US008067664B2

(12) United States Patent
Huang

(10) Patent No.: US 8,067,664 B2
(45) Date of Patent: Nov. 29, 2011

(54) PRO224 GENE DISRUPTIONS, AND METHODS RELATED THERETO

(75) Inventor: Wenhu Huang, San Diego, CA (US)

(73) Assignee: Genentech, Inc., South San Francisco, CA (US)

( * ) Notice: Subject to any disclaimer, the term of this patent is extended or adjusted under 35 U.S.C. 154(b) by 726 days.

(21) Appl. No.: 10/583,466

(22) PCT Filed: Dec. 13, 2004

(86) PCT No.: PCT/US2004/041721
§ 371 (c)(1),
(2), (4) Date: Sep. 5, 2007

(87) PCT Pub. No.: WO2005/058028
PCT Pub. Date: Jun. 30, 2005

(65) Prior Publication Data
US 2007/0292438 A1    Dec. 20, 2007

Related U.S. Application Data

(60) Provisional application No. 60/530,043, filed on Dec. 16, 2003.

(51) Int. Cl.
*G01N 33/00* (2006.01)
*C12N 15/00* (2006.01)
(52) U.S. Cl. .............................................. 800/3; 800/21
(58) Field of Classification Search ................... 800/3, 21
See application file for complete search history.

(56) References Cited

U.S. PATENT DOCUMENTS

| 6,436,707 B1 | 8/2002 | Zambrowicz et al. |
| 2002/0137900 A1 | 9/2002 | Ferrara et al. |
| 2004/0067553 A1 | 4/2004 | Masanori |

FOREIGN PATENT DOCUMENTS

| WO | WO 99/14328 | 3/1999 |
| WO | WO 01/87932 | 11/2001 |
| WO | WO 02/053593 | 7/2002 |

OTHER PUBLICATIONS

Upton et al., Lack of 5-HT1B receptor and of serotonin transporter have different effects on the segregation of retinal axons in the lateral geniculate nucleus compared to the superior colliculus, Neuroscience, 111(3):597-610, 2002.*
Ristevski, Making better transgenic models: conditional, temporal, and spatial approaches. Mol Biotechnol. 29(2): 153-63, 2005.*
Montoliu, Gene transfer strategies in animal transgenesis. Cloning Stem Cells. 4(1): 39-46, 2002.*
Clark et al., The mammary gland as a bioreactor: expression, processing, and production of recombinant proteins, J Mammary Gland Biol Neoplasia. 3(3):337-50, 1998.*
Williams, Death of Dolly marks cloning milestone, Curr Biol. 13(6):R209-10, 2003.*
Denning et al, New frontiers in gene targeting and cloning: success, application and challenges in domestic animals and human embryonic stem cells. 2003, Reproduction, 126: 1-11, 2003.*
Matthaei, Genetically manipulated mice: a powerful tool with unsuspected caveats. J Physiol. 582(Pt 2):481-8, 2007.*
Skolnick et al., From genes to protein structure and function: novel applications of computational approaches in the genomic era, Trends in Biotechnol. 18(1):34-39, 2000.*
Abu-Elheiga, L. et al., "Continuous Fatty Acid Oxidation and Reduced Fat Storage in Mice Lacking Acetyl-CoA Carboxylase 2" *Science* 291:2613-16 (Mar. 30, 2001).
Abud, H. E, et al., "The murine A33 antigen is expressed at two distinct sites during development, the ICM of the blastocyst and the intestinal epithelium" *Mechanisms of Development* 98:111-14 (2000).
Beltowski, J., "Adiponectin and resistin—new hormones of white adipose tissue." *Med Sci Monit.* 9(2) :RA55-61 (Feb. 2003).
Bromme, N. C., et al., "Cloning, Characterization, and Expression of the Human TIN-ag-RP Gene Encoding a Novel Putative Extracellular Matrix Protein" *Biochemical and Biophysical Research Communications* 271:474-80 (2000).
Chang, B., et al., "Identification of a missense mutation in the αA-crystallin gene of the lop18 mouse" *Molecular Vision* 5:21-5 (1999).
Daly, N.L., et al., "Three-dimensional structure of a cysteine-rich repeat from the low-density lipoprotein receptor" *Proc. Natl. Acad. Sci.* 92:6334-38 (Jul. 1995).
DeLorey, T.M. et al., "Mice lacking the beta3 subunit of the GABAA receptor have the epilepsy phenotype and many of the behavorial characteristics of Angelman syndrome." *Neuroscience* 18(20) :8505-14 (Oct. 15, 1998).
Dumoutier et al., "Cloning and Characterization of IL-22 Binding Protein, a Natural Antagonist of IL-10-Related T Cell-Derived Inducible Factor/IL-22" *Journal of Immunology* 166:7090-7095 (2001).
Eby, M. T., et al., "TAJ, a Novel Member of the Tumor Necrosis Factor Receptor Family, Activates the c-Jun N-Terminal Kinase Pathway and Mediates Caspase-independent Cell Death" *The Journal of Biological Chemistry* 275(20) :15336-42 (May 19, 2000).

(Continued)

*Primary Examiner* — Wu-Cheng Winston Shen
(74) *Attorney, Agent, or Firm* — Bonny Yeung; James A. Fox; Arnold & Porter LLP

(57) ABSTRACT

The present invention relates to transgenic animals, as well as compositions and methods relating to the characterization of gene function. Specifically, the present invention provides transgenic mice comprising disruptions in PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 genes. Such in vivo studies and characterizations may provide valuable identification and discovery of therapeutics and/or treatments useful in the prevention, amelioration or correction of diseases or dysfunctions associated with gene disruptions such as neurological disorders; cardiovascular, endothelial or angiogenic disorders; eye abnormalities; immunological disorders; oncological disorders; bone metabolic abnormalities or disorders; lipid metabolic disorders; or developmental abnormalities.

8 Claims, 40 Drawing Sheets

OTHER PUBLICATIONS

Esther, R.C. et al., "Mice Lacking angiotensin-converting enzyme have low blood pressure, renal pathology, and reduced male fertility." *Laboratory Investigation* 74(5) :953-65 (May 1996).

Giese, A., et al., "Molecular characterization of the equine testis-specific protein 1 (TPX1) and acidic epididymal glycoprotein 2 (AEG2) genes encoding members of the cysteine-rich secretory protein (CRISP) family" *Gene* 299:101-109 (2002).

Giros, B., et al., "Hyperlocomotion and indifference to cocaine and amphetamine in mice lacking the dopamine transporter" *Nature* 379:606-12 (Feb. 15, 1996).

Hara, Y., et al., "LTRPC2$Ca^{2+}$-Permeable Channel Activated by Changes in Redox Status Confers Susceptibility to Cell Death" *Molecular Cell* 9:163-73 (Jan. 2002).

Hawes, N. L., et al., "Mouse fundus photography and angiography: A catalogue of normal and mutant phenotypes" *Molecular Vision* 5:22 (Aug. 1999).

Holcomb et al., "FIZZ1, a novel cysteine-rich secreted protein associated with pulmonary inflammation, defines a new gene family" *EMBO Journal* 19(15) :4046-4055 (2000).

Holmes, G., et al., "Expression of slit-2 and slit-3 during chick development." *Dev Dyn.* 222(2) :301-7 (Oct. 2001).

Homanics, G. E., et al., "Mice devoid of γ-aminobutyrate type A receptor β3 subunit have epilepsy, cleft palate, and hypersensitive behavior" *Proc. Natl. Acad. Sci. USA* 94:4143-8 (Apr. 1997).

Hu et al., "Characterization of TNFRSF19, a novel member of the tumor necrosis factor receptor superfamily" *Genomics* 62(1) :103-107 (Nov. 15, 1999).

Kim, I., et al., "A novel fibroblast growth factor receptor-5 preferentially expressed in the pancreas(1)." *Biochim Biophys Acta* 1518(1-2) :152-6 (Mar. 19, 2001).

Kobayashi, M., et al., "Isolation of an androgen-inducible novel lipocalin gene, Argl, from androgen-dependent mouse mammary Shionogi carcinoma cells." *Steroid Biochem Mol Biol* 77(2-3) :109-15 (May 2001).

Kojima, T., et al., "TROY, a Newly Identified Member of the Tumor Necrosis Factor Receptor Superfamily, Exhibits a Homology with Edar and Is Expressed in Embryonic Skin and Hair Follicles" *The Journal of Biological Chemistry* 275(27) :20742-47 (Jul. 7, 2000).

Kotenko et al., "Identification, Cloning, and Characterization of a Novel Soluble Receptor That Binds IL-22 and Neutralizes Its Activity[1,2]" *J. Immunol.* 166:7096-7103 (2001).

Langenbach, R. et al., "Prostaglandin Synthase 1 Gene Disruption in Mice Reduced Arachidonic Acid-Induced Inflammation and Indomethancin-Induced Gastric Ulceration" *Cell* 83:483-92 (Nov. 3, 1995).

Leung, D.W., "The structure and functions of human lysophosphatidic acid acyltransferases." *Frontiers in Bioscience* 6:D944-53 (Aug. 2001).

Li, L., et al., "Identification of a Human Follicular Dendritic Cell Molecule That Stimulates Germinal Center B Cell Growth" *Journal of Experimental Medicine* 191(6) :1077-83 (Mar. 20, 2000).

Little, M. H., et al., "Dual trafficking of Slit3 to mitochondria and cell surface demonstrates novel localization for Slit protein" *Am J Physiol Cell Physiol* 281:C486-95 (2001).

Liu, M., et al., "GPR56, a Novel Secretin—like Human G-Protein-Coupled Receptor Gene" *Genomics* 55:296-305 (1999).

Louie and Edwards, "Hypertrophic Cardiomyopathy" *Prog. Cardiovasc. Dis.* 36:275-308 (1994).

Milne, T. J., et al., "Isolation and Characterization of a Cone Snail Protease with Homology to CRISP Proteins of the Pathogenesis-related Protein Superfamily" *Journal of Biological Chemistry* 278(33) :31105-10 (Aug. 15, 2003).

Mukai, K., et al., "An Inverse Correlation between Expression of a Preprocathepsin B-related Protein with Cysteine-rich Sequences and Steroid 11β-Hydroxylase in Adrenocortical Cells" *The Journal of Biological Chemistry* 278(19) :17084-92 (May 9, 2003).

Perraud, A., et al., "ADP-ribose gating of the calcium-permeable LTRPC2 channel revealed by Nudix motif homology" *Nature* 411:595-9 (May 2001).

Pizzuti, A., et al., "An ATG Repeat in the 3' -Untranslated Region of the Human Resistin Gene Is Associated with a Decreased Risk of Insulin Resistance" *Journal of Clinical Endocrinology & Metabolism* 87(9) :4403-6 (2002).

Sano, Y., et al., "Immunocyte $Ca^{2+}$ Influx System Mediated by LTRPC2" *Science* 293:1327-30 (Aug. 17, 2001).

Schultz, J., et al., "SMART: a web-based tool for the study of genetically mobile domains" *Nucleic Acids Research* 28(1) :231-4 (2000).

Sleeman, M., et al., "Identification of a new fibroblast growth factor receptor, FGFR5" *Gene* 271:171-82 (2001).

Spirito et al., "The Management of Hypertrophic Cardiomyopathy" *New England J. of Medicine* 336:775-785 (1997).

Steppan, C. M., et al., "The hormone resistin links obesity to diabetes" *Nature* 409:307-12 (Jan. 2001).

Sutphen, R. et al., "Lysophospholipids Are Potential Biomarkers of Ovarian Cancer" *Cancer Epidemiology Biomarkers & Prevention* 13(7) :1185-91 (Jul. 2004).

Vassilatis, D. K., et al, "The G protein-coupled receptor repertoires of human and mouse" *Proc. Natl. Acad. Sci. USA* 100(8) :4903-8 (Apr. 15, 2003).

Wehage, E., et al., "Activation of the Cation Channel Long Transient Receptor Potential Channel 2 (LTRPC2) by Hydrogen Peroxide" *The Journal of Biological Chemistry* 277(26):23150-6 (Jun. 28, 2002).

Wex, T., et al., "TIN-ag-RP, a Novel Catalytically Inactive Cathepsin B-Related Protein with EGF Domains, Is Predominantly Expressed in Vascular Smooth Muscle Cells" *Biochemistry* 40:1350-7 (2001).

Wiedemann, M., et al., "Characterization of a Novel Protein (FGFRL1) from Human Cartilage Related to FGF Receptors" *Genomics* 69:275-9 (2000).

Wiedemann, M., et al., "The mouse Fgfrl1 gene coding for a novel FGF receptor-like protein." *Biochim Biophys Acta* 1520(3) :247-50 (Sep. 21, 2001).

Wigle et al., "Hypertrophic cardiomyopathy, clinical spectrum and treatment" *Circulation* 92:1680-1692 (1995).

Wu, H. et al, "Generation of Committed Erythroid BFU-E and CFU-E Progenitors Does Not Require Erythropoietin or the Erythropoietin Receptor" *Cell* 83:59-67 (Oct. 6, 1995).

Xu et al., "A soluble class II cytokine receptor, IL-22RA2, is a naturally occurring IL-22 antagonist" *Proc. Natl. Acad. Sci. USA* 98:9511-9516 (Aug. 14, 2001).

Xu, X, et al., "Presence of a vertebrate fibrinogen-like sequence in an echinoderm" *Proc. Natl. Acad. Sci. USA* 87:2097-2101 (Mar. 1990).

Zendman, A., et al., "TM7XN1, a novel human EGF-TM7-like cDNA, detected with mRNA differential display using human melanoma cell lines with different metastatic potential" *FEBS Letters* 446:292-8 (1999).

Zhang, Q., et al., "Cloning and Functional Analysis of cDNAs with Open Reading Frames for 300 Previously Undefined Genes Expressed in CD34+ Hematopoietic Stem/Progenitor Cells" *Genome Research* 10:1546-60 (2000).

Clark, et al., "The secreted protein discovery initiative (SPDI), a large scale effort to identify novel human secreted and transmembrane proteins; A bioinformatics assessment", Genome Research, vol. 13, pp. 2265-2270, (2003).

Database EMBL, "Homo sapiens clone DNA203528 GPR113 (UNQ9196) mRNA, complete eds", EBI Accession No. AY358172, Oct. 9, 2003.

* cited by examiner

FIGURE 1

CAGCGCGTGGCCGGCGCCGCTGTGGGGACAGCATGAGCGGCGGTTGGATGGCGCAGGTTGGAGCGTGGCGAACA
GGGGCTCTGGGCCTGGCGCTGCTGCTGCTGCTCGGCCTCGGACTAGGCCTGGAGGCCGCCGCGAGCCCGCTTTC
CACCCCGACCTCTGCCCAGGCCGCAGGCCCCAGCTCAGGCTCGTGCCCACCCACCAAGTTCCAGTGCCGCACCA
GTGGCTTATGCGTGCCCCTCACCTGGCGCTGCGACAGGGACTTGGACTGCAGCGATGGCAGCGATGAGGAGGAG
TGCAGGATTGAGCCATGTACCCAGAAAGGGCAATGCCCACCGCCCCTGGCCTCCCCTGCCCTGCACCGGCGT
CAGTGACTGCTCTGGGGGAACTGACAAGAAACTGCGCAACTGCAGCCGCCTGGCCTGCCTAGCAGGCGAGCTCC
GTTGCACGCTGAGCGATGACTGCATTCCACTCACGTGGCGCTGCGACGGCCACCCAGACTGTCCCGACTCCAGC
GACGAGCTCGGCTGTGGAACCAATGAGATCCTCCCGGAAGGGGATGCCACAACCATGGGGCCCCCTGTGACCCT
GGAGAGTGTCACCTCTCTCAGGAATGCCACAACCATGGGGCCCCCTGTGACCCTGGAGAGTGTCCCCTCTGTCG
GGAATGCCACATCCTCCTCTGCCGGAGACCAGTCTGGAAGCCCAACTGCCTATGGGGTTATTGCAGCTGCTGCG
GTGCTCAGTGCAAGCCTGGTCACCGCCACCCTCCTCCTTTTGTCCTGGCTCCGAGCCCAGGAGCGCCTCCGCCC
ACTGGGGTTACTGGTGGCCATGAAGGAGTCCCTGCTGCTGTCAG AACAGAAGACCTCGCTGCCCTGAGGACAAG
CACTTGCCACCACCGTCACTCAGCCCTGGGCGTAGCCGGACAGGAGGAGAGCAGTGATGCGGATGGGTACCCGG
GCACACCAGCCCTCAGAGACCTGAGTTCTTCTGGCCACGTGGAACCTCGAACCCGAGCTCCTGCAGAAGTGGCC
CTGGAGATTGAGGGTCCCTGGACACTCCCTATGGAGATCCGGGGAGCTAGGATGGGGAACCTGCCACAGCCAGA
ACTGAGGGGCTGGCCCCAGGCAGCTCCCAGGGGGTAGAACGGCCCTGTGCTTAAGACACTCCCTGCTGCCCCGT
CTGAGGGTGGCGATTAAAGTTGCTTC

FIGURE 2

MSGGWMAQVGAWRTGALGLALLLLLGLGLGLEAAASPLSTPTSAQAAGPSSGSCPPTKFQCRTSGLCVPLTWRC
DRDLDCSDGSDEEECRIEPCTQKGQCPPPPGLPCPCTGVSDCSGGTDKKLRNCSRLACLAGELRCTLSDDCIPL
TWRCDGHPDCPDSSDELGCGTNEILPEGDATTMGPPVTLESVTSLRNATTMGPPVTLESVPSVGNATSSSAGDQ
SGSPTAYGVIAAAAVLSASLVTATLLLLSWLRAQERLRPLGLLVAMKESLLLSEQKTSLP

Signal sequence:
amino acids 1-30

Transmembrane domain:
amino acids 230-246

N-glycosylation site.
amino acids 126-130, 195-199, 213-217

Casein kinase II phosphorylation site.
amino acids 84-88, 140-144, 161-165, 218-222

N-myristoylation site.
amino acids 3-9, 10-16, 26-32, 30-36, 112-118, 166-172, 212-218, 224-230, 230-236, 263-269

Prokaryotic membrane lipoprotein lipid attachment site.
amino acids 44-55

Leucine zipper pattern.
amino acids 17-39

FIGURE 3

ACACTGGCCAAACACTCGCATCCCAGGGCGTCTCCGGCTGCTCCCATTGAGCTGTCTGCT
CGCTGTGCCCGCTGTGCCTGCTGTGCCCGCGCTGTCGCCGCTGCTACCGCGTCTGCTGGA
CGCGGGAGACGCCAGCGAGCTGGTGATTGGAGCCCTGCGGAGAGCTCAAGCGCCCAGCTC
TGCCCGAGGAGCCCAGGCTGCCCCGTGAGTCCATAGTTGCTGCAGGAGTGGAGCCTTTC
CCTTTGCGATCGCTAAACCACCATGAGCTGCGTCCTGGGTGGTGTCATCCCCTTGGGGCT
GCTGTTCCTGGTCTGCGGATCCCAAGGCTACCTCCTGCCCAACGTCACTCTCTTAGAGGA
GCTGCTCAGCAAATACCAGCACAACGAGTCTCACTCCCGGGTCCGCAGAGCCATCCCCAG
GGAGGACAAGGAGGAGATCCTCATGCTGCACAACAAGCTTCGGGGCCAGGTGCAGCCTCA
GGCCTCCAACATGGAGTACATGACCTGGGATGACGAACTGGAGAAGTCTGCTGCAGCGTG
GGCCAGTCAGTGCATCTGGGAGCACGGGCCCACCAGTCTGCTGGTGTCCATCGGGCAGAA
CCTGGGCGCTCACTGGGGCAGGTATCGCTCTCCGGGGTTCCATGTGCAGTCCTGGTATGA
CGAGGTGAAGGACTACACCTACCCCTACCCGAGCGAGTGCAACCCCTGGTGTCCAGAGAG
GTGCTCGGGGCCTATGTGCACGCACTACACACAGATAGTTTGGGCCACCACCAACAAGAT
CGGTTGTGCTGTGAACACCTGCCGGAAGATGACTGTCTGGGGAGAAGTTTGGGAGAACGC
GGTCTACTTTGTCTGCAATTATTCTCCAAAGGGGAACTGGATTGGAGAAGCCCCCTACAA
GAATGGCCGGCCCTGCTCTGAGTGCCCACCCAGCTATGGAGGCAGCTGCAGGAACAACTT
GTGTTACCGAGAAGAAACCTACACTCCAAAACCTGAAACGGACGAGATGAATGAGGTGGA
AACGGCTCCCATTCCTGAAGAAAACCATGTTTGGCTCCAACCGAGGGTGATGAGACCCAC
CAAGCCCAAGAAAACCTCTGCGGTCAACTACATGACCCAAGTCGTCAGATGTGACACCAA
GATGAAGGACAGGTGCAAAGGGTCCACGTGTAACAGGTACCAGTGCCCAGCAGGCTGCCT
GAACCACAAGGCGAAGATCTTTGGAAGTCTGTTCTATGAAAGCTCGTCTAGCATATGCCG
CGCCGCCATCCACTACGGGATCCTGGATGACAAGGGAGGCCTGGTGGATATCACCAGGAA
CGGGAAGGTCCCCTTCTTCGTGAAGTCTGAGAGACACGGCGTGCAGTCCCTCAGCAAATA
CAAACCTTCCAGCTCATTCATGGTGTCAAAAGTGAAAGTGCAGGATTTGGACTGCTACAC
GACCGTTGCTCAGCTGTGCCCGTTTGAAAAGCCAGCAACTCACTGCCCAAGAATCCATTG
TCCGGCACACTGCAAAGACGAACCTTCCTACTGGGCTCCGGTGTTTGGAACCAACATCTA
TGCAGATACCTCAAGCATCTGCAAGACAGCTGTGCACGCGGGAGTCATCAGCAACGAGAG
TGGGGGTGACGTGGACGTGATGCCCGTGGATAAAAAGAAGACCTACGTGGGCTCGCTCAG
GAATGGAGTTCAGTCTGAAAGCCTGGGGACTCCTCGGGATGGAAAGGCCTTCCGGATCTT
TGCTGTCAGGCATTTCCCTTTGCGGCCGCGTGAATTTCCAGCACCAGGGGAGAAGGGGCG
TCTTCAGGAGGGCTTCGGGGTTTTGCTTTTATTTTTATTTTGTCATTGCGGGGTATATGG
AGAGTCA

FIGURE 4

MSCVLGGVIPLGLLFLVCGSQGYLLPNVTLLEELLSKYQHNESHSRVRRAIPREDKEEIL
MLHNKLRGQVQPQASNMEYMTWDDELEKSAAAWASQCIWEHGPTSLLVSIGQNLGAHWGR
YRSPGFHVQSWYDEVKDYTYPYPSECNPWCPERCSGPMCTHYTQIVWATTNKIGCAVNTC
RKMTVWGEVWENAVYFVCNYSPKGNWIGEAPYKNGRPCSECPPSYGGSCRNNLCYREETY
TPKPETDEMNEVETAPIPEENHVWLQPRVMRPTKPKKTSAVNYMTQVVRCDTKMKDRCKG
STCNRYQCPAGCLNHKAKIFGSLFYESSSSICRAAIHYGILDDKGGLVDITRNGKVPFFV
KSERHGVQSLSKYKPSSSFMVSKVKVQDLDCYTTVAQLCPFEKPATHCPRIHCPAHCKDE
PSYWAPVFGTNIYADTSSICKTAVHAGVISNESGGDVDVMPVDKKKTYVGSLRNGVQSES
LGTPRDGKAFRIFAVRQ

Important features of the protein:
Signal peptide:
1-22
N-glycosylation site:
    27-31
    41-45
    451-455
cAMP- and cGMP-dependent protein kinase phosphorylation site.
    181-185
    276-280
    464-468
Tyrosine kinase phosphorylation site.
    385-393
N-myristoylation site.
    111-117
    115-121
    174-180
    204-210
    227-233
    300-306
    447-453
    470-476
Extracellular proteins SCP/Tpx-1/Ag5/PR-1/Sc7 signature 2.
    195-207
SCP-like extracellular protein
    56-208

FIGURE 5

CTGTCAGGAAGGACCATCTGAAGGCTGCAATTTGTTCTTAGGGAGGCAGGTGCTGGCCTGGCCTGGATCTTCCA
CCATGTTCCTGTTGCTGCCTTTTGATAGCCTGATTGTCAACCTTCTGGGCATCTCCCTGACTGTCCTCTTCACC
CTCCTTCTCGTTTTCATCATAGTGCCAGCCATTTTTGGAGTCTCCTTTGGTATCCGCAAACTCTACATGAAAAG
TCTGTTAAAAATCTTTGCGTGGCTACCTTGAGAATGGAGCGAGGAGCCAAGGAGAAGAACCACCAGCTTTACA
AGCCCTACACCAACGGAATCATTGCAAAGGATCCCACTTCACTAGAAGAAGAGATCAAAGAGATTCGTCGAAGT
GGTAGTAGTAAGGCTCTGGACAACACTCCAGAGTTCGAGCTCTCTGACATTTTCTACTTTTGCCGGAAAGGAAT
GGAGACCATTATGGATGATGAGGTGACAAAGAGATTCTCAGCAGAAGAACTGGAGTCCTGGAACCTGCTGAGCA
GAACCAATTATAACTTCCAGTACATCAGCCTTCGGCTCACGGTCCTGTGGGGGTTAGGAGTGCTGATTCGGTAC
TGCTTTCTGCTGCCGCTCAGGATAGCACTGGCTTTCACAGGGATTAGCCTTCTGGTGGTGGGCACAACTGTGGT
GGGATACTTGCCAAATGGGAGGTTTAAGGAATTCATGAGTAAACATGTTCACTTAATGTGTTACCGGATCTGCG
TGCGAGCGCTGACAGCCATCATCACCTACCATGACAGGGAAAACAGACCAAGAAATGGTGGCATCTGTGTGGCC
AATCATACCTCACCGATCGATGTGATCATCTTGGCCAGCGATGGCTATTATGCCATGGTGGGTCAAGTGCACGG
GGGACTCATGGGTGTGATTCAGAGAGCCATGGTGAAGGCCTGCCCACACGTCTGGTTTGAGCGCTCGGAAGTGA
AGGATCGCCACCTGGTGGCTAAGAGACTGACTGAACATGTGCAAGATAAAAGCAAGCTGCCTATCCTCATCTTC
CCAGAAGGAACCTGCATCAATAATACATCGGTGATGATGTTCAAAAAGGGAAGTTTTGAAATTGGAGCCACAGT
TTACCCTGTTGCTATCAAGTATGACCCTCAATTTGGCGATGCCTTCTGGAACAGCAGCAAATACGGGATGGTGA
CGTACCTGCTGCGAATGATGACCAGCTGGGCCATTGTCTGCAGCGTGTGGTACCTGCCTCCCATGACTAGAGAG
GCAGATGAAGATGCTGTCCAGTTTGCGAATAGGGTGAAATCTGCCATTGCCAGGCAGGGAGGACTTGTGGACCT
GCTGTGGGATGGGGCCTGAAGAGGGAGAAGGTGAAGGACACGTTCAAGGAGGAGCAGCAGAAGCTGTACAGCA
AGATGATCGTGGGGAACCACAAGGACAGGAGCCGCTCCTGAGCCTGCCTCCAGCTGGCTGGGGCCACCGTGCGG
GGTGCCAACGGGCTCAGAGCTGGAGTTGCCGCCGCCGCCCCCACTGCTGTGTCCTTTCCAGACTCCAGGGCTCC
CCGGGCTGCTCTGGATCCCAGGACTCCGGCTTTCGCCGAGCCGCAGCGGGATCCCTGTGCACCCGGCGCAGCCT
ACCCTTGGTGGTCTAAACGGATGCTGCTGGGTGTTGCGACCCAGGACGAGATGCCTTGTTTCTTTTACAATAAG
TCGTTGGAGGAATGCCATTAAAGTGAACTCCCCACCTTTGCACGCTGTGCGGGCTGAGTGGTTGGGGAGATGTG
GCCATGGTCTTGTGCTAGAGATGGCGGTACAAGAGTCTGTTATGCAAGCCCGTGTGCCAGGGATGTGCTGGGGG
CGGCCACCCGCTCTCCAGGAAAGGCACAGCTGAGGCACTGTGGCTGGCTTCGGCCTCAACATCGCCCCCAGCCT
TGGAGCTCTGCAGACATGATAGGAAGGAAACTGTCATCTGCAGGGGCTTTCAGCAAAATGAAGGGTTAGATTTT
TATGCTGCTGCTGATGGGGTTACTAAAGGGAGGGGAAGAGGCCAGGTGGGCCGCTGACTGGGCCATGGGGAGAA
CGTGTGTTCGTACTCCAGGCTAACCCTGAACTCCCCATGTGATGCGCGCTTTGTTGAATGTGTGTCTCGGTTTC
CCCATCTGTAATATGAGTCGGGGGGAATGGTGGTGATTCCTACCTCACAGGGCTGTTGTGGGGATTAAAGTGCT
GCGGGTGAGTGAAGGACACATCACGTTCAGTGTTTCAAGTACAGGCCCACAAAACGGGGCACGGCAGGCCTGAG
CTCAGAGCTGCTGCACTGGGCTTTGGATTTGTTCTTGTGAGTAAATAAAACTGGCTGGTGAATGA

FIGURE 6

MFLLLPFDSLIVNLLGISLTVLFTLLLVFIIVPAIFGVSFGIRKLYMKSLLKIFAWATLRMERGAKEKNHQLYK
PYTNGIIAKDPTSLEEEIKEIRRSGSSKALDNTPEFELSDIFYFCRKGMETIMDDEVTKRFSAEELESWNLLSR
TNYNFQYISLRLTVLWGLGVLIRYCFLLPLRIALAFTGISLLVVGTTVVGYLPNGRFKEFMSKHVHLMCYRICV
RALTAIITYHDRENRPRNGGICVANHTSPIDVIILASDGYYAMVGQVHGGLMGVIQRAMVKACPHVWFERSEVK
DRHLVAKRLTEHVQDKSKLPILIFPEGTCINNTSVMMFKKGSFEIGATVYPVAIKYDPQFGDAFWNSSKYGMVT
YLLRMMTSWAIVCSVWYLPPMTREADEDAVQFANRVKSAIARQGGLVDLLWDGGLKREKVKDTFKEEQQKLYSK
MIVGNHKDRSRS

FIGURE 7A

```
CTCCCTTTCATCTGGTGGCCCTAGCGCCACAAGCTGCCGCTTAGGAAGTCCCTGCCGGGA
GCAGAAGTGGAGACATCAGCAGGATGGCATCGGCAAGTCGCTCCCCTCCCGGGCCTCATC
TGCCAAACGATCATCTCCTCCTCCGAAGTTGTATGCATGACAGGCGAGTGGAAACTTCAC
TAAAATGAAGGCGATTGACACAACAGAAGGAACTCCATCCTTTCGGGGGCTTACGAAAAT
AATAAGTTTAAAAAAAATAGGAAGGGAATTCCCTCGCTCCATGATCACTGAGCGCTCTCC
TAAGGAAAAGGAAATCTCCCGGGGGTGCCGACTACGGGCGGCGGGCTTAGGATGCTCCC
ACGCTCCCCGACCCCCAATCCCCAGGACCCGCAGGACCTCCGGAGGAACGCCCGCCAGCC
CGCCCGGAGCCACGCGGCACAAGGTGACACGGACCGCGCCGCGCGGGCCCCTCAGCCGCC
TGGGCGAGGCCGGGAGCAGGGAGAGGGGCATCCGCCGGCCCGCGGTACCTTGTACTTATC
AAAGCCAGCCAGCTGCTCCGGGCTCACGTATTCGTAGCCAGCCATGACGACCCGAAAACT
GAGCGCCCACTCGGCAGCGACTCCCGGCTACAAGGCTGTGACACACAAGCACCACACCGG
CTGGGCAAGGATGGCAAAGACTGGGCTGCCCGAGAAGGGACAGAGTCAGGCTGGAGGGGA
ATCTGGATCTGGGCAGCTCCTGGACCAAGAGAATGGAGCAGGGGAATCAGCGCTGGTCTC
CGTCTATGTACATCTGGACTTTCCAGATAAGACCTGGCCCCCTGAACTCTCCAGGACACT
GACTCTCCCTGCTGCCTCAGCTTCCTCTTCCCCAAGGCCTCTTCTCACTGGCCTCAGACT
CACAACAGGTGAGTACATGAGCTGCTTCGAGGCCCAGGGCTTCAAGTGGAACCTGTATGA
GGTGGTGAGGGTGCCCTTGAAGGCGACAGATGTGGCTCGACTTCCATACCAGCTGTCCAT
CTCCTGTGTCACCTCCCCTGGCTTCCAGCTGAGCTGCTGCATCCCCAGCACAAACCTGGC
CTACACCGCGGCCTGGAGCCCTGGAGAGGGCAGCAAAGCTTCCTCCTTCAACGAGTCAGG
CTCTCAGTGCTTTGTGCTGGCTGTTCAGCGCTGCCCGATGGCTGACACCACGTACACTTG
TGACCTGCAGAGCCTGGGCCTGGCTCCACTCAGGGTCCCCATCTCCATCACCATCATCCA
GGATGGAGACATCACCTGCCCTGAGGACGCCTCGGTGCTCACCTGGAATGTCACCAAGGC
TGGCCACGTGGCACAGGCCCCATGTCCTGAGAGCAAGAGGGGCATAGTGAGGAGGCTCTG
TGGGGCTGACGGAGTCTGGGGGCCGGTCCACAGCAGCTGCACAGATGCGAGGCTCCTGGC
CTTGTTCACTAGAACCAAGCTGCTGCAGGCAGGCCAGGGCAGTCCTGCTGAGGAGGTGCC
ACAGATCCTGGCACAGCTGCCAGGGCAGGCGGCAGAGGCAAGTTCACCCTCCGACTTACT
GACCCTGCTGAGCACCATGAAATACGTGGCCAAGGTGGTGGCAGAGGCCAGAATACAGCT
TGACCGCAGAGCCCTGAAGAATCTCCTGATTGCCACAGACAAGGTCCTAGATATGGACAC
CAGGTCTCTGTGGACCCTGGCCCAAGCCCGGAAGCCCTGGGCAGGCTCGACTCTCCTGCT
GGCTGTGGAGACCCTGGCATGCAGCCTGTGCCCACAGGACTACCCCTTCGCCTTCAGCTT
ACCCAATGTGCTGCTGCAGAGCCAGCTGTTTGGACCCACGTTTCCTGCTGACTACAGCAT
CTCCTTCCCTACTCGTCCCCCACTGCAGGCTCAGATTCCCAGGCACTCACTGGCCCCATT
GGTCCGTAATGGAACTGAAATAAGTATTACTAGCCTGGTGCTGCGAAAACTGGACCACCT
TCTGCCCTCAAACTATGGACAAGGGCTGGGGATTCCCTCTATGCCACTCCTGGCCTGGT
CCTTGTCATTTCCATCATGGCAGGTGACCGGGCCTTCAGCCAGGGAGAGGTCATCATGGA
CTTTGGGAACACAGATGGTTCCCCTCACTGTGTCTTCTGGGATCACAGTCTCTTCCAGGG
CAGGGGGGGTTGGTCCAAAGAAGGGTGCCAGGCACAGGTGGCCAGTGCCAGCCCCACTGC
```

FIGURE 7B

```
TCAGTGCCTCTGCCAGCACCTCACTGCCTTCTCCGTCCTCATGTCCCCACACACTGTTCC
GGAAGAACCCGCTCTGGCGCTGCTGACTCAAGTGGGCTTGGGAGCTTCCATACTGGCGCT
GCTTGTGTGCCTGGGTGTGTACTGGCTGGTGTGGAGAGTCGTGGTGCGGAACAAGATCTC
CTATTTCCGCCACGCCGCCCTGCTCAACATGGTGTTCTGCTTGCTGGCCGCAGACACTTG
CTTCCTGGGCGCCCCATTCCTCTCTCCAGGGCCCCGAAGCCCGCTCTGCCTTGCTGCCGC
CTTCCTCTGTCATTTCCTCTACCTGGCCACCTTTTTCTGGATGCTGGCGCAGGCCCTGGT
GTTGGCCCACCAGCTGCTATTTGTCTTTCACCAGCTGGCAAAGCACCGAGTTCTCCCCCT
CATGGTGCTCCTGGGCTACCTGTGCCCACTGGGGTTGGCAGGTGTCACCCTGGGGCTCTA
CCTACCTCAAGGGCAATACCTGAGGGAGGGGGAATGCTGGTTGGATGGGAAGGGAGGGGC
GTTATACACCTTCGTGGGGCCAGTGCTGGCCATCATAGGCGTGAATGGGCTGGTACTAGC
CATGGCCATGCTGAAGTTGCTGAGACCTTCGCTGTCAGAGGGACCCCCAGCAGAGAAGCG
CCAAGCTCTGCTGGGGGTGATCAAAGCCCTGCTCATTCTTACACCCATCTTTGGCCTCAC
CTGGGGGCTGGGCCTGGCCACTCTGTTAGAGGAAGTCTCCACGGTCCCTCATTACATCTT
CACCATTCTCAACACCCTCCAGGGCGTCTTCATCCTATTGTTTGGTTGCCTCATGGACAG
GAAGATACAAGAAGCTTTGCGCAAACGCTTCTGCCGCGCCCAAGCCCCCAGCTCCACCAT
CTCCCTGGCCACAAATGAAGGCTGCATCTTGGAACACAGCAAAGGAGGAAGCGACACTGC
CAGGAAGACAGATGCTTCAGAGTGAACCACACACGGACCCATGTTCCTGCAAGGGAGTTG
AGGCTGTGTGCTTGAACCCACCAGATGAGCCCTGGCCCAATGCTCTGAACTCTTCCCGCC
TCCCGGAGCTCAGCCCTTGAGAAAGTTATGAAGAAAGGATGACTTACTTGACAGGAACCT
CTGATCTTTCAAACATTGGAGATGAAGGGCAGAATTTGGTTTGTCTTTTCAAGTTTAGGA
AAAGGTGAAGTTAATTGGTCCCTCTTTCTTTAACCTTTAAAAAATCAATATAAAATGTAA
GTTTCTTAACCAT
```

FIGURE 8A

```
MTTRKLSAHSAATPGYKAVTHKHHTGWARMAKTGLPEKGQSQAGGESGSGQLLDQENGAG
ESALVSVYVHLDFPDKTWPPELSRTLTLPAASASSSPRPLLTGLRLTTGEYMSCFEAQGF
KWNLYEVVRVPLKATDVARLPYQLSISCVTSPGFQLSCCIPSTNLAYTAAWSPGEGSKAS
SFNESGSQCFVLAVQRCPMADTTYTCDLQSLGLAPLRVPISITIIQDGDITCPEDASVLT
WNVTKAGHVAQAPCPESKRGIVRRLCGADGVWGPVHSSCTDARLLALFTRTKLLQAGQGS
PAEEVPQILAQLPGQAAEASSPSDLLTLLSTMKYVAKVVAEARIQLDRRALKNLLIATDK
VLDMDTRSLWTLAQARKPWAGSTLLLAVETLACSLCPQDYPFAFSLPNVLLQSQLFGPTF
PADYSISFPTRPPLQAQIPRHSLAPLVRNGTEISITSLVLRKLDHLLPSNYGQGLGDSLY
ATPGLVLVISIMAGDRAFSQGEVIMDFGNTDGSPHCVFWDHSLFQGRGGWSKEGCQAQVA
SASPTAQCLCQHLTAFSVLMSPHTVPEEPALALLTQVGLGASILALLVCLGVYWLVWRVV
VRNKISYFRHAALLNMVFCLLAADTCFLGAPFLSPGPRSPLCLAAAFLCHFLYLATFFWM
LAQALVLAHQLLFVFHQLAKHRVLPLMVLLGYLCPLGLAGVTLGLYLPQGQYLREGECWL
DGKGGALYTFVGPVLAIIGVNGLVLAMAMLKLLRPSLSEGPPAEKRQALLGVIKALLILT
PIFGLTWGLGLATLLEEVSTVPHYIFTILNTLQGVFILLFGCLMDRKIQEALRKRFCRAQ
APSSTISLATNEGCILEHSKGGSDTARKTDASE
```

Transmembrane domain:
573-593
609-629
648-668
685-705
728-748
770-790
803-823

N-glycosylation site.
183-186
242-245
449-452

Glycosaminoglycan attachment site.
47-50 cAMP- and cGMP-dependent protein kinase phosphorylation site.
4-7

FIGURE 8B

N-myristoylation site.
39-44
44-49
58-63
103-108
176-181
450-455
472-477
474-479
508-513
512-517
578-583
700-705
725-730
742-747
771-776
784-789
788-793
861-866
862-867

G-protein coupled receptor
231-258
642-671
727-757
771-790
578-597
811-836

7 transmembrane receptor (Secretin family)
568-828

Latrophilin/CL-1-like GPS domain
512-565

FIGURE 9

GGGAACGGAAAATGGCGCCTCACGGCCCGGGTAGTCTTACGACCCTGGTGCCCTGGGCTGCCGCCCTGCTCCTC
GCTCTGGGCGTGGAAAGGGCTCTGGCGCTACCCGAGATATGCACCCAATGTCCAGGGAGCGTGCAAAATTTGTC
AAAAGTGGCCTTTTATTGTAAAACGACACGAGAGCTAATGCTGCATGCCCGTTGCTGCCTGAATCAGAAGGGCA
CCATCTTGGGGCTGGATCTCCAGAACTGTTCTCTGGAGGACCCTGGTCCAAACTTTCATCAGGCACATACCACT
GTCATCATAGACCTGCAAGCAAACCCCCTCAAAGGTGACTTGGCCAACACCTTCCGTGGCTTTACTCAGCTCCA
GACTCTGATACTGCCACAACATGTCAACTGTCCTGGAGGAATTAATGCCTGGAATACTATCACCTCTTATATAG
ACAACCAAATCTGTCAAGGGCAAAAGAACCTTTGCAATAACACTGGGGACCCAGAAATGTGTCCTGAGAATGGA
TCTTGTGTACCTGATGGTCCAGGTCTTTTGCAGTGTGTTTGTGCTGATGGTTTCCATGGATACAAGTGTATGCG
CCAGGGCTCGTTCTCACTGCTTATGTTCTTCGGGATTCTGGGAGCCACCACTCTATCCGTCTCCATTCTGCTTT
GGGCGACCCAGCGCCGAAAAGCCAAGACTTCATGAACTACATAGGTCTTACCATTGACCTAAGATCAATCTGAA
CTATCTTAGCCCAGTCAGGGAGCTCTGCTTCCTAGAAAGGCATCTTTCGCCAGTGGATTCGCCTCAAGGTTGAG
GCCGCCATTGGAAGATGAAAAATTGCACTCCCTTGGTGTAGACAAATACCAGTTCCCATTGGTGTTGTTGCCTA
TAATAAACACTTTTTCTTTTTTNAAAAAAAAAAAAAAAAAAAAA

FIGURE 10

Signal Peptide:

Amino acids 1-30

Transmembrane:

Amino acids 198-212

MAPHGPGSLTTLVPWAAALLLALGVERALALPEICTQCPGSVQNLSKVAFYCKTTRELMLH
ARCCLNQKGTILGLDLQNCSLEDPGPNFHQAHTTVIIDLQANPLKGDLANTFRGFTQLQTL
ILPQHVNCPGGINAWNTITSYIDNQICQGQKNLCNNTGDPEMCPENGSCVPDGPGLLQCVC
ADGFHGYKCMRQGSFSLLMFFGILGATTLSVSILLWATQRRKAKTS

FIGURE 11

```
GCCGCCCCGCCCCGAGACCGGGCCCGGGGGCGCGGGGCGGCGGGATGCGGCGCCCGGGGCG
GCGATGACCGCGGAGCGCACGCCGCGGGCCCGGCCCTGACCCCGCCGCCCGCCCGCTGAGC
CCCCCGCCGAGGTCCGGACAGGCCGAGATGACGCCGAGCCCCCTGTTGCTGCTCCTGCTGC
CGCCGCTGCTGCTGGGGGCCCTTCCCACCGGCCGCCGCCGCCCGAGGCCCCCCAAAGATGGC
GGACAAGGTGGTCCCACGGCAGGTGGCCCGGCTGGGCCGCACTGTGCGGCTGCAGTGCCCA
GTGGAGGGGGACCCGCCGCCGCTGACCATGTGGACCAAGGATGGCCGCACCATCCACAGCG
GCTGGAGCCGCTTCCGCGTGCTGCCGCAGGGGCTGAAGGTGAAGCAGGTGGAGCGGGAGGA
TGCCGGCGTGTACGTGTGCAAGGCCACCAACGGCTTCGGCAGCCTGAGCGTCAACTACACC
CTCGTCGTGCTGGATGACATTAGCCCAGGGAAGGAGAGCCTGGGGCCCGACAGCTCCTCTG
GGGGTCAAGAGGACCCCGCCAGCCAGCAGTGGGCACGACCGCGCTTCACACAGCCCTCCAA
GATGAGGCGCCGGGTGATCGCACGGCCCGTGGGTAGCTCCGTGCGGCTCAAGTGCGTGGCC
AGCGGGCACCCTCGGCCCGACATCACGTGGATGAAGGACGACCAGGCCTTGACGCGCCCAG
AGGCCGCTGAGCCCAGGAAGAAGAAGTGGACACTGAGCCTGAAGAACCTGCGGCCGGAGGA
CAGCGGCAAATACACCTGCCGCGTGTCGAACCGCGCGGGCGCCATCAACGCCACCTACAAG
GTGGATGTGATCCAGCGGACCCGTTCCAAGCCCGTGCTCACAGGCACGCACCCCGTGAACA
CGACGGTGGACTTCGGGGGGACCACGTCCTTCCAGTGCAAGGTGCGCAGCGACGTGAAGCC
GGTGATCCAGTGGCTGAAGCGCGTGGAGTACGGCGCCGAGGGCCGCCACAACTCCACCATC
GATGTGGGCGGCCAGAAGTTTGTGGTGCTGCCCACGGGTGACGTGTGGTCGGCCCGACG
GCTCCTACCTCAATAAGCTGCTCATCACCCGTGCCCGCCAGGACGATGCGGGCATGTACAT
CTGCCTTGGCGCCAACACCATGGGCTACAGCTTCCGCAGCGCCTTCCTCACCGTGCTGCCA
GACCCAAAACCGCCAGGGCCACCTGTGGCCTCCTCGTCCTCGGCCACTAGCCTGCCGTGGC
CCGTGGTCATCGGCATCCCAGCCGGCGCTGTCTTCATCCTGGGCACCCTGCTCCTGTGGCT
TTGCCAGGCCCAGAAGAAGCCGTGCACCCCCGCGCCTGCCCCTCCCCTGCCTGGGCACCGC
CCGCCGGGGACGGCCCGCGACCGCAGCGGAGACAAGGACCTTCCCTCGTTGGCCGCCCTCA
GCGCTGGCCCTGGTGTGGGGCTGTGTGAGGAGCATGGGTCTCCGGCAGCCCCCCAGCACTT
ACTGGGCCCAGGCCCAGTTGCTGGCCCTAAGTTGTACCCCAAACTCTACACAGACATCCAC
ACACACACACACACACTCTCACACACACTCACACGTGGAGGGCAAGGTCCACCAGCACA
TCCACTATCAGTGCTAGACGGCACCGTATCTGCAGTGGGCACGGGGGGCCGGCCAGACAG
GCAGACTGGGAGGATGGAGGACGGAGCTGCAGACGAAGGCAGGGGACCCATGGCGAGGAGG
AATGGCCAGCACCCCAGGCAGTCTGTGTGTGAGGCATAGCCCCTGGACACACACACACAGA
CACACACACTACCTGGATGCATGTATGCACACATGCGCGCACACGTGCTCCCTGAAGGC
ACACGTACGCACACGCACATGCACAGATATGCCGCCTGGGCACACAGATAAGCTGCCCAAA
TGCACGCACACGCACAGAGACATGCCAGAACATACAAGGACATGCTGCCTGAACATACACA
CGCACACCCATGCGCAGATGTGCTGCCTGGACACACACACACACACGGATATGCTGTCTGG
ACGCACACACGTGCAGATATGGTATCCGGACACACACGTGCACAGATATGCTGCCTGGACA
CACAGATAATGCTGCCTTGACACACACATGCACGGATATTGCCTGGACACACACACACACA
CACGCGTGCACAGATATGCTGTCTGGACACGCACACATGCAGATATGCTGCCTGGACAC
ACACTTCCAGACACACGTGCACAGGCGCAGATATGCTGCCTGGACACACGCAGATATGCTG
TCTAGTCACACACACACGCAGACATGCTGTCCGGACACACACACGCATGCACAGATATGCT
GTCCGGACACACACACGCACGCAGATATGCTGCCTGGACACACACACAGATAATGCTGCCT
CAACACTCACACACGTGCAGATATTGCCTGGACACACACATGTGCACAGATATGCTGTCTG
GACATGCACACACGTGCAGATATGCTGTCCGGATACACACGCACGCACACATGCAGATATG
CTGCCTGGGCACACACTTCCGGACACACATGCACACACAGGTGCAGATATGCTGCCTGGAC
ACACACAGATAATGCTGCCTCAACACTCACACACGTGCAGATATTGCCTGGACACACAC
ATGTGCACAGATATGCTGTCTGGACATGCACACACGTGCAGATATGCTGTCCGGATACACA
CGCACGCACACATGCAGATATGCTGCCTGGGCACACACTTCCGGACACACATGCACACACA
GGTGCAGATATGCTGCCTGGACACACGCAGACTGACGTGCTTTTGGGAGGGTGTGCCGTGA
AGCCTGCAGTACGTGTGCCGTGAGGCTCATAGTTGATGAGGGACTTTCCCTGCTCCACCGT
CACTCCCCCAACTCTGCCCGCCTCTGTCCCCGCCTCAGTCCCCGCCTCCATCCCCGCCTCT
GTCCCCTGGCCTTGGCGGCTATTTTTGCCACCTGCCTTGGGTGCCCAGGAGTCCCCTACTG
CTGTGGGCTGGGGTTGGGGGCACAGCAGCCCCAAGCCTGAGAGGCTGGAGCCCATGGCTAG
TGGCTCATCCCCAGTGCATTCTCCCCCTGACACAGAGAAGGGGCCTTGGTATTTATATTTA
AGAAATGAAGATAATATTAATAATGATGGAAGGAAGACTGGGTTGCAGGGACTGTGGTCTC
TCCTGGGGCCCGGGACCCGCCTGGTCTTTCAGCCATGCTGATGACCACACCCCGTCCAGGC
CAGACACCACCCCCCACCCCACTGTCGTGGTGGCCCCAGATCTCTGTAATTTTATGTAGAG
TTTGAGCTGAAGCCCCGTATATTTAATTTATTTTGTTAAACACAAAA
```

FIGURE 12

```
MTPSPLLLLLLPPLLLGAFPPAAAARGPPKMADKVVPRQVARLGRTVRLQCPVEGDPPPLT
MWTKDGRTIHSGWSRFRVLPQGLKVKQVEREDAGVYVCKATNGFGSLSVNYTLVVLDDISP
GKESLGPDSSSGGQEDPASQQWARPRFTQPSKMRRRVIARPVGSSVRLKCVASGHPRPDIT
WMKDDQALTRPEAAEPRKKKWTLSLKNLRPEDSGKYTCRVSNRAGAINATYKVDVIQRTRS
KPVLTGTHPVNTTVDFGGTTSFQCKVRSDVKPVIQWLKRVEYGAEGRHNSTIDVGGQKFVV
LPTGDVWSRPDGSYLNKLLITRARQDDAGMYICLGANTMGYSFRSAFLTVLPDPKPPGPPV
ASSSSATSLPWPVVIGIPAGAVFILGTLLLWLCQAQKKPCTPAPAPPLPGHRPPGTARDRS
GDKDLPSLAALSAGPGVGLCEEHGSPAAPQHLLGPGPVAGPKLYPKLYTDIHTHTHTHSHT
HSHVEGKVHQHIHYQC
```

FIGURE 13

```
CGGACGCGTGGGCGTCCGGCGGTCGCAGAGCCAGGAGGCGGAGGCGCGCGGGCCAGCCTGG
GCCCCAGCCCACACCTTCACCAGGGCCCAGGAGCCACCATGTGGCGATGTCCACTGGGGCT
ACTGCTGTTGCTGCCGCTGGCTGGCCACTTGGCTCTGGGTGCCCAGCAGGGTCGTGGGCGC
CGGGAGCTAGCACCGGGTCTGCACCTGCGGGGCATCCGGGACGCGGGAGGCCGGTACTGCC
AGGAGCAGGACCTGTGCTGCCGCGGCCGTGCCGACGACTGTGCCCTGCCCTACCTGGGCGC
CATCTGTTACTGTGACCTCTTCTGCAACCGCACGGTCTCCGACTGCTGCCCTGACTTCTGG
GACTTCTGCCTCGGCGTGCCACCCCCTTTTCCCCCGATCCAAGGATGTATGCATGGAGGTC
GTATCTATCCAGTCTTGGGAACGTACTGGGACAACTGTAACCGTTGCACCTGCCAGGAGAA
CAGGCAGTGGCATGGTGGATCCAGACATGATCAAAGCCATCAACCAGGGCAACTATGGCTG
GCAGGCTGGGAACCACAGCGCCTTCTGGGGCATGACCCTGGATGAGGGCATTCGCTACCGC
CTGGGCACCATCCGCCCATCTTCCTCGGTCATGAACATGCATGAAATTTATACAGTGCTGA
ACCCAGGGGAGGTGCTTCCCACAGCCTTCGAGGCCTCTGAGAAGTGGCCCAACCTGATTCA
TGAGCCTCTTGACCAAGGCAACTGTGCAGGCTCCTGGGCCTTCTCCACAGCAGCTGTGGCA
TCCGATCGTGTCTCAATCCATTCTCTGGGACACATGACGCCTGTCCTGTCGCCCCAGAACC
TGCTGTCTTGTGACACCCACCAGCAGCAGGGCTGCCGCGGTGGGCGTCTCGATGGTGCCTG
GTGGTTCCTGCGTCGCCGAGGGGTGGTGTCTGACCACTGCTACCCCTTCTCGGGCCGTGAA
CGAGACGAGGCTGGCCCTGCGCCCCCCTGTATGATGCACAGCCGAGCCATGGGTCGGGGCA
AGCGCCAGGCCACTGCCCACTGCCCCAACAGCTATGTTAATAACAATGACATCTACCAGGT
CACTCCTGTCTACCGCCTCGGCTCCAACGACAAGGAGATCATGAAGGAGCTGATGGAGAAT
GGCCCTGTCCAAGCCCTCATGGAGGTGCATGAGGACTTCTTCCTATACAAGGGAGGCATCT
ACAGCCACACGCCAGTGAGCCTTGGGAGGCCAGAGAGATACCGCCGGCATGGGACCCACTC
AGTCAAGATCACAGGATGGGGAGAGGAGACGCTGCCAGATGGAAGGACGCTCAAATACTGG
ACTGCGGCCAACTCCTGGGGCCCAGCCTGGGGCGAGAGGGGCCACTTCCGCATCGTGCGCG
GCGTCAATGAGTGCGACATCGAGAGCTTCGTGCTGGGCGTCTGGGGCCGCGTGGGCATGGA
GGACATGGGTCATCACTGAGGCTGCGGGCACCACGCGGGTCCGGCCTGGGATCCAGGCTA
AGGGCCGGCGGAAGAGGCCCCAATGGGGCGGTGACCCCAGCCTCGCCCGACAGAGCCCGGG
GCGCAGGCGGGCGCCAGGGCGCTAATCCCGGCGCGGGTTCCGCTGACGCAGCGCCCCGCCT
GGGAGCCGCGGGCAGGCGAGACTGGCGGAGCCCCAGACCTCCCAGTGGGGACGGGGCAGG
GCCTGGCCTGGGAAGAGCACAGCTGCAGATCCCAGGCCTCTGGCGCCCCACTCAAGACTA
CCAAAGCCAGGACACCTCAAGTCTCCAGCCCCAATACCCCACCCCAATCCCGTATTCTTTT
TTTTTTTTTTTAGACAGGGTCTTGCTCCGTTGCCCAGGTTGGAGTGCAGTGGCCCATCAG
GGCTCACTGTAACCTCCGACTCCTGGGTTCAAGTGACCCTCCCACCTCAGCCTCTCAAGTA
GCTGGGACTACAGGTGCACCACCACACCTGGCTAATTTTTGTATTTTTTGTAAAGAGGGGG
GTCTCACTGTGTTGCCCAGGCTGGTTTCGAACTCCTGGGCTCAAGCGGTCCACCTGCCTCC
GCCTCCCAAAGTGCTGGGATTGCAGGCATGAGCCACTGCACCCAGCCCTGTATTCTTATTC
TTCAGATATTTATTTTTCTTTTCACTGTTTTAAAATAAAACCAAAGTATTGATAAAAAAAAA
```

FIGURE 14

```
></usr/seqdb2/sst/DNA/Dnaseqs.min/ss.DNA33223
><subunit 1 of 1, 164 aa, 1 stop
><MW: 18359, pI: 7.45, NX(S/T): 1
MWRCPLGLLLLLLPLAGHLALGAQQGRGRRELAPGLHLRGIRDAGGRYCQEQDLCCRGRADD
CALPYLGAICYCDLFCNRTVSDCCPDFWDFCLGVPPPFPPIQGCMHGGRIYPVLGTYWDNC
NRCTCQENRQWHGGSRHDQSHQPGQLWLAGWEPQRLLGHDPG
```

N-glycosylation site.

amino acids 78-82, 161-165

Casein kinase II phosphorylation site.

amino acids 80-84, 117-121, 126-130, 169-173, 205-209, 296-300, 411-415

N-myristoylation site.

amino acids 21-27, 39-45, 44-50, 104-110, 160-164, 224-230, 269-275, 378-384, 442-448

Amidation site.

amino acids 26-30, 318-322

Eukaryotic thiol (cysteine) proteases histidine active site.

amino acids 398-409

FIGURE 15

GGCTCAGAGGCCCCACTGGACCCTCGGCTCTTCCTTGGACTTCTTGTGTGTTCTGTGAGCTTCGCTGGATTCAG
GGTCTTGGGCATCAGAGGTGAGAGGGTGGGAAGGTCCGCCGCGATGGGGAAGCCCTGGCTGCGTGCGCTACAGC
TGCTGCTCCTGCTGGGCGCGTCGTGGGCGCGGGCGGGCGCCCCGCGCTGCACCTACACCTTCGTGCTGCCCCCG
CAGAAGTTCACGGGCGCTGTGTGCTGGAGCGGCCCCGCATCCACGCGGGCGACGCCCGAGGCCGCCAACGCCAG
CGAGCTGGCGGCGCTGCGCATGCGCGTCGGCCGCCACGAGGAGCTGTTACGCGAGCTGCAGAGGCTGGCGGCGG
CCGACGGCGCCGTGGCCGGCGAGGTGCGCGCGCTGCGCAAGGAGAGCCGCGGCCTGAGCGCGCGCCTGGGCCAG
TTGCGCGCGCAGCTGCAGCACGAGGCGGGGCCCGGGGCGGGCCCGGGGGCGGATCTGGGGCGGAGCCTGCCGC
GGCGCTGGCGCTGCTCGGGGAGCGCGTGCTCAACGCGTCCGCCGAGGCTCAGCGCGCAGCCGCCCGGTTCCACC
AGCTGGACGTCAAGTTCCGCGAGCTGGCGCAGCTCGTCACCCAGCAGAGCAGTCTCATCGCCCGCCTGGAGCGC
CTGTGCCCGGGAGGCGCGGGCGGGCAGCAGCAGGTCCTGCCGCCACCCCCACTGGTGCCTGTGGTTCCGGTCCG
TCTTGTGGGTAGCACCAGTGACACCAGTAGGATGCTGGACCCAGCCCCAGAGCCCCAGAGAGACCAGACCCAGA
GACAGCAGGAGCCCATGGCTTCTCCCATGCCTGCAGGTCACCCTGCGGTCCCCACCAAGCCTGTGGGCCCGTGG
CAGGATTGTGCAGAGGCCCGCCAGGCAGGCCATGAACAGAGTGGAGTGTATGAACTGCGAGTGGGCCGTCACGT
AGTGTCAGTATGGTGTGAGCAGCAACTGGAGGGTGGAGGCTGGACTGTGATCCAGCGGAGGCAAGATGGTTCAG
TCAACTTCTTCACTACCTGGCAGCACTATAAGGCGGGCTTTGGGCGGCCAGACGGAGAATACTGGCTGGGCCTT
GAACCCGTGTATCAGCTGACCAGCCGTGGGGACCATGAGCTGCTGGTTCTCCTGGAGGACTGGGGGGGCCGTGG
AGCACGTGCCCACTATGATGGCTTCTCCCTGGAACCCGAGAGCGACCACTACCGCCTGCGGCTTGGCCAGTACC
ATGGTGATGCTGGAGACTCTCTTTCCTGGCACAATGACAAGCCCTTCAGCACCGTGGATAGGGACCGAGACTCC
TATTCTGGTAACTGTGCCCTGTACCAGCGGGGAGGCTGGTGGTACCATGCCTGTGCCCACTCCAACCTCAACGG
TGTGTGGCACCACGGCGGCCACTACCGAAGCCGCTACCAGGATGGTGTCTACTGGGCTGAGTTTCGTGGTGGGG
CATATTCTCTCAGGAAGGCCGCCATGCTCATTCGGCCCCTGAAGCTGTGACTCTGTGTTCCTCTGTCCCCTAGG
CCCTAGAGGACATTGGTCAGCAGGAGCCCAAGTTGTTCTGGCCACACCTTCTTTGTGGCTCAGTGCCAATGTGT
CCCACAGAACTTCCCACTGTGGATCTGTGACCCTGGGCGCTGAAAATGGGACCCAGGAATCCCCCCCGTCAATA
TCTTGGCCTCAGATGGCTCCCCAAGGTCATTCATATCTCGGTTTGAGCTCATATCTTATAATAACACAAAGTAG
CCAC

FIGURE 16

Signal sequence:                                   Amino acids 1-20

N-glycosylation sites:          Amino acids 58-62;145-149 cAMP- and cGMP-dependent protein kinase phosphorylation site:
                                Amino acids 97-101

Tyrosine kinase phosphorylation site:   Amino acids 441-448

N-myristoylation sites:         Amino acids 16-22;23-29;87-93;
                                108-114;121-127;125-131;129-135;
                                187-193;293-299;353-359;378-384;
                                445-451;453-459

Cell attachment sequence:       Amino acids 340-343

Fibrinogen beta and gamma chains C-terminal domain signature:
                                Amino acids 418-431

MGKPWLRALQLLLLLGASWARAGAPRCTYTFVLPPQKFTGAVCWSGPASTRATPEAANASE
LAALRMRVGRHEELLRELQRLAAADGAVAGEVRALRKESRGLSARLGQLRAQLQHEAGPGA
GPGADLGAEPAAALALLGERVLNASAEAQRAAARFHQLDVKFRELAQLVTQQSSLIARLER
LCPGGAGGQQQVLPPPPLVPVVPVRLVGSTSDTSRMLDPAPEPQRDQTQRQQEPMASPMPA
GHPAVPTKPVGPWQDCAEARQAGHEQSGVYELRVGRHVVSVWCEQQLEGGGWTVIQRRQDG
SVNFFTTWQHYKAGFGRPDGEYWLGLEPVYQLTSRGDHELLVLLEDWGGRGARAHYDGFSL
EPESDHYRLRLGQYHGDAGDSLSWHNDKPFSTVDRDRDSYSGNCALYQRGGWWYHACAHSN
LNGVWHHGGHYRSRYQDGVYWAEFRGGAYSLRKAAMLIRPLKL

FIGURE 17

AGCCCACCGAGAGGCGCCTGCAGGATGAAAGCTCTCTGTCTCCTCCTCCTCCCTGTCCTGGGGCTGTTGGTGTC
TAGCAAGACCCTGTGCTCCATGGAAGAAGCCATCAATGAGAGGATCCAGGAGGTCGCCGGCTCCCTAATATTTA
GGGCAATAAGCAGCATTGGCCTGGAGTGCCAGAGCGTCACCTCCAGGGGGGACCTGGCTACTTGCCCCCGAGGC
TTCGCCGTCACCGGCTGCACTTGTGGCTCCGCCTGTGGCTCGTGGGATGTGCGCGCCGAGACCACATGTCACTG
CCAGTGCGCGGGCATGGACTGGACCGGAGCGCGCTGCTGTCGTGTGCAGCCCTGAGGTCGCGCGCAGCGCGTGC
ACAGCGCGGGCGGAGGCGGCTCCAGGTCCGGAGGGGTTGCGGGGAGCTGGAAATAAACCTGGAGATGATGATG
ATGATGATGATGGAAAAA

FIGURE 18

MKALCLLLLPVLGLLVSSKTLCSMEEAINERIQEVAGSLIFRAISSIGLECQSVTSRGD
LATCPRGFAVTGCTCGSACGSWDVRAETTCHCQCAGMDWTGARCCRVQP

Signal peptide:
1-18

Transmembrane domain:
none

Cell attachment sequence.
57-60

N-myristoylation site.

```
   1 tcagggtcag gtgattctcc cacctcagcc tcctgagtag ctgggagtac aggcacatgc
  61 caccacaccc agataatttt taaattttt gtagagatgg ggtctcactg tgttgcccag
 121 gctggtctcg agctcctggg ctgaagtgat ccatccacct ccgtccacca aagtgctggg
 181 attacaggtg tgagccaccg tgccctgcct gcatttcttt taatagacat gtctctggat
 241 ggtcaactgg acagttgtgc tcaccctcca catttcctcc cctctactca caccccaagg
 301 tgataatgga ttggcaaccc tgggtgactt aagaattcca tgagcttcat aaatgtcaaa
 361 taagctgtct taccctacta acccctctac catcacaatg atcaaagcaa agccaaatag
 421 cccacacctc tcatcccaca cataccatag tcatcctttc atccatttat ccatccattt
 481 accaacttaa aatattcatt gattacctac tacatatgac actttacttg accaaaattg
 541 gcaaaacaca tagcttaaag ttgtcttct tcctagttag gtggaatgat gcctggtata
 601 tcgtatcatt agaaatggct gaatgaatga gctcactgtt tattaggaga atgagacaca
 661 gaccaaataa ctcaagcata agagagaatg tagttagtgt cctaaaagag atccagagtg
 721 ctgtgtgagt tcaaggtga gaaagagccc ttctgactga agaaatcagg aaagacttca
 781 tagaagcagt ggtgatatat gagctgactt ctaaaggaca agtaagatta taatagcaga
 841 tatagtaggg gaagggaatt accgaggggg tggcatcaat aaagttttgg gggtaaggaa
 901 gtatgagttc tgggtatgaa aatatgtcta acttggtcag agcataaatt acgtattctg
 961 gaaggtagac tgtgtttgag aacaaatgct agaatacctt aaaagctaat tgttaggtt
1021 ctgcagagtc agtgatagga cccaagcaga caagtaatta ggaagactaa tttggcaaag
1081 atattataaa atgttggggc tgaacaatta ttacatataa taagagaatt aacaaggtgc
1141 ctgagtgaaa tgtaataaac agaaacaac aaatttgta tgtcaaccaa acctagcagt
1201 caaaaggatt aataacaata agtcatgtag gatactatga attcataaca caaagaaatg
1261 ctaggggaaa tatttgcaat gcttatcaca tccaaaagtt cctttcccta atatacaaag
1321 atctgctaga agtcaacaag ctaaagatca acagctcaat agaaatatgg ccaaacggct
1381 ggacgtggtg gctcatgcct gtaatcccag catttggga gactgaggca ggattgcttg
1441 agcccaggaa ttcaagacca gcctggtcaa cgtagcgaga ttctgtgtct atatttttaa
1501 aaatttatta aaaaagaaa tacggcaaa tgagctacct agtctcagaa aagaaaatat
1561 atatgatgtg caactatatt aaaagatttt caatttcact aataattttt tttttgaga
1621 cagagtcttg ctctgtcgcc aggctggagt gcagtggcac catcttggct cactgcaagc
1681 tctgcctccc gagttcacca ttctcctgcc tcagcctccc aagtagctgg gattacaggc
1741 gcacaccacc acacctggct aatgttttgt attttagta gaggcggggt ttcaccgtgt
1801 tagccaggat ggcctcgatc tcttgacctc gtgatcagcc accttggcc tctcaaagtg
1861 ctgtgattac aggcgtgagc caccgcgcct ggccaaattt cactaataat tttaaaagt
1921 aaattatata tacatgggat atcatgttca cttagattgg cgatgagcag aaagtttgat
1981 aactgtgtca taaacacttg gtaactgtgt tagtgagtgt gtgggagat aggtatcctt
2041 atatgctgct aataggagtg taggctgtaa aattctcatg gtagctagtt tagcaatatc
2101 tataaaaatt acaaatatgc ataactttca gtgagtcaga aattttactt ttaagaattt
```

FIGURE 19B

```
2161 atcttacatg tataatcaca acacgtgtga aatatcgtac acataataga tattggttgc
2221 aatcttttca tagttgtgaa agatgaggaa aaacaatctt aaaagtagtt tggttaaata
2281 aatcatgtca ctcatataca gtgaaatatc atccccattt taaaaagatg atggtggtgg
2341 tgctatacat accgatacag aaagctttct aaaacctttc attaaatgaa aaatgaataa
2401 atcattgcag aacagtgtat atatatctaa aatatctatg gaagaaacca gcaacagcca
2461 ctgctcctgg agaattatgg tcccacacca ctgatcattc tttcagtagg gtgaccatca
2521 tccaaatttg cttgggactg aggggttcc ttttggtttg aaaaccagga cagtcctagg
2581 aaaagtgaga caagttggtc acatgtcccc aagatgatct tctttcactt atgaacttgc
2641 tactttccca gtcagaatat aaactctgag gggggagact tcctgttttc ttcatgacta
2701 tatctcttgc gcactgtggg gtggaggctg tagaagagga gagaagtaga gaaacagatc
2761 acattgtgtc ttgaagtgtt tcagcaaata tgggcaacac ccttctttta ctagcttgga
2821 accctacctc tgagtgcatt tccttttta ttatttattt cctgtcagtt ataagagagg
2881 cctaccccctt tgtgagcagt ctaggacttt gtacacctgc taagtaggga gaaggcaggg
2941 gaggtggctg gtttaagggg aacttgaggg aagtagggaa gactcctctc gggaccttg
3001 gagtaggtga cacatgagcc cagccccagc tcacctgcca atccagctga ggagctcacc
3061 tgccaatcca gctgaggctg gcagaggtg ggtgagaaga gggaaaattg cagggacctc
3121 cagttgggcc aggccagaag ctgctgtagc tttaaccaga cagctcagac ctgtatggag
3181 gctgccagtg acaggttagg tttagggcag agaagaagca agaccatg
```

FIGURE 20

MVGKMWPVLWTLCAVRVTVDAISVETPQDVLRASQGKSVTLPCTYHTSTSSREGLIQWDKLLLTHTERVVIWPF
SNKNYIHGELYKNRVSISNNAEQSDASITIDQLTMADNGTYECSVSLMSDLEGNTKSRVRLLVLVPPSKPECGI
EGETIIGNNIQLTCQSKEGSPTPQYSWKRYNILNQEQPLAQPASGQPVSLKNISTDTSGYYICTSSNEEGTQFC
NITVAVRSPSMNVALYVGIAVGVVAALIIIGIIIYCCCCRGKDDNTEDKEDARPNREAYEEPPEQLRELSRERE
EEDDYRQEEQRSTGRESPDHLDQ

FIGURE 21A

```
CGCGGAGCCCTGCGCTGGGAGGTGCACGGTGTGCACGCTGGACTGGACCCCCATGCAACCCCGCGCCCTGCGCC
TTAACCAGGACTGCTCCGCGCGCCCCTGAGCCTCGGGCTCCGGCCCGGACCTGCAGCCTCCCAGGTGGCTGGGA
AGAACTCTCCAACAATAAATACATTTGATAAGAAAGATGGCTTTAAAAGTGCTACTAGAACAAGAGAAAACGTT
TTTCACTCTTTTAGTATTACTAGGCTATTTGTCATGTAAAGTGACTTGTGAATCAGGAGACTGTAGACAGCAAG
AATTCAGGGATCGGTCTGGAAACTGTGTTCCCTGCAACCAGTGTGGGCCAGGCATGGAGTTGTCTAAGGAATGT
GGCTTCGGCTATGGGGAGGATGCACAGTGTGTGACGTGCCGGCTGCACAGGTTCAAGGAGGACTGGGGCTTCCA
GAAATGCAAGCCCTGTCTGGACTGCGCAGTGGTGAACCGCTTTCAGAAGGCAAATTGTTCAGCCACCAGTGATG
CCATCTGCGGGGACTGCTTGCCAGGATTTTATAGGAAGACGAAACTTGTCGGCTTTCAAGACATGGAGTGTGTG
CCTTGTGGAGACCCTCCTCCTCCTTACGAACCGCACTGTGCCAGCAAGGTCAACCTCGTGAAGATCGCGTCCAC
GGCCTCCAGCCCACGGGACACGGCGCTGGCTGCCGTTATCTGCAGCGCTCTGGCCACCGTCCTGCTGGCCCTGC
TCATCCTCTGTGTCATCTATTGTAAGAGACAGTTTATGGAGAAGAAACCCAGCTGGTCTCTGCGGTCGCAGGAC
ATTCAGTACAACGGCTCTGAGCTGTCGTGTTTTGACAGACCTCAGCTCCACGAATATGCCCACAGAGCCTGCTG
CCAGTGCCGCCGTGACTCAGTGCAGACCTGCGGGCCGGTGCGCTTGCTCCCATCCATGTGCTGTGAGGAGGCCT
GCAGCCCCAACCCGGCGACTCTTGGTTGTGGGGTGCATTCTGCAGCCAGTCTTCAGGCAAGAAACGCAGGCCCA
GCCGGGGAGATGGTGCCGACTTTCTTCGGATCCCTCACGCAGTCCATCTGTGGCGAGTTTTCAGATGCCTGGCC
TCTGATGCAGAATCCCATGGGTGGTGACAACATCTCTTTTTGTGACTCTTATCCTGAACTCACTGGAGAAGACA
TTCATTCTCTCAATCCAGAACTTGAAAGCTCAACGTCTTTGGATTCAAATAGCAGTCAAGATTTGGTTGGTGGG
GCTGTTCCAGTCCAGTCTCATTCTGAAAACTTTACAGCAGCTACTGATTTATCTAGATATAACAACACACTGGT
AGAATCAGCATCAACTCAGGATGCACTAACTATGAGAAGCCAGCTAGATCAGGAGAGTGGCGCTGTCATCCACC
CAGCCACTCAGACGTCCCTCCAGGAAGCTTAAAGAACCTGCTTCTTTCTGCAGTAGAAGCGTGTGCTGGAACCC
AAAGAGTACTCCTTTGTTAGGCTTATGGACTGAGCAGTCTGGACCTTGCATGGCTTCTGGGGCAAAAATAAATC
TGAACCAAACTGACGGCATTTGAAGCCTTTCAGCCAGTTGCTTCTGAGCCAGACCAGCTGTAAGCTGAAACCTC
AATGAATAACAAGAAAAGACTCCAGGCCGACTCATGATACTCTGCATCTTTCCTACATGAGAAGCTTCTCTGCCAC
AAAAGTGACTTCAAAGACTGATGGGTTGAGCTGGCAGCCTATGAGATTGTGGACATATAACAAGAAACAGAAAT
GCCCTCATGCTTATTTTCATGGTGATTGTGGTTTTACAAGACTGAAGACCCAGAGTATACTTTTTCTTTCCAGA
AATAATTTCATACCGCCTATGAAATATCAGATAAATTACCTTAGCTTTTATGTAGAATGGGTTCAAAAGTGAGT
GTTTCTATTTGAGAAGGACACTTTTTCATCATCTAAACTGATTCGCATAGGTGGTTAGAATGGCCCTCATATTG
CCTGCCTAAATCTTGGGTTTATTAGATGAAGTTTACTGAATCAGAGGAATCAGACAGAGGAGGATAGCTCTTTC
CAGAATCCACACTTCTGACCTCAGCCTCGGTCTCATGAACACCCGCTGATCTCAGGAGAACACCTGGGCTAGGG
AATGTGGTCGAGAAAGGGCAGCCCATTGCCCAGAATTAACACATATTGTAGAGACTTGTATGCAAAGGTTGGCA
TATTTATATGAAAATTAGTTGCTATAGAAACATTTGTTGCATCTGTCCCTCTGCCTGAGCTTAGAAGGTTATAG
AAAAAGGGTATTTATAAACATAAATGACCTTTTACTTGCATTGTATCTTATACTAAAGGCTTTAGAAATTACAA
CATATCAGGTTCCCCTACTACTGAAGTAGCCTTCCGTGAGAACACACCACATGTTAGGACTAGAAGAAAATGCA
CAATTTGTAGGGGTTTGGATGAAGCAGCTGTAACTGCCCTAGTGTAGTTTGACCAGGACATTGTCGTGCTCCTT
CCAATTGTGTAAGATTAGTTAGCACATCATCTCCTACTTTAGCCATCCGGTGTTGGATTTAAGAGGACGGTGCT
TCTTTCTATTAAAGTGCTCCATCCCCTACCATCTACACATTAGCATTGTCTCTAGAGCTAAGACAGAAATTAAC
```

FIGURE 21B

CCCGTTCAGTCACAAAGCAGGGAATGGTTCATTTACTCTTAATCTTTATGCCCTGGAGAAGACCTACTTGAACA
GGGCATATTTTTTAGACTTCTGAACATCAGTATGTTCGAGGGTACTATGATATTTTGGTTTGGAATTGCCCTGC
CCAAGTCACTGTCTTTTAACTTTTAAACTGAATATTAAAATGTATCTGTCTTTCCT

FIGURE 22

></usr/seqdb2/sst/DNA/Dnaseqs.min/ss.DNA84210
><subunit 1 of 1, 417 aa, 1 stop
><MW: 45305, pI: 5.12, NX(S/T): 6
MALKVLLEQEKTFFTLLVLLGYLSCKVTCESGDCRQQEFRDRSGNCVPCNQCGPGMELSK
ECGFGYGEDAQCVTCRLHRFKEDWGFQKCKPCLDCAVVNRFQKANCSATSDAICGDCLPG
FYRKTKLVGFQDMECVPCGDPPPPYEPHCASKVNLVKIASTASSPRDTALAAVICSALAT
VLLALLILCVIYCKRQFMEKKPSWSLRSQDIQYNGSELSCFDRPQLHEYAHRACCQCRRD
SVQTCGPVRLLPSMCCEEACSPNPATLGCGVHSAASLQARNAGPAGEMVPTFFGSLTQSI
CGEFSDAWPLMQNPMGGDNISFCDSYPELTGEDIHSLNPELESSTSLDSNSSQDLVGGAV
PVQSHSENFTAATDLSRYNNTLVESASTQDALTMRSQLDQESGAVIHPATQTSLQEA

FIGURE 23A

CGCGCTCCCCGCGCGCCTCCTCGGGCTCCACGCGTCTTGCCCCGCAGAGGCAGCCTCCTCCAGGAGCGGGGCCC
TGCACACCATGGCCCCCGGGTGGGCAGGGGTCGGCGCCGCCGTGCGCGCCCGCCTGGCGCTGGCCTTGGCGCTG
GCGAGCGTCCTGAGTGGGCCTCCAGCCGTCGCCTGCCCCACCAAGTGTACCTGCTCCGCTGCCAGCGTGGACTG
CCACGGGCTGGGCCTCCGCGCGGTTCCTCGGGGCATCCCCCGCAACGCTGAGCGCCTTGACCTGGACAGAAATA
ATATCACCAGGATCACCAAGATGGACTTCGCTGGGCTCAAGAACCTCCGAGTCTTGCATCTGGAAGACAACCAG
GTCAGCGTCATCGAGAGAGGCGCCTTCCAGGACCTGAAGCAGCTAGAGCGACTGCGCCTGAACAAGAATAAGCT
GCAAGTCCTTCCAGAATTGCTTTTCCAGAGCACGCCGAAGCTCACCAGACTAGATTTGAGTGAAAACCAGATCC
AGGGGATCCCGAGGAAGGCGTTCCGCGGCATCACCGATGTGAAGAACCTGCAACTGGACAACAACCACATCAGC
TGCATTGAAGATGGAGCCTTCCGAGCGCTGCGCGATTTGGAGATCCTTACCCTCAACAACAACAACATCAGTCG
CATCCTGGTCACCAGCTTCAACCACATGCCGAAGATCCGAACTCTGCGCCTCCACTCCAACCACCTCTACTGCG
ACTGCCACCTGGCCTGGCTCTCGGATTGGCTGCGACAGCGACGGACAGTTGGCCAGTTCACACTCTGCATGGCT
CCTGTGCATTTGAGGGGCTTCAACGTGGCGGATGTGCAGAAGAAGGAGTACGTGTGCCCAGCCCCCCACTCGGA
GCCCCCATCCTGCAATGCCAACTCCATCTCCTGCCCTTCGCCCTGCACGTGCAGCAATAACATCGTGGACTGTC
GAGGAAAGGGCTTGATGGAGATTCCTGCCAACTTGCCGGAGGGCATCGTCGAAATACGCCTAGAACAGAACTCC
ATCAAAGCCATCCCTGCAGGAGCCTTCACCCAGTACAAGAAACTGAAGCGAATAGACATCAGCAAGAATCAGAT
ATCGGATATTGCTCCAGATGCCTTCCAGGGCCTGAAATCACTCACATCGCTGGTCCTGTATGGGAACAAGATCA
CCGAGATTGCCAAGGGACTGTTTGATGGGCTGGTGTCCCTACAGCTGCTCCTCCTCAATGCCAACAAGATCAAC
TGCCTGCGGGTGAACACGTTTCAGGACCTGCAGAACCTCAACTTGCTCTCCCTGTATGACAACAAGCTGCAGAC
CATCAGCAAGGGGCTCTTCGCCCCTCTGCAGTCCATCCAGACACTCCACTTAGCCCAAAACCCATTTGTGTGCG
ACTGCCACTTGAAGTGGCTGGCCGACTACCTCCAGGACAACCCCATCGAGACAAGCGGGGCCCGCTGCAGCAGC
CCGCGCCGACTCGCCAACAAGCGCATCAGCCAGATCAAGAGCAAGAAGTTCCGCTGCTCAGGCTCCGAGGATTA
CCGCAGCAGGTTCAGCAGCGAGTGCTTCATGGACCTCGTGTGCCCCGAGAAGTGTCGCTGTGAGGGCACGATTG
TGGACTGCTCCAACCAGAAGCTGGTCCGCATCCCAAGCCACCTCCCTGAATATGTCACCGACCTGCGACTGAAT
GACAATGAGGTATCTGTTCTGGAGGCCACTGGCATCTTCAAGAAGTTGCCCAACCTGCGGAAAATAAATCTGAG
TAACAATAAGATCAAGGAGGTGCGAGAGGGAGCTTTCGATGGAGCAGCCAGCGTGCAGGAGCTGATGCTGACAG
GGAACCAGCTGGAGACCGTGCACGGGCGCGTGTTCCGTGGCCTCAGTGGCCTCAAAACCTTGATGCTGAGGAGT
AACTTGATCAGCTGTGTGAGTAATGACACCTTTGCCGGCCTGAGTTCGGTGAGACTGCTGTCCCTCTATGACAA
TCGGATCACCACCATCACCCCTGGGGCCTTCACCACGCTTGTCTCCCTGTCCACCATAAACCTCCTGTCCAACC
CCTTCAACTGCAACTGCCACCTGGCCTGGCTCGGCAAGTGGTTGAGGAAGAGGCGGATCGTCAGTGGGAACCCT
AGGTGCCAGAAGCCATTTTTCCTCAAGGAGATTCCCATCCAGGATGTGGCCATCCAGGACTTCACCTGTGATGG
CAACGAGGAGAGTAGCTGCCAGCTGAGCCCGCGCTGCCCGGAGCAGTGCACCTGTATGGAGACAGTGGTGCGAT
GCAGCAACAAGGGGCTCCGCGCCCTCCCCAGAGGCATGCCCAAGGATGTGACCGAGCTGTACCTGGAAGGAAAC
CACCTAACAGCCGTGCCCAGAGAGCTGTCCGCCCTCCGACACCTGACGCTTATTGACCTGAGCAACAACAGCAT
CAGCATGCTGACCAATTACACCTTCAGTAACATGTCTCACCTCTCCACTCTGATCCTGAGCTACAACCGGCTGA
GGTGCATCCCCGTCCACGCCTTCAACGGGCTGCGGTCCCTGCGAGTGCTAACCCTCCATGGCAATGACATTTCC
AGCGTTCCTGAAGGCTCCTTCAACGACCTCACATCTCTTTCCCATCTGGCGCTGGGAACCAACCCACTCCACTG

FIGURE 23B

```
TGACTGCAGTCTTCGGTGGCTGTCGGAGTGGGTGAAGGCGGGGTACAAGGAGCCTGGCATCGCCCGCTGCAGTA
GCCCTGAGCCCATGGCTGACAGGCTCCTGCTCACCACCCCAACCCACCGCTTCCAGTGCAAAGGGCCAGTGGAC
ATCAACATTGTGGCCAAATGCAATGCCTGCCTCTCCAGCCCGTGCAAGAATAACGGGACATGCACCCAGGACCC
TGTGGAGCTGTACCGCTGTGCCTGCCCCTACAGCTACAAGGGCAAGGACTGCACTGTGCCCATCAACACCTGCA
TCCAGAACCCCTGTCAGCATGGAGGCACCTGCCACCTGAGTGACAGCCACAAGGATGGGTTCAGCTGCTCCTGC
CCTCTGGGCTTTGAGGGGCAGCGGTGTGAGATCAACCCAGATGACTGTGAGGACAACGACTGCGAAAACAATGC
CACCTGCGTGGACGGGATCAACAACTACGTGTGTATCTGTCCGCCTAACTACACAGGTGAGCTATGCGACGAGG
TGATTGACCACTGTGTGCCTGAGCTGAACCTCTGTCAGCATGAGGCCAAGTGCATCCCCCTGGACAAAGGATTC
AGCTGCGAGTGTGTCCCTGGCTACAGCGGGAAGCTCTGTGAGACAGACAATGATGACTGTGTGGCCCACAAGTG
CCGCCACGGGCCCAGTGCGTGGACACAATCAATGGCTACACATGCACCTGCCCCCAGGGCTTCAGTGGACCCT
TCTGTGAACACCCCCACCCATGGTCCTACTGCAGACCAGCCCATGCGACCAGTACGAGTGCCAGAACGGGGCC
CAGTGCATCGTGGTGCAGCAGGAGCCCACCTGCCGCTGCCCACCAGGCTTCGCCGGCCCCAGATGCGAGAAGCT
CATCACTGTCAACTTCGTGGGCAAAGACTCCTACGTGGAACTGGCCTCCGCCAAGGTCCGACCCCAGGCCAACA
TCTCCCTGCAGGTGGCCACTGACAAGGACAACGGCATCCTTCTCTACAAAGGAGACAATGACCCCCTGGCACTG
GAGCTGTACCAGGGCCACGTGCGGCTGGTCTATGACAGCCTGAGTTCCCCTCCAACCACAGTGTACAGTGTGGA
GACAGTGAATGATGGGCAGTTTCACAGTGTGGAGCTGGTGACGCTAAACCAGACCCTGAACCTAGTAGTGGACA
AAGGAACTCCAAAGAGCCTGGGGAAGCTCCAGAAGCAGCCAGCAGTGGGCATCAACAGCCCCCTCTACCTTGGA
GGCATCCCCACCTCCACCGGCCTCTCCGCCTTGCGCCAGGGCACGGACCGGCCTCTAGGCGGCTTCCACGGATG
CATCCATGAGGTGCGCATCAACAACGAGCTGCAGGACTTCAAGGCCCTCCCACCACAGTCCCTGGGGGTGTCAC
CAGGCTGCAAGTCCTGCACCGTGTGCAAGCACGGCCTGTGCCGCTCCGTGGAGAAGGACAGCGTGGTGTGCGAG
TGCCGCCCAGGCTGGACCGGCCCACTCTGCGACCAGGAGGCCCGGGACCCCTGCCTCGGCCACAGATGCCACCA
TGGAAAATGTGTGGCAACTGGGACCTCATACATGTGCAAGTGTGCCGAGGGCTATGGAGGGACTTGTGTGACA
ACAAGAATGACTCTGCCAATGCCTGCTCAGCCTTCAAGTGTCACCATGGGCAGTGCCACATCTCAGACCAAGGG
GAGCCCTACTGCCTGTGCCAGCCCGGCTTTAGCGGCGAGCACTGCCAACAAGAGAATCCGTGCCTGGGACAAGT
AGTCCGAGAGGTGATCCGCCGCCAGAAAGGTTATGCATCATGTGCCACAGCCTCCAAGGTGCCCATCATGGAAT
GTCGTGGGGGCTGTGGGCCCCAGTGCTGCCAGCCCACCCGCAGCAAGCGGCGGAAATACGTCTTCCAGTGCACG
GACGGCTCCTCGTTTGTAGAAGAGGTGGAGAGACACTTAGAGTGCGGCTGCCTCGCGTGTTCCTAAGCCCCTGC
CCGCCTGCCTGCCACCTCTCGGACTCCAGCTTGATGGAGTTGGGACAGCCATGTGGGACCCCCTGGTGATTCAG
CATGAAGGAAATGAAGCTGGAGAGGAAGGTAAAGAAGAAGAGAATATTAAGTATATTGTAAAATAAACAAAAAA
TAGAACTTAAAAAAAAAAAAAAAAAAAAAAAAA
```

FIGURE 24A

MAPGWAGVGAAVRARLALALALASVLSGPPAVACPTKCTCSAASVDCHGLGLRAVPRGIPR
NAERLDLDRNNITRITKMDFAGLKNLRVLHLEDNQVSVIERGAFQDLKQLERLRLNKNKLQ
VLPELLFQSTPKLTRLDLSENQIQGIPRKAFRGITDVKNLQLDNNHISCIEDGAFRALRDL
EILTLNNNNISRILVTSFNHMPKIRTLRLHSNHLYCDCHLAWLSDWLRQRRTVGQFTLCMA
PVHLRGFNVADVQKKEYVCPAPHSEPPSCNANSISCPSPCTCSNNIVDCRGKGLMEIPANL
PEGIVEIRLEQNSIKAIPAGAFTQYKKLKRIDISKNQISDIAPDAFQGLKSLTSLVLYGNK
ITEIAKGLFDGLVSLQLLLLNANKINCLRVNTFQDLQNLNLLSLYDNKLQTISKGLFAPLQ
SIQTLHLAQNPFVCDCHLKWLADYLQDNPIETSGARCSSPRRLANKRISQIKSKKFRCSGS
EDYRSRFSSECFMDLVCPEKCRCEGTIVDCSNQKLVRIPSHLPEYVTDLRLNDNEVSVLEA
TGIFKKLPNLRKINLSNNKIKEVREGAFDGAASVQELMLTGNQLETVHGRVFRGLSGLKTL
MLRSNLISCVSNDTFAGLSSVRLLSLYDNRITTITPGAFTTLVSLSTINLLSNPFNCNCHL
AWLGKWLRKRRIVSGNPRCQKPFFLKEIPIQDVAIQDFTCDGNEESSCQLSPRCPEQCTCM
ETVVRCSNKGLRALPRGMPKDVTELYLEGNHLTAVPRELSALRHLTLIDLSNNSISMLTNY
TFSNMSHLSTLILSYNRLRCIPVHAFNGLRSLRVLTLHGNDISSVPEGSFNDLTSLSHLAL
GTNPLHCDCSLRWLSEWVKAGYKEPGIARCSSPEPMADRLLLTTPTHRFQCKGPVDINIVA
KCNACLSSPCKNNGTCTQDPVELYRCACPYSYKGKDCTVPINTCIQNPCQHGGTCHLSDSH
KDGFSCSCPLGFEGQRCEINPDDCEDNDCENNATCVDGINNYVCICPPNYTGELCDEVIDH
CVPELNLCQHEAKCIPLDKGFSCECVPGYSGKLCETDNDDCVAHKCRHGAQCVDTINGYTC
TCPQGFSGPFCEHPPPMVLLQTSPCDQYECQNGAQCIVVQQEPTCRCPPGFAGPRCEKLIT
VNFVGKDSYVELASAKVRPQANISLQVATDKDNGILLYKGDNDPLALELYQGHVRLVYDSL
SSPPTTVYSVETVNDGQFHSVELVTLNQTLNLVVDKGTPKSLGKLQKQPAVGINSPLYLGG
IPTSTGLSALRQGTDRPLGGFHGCIHEVRINNELQDFKALPPQSLGVSPGCKSCTVCKHGL
CRSVEKDSVVCECRPGWTGPLCDQEARDPCLGHRCHHGKCVATGTSYMCKCAEGYGGDLCD
NKNDSANACSAFKCHHGQCHISDQGEPYCLCQPGFSGEHCQQENPCLGQVVREVIRRQKGY
ASCATASKVPIMECRGGCGPQCCQPTRSKRRKYVFQCTDGSSFVEEVERHLECGCLACS

FIGURE 24B

Signal peptide:

amino acids 1-27

Important features of the protein:

Signal peptide:

Amino acids 1-25

Transmembrane domain:

Amino acids 169-192

N-glycosylation sites:

Amino acids 105-109;214-218;319-323;350-354;368-372;379-383 cAMP- and cGMP-dependent protein kinase phosphorylation sites:

Amino acids 200-204;238-242

Tyrosine kinase phosphorylation site:

Amino acids 207-214

N-myristoylation sites:

Amino acids 55-61;215-221;270-276

Prokaryotic membrane lipoprotein lipid attachment site:

Amino acids 259-270

TNFR/NGFR family cysteine-rich region proteins:

Amino acids 89-96

FIGURE 25

```
CAGTTTCTTCATCTGTAACATCAAATGAATAATAATACCAATCTCCTAGACTTCATAAGA
GGATTAACAAAGACAAAATATGGGAAAAACATAACATGGCGTCCCATAATTATTAGATCT
TATTATTGACACTAAAATGGCATTAAAATTACCAAAAGGAAGACAGCATCTGTTTCCTCT
TTGGTCCTGAGCTGGTTAAAAGGAACACTGGTTGCCTGAACAGTCACACTTGCAACCATG
ATGCCTAAACATTGCTTTCTAGGCTTCCTCATCAGTTTCTTCCTTACTGGTGTAGCAGGA
ACTCAGTCAACGCATGAGTCTCTGAAGCCTCAGAGGGTACAATTTCAGTCCCGAAATTTT
CACAACATTTTGCAATGGCAGCCTGGGAGGGCACTTACTGGCAACAGCAGTGTCTATTTT
GTGCAGTACAAAATCATGTTCTCATGCAGCATGAAAAGCTCTCACCAGAAGCCAAGTGGA
TGCTGGCAGCACATTTCTTGTAACTTCCAGGCTGCAGAACATTGGCTAAATATGGACAG
AGACAATGGAAAAATAAAGAAGACTGTTGGGGTACTCAAGAACTCTCTTGTGACCTTACC
AGTGAAACCTCAGACATACAGGAACCTTATTACGGGAGGGTGAGGGCGGCCTCGGCTGGG
AGCTACTCAGAATGGAGCATGACGCCGCGGTTCACTCCCTGGTGGGAAACAAAATAGAT
CCTCCAGTCATGAATATAACCCAAGTCAATGGCTCTTTGTTGGTAATTCTCCATGCTCCA
AATTTACCATATAGATACCAAAAGGAAAAAAATGTATCTATAGAAGATTACTATGAACTA
CTATACCGAGTTTTTATAATTAACAATTCACTAGAAAAGGAGCAAAAGGTTTATGAAGGG
GCTCACAGAGCGGTTGAAATTGAAGCTCTAACACCACACTCCAGCTACTGTGTAGTGGCT
GAAATATATCAGCCCATGTTAGACAGAAGAAGTCAGAGAAGTGAAGAGAGATGTGTGGAA
ATTCCATGACTTGTGGAATTTGGCATTCAGCAATGTGGAAATTCTAAAGCTCCCTGAGAA
CAGGATGACTCGTGTTTGAAGGATCTTATTTAAAATTGTTTTTGTATTTTCTTAAAGCAA
TATTCACTGTTACACCTTGGGGACTTCTTTGTTTATCCATTCTTTTATCCTTTATATTTC
ATTTGTAAACTATATTTGAACGACATTCCCCCCGAAAAATTGAAATGTAAGATGAGGCA
GAGAATAAAGTGTTCTATGAAAAAAAAAAAAAAAAAAAAAAAAAAAAAAAAAAAAAAAA
```

FIGURE 26

></usr/seqdb2/sst/DNA/Dnaseqs.min/ss.DNA145887
><subunit 1 of 1, 262 aa, 1 stop
><MW: 30419, pI: 8.44, NX(S/T): 5
MPKHCFLGFLISFFLTGVAGTQSTHESLKPQRVQFQSRNFHNILQWQPGRALTGNSSVYF
VQYKIMFSCSMKSSHQKPSGCWQHISCNFPGCRTLAKYGQRQWKNKEDCWGTQELSCDLT
SETSDIQEPYYGRVRAASAGSYSEWSMTPRFTPWWETKIDPPVMNITQVNGSLLVILHAP
NLPYRYQKEKNVSIEDYYELLYRVFIINNSLEKEQKVYEGAHRAVEIEALTPHSSYCVVA
EIYQPMLDRRSQRSEERCVEIP Important features of the protein:
Signal peptide:
Amino Acids       1-20

N-glycosylation sites:
Amino acids       55-59;165-169;170-174;191-195;208-212

N-myristoylation sites:
Amino acids       17-23;20-26;220-226

FIGURE 27

```
GGAAGGGGAGGAGCAGGCCACACAGGCACAGGCCGGTGAGGGACCTGCCCAGACCTGGAGGGTCTCGCTCTGTC
ACACAGGCTGGAGTGCAGTGGTGTGATCTTGGCTCATCGTAACCTCCACCTCCCGGGTTCAAGTGATTCTCATG
CCTCAGCCTCCCGAGTAGCTGGGATTACAGGTGGTGACTTCCAAGAGTGACTCCGTCGGAGGAAAATGACTCCC
CAGTCGCTGCTGCAGACGACACTGTTCCTGCTGAGTCTGCTCTTCCTGGTCCAAGGTGCCCACGGCAGGGGCCA
CAGGGAAGACTTTCGCTTCTGCAGCCAGCGGAACCAGACACACAGGAGCAGCCTCCACTACAAACCCACACCAG
ACCTGCGCATCTCCATCGAGAACTCCGAAGAGGCCCTCACAGTCCATGCCCCTTTCCCTGCAGCCCACCCTGCT
TCCCGATCCTTCCCTGACCCCAGGGGCCTCTACCACTTCTGCCTCTACTGGAACCGACATGCTGGGAGATTACA
TCTTTCTCTATGGCAAGCGTGACTTCTTGCTGAGTGACAAAGCCTCTAGCCTCCTCTGCTTCCAGCACCAGGAGG
AGAGCCTGGCTCAGGGCCCCCCGCTGTTAGCCACTTCTGTCACCTCCTGGTGGAGCCCTCAGAACATCAGCCTG
CCCAGTGCCGCCAGCTTCACCTTCTCCTTCCACAGTCCTCCCCACACGGCCGCTCACAATGCCTCGGTGGACAT
GTGCGAGCTCAAAAGGGACCTCCAGCTGCTCAGCCAGTTCCTGAAGCATCCCCAGAAGGCCTCAAGGAGGCCCT
CGGCTGCCCCCGCCAGCCAGCAGTTGCAGAGCCTGGAGTCGAAACTGACCTCTGTGAGATTCATGGGGACATG
GTGTCCTTCGAGGAGGACCGGATCAACGCCACGGTGTGGAAGCTCCAGCCCACAGCCGGCCTCCAGGACCTGCA
CATCCACTCCCGGCAGGAGGAGGAGCAGAGCGAGATCATGGAGTACTCGGTGCTGCTGCCTCGAACACTCTTCC
AGAGGACGAAAGGCCGGAGCGGGGAGGCTGAGAAGAGACTCCTCCTGGTGGACTTCAGCAGCCAAGCCCTGTTC
CAGGACAAGAATTCCAGCCAAGTCCTGGGTGAGAAGGTCTTGGGGATTGTGGTACAGAACACCAAAGTAGCCAA
CCTCACGGAGCCCGTGGTGCTCACTTTCCAGCACCAGCTACAGCCGAAGAATGTGACTCTGCAATGTGTGTTCT
GGGTTGAAGACCCCACATTGAGCAGCCCGGGGCATTGGAGCAGTGCTGGGTGTGAGACCGTCAGGAGAGAAACC
CAAACATCCTGCTTCTGCAACCACTTGACCTACTTTGCAGTGCTGATGGTCTCCTCGGTGGAGGTGGACGCCGT
GCACAAGCACTACCTGAGCCTCCTCTCCTACGTGGGCTGTGTCGTCTCTGCCCTGGCCTGCCTTGTCACCATTG
CCGCCTACCTCTGCTCCAGGGTGCCCCTGCCGTGCAGGAGGAAACCTCGGGACTACACCATCAAGGTGCACATG
AACCTGCTGCTGGCCGTCTTCCTGCTGGACACAGGCTTCCTGCTCAGCGAGCCGGTGGCCCTGACAGGCTCTGA
GGCTGGCTGCCGAGCCAGTGCCATCTTCCTGCACTTCTCCTGCTCACCTGCCCTTTCCTGGATGGCCTCGAGG
GGTACAACCTCTACCGACTCGTGGTGGAGGTCTTTGGCACCTATGTCCCTGGCTACCTACTCAAGCTGAGCGCC
ATGGGCTGGGGCTTCCCCATCTTTCTGGTGACGCTGGTGGCCCTGGTGGATGTGGACAACTATGGCCCCATCAT
CTTGGCTGTGCATAGGACTCCAGAGGGCGTCATCTACCCTTCCATGTGCTGGATCCGGGACTCCCTGGTCAGCT
ACATCACCAACCTGGGCCTCTTCAGCCTGGTGTTTCTGTTCAACATGGCCATGCTAGCCACCATGGTGGTGCAG
ATCCTGCGGCTGCGCCCCCACACCCAAAAGTGGTCACATGTGCTGACACTGCTGGGCCTCAGCCTGGTCCTTGG
CCTGCCCTGGGCCTTGATCTTCTTCTCCTTTGCTTCTGGCACCTTCCAGCTTGTCGTCCTCTACCTTTTCAGCA
TCATCACCTCCTTCCAAGGCTTCCTCATCTTCATCTGGTACTGGTCCATGCGGCTGCAGGCCCGGGGTGGCCCC
TCCCCTCTGAAGAGCAACTCAGACAGCGCCAGGCTCCCCATCAGCTCGGGCAGCACCTCGTCCAGCCGCATCTA
GGCCTCCAGCCCACCTGCCCATGTGATGAAGCAGAGATGCGGCCTCGTCGCACACTGCCTGTGGCCCCCGAGCC
AGGCCCAGCCCCAGGCCAGTCAGCCGCAGACTTTGGAAAGCCCAACGACCATGGAGAGATGGGCCGTTGCCATG
GTGGACGGACTCCCGGGCTGGGCTTTTGAATTGGCCTTGGGGACTACTCGGCTCTCACTCAGCTCCCACGGGAC
TCAGAAGTGCGCCGCCATGCTGCCTAGGGTACTGTCCCCACATCTGTCCCAACCCAGCTGGAGGCCTGGTCTCT
CCTTACAACCCCTGGGCCCAGCCCTCATTGCTGGGGGCCAGGCCTTGGATCTTGAGGGTCTGGCACATCCTTAA
TCCTGTGCCCCTGCCTGGGACAGAAATGTGGCTCCAGTTGCTCTGTCTCTCGTGGTCACCCTGAGGGCACTCTG
CATCCTCTGTCATTTTAACCTCAGGTGGCACCCAGGGCGAATGGGGCCCAGGGCAGACCTTCAGGGCCAGAGCC
CTGGCGGAGGAGAGGCCCTTTGCCAGGAGCACAGCAGCAGCTCGCCTACCTCTGAGCCCAGGCCCCTCCCTCC
CTCAGCCCCCCAGTCCTCCCTCCATCTTCCCTGGGGTTCTCCTCCTCTCCCAGGGCCTCCTTGCTCCTTCGTTC
ACAGCTGGGGGTCCCCGATTCCAATGCTGTTTTTTGGGGAGTGGTTTCCAGGAGCTGCCTGGTGTCTGCTGTAA
ATGTTTGTCTACTGCACAAGCCTCGGCCTGCCCCTGAGCCAGGCTCGGTACCGATGCGTGGGCTGGGCTAGGTC
CCTCTGTCCATCTGGGCCTTTGTATGAGCTGCATTGCCCTTGCTCACCCTGACCAAGCACACGCCTCAGAGGGG
CCCTCAGCCTCTCCTGAAGCCCTCTTGTGGCAAGAACTGTGGACCATGCCAGTCCCGTCTGGTTTCCATCCCAC
CACTCCAAGGACTGAGACTGACCTCCTCTGGTGACACTGGCCTAGAGCCTGACACTCTCCTAAGAGGTTCTCTC
CAAGCCCCCAAATAGCTCCAGGCGCCCTCGGCCGCCCATCATGGTTAATTCTGTCCAACAAACACACACGGGTA
GATTGCTGGCCTGTTGTAGGTGGTAGGGACACAGATGACCGACCTGGTCACTCCTCCTGCCAACATTCAGTCTG
GTATGTGAGGCGTGCGTGAAGCAAGAACTCCTGGAGCTACAGGGACAGGGAGCCATCATTCCTGCCTGGGAATC
CTGGAAGACTTCCTGCAGGAGTCAGCGTTCAATCTTGACCTTGAAGATGGGAAGGATGTTCTTTTTACGTACCA
ATTCTTTTGTCTTTTGATATTAAAAGAAGTACATGTTCATTGTAGAGAATTTGGAAACTGTAGAAGAGAATCA
AGAAGAAAAATAAAAATCAGCTGTTGTAATCGCCTAGCAAAAAAAAAAAAAAAAAAAAAAAAAAAAAAAAAAAA
AAAAAAAAAAAAAAAAAAAAAAAAAAAAAAAAAAAAAAAAAAAAAAAA
```

FIGURE 28

```
</usr/seqdb2/sst/DNA/Dnaseqs.min/ss.DNA50921
<subunit 1 of 1, 693 aa, 1 stop
<MW: 77738, pI: 8.87, NX(S/T): 7
MTPQSLLQTTLFLLSLLFLVQGAHGRGHREDFRFCSQRNQTHRSSLHYKPTPDLRISIENS
EEALTVHAPFPAAHPASRSFPDPRGLYHFCLYWNRHAGRLHLLYGKRDFLLSDKASSLLCF
QHQEESLAQGPPLLATSVTSWWSPQNISLPSAASFTFSFHSPPHTAAHNASVDMCELKRDL
QLLSQFLKHPQKASRRPSAAPASQQLQSLESKLTSVRFMGDMVSFEEDRINATVWKLQPTA
GLQDLHIHSRQEEEQSEIMEYSVLLPRTLFQRTKGRSGEAEKRLLLVDFSSQALFQDKNSS
QVLGEKVLGIVVQNTKVANLTEPVVLTFQHQLQPKNVTLQCVFWVEDPTLSSPGHWSSAGC
ETVRRETQTSCFCNHLTYFAVLMVSSVEVDAVHKHYLSLLSYVGCVVSALACLVTIAAYLC
SRVPLPCRRKPRDYTIKVHMNLLLAVFLLDTSFLLSEPVALTGSEAGCRASAIFLHFSLLT
CLSWMGLEGYNLYRLVVEVFGTYVPGYLLKLSAMGWGFPIFLVTLVALVDVDNYGPIILAV
HRTPEGVIYPSMCWIRDSLVSYITNLGLFSLVFLFNMAMLATMVVQILRLRPHTQKWSHVL
TLLGLSLVLGLPWALIFFSFASGTFQLVVLYLFSIITSFQGFLIFIWYWSMRLQARGGPSP
LKSNSDSARLPISSGSTSSSRI
```

Important features:
Signal peptide:
amino acids 1-25
Putative transmembrane domains:
amino acids 382-398, 402-420, 445-468, 473-491, 519-537, 568-590
and 634-657
Microbodies C-terminal targeting signal.
amino acids 691-693
cAMP- and cGMP-dependent protein kinase phosphorylation sites.
amino acids 198-201 and 370-373
N-glycosylation sites.
amino acids 39-42, 148-151, 171-174, 234-237, 303-306, 324-327
and 341-344
G-protein coupled receptors family 2 proteins
amino acids 475-504

FIGURE 29A

```
TGTGCAGAATTGTACAGTTGCGAAACCATGTCGCTGGCAGCTGGTGCTGGCGGTGGAGAC
TTCCCTGTGCGGTGCTCAGTGCATCTGCACCCGTGGGGAGGGAGCTCTTTCTCTGGCCC
TGCAGTCACCTGAGGTTGTTACCATTATGAACGGCCGCTGGGACCCCCGCATGTGCATGT
ACTCCCCCAGAGTGTCCGGGGGCCCCAGCCAAGGGACACATCTCACGCAGCTGGGAACAT
GTGCAGGCTGATGAAGAGAACCGGATGAGGGCTTCACATGAGGAAGCATGTGGCCAGGTC
CTCTCAGAACATCAGCCTCATCTTCCTGTCTCTGATCTATTTCACCAACCACCCCATGTG
TCTCTAGAACCCCAGTGTAGCGAGCTGGAGAGAGGACTGTCCTGAGGGCAGCAGGCCTGG
TTGCAGCTGGCGTGGGGGTCTCAGAATGGAGCCCTCAGCCCTGAGGAAAGCTGGCTCGGA
GCAGGAGGAGGGCTTTGAGGGGCTGCCCAGAAGGGTCACTGACCTGGGGATGGTCTCCAA
TCTCCGGCGCAGCAACAGCAGCCTCTTCAAGAGCTGGAGGCTACAGTGCCCCTTCGGCAA
CAATGACAAGCAAGAAAGCCTCAGTTCGTGGATTCCTGAAAACATCAAGAAGAAAGAATG
CGTGTATTTTGTGGAAAGTTCCAAACTGTCTGATGCTGGGAAGGTGGTGTGTCAGTGTGG
CTACACGCATGAGCAGCACTTGGAGGAGGCTACCAAGCCCCACACCTTCCAGGGCACACA
GTGGGACCCAAAGAAACATGTCCAGGAGATGCCAACCGATGCCTTTGGCGACATCGTCTT
CACGGGCCTGAGCCAGAAGGTGAAAAAGTACGTCCGAGTCTCCCAGGACACGCCCTCCAG
CGTGATCTACCACCTCATGACCCAGCACTGGGGCTGGACGTCCCCAATCTCTTGATCTC
GGTGACCGGGGGGCCAAGAACTTCAACATGAAGCCGCGGCTGAAGAGCATTTTCCGCAG
AGGCCTGGTCAAGGTGGCTCAGACCACAGGGGCCTGGATCATCACAGGGGGGTCCCACAC
CGGCGTCATGAAGCAGGTAGGCGAGGCGGTGCGGGACTTCAGCCTGAGCAGCAGCTACAA
GGAAGGCGAGCTCATCACCATCGGAGTCGCCACCTGGGGCACTGTCCACCGCCGCGAGGG
CCTGATCCATCCCACGGGCAGCTTCCCCGCCGAGTACATACTGGATGAGGATGGCCAAGG
GAACCTGACCTGCCTAGACAGCAACCACTCTCACTTCATCCTCGTGGACGACGGGACCCA
CGGCCAGTACGGGGTGGAGATTCCTCTGAGGACCAGGCTGGAGAAGTTCATATCGGAGCA
GACCAAGGAAAGAGGAGGTGTGGCCATCAAGATCCCCATCGTGTGCGTGGTGCTGGAGGG
CGGCCCGGGCACGTTGCACACCATCGACAACGCCACCACCAACGGCACCCCCTGTGTGGT
TGTGGAGGGCTCGGGCCGCGTGGCCGACGTCATTGCCCAGGTGGCCAACCTGCCTGTCTC
GGACATCACTATCTCCCTGATCCAGCAGAAACTGAGCGTGTTCTTCCAGGAGATGTTTGA
GACCTTCACGGAAAGCAGGATTGTCGAGTGGACCAAAAAGATCCAAGATATTGTCCGGAG
GCGGCAGCTGCTGACTGTCTTCCGGGAAGGCAAGGATGGTCAGCAGGACGTGGATGTGGC
CATCTTGCAGGCCTTGCTGAAAGCCTCACGGAGCCAAGACCACTTTGGCCACGAGAACTG
GGACCACCAGCTGAAACTGGCAGTGGCATGGAATCGCGTGGACATTGCCCGCAGTGAGAT
CTTCATGGATGAGTGGCAGTGGAAGCCTTCAGATCTGCACCCCACGATGACAGCTGCACT
CATCTCCAACAAGCCTGAGTTTGTGAAGCTCTTCCTGGAAAACGGGGTGCAGCTGAAGGA
GTTTGTCACCTGGGACACCTTGCTCTACCTGTACGAGAACCTGGACCCCTCCTGCCTGTT
CCACAGCAAGCTGCAAAAGGTGCTGGTGGAGGATCCCGAGCGCCCGGCTTGCGCGCCCGC
GGCGCCCCGCCTGCAGATGCACCACGTGGCCCAGGTGCTGCGGGAGCTGCTGGGGGACTT
```

FIGURE 29B

```
CACGCAGCCGCTTTATCCCCGGCCCCGGCACAACGACCGGCTGCGGCTCCTGCTGCCCGT
TCCCCACGTCAAGCTCAACGTGCAGGGAGTGAGCCTCCGGTCCCTCTACAAGCGTTCCTC
AGGCCATGTGACCTTCACCATGGACCCCATCCGTGACCTTCTCATTTGGGCCATTGTCCA
GAACCGTCGGGAGCTGGCAGGAATCATCTGGGCTCAGAGCCAGGACTGCATCGCAGCGGC
CTTGGCCTGCAGCAAGATCCTGAAGGAACTGTCCAAGGAGGAGGAGGACACGGACAGCTC
GGAGGAGATGCTGGCGCTGGCGGAGGAGTATGAGCACAGAGCCATCGGGGTCTTCACCGA
GTGCTACCGGAAGGACGAAGAGAGAGCCCAGAAACTGCTCACCCGCGTGTCCGAGGCCTG
GGGGAAGACCACCTGCCTGCAGCTCGCCCTGGAGGCCAAGGACATGAAGTTTGTGTCTCA
CGGGGGCATCCAGGCCTTCCTGACCAAGGTGTGGTGGGCCAGCTCTCCGTGGACAATGG
GCTGTGGCGTGTGACCCTGTGCATGCTGGCCTTCCCGCTGCTCCTCACCGGCCTCATCTC
CTTCAGGGAGAAGAGGCTGCAGGATGTGGGCACCCCGCGGCCCGCGCCCGTGCCTTCTT
CACCGCACCCGTGGTGGTCTTCCACCTGAACATCCTCTCCTACTTCGCCTTCCTCTGCCT
GTTCGCCTACGTGCTCATGGTGGACTTCCAGCCTGTGCCCTCCTGGTGCGAGTGTGCCAT
CTACCTCTGGCTCTTCTCCTTGGTGTGCGAGGAGATGCGGCAGCTCTTCTATGACCCTGA
CGAGTGCGGGCTGATGAAGAAGGCAGCCTTGTACTTCAGTGACTTCTGGAATAAGCTGGA
CGTCGGCGCAATCTTGCTCTTCGTGGCAGGGCTGACCTGCAGGCTCATCCCGGCGACGCT
GTACCCCGGGCGCGTCATCCTCTCTCTGGACTTCATCCTGTTCTGCCTCCGGCTCATGCA
CATTTTTACCATCAGTAAGACGCTGGGGCCCAAGATCATCATTGTGAAGCGGATGATGAA
GGACGTCTTCTTCTTCCTCTTCCTGCTGGCTGTGTGGGTGGTGTCCTTCGGGGTGGCCAA
GCAGGCCATCCTCATCCACAACGAGCGCCGGGTGGACTGGCTGTTCGAGGGGCCGTCTA
CCACTCCTACCTCACCATCTTCGGGCAGATCCCGGGCTACATCGACGGTGTGAACTTCAA
CCCGGAGCACTGCAGCCCCAATGGCACCGACCCCTACAAGCCTAAGTGCCCCGAGAGCGA
CGCGACGCAGCAGAGGCCGGCCTTCCCTGAGTGGCTGACGGTCCTCCTACTCTGCCTCTA
CCTGCTCTTCACCAACATCCTGCTGCTCAACCTCCTCATCGCCATGTTCAACTACACCTT
CCAGCAGGTGCAGGAGCACACGGACCAGATTTGGAAGTTCCAGCGCCATGACCTGATCGA
GGAGTACCACGGCCGCCCCGCCGCGCCGCCCCCCTTCATCCTCCTCAGCCACCTGCAGCT
CTTCATCAAGAGGGTGGTCCTGAAGACTCCGGCCAAGAGGCACAAGCAGCTCAAGAACAA
GCTGGAGAAGAACGAGGAGGCGGCCCTGCTATCCTGGGAGATCTACCTGAAGGAGAACTA
CCTCCAGAACCGACAGTTCCAGCAAAAGCAGCGGCCCGAGCAGAAGATCGAGGACATCAG
CAATAAGGTTGACGCCATGGTGGACCTGCTGGACCTGGACCCACTGAAGAGGTCGGGCTC
CATGGAGCAGAGGTTGGCCTCCCTGGAGGAGCAGGTGGCCCAGACAGCCCGAGCCCTGCA
CTGGATCGTGAGGACGCTGCGGGCCAGCGGCTTCAGCTCGGAGGCGGACGTCCCCACTCT
GGCCTCCCAGAAGGCCGCGGAGGAGCCGGATGCTGAGCCGGGAGGCAGGAAGAAGACGGA
GGAGCCGGGCGACAGCTACCACGTGAATGCCCGGCACCTCCTCTACCCCAACTGCCCTGT
CACGCGCTTCCCCGTGCCCAACGAGAAGGTGCCCTGGGAGACGGAGTTCCTGATCTATGA
```

FIGURE 29C

```
CCCACCCTTTTACACGGCAGAGAGGAAGGACGCGGCCGCCATGGACCCCATGGGAGACAC
CTGGAGCCACTGTCCACGATCCAGTACAACGTGGTGGATGGCCTGAGGGACCGCCGGAG
CTTCCACGGGCCGTACACAGTGCAGGCCGGGTTGCCCCTGAACCCCATGGGCCGCACAGG
ACTGCGTGGGCGCGGGAGCCTCAGCTGCTTCGGACCCAACCACACGCTGTACCCCATGGT
CACGCGGTGGAGGCGGAACGAGGATGGAGCCATCTGCAGGAAGAGCATAAAGAAGATGCT
GGAAGTGCTGGTGGTGAAGCTCCCTCTCTCCGAGCACTGGGCCCTGCCTGGGGGCTCCCG
GGAGCCAGGGGAGATGCTACCTCGGAAGCTGAAGCGGATCCTCCGGCAGGAGCACTGGCC
GTCTTTTGAAAACTTGCTGAAGTGCGGCATGGAGGTGTACAAAGGCTACATGGATGACCC
GAGGAACACGGACAATGCCTGGATCGAGACGGTGGCCGTCAGCGTCCACTTCCAGGACCA
GAATGACGTGGAGCTGAACAGGCTGAACTCTAACCTGCACGCCTGCGACTCGGGGGCCTC
CATCCGATGGCAGGTGGTGGACAGGCGCATCCCACTCTATGCGAACCACAAGACCCTCCT
CCAGAAGGCAGCCGCTGAGTTCGGGGCTCACTACTGACTGTGCCCTCAGGCTGGGCGGCT
CCAGTCCATAGACGTTCCCCCCAGAAACCAGGGCTTCTCTCTCCTGAGCCTGGCCAGGAC
TCAGGCTGTTCCTGGGCCCTGCACATGATGGGGTTTGGTGGACCCAGTGCCCCTCACGGC
TGCCGCAAGTCTGCTGCAGATGACCTCATGAACTGGAAGGGGTCAAGGTGACCCGGGAGG
AGAGCTCAAGACAGGGCACAGGCTACTCAGAGCTGAGGGGCCCCTGGGACCCTTGGCCAT
CAGGCGAGGGGCTGGGCCTGTGCAGCTGGGCCCTTGGCCAGAGTCCACTCCCTTCCTGGC
TGTGTCACCCCGAGCAGCTCATCCACCATGGAGGTCATTGGCCTGAGGCAAGTTCCCCGG
AGAGTCGGGATCCCCTGTGGCCCCCTCAGGCCTATGTCTGTGAGGAAGGGGCCCTGCCAC
TCTCCCCAAGAGGGCCTCCATGTTTCGAGGTGCCTCAACATGGAGCCTTGCCTGGCCTGG
GCTAGGGGCACTGTCTGAACTCCTGACTGTCAGGATAAACTCCGTGGGGGTACAGGAGCC
CAGACAAAGCCCAGGCCTGTCAAGAGACGCAGAGGGCCCCTGCCAGGGTTGGCCCCAGGG
ACCCTGGGACGAGGCTGCAGAAGCTCTCCCTCCCTACTCCCTGGGAGCCACGTGCTGGCC
ATGTGGCCAGGGACGGCATGAGCAGGAGGCGGGGACGTGGGGGCCTTCTGGTTTGGTGTC
AACAGCTCACAGGAGCGTGAACCATGAGGGCCCTCAGGAGGGGAACGTGGTAAAACCCAA
GACATTAAATCTGCCATCTCAGGCCTGGCTGGCTCTTCTGTGCTTTCCACAAATAAAGTT
CCTGACACGTCCAGGGCCAGGGGCTGTGTGACGGCTGCCTGAAGTTCTCCTCGATCCCCC
GGTGAGCTTCCTGCAGCCTGTGGATGTCCTGCAGCCCCTCAGCCCTACCCCCAAGTTTCT
CCTCTGACCCATCAGCTCCCTGTCTTCATTTTCCTAAACCTGGGCTCCAGCATCGTCCCC
AAGCCCACCAGGCCAGGATGCAGGCATCCACATGCCCTCCTCCTTGGCTTCCCCTGCGTG
GTGGTGCCAATGTGCCCTGGCACCCCTGCAGAGGCTCCGGATGGAGCCTGGGGCTGCCTG
GCCACTGAGCACTGGCCGAGGTGATGCCCACCCTTCCCTGGACAGGCCTCTGTCTTCCAC
CTGACCCAAAGCTCTCTAGCCACCCCCTTGTCCCCAGTAT
```

FIGURE 30

><DNA226659 [min]
></usr/seqdb2/sst/DNA/Dnaseqs.min/ss.DNA226659
><subunit 1 of 1, 1503 aa, 1 stop
><MW: 171226, pI: 7.73, NX(S/T): 8

MEPSALRKAGSEQEEGFEGLPRRVTDLGMVSNLRRSNSSLFKSWRLQCPFGNNDKQESLS
SWIPENIKKKECVYFVESSKLSDAGKVVCQCGYTHEQHLEEATKPHTFQGTQWDPKKHVQ
EMPTDAFGDIVFTGLSQKVKKYVRVSQDTPSSVIYHLMTQHWGLDVPNLLISVTGGAKNF
NMKPRLKSIFRRGLVKVAQTTGAWIITGGSHTGVMKQVGEAVRDFSLSSSYKEGELITIG
VATWGTVHRREGLIHPTGSFPAEYILDEDGQGNLTCLDSNHSHFILVDDGTHGQYGVEIP
LRTRLEKFISEQTKERGGVAIKIPIVCVVLEGGPGTLHTIDNATTNGTPCVVVEGSGRVA
DVIAQVANLPVSDITISLIQQKLSVFFQEMFETFTESRIVEWTKKIQDIVRRRQLLTVFR
EGKDGQQDVDVAILQALLKASRSQDHFGHENWDHQLKLAVAWNRVDIARSEIFMDEWQWK
PSDLHPTMTAALISNKPEFVKLFLENGVQLKEFVTWDTLLYLYENLDPSCLFHSKLQKVL
VEDPERPACAPAAPRLQMHHVAQVLRELLGDFTQPLYPRPRHNDRLRLLLPVPHVKLNVQ
GVSLRSLYKRSSGHVTFTMDPIRDLLIWAIVQNRRELAGIIWAQSQDCIAAALACSKILK
ELSKEEEDTDSSEEMLALAEEYEHRAIGVFTECYRKDEERAQKLLTRVSEAWGKTTCLQL
ALEAKDMKFVSHGGIQAFLTKVWWGQLSVDNGLWRVTLCMLAFPLLLTGLISFREKRLQD
VGTPAARARAFFTAPVVVFHLNILSYFAFLCLFAYVLMVDFQPVPSWCECAIYLWLFSLV
CEEMRQLFYDPDECGLMKKAALYFSDFWNKLDVGAILLFVAGLTCRLIPATLYPGRVILS
LDFILFCLRLMHIFTISKTLGPKIIIVKRMMKDVFFFLFLLAVWVVSFGVAKQAILIHNE
RRVDWLFRGAVYHSYLTIFGQIPGYIDGVNFNPEHCSPNGTDPYKPKCPESDATQQRPAF
PEWLTVLLLCLYLLFTNILLLNLLIAMFNYTFQQVQEHTDQIWKFQRHDLIEEYHGRPAA
PPPFILLSHLQLFIKRVVLKTPAKRHKQLKNKLEKNEEAALLSWEIYLKENYLQNRQFQQ
KQRPEQKIEDISNKVDAMVDLLDLDPLKRSGSMEQRLASLEEQVAQTARALHWIVRTLRA
SGFSSEADVPTLASQKAAEEPDAEPGGRKKTEEPGDSYHVNARHLLYPNCPVTRFPVPNE
KVPWETEFLIYDPPFYTAERKDAAAMDPMGDTLEPLSTIQYNVVDGLRDRRSFHGPYTVQ
AGLPLNPMGRTGLRGRGSLSCFGPNHTLYPMVTRWRRNEDGAICRKSIKKMLEVLVVKLP
LSEHWALPGGSREPGEMLPRKLKRILRQEHWPSFENLLKCGMEVYKGYMDDPRNTDNAWI
ETVAVSVHFQDQNDVELNRLNSNLHACDSGASIRWQVVDRRIPLYANHKTLLQKAAAEFG
AHY

FIGURE 31

```
GATGGCGCAGCCACAGCTTCTGTGAGATTCGATTTCTCCCCAGTTCCCCTGTGGGTCTGAGGGGACCAGAAGGG
TGAGCTACGTTGGCTTTCTGGAAGGGGAGGCTATATGCGTCAATTCCCCAAAACAAGTTTTGACATTTCCCCTG
AAATGTCATTCTCTATCTATTCACTGCAAGTGCCTGCTGTTCCAGGCCTTACCTGCTGGGCACTAACGGCGGAG
CCAGGATGGGGACAGAATAAAGGAGCCACGACCTGTGCCACCAACTCGCACTCAGACTCTGAACTCAGACCTGA
AATCTTCTCTTCACGGGAGGCTTGGCAGTTTTTCTTACTCCTGTGGTCTCCAGATTTCAGGCCTAAGATGAAAG
CCTCTAGTCTTGCCTTCAGCCTTCTCTCTGCTGCGTTTTATCTCCTATGGACTCCTTCCACTGGACTGAAGACA
CTCAATTTGGGAAGCTGTGTGATCGCCACAAACCTTCAGGAAATACGAAATGGATTTTCTGAGATACGGGGCAG
TGTGCAAGCCAAAGATGGAAACATTGACATCAGAATCTTAAGGAGGACTGAGTCTTTGCAAGACACAAAGCCTG
CGAATCGATGCTGCCTCCTGCGCCATTTGCTAAGACTCTATCTGGACAGGGTATTTAAAAACTACCAGACCCCT
GACCATTATACTCTCCGGAAGATCAGCAGCCTCGCCAATTCCTTTCTTACCATCAAGAAGGACCTCCGGCTCTC
TCATGCCCACATGACATGCCATTGTGGGGAGGAAGCAATGAAGAAATACAGCCAGATTCTGAGTCACTTTGAAA
AGCTGGAACCTCAGGCAGCAGTTGTGAAGGCTTTGGGGGAACTAGACATTCTTCTGCAATGGATGGAGGAGACA
GAATAGGAGGAAAGTGATGCTGCTGCTAAGAATATTCGAGGTCAAGAGCTCCAGTCTTCAATACCTGCAGAGGA
GGCATGACCCCAAACCACCATCTCTTTACTGTACTAGTCTTGTGCTGGTCACAGTGTATCTTATTTATGCATTA
CTTGCTTCCTTGCATGATTGTCTTTATGCATCCCCAATCTTAATTGAGACCATACTTGTATAAGATTTTTGTAA
TATCTTTCTGCTATTGGATATATTTATTAGTTAATATATTTATTTATTTTTTGCTATTTAATGTATTTATTTTT
TTACTTGGACATGAAACTTTAAAAAAATTCACAGATTATATTTATAACCTGACTAGAGCAGGTGATGTATTTTT
ATACAGTAAAAAAAAAAAAACCTTGTAAATTCTAGAAGAGTGGCTAGGGGGGTTATTCATTTGTATTCAACTAAG
GACATATTTACTCATGCTGATGCTCTGTGAGATATTTGAAATTGAACCAATGACTACTTAGGATGGGTTGTGGA
ATAAGTTTTGATGTGGAATTGCACATCTACCTTACAATTACTGACCATCCCCAGTAGACTCCCCAGTCCCATAA
TTGTGTATCTTCCAGCCAGGAATCCTACACGGCCAGCATGTATTTCTACAAATAAAGTTTTCTTTGCATACCAA
AAAAAAAAAAAAAAAA
```

FIGURE 32

></usr/seqdb2/sst/DNA/Dnaseqs.min/ss.DNA83500

><subunit 1 of 1, 176 aa, 1 stop

><MW: 20056, pI: 9.13, NX(S/T): 0

MKASSLAFSLLSAAFYLLWTPSTGLKTLNLGSCVIATNLQEIRNGFSEIRGSVQAKDGNI
DIRILRRTESLQDTKPANRCCLLRHLLRLYLDRVFKNYQTPDHYTLRKISSLANSFLTIK
KDLRLSHAHMTCHCGEEAMKKYSQILSHFEKLEPQAAVVKALGELDILLQWMEETE

PRO224 GENE DISRUPTIONS, AND METHODS RELATED THERETO

RELATED APPLICATIONS

This application is a US national stage continuation application claiming priority under 35 USC §371 of international application PCT/US2004/041721, filed Dec. 13, 2004, which claims priority under 35 USC §119 to U.S. Provisional Application No. 60/530,043 filed Dec. 16, 2003.

FIELD OF THE INVENTION

The present invention relates to compositions, including transgenic and knockout animals and methods of using such compositions for the diagnosis and treatment of diseases or disorders.

The disclosure includes a Computer Program Listing Appendix, provided on a single compact disc created on Sep. 21, 2011, which is hereby incorporated by reference in its entirety.

BACKGROUND OF THE INVENTION

Extracellular proteins play important roles in, among other things, the formation, differentiation and maintenance of multicellular organisms. The fate of many individual cells, e.g., proliferation, migration, differentiation, or interaction with other cells, is typically governed by information received from other cells and/or the immediate environment. This information is often transmitted by secreted polypeptides (for instance, mitogenic factors, survival factors, cytotoxic factors, differentiation factors, neuropeptides, and hormones) which are, in turn, received and interpreted by diverse cell receptors or membrane-bound proteins. These secreted polypeptides or signaling molecules normally pass through the cellular secretory pathway to reach their site of action in the extracellular environment.

Secreted proteins have various industrial applications, including as pharmaceuticals, diagnostics, biosensors and bioreactors. Most protein drugs available at present, such as thrombolytic agents, interferons, interleukins, erythropoietins, colony stimulating factors, and various other cytokines, are secretory proteins. Their receptors, which are membrane proteins, also have potential as therapeutic or diagnostic agents. Efforts are being undertaken by both industry and academia to identify new, native secreted proteins. Many efforts are focused on the screening of mammalian recombinant DNA libraries to identify the coding sequences for novel secreted proteins. Examples of screening methods and techniques are described in the literature [see, for example, Klein et al., *Proc. Natl. Acad. Sci.* 93:7108-7113 (1996); U.S. Pat. No. 5,536,637].

Membrane-bound proteins and receptors can play important roles in, among other things, the formation, differentiation and maintenance of multicellular organisms. The fate of many individual cells, e.g., proliferation, migration, differentiation, or interaction with other cells, is typically governed by information received from other cells and/or the immediate environment. This information is often transmitted by secreted polypeptides (for instance, mitogenic factors, survival factors, cytotoxic factors, differentiation factors, neuropeptides, and hormones) which are, in turn, received and interpreted by diverse cell receptors or membrane-bound proteins. Such membrane-bound proteins and cell receptors include, but are not limited to, cytokine receptors, receptor kinases, receptor phosphatases, receptors involved in cell-cell interactions, and cellular adhesion molecules like selectins and integrins. For instance, transduction of signals that regulate cell growth and differentiation is regulated in part by phosphorylation of various cellular proteins. Protein tyrosine kinases, enzymes that catalyze that process, can also act as growth factor receptors. Examples include fibroblast growth factor receptor and nerve growth factor receptor.

Membrane-bound proteins and receptor molecules have various industrial applications, including as pharmaceutical and diagnostic agents. Receptor immuno-adhesions, for instance, can be employed as therapeutic agents to block receptor-ligand interactions. The membrane-bound proteins can also be employed for screening of potential peptide or small molecule inhibitors of the relevant receptor/ligand interaction.

Efforts are being undertaken by both industry and academia to identify new, native receptor or membrane-bound proteins. Many efforts are focused on the screening of mammalian recombinant DNA libraries to identify the coding sequences for novel receptor or membrane-bound proteins.

Given the importance of secreted and membrane-bound proteins in biological and disease processes, in vivo studies and characterizations may provide valuable identification and discovery of therapeutics and/or treatments useful in the prevention, amelioration or correction of diseases or dysfunctions. In this regard, genetically engineered mice have proven to be invaluable tools for the functional dissection of biological processes relevant to human disease, including immunology, cancer, neuro-biology, cardiovascular biology, obesity and many others. Gene knockouts can be viewed as modeling the biological mechanism of drug action by presaging the activity of highly specific antagonists in vivo. Knockout mice have been shown to model drug activity; phenotypes of mice deficient for specific pharmaceutical target proteins can resemble the human clinical phenotype caused by the corresponding antagonist drug. Gene knockouts enable the discovery of the mechanism of action of the target, the predominant physiological role of the target, and mechanism-based side-effects that might result from inhibition of the target in mammals. Examples of this type include mice deficient in the angiotensin converting enzyme (ACE) [Esther, C. R. et al., *Lab. Invest.*, 74:953-965 (1996)] and cyclooxygenase-1 (COX1) genes [Langenbach, R. et al., *Cell* 83:483-492 (1995)]. Conversely, knocking the gene out in the mouse can have an opposite phenotypic effect to that observed in humans after administration of an agonist drug to the corresponding target. Examples include the erythropoietin knockout [Wu, C. S. et al., *Cell* 83:59-67 (1996)], in which a consequence of the mutation is deficient red blood cell production, and the GABA(A)-R-β3 knockout [DeLorey, T. M., *J. Neurosci.*, 18:8505-8514 (1998)], in which the mutant mice show hyperactivity and hyper-responsiveness. Both these phenotypes are opposite to the effects of erythropoietin and benzodiazepine administration in humans. A striking example of a target validated using mouse genetics is the ACC2 gene. Although the human ACC2 gene had been identified several years ago, interest in ACC2 as a target for drug development was stimulated only recently after analysis of ACC2 function using a knockout mouse. ACC2 mutant mice eat more than their wild-type littermates, yet burn more fat and store less fat in their adipocytes, making this enzyme a probable target for chemical antagonism in the treatment of obesity [Abu-Elheiga, L. et al., *Science,* 291:2613-2616 (2001)].

In the instant application, mutated gene disruptions have resulted in phenotypic observations related to various disease conditions or dysfunctions including: CNS/neurological disturbances or disorders such as anxiety; eye abnormalities and associated diseases; cardiovascular, endothelial or angiogenic disorders including atherosclerosis; abnormal metabolic disorders including diabetes and dyslipidemias associated with elevated serum triglycerides and cholesterol levels; immunological and inflammatory disorders; oncological disorders; bone metabolic abnormalities or disorders such as arthritis, osteoporosis and osteopetrosis; or a developmental disease such as embryonic lethality.

SUMMARY OF THE INVENTION

A. Embodiments

The invention provides an isolated nucleic acid molecule comprising a nucleotide sequence that encodes a PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide.

In one aspect, the isolated nucleic acid molecule comprises a nucleotide sequence having at least about 80% nucleic acid sequence identity, alternatively at least about 81% nucleic acid sequence identity, alternatively at least about 82% nucleic acid sequence identity, alternatively at least about 83% nucleic acid sequence identity, alternatively at least about 84% nucleic acid sequence identity, alternatively at least about 85% nucleic acid sequence identity, alternatively at least about 86% nucleic acid sequence identity, alternatively at least about 87% nucleic acid sequence identity, alternatively at least about 88% nucleic acid sequence identity, alternatively at least about 89% nucleic acid sequence identity, alternatively at least about 90% nucleic acid sequence identity, alternatively at least about 91% nucleic acid sequence identity, alternatively at least about 92% nucleic acid sequence identity, alternatively at least about 93% nucleic acid sequence identity, alternatively at least about 94% nucleic acid sequence identity, alternatively at least about 95% nucleic acid sequence identity, alternatively at least about 96% nucleic acid sequence identity, alternatively at least about 97% nucleic acid sequence identity, alternatively at least about 98% nucleic acid sequence identity and alternatively at least about 99% nucleic acid sequence identity to (a) a DNA molecule encoding a PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide having a full-length amino acid sequence as disclosed herein, an amino acid sequence lacking the signal peptide as disclosed herein, an extracellular domain of a transmembrane protein, with or without the signal peptide, as disclosed herein or any other specifically defined fragment of the full-length amino acid sequence as disclosed herein, or (b) the complement of the DNA molecule of (a).

In other aspects, the isolated nucleic acid molecule comprises a nucleotide sequence having at least about 80% nucleic acid sequence identity, alternatively at least about 81% nucleic acid sequence identity, alternatively at least about 82% nucleic acid sequence identity, alternatively at least about 83% nucleic acid sequence identity, alternatively at least about 84% nucleic acid sequence identity, alternatively at least about 85% nucleic acid sequence identity, alternatively at least about 86% nucleic acid sequence identity, alternatively at least about 87% nucleic acid sequence identity, alternatively at least about 88% nucleic acid sequence identity, alternatively at least about 89% nucleic acid sequence identity, alternatively at least about 90% nucleic acid sequence identity, alternatively at least about 91% nucleic acid sequence identity, alternatively at least about 92% nucleic acid sequence identity, alternatively at least about 93% nucleic acid sequence identity, alternatively at least about 94% nucleic acid sequence identity, alternatively at least about 95% nucleic acid sequence identity, alternatively at least about 96% nucleic acid sequence identity, alternatively at least about 97% nucleic acid sequence identity, alternatively at least about 98% nucleic acid sequence identity and alternatively at least about 99% nucleic acid sequence identity to (a) a DNA molecule comprising the coding sequence of a full-length PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide cDNA as disclosed herein, the coding sequence of a PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide lacking the signal peptide as disclosed herein, the coding sequence of an extracellular domain of a transmembrane PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide, with or without the signal peptide, as disclosed herein or the coding sequence of any other specifically defined fragment of the full-length amino acid sequence as disclosed herein, or (b) the complement of the DNA molecule of (a).

In a further aspect, the invention concerns an isolated nucleic acid molecule comprising a nucleotide sequence having at least about 80% nucleic acid sequence identity, alternatively at least about 81% nucleic acid sequence identity, alternatively at least about 82% nucleic acid sequence identity, alternatively at least about 83% nucleic acid sequence identity, alternatively at least about 84% nucleic acid sequence identity, alternatively at least about 85% nucleic acid sequence identity, alternatively at least about 86% nucleic acid sequence identity, alternatively at least about 87% nucleic acid sequence identity, alternatively at least about 88% nucleic acid sequence identity, alternatively at least about 89% nucleic acid sequence identity, alternatively at least about 90% nucleic acid sequence identity, alternatively at least about 91% nucleic acid sequence identity, alternatively at least about 92% nucleic acid sequence identity, alternatively at least about 93% nucleic acid sequence identity, alternatively at least about 94% nucleic acid sequence identity, alternatively at least about 95% nucleic acid sequence identity, alternatively at least about 96% nucleic acid sequence identity, alternatively at least about 97% nucleic acid sequence identity, alternatively at least about 98% nucleic acid sequence identity and alternatively at least about 99% nucleic acid sequence identity to (a) a DNA molecule that encodes the same mature polypeptide encoded by any of the human protein cDNAs deposited with the ATCC as disclosed herein, or (b) the complement of the DNA molecule of (a).

Another aspect of the invention provides an isolated nucleic acid molecule comprising a nucleotide sequence encoding a PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide which is either transmembrane domain-deleted or transmembrane domain-inactivated, or is complementary to such encoding nucleotide sequence, wherein the transmembrane domain(s) of such polypeptide are disclosed herein. Therefore, soluble extracellular domains of the herein described PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptides are contemplated.

The invention also provides fragments of a PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide coding sequence, or the complement thereof, that may find use as, for example, hybridization probes, for encoding fragments of a PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide that may optionally encode a polypeptide comprising a binding site for an anti-PRO224, anti-PRO9783, anti-PRO1108, anti-PRO34000, anti-PRO240, anti-PRO943, anti-hu A33, anti-PRO230, anti-PRO178, anti-PRO1199, anti-PRO4333, anti-PRO1336, anti-PRO19598, anti-PRO1083, anti-hu TRPM2 or anti-PRO1801 antibody or as antisense oligonucleotide probes. Such nucleic acid fragments usually are or are at least about 10 nucleotides in length, alternatively are or are at least about 15 nucleotides in length, alternatively are or are at least about 20 nucleotides in length, alternatively are or are at least about 30 nucleotides in length, alternatively are or are at least about 40 nucleotides in length, alternatively are or are at least about 50 nucleotides in length, alternatively are or are at least about 60 nucleotides in length, alternatively are or are at least about 70 nucleotides in length, alternatively are or are at least about 80 nucleotides in length, alternatively are or are at least about 90 nucleotides in length, alternatively are or are at least about 100 nucleotides in length, alternatively are or are at least about 110 nucleotides in length, alternatively are or are at least about 120 nucleotides in length, alternatively are or are at least about 130 nucleotides in length, alternatively are or are at least about 140 nucleotides in length, alternatively are or are at least about 150 nucleotides in length, alternatively are or are at least about 160 nucleotides in length, alternatively are or are at least about 170 nucleotides in length, alternatively are or are at least about 180 nucleotides in length, alternatively are or are at least about 190 nucleotides in length, alternatively are or are at least about 200 nucleotides in length, alternatively are or are at least about 250 nucleotides in length, alternatively are or are at least about 300 nucleotides in length, alternatively are or are at least about 350 nucleotides in length, alternatively are or are at least about 400 nucleotides in length, alternatively are or are at least about 450 nucleotides in length, alternatively are or are at least about 500 nucleotides in length, alternatively are or are at least about 600 nucleotides in length, alternatively are or are at least about 700 nucleotides in length, alternatively are or are at least about 800 nucleotides in length, alternatively are or are at least about 900 nucleotides in length and alternatively are or are at least about 1000 nucleotides in length, wherein in this context the term "about" means the referenced nucleotide sequence length plus or minus 10% of that referenced length. It is noted that novel fragments of a PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide-encoding nucleotide sequence may be determined in a routine manner by aligning the PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide-encoding nucleotide sequence with other known nucleotide sequences using any of a number of well known sequence alignment programs and determining which PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide-encoding nucleotide sequence fragment(s) are novel. All of such PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide-encoding nucleotide sequences are contemplated herein. Also contemplated are the PRO224, PRO9783, PRO1108, PRO34000, PRO240, PRO943, hu A33, PRO230, PRO178, PRO199, PRO4333, PRO1336, PRO19598, PRO1083, hu TRPM2 or PRO1801 polypeptide fragments encoded by these nucleotide molecule fragments, preferably those PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide fragments that comprise a binding site for an anti-PRO224, anti-PRO9783, anti-PRO1108, anti-PRO34000, anti-PRO240, anti-PRO943, anti-hu A33, anti-PRO230, anti-PRO178, anti-PRO1199, anti-PRO4333, anti-PRO1336, anti-PRO19598, anti-PRO1083, anti-hu TRPM2 or anti-PRO1801 antibody.

The invention provides isolated PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptides encoded by any of the isolated nucleic acid sequences hereinabove identified.

In a certain aspect, the invention concerns an isolated PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide, comprising an amino acid sequence having at least about 80% amino acid sequence identity, alternatively at least about 81% amino acid sequence identity, alternatively at least about 82% amino acid sequence identity, alternatively at least about 83% amino acid sequence identity, alternatively at least about 84% amino acid sequence identity, alternatively at least about 85% amino acid sequence identity, alternatively at least about 86% amino acid sequence identity, alternatively at least about 87% amino acid sequence identity, alternatively at least about 88% amino acid sequence identity, alternatively at least about 89% amino acid sequence identity, alternatively at least about 90% amino acid sequence identity, alternatively at least about 91% amino acid sequence identity, alternatively at least about 92% amino acid sequence identity, alternatively at least about 93% amino acid sequence identity, alternatively at least about 94% amino acid sequence identity, alternatively at least about 95% amino acid sequence identity, alternatively at least about 96% amino acid sequence identity, alternatively at least about 97% amino acid sequence identity, alternatively at least about 98% amino acid sequence identity and alternatively at least about 99% amino acid sequence identity to a PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide having a full-length amino acid sequence as disclosed herein, an amino acid sequence lacking the signal peptide as disclosed herein, an extracellular domain of a transmembrane protein, with or without the signal peptide, as disclosed herein or any other specifically defined fragment of the full-length amino acid sequence as disclosed herein.

In a further aspect, the invention concerns an isolated PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide comprising an amino acid sequence having at least about 80% amino acid sequence identity, alternatively at least about 81% amino acid sequence identity, alternatively at least about 82% amino acid sequence identity, alternatively at least about 83% amino acid sequence identity, alternatively at least about 84% amino acid sequence identity, alternatively at least about 85% amino acid sequence identity, alternatively at least about 86% amino acid sequence identity, alternatively at least about 87% amino acid sequence identity, alternatively at least about 88% amino acid sequence identity, alternatively at least about 89% amino acid sequence identity, alternatively at least about 90% amino acid sequence identity, alternatively at least about 91% amino acid sequence identity, alternatively at least about 92% amino acid sequence identity, alternatively at least about 93% amino acid sequence identity, alternatively at least about 94% amino acid sequence identity, alternatively at least about 95% amino acid sequence identity, alternatively at least about 96% amino acid sequence identity, alternatively at least about 97% amino acid sequence identity, alternatively at least about 98% amino acid sequence identity and alternatively at least about 99% amino acid sequence identity to an amino acid sequence encoded by any of the human protein cDNAs deposited with the ATCC as disclosed herein.

In one aspect, the invention concerns PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 variant polypeptides which are or are at least about 10 amino acids in length, alternatively are or are at least about 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600 amino acids in length, or more. Optionally, PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 variant polypeptides will have or have no more than one conservative amino acid substitution as compared to the native PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide sequence, alternatively will have or will have no more than 2, 3, 4, 5, 6, 7, 8, 9, or 10 conservative amino acid substitution as compared to the native PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide sequence.

In a specific aspect, the invention provides an isolated PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide without the N-terminal signal sequence and/or the initiating methionine and is encoded by a nucleotide sequence that encodes such an amino acid sequence as hereinbefore described. Processes for producing the same are also herein described, wherein those processes comprise culturing a host cell comprising a vector which comprises the appropriate encoding nucleic acid molecule under conditions suitable for expression of the PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide and recovering the PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide from the cell culture.

Another aspect the invention provides an isolated PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide which is either transmembrane domain-deleted or transmembrane domain-inactivated. Processes for producing the same are also herein described, wherein those processes comprise culturing a host cell comprising a vector which comprises the appropriate encoding nucleic acid molecule under conditions suitable for expression of the PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide and recovering the PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide from the cell culture.

The invention provides agonists and antagonists of a native PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide as defined herein. In particular, the agonist or antagonist is an anti-PRO224, anti-PRO9783, anti-PRO1108, anti-PRO34000, anti-PRO240, anti-PRO943, anti-hu A33, anti-PRO230, anti-PRO178, anti-PRO1199, anti-PRO4333, anti-PRO1336, anti-PRO19598, anti-PRO1083, anti-hu TRPM2 or anti-PRO1801 antibody or a small molecule.

The invention provides a method of identifying agonists or antagonists to a PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide which comprise contacting the PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide with a candidate molecule and monitoring a biological activity mediated by said PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide. Preferably, the PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide is a native PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide.

The invention provides a composition of matter comprising a PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide, or an agonist or antagonist of a PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide as herein described, or an anti-PRO224, anti-PRO9783, anti-PRO1108, anti-PRO34000, anti-PRO240, anti-PRO943, anti-hu A33, anti-PRO230, anti-PRO178, anti-PRO1199, anti-PRO4333, anti-PRO1336, anti-PRO19598, anti-PRO1083, anti-hu TRPM2 or anti-PRO1801 antibody, in combination with a carrier. Optionally, the carrier is a pharmaceutically acceptable carrier.

The invention provides the use of a PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide, or an agonist or antagonist thereof as hereinbefore described, or an anti- PRO224, anti-PRO9783, anti-PRO1108, anti-PRO34000, anti-PRO240, anti-PRO943, anti-hu A33, anti-PRO230, anti-PRO178, anti-PRO1199, anti-PRO4333, anti-PRO1336, anti-PRO19598, anti-PRO1083, anti-hu TRPM2 or anti-PRO1801 antibody, for the preparation of a medicament useful in the treatment of a condition which is responsive to the anti-PRO224, anti-PRO9783, anti-PRO1108, anti-PRO34000, anti-PRO240, anti-PRO943, anti-hu A33, anti-PRO230, anti-PRO178, anti-PRO1199, anti-PRO4333, anti-PRO1336, anti-PRO19598, anti-PRO1083, anti-hu TRPM2 or anti-PRO1801 antibody.

The invention provides vectors comprising DNA encoding any of the herein described polypeptides. Host cell comprising any such vector are also provided. By way of example, the host cells may be CHO cells, E. coli, or yeast. A process for producing any of the herein described polypeptides is further provided and comprises culturing host cells under conditions suitable for expression of the desired polypeptide and recovering the desired polypeptide from the cell culture.

The invention provides chimeric molecules comprising any of the herein described polypeptides fused to a heterologous polypeptide or amino acid sequence. Example of such chimeric molecules comprise any of the herein described polypeptides fused to an epitope tag sequence or a Fc region of an immunoglobulin.

The invention provides an antibody which binds, preferably specifically, to any of the above or below described polypeptides. Optionally, the antibody is a monoclonal antibody, humanized antibody, antibody fragment or single-chain antibody.

The invention provides oligonucleotide probes which may be useful for isolating genomic and cDNA nucleotide sequences, measuring or detecting expression of an associated gene or as antisense probes, wherein those probes may be derived from any of the above or below described nucleotide sequences. Preferred probe lengths are described above.

The invention also provides a method of identifying a phenotype associated with a disruption of a gene which encodes for a PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide, the method comprising:

(a) providing a non-human transgenic animal whose genome comprises a disruption of the gene which encodes for a PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide;

(b) measuring a physiological characteristic of the non-human transgenic animal; and (c) comparing the measured physiological characteristic with that of a gender matched wild-type animal, wherein the physiological characteristic of the non-human transgenic animal that differs from the physiological characteristic of the wild-type animal is identified as a phenotype resulting from the gene disruption in the non-human transgenic animal. In one aspect, the non-human transgenic animal is a mammal. In another aspect, the mammal is a rodent. In still another aspect, the mammal is a rat or a mouse. In one aspect, the non-human transgenic animal is heterozygous for the disruption of a gene which encodes for a PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide. In another aspect, the phenotype exhibited by the non-human transgenic animal as compared with gender matched wild-type littermates is at least one of the following: a neurological disorder; a cardio-vascular, endothelial or angiogenic disorder; an eye abnormality; an immunological disorder; an oncological disorder; a bone metabolic abnormality or disorder; a lipid metabolic disorder; or a developmental abnormality.

In yet another aspect, the neurological disorder is an increased anxiety-like response during open field activity testing. In yet another aspect, the neurological disorder is a decreased anxiety-like response during open field activity testing. In yet another aspect, the neurological disorder is an abnormal circadian rhythm during home-cage activity testing. In yet another aspect, the neurological disorder is an enhanced motor coordination during inverted screen testing. In yet another aspect, the neurological disorder is impaired motor coordination during inverted screen testing. In yet another aspect, the neurological disorder includes depression, generalized anxiety disorders, attention deficit disorder, sleep disorder, hyperactivity disorder, obsessive compulsive disorder, schizophrenia, cognitive disorders, hyperalgesia and sensory disorders. Such neurological disorders include the category defined as "anxiety disorders" which include but are not limited to: mild to moderate anxiety, anxiety disorder due to a general medical condition, anxiety disorder not otherwise specified, generalized anxiety disorder, panic attack, panic disorder with agoraphobia, panic disorder without agoraphobia, posttraumatic stress disorder, social phobia, social anxiety, autism, specific phobia, substance-induced anxiety disorder, acute alcohol withdrawal, obsessive compulsive disorder, agoraphobia, monopolar disorders, bipolar disorder I or II, bipolar disorder not otherwise specified, cyclothymic disorder, depressive disorder, major depressive disorder, mood disorder, substance-induced mood disorder, enhancement of cognitive function, loss of cognitive function associated with but not limited to Alzheimer's disease, stroke, or traumatic injury to the brain, seizures resulting from disease or injury including but not limited to epilepsy, learning disorders/disabilities, cerebral palsy. In addition, anxiety disorders may apply to personality disorders including but not limited to the following types: paranoid, antisocial, avoidant behavior, borderline personality disorders, dependent, histronic, narcissistic, obsessive-compulsive, schizoid, and schizotypal.

In another aspect, the eye abnormality is a retinal abnormality. In still another aspect, the eye abnormality is consistent with vision problems or blindness. In yet another aspect, the retinal abnormality is consistent with retinitis pigmentosa or is characterized by retinal degeneration or retinal dysplasia.

In still another aspect, the retinal abnormalities are consistent with retinal dysplasia, various retinopathies, including retinopathy of prematurity, retrolental fibroplasia, neovascular glaucoma, age-related macular degeneration, diabetic macular edema, corneal neovascularization, corneal graft neovascularization, corneal graft rejection, retinal/choroidal neovascularization, neovascularization of the angle (rubeosis), ocular neovascular disease, vascular restenosis, arteriovenous malformations (AVM), meningioma, hemangioma, angiofibroma, thyroid hyperplasias (including Grave's disease), corneal and other tissue transplantation, retinal artery obstruction or occlusion; retinal degeneration causing secondary atrophy of the retinal vasculature, retinitis pigmentosa, macular dystrophies, Stargardt's disease, congenital stationary night blindness, choroideremia, gyrate atrophy, Leber's congenital amaurosis, retinoschisis disorders, Wagner's syndrome, Usher syndromes, Zellweger syndrome, Saldino-Mainzer syndrome, Senior-Loken syndrome, Bardet-Biedl syndrome, Alport's syndrome, Alstrom's syndrome, Cockayne's syndrome, dysplaisa spondyloepiphysaria congentia, Flynn-Aird syndrome, Friedreich ataxia, Hallgren syndrome, Marshall syndrome, Albers-Schnoberg disease, Refsum's disease, Kearns-Sayre syndrome, Waardenburg's syndrome, Alagile syndrome, myotonic dystrophy, olivopontocerebellar atrophy, Pierre-Marie dunsdrome, Stickler syndrome, carotinemeia, cystinosis, Wolfram syndrome, Bassen-Kornzweig syndrome, abetalipoproteinemia, incontinentia pigmenti, Baften's disease, mucopolysaccharidoses, homocystinuria, or mannosidosis.

In still another aspect, the eye abnormality is a cataract. In still yet another aspect, the cataract is a systemic disease such as human Down's syndrome, Hallerman-Streiff syndrome, Lowe syndrome, galactosemia, Marfan syndrome, Trismoy 13-15, Alport syndrome, myotonic dystrophy, Fabry disease, hypoparathroidism or Conradi syndrome.

In still another aspect, the developmental abnormality comprises embryonic lethality or reduced viability.

In still yet another aspect, the cardiovascular, endothelial or angiogenic disorders are arterial diseases, such as diabetes mellitus; papilledema; optic atrophy; atherosclerosis; angina; myocardial infarctions such as acute myocardial infarctions, cardiac hypertrophy, and heart failure such as congestive heart failure; hypertension; inflammatory vasculitides; Reynaud's disease and Reynaud's phenomenon; aneurysms and arterial restenosis; venous and lymphatic disorders such as thrombophlebitis, lymphangitis, and lymphedema; peripheral vascular disease; cancer such as vascular tumors, e.g., hemangioma (capillary and cavernous), glomus tumors, telangiectasia, bacillary angiomatosis, hemangioendothelioma, angiosarcoma, haemangiopericytoma, Kaposi's sarcoma, lymphangioma, and lymphangiosarcoma; tumor angiogenesis; trauma such as wounds, burns, and other injured tissue, implant fixation, scarring; ischemia reperfusion injury; rheumatoid arthritis; cerebrovascular disease; renal diseases such as acute renal failure, or osteoporosis.

In still another aspect, the immunological disorders are consistent with systemic lupus erythematosis; rheumatoid arthritis; juvenile chronic arthritis; spondyloarthropathies; systemic sclerosis (scleroderma); idiopathic inflammatory myopathies (dermatomyositis, polymyositis); Sjögren's syndrome; systemic vasculitis; sarcoidosis; autoimmune hemolytic anemia (immune pancytopenia, paroxysmal nocturnal hemoglobinuria); autoimmune thrombocytopenia (idiopathic thrombocytopenic purpura, immune-mediated thrombocytopenia); thyroiditis (Grave's disease, Hashimoto's thyroiditis, juvenile lymphocytic thyroiditis, atrophic thyroiditis); diabetes mellitus; immune-mediated renal disease (glomerulonephritis, tubulointerstitial nephritis); demyelinating diseases of the central and peripheral nervous systems such as multiple sclerosis, idiopathic demyelinating polyneuropathy or Guillain-Barré syndrome, and chronic inflammatory demyelinating polyneuropathy; hepatobiliary diseases such as infectious hepatitis (hepatitis A, B, C, D, E and other non-hepatotropic viruses), autoimmune chronic active hepatitis, primary biliary cirrhosis, granulomatous hepatitis, and sclerosing cholangitis; inflammatory bowel disease (ulcerative colitis: Crohn's disease); gluten-sensitive enteropathy, and Whipple's disease; autoimmune or immune-mediated skin diseases including bullous skin diseases, erythema multiforme and contact dermatitis, psoriasis; allergic diseases such as asthma, allergic rhinitis, atopic dermatitis, food hypersensitivity and urticaria; immunologic diseases of the lung such as eosinophilic pneumonia, idiopathic pulmonary fibrosis and hypersensitivity pneumonitis; or transplantation associated diseases including graft rejection and graft-versus-host disease.

In still another aspect, the bone metabolic abnormality or disorder is arthritis, osteoporosis, osteopenia or osteopetrosis.

In another aspect, the non-human transgenic animal exhibits at least one of the following physiological characteristics compared with gender matched wildtype littermates: a decreased anxiety-like response during open field activity testing; an increased anxiety-like response during open field activity testing; balding, exothalamus observations, and piloerection observations in functional observation battery (FOB) testing; an increased mean artery-to-vein ratio associated with retinal degeneration; developing cataracts; an increased mean serum cholesterol level; an increased mean serum triglyceride level; a decreased mean serum insulin level, a decreased mean percentage of B cells in the spleen and lymph node; a decreased mean serum IgG2a response to an ovalbumin challenge; decreased mean serum IgA levels; an increased mean serum IgG2a response to an ovalbumin challenge; increased mean serum IgM, IgG1, IgG2a and IgG2b levels; increased mean serum IgM, IgA and IgG3 levels; increased mean serum IgM, IgG1, IgG2a and IgG2b levels; an increased mean percentage of CD4 cells and a decreased mean percentage of CD8 cells in spleen and thymus; mobilization of neutrophils in response to peritoneal inflammation; an enhanced DDS-induced colitis response; an enhanced ConA-induced hepatitis response; a decreased skin fibroblast proliferation; a decreased volumetric bone mineral density, a decreased bone mineral content index (BMC/LBM), and a decreased mean bone mineral density in total body, femur and vertebrate; a decreased mean bone mineral density, a decreased mean trabecular bone volume, decreased thickness, and decreased connectivity density; a decreased body weight and length, decreased total tissue mass and lean body mass, a decreased femoral midshaft cross-sectional area with decreased alkaline phosphatase levels; growth retardation with decreased body weight and length, total tissue mass, and lean body mass; a diaphragmatic hernia; an increased total tissue mass, increased lean body mass, increased bone mineral content, increased total body and increased femoral bone mineral density; an enhanced glucose tolerance; developmental disorders including abnormal kidney development marked by kidney agenesis; embryonic lethality; or embryonic lethality wherein heterozygous adults exhibited decreased serum IgM, IgG1, IgG2a, IgG2b and IgG3 levels.

The invention also provides an isolated cell derived from a non-human transgenic animal whose genome comprises a disruption of the gene which encodes for a PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide. In one aspect, the isolated cell is a murine cell. In yet another aspect, the murine cell is an embryonic stem cell. In still another aspect, the isolated cell is derived from a non-human transgenic animal which exhibits at least one of the following phenotypes compared with gender matched wild-type littermates: a neurological disorder; a cardiovascular, endothelial or angiogenic disorder; an eye abnormality; an immunological disorder; an oncological disorder; a bone metabolic abnormality or disorder; a lipid metabolic disorder; or a developmental abnormality.

The invention also provides a method of identifying an agent that modulates a phenotype associated with a disruption of a gene which encodes for a PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide, the method comprising:

(a) providing a non-human transgenic animal whose genome comprises a disruption of the gene which encodes for the PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide;

(b) measuring a physiological characteristic of the non-human transgenic animal of (a);

(c) comparing the measured physiological characteristic of (b) with that of a gender matched wild-type animal, wherein the physiological characteristic of the non-human transgenic animal that differs from the physiological characteristic of the wild-type animal is identified as a phenotype resulting from the gene disruption in the non-human transgenic animal;

(d) administering a test agent to the non-human transgenic animal of (a); and (e) determining whether the test agent modulates the identified phenotype associated with gene disruption in the non-human transgenic animal.

In one aspect, the phenotype associated with the gene disruption comprises a neurological disorder; a cardiovascular, endothelial or angiogenic disorder; an eye abnormality; an immunological disorder; an oncological disorder; a bone metabolic abnormality or disorder; a lipid metabolic disorder; or a developmental abnormality.

In yet another aspect, the neurological disorder is an increased anxiety-like response during open field activity testing. In yet another aspect, the neurological disorder is a decreased anxiety-like response during open field activity testing. In yet another aspect, the neurological disorder is an abnormal circadian rhythm during home-cage activity testing. In yet another aspect, the neurological disorder is an enhanced motor coordination during inverted screen testing. In yet another aspect, the neurological disorder is impaired motor coordination during inverted screen testing. In yet another aspect, the neurological disorder includes depression, generalized anxiety disorders, attention deficit disorder, sleep disorder, hyperactivity disorder, obsessive compulsive disorder, schizophrenia, cognitive disorders, hyperalgesia and sensory disorders. Such neurological disorders include the category defined as "anxiety disorders" which include but are not limited to: mild to moderate anxiety, anxiety disorder due to a general medical condition, anxiety disorder not otherwise specified, generalized anxiety disorder, panic attack, panic disorder with agoraphobia, panic disorder without agoraphobia, posttraumatic stress disorder, social phobia, social anxiety, autism, specific phobia, substance-induced anxiety disorder, acute alcohol withdrawal, obsessive compulsive disorder, agoraphobia, monopolar disorders, bipolar disorder I or II, bipolar disorder not otherwise specified, cyclothymic disorder, depressive disorder, major depressive disorder, mood disorder, substance-induced mood disorder, enhancement of cognitive function, loss of cognitive function associated with but not limited to Alzheimer's disease, stroke, or traumatic injury to the brain, seizures resulting from disease or injury including but not limited to epilepsy, learning disorders/disabilities, cerebral palsy. In addition, anxiety disorders may apply to personality disorders including but not limited to the following types: paranoid, antisocial, avoidant behavior, borderline personality disorders, dependent, histronic, narcissistic, obsessive-compulsive, schizoid, and schizotypal.

In yet another aspect, the eye abnormality is a retinal abnormality. In still another aspect, the eye abnormality is consistent with vision problems or blindness. In yet another aspect, the retinal abnormality is consistent with retinitis pigmentosa or is characterized by retinal degeneration or retinal dysplasia.

In still another aspect, the retinal abnormalities are consistent with retinal dysplasia, various retinopathies, including retinopathy of prematurity, retrolental fibroplasia, neovascular glaucoma, age-related macular degeneration, diabetic macular edema, corneal neovascularization, corneal graft neovascularization, corneal graft rejection, retinal/choroidal neovascularization, neovascularization of the angle (rubeosis), ocular neovascular disease, vascular restenosis, arteriovenous malformations (AVM), meningioma, hemangioma, angiofibroma, thyroid hyperplasias (including Grave's disease), corneal and other tissue transplantation, retinal artery obstruction or occlusion; retinal degeneration causing secondary atrophy of the retinal vasculature, retinitis pigmentosa, macular dystrophies, Stargardt's disease, congenital stationary night blindness, choroideremia, gyrate atrophy, Leber's congenital amaurosis, retinoschisis disorders, Wagner's syndrome, Usher syndromes, Zellweger syndrome, Saldino-Mainzer syndrome, Senior-Loken syndrome, Bardet-Biedl syndrome, Alport's syndrome, Alstrom's syndrome, Cockayne's syndrome, dysplasia spondyloepiphysaria congentia, Flynn-Aird syndrome, Friedreich ataxia, Hallgren syndrome, Marshall syndrome, Albers-Schnoberg disease, Refsum's disease, Kearns-Sayre syndrome, Waardenburg's syndrome, Alagile syndrome, myotonic dystrophy, olivopontocerebellar atrophy, Pierre-Marie dunsdrome, Stickler syndrome, carotinemeia, cystinosis, Wolfram syndrome, Bassen-Kornzweig syndrome, abetalipoproteinemia, incontinentia pigmenti, Batten's disease, mucopolysaccharidoses, homocystinuria, or mannosidosis.

In still another aspect, the eye abnormality is a cataract. In still yet another aspect, the cataract is a systemic disease such as human Down's syndrome, Hallerman-Streiff syndrome, Lowe syndrome, galactosemia, Marfan syndrome, Trismoy 13-15, Alport syndrome, myotonic dystrophy, Fabry disease, hypoparathroidism, or Conradi syndrome.

In still another aspect, the developmental abnormality comprises embryonic lethality or reduced viability.

In still another aspect, the cardiovascular, endothelial or angiogenic disorders are arterial diseases, such as diabetes mellitus; papilledema; optic atrophy; atherosclerosis; angina; myocardial infarctions such as acute myocardial infarctions, cardiac hypertrophy, and heart failure such as congestive heart failure; hypertension; inflammatory vasculitides; Reynaud's disease and Reynaud's phenomenon; aneurysms and arterial restenosis; venous and lymphatic disorders such as thrombophlebitis, lymphangitis, and lymphedema; peripheral vascular disease; cancer such as vascular tumors, e.g., hemangioma (capillary and cavernous), glomus tumors, telangiectasia, bacillary angiomatosis, hemangioendothelioma, angiosarcoma, haemangiopericytoma, Kaposi's sarcoma, lymphangioma, and lymphangiosarcoma; tumor angiogenesis; trauma such as wounds, burns, and other injured tissue, implant fixation, scarring; ischemia reperfusion injury; rheumatoid arthritis; cerebrovascular disease; renal diseases such as acute renal failure, or osteoporosis.

In still another aspect, the immunological disorders are consistent with systemic lupus erythematosis; rheumatoid arthritis; juvenile chronic arthritis; spondyloarthropathies; systemic sclerosis (scleroderma); idiopathic inflammatory myopathies (dermatomyositis, polymyositis); Sjögren's syndrome; systemic vasculitis; sarcoidosis; autoimmune hemolytic anemia (immune pancytopenia, paroxysmal nocturnal hemoglobinuria); autoimmune thrombocytopenia (idiopathic thrombocytopenic purpura, immune-mediated thrombocytopenia); thyroiditis (Grave's disease, Hashimoto's thyroiditis, juvenile lymphocytic thyroiditis, atrophic thyroiditis); diabetes mellitus; immune-mediated renal disease (glomerulonephritis, tubulointerstitial nephritis); demyelinating diseases of the central and peripheral nervous systems such as multiple sclerosis, idiopathic demyelinating polyneuropathy or Guillain-Barré syndrome, and chronic inflammatory demyelinating polyneuropathy; hepatobiliary diseases such as infectious hepatitis (hepatitis A, B, C, D, E and other non-hepatotropic viruses), autoimmune chronic active hepatitis, primary biliary cirrhosis, granulomatous hepatitis, and sclerosing cholangitis; inflammatory bowel disease (ulcerative colitis: Crohn's disease); gluten-sensitive enteropathy, and Whipple's disease; autoimmune or immune-mediated skin diseases including bullous skin diseases, erythema multiforme and contact dermatitis, psoriasis; allergic diseases such as asthma, allergic rhinitis, atopic dermatitis, food hypersensitivity and urticaria; immunologic diseases of the lung such as eosinophilic pneumonia, idiopathic pulmonary fibrosis and hypersensitivity pneumonitis; or transplantation associated diseases including graft rejection and graft-versus-host disease.

In yet another aspect, the bone metabolic abnormality or disorder is arthritis, osteoporosis, osteopenia or osteopetrosis.

In still another aspect, the non-human transgenic animal exhibits at least one of the following physiological characteristics compared with gender matched wild-type littermates: a decreased anxiety-like response during open field activity testing; an increased anxiety-like response during open field activity testing; balding, exothalamus observations, and piloerection observations in functional observation battery (FOB) testing; an increased mean artery-to-vein ratio associated with retinal degeneration; developing cataracts; an increased mean serum cholesterol level; an increased mean serum triglyceride level; a decreased mean serum insulin level, a decreased mean percentage of B cells in the spleen and lymph node; a decreased mean serum IgG2a response to an ovalbumin challenge; decreased mean serum IgA levels; an increased mean serum IgG2a response to an ovalbumin challenge; increased mean serum IgM, IgG1, IgG2a and IgG2b levels; increased mean serum IgM, IgA and IgG3 levels; increased mean serum IgM, IgG1, IgG2a and IgG2b levels; an increased mean percentage of CD4 cells and a decreased mean percentage of CD8 cells in spleen and thymus; mobilization of neutrophils in response to peritoneal inflammation; an enhanced DDS-induced colitis response; an enhanced ConA-induced hepatitis response; a decreased skin fibroblast proliferation; a decreased volumetric bone mineral density, a decreased bone mineral content index (BMC/LBM), and a decreased mean bone mineral density in total body, femur and vertebrate; a decreased mean bone mineral density, a decreased mean trabecular bone volume, decreased thickness, and decreased connectivity density; a decreased body weight and length, decreased total tissue mass and lean body mass, a decreased femoral midshaft cross-sectional area with decreased alkaline phosphatase levels; growth retardation with decreased body weight and length, total tissue mass, and lean body mass; a diaphragmatic hernia; an increased total tissue mass, increased lean body mass, increased bone mineral content, increased total body and increased femoral bone mineral density; an enhanced glucose tolerance; developmental disorders including abnormal kidney development marked by kidney agenesis; embryonic lethality; or embryonic lethality wherein heterozygous adults exhibited decreased serum IgM, IgG1, IgG2a, IgG2b and IgG3 levels.

The invention also provides an agent which modulates the phenotype associated with gene disruption. In one aspect, the agent is an agonist or antagonist of a PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide. In yet another aspect, the agonist agent is an anti-PRO224, anti-PRO9783, anti-PRO1108, anti-PRO34000, anti-PRO240, anti-PRO943, anti-hu A33, anti-PRO230, anti-PRO178, anti-PRO1199, anti-PRO4333, anti-PRO1336, anti-PRO19598, anti-PRO1083, anti-hu TRPM2 or anti-PRO1801 antibody. In still another aspect, the antagonist agent is an anti-PRO224, anti-PRO9783, anti-PRO1108, anti-PRO34000, anti-PRO240, anti-PRO943, anti-hu A33, anti-PRO230, anti-PRO178, anti-PRO1199, anti-PRO4333, anti-PRO1336, anti-PRO19598, anti-PRO1083, anti-hu TRPM2 or anti-PRO1801 antibody.

The invention also provides a method of identifying an agent that modulates a physiological characteristic associated with a disruption of the gene which encodes for a PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide, the method comprising:

(a) providing a non-human transgenic animal whose genome comprises a disruption of the gene which encodes for a PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide;

(b) measuring a physiological characteristic exhibited by the non-human transgenic animal of (a);

(c)) comparing the measured physiological characteristic of (b) with that of a gender matched wild-type animal, wherein the physiological characteristic exhibited by the non-human transgenic animal that differs from the physiological characteristic exhibited by the wild-type animal is identified as a physiological characteristic associated with gene disruption;

(d) administering a test agent to the non-human transgenic animal of (a); and (e) determining whether the physiological characteristic associated with gene disruption is modulated.

In one aspect, the non-human transgenic animal exhibits at least one of the following physiological characteristics compared with gender matched wild-type littermates: a decreased anxiety-like response during open field activity testing; an increased anxiety-like response during open field activity testing; balding, exothalamus observations, and piloerection observations in functional observation battery (FOB) testing; an increased mean artery-to-vein ratio associated with retinal degeneration; developing cataracts; an increased mean serum cholesterol level; an increased mean serum triglyceride level; a decreased mean serum insulin level, a decreased mean percentage of B cells in the spleen and lymph node; a decreased mean serum IgG2a response to an ovalbumin challenge; decreased mean serum IgA levels; an increased mean serum IgG2a response to an ovalbumin challenge; increased mean serum IgM, IgG1, IgG2a and IgG2b levels; increased mean serum IgM, IgA and IgG3 levels; increased mean serum IgM, IgG1, IgG2a and IgG2b levels; an increased mean percentage of CD4 cells and a decreased mean percentage of CD8 cells in spleen and thymus; mobilization of neutrophils in response to peritoneal inflammation; an enhanced DDS-induced colitis response; an enhanced ConA-induced hepatitis response; a decreased skin fibroblast proliferation; a decreased volumetric bone mineral density, a decreased bone mineral content index (BMC/LBM), and a decreased mean bone mineral density in total body, femur and vertebrate; a decreased mean bone mineral density, a decreased mean trabecular bone volume, decreased thickness, and decreased connectivity density; a decreased body weight and length, decreased total tissue mass and lean body mass, a decreased femoral midshaft cross-sectional area with decreased alkaline phosphatase levels; growth retardation with decreased body weight and length, total tissue mass, and lean body mass; a diaphragmatic hernia; an increased total tissue mass, increased lean body mass, increased bone mineral content, increased total body and increased femoral bone mineral density; an enhanced glucose tolerance; developmental disorders including abnormal kidney development marked by kidney agenesis; embryonic lethality; or embryonic lethality wherein heterozygous adults exhibited decreased serum IgM, IgG1, IgG2a, IgG2b and IgG3 levels.

The invention also provides an agent that modulates a physiological characteristic which is associated with gene disruption. In one aspect, the agent is an agonist or antagonist of the phenotype associated with a disruption of a gene which encodes for a PRO224, PRO9783, PRO1108, PRO34000, PRO240, PRO943, hu A33, PRO230, PRO178, PRO199, PRO4333, PRO1336, PRO19598, PRO1083, hu TRPM2 or PRO1801 polypeptide. In yet another aspect, the agent is an agonist or antagonist of a PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide. In yet another aspect, the agonist agent is an anti-PRO224, anti-PRO9783, anti-PRO1108, anti-PRO34000, anti-PRO240, anti-PRO943, anti-hu A33, anti-PRO230, anti-PRO178, anti-PRO1199, anti-PRO4333, anti-PRO1336, anti-PRO19598, anti-PRO1083, anti-hu TRPM2 or anti-PRO1801 antibody. In still another aspect, the antagonist agent is an anti-PRO224, anti-PRO9783, anti-PRO1108, anti-PRO34000, anti-PRO240, anti-PRO943, anti-hu A33, anti-PRO230, anti-PRO178, anti-PRO1199, anti-PRO4333, anti-PRO1336, anti-PRO19598, anti-PRO1083, anti-hu TRPM2 or anti-PRO1801 antibody.

The invention also provides a method of identifying an agent which modulates a behavior associated with a disruption of the gene which encodes for a PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide, the method comprising:

(a) providing a non-human transgenic animal whose genome comprises a disruption of the gene which encodes for a PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide;

(b) observing the behavior exhibited by the non-human transgenic animal of (a);

(c) comparing the observed behavior of (b) with that of a gender matched wild-type animal, wherein the observed behavior exhibited by the non-human transgenic animal that differs from the observed behavior exhibited by the wild-type animal is identified as a behavior associated with gene disruption;

(d) administering a test agent to the non-human transgenic animal of (a); and (e) determining whether the agent modulates the behavior associated with gene disruption.

In one aspect, the observed behavior is an increased anxiety-like response during open field activity testing. In yet another aspect, the observed behavior is a decreased anxiety-like response during open field activity testing. In yet another aspect, the observed behavior is an abnormal circadian rhythm during home-cage activity testing. In yet another aspect, the observed behavior is an enhanced motor coordination during inverted screen testing. In yet another aspect, the observed behavior is impaired motor coordination during inverted screen testing. In yet another aspect, the observed behavior includes depression, generalized anxiety disorders, attention deficit disorder, sleep disorder, hyperactivity disorder, obsessive compulsive disorder, schizophrenia, cognitive disorders, hyperalgesia and sensory disorders. Such disorders include the category defined as "anxiety disorders" which include but are not limited to: mild to moderate anxiety, anxiety disorder due to a general medical condition, anxiety disorder not otherwise specified, generalized anxiety disorder, panic attack, panic disorder with agoraphobia, panic disorder without agoraphobia, posttraumatic stress disorder, social phobia, social anxiety, autism, specific phobia, substance-induced anxiety disorder, acute alcohol withdrawal, obsessive compulsive disorder, agoraphobia, monopolar disorders, bipolar disorder I or II, bipolar disorder not otherwise specified, cyclothymic disorder, depressive disorder, major depressive disorder, mood disorder, substance-induced mood disorder, enhancement of cognitive function, loss of cognitive function associated with but not limited to Alzheimer's disease, stroke, or traumatic injury to the brain, seizures resulting from disease or injury including but not limited to epilepsy, learning disorders/disabilities, cerebral palsy. In addition, anxiety disorders may apply to personality disorders including but not limited to the following types: paranoid, antisocial, avoidant behavior, borderline personality disorders, dependent, histronic, narcissistic, obsessive-compulsive, schizoid, and schizotypal.

The invention also provides an agent that modulates a behavior which is associated with gene disruption. In one aspect, the agent is an agonist or antagonist of the phenotype associated with a disruption of a gene which encodes for a PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide. In yet another aspect, the agent is an agonist or antagonist of a PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide. In yet another aspect, the agonist agent is an anti-PRO224, anti-PRO9783, anti-PRO1108, anti-PRO34000, anti-PRO240, anti-PRO943, anti-hu A33, anti-PRO230, anti-PRO178, anti-PRO1199, anti-PRO4333, anti-PRO1336, anti-PRO19598, anti-PRO1083, anti-hu TRPM2 or anti-PRO1801 antibody. In still another aspect, the antagonist agent is an anti-PRO224, anti-PRO9783, anti-PRO1108, anti-PRO34000, anti-PRO240, anti-PRO943, anti-hu A33, anti-PRO230, anti-PRO178, anti-PRO1199, anti-PRO4333, anti-PRO1336, anti-PRO19598, anti-PRO1083, anti-hu TRPM2 or anti-PRO1801 antibody.

The invention also provides a method of identifying an agent that ameliorates or modulates a neurological disorder; a cardiovascular, endothelial or angiogenic disorder; an eye abnormality; an immunological disorder; an oncological disorder; a bone metabolic abnormality or disorder; a lipid metabolic disorder; or a developmental abnormality associated with a disruption in the gene which encodes for a PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide, the method comprising:

(a) providing a non-human transgenic animal whose genome comprises a disruption of the gene which encodes for a PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide;

(b) administering a test agent to said non-human transgenic animal; and (c) determining whether the test agent ameliorates or modulates the neurological disorder; cardiovascular, endothelial or angiogenic disorder; eye abnormality; immunological disorder; oncological disorder; bone metabolic abnormality or disorder; lipid metabolic disorder; or developmental abnormality associated with the gene disruption in the non-human transgenic animal.

In yet another aspect, the neurological disorder is an increased anxiety-like response during open field activity testing. In yet another aspect, the neurological disorder is a decreased anxiety-like response during open field activity testing. In yet another aspect, the neurological disorder is an abnormal circadian rhythm during home-cage activity testing. In yet another aspect, the neurological disorder is an enhanced motor coordination during inverted screen testing. In yet another aspect, the neurological disorder is impaired motor coordination during inverted screen testing. In yet another aspect, the neurological disorder includes depression, generalized anxiety disorders, attention deficit disorder, sleep disorder, hyperactivity disorder, obsessive compulsive disorder, schizophrenia, cognitive disorders, hyperalgesia and sensory disorders. Such neurological disorders include the category defined as "anxiety disorders" which include but are not limited to: mild to moderate anxiety, anxiety disorder due to a general medical condition, anxiety disorder not otherwise specified, generalized anxiety disorder, panic attack, panic disorder with agoraphobia, panic disorder without agoraphobia, posttraumatic stress disorder, social phobia, social anxiety, autism, specific phobia, substance-induced anxiety disorder, acute alcohol withdrawal, obsessive compulsive disorder, agoraphobia, monopolar disorders, bipolar disorder I or II, bipolar disorder not otherwise specified, cyclothymic disorder, depressive disorder, major depressive disorder, mood disorder, substance-induced mood disorder, enhancement of cognitive function, loss of cognitive function associated with but not limited to Alzheimer's disease, stroke, or traumatic injury to the brain, seizures resulting from disease or injury including but not limited to epilepsy, learning disorders/disabilities, cerebral palsy. In addition, anxiety disorders may apply to personality disorders including but not limited to the following types: paranoid, antisocial, avoidant behavior, borderline personality disorders, dependent, histronic, narcissistic, obsessive-compulsive, schizoid, and schizotypal.

In another aspect, the eye abnormality is a retinal abnormality. In still another aspect, the eye abnormality is consistent with vision problems or blindness. In yet another aspect, the retinal abnormality is consistent with retinitis pigmentosa or is characterized by retinal degeneration or retinal dysplasia.

In still another aspect, the retinal abnormalities the retinal abnormalities are consistent with retinal dysplasia, various retinopathies, including retinopathy of prematurity, retrolental fibroplasia, neovascular glaucoma, age-related macular degeneration, diabetic macular edema, corneal neovascularization, corneal graft neovascularization, corneal graft rejection, retinal/choroidal neovascularization, neovascularization of the angle (rubeosis), ocular neovascular disease, vascular restenosis, arteriovenous malformations (AVM), meningioma, hemangioma, angiofibroma, thyroid hyperplasias (including Grave's disease), corneal and other tissue transplantation, retinal artery obstruction or occlusion; retinal degeneration causing secondary atrophy of the retinal vasculature, retinitis pigmentosa, macular dystrophies, Stargardt's disease, congenital stationary night blindness, choroideremia, gyrate atrophy, Leber's congenital amaurosis, retinoschisis disorders, Wagner's syndrome, Usher syndromes, Zellweger syndrome, Saldino-Mainzer syndrome, Senior-Loken syndrome, Bardet-Biedl syndrome, Alport's syndrome, Alstrom's syndrome, Cockayne's syndrome, dysplaisa spondyloepiphysaria congenita, Flynn-Aird syndrome, Friedreich ataxia, Hallgren syndrome, Marshall syndrome, Albers-Schnoberg disease, Refsum's disease, Kearns-Sayre syndrome, Waardenburg's syndrome, Alagile syndrome, myotonic dystrophy, olivopontocerebellar atrophy, Pierre-Marie dunsdrome, Stickler syndrome, carotinemeia, cystinosis, Wolfram syndrome, Bassen-Kornzweig syndrome, abetalipoproteinemia, incontinentia pigmenti, Batten's disease, mucopolysaccharidoses, homocystinuria, or mannosidosis.

In still another aspect, the developmental abnormality comprises embryonic lethality or reduced viability.

In yet another aspect, the cardiovascular, endothelial or angiogenic disorders are arterial diseases, such as diabetes mellitus; papilledema; optic atrophy; atherosclerosis; angina; myocardial infarctions such as acute myocardial infarctions, cardiac hypertrophy, and heart failure such as congestive heart failure; hypertension; inflammatory vasculitides; Reynaud's disease and Reynaud's phenomenon; aneurysms and arterial restenosis; venous and lymphatic disorders such as thrombophlebitis, lymphangitis, and lymphedema; peripheral vascular disease; cancer such as vascular tumors, e.g., hemangioma (capillary and cavernous), glomus tumors, telangiectasia, bacillary angiomatosis, hemangioendothelioma, angiosarcoma, haemangiopericytoma, Kaposi's sarcoma, lymphangioma, and lymphangiosarcoma; tumor angiogenesis; trauma such as wounds, burns, and other injured tissue, implant fixation, scarring; ischemia reperfusion injury; rheumatoid arthritis; cerebrovascular disease; renal diseases such as acute renal failure, or osteoporosis.

In still yet another, aspect, the immunological disorders are consistent with systemic lupus erythematosis; rheumatoid arthritis; juvenile chronic arthritis; spondyloarthropathies; systemic sclerosis (scleroderma); idiopathic inflammatory myopathies (dermatomyositis, polymyositis); Sjögren's syndrome; systemic vasculitis; sarcoidosis; autoimmune hemolytic anemia (immune pancytopenia, paroxysmal nocturnal hemoglobinuria); autoimmune thrombocytopenia (idiopathic thrombocytopenic purpura, immune-mediated thrombocytopenia); thyroiditis (Grave's disease, Hashimoto's thyroiditis, juvenile lymphocytic thyroiditis, atrophic thyroiditis); diabetes mellitus; immune-mediated renal disease (glomerulonephritis, tubulointerstitial nephritis); demyelinating diseases of the central and peripheral nervous systems such as multiple sclerosis, idiopathic demyelinating polyneuropathy or Guillain-Barré syndrome, and chronic inflammatory demyelinating polyneuropathy; hepatobiliary diseases such as infectious hepatitis (hepatitis A, B, C, D, E and other non-hepatotropic viruses), autoimmune chronic active hepatitis, primary biliary cirrhosis, granulomatous hepatitis, and sclerosing cholangitis; inflammatory bowel disease (ulcerative colitis: Crohn's disease); gluten-sensitive enteropathy, and Whipple's disease; autoimmune or immune-mediated skin diseases including bullous skin diseases, erythema multiforme and contact dermatitis, psoriasis; allergic diseases such as asthma, allergic rhinitis, atopic dermatitis, food hypersensitivity and urticaria; immunologic diseases of the lung such as eosinophilic pneumonia, idiopathic pulmonary fibrosis and hypersensitivity pneumonitis; or transplantation associated diseases including graft rejection and graft-versus-host disease.

In yet another aspect, the bone metabolic abnormality or disorder is arthritis, osteoporosis, osteopenia or osteopetrosis.

In still another aspect, the non-human transgenic animal exhibits at least one of the following physiological characteristics compared with gender matched wild-type littermates: a decreased anxiety-like response during open field activity testing; an increased anxiety-like response during open field activity testing; balding, exothalamus observations, and piloerection observations in functional observation battery (FOB) testing; an increased mean artery-to-vein ratio associated with retinal degeneration; developing cataracts; an increased mean serum cholesterol level; an increased mean serum triglyceride level; a decreased mean serum insulin level, a decreased mean percentage of B cells in the spleen and lymph node; a decreased mean serum IgG2a response to an ovalbumin challenge; decreased mean serum IgA levels; an increased mean serum IgG2a response to an ovalbumin challenge; increased mean serum IgM, IgG1, IgG2a and IgG2b levels; increased mean serum IgM, IgA and IgG3 levels; increased mean serum IgM, IgG1, IgG2a and IgG2b levels; an increased mean percentage of CD4 cells and a decreased mean percentage of CD8 cells in spleen and thymus; mobilization of neutrophils in response to peritoneal inflammation; an enhanced DDS-induced colitis response; an enhanced ConA-induced hepatitis response; a decreased skin fibroblast proliferation; a decreased volumetric bone mineral density, a decreased bone mineral content index (BMC/LBM), and a decreased mean bone mineral density in total body, femur and vertebrate; a decreased mean bone mineral density, a decreased mean trabecular bone volume, decreased thickness, and decreased connectivity density; a decreased body weight and length, decreased total tissue mass and lean body mass, a decreased femoral midshaft cross-sectional area with decreased alkaline phosphatase levels; growth retardation with decreased body weight and length, total tissue mass, and lean body mass; a diaphragmatic hernia; an increased total tissue mass, increased lean body mass, increased bone mineral content, increased total body and increased femoral bone mineral density; an enhanced glucose tolerance; developmental disorders including abnormal kidney development marked by kidney agenesis; embryonic lethality; or embryonic lethality wherein heterozygous adults exhibited decreased serum IgM, IgG1, IgG2a, IgG2b and IgG3 levels.

The invention also provides an agent that ameliorates or modulates a neurological disorder; a cardiovascular, endothelial or angiogenic disorder; an eye abnormality; an immunological disorder; an oncological disorder; a bone metabolic abnormality or disorder; a lipid metabolic disorder; or a developmental abnormality which is associated with gene disruption. In one aspect, the agent is an agonist or antagonist of the phenotype associated with a disruption of a gene which encodes for a PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide. In yet another aspect, the agent is an agonist or antagonist of a PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide. In yet another aspect, the agonist agent is an anti-PRO224, anti-PRO9783, anti-PRO1108, anti-PRO34000, anti-PRO240, anti-PRO943, anti-hu A33, anti-PRO230, anti-PRO178, anti-PRO1199, anti-PRO4333, anti-PRO1336, anti-PRO19598, anti-PRO1083, anti-hu TRPM2 or anti-PRO1801 antibody. In still another aspect, the antagonist agent is an anti-PRO224, anti-PRO9783, anti-PRO1108, anti-PRO34000, anti-PRO240, anti-PRO943, anti-hu A33, anti-PRO230, anti-PRO178, anti-PRO1199, anti-PRO4333, anti-PRO1336, anti-PRO19598, anti-PRO1083, anti-hu TRPM2 or anti-PRO1801 antibody.

The invention also provides a therapeutic agent for the treatment of a neurological disorder; a cardiovascular, endothelial or angiogenic disorder; an eye abnormality; an immunological disorder; an oncological disorder; a bone metabolic abnormality or disorder; a lipid metabolic disorder; or a developmental abnormality.

The invention also provides a method of identifying an agent that modulates the expression of a PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide, the method comprising:

(a) contacting a test agent with a host cell expressing a PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide; and (b) determining whether the test agent modulates the expression of the PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide by the host cell.

The invention also provides an agent that modulates the expression of a PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide. In one aspect, the agent is an agonist or antagonist of the phenotype associated with a disruption of a gene which encodes for a PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide. In yet another aspect, the agent is an agonist or antagonist of a PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide. In yet another aspect, the agonist agent is an anti-PRO224, anti-PRO9783, anti-PRO1108, anti-PRO34000, anti-PRO240, anti-PRO943, anti-hu A33, anti-PRO230, anti-PRO178, anti-PRO1199, anti-PRO4333, anti-PRO1336, anti-PRO19598, anti-PRO1083, anti-hu TRPM2 or anti-PRO1801 antibody. In still another aspect, the antagonist agent is an anti-PRO224, anti-PRO9783, anti-PRO1108, anti-PRO34000, anti-PRO240, anti-PRO943, anti-hu A33, anti-PRO230, anti-PRO178, anti-PRO1199, anti-PRO4333, anti-PRO1336, anti-PRO19598, anti-PRO1083, anti-hu TRPM2 or anti-PRO1801 antibody.

The invention also provides a method of evaluating a therapeutic agent capable of affecting a condition associated with a disruption of a gene which encodes for a PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide, the method comprising:

(a) providing a non-human transgenic animal whose genome comprises a disruption of the gene which encodes for the PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide;

(b) measuring a physiological characteristic of the non-human transgenic animal of (a);

(c)) comparing the measured physiological characteristic of (b) with that of a gender matched wild-type animal, wherein the physiological characteristic of the non-human transgenic animal that differs from the physiological characteristic of the wild-type animal is identified as a condition resulting from the gene disruption in the non-human transgenic animal;

(d) administering a test agent to the non-human transgenic animal of (a); and (e) evaluating the effects of the test agent on the identified condition associated with gene disruption in the non-human transgenic animal.

In one aspect, the condition is a neurological disorder; a cardiovascular, endothelial or angiogenic disorder; an eye abnormality; an immunological disorder; an oncological disorder; a bone metabolic abnormality or disorder; a lipid metabolic disorder; or a developmental abnormality.

The invention also provides a therapeutic agent which is capable of affecting a condition associated with gene disruption. In one aspect, the agent is an agonist or antagonist of the phenotype associated with a disruption of a gene which encodes for a PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide. In yet another aspect, the agent is an agonist or antagonist of a PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide. In yet another aspect, the agonist agent is an anti-PRO224, anti-PRO9783, anti-PRO1108, anti-PRO34000, anti-PRO240, anti-PRO943, anti-hu A33, anti-PRO230, anti-PRO178, anti-PRO1199, anti-PRO4333, anti-PRO1336, anti-PRO19598, anti-PRO1083, anti-hu TRPM2 or anti-PRO1801 antibody. In still another aspect, the antagonist agent is an anti-PRO224, anti-PRO9783, anti-PRO1108, anti-PRO34000, anti-PRO240, anti-PRO943, anti-hu A33, anti-PRO230, anti-PRO178, anti-PRO1199, anti-PRO4333, anti-PRO1336, anti-PRO19598, anti-PRO1083, anti-hu TRPM2 or anti-PRO1801 antibody.

The invention also provides a pharmaceutical composition comprising a therapeutic agent capable of affecting the condition associated with gene disruption.

The invention also provides a method of treating or preventing or ameliorating a neurological disorder; cardiovascular, endothelial or angiogenic disorder; immunological disorder; oncological disorder; bone metabolic abnormality or disorder, or embryonic lethality associated with the disruption of a gene which encodes for a PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide, the method comprising administering to a subject in need of such treatment whom may already have the disorder, or may be prone to have the disorder or may be in whom the disorder is to be prevented, a therapeutically effective amount of a therapeutic agent, or agonists or antagonists thereof, thereby effectively treating or preventing or ameliorating said disorder or disease.

In yet another aspect, the neurological disorder is an increased anxiety-like response during open field activity testing. In yet another aspect, the neurological disorder is a decreased anxiety-like response during open field activity testing. In yet another aspect, the neurological disorder is an abnormal circadian rhythm during home-cage activity testing. In yet another aspect, the neurological disorder is an enhanced motor coordination during inverted screen testing. In yet another aspect, the neurological disorder is impaired motor coordination during inverted screen testing. In yet another aspect, the neurological disorder includes depression, generalized anxiety disorders, attention deficit disorder, sleep disorder, hyperactivity disorder, obsessive compulsive disorder, schizophrenia, cognitive disorders, hyperalgesia and sensory disorders. Such neurological disorders include the category defined as "anxiety disorders" which include but are not limited to: mild to moderate anxiety, anxiety disorder due to a general medical condition, anxiety disorder not otherwise specified, generalized anxiety disorder, panic attack, panic disorder with agoraphobia, panic disorder without agoraphobia, posttraumatic stress disorder, social phobia, social anxiety, autism, specific phobia, substance-induced anxiety disorder, acute alcohol withdrawal, obsessive compulsive disorder, agoraphobia, monopolar disorders, bipolar disorder I or II, bipolar disorder not otherwise specified, cyclothymic disorder, depressive disorder, major depressive disorder, mood disorder, substance-induced mood disorder, enhancement of cognitive function, loss of cognitive function associated with but not limited to Alzheimer's disease, stroke, or traumatic injury to the brain, seizures resulting from disease or injury including but not limited to epilepsy, learning disorders/disabilities, cerebral palsy. In addition, anxiety disorders may apply to personality disorders including but not limited to the following types: paranoid, antisocial, avoidant behavior, borderline personality disorders, dependent, histronic, narcissistic, obsessive-compulsive, schizoid, and schizotypal.

In another aspect, the eye abnormality is a retinal abnormality. In still another aspect, the eye abnormality is consistent with vision problems or blindness. In yet another aspect, the retinal abnormality is consistent with retinitis pigmentosa or is characterized by retinal degeneration or retinal dysplasia.

In still another aspect, the retinal abnormalities are consistent with retinal dysplasia, various retinopathies, including retinopathy of prematurity, retrolental fibroplasia, neovascular glaucoma, age-related macular degeneration, diabetic macular edema, corneal neovascularization, corneal graft neovascularization, corneal graft rejection, retinal/choroidal neovascularization, neovascularization of the angle (rubeosis), ocular neovascular disease, vascular restenosis, arteriovenous malformations (AVM), meningioma, hemangioma, angiofibroma, thyroid hyperplasias (including Grave's disease), corneal and other tissue transplantation, retinal artery obstruction or occlusion; retinal degeneration causing secondary atrophy of the retinal vasculature, retinitis pigmentosa, macular dystrophies, Stargardt's disease, congenital stationary night blindness, choroideremia, gyrate atrophy, Leber's congenital amaurosis, retinoschisis disorders, Wagner's syndrome, Usher syndromes, Zellweger syndrome, Saldino-Mainzer syndrome, Senior-Loken syndrome, Bardet-Biedl syndrome, Alport's syndrome, Alstrom's syndrome, Cockayne's syndrome, dysplaisa spondyloepiphysaria congentia, Flynn-Aird syndrome, Friedreich ataxia, Hallgren syndrome, Marshall syndrome, Albers-Schnoberg disease, Refsum's disease, Kearns-Sayre syndrome, Waardenburg's syndrome, Alagile syndrome, myotonic dystrophy, olivopontocerebellar atrophy, Pierre-Marie dunsdrome, Stickler syndrome, carotinemeia, cystinosis, Wolfram syndrome, Bassen-Kornzweig syndrome, abetalipoproteinemia, incontinentia pigmenti, Batten's disease, mucopolysaccharidoses, homocystinuria, or mannosidosis.

In still another aspect, the eye abnormality is a cataract. In still yet another aspect, the cataract is a systemic disease such as human Down's syndrome, Hallerman-Streiff syndrome, Lowe syndrome, galactosemia, Marfan syndrome, Trismoy 13-15, Alport syndrome, myotonic dystrophy, Fabry disease, hypoparathroidism or Conradi syndrome.

In still another aspect, the developmental abnormality comprises embryonic lethality or reduced viability.

In yet another aspect, the cardiovascular, endothelial or angiogenic disorders are arterial diseases, such as diabetes mellitus; papilledema; optic atrophy; atherosclerosis; angina; myocardial infarctions such as acute myocardial infarctions, cardiac hypertrophy, and heart failure such as congestive heart failure; hypertension; inflammatory vasculitides; Reynaud's disease and Reynaud's phenomenon; aneurysms and arterial restenosis; venous and lymphatic disorders such as thrombophlebitis, lymphangitis, and lymphedema; peripheral vascular disease; cancer such as vascular tumors, e.g., hemangioma (capillary and cavernous), glomus tumors, telangiectasia, bacillary angiomatosis, hemangioendothelioma, angiosarcoma, haemangiopericytoma, Kaposi's sarcoma, lymphangioma, and lymphangiosarcoma; tumor angiogenesis; trauma such as wounds, burns, and other injured tissue, implant fixation, scarring; ischemia reperfusion injury; rheumatoid arthritis; cerebrovascular disease; renal diseases such as acute renal failure, or osteoporosis.

In still yet another aspect, the immunological disorders are consistent with systemic lupus erythematosis; rheumatoid arthritis; juvenile chronic arthritis; spondyloarthropathies; systemic sclerosis (scleroderma); idiopathic inflammatory myopathies (dermatomyositis, polymyositis); Sjögren's syndrome; systemic vasculitis; sarcoidosis; autoimmune hemolytic anemia (immune pancytopenia, paroxysmal nocturnal hemoglobinuria); autoimmune thrombocytopenia (idiopathic thrombocytopenic purpura, immune-mediated thrombocytopenia); thyroiditis (Grave's disease, Hashimoto's thyroiditis, juvenile lymphocytic thyroiditis, atrophic thyroiditis); diabetes mellitus; immune-mediated renal disease (glomerulonephritis, tubulointerstitial nephritis); demyelinating diseases of the central and peripheral nervous systems such as multiple sclerosis, idiopathic demyelinating polyneuropathy or Guillain-Barré syndrome, and chronic inflammatory demyelinating polyneuropathy; hepatobiliary diseases such as infectious hepatitis (hepatitis A, B, C, D, E and other non-hepatotropic viruses), autoimmune chronic active hepatitis, primary biliary cirrhosis, granulomatous hepatitis, and sclerosing cholangitis; inflammatory bowel disease (ulcerative colitis: Crohn's disease); gluten-sensitive enteropathy, and Whipple's disease; autoimmune or immune-mediated skin diseases including bullous skin diseases, erythema multiforme and contact dermatitis, psoriasis; allergic diseases such as asthma, allergic rhinitis, atopic dermatitis, food hypersensitivity and urticaria; immunologic diseases of the lung such as eosinophilic pneumonia, idiopathic pulmonary fibrosis and hypersensitivity pneumonitis; or transplantation associated diseases including graft rejection and graft-versus-host disease.

In yet another aspect, the bone metabolic abnormality or disorder is arthritis, osteoporosis, osteopenia or osteopetrosis.

In another aspect the therapeutic agent is an agonist or antagonist of the phenotype associated with a disruption of a gene which encodes for a PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide. In yet another aspect, the agent is an agonist or antagonist of a PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide. In yet another aspect, the agonist agent is an anti-PRO224, anti-PRO9783, anti-PRO1108, anti-PRO34000, anti-PRO240, anti-PRO943, anti-hu A33, anti-PRO230, anti-PRO178, anti-PRO1199, anti-PRO4333, anti-PRO1336, anti-PRO19598, anti-PRO1083, anti-hu TRPM2 or anti-PRO1801 antibody. In still another aspect, the antagonist agent is an anti-PRO224, anti-PRO9783, anti-PRO1108, anti-PRO34000, anti-PRO240, anti-PRO943, anti-hu A33, anti-PRO230, anti-PRO178, anti-PRO1199, anti-PRO4333, anti-PRO1336, anti-PRO19598, anti-PRO1083, anti-hu TRPM2 or anti-PRO1801 antibody.

The invention also provides a method of identifying an agent that ameliorates or modulates a neurological disorder; a cardiovascular, endothelial or angiogenic disorder; an eye abnormality; an immunological disorder; an oncological disorder; a bone metabolic abnormality or disorder; a lipid metabolic disorder; or a developmental abnormality associated with a disruption in the gene which encodes for a PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide, the method comprising:

(a) providing a non-human transgenic animal cell culture, each cell of said culture comprising a disruption of the gene which encodes for a PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide;

(b) administering a test agent to said cell culture; and (c) determining whether the test agent ameliorates or modulates the neurological disorder; cardiovascular, endothelial or angiogenic disorder; eye abnormality; immunological disorder; oncological disorder; bone metabolic abnormality or disorder; lipid metabolic disorder; or developmental abnormality in said culture.

In yet another aspect, the neurological disorder is an increased anxiety-like response during open field activity testing. In yet another aspect, the neurological disorder is a decreased anxiety-like response during open field activity testing. In yet another aspect, the neurological disorder is an abnormal circadian rhythm during home-cage activity testing. In yet another aspect, the neurological disorder is an enhanced motor coordination during inverted screen testing. In yet another aspect, the neurological disorder is impaired motor coordination during inverted screen testing. In yet another aspect, the neurological disorder includes depression, generalized anxiety disorders, attention deficit disorder, sleep disorder, hyperactivity disorder, obsessive compulsive disorder, schizophrenia, cognitive disorders, hyperalgesia and sensory disorders. Such neurological disorders include the category defined as "anxiety disorders" which include but are not limited to: mild to moderate anxiety, anxiety disorder due to a general medical condition, anxiety disorder not otherwise specified, generalized anxiety disorder, panic attack, panic disorder with agoraphobia, panic disorder without agoraphobia, posttraumatic stress disorder, social phobia, social anxiety, autism, specific phobia, substance-induced anxiety disorder, acute alcohol withdrawal, obsessive compulsive disorder, agoraphobia, monopolar disorders, bipolar disorder I or II, bipolar disorder not otherwise specified, cyclothymic disorder, depressive disorder, major depressive disorder, mood disorder, substance-induced mood disorder, enhancement of cognitive function, loss of cognitive function associated with but not limited to Alzheimer's disease, stroke, or traumatic injury to the brain, seizures resulting from disease or injury including but not limited to epilepsy, learning disorders/disabilities, cerebral palsy. In addition, anxiety disorders may apply to personality disorders including but not limited to the following types: paranoid, antisocial, avoidant behavior, borderline personality disorders, dependent, histronic, narcissistic, obsessive-compulsive, schizoid, and schizotypal.

In another aspect, the eye abnormality is a retinal abnormality. In still another aspect, the eye abnormality is consistent with vision problems or blindness. In yet another aspect, the retinal abnormality is consistent with retinitis pigmentosa or is characterized by retinal degeneration or retinal dysplasia.

In still another aspect, the retinal abnormalities are consistent with retinal dysplasia, various retinopathies, including retinopathy of prematurity, retrolental fibroplasia, neovascular glaucoma, age-related macular degeneration, diabetic macular edema, corneal neovascularization, corneal graft neovascularization, corneal graft rejection, retinal/choroidal neovascularization, neovascularization of the angle (rubeosis), ocular neovascular disease, vascular restenosis, arteriovenous malformations (AVM), meningioma, hemangioma, angiofibroma, thyroid hyperplasias (including Grave's disease), corneal and other tissue transplantation, retinal artery obstruction or occlusion; retinal degeneration causing secondary atrophy of the retinal vasculature, retinitis pigmentosa, macular dystrophies, Stargardt's disease, congenital stationary night blindness, choroideremia, gyrate atrophy, Leber's congenital amaurosis, retinoschisis disorders, Wagner's syndrome, Usher syndromes, Zellweger syndrome, Saldino-Mainzer syndrome, Senior-Loken syndrome, Bardet-Biedl syndrome, Alport's syndrome, Alstrom's syndrome, Cockayne's syndrome, dysplaisa spondyloepiphysaria congentia, Flynn-Aird syndrome, Friedreich ataxia, Hallgren syndrome, Marshall syndrome, Albers-Schnoberg disease, Refsum's disease, Kearns-Sayre syndrome, Waardenburg's syndrome, Alagile syndrome, myotonic dystrophy, olivopontocerebellar atrophy, Pierre-Marie dunsdrome, Stickler syndrome, carotinemeia, cystinosis, Wolfram syndrome, Bassen-Kornzweig syndrome, abetalipoproteinemia, incontinentia pigmenti, Batten's disease, mucopolysaccharidoses, homocystinuria, or mannosidosis.

In still another aspect, the eye abnormality is a cataract. In still yet another aspect, the cataract is a systemic disease such as human Down's syndrome, Hallerman-Streiff syndrome, Lowe syndrome, galactosemia, Marfan syndrome, Trismoy 13-15, Alport syndrome, myotonic dystrophy, Fabry disease, hypoparathroidism or Conradi syndrome.

In still another aspect, the developmental abnormality comprises embryonic lethality or reduced viability.

In yet another aspect, the cardiovascular, endothelial or angiogenic disorders are arterial diseases, such as diabetes mellitus; papilledema; optic atrophy; atherosclerosis; angina; myocardial infarctions such as acute myocardial infarctions, cardiac hypertrophy, and heart failure such as congestive heart failure; hypertension; inflammatory vasculitides; Reynaud's disease and Reynaud's phenomenon; aneurysms and arterial restenosis; venous and lymphatic disorders such as thrombophlebitis, lymphangitis, and lymphedema; peripheral vascular disease; cancer such as vascular tumors, e.g., hemangioma (capillary and cavernous), glomus tumors, telangiectasia, bacillary angiomatosis, hemangioendothelioma, angiosarcoma, haemangiopericytoma, Kaposi's sarcoma, lymphangioma, and lymphangiosarcoma; tumor angiogenesis; trauma such as wounds, burns, and other injured tissue, implant fixation, scarring; ischemia reperfusion injury; rheumatoid arthritis; cerebrovascular disease; renal diseases such as acute renal failure, or osteoporosis.

In still yet another aspect, the immunological disorders are consistent with systemic lupus erythematosis; rheumatoid arthritis; juvenile chronic arthritis; spondyloarthropathies; systemic sclerosis (scleroderma); idiopathic inflammatory myopathies (dermatomyositis, polymyositis); Sjögren's syndrome; systemic vasculitis; sarcoidosis; autoimmune hemolytic anemia (immune pancytopenia, paroxysmal nocturnal hemoglobinuria); autoimmune thrombocytopenia (idiopathic thrombocytopenic purpura, immune-mediated thrombocytopenia); thyroiditis (Grave's disease, Hashimoto's thyroiditis, juvenile lymphocytic thyroiditis, atrophic thyroiditis); diabetes mellitus; immune-mediated renal disease (glomerulonephritis, tubulointerstitial nephritis); demyelinating diseases of the central and peripheral nervous systems such as multiple sclerosis, idiopathic demyelinating polyneuropathy or Guillain-Barré syndrome, and chronic inflammatory demyelinating polyneuropathy; hepatobiliary diseases such as infectious hepatitis (hepatitis A, B, C, D, E and other non-hepatotropic viruses), autoimmune chronic active hepatitis, primary biliary cirrhosis, granulomatous hepatitis, and sclerosing cholangitis; inflammatory bowel disease (ulcerative colitis: Crohn's disease); gluten-sensitive enteropathy, and Whipple's disease; autoimmune or immune-mediated skin diseases including bullous skin diseases, erythema multiforme and contact dermatitis, psoriasis; allergic diseases such as asthma, allergic rhinitis, atopic dermatitis, food hypersensitivity and urticaria; immunologic diseases of the lung such as eosinophilic pneumonia, idiopathic pulmonary fibrosis and hypersensitivity pneumonitis; or transplantation associated diseases including graft rejection and graft-versus-host disease.

In yet another aspect, the bone metabolic abnormality or disorder is arthritis, osteoporosis, osteopenia or osteopetrosis.

The invention also provides an agent that ameliorates or modulates a neurological disorder; a cardiovascular, endothelial or angiogenic disorder; an eye abnormality; an immunological disorder; an oncological disorder; a bone metabolic abnormality or disorder; a lipid metabolic disorder; or a developmental abnormality which is associated with gene disruption in said culture. In one aspect, the agent is an agonist or antagonist of the phenotype associated with a disruption of a gene which encodes for a PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide. In yet another aspect, the agent is an agonist or antagonist of a PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide. In yet another aspect, the agonist agent is an anti-PRO224, anti-PRO9783, anti-PRO1108, anti-PRO34000, anti-PRO240, anti-PRO943, anti-hu A33, anti-PRO230, anti-PRO178, anti-PRO1199, anti-PRO4333, anti-PRO1336, anti-PRO19598, anti-PRO1083, anti-hu TRPM2 or anti-PRO1801 antibody. In still another aspect, the antagonist agent is an anti-PRO224, anti-PRO9783, anti-PRO1108, anti-PRO34000, anti-PRO240, anti-PRO943, anti-hu A33, anti-PRO230, anti-PRO178, anti-PRO1199, anti-PRO4333, anti-PRO1336, anti-PRO19598, anti-PRO1083, anti-hu TRPM2 or anti-PRO1801 antibody.

The invention also provides a method of modulating a phenotype associated with a disruption of a gene which encodes for a PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide, the method comprising administering to a subject whom may already have the phenotype, or may be prone to have the phenotype or may be in whom the phenotype is to be prevented, an effective amount of an agent identified as modulating said phenotype, or agonists or antagonists thereof, thereby effectively modulating the phenotype.

The invention also provides a method of modulating a physiological characteristic associated with a disruption of a gene which encodes for a PRO224, PRO9783, PRO1108, PRO34000, PRO240, PRO943, hu A33, PRO230, PRO178, PRO199, PRO4333, PRO1336, PRO19598, PRO1083, hu TRPM2 or PRO1801 polypeptide, the method comprising administering to a subject whom may already exhibit the physiological characteristic, or may be prone to exhibit the physiological characteristic or may be in whom the physiological characteristic is to be prevented, an effective amount of an agent identified as modulating said physiological characteristic, or agonists or antagonists thereof, thereby effectively modulating the physiological characteristic.

The invention also provides a method of modulating a behavior associated with a disruption of a gene which encodes for a PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide, the method comprising administering to a subject whom may already exhibit the behavior, or may be prone to exhibit the behavior or may be in whom the exhibited behavior is to be prevented, an effective amount of an agent identified as modulating said behavior, or agonists or antagonists thereof, thereby effectively modulating the behavior.

The invention also provides a method of modulating the expression of a PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide, the method comprising administering to a host cell expressing said PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide, an effective amount of an agent identified as modulating said expression, or agonists or antagonists thereof, thereby effectively modulating the expression of said polypeptide.

The invention also provides a method of modulating a condition associated with a disruption of a gene which encodes for a PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide, the method comprising administering to a subject whom may have the condition, or may be prone to have the condition or may be in whom the condition is to be prevented, a therapeutically effective amount of a therapeutic agent identified as modulating said condition, or agonists or antagonists thereof, thereby effectively modulating the condition.

The invention also provides a method of treating or preventing or ameliorating a neurological disorder; cardiovascular, endothelial or angiogenic disorder; immunological disorder; oncological disorder; bone metabolic abnormality or disorder, or embryonic lethality associated with the disruption of a gene which encodes for a PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide, the method comprising administering to a non-human transgenic animal cell culture, each cell of said culture comprising a disruption of the gene which encodes for a PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide, an effective amount of an agent identified as treating or preventing or ameliorating said disorder, or agonists or antagonists thereof, thereby effectively treating or preventing or ameliorating said disorder.

B. Further Embodiments

In yet further embodiments, the invention is directed to the following set of potential claims for this application:

1. A method of identifying a phenotype associated with a disruption of a gene which encodes for a PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide, the method comprising:

(a) providing a non-human transgenic animal whose genome comprises a disruption of the gene which encodes for a PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide;

(b) measuring a physiological characteristic of the non-human transgenic animal; and (c) comparing the measured physiological characteristic with that of a gender matched wild-type animal, wherein the physiological characteristic of the non-human transgenic animal that differs from the physiological characteristic of the wild-type animal is identified as a phenotype resulting from the gene disruption in the non-human transgenic animal.

2. The method of claim 1, wherein the non-human transgenic animal is heterozygous for the disruption of a gene which encodes for a PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide.

3. The method of claim 1, wherein the phenotype exhibited by the non-human transgenic animal as compared with gender matched wild-type littermates is at least one of the following: a neurological disorder; a cardiovascular, endothelial or angiogenic disorder; an eye abnormality; an immunological disorder; an oncological disorder; a bone metabolic abnormality or disorder; a lipid metabolic disorder; or a developmental abnormality.

4. The method of claim 3, wherein the neurological disorder is an increased anxiety-like response during open field activity testing.

5. The method of claim 3, wherein the neurological disorder is a decreased anxiety-like response during open field activity testing.

6. The method of claim 3, wherein the neurological disorder is an abnormal circadian rhythm during home-cage activity testing.

7. The method of claim 3, wherein the neurological disorder is an enhanced motor coordination during inverted screen testing.

8. The method of claim 3, wherein the neurological disorder is an impaired motor coordination during inverted screen testing.

9. The method of claim 3, wherein the neurological disorder is depression, generalized anxiety disorders, attention deficit disorder, sleep disorder, hyperactivity disorder, obsessive compulsive disorder, schizophrenia, cognitive disorders, hyperalgesia or sensory disorders.

10. The method of claim 3, wherein the eye abnormality is a retinal abnormality.

11. The method of claim 3, wherein the eye abnormality is consistent with vision problems or blindness.

12. The method of claim 10, wherein the retinal abnormality is consistent with retinitis pigmentosa.

13. The method of claim 10, wherein the retinal abnormality is characterized by retinal degeneration or retinal dysplasia.

14. The method of claim 10, wherein the retinal abnormality is consistent with retinal dysplasia, various retinopathies, including retinopathy of prematurity, retrolental fibroplasia, neovascular glaucoma, age-related macular degeneration, diabetic macular edema, corneal neovascularization, corneal graft neovascularization, corneal graft rejection, retinal/choroidal neovascularization, neovascularization of the angle (rubeosis), ocular neovascular disease, vascular restenosis, arteriovenous malformations (AVM), meningioma, hemangioma, angiofibroma, thyroid hyperplasias (including Grave's disease), corneal and other tissue transplantation, retinal artery obstruction or occlusion; retinal degeneration causing secondary atrophy of the retinal vasculature, retinitis pigmentosa, macular dystrophies, Stargardt's disease, congenital stationary night blindness, choroideremia, gyrate atrophy, Leber's congenital amaurosis, retinoschisis disorders, Wagner's syndrome, Usher syndromes, Zellweger syndrome, Saldino-Mainzer syndrome, Senior-Loken syndrome, Bardet-Biedl syndrome, Alport's syndrome, Alstrom's syndrome, Cockayne's syndrome, dysplaisa spondyloepiphysaria congentia, Flynn-Aird syndrome, Friedreich ataxia, Hallgren syndrome, Marshall syndrome, Albers-Schnoberg disease, Refsum's disease, Kearns-Sayre syndrome, Waardenburg's syndrome, Alagile syndrome, myotonic dystrophy, olivopontocerebellar atrophy, Pierre-Marie dunsdrome, Stickler syndrome, carotinemeia, cystinosis, Wolfram syndrome, Bassen-Kornzweig syndrome, abetalipoproteinemia, incontinentia pigmenti, Batten's disease, mucopolysaccharidoses, homocystinuria, or mannosidosis.

15. The method of claim 3, wherein the eye abnormality is a cataract.

16. The method of claim 15, wherein the cataract is consistent with systemic diseases such as human Down's syndrome, Hallerman-Streiff syndrome, Lowe syndrome, galactosemia, Marfan syndrome, Trismoy 13-15, Alport syndrome, myotonic dystrophy, Fabry disease, hypoparathroidism or Conradi syndrome.

17. The method of claim 3, wherein the developmental abnormality comprises embryonic lethality or reduced viability.

18. The method of claim 3, wherein the cardiovascular, endothelial or angiogenic disorders are arterial diseases, such as diabetes mellitus; papilledema; optic atrophy; atherosclerosis; angina; myocardial infarctions such as acute myocardial infarctions, cardiac hypertrophy, and heart failure such as congestive heart failure; hypertension; inflammatory vasculitides; Reynaud's disease and Reynaud's phenomenon; aneurysms and arterial restenosis; venous and lymphatic disorders such as thrombophlebitis, lymphangitis, and lymphedema; peripheral vascular disease; cancer such as vascular tumors, e.g., hemangioma (capillary and cavernous), glomus tumors, telangiectasia, bacillary angiomatosis, hemangioendothelioma, angiosarcoma, haemangiopericytoma, Kaposi's sarcoma, lymphangioma, and lymphangiosarcoma; tumor angiogenesis; trauma such as wounds, burns, and other injured tissue, implant fixation, scarring; ischemia reperfusion injury; rheumatoid arthritis; cerebrovascular disease; renal diseases such as acute renal failure, or osteoporosis.

19. The method of claim 3, wherein the immunological disorders are systemic lupus erythematosis; rheumatoid arthritis; juvenile chronic arthritis; spondyloarthropathies; systemic sclerosis (scleroderma); idiopathic inflammatory myopathies (dermatomyositis, polymyositis); Sjögren's syndrome; systemic vasculitis; sarcoidosis; autoimmune hemolytic anemia (immune pancytopenia, paroxysmal nocturnal hemoglobinuria); autoimmune thrombocytopenia (idiopathic thrombocytopenic purpura, immune-mediated thrombocytopenia); thyroiditis (Grave's disease, Hashimoto's thyroiditis, juvenile lymphocytic thyroiditis, atrophic thyroiditis); diabetes mellitus; immune-mediated renal disease (glomerulonephritis, tubulointerstitial nephritis); demyelinating diseases of the central and peripheral nervous systems such as multiple sclerosis, idiopathic demyelinating polyneuropathy or Guillain-Barré syndrome, and chronic inflammatory demyelinating polyneuropathy; hepatobiliary diseases such as infectious hepatitis (hepatitis A, B, C, D, E and other non-hepatotropic viruses), autoimmune chronic active hepatitis, primary biliary cirrhosis, granulomatous hepatitis, and sclerosing cholangitis; inflammatory bowel disease (ulcerative colitis: Crohn's disease); gluten-sensitive enteropathy, and Whipple's disease; autoimmune or immune-mediated skin diseases including bullous skin diseases, erythema multiforme and contact dermatitis, psoriasis; allergic diseases such as asthma, allergic rhinitis, atopic dermatitis, food hypersensitivity and urticaria; immunologic diseases of the lung such as eosinophilic pneumonias, idiopathic pulmonary fibrosis and hypersensitivity pneumonitis; or transplantation associated diseases including graft rejection and graft-versus-host disease.

20. The method of claim 3, wherein the bone metabolic abnormality or disorder is arthritis, osteoporosis or osteopetrosis.

21. The method of claim 1, wherein the non-human transgenic animal exhibits at least one of the following physiological characteristics compared with gender matched wild-type littermates: a decreased anxiety-like response during open field activity testing; an increased anxiety-like response during open field activity testing; balding, exothalamus observations, and piloerection observations in functional observation battery (FOB) testing; an increased mean artery-to-vein ratio associated with retinal degeneration; developing cataracts; an increased mean serum cholesterol level; an increased mean serum triglyceride level; a decreased mean serum insulin level, a decreased mean percentage of B cells in the spleen and lymph node; a decreased mean serum IgG2a response to an ovalbumin challenge; decreased mean serum IgA levels; an increased mean serum IgG2a response to an ovalbumin challenge; increased mean serum IgM, IgG1, IgG2a and IgG2b levels; increased mean serum IgM, IgA and IgG3 levels; increased mean serum IgM, IgG1, IgG2a and IgG2b levels; an increased mean percentage of CD4 cells and a decreased mean percentage of CD8 cells in spleen and thymus; mobilization of neutrophils in response to peritoneal inflammation; an enhanced DDS-induced colitis response; an enhanced ConA-induced hepatitis response; a decreased skin fibroblast proliferation; a decreased volumetric bone mineral density, a decreased bone mineral content index (BMC/LBM), and a decreased mean bone mineral density in total body, femur and vertebrate; a decreased mean bone mineral density, a decreased mean trabecular bone volume, decreased thickness, and decreased connectivity density; a decreased body weight and length, decreased total tissue mass and lean body mass, a decreased femoral midshaft cross-sectional area with decreased alkaline phosphatase levels; growth retardation with decreased body weight and length, total tissue mass, and lean body mass; a diaphragmatic hernia; an increased total tissue mass, increased lean body mass, increased bone mineral content, increased total body and increased femoral bone mineral density; an enhanced glucose tolerance; developmental disorders including abnormal kidney development marked by kidney agenesis; embryonic lethality; or embryonic lethality wherein heterozygous adults exhibited decreased serum IgM, IgG1, IgG2a, IgG2b and IgG3 levels.

22. An isolated cell derived from a non-human transgenic animal whose genome comprises a disruption of the gene which encodes for a PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide.

23. The isolated cell of claim 22 which is a murine cell.

24. The isolated cell of claim 23, wherein the murine cell is an embryonic stem cell.

25. The isolated cell of claim 22, wherein the non-human transgenic animal exhibits at least one of the following phenotypes compared with gender matched wild-type littermates: a neurological disorder; a cardiovascular, endothelial or angiogenic disorder; an eye abnormality; an immunological disorder; an oncological disorder; a bone metabolic abnormality or disorder; a lipid metabolic disorder; or a developmental abnormality.

26. A method of identifying an agent that modulates a phenotype associated with a disruption of a gene which encodes for a PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide, the method comprising:
(a) providing a non-human transgenic animal whose genome comprises a disruption of the gene which encodes for the PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide;
(b) measuring a physiological characteristic of the non-human transgenic animal of (a);
(c) comparing the measured physiological characteristic of (b) with that of a gender matched wild-type animal, wherein the physiological characteristic of the non-human transgenic animal that differs from the physiological characteristic of the wild-type animal is identified as a phenotype resulting from the gene disruption in the non-human transgenic animal;
(d) administering a test agent to the non-human transgenic animal of (a); and
(e) determining whether the test agent modulates the identified phenotype associated with gene disruption in the non-human transgenic animal.

27. The method of claim 26, wherein the phenotype associated with the gene disruption comprises a neurological disorder; a cardiovascular, endothelial or angiogenic disorder; an eye abnormality; an immunological disorder; an oncological disorder; a bone metabolic abnormality or disorder; a lipid metabolic disorder; or a developmental abnormality.

28. The method of claim 27, wherein the neurological disorder is an increased anxiety-like response during open field activity testing.

29. The method of claim 27, wherein the neurological disorder is a decreased anxiety-like response during open field activity testing.

30. The method of claim 27, wherein the neurological disorder is an abnormal circadian rhythm during home-cage activity testing.

31. The method of claim 27, wherein the neurological disorder is an enhanced motor coordination during inverted screen testing.

32. The method of claim 27, wherein the neurological disorder is an impaired motor coordination during inverted screen testing.

33. The method of claim 27, wherein the neurological disorder is depression, generalized anxiety disorders, attention deficit disorder, sleep disorder, hyperactivity disorder, obsessive compulsive disorder, schizophrenia, cognitive disorders, hyperalgesia or sensory disorders.

34. The method of claim 27, wherein the eye abnormality is a retinal abnormality.

35. The method of claim 27, wherein the eye abnormality is consistent with vision problems or blindness.

36. The method of claim 34, wherein the retinal abnormality is consistent with retinitis pigmentosa.

37. The method of claim 34, wherein the retinal abnormality is characterized by retinal degeneration or retinal dysplasia.

38. The method of claim 34, wherein the retinal abnormality is consistent with retinal dysplasia, various retinopathies, including retinopathy of prematurity, retrolental fibroplasia, neovascular glaucoma, age-related macular degeneration, diabetic macular edema, corneal neovascularization, corneal graft neovascularization, corneal graft rejection, retinal/choroidal neovascularization, neovascularization of the angle (rubeosis), ocular neovascular disease, vascular restenosis, arteriovenous malformations (AVM), meningioma, hemangioma, angiofibroma, thyroid hyperplasias (including Grave's disease), corneal and other tissue transplantation, retinal artery obstruction or occlusion; retinal degeneration causing secondary atrophy of the retinal vasculature, retinitis pigmentosa, macular dystrophies, Stargardt's disease, congenital stationary night blindness, choroideremia, gyrate atrophy, Leber's congenital amaurosis, retinoschisis disorders, Wagner's syndrome, Usher syndromes, Zellweger syndrome, Saldino-Mainzer syndrome, Senior-Loken syndrome, Bardet-Biedl syndrome, Alport's syndrome, Alstrom's syndrome, Cockayne's syndrome, dysplaisa spondyloepiphysaria congentia, Flynn-Aird syndrome, Friedreich ataxia, Hallgren syndrome, Marshall syndrome, Albers-Schnoberg disease, Refsum's disease, Kearns-Sayre syndrome, Waardenburg's syndrome, Alagile syndrome, myotonic dystrophy, olivopontocerebellar atrophy, Pierre-Marie dunsdrome, Stickler syndrome, carotinemeia, cystinosis, Wolfram syndrome, Bassen-Kornzweig syndrome, abetalipoproteinemia, incontinentia pigmenti, Batten's disease, mucopolysaccharidoses, homocystinuria, or mannosidosis.

39. The method of claim 27, wherein the eye abnormality is a cataract.

40. The method of claim 39, wherein the cataract is consistent with systemic diseases such as human Down's syndrome, Hallerman-Streiff syndrome, Lowe syndrome, galactosemia, Marfan syndrome, Trismoy 13-15, Alport syndrome, myotonic dystrophy, Fabry disease, hypoparathroidism or Conradi syndrome.

41. The method of claim 27, wherein the developmental abnormality comprises embryonic lethality or reduced viability.

42. The method of claim 27, wherein the cardiovascular, endothelial or angiogenic disorders are arterial diseases, such as diabetes mellitus; papilledema; optic atrophy; atherosclerosis; angina; myocardial infarctions such as acute myocardial infarctions, cardiac hypertrophy, and heart failure such as congestive heart failure; hypertension; inflammatory vasculitides; Reynaud's disease and Reynaud's phenomenon; aneurysms and arterial restenosis; venous and lymphatic disorders such as thrombophlebitis, lymphangitis, and lymphedema; peripheral vascular disease; cancer such as vascular tumors, e.g., hemangioma (capillary and cavernous), glomus tumors, telangiectasia, bacillary angiomatosis, hemangioendothelioma, angiosarcoma, haemangiopericytoma, Kaposi's sarcoma, lymphangioma, and lymphangiosarcoma; tumor angiogenesis; trauma such as wounds, burns, and other injured tissue, implant fixation, scarring; ischemia reperfusion injury; rheumatoid arthritis; cerebrovascular disease; renal diseases such as acute renal failure, or osteoporosis.

43. The method of claim 27, wherein the immunological disorders are systemic lupus erythematosis; rheumatoid arthritis; juvenile chronic arthritis; spondyloarthropathies; systemic sclerosis (scleroderma); idiopathic inflammatory myopathies (dermatomyositis, polymyositis); Sjögren's syndrome; systemic vasculitis; sarcoidosis; autoimmune hemolytic anemia (immune pancytopenia, paroxysmal nocturnal hemoglobinuria); autoimmune thrombocytopenia (idiopathic thrombocytopenic purpura, immune-mediated thrombocytopenia); thyroiditis (Grave's disease, Hashimoto's thyroiditis, juvenile lymphocytic thyroiditis, atrophic thyroiditis); diabetes mellitus; immune-mediated renal disease (glomerulonephritis, tubulointerstitial nephritis); demyelinating diseases of the central and peripheral nervous systems such as multiple sclerosis, idiopathic demyelinating polyneuropathy or Guillain-Barré syndrome, and chronic inflammatory demyelinating polyneuropathy; hepatobiliary diseases such as infectious hepatitis (hepatitis A, B, C, D, E and other non-hepatotropic viruses), autoimmune chronic active hepatitis, primary biliary cirrhosis, granulomatous hepatitis, and sclerosing cholangitis; inflammatory bowel disease (ulcerative colitis: Crohn's disease); gluten-sensitive enteropathy, and Whipple's disease; autoimmune or immune-mediated skin diseases including bullous skin diseases, erythema multiforme and contact dermatitis, psoriasis; allergic diseases such as asthma, allergic rhinitis, atopic dermatitis, food hypersensitivity and urticaria; immunologic diseases of the lung such as eosinophilic pneumonia, idiopathic pulmonary fibrosis and hypersensitivity pneumonitis; or transplantation-associated diseases including graft rejection and graft-versus-host disease.

44. The method of claim 27, wherein said bone metabolic abnormality or disorder is arthritis, osteoporosis or osteopetrosis.

45. The method of claim 26, wherein the non-human transgenic animal exhibits at least one of the following physiological characteristics compared with gender matched wild-type littermates: a decreased anxiety-like response during open field activity testing; an increased anxiety-like response during open field activity testing; balding, exothalamus observations, and piloerection observations in functional observation battery (FOB) testing; an increased mean artery-to-vein ratio associated with retinal degeneration; developing cataracts; an increased mean serum cholesterol level; an increased mean serum triglyceride level; a decreased mean serum insulin level, a decreased mean percentage of B cells in the spleen and lymph node; a decreased mean serum IgG2a response to an ovalbumin challenge; decreased mean serum IgA levels; an increased mean serum IgG2a response to an ovalbumin challenge; increased mean serum IgM, IgG1, IgG2a and IgG2b levels; increased mean serum IgM, IgA and IgG3 levels; increased mean serum IgM, IgG1, IgG2a and IgG2b levels; an increased mean percentage of CD4 cells and a decreased mean percentage of CD8 cells in spleen and thymus; mobilization of neutrophils in response to peritoneal inflammation; an enhanced DDS-induced colitis response; an enhanced ConA-induced hepatitis response; a decreased skin fibroblast proliferation; a decreased volumetric bone mineral density, a decreased bone mineral content index (BMC/LBM), and a decreased mean bone mineral density in total body, femur and vertebrate; a decreased mean bone mineral density, a decreased mean trabecular bone volume, decreased thickness, and decreased connectivity density; a decreased body weight and length, decreased total tissue mass and lean body mass, a decreased femoral midshaft cross-sectional area with decreased alkaline phosphatase levels; growth retardation with decreased body weight and length, total tissue mass, and lean body mass; a diaphragmatic hernia; an increased total tissue mass, increased lean body mass, increased bone mineral content, increased total body and increased femoral bone mineral density; an enhanced glucose tolerance; developmental disorders including abnormal kidney development marked by kidney agenesis; embryonic lethality; or embryonic lethality wherein heterozygous adults exhibited decreased serum IgM, IgG1, IgG2a, IgG2b and IgG3 levels.

46. An agent identified by the method of claim 26.

47. The agent of claim 46 which is an agonist or antagonist of a PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide.

48. The agent of claim 47, wherein the agonist is an anti-PRO224, anti-PRO9783, anti-PRO1108, anti-PRO34000, anti-PRO240, anti-PRO943, anti-hu A33, anti-PRO230, anti-PRO178, anti-PRO1199, anti-PRO4333, anti-PRO1336, anti-PRO19598, anti-PRO1083, anti-hu TRPM2 or anti-PRO1801 antibody.

49. The agent of claim 47, wherein the antagonist is an anti-PRO224, anti-PRO9783, anti-PRO1108, anti-PRO34000, anti-PRO240, anti-PRO943, anti-hu A33, anti-PRO230, anti-PRO178, anti-PRO1199, anti-PRO4333, anti-PRO1336, anti-PRO19598, anti-PRO1083, anti-hu TRPM2 or anti-PRO1801 antibody.

50. A method of identifying an agent that modulates a physiological characteristic associated with a disruption of the gene which encodes for a PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide, the method comprising:

(a) providing a non-human transgenic animal whose genome comprises a disruption of the gene which encodes for a PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide;

(b) measuring a physiological characteristic exhibited by the non-human transgenic animal of (a);

(c) comparing the measured physiological characteristic of (b) with that of a gender matched wild-type animal, wherein the physiological characteristic exhibited by the non-human transgenic animal that differs from the physiological characteristic exhibited by the wild-type animal is identified as a physiological characteristic associated with gene disruption;

(d) administering a test agent to the non-human transgenic animal of (a); and (e) determining whether the physiological characteristic associated with gene disruption is modulated.

51. The method of claim 50, wherein the non-human transgenic animal exhibits at least one of the following physiological characteristics compared with gender matched wild-type littermates: a decreased anxiety-like response during open field activity testing; an increased anxiety-like response during open field activity testing; balding, exothalamus observations, and piloerection observations in functional observation battery (FOB) testing; an increased mean artery-to-vein ratio associated with retinal degeneration; developing cataracts; an increased mean serum cholesterol level; an increased mean serum triglyceride level; a decreased mean serum insulin level, a decreased mean percentage of B cells in the spleen and lymph node; a decreased mean serum IgG2a response to an ovalbumin challenge; decreased mean serum IgA levels; an increased mean serum IgG2a response to an ovalbumin challenge; increased mean serum IgM, IgG1, IgG2a and IgG2b levels; increased mean serum IgM, IgA and IgG3 levels; increased mean serum IgM, IgG1, IgG2a and IgG2b levels; an increased mean percentage of CD4 cells and a decreased mean percentage of CD8 cells in spleen and thymus; mobilization of neutrophils in response to peritoneal inflammation; an enhanced DDS-induced colitis response; an enhanced ConA-induced hepatitis response; a decreased skin fibroblast proliferation; a decreased volumetric bone mineral density, a decreased bone mineral content index (BMC/LBM), and a decreased mean bone mineral density in total body, femur and vertebrate; a decreased mean bone mineral density, a decreased mean trabecular bone volume, decreased thickness, and decreased connectivity density; a decreased body weight and length, decreased total tissue mass and lean body mass, a decreased femoral midshaft cross-sectional area with decreased alkaline phosphatase levels; growth retardation with decreased body weight and length, total tissue mass, and lean body mass; a diaphragmatic hernia; an increased total tissue mass, increased lean body mass, increased bone mineral content, increased total body and increased femoral bone mineral density; an enhanced glucose tolerance; developmental disorders including abnormal kidney development marked by kidney agenesis; embryonic lethality; or embryonic lethality wherein heterozygous adults exhibited decreased serum IgM, IgG1, IgG2a, IgG2b and IgG3 levels.

52. An agent identified by the method of claim 50.

53. The agent of claim 52 which is an agonist or antagonist of a PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide.

54. The agent of claim 53, wherein the agonist is an anti-PRO224, anti-PRO9783, anti-PRO1108, anti-PRO34000, anti-PRO240, anti-PRO943, anti-hu A33, anti-PRO230, anti-PRO178, anti-PRO1199, anti-PRO4333, anti-PRO1336, anti-PRO19598, anti-PRO1083, anti-hu TRPM2 or anti-PRO1801 antibody.

55. The agent of claim 53, wherein the antagonist is an anti-PRO224, anti-PRO9783, anti-PRO1108, anti-PRO34000, anti-PRO240, anti-PRO943, anti-hu A33, anti-PRO230, anti-PRO178, anti-PRO1199, anti-PRO4333, anti-PRO1336, anti-PRO19598, anti-PRO1083, anti-hu TRPM2 or anti-PRO1801 antibody.

56. A method of identifying an agent which modulates a behavior associated with a disruption of the gene which encodes for a PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide, the method comprising:

(a) providing a non-human transgenic animal whose genome comprises a disruption of the gene which encodes for a PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide;

(b) observing the behavior exhibited by the non-human transgenic animal of (a);

(c) comparing the observed behavior of (b) with that of a gender matched wild-type animal, wherein the observed behavior exhibited by the non-human transgenic animal that differs from the observed behavior exhibited by the wild-type animal is identified as a behavior associated with gene disruption;

(d) administering a test agent to the non-human transgenic animal of (a); and (e) determining whether the agent modulates the behavior associated with gene disruption.

57. The method of claim 56, wherein the behavior is an increased anxiety-like response during open field activity testing.

58. The method of claim 56, wherein the behavior is a decreased anxiety-like response during open field activity testing.

59. The method of claim 56, wherein the behavior is an abnormal circadian rhythm during home-cage activity testing.

60. The method of claim 56, wherein the behavior is an enhanced motor coordination during inverted screen testing.

61. The method of claim 56, wherein the behavior is an impaired motor coordination during inverted screen testing.

62. The method of claim 56, wherein the behavior is depression, generalized anxiety disorders, attention deficit disorder, sleep disorder, hyperactivity disorder, obsessive compulsive disorder, schizophrenia, cognitive disorders, hyperalgesia or sensory disorders.

63. An agent identified by the method of claim 56.

64. The agent of claim 63 which is an agonist or antagonist of aPRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide.

65. The agent of claim 64, wherein the agonist is an anti-PRO224, anti-PRO9783, anti-PRO1108, anti-PRO34000, anti-PRO240, anti-PRO943, anti-hu A33, anti-PRO230, anti-PRO178, anti-PRO1199, anti-PRO4333, anti-PRO1336, anti-PRO19598, anti-PRO1083, anti-hu TRPM2 or anti-PRO1801 antibody.

66. The agent of claim 64, wherein the antagonist is an anti-PRO224, anti-PRO9783, anti-PRO1108, anti-PRO34000, anti-PRO240, anti-PRO943, anti-hu A33, anti-PRO230, anti-PRO178, anti-PRO1199, anti-PRO4333, anti- PRO1336, anti-PRO19598, anti-PRO1083, anti-hu TRPM2 or anti-PRO1801 antibody.

67. A method of identifying an agent that ameliorates or modulates a neurological disorder; a cardiovascular, endothelial or angiogenic disorder; an eye abnormality; an immunological disorder; an oncological disorder; a bone metabolic abnormality or disorder; a lipid metabolic disorder; or a developmental abnormality associated with a disruption in the gene which encodes for a PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide, the method comprising:

(a) providing a non-human transgenic animal whose genome comprises a disruption of the gene which encodes for a PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide;

(b) administering a test agent to said non-human transgenic animal; and (c) determining whether said test agent ameliorates or modulates the neurological disorder; cardiovascular, endothelial or angiogenic disorder; eye abnormality; immunological disorder; oncological disorder; bone metabolic abnormality or disorder; lipid metabolic disorder; or developmental abnormality in the non-human transgenic animal.

68. The method of claim 67, wherein the neurological disorder is an increased anxiety-like response during open field activity testing.

69. The method of claim 67, wherein the neurological disorder is a decreased anxiety-like response during open field activity testing.

70. The method of claim 67, wherein the neurological disorder is an abnormal circadian rhythm during home-cage activity testing.

71. The method of claim 67, wherein the neurological disorder is an enhanced motor coordination during inverted screen testing.

72. The method of claim 67, wherein the neurological disorder is an impaired motor coordination during inverted screen testing.

73. The method of claim 67, wherein the neurological disorder is depression, generalized anxiety disorders, attention deficit disorder, sleep disorder, hyperactivity disorder, obsessive compulsive disorder, schizophrenia, cognitive disorders, hyperalgesia or sensory disorders.

74. The method of claim 67, wherein the eye abnormality is a retinal abnormality.

75. The method of claim 67, wherein the eye abnormality is consistent with vision problems or blindness.

76. The method of claim 74, wherein the retinal abnormality is consistent with retinitis pigmentosa.

77. The method of claim 74, wherein the retinal abnormality is characterized by retinal degeneration or retinal dysplasia.

78. The method of claim 74, wherein the retinal abnormality is consistent with retinal dysplasia, various retinopathies, including retinopathy of prematurity, retrolental fibroplasia, neovascular glaucoma, age-related macular degeneration, diabetic macular edema, corneal neovascularization, corneal graft neovascularization, corneal graft rejection, retinal/choroidal neovascularization, neovascularization of the angle (rubeosis), ocular neovascular disease, vascular restenosis, arteriovenous malformations (AVM), meningioma, hemangioma, angiofibroma, thyroid hyperplasias (including Grave's disease), corneal and other tissue transplantation, retinal artery obstruction or occlusion; retinal degeneration causing secondary atrophy of the retinal vasculature, retinitis pigmentosa, macular dystrophies, Stargardt's disease, congenital stationary night blindness, choroideremia, gyrate atrophy, Leber's congenital amaurosis, retinoschisis disorders, Wagner's syndrome, Usher syndromes, Zellweger syndrome, Saldino-Mainzer syndrome, Senior-Loken syndrome, Bardet-Biedl syndrome, Alport's syndrome, Alstrom's syndrome, Cockayne's syndrome, dysplaisa spondyloepiphysaria congentia, Flynn-Aird syndrome, Friedreich ataxia, Hallgren syndrome, Marshall syndrome, Albers-Schnoberg disease, Refsum's disease, Kearns-Sayre syndrome, Waardenburg's syndrome, Alagile syndrome, myotonic dystrophy, olivopontocerebellar atrophy, Pierre-Marie dunsdrome, Stickler syndrome, carotinemeia, cystinosis, Wolfram syndrome, Bassen-Kornzweig syndrome, abetalipoproteinemia, incontinentia pigmenti, Batten's disease, mucopolysaccharidoses, homocystinuria, or mannosidosis.

79. The method of claim 67, wherein the eye abnormality is a cataract.

80. The method of claim 79, wherein the cataract is a systemic disease such as human Down's syndrome, Hallerman-Streiff syndrome, Lowe syndrome, galactosemia, Marfan syndrome, Trismoy 13-15, Alport syndrome, myotonic dystrophy, Fabry disease, hypoparathroidism or Conradi syndrome.

81. The method of claim 67, wherein the developmental abnormality comprises embryonic lethality or reduced viability.

82. The method of claim 67, wherein the cardiovascular, endothelial or angiogenic disorders are arterial diseases, such as diabetes mellitus; papilledema; optic atrophy; atherosclerosis; angina; myocardial infarctions such as acute myocardial infarctions, cardiac hypertrophy, and heart failure such as congestive heart failure; hypertension; inflammatory vasculitides; Reynaud's disease and Reynaud's phenomenon; aneurysms and arterial restenosis; venous and lymphatic disorders such as thrombophlebitis, lymphangitis, and lymphedema; peripheral vascular disease; cancer such as vascular tumors, e.g., hemangioma (capillary and cavernous), glomus tumors, telangiectasia, bacillary angiomatosis, hemangioendothelioma, angiosarcoma, haemangiopericytoma, Kaposi's sarcoma, lymphangioma, and lymphangiosarcoma; tumor angiogenesis; trauma such as wounds, burns, and other injured tissue, implant fixation, scarring; ischemia reperfusion injury; rheumatoid arthritis; cerebrovascular disease; renal diseases such as acute renal failure, or osteoporosis.

83. The method of claim 67, wherein the immunological disorders are systemic lupus erythematosis; rheumatoid arthritis; juvenile chronic arthritis; spondyloarthropathies; systemic sclerosis (scleroderma); idiopathic inflammatory myopathies (dermatomyositis, polymyositis); Sjögren's syndrome; systemic vasculitis; sarcoidosis; autoimmune hemolytic anemia (immune pancytopenia, paroxysmal nocturnal hemoglobinuria); autoimmune thrombocytopenia (idiopathic thrombocytopenic purpura, immune-mediated thrombocytopenia); thyroiditis (Grave's disease, Hashimoto's thyroiditis, juvenile lymphocytic thyroiditis, atrophic thyroiditis); diabetes mellitus; immune-mediated renal disease (glomerulonephritis, tubulointerstitial nephritis); demyelinating diseases of the central and peripheral nervous systems such as multiple sclerosis, idiopathic demyelinating polyneuropathy or Guillain-Barré syndrome, and chronic inflammatory demyelinating polyneuropathy; hepatobiliary diseases such as infectious hepatitis (hepatitis A, B, C, D, E and other non-hepatotropic viruses), autoimmune chronic active hepatitis, primary biliary cirrhosis, granulomatous hepatitis, and sclerosing cholangitis; inflammatory bowel disease (ulcerative colitis: Crohn's disease); gluten-sensitive enteropathy, and Whipple's disease; autoimmune or immune-mediated skin diseases including bullous skin diseases, erythema multiforme and contact dermatitis, psoriasis; allergic diseases such as asthma, allergic rhinitis, atopic dermatitis, food hypersensitivity and urticaria; immunologic diseases of the lung such as eosinophilic pneumonia, idiopathic pulmonary fibrosis and hypersensitivity pneumonitis; or transplantation associated diseases including graft rejection and graft-versus-host disease.

84. The method of claim 67, wherein said bone metabolic abnormality or disorder is arthritis, osteoporosis or osteopetrosis.

85. The method of claim 67, wherein the non-human transgenic animal exhibits at least one of the following physiological characteristics compared with gender matched wild-type littermates: a decreased anxiety-like response during open field activity testing; an increased anxiety-like response during open field activity testing; balding, exothalamus observations, and piloerection observations in functional observation battery (FOB) testing; an increased mean artery-to-vein ratio associated with retinal degeneration; developing cataracts; an increased mean serum cholesterol level; an increased mean serum triglyceride level; a decreased mean serum insulin level, a decreased mean percentage of B cells in the spleen and lymph node; a decreased mean serum IgG2a response to an ovalbumin challenge; decreased mean serum IgA levels; an increased mean serum IgG2a response to an ovalbumin challenge; increased mean serum IgM, IgG1, IgG2a and IgG2b levels; increased mean serum IgM, IgA and IgG3 levels; increased mean serum IgM, IgG1, IgG2a and IgG2b levels; an increased mean percentage of CD4 cells and a decreased mean percentage of CD8 cells in spleen and thymus; mobilization of neutrophils in response to peritoneal inflammation; an enhanced DDS-induced colitis response; an enhanced ConA-induced hepatitis response; a decreased skin fibroblast proliferation; a decreased volumetric bone mineral density, a decreased bone mineral content index (BMC/LBM), and a decreased mean bone mineral density in total body, femur and vertebrate; a decreased mean bone mineral density, a decreased mean trabecular bone volume, decreased thickness, and decreased connectivity density; a decreased body weight and length, decreased total tissue mass and lean body mass, a decreased femoral midshaft cross-sectional area with decreased alkaline phosphatase levels; growth retardation with decreased body weight and length, total tissue mass, and lean body mass; a diaphragmatic hernia; an increased total tissue mass, increased lean body mass, increased bone mineral content, increased total body and increased femoral bone mineral density; an enhanced glucose tolerance; developmental disorders including abnormal kidney development marked by kidney agenesis; embryonic lethality; or embryonic lethality wherein heterozygous adults exhibited decreased serum IgM, IgG1, IgG2a, IgG2b and IgG3 levels.

86. An agent identified by the method of claim 67.

87. The agent of claim 86 which is an agonist or antagonist of a PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide.

88. The agent of claim 87, wherein the agonist is an anti-PRO224, anti-PRO9783, anti-PRO1108, anti-PRO34000, anti-PRO240, anti-PRO943, anti-hu A33, anti-PRO230, anti-PRO178, anti-PRO1199, anti-PRO4333, anti-PRO1336, anti-PRO19598, anti-PRO1083, anti-hu TRPM2 or anti-PRO1801 antibody.

89. The agent of claim 87, wherein the antagonist is an anti-PRO224, anti-PRO9783, anti-PRO1108, anti-PRO34000, anti-PRO240, anti-PRO943, anti-hu A33, anti-PRO230, anti-PRO178, anti-PRO1199, anti-PRO4333, anti-PRO1336, anti-PRO19598, anti-PRO1083, anti-hu TRPM2 or anti-PRO1801 antibody.

90. A therapeutic agent identified by the method of claim 67.

91. A method of identifying an agent that modulates the expression of a PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide, the method comprising:

(a) contacting a test agent with a host cell expressing a PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide; and (b) determining whether the test agent modulates the expression of the PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide by the host cell.

92. An agent identified by the method of claim 91.

93. The agent of claim 92 which is an agonist or antagonist of a PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide.

94. The agent of claim 93, wherein the agonist is an anti-PRO224, anti-PRO9783, anti-PRO1108, anti-PRO34000, anti-PRO240, anti-PRO943, anti-hu A33, anti-PRO230, anti-PRO178, anti-PRO1199, anti-PRO4333, anti-PRO1336, anti-PRO19598, anti-PRO1083, anti-hu TRPM2 or anti-PRO1801 antibody.

95. The agent of claim 93, wherein the antagonist is an anti-PRO224, anti-PRO9783, anti-PRO1108, anti-PRO34000, anti-PRO240, anti-PRO943, anti-hu A33, anti-PRO230, anti-PRO178, anti-PRO1199, anti-PRO4333, anti-PRO1336, anti-PRO19598, anti-PRO1083, anti-hu TRPM2 or anti-PRO1801 antibody.

96. A method of evaluating a therapeutic agent capable of affecting a condition associated with a disruption of a gene which encodes foraPRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide, the method comprising:

(a) providing a non-human transgenic animal whose genome comprises a disruption of the gene which encodes for the PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide;

(b) measuring a physiological characteristic of the non-human transgenic animal of (a);

(c) comparing the measured physiological characteristic of (b) with that of a gender matched wild-type animal, wherein the physiological characteristic of the non-human transgenic animal that differs from the physiological characteristic of the wild-type animal is identified as a condition resulting from the gene disruption in the non-human transgenic animal;

(d) administering a test agent to the non-human transgenic animal of (a); and (e) evaluating the effects of the test agent on the identified condition associated with gene disruption in the non-human transgenic animal.

97. The method of claim 96, wherein the condition is a neurological disorder; a cardiovascular, endothelial or angiogenic disorder; an eye abnormality; an immunological disorder; an oncological disorder; a bone metabolic abnormality or disorder; a lipid metabolic disorder; or a developmental abnormality.

98. A therapeutic agent identified by the method of claim 96.

99. The therapeutic agent of claim 98 which is an agonist or antagonist of a PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide.

100. The therapeutic agent of claim 99, wherein the agonist is an anti-PRO224, anti-PRO9783, anti-PRO1108, anti-PRO34000, anti-PRO240, anti-PRO943, anti-hu A33, anti-PRO230, anti-PRO178, anti-PRO1199, anti-PRO4333, anti-PRO1336, anti-PRO19598, anti-PRO1083, anti-hu TRPM2 or anti-PRO1801 antibody.

101. The therapeutic agent of claim 99, wherein the antagonist is an anti-PRO224, anti-PRO9783, anti-PRO1108, anti-PRO34000, anti-PRO240, anti-PRO943, anti-hu A33, anti-PRO230, anti-PRO178, anti-PRO1199, anti-PRO4333, anti-PRO1336, anti-PRO19598, anti-PRO1083, anti-hu TRPM2 or anti-PRO1801 antibody.

102. A pharmaceutical composition comprising the therapeutic agent of claim 98.

103. A method of treating or preventing or ameliorating a neurological disorder; cardiovascular, endothelial or angiogenic disorder; immunological disorder; oncological disorder; bone metabolic abnormality or disorder, or embryonic lethality associated with the disruption of a gene which encodes for a PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide, the method comprising administering to a subject in need of such treatment whom may already have the disorder, or may be prone to have the disorder or may be in whom the disorder is to be prevented, a therapeutically effective amount of the therapeutic agent of claim 94, or agonists or antagonists thereof, thereby effectively treating or preventing or ameliorating said disorder.

104. The method of claim 103, wherein the neurological disorder is an increased anxiety-like response during open field activity testing.

105. The method of claim 103, wherein the neurological disorder is a decreased anxiety-like response during open field activity testing.

106. The method of claim 103, wherein the neurological disorder is an abnormal circadian rhythm during home-cage activity testing.

107. The method of claim 103, wherein the neurological disorder is an enhanced motor coordination during inverted screen testing.

108. The method of claim 103, wherein the neurological disorder is an impaired motor coordination during inverted screen testing.

109. The method of claim 103, wherein the neurological disorder is depression, generalized anxiety disorders, attention deficit disorder, sleep disorder, hyperactivity disorder, obsessive compulsive disorder, schizophrenia, cognitive disorders, hyperalgesia or sensory disorders.

110. The method of claim 103, wherein the eye abnormality is a retinal abnormality.

111. The method of claim 103, wherein the eye abnormality is consistent with vision problems or blindness.

112. The method of claim 110, wherein the retinal abnormality is consistent with retinitis pigmentosa.

113. The method of claim 110, wherein the retinal abnormality is characterized by retinal degeneration or retinal dysplasia.

114. The method of 110, wherein the retinal abnormality is consistent with retinal dysplasia, various retinopathies, including retinopathy of prematurity, retrolental fibroplasia, neovascular glaucoma, age-related macular degeneration, diabetic macular edema, corneal neovascularization, corneal graft neovascularization, corneal graft rejection, retinal/choroidal neovascularization, neovascularization of the angle (rubeosis), ocular neovascular disease, vascular restenosis, arteriovenous malformations (AVM), meningioma, hemangioma, angiofibroma, thyroid hyperplasias (including Grave's disease), corneal and other tissue transplantation, retinal artery obstruction or occlusion; retinal degeneration causing secondary atrophy of the retinal vasculature, retinitis pigmentosa, macular dystrophies, Stargardt's disease, congenital stationary night blindness, choroideremia, gyrate atrophy, Leber's congenital amaurosis, retinoschisis disorders, Wagner's syndrome, Usher syndromes, Zellweger syndrome, Saldino-Mainzer syndrome, Senior-Loken syndrome, Bardet-Biedl syndrome, Alport's syndrome, Alstrom's syndrome, Cockayne's syndrome, dysplaisa spondyloepiphysaria congentia, Flynn-Aird syndrome, Friedreich ataxia, Hallgren syndrome, Marshall syndrome, Albers-Schnoberg disease, Refsum's disease, Kearns-Sayre syndrome, Waardenburg's syndrome, Alagile syndrome, myotonic dystrophy, olivopontocerebellar atrophy, Pierre-Marie dunsdrome, Stickler syndrome, carotinemeia, cystinosis, Wolfram syndrome, Bassen-Kornzweig syndrome, abetalipoproteinemia, incontinentia pigmenti, Batten's disease, mucopolysaccharidoses, homocystinuria, or mannosidosis.

115. The method of claim 103, wherein the eye abnormality is a cataract.

116. The method of claim 115, wherein the cataract is a systemic disease such as human Down's syndrome, Hallerman-Streiff syndrome, Lowe syndrome, galactosemia, Marfan syndrome, Trismoy 13-15, Alport syndrome, myotonic dystrophy, Fabry disease, hypoparathroidism or Conradi syndrome.

117. The method of claim 103, wherein the developmental abnormality comprises embryonic lethality or reduced viability.

118. The method of claim 103, wherein the cardiovascular, endothelial or angiogenic disorders are arterial diseases, such as diabetes mellitus; papilledema; optic atrophy; atherosclerosis; angina; myocardial infarctions such as acute myocardial infarctions, cardiac hypertrophy, and heart failure such as congestive heart failure; hypertension; inflammatory vasculitides; Reynaud's disease and Reynaud's phenomenon; aneurysms and arterial restenosis; venous and lymphatic disorders such as thrombophlebitis, lymphangitis, and lymphedema; peripheral vascular disease; cancer such as vascular tumors, e.g., hemangioma (capillary and cavernous), glomus tumors, telangiectasia, bacillary angiomatosis, hemangioendothelioma, angiosarcoma, haemangiopericytoma, Kaposi's sarcoma, lymphangioma, and lymphangiosarcoma; tumor angiogenesis; trauma such as wounds, burns, and other injured tissue, implant fixation, scarring; ischemia reperfusion injury; rheumatoid arthritis; cerebrovascular disease; renal diseases such as acute renal failure, or osteoporosis.

119. The method of claim 103, wherein the immunological disorders are systemic lupus erythematosis; rheumatoid arthritis; juvenile chronic arthritis; spondyloarthropathies; systemic sclerosis (scleroderma); idiopathic inflammatory myopathies (dermatomyositis, polymyositis); Sjögren's syndrome; systemic vasculitis; sarcoidosis; autoimmune hemolytic anemia (immune pancytopenia, paroxysmal nocturnal hemoglobinuria); autoimmune thrombocytopenia (idiopathic thrombocytopenic purpura, immune-mediated thrombocytopenia); thyroiditis (Grave's disease, Hashimoto's thyroiditis, juvenile lymphocytic thyroiditis, atrophic thyroiditis); diabetes mellitus; immune-mediated renal disease (glomerulonephritis, tubulointerstitial nephritis); demyelinating diseases of the central and peripheral nervous systems such as multiple sclerosis, idiopathic demyelinating polyneuropathy or Guillain-Barré syndrome, and chronic inflammatory demyelinating polyneuropathy; hepatobiliary diseases such as infectious hepatitis (hepatitis A, B, C, D, E and other non-hepatotropic viruses), autoimmune chronic active hepatitis, primary biliary cirrhosis, granulomatous hepatitis, and sclerosing cholangitis; inflammatory bowel disease (ulcerative colitis: Crohn's disease); gluten-sensitive enteropathy, and Whipple's disease; autoimmune or immune-mediated skin diseases including bullous skin diseases, erythema multiforme and contact dermatitis, psoriasis; allergic diseases such as asthma, allergic rhinitis, atopic dermatitis, food hypersensitivity and urticaria; immunologic diseases of the lung such as eosinophilic pneumonia, idiopathic pulmonary fibrosis and hypersensitivity pneumonitis; or transplantation associated diseases including graft rejection and graft-versus-host disease.

120. The method of claim 103, wherein said bone metabolic abnormality or disorder is arthritis, osteoporosis or osteopetrosis.

121. A method of identifying an agent that ameliorates or modulates a neurological disorder; a cardiovascular, endothelial or angiogenic disorder; an eye abnormality; an immunological disorder; an oncological disorder; a bone metabolic abnormality or disorder; a lipid metabolic disorder; or a developmental abnormality associated with a disruption in the gene which encodes for a PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide, the method comprising:

(a) providing a non-human transgenic animal cell culture, each cell of said culture comprising a disruption of the gene which encodes for a PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide;

(b) administering a test agent to said cell culture; and (c) determining whether said test agent ameliorates or modulates the neurological disorder; cardiovascular, endothelial or angiogenic disorder; eye abnormality; immunological disorder; oncological disorder; bone metabolic abnormality or disorder; lipid metabolic disorder; or developmental abnormality in said cell culture.

122. The method of claim 121, wherein the neurological disorder is an increased anxiety-like response during open field activity testing.

123. The method of claim 121, wherein the neurological disorder is a decreased anxiety-like response during open field activity testing.

124. The method of 121, wherein the neurological disorder is an abnormal circadian rhythm during home-cage activity testing.

125. The method of claim 121, wherein the neurological disorder is an enhanced motor coordination during inverted screen testing.

126. The method of claim 121, wherein the neurological disorder is an impaired motor coordination during inverted screen testing.

127. The method of claim 121, wherein the neurological disorder is depression, generalized anxiety disorders, attention deficit disorder, sleep disorder, hyperactivity disorder, obsessive compulsive disorder, schizophrenia, cognitive disorders, hyperalgesia or sensory disorders.

128. The method of claim 121, wherein the eye abnormality is a retinal abnormality.

129. The method of claim 121, wherein the eye abnormality is consistent with vision problems or blindness.

130. The method of claim 128, wherein the retinal abnormality is consistent with retinitis pigmentosa.

131. The method of claim 128, wherein the retinal abnormality is characterized by retinal degeneration or retinal dysplasia.

132. The method of claim 128, wherein the retinal abnormality is consistent with retinal dysplasia, various retinopathies, including retinopathy of prematurity, retrolental fibroplasia, neovascular glaucoma, age-related macular degeneration, diabetic macular edema, corneal neovascularization, corneal graft neovascularization, corneal graft rejection, retinal/choroidal neovascularization, neovascularization of the angle (rubeosis), ocular neovascular disease, vascular restenosis, arteriovenous malformations (AVM), meningioma, hemangioma, angiofibroma, thyroid hyperplasias (including Grave's disease), corneal and other tissue transplantation, retinal artery obstruction or occlusion; retinal degeneration causing secondary atrophy of the retinal vasculature, retinitis pigmentosa, macular dystrophies, Stargardt's disease, congenital stationary night blindness, choroideremia, gyrate atrophy, Leber's congenital amaurosis, retinoschisis disorders, Wagner's syndrome, Usher syndromes, Zellweger syndrome, Saldino-Mainzer syndrome, Senior-Loken syndrome, Bardet-Biedl syndrome, Alport's syndrome, Alstrom's syndrome, Cockayne's syndrome, dysplaisa spondyloepiphysaria congentia, Flynn-Aird syndrome, Friedreich ataxia, Hallgren syndrome, Marshall syndrome, Albers-Schnoberg disease, Refsum's disease, Kearns-Sayre syndrome, Waardenburg's syndrome, Alagile syndrome, myotonic dystrophy, olivopontocerebellar atrophy, Pierre-Marie dunsdrome, Stickler syndrome, carotinemeia, cystinosis, Wolfram syndrome, Bassen-Kornzweig syndrome, abetalipoproteinemia, incontinentia pigmenti, Batten's disease, mucopolysaccharidoses, homocystinuria, or mannosidosis.

133. The method of claim 121, wherein the eye abnormality is a cataract.

134. The method of claim 133, wherein the cataract is a systemic disease such as human Down's syndrome, Hallerman-Streiff syndrome, Lowe syndrome, galactosemia, Marfan syndrome, Trismoy 13-15, Alport syndrome, myotonic dystrophy, Fabry disease, hypoparathroidism or Conradi syndrome.

135. The method of claim 121, wherein the developmental abnormality comprises embryonic lethality or reduced viability.

136. The method of claim 121, wherein the cardiovascular, endothelial or angiogenic disorders are arterial diseases, such as diabetes mellitus; papilledema; optic atrophy; atherosclerosis; angina; myocardial infarctions such as acute myocardial infarctions, cardiac hypertrophy, and heart failure such as congestive heart failure; hypertension; inflammatory vasculitides; Reynaud's disease and Reynaud's phenomenon; aneurysms and arterial restenosis; venous and lymphatic disorders such as thrombophlebitis, lymphangitis, and lymphedema; peripheral vascular disease; cancer such as vascular tumors, e.g., hemangioma (capillary and cavernous), glomus tumors, telangiectasia, bacillary angiomatosis, hemangioendothelioma, angiosarcoma, haemangiopericytoma, Kaposi's sarcoma, lymphangioma, and lymphangiosarcoma; tumor angiogenesis; trauma such as wounds, burns, and other injured tissue, implant fixation, scarring; ischemia reperfusion injury; rheumatoid arthritis; cerebrovascular disease; renal diseases such as acute renal failure, or osteoporosis.

137. The method of claim 121, wherein the immunological disorders are systemic lupus erythematosis; rheumatoid arthritis; juvenile chronic arthritis; spondyloarthropathies; systemic sclerosis (scleroderma); idiopathic inflammatory myopathies (dermatomyositis, polymyositis); Sjögren's syndrome; systemic vasculitis; sarcoidosis; autoimmune hemolytic anemia (immune pancytopenia, paroxysmal nocturnal hemoglobinuria); autoimmune thrombocytopenia (idiopathic thrombocytopenic purpura, immune-mediated thrombocytopenia); thyroiditis (Grave's disease, Hashimoto's thyroiditis, juvenile lymphocytic thyroiditis, atrophic thyroiditis); diabetes mellitus; immune-mediated renal disease (glomerulonephritis, tubulointerstitial nephritis); demyelinating diseases of the central and peripheral nervous systems such as multiple sclerosis, idiopathic demyelinating polyneuropathy or Guillain-Barré syndrome, and chronic inflammatory demyelinating polyneuropathy; hepatobiliary diseases such as infectious hepatitis (hepatitis A, B, C, D, E and other non-hepatotropic viruses), autoimmune chronic active hepatitis, primary biliary cirrhosis, granulomatous hepatitis, and sclerosing cholangitis; inflammatory bowel disease (ulcerative colitis: Crohn's disease); gluten-sensitive enteropathy, and Whipple's disease; autoimmune or immune-mediated skin diseases including bullous skin diseases, erythema multiforme and contact dermatitis, psoriasis; allergic diseases such as asthma, allergic rhinitis, atopic dermatitis, food hypersensitivity and urticaria; immunologic diseases of the lung such as eosinophilic pneumonia, idiopathic pulmonary fibrosis and hypersensitivity pneumonitis; or transplantation associated diseases including graft rejection and graft-versus-host disease.

138. The method of claim 121, wherein said bone metabolic abnormality or disorder is arthritis, osteoporosis or osteopetrosis.

139. An agent identified by the method of claim 121.

140. The agent of claim 139 which is an agonist or antagonist of a PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide.

141. The agent of claim 140, wherein the agonist is an anti-PRO224, anti-PRO9783, anti-PRO1108, anti-PRO34000, anti-PRO240, anti-PRO943, anti-hu A33, anti-PRO230, anti-PRO178, anti-PRO1199, anti-PRO4333, anti-PRO1336, anti-PRO19598, anti-PRO1083, anti-hu TRPM2 or anti-PRO1801 antibody.

142. The agent of claim 140, wherein the antagonist is an anti-PRO224, anti-PRO9783, anti-PRO1108, anti-PRO34000, anti-PRO240, anti-PRO943, anti-hu A33, anti-PRO230, anti-PRO178, anti-PRO1199, anti-PRO4333, anti-PRO1336, anti-PRO19598, anti-PRO1083, anti-hu TRPM2 or anti-PRO1801 antibody.

143. A therapeutic agent identified by the method of claim 121.

144. A method of modulating a phenotype associated with a disruption of a gene which encodes for a PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide, the method comprising administering to a subject whom may already have the phenotype, or may be prone to have the phenotype or may be in whom the phenotype is to be prevented, an effective amount of the agent of claim 46, or agonists or antagonists thereof, thereby effectively modulating the phenotype.

145. A method of modulating a physiological characteristic associated with a disruption of a gene which encodes for a PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide, the method comprising administering to a subject whom may already exhibit the physiological characteristic, or may be prone to exhibit the physiological characteristic or may be in whom the physiological characteristic is to be prevented, an effective amount of the agent of claim 52, or agonists or antagonists thereof, thereby effectively modulating the physiological characteristic.

146. A method of modulating a behavior associated with a disruption of a gene which encodes for a PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide, the method comprising administering to a subject whom may already exhibit the behavior, or may be prone to exhibit the behavior or may be in whom the exhibited behavior is to be prevented, an effective amount of the agent of claim 63, or agonists or antagonists thereof, thereby effectively modulating the behavior.

147. A method of modulating the expression of a PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide, the method comprising administering to a host cell expressing said PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide, an effective amount of the agent of claim 92, or agonists or antagonists thereof, thereby effectively modulating the expression of said polypeptide.

148. A method of modulating a condition associated with a disruption of a gene which encodes for a PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide, the method comprising administering to a subject whom may have the condition, or may be prone to have the condition or may be in whom the condition is to be prevented, a therapeutically effective amount of the therapeutic agent of claim 98, or agonists or antagonists thereof, thereby effectively modulating the condition.

149. A method of treating or preventing or ameliorating a neurological disorder; cardiovascular, endothelial or angiogenic disorder; immunological disorder; oncological disorder; bone metabolic abnormality or disorder, or embryonic lethality associated with the disruption of a gene which encodes for a PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide, the method comprising administering to a non-human transgenic animal cell culture, each cell of said culture comprising a disruption of the gene which encodes for a PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide, a therapeutically effective amount of the agent of claim 94, or agonists or antagonists thereof, thereby effectively treating or preventing or ameliorating said disorder.

BRIEF DESCRIPTION OF THE DRAWINGS

FIG. 1 shows a nucleotide sequence (SEQ ID NO:1) of a native sequence PRO224 cDNA, wherein SEQ ID NO:1 is a clone designated herein as "DNA33221-1133" (UNQ198).

FIG. 2 shows the amino acid sequence (SEQ ID NO:2) derived from the coding sequence of SEQ ID NO:1 shown in FIG. 1.

FIG. 3 shows a nucleotide sequence (SEQ ID NO:3) of a native sequence PRO9783 cDNA, wherein SEQ ID NO:3 is a clone designated herein as "DNA131590-2962" (UNQ2914).

FIG. 4 shows the amino acid sequence (SEQ ID NO:4) derived from the coding sequence of SEQ ID NO:3 shown in FIG. 3.

FIG. 5 shows a nucleotide sequence (SEQ ID NO:5) of a native sequence PRO1108 cDNA, wherein SEQ ID NO:5 is a clone designated herein as "DNA58848-1472" (UNQ551).

FIG. 6 shows the amino acid sequence (SEQ ID NO:6) derived from the coding sequence of SEQ ID NO:5 shown in FIG. 5.

FIGS. 7A-B show a nucleotide sequence (SEQ ID NO:7) of a native sequence PRO34000 cDNA, wherein SEQ ID NO:7 is a clone designated herein as "DNA203528-3014" (UNQ9196).

FIGS. 8A-B show the amino acid sequence (SEQ ID NO:8) derived from the coding sequence of SEQ ID NO:7 shown in FIGS. 7A-B.

FIG. 9 shows a nucleotide sequence (SEQ ID NO:9) of a native sequence PRO240 cDNA, wherein SEQ ID NO:9 is a clone designated herein as "DNA34387-1138" (UNQ214).

FIG. 10 shows the amino acid sequence (SEQ ID NO:10) derived from the coding sequence of SEQ ID NO:9 shown in FIG. 9.

FIG. 11 shows a nucleotide sequence (SEQ ID NO:11) of a native sequence PRO943 cDNA, wherein SEQ ID NO:11 is a clone designated herein as "DNA52192-1369" (UNQ480).

FIG. 12 shows the amino acid sequence (SEQ ID NO:12) derived from the coding sequence of SEQ ID NO:11 shown in FIG. 11.

FIG. 13 shows a nucleotide sequence (SEQ ID NO:13) of a native sequence PRO230 cDNA, wherein SEQ ID NO:13 is a clone designated herein as "DNA33223-1136" (UNQ204).

FIG. 14 shows the amino acid sequence (SEQ ID NO:14) derived from the coding sequence of SEQ ID NO:13 shown in FIG. 13.

FIG. 15 shows a nucleotide sequence (SEQ ID NO:15) of a native sequence PRO178 cDNA, wherein SEQ ID NO:15 is a clone designated herein as "DNA23339-1130" (UNQ152).

FIG. 16 shows the amino acid sequence (SEQ ID NO:16) derived from the coding sequence of SEQ ID NO:15 shown in FIG. 15.

FIG. 17 shows a nucleotide sequence (SEQ ID NO:17) of a native sequence PRO1199 cDNA, wherein SEQ ID NO:17 is a clone designated herein as "DNA65351-1366-2" (UNQ407).

FIG. 18 shows the amino acid sequence (SEQ ID NO:18) derived from the coding sequence of SEQ ID NO:17 shown in FIG. 17.

FIGS. 19A-B show a nucleotide sequence (SEQ ID NO:19) of a native sequence hu A33 cDNA, wherein SEQ ID NO:19 is a clone designated herein as "DNA98557" (UNQ1425).

FIG. 20 shows the amino acid sequence (SEQ ID NO:20) derived from the coding sequence of SEQ ID NO:19 shown in FIGS. 19A-B.

FIGS. 21A-B show a nucleotide sequence (SEQ ID NO:21) of a native sequence PRO4333 cDNA, wherein SEQ ID NO:21 is a clone designated herein as "DNA84210-2576" (UNQ1888).

FIG. 22 shows the amino acid sequence (SEQ ID NO:22) derived from the coding sequence of SEQ ID NO:21 shown in FIGS. 21A-B.

FIGS. 23A-B show a nucleotide sequence (SEQ ID NO:23) of a native sequence PRO1336 cDNA, wherein SEQ ID NO:23 is a clone designated herein as "DNA65423-1595" (UNQ691).

FIGS. 24A-B show the amino acid sequence (SEQ ID NO:24) derived from the coding sequence of SEQ ID NO:23 shown in FIGS. 23A-B.

FIG. 25 shows a nucleotide sequence (SEQ ID NO:25) of a native sequence PRO19598 cDNA, wherein SEQ ID NO:25 is a clone designated herein as "DNA145887-2849" (UNQ5793).

FIG. 26 shows the amino acid sequence (SEQ ID NO:26) derived from the coding sequence of SEQ ID NO:25 shown in FIG. 25.

FIG. 27 shows a nucleotide sequence (SEQ ID NO:27) of a native sequence PRO1083 cDNA, wherein SEQ ID NO:27 is a clone designated herein as "DNA50921-1458" (UNQ540).

FIG. 28 shows the amino acid sequence (SEQ ID NO:28) derived from the coding sequence of SEQ ID NO:27 shown in FIG. 27.

FIGS. 29A-C show a nucleotide sequence (SEQ ID NO:29) of a native sequence hu TRPM2 cDNA, wherein SEQ ID NO:29 is a clone designated herein as "DNA226659" (UNQ5070).

FIG. 30 shows the amino acid sequence (SEQ ID NO:30) derived from the coding sequence of SEQ ID NO:29 shown in FIGS. 29A-C.

FIG. 31 shows a nucleotide sequence (SEQ ID NO:67) of a native sequence PRO1801 cDNA, wherein SEQ ID NO:67 is a clone designated herein as "DNA83500-2506" (UNQ852).

FIG. 32 shows the amino acid sequence (SEQ ID NO:68) derived from the coding sequence of SEQ ID NO:67 shown in FIG. 31.

DETAILED DESCRIPTION OF THE PREFERRED EMBODIMENTS

I. Definitions

The terms "PRO polypeptide" and "PRO" as used herein and when immediately followed by a numerical designation refer to various polypeptides, wherein the complete designation (i.e., PRO/number) refers to specific polypeptide sequences as described herein. The terms "PRO/number polypeptide" and "PRO/number" wherein the term "number" is provided as an actual numerical designation as used herein encompass native sequence polypeptides and polypeptide variants (which are further defined herein). The PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide described herein may be isolated from a variety of sources, such as from human tissue types or from another source, or prepared by recombinant or synthetic methods. The term "PRO polypeptide" refers to each individual PRO/number polypeptide disclosed herein. All disclosures in this specification which refer to the "PRO polypeptide" refer to each of the polypeptides individually as well as jointly. For example, descriptions of the preparation of, purification of, derivation of, formation of antibodies to or against, administration of, compositions containing, treatment of a disease with, etc., pertain to each polypeptide of the invention individually. The term "PRO polypeptide" also includes variants of the PRO/number polypeptides disclosed herein.

A "native sequence PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide" comprises a polypeptide having the same amino acid sequence as the corresponding PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide derived from nature. Such native sequence PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptides can be isolated from nature or can be produced by recombinant or synthetic means. The term "native sequence PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide" specifically encompasses naturally-occurring truncated or secreted forms of the specific PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide (e.g., an extracellular domain sequence), naturally-occurring variant forms (e.g., alternatively spliced forms) and naturally-occurring allelic variants of the polypeptide. The invention provides native sequence PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptides disclosed herein which are mature or full-length native sequence polypeptides comprising the full-length amino acids sequences shown in the accompanying figures. Start and stop codons are shown in bold font and underlined in the figures. However, while the PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide disclosed in the accompanying figures are shown to begin with methionine residues designated herein as amino acid position 1 in the figures, it is conceivable and possible that other methionine residues located either upstream or downstream from the amino acid position 1 in the figures may be employed as the starting amino acid residue for the PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptides.

The PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide "extracellular domain" or "ECD" refers to a form of the PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide which is essentially free of the transmembrane and cytoplasmic domains. Ordinarily, a PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide ECD will have less than 1% of such transmembrane and/or cytoplasmic domains and preferably, will have less than 0.5% of such domains. It will be understood that any transmembrane domains identified for the PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptides of the present invention are identified pursuant to criteria routinely employed in the art for identifying that type of hydrophobic domain. The exact boundaries of a transmembrane domain may vary but most likely by no more than about 5 amino acids at either end of the domain as initially identified herein. Optionally, therefore, an extracellular domain of a PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide may contain from about 5 or fewer amino acids on either side of the transmembrane domain/extracellular domain boundary as identified in the Examples or specification and such polypeptides, with or without the associated signal peptide, and nucleic acid encoding them, are contemplated by the present invention.

The approximate location of the "signal peptides" of the various PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptides disclosed herein are shown in the present specification and/or the accompanying figures. It is noted, however, that the C-terminal boundary of a signal peptide may vary, but most likely by no more than about 5 amino acids on either side of the signal peptide C-terminal boundary as initially identified herein, wherein the C-terminal boundary of the signal peptide may be identified pursuant to criteria routinely employed in the art for identifying that type of amino acid sequence element (e.g., Nielsen et al., *Prot. Eng.* 10:1-6 (1997) and von Heinje et al., *Nucl. Acids. Res.* 14:4683-4690 (1986)). Moreover, it is also recognized that, in some cases, cleavage of a signal sequence from a secreted polypeptide is not entirely uniform, resulting in more than one secreted species. These mature polypeptides, where the signal peptide is cleaved within no more than about 5 amino acids on either side of the C-terminal boundary of the signal peptide as identified herein, and the polynucleotides encoding them, are contemplated by the present invention.

"PRO224. PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide variant" means a PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide, preferably an active PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide, as defined herein having at least about 80% amino acid sequence identity with a full-length native sequence PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide sequence as disclosed herein, a PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide sequence lacking the signal peptide as disclosed herein, an extracellular domain of a PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide, with or without the signal peptide, as disclosed herein or any other fragment of a full-length PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide sequence as disclosed herein (such as those encoded by a nucleic acid that represents only a portion of the complete coding sequence for a full-length PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide). Such PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide variants include, for instance, PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptides wherein one or more amino acid residues are added, or deleted, at the N- or C-terminus of the full-length native amino acid sequence. Ordinarily, a PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide variant will have or will have at least about 80% amino acid sequence identity, alternatively will have or will have at least about 81%, 82%, 83%, 84%, 85%, 86%, 87%, 88%, 89%, 90%, 91%, 92%, 93%, 94%, 95%, 96%, 97%, 98%, or 99% amino acid sequence identity, to a full-length native sequence PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide sequence as disclosed herein, a PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide sequence lacking the signal peptide as disclosed herein, an extracellular domain of a PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide, with or without the signal peptide, as disclosed herein or any other specifically defined fragment of a full-length PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide sequence as disclosed herein. Ordinarily, PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 variant polypeptides are or are at least about 10 amino acids in length, alternatively are or are at least about 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600 amino acids in length, or more. Optionally, PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 variant polypeptides will have no more than one conservative amino acid substitution as compared to the native PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide sequence, alternatively will have or will have no more than 2, 3, 4, 5, 6, 7, 8, 9, or 10 conservative amino acid substitution as compared to the native PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide sequence.

"Percent (%) amino acid sequence identity" with respect to the PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide sequences identified herein is defined as the percentage of amino acid residues in a candidate sequence that are identical with the amino acid residues in the specific PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for measuring alignment, including any algorithms needed to achieve maximal alignment over the full length of the sequences being compared. For purposes herein, however, % amino acid sequence identity values are generated using the sequence comparison computer program ALIGN-2, wherein the complete source code for the ALIGN-2 program is provided in Table 1 below. The ALIGN-2 sequence comparison computer program was authored by Genentech, Inc. and the source code shown in Table 1 below has been filed with user documentation in the U.S. Copyright Office, Washington D.C., 20559, where it is registered under U.S. Copyright Registration No. TXU510087. The ALIGN-2 program is publicly available through Genentech, Inc., South San Francisco, Calif. or may be compiled from the source code provided in Table 1 below. The ALIGN-2 program should be compiled for use on a UNIX operating system, preferably digital UNIX V4.0D. All sequence comparison parameters are set by the ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

100 times the fraction X/Y where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. As examples of % amino acid sequence identity calculations using this method, Tables 2 and 3 demonstrate how to calculate the % amino acid sequence identity of the amino acid sequence designated "Comparison Protein" to the amino acid sequence designated "PRO", wherein "PRO" represents the amino acid sequence of a hypothetical PRO polypeptide of interest, "Comparison Protein" represents the amino acid sequence of a polypeptide against which the "PRO" polypeptide of interest is being compared, and "X", "Y" and "Z" each represent different hypothetical amino acid residues. Unless specifically stated otherwise, all % amino acid sequence identity values used herein are obtained as described in the immediately preceding paragraph using the ALIGN-2 computer program.

"PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 variant polynucleotide" or "PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 variant nucleic acid sequence" means a nucleic acid molecule which encodes a PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide, preferably an active PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide, as defined herein and which has at least about 80% nucleic acid sequence identity with a nucleotide acid sequence encoding a full-length native sequence PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide sequence as disclosed herein, a full-length native sequence PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide sequence lacking the signal peptide as disclosed herein, an extracellular domain of a PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide, with or without the signal peptide, as disclosed herein or any other fragment of a full-length PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide sequence as disclosed herein (such as those encoded by a nucleic acid that represents only a portion of the complete coding sequence for a full-length PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide). Ordinarily, a PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 variant polynucleotide will have or will have at least about 80% nucleic acid sequence identity, alternatively will have or will have at least about 81%, 82%, 83%, 84%, 85%, 86%, 87%, 88%, 89%, 90%, 91%, 92%, 93%, 94%, 95%, 96%, 97%, 98%, or 99% nucleic acid sequence identity with a nucleic acid sequence encoding a full-length native sequence PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide sequence as disclosed herein, a full-length native sequence PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide sequence lacking the signal peptide as disclosed herein, an extracellular domain of a PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide, with or without the signal sequence, as disclosed herein or any other fragment of a full-length PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide sequence as disclosed herein. Variants do not encompass the native nucleotide sequence.

Ordinarily, PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 variant polynucleotides are or are at least about 5 nucleotides in length, alternatively are or are at least about 6, 7, 8, 9, 10, 11, 12, 13, 14, 15, 16, 17, 18, 19, 20, 21, 22, 23, 24, 25, 26, 27, 28, 29, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, or 1000 nucleotides in length, wherein in this context the term "about" means the referenced nucleotide sequence length plus or minus 10% of that referenced length.

"Percent (%) nucleic acid sequence identity" with respect to PRO224-, PRO9783-, PRO1108-, PRO34000-, PRO240-, PRO943-, hu A33-, PRO230-, PRO178-, PRO1199-, PRO4333-, PRO1336-, PRO19598-, PRO1083-, hu TRPM2- or PRO1801-encoding nucleic acid sequences identified herein is defined as the percentage of nucleotides in a candidate sequence that are identical with the nucleotides in the PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 nucleic acid sequence of interest, after aligning the sequences and introducing gaps, if necessary, to achieve the maximum percent sequence identity. Alignment for purposes of determining percent nucleic acid sequence identity can be achieved in various ways that are within the skill in the art, for instance, using publicly available computer software such as BLAST, BLAST-2, ALIGN or Megalign (DNASTAR) software. For purposes herein, however, % nucleic acid sequence identity values are generated using the sequence comparison computer program ALIGN-2, wherein the complete source code for the ALIGN-2 program is provided in Table 1 below. The ALIGN-2 sequence comparison computer program was authored by Genentech, Inc. and the source code shown in Table 1 below has been filed with user documentation in the U.S. Copyright Office, Washington D.C., 20559, where it is registered under U.S. Copyright Registration No. TXU510087. The ALIGN-2 program is publicly available through Genentech, Inc., South San Francisco, Calif. or may be compiled from the source code provided in Table 1 below. The ALIGN-2 program should be compiled for use on a UNIX operating system, preferably digital UNIX V4.0D. All sequence comparison parameters are set by the ALIGN-2 program and do not vary.

In situations where ALIGN-2 is employed for nucleic acid sequence comparisons, the % nucleic acid sequence identity of a given nucleic acid sequence C to, with, or against a given nucleic acid sequence D (which can alternatively be phrased as a given nucleic acid sequence C that has or comprises a certain % nucleic acid sequence identity to, with, or against a given nucleic acid sequence D) is calculated as follows:

100 times the fraction W/Z where W is the number of nucleotides scored as identical matches by the sequence alignment program ALIGN-2 in that program's alignment of C and D, and where Z is the total number of nucleotides in D. It will be appreciated that where the length of nucleic acid sequence C is not equal to the length of nucleic acid sequence D, the % nucleic acid sequence identity of C to D will not equal the % nucleic acid sequence identity of D to C. As examples of % nucleic acid sequence identity calculations, Tables 4 and 5, demonstrate how to calculate the % nucleic acid sequence identity of the nucleic acid sequence designated "Comparison DNA" to the nucleic acid sequence designated "PRO-DNA", wherein "PRO-DNA" represents a hypothetical PRO-encoding nucleic acid sequence of interest, "Comparison DNA" represents the nucleotide sequence of a nucleic acid molecule against which the "PRO-DNA" nucleic acid molecule of interest is being compared, and "N", "L" and "V" each represent different hypothetical nucleotides. Unless specifically stated otherwise, all % nucleic acid sequence identity values used herein are obtained as described in the immediately preceding paragraph using the ALIGN-2 computer program.

The invention also provides PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 variant polynucleotides which are nucleic acid molecules that encode a PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide and which are capable of hybridizing, preferably under stringent hybridization and wash conditions, to nucleotide sequences encoding a full-length PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide as disclosed herein. PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 variant polypeptides may be those that are encoded by a PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 variant polynucleotide.

The term "full-length coding region" when used in reference to a nucleic acid encoding a PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide refers to the sequence of nucleotides which encode the full-length PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide of the invention (which is often shown between start and stop codons, inclusive thereof, in the accompanying figures). The term "full-length coding region" when used in reference to an ATCC deposited nucleic acid refers to the PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide-encoding portion of the cDNA that is inserted into the vector deposited with the ATCC (which is often shown between start and stop codons, inclusive thereof, in the accompanying figures).

"Isolated," when used to describe the various polypeptides disclosed herein, means polypeptide that has been identified and separated and/or recovered from a component of its natural environment. Contaminant components of its natural environment are materials that would typically interfere with diagnostic or therapeutic uses for the polypeptide, and may include enzymes, hormones, and other proteinaceous or non-proteinaceous solutes. The invention provides that the polypeptide will be purified (1) to a degree sufficient to obtain at least 15 residues of N-terminal or internal amino acid sequence by use of a spinning cup sequenator, or (2) to homogeneity by SDS-PAGE under non-reducing or reducing conditions using Coomassie blue or, preferably, silver stain. Isolated polypeptide includes polypeptide in situ within recombinant cells, since at least one component of the PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide natural environment will not be present. Ordinarily, however, isolated polypeptide will be prepared by at least one purification step.

An "isolated" PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide-encoding nucleic acid or other polypeptide-encoding nucleic acid is a nucleic acid molecule that is identified and separated from at least one contaminant nucleic acid molecule with which it is ordinarily associated in the natural source of the polypeptide-encoding nucleic acid. An isolated polypeptide-encoding nucleic acid molecule is other than in the form or setting in which it is found in nature. Isolated polypeptide-encoding nucleic acid molecules therefore are distinguished from the specific polypeptide-encoding nucleic acid molecule as it exists in natural cells. However, an isolated polypeptide-encoding nucleic acid molecule includes polypeptide-encoding nucleic acid molecules contained in cells that ordinarily express the polypeptide where, for example, the nucleic acid molecule is in a chromosomal location different from that of natural cells.

The term "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

"Stringency" of hybridization reactions is readily determinable by one of ordinary skill in the art, and generally is an empirical calculation dependent upon probe length, washing temperature, and salt concentration. In general, longer probes require higher temperatures for proper annealing, while shorter probes need lower temperatures. Hybridization generally depends on the ability of denatured DNA to reanneal when complementary strands are present in an environment below their melting temperature. The higher the degree of desired homology between the probe and hybridizable sequence, the higher the relative temperature which can be used. As a result, it follows that higher relative temperatures would tend to make the reaction conditions more stringent, while lower temperatures less so. For additional details and explanation of stringency of hybridization reactions, see Ausubel et al., *Current Protocols in Molecular Biology*, Wiley Interscience Publishers, (1995).

"Stringent conditions" or "high stringency conditions", as defined herein, may be identified by those that: (1) employ low ionic strength and high temperature for washing, for example 0.015 M sodium chloride/0.0015 M sodium citrate/ 0.1% sodium dodecyl sulfate at 50° C.; (2) employ during hybridization a denaturing agent, such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; or (3) employ 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 µg/ml), 0.1% SDS, and 10% dextran sulfate at 42° C., with washes at 42° C. in 0.2×SSC (sodium chloride/sodium citrate) and 50% formamide at 55° C., followed by a high-stringency wash consisting of 0.1×SSC containing EDTA at 55° C.

"Moderately stringent conditions" may be identified as described by Sambrook et al., *Molecular Cloning: A Laboratory Manual*, New York: Cold Spring Harbor Press, 1989, and include the use of washing solution and hybridization conditions (e.g., temperature, ionic strength and % SDS) less stringent that those described above. An example of moderately stringent conditions is overnight incubation at 37° C. in a solution comprising: 20% formamide, 5×SSC (150 mM NaCl, 15 mM trisodium citrate), 50 mM sodium phosphate (pH 7.6), 5×Denhardt's solution, 10% dextran sulfate, and 20 mg/ml denatured sheared salmon sperm DNA, followed by washing the filters in 1×SSC at about 37-50° C. The skilled artisan will recognize how to adjust the temperature, ionic strength, etc. as necessary to accommodate factors such as probe length and the like.

The term "epitope tagged" when used herein refers to a chimeric polypeptide comprising a PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide fused to a "tag polypeptide". The tag polypeptide has enough residues to provide an epitope against which an antibody can be made, yet is short enough such that it does not interfere with activity of the polypeptide to which it is fused. The tag polypeptide preferably also is fairly unique so that the antibody does not substantially cross-react with other epitopes. Suitable tag polypeptides generally have at least six amino acid residues and usually between about 8 and 50 amino acid residues (preferably, between about 10 and 20 amino acid residues).

"Active" or "activity" for the purposes herein refers to form(s) of a PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide which retain a biological and/or an immunological activity of native or naturally-occurring PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide, wherein "biological" activity refers to a biological function (either inhibitory or stimulatory) caused by a native or naturally-occurring PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide other than the ability to induce the production of an antibody against an antigenic epitope possessed by a native or naturally-occurring PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide and an "immunological" activity refers to the ability to induce the production of an antibody against an antigenic epitope possessed by a native or naturally-occurring PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide.

The term "antagonist" is used in the broadest sense [unless otherwise qualified], and includes any molecule that partially or fully blocks, inhibits, or neutralizes a biological activity of a native PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide disclosed herein. In a similar manner, the term "agonist" is used in the broadest sense [unless otherwise qualified] and includes any molecule that mimics a biological activity of a native PRO224, PRO9783, PRO1108, PRO34000, PRO240, PRO943, hu A33, PRO230, PRO178, PRO199, PRO4333, PRO1336, PRO19598, PRO1083, hu TRPM2 or PRO1801 polypeptide disclosed herein. Suitable agonist or antagonist molecules specifically include agonist or antagonist antibodies or antibody fragments, fragments or amino acid sequence variants of native PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptides, peptides, antisense oligonucleotides, small organic molecules, etc. Methods for identifying agonists or antagonists of a PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide may comprise contacting a PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide with a candidate agonist or antagonist molecule and measuring a detectable change in one or more biological activities normally associated with the PRO224, PRO9783, PRO1108, PRO340DO, PRO240, PRO943, hu A33, PRO230, PRO178, PRO1199, PRO4333, PRO1336, PRO19598, PRO1083, hu TRPM2 or PRO1801 polypeptide.

"Treating" or "treatment" or "alleviation" refers to both therapeutic treatment and prophylactic or preventative measures, wherein the object is to prevent or slow down (lessen) the targeted pathologic condition or disorder. A subject in need of treatment may already have the disorder, or may be prone to have the disorder or may be in whom the disorder is to be prevented.

"Chronic" administration refers to administration of the agent(s) in a continuous mode as opposed to an acute mode, so as to maintain the initial therapeutic effect (activity) for an extended period of time. "Intermittent" administration is treatment that is not consecutively done without interruption, but rather is cyclic in nature.

"Mammal" for purposes of treatment refers to any animal classified as a mammal, including humans, rodents such as rats or mice, domestic and farm animals, and zoo, sports, or pet animals, such as dogs, cats, cattle, horses, sheep, pigs, goats, rabbits, etc. Preferably, the mammal is human.

Administration "in combination with" one or more further therapeutic agents includes simultaneous (concurrent) and consecutive administration in any order.

"Carriers" as used herein include pharmaceutically acceptable carriers, excipients, or stabilizers which are nontoxic to the cell or mammal being exposed thereto at the dosages and concentrations employed. Often the physiologically acceptable carrier is an aqueous pH buffered solution. Examples of physiologically acceptable carriers include buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™, polyethylene glycol (PEG), and PLURONICS™.

By "solid phase" is meant a non-aqueous matrix to which the antibody of the present invention can adhere. Examples of solid phases encompassed herein include those formed partially or entirely of glass (e.g., controlled pore glass), polysaccharides (e.g., agarose), polyacrylamides, polystyrene, polyvinyl alcohol and silicones. Depending on the context, the solid phase can comprise the well of an assay plate; in others it is a purification column (e.g., an affinity chromatography column). This term also includes a discontinuous solid phase of discrete particles, such as those described in U.S. Pat. No. 4,275,149.

A "liposome" is a small vesicle composed of various types of lipids, phospholipids and/or surfactant which is useful for delivery of a drug (such as a PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide or antibody thereto) to a mammal. The components of the liposome are commonly arranged in a bilayer formation, similar to the lipid arrangement of biological membranes.

A "small molecule" is defined herein to have a molecular weight below about 500 Daltons.

An "effective amount" of a PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide, an anti-PRO224, anti-PRO9783, anti-PRO1108, anti-PRO34000, anti-PRO240, anti-PRO943, anti-hu A33, anti-PRO230, anti-PRO178, anti-PRO1199, anti-PRO4333, anti-PRO1336, anti-PRO19598, anti-PRO1083, anti-hu TRPM2 or anti-PRO1801 antibody, a PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 binding oligopeptide, a PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 binding organic molecule or an agonist or antagonist thereof as disclosed herein is an amount sufficient to carry out a specifically stated purpose. An "effective amount" may be determined empirically and in a routine manner, in relation to the stated purpose.

The term "therapeutically effective amount" refers to an amount of an anti-PRO224, anti-PRO9783, anti-PRO1108, anti-PRO34000, anti-PRO240, anti-PRO943, anti-hu A33, anti-PRO230, anti-PRO178, anti-PRO1199, anti-PRO4333, anti-PRO1336, anti-PRO19598, anti-PRO1083, anti-hu TRPM2 or anti-PRO1801 antibody, a PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide, a PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 binding oligopeptide, a PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 binding organic molecule or other drug effective to "treat" a disease or disorder in a subject or mammal. In the case of cancer, the therapeutically effective amount of the drug may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the cancer. See the definition herein of "treating". To the extent the drug may prevent growth and/or kill existing cancer cells, it may be cytostatic and/or cytotoxic.

The phrases "cardiovascular, endothelial and angiogenic disorder", "cardiovascular, endothelial and angiogenic dysfunction", "cardiovascular, endothelial or angiogenic disorder" and "cardiovascular, endothelial or angiogenic dysfunction" are used interchangeably and refer in part to systemic disorders that affect vessels, such as diabetes mellitus, as well as diseases of the vessels themselves, such as of the arteries, capillaries, veins, and/or lymphatics. This would include indications that stimulate angiogenesis and/or cardiovascularization, and those that inhibit angiogenesis and/or cardiovascularization. Such disorders include, for example, arterial disease, such as atherosclerosis, hypertension, inflammatory vasculitides, Reynaud's disease and Reynaud's phenomenon, aneurysms, and arterial restenosis; venous and lymphatic disorders such as thrombophlebitis, lymphangitis, and lymphedema; and other vascular disorders such as peripheral vascular disease, cancer such as vascular tumors, e.g., hemangioma (capillary and cavernous), glomus tumors, telangiectasia, bacillary angiomatosis, hemangioendothelioma, angiosarcoma, haemangiopericytoma, Kaposi's sarcoma, lymphangioma, and lymphangiosarcoma, tumor angiogenesis, trauma such as wounds, burns, and other injured tissue, implant fixation, scarring, ischemia reperfusion injury, rheumatoid arthritis, cerebrovascular disease, renal diseases such as acute renal failure, or osteoporosis. This would also include angina, myocardial infarctions such as acute myocardial infarctions, cardiac hypertrophy, and heart failure such as CHF.

"Hypertrophy", as used herein, is defined as an increase in mass of an organ or structure independent of natural growth that does not involve tumor formation. Hypertrophy of an organ or tissue is due either to an increase in the mass of the individual cells (true hypertrophy), or to an increase in the number of cells making up the tissue (hyperplasia), or both. Certain organs, such as the heart, lose the ability to divide shortly after birth. Accordingly, "cardiac hypertrophy" is defined as an increase in mass of the heart, which, in adults, is characterized by an increase in myocyte cell size and contractile protein content without concomitant cell division. The character of the stress responsible for inciting the hypertrophy, (e.g., increased preload, increased afterload, loss of myocytes, as in myocardial infarction, or primary depression of contractility), appears to play a critical role in determining the nature of the response. The early stage of cardiac hypertrophy is usually characterized morphologically by increases in the size of myofibrils and mitochondria, as well as by enlargement of mitochondria and nuclei. At this stage, while muscle cells are larger than normal, cellular organization is largely preserved. At a more advanced stage of cardiac hypertrophy, there are preferential increases in the size or number of specific organelles, such as mitochondria, and new contractile elements are added in localized areas of the cells, in an irregular manner. Cells subjected to long-standing hypertrophy show more obvious disruptions in cellular organization, including markedly enlarged nuclei with highly lobulated membranes, which displace adjacent myofibrils and cause breakdown of normal Z-band registration. The phrase "cardiac hypertrophy" is used to include all stages of the progression of this condition, characterized by various degrees of structural damage of the heart muscle, regardless of the underlying cardiac disorder. Hence, the term also includes physiological conditions instrumental in the development of cardiac hypertrophy, such as elevated blood pressure, aortic stenosis, or myocardial infarction.

"Heart failure" refers to an abnormality of cardiac function where the heart does not pump blood at the rate needed for the requirements of metabolizing tissues. The heart failure can be caused by a number of factors, including ischemic, congenital, rheumatic, or idiopathic forms.

"Congestive heart failure" (CHF) is a progressive pathologic state where the heart is increasingly unable to supply adequate cardiac output (the volume of blood pumped by the heart over time) to deliver the oxygenated blood to peripheral tissues. As CHF progresses, structural and hemodynamic damages occur. While these damages have a variety of manifestations, one characteristic symptom is ventricular hypertrophy. CHF is a common end result of a number of various cardiac disorders.

"Myocardial infarction" generally results from atherosclerosis of the coronary arteries, often with superimposed coronary thrombosis. It may be divided into two major types: transmural infarcts, in which myocardial necrosis involves the full thickness of the ventricular wall, and subendocardial (nontransmural) infarcts, in which the necrosis involves the subendocardium, the intramural myocardium, or both, without extending all the way through the ventricular wall to the epicardium. Myocardial infarction is known to cause both a change in hemodynamic effects and an alteration in structure in the damaged and healthy zones of the heart. Thus, for example, myocardial infarction reduces the maximum cardiac output and the stroke volume of the heart. Also associated with myocardial infarction is a stimulation of the DNA synthesis occurring in the interstice as well as an increase in the formation of collagen in the areas of the heart not affected.

As a result of the increased stress or strain placed on the heart in prolonged hypertension due, for example, to the increased total peripheral resistance, cardiac hypertrophy has long been associated with "hypertension". A characteristic of the ventricle that becomes hypertrophic as a result of chronic pressure overload is an impaired diastolic performance. Fouad et al., *J. Am. Coll. Cardiol.*, 4: 1500-1506 (1984); Smith et al., *J. Am. Coll. Cardiol.*, 5: 869-874 (1985). A prolonged left ventricular relaxation has been detected in early essential hypertension, in spite of normal or supranormal systolic function. Hartford et al., *Hypertension*, 6: 329-338 (1984). However, there is no close parallelism between blood pressure levels and cardiac hypertrophy. Although improvement in left ventricular function in response to antihypertensive therapy has been reported in humans, patients variously treated with a diuretic (hydrochlorothiazide), a β-blocker (propranolol), or a calcium channel blocker (diltiazem), have shown reversal of left ventricular hypertrophy, without improvement in diastolic function. Inouye et al., *Am. J. Cardiol.*, 53: 1583-7 (1984).

Another complex cardiac disease associated with cardiac hypertrophy is "hypertrophic cardiomyopathy". This condition is characterized by a great diversity of morphologic, functional, and clinical features (Maron et al., *N. Engl. J. Med.*, 316: 780-789 (1987); Spirito et al., *N. Engl. J. Med.*, 320: 749-755 (1989); Louie and Edwards, *Prog. Cardiovasc. Dis.*, 36: 275-308 (1994); Wigle et al., *Circulation*, 92: 1680-1692 (1995)), the heterogeneity of which is accentuated by the fact that it afflicts patients of all ages. Spirito et al., *N. Engl. J. Med.*, 336: 775-785 (1997). The causative factors of hypertrophic cardiomyopathy are also diverse and little understood. In general, mutations in genes encoding sarcomeric proteins are associated with hypertrophic cardiomyopathy. Recent data suggest that β-myosin heavy chain mutations may account for approximately 30 to 40 percent of cases of familial hypertrophic cardiomyopathy. Watkins et al., *N. Engl. J. Med.*, 326: 1108-1114 (1992); Schwartz et al, *Circulation*, 91: 532-540 (1995); Marian and Roberts, *Circulation*, 92: 1336-1347 (1995); Thierfelder et al., *Cell*, 77: 701-712 (1994); Watkins et al., *Nat. Gen.* 11: 434-437 (1995). Besides β-myosin heavy chain, other locations of genetic mutations include cardiac troponin T, alpha topomyosin, cardiac myosin binding protein C, essential myosin light chain, and regulatory myosin light chain. See, Malik and Watkins, *Curr. Opin. Cardiol.*, 12: 295-302 (1997).

Supravalvular "aortic stenosis" is an inherited vascular disorder characterized by narrowing of the ascending aorta, but other arteries, including the pulmonary arteries, may also be affected. Untreated aortic stenosis may lead to increased intracardiac pressure resulting in myocardial hypertrophy and eventually heart failure and death. The pathogenesis of this disorder is not fully understood, but hypertrophy and possibly hyperplasia of medial smooth muscle are prominent features of this disorder. It has been reported that molecular variants of the elastin gene are involved in the development and pathogenesis of aortic stenosis. U.S. Pat. No. 5,650,282 issued Jul. 22, 1997.

"Valvular regurgitation" occurs as a result of heart diseases resulting in disorders of the cardiac valves. Various diseases, like rheumatic fever, can cause the shrinking or pulling apart of the valve orifice, while other diseases may result in endocarditis, an inflammation of the endocardium or lining membrane of the atrioventricular orifices and operation of the heart. Defects such as the narrowing of the valve stenosis or the defective closing of the valve result in an accumulation of blood in the heart cavity or regurgitation of blood past the valve. If uncorrected, prolonged valvular stenosis or insufficiency may result in cardiac hypertrophy and associated damage to the heart muscle, which may eventually necessitate valve replacement.

The term "immune related disease" means a disease in which a component of the immune system of a mammal causes, mediates or otherwise contributes to a morbidity in the mammal. Also included are diseases in which stimulation or intervention of the immune response has an ameliorative effect on progression of the disease. Included within this term are immune-mediated inflammatory diseases, non-immune-mediated inflammatory diseases, infectious diseases, immunodeficiency diseases, neoplasia, etc.

The term "T cell mediated disease" means a disease in which T cells directly or indirectly mediate or otherwise contribute to a morbidity in a mammal. The T cell mediated disease may be associated with cell mediated effects, lymphokine mediated effects, etc., and even effects associated with B cells if the B cells are stimulated, for example, by the lymphokines secreted by T cells.

Examples of immune-related and inflammatory diseases, some of which are immune or T cell mediated, include systemic lupus erythematosis, rheumatoid arthritis, juvenile chronic arthritis, spondyloarthropathies, systemic sclerosis (scleroderma), idiopathic inflammatory myopathies (dermatomyositis, polymyositis), Sjögren's syndrome, systemic vasculitis, sarcoidosis, autoimmune hemolytic anemia (immune pancytopenia, paroxysmal nocturnal hemoglobinuria), autoimmune thrombocytopenia (idiopathic thrombocytopenic purpura, immune-mediated thrombocytopenia), thyroiditis (Grave's disease, Hashimoto's thyroiditis, juvenile lymphocytic thyroiditis, atrophic thyroiditis), diabetes mellitus, immune-mediated renal disease (glomerulonephritis, tubulointerstitial nephritis), demyelinating diseases of the central and peripheral nervous systems such as multiple sclerosis, idiopathic demyelinating polyneuropathy or Guillain-Barré syndrome, and chronic inflammatory demyelinating polyneuropathy, hepatobiliary diseases such as infectious hepatitis (hepatitis A, B, C, D, E and other non-hepatotropic viruses), autoimmune chronic active hepatitis, primary biliary cirrhosis, granulomatous hepatitis, and sclerosing cholangitis, inflammatory bowel disease (ulcerative colitis: Crohn's disease), gluten-sensitive enteropathy, and Whipple's disease, autoimmune or immune-mediated skin diseases including bullous skin diseases, erythema multiforme and contact dermatitis, psoriasis, allergic diseases such as asthma, allergic rhinitis, atopic dermatitis, food hypersensitivity and urticaria, immunologic diseases of the lung such as eosinophilic pneumonia, idiopathic pulmonary fibrosis and hypersensitivity pneumonitis, or transplantation associated diseases including graft rejection and graft-versus-host-disease. Infectious diseases including viral diseases such as AIDS (HIV infection), hepatitis A, B, C, D, and E, herpes, etc., bacterial infections, fungal infections, protozoal infections and parasitic infections.

An "autoimmune disease" herein is a disease or disorder arising from and directed against an individual's own tissues or a co-segregate or manifestation thereof or resulting condition therefrom. Examples of autoimmune diseases or disorders include, but are not limited to arthritis (rheumatoid arthritis, juvenile rheumatoid arthritis, osteoarthritis, psoriatic arthritis, and ankylosing spondylitis), psoriasis, dermatitis including atopic dermatitis; chronic idiopathic urticaria, including chronic autoimmune urticaria, polymyositis/dermatomyositis, toxic epidermal necrolysis, systemic scleroderma and sclerosis, responses associated with inflammatory bowel disease (IBD) (Crohn's disease, ulcerative colitis), and IBD with co-segregate of pyoderma gangrenosum, erythema nodosum, primary sclerosing cholangitis, and/or episcleritis), respiratory distress syndrome, including adult respiratory distress syndrome (ARDS), meningitis, IgE-mediated diseases such as anaphylaxis and allergic rhinitis, encephalitis such as Rasmussen's encephalitis, uveitis, colitis such as microscopic colitis and collagenous colitis, glomerulonephritis (GN) such as membranous GN, idiopathic membranous GN, membranous proliferative GN (MPGN), including Type I and Type II, and rapidly progressive GN, allergic conditions, eczema, asthma, conditions involving infiltration of T cells and chronic inflammatory responses, atherosclerosis, autoimmune myocarditis, leukocyte adhesion deficiency, systemic lupus erythematosus (SLE) such as cutaneous SLE, lupus (including nephritis, cerebritis, pediatric, non-renal, discoid, alopecia), juvenile onset diabetes, multiple sclerosis (MS) such as spino-optical MS, allergic encephalomyelitis, immune responses associated with acute and delayed hypersensitivity mediated by cytokines and T-lymphocytes, tuberculosis, sarcoidosis, granulomatosis including Wegener's granulomatosis, agranulocytosis, vasculitis (including Large Vessel vasculitis (including Polymyalgia Rheumatica and Giant Cell (Takayasu's) Arteritis), Medium Vessel vasculitis (including Kawasaki's Disease and Polyarteritis Nodosa), CNS vasculitis, and ANCA-associated vasculitis, such as Churg-Strauss vasculitis or syndrome (CSS)), aplastic anemia, Coombs positive anemia, Diamond Blackfan anemia, immune hemolytic anemia including autoimmune hemolytic anemia (AIHA), pernicious anemia, pure red cell aplasia (PRCA), Factor VIII deficiency, hemophilia A, autoimmune neutropenia, pancytopenia, leukopenia, diseases involving leukocyte diapedesis, CNS inflammatory disorders, multiple organ injury syndrome, myasthenia gravis, antigen-antibody complex mediated diseases, anti-glomerular basement membrane disease, anti-phospholipid antibody syndrome, allergic neuritis, Bechet disease, Castleman's syndrome, Goodpasture's Syndrome, Lambert-Eaton Myasthenic Syndrome, Reynaud's syndrome, Sjorgen's syndrome, Stevens-Johnson syndrome, solid organ transplant rejection (including pretreatment for high panel reactive antibody titers, IgA deposit in tissues, and rejection arising from renal transplantation, liver transplantation, intestinal transplantation, cardiac transplantation, etc.), graft versus host disease (GVHD), pemphigoid bullous, pemphigus (including vulgaris, foliaceus, and pemphigus mucus-membrane pemphigoid), autoimmune polyendocrinopathies, Reiter's disease, stiff-man syndrome, immune complex nephritis, IgM polyneuropathies or IgM mediated neuropathy, idiopathic thrombocytopenic purpura (ITP), thrombotic throbocytopenic purpura (TTP), thrombocytopenia (as developed by myocardial infarction patients, for example), including autoimmune thrombocytopenia, autoimmune disease of the testis and ovary including autoimmune orchitis and oophoritis, primary hypothyroidism; autoimmune endocrine diseases including autoimmune thyroiditis, chronic thyroiditis (Hashimoto's Thyroiditis), subacute thyroiditis, idiopathic hypothyroidism, Addison's disease, Grave's disease, autoimmune polyglandular syndromes (or polyglandular endocrinopathy syndromes), Type I diabetes also referred to as insulin-dependent diabetes mellitus (IDDM), including pediatric IDDM, and Sheehan's syndrome; autoimmune hepatitis, Lymphoid interstitial pneumonitis (HIV), bronchiolitis obliterans (non-transplant) vs NSIP, Guillain-Barré Syndrome, Berger's Disease (IgA nephropathy), primary biliary cirrhosis, celiac sprue (gluten enteropathy), refractory sprue with co-segregate dermatitis herpetiformis, cryoglobulinemia, amylotrophic lateral sclerosis (ALS; Lou Gehrig's disease), coronary artery disease, autoimmune inner ear disease (AIED), autoimmune hearing loss, opsoclonus myoclonus syndrome (OMS), polychondritis such as refractory polychondritis, pulmonary alveolar proteinosis, amyloidosis, giant cell hepatitis, scleritis, monoclonal gammopathy of uncertain/unknown significance (MGUS), peripheral neuropathy, paraneoplastic syndrome, channelopathies such as epilepsy, migraine, arrhythmia, muscular disorders, deafness, blindness, periodic paralysis, and channelopathies of the CNS; autism, inflammatory myopathy, and focal segmental glomerulosclerosis (FSGS).

The phrase "anxiety related disorders" refers to disorders of anxiety, mood, and substance abuse, including but not limited to: depression, generalized anxiety disorders, attention deficit disorder, sleep disorder, hyperactivity disorder, obsessive compulsive disorder, schizophrenia, cognitive disorders, hyperalgesia and sensory disorders. Such disorders include the mild to moderate anxiety, anxiety disorder due to a general medical condition, anxiety disorder not otherwise specified, generalized anxiety disorder, panic attack, panic disorder with agoraphobia, panic disorder without agoraphobia, posttraumatic stress disorder, social phobia, social anxiety, autism, specific phobia, substance-induced anxiety disorder, acute alcohol withdrawal, obsessive compulsive disorder, agoraphobia, monopolar disorders, bipolar disorder I or II, bipolar disorder not otherwise specified, cyclothymic disorder, depressive disorder, major depressive disorder, mood disorder, substance-induced mood disorder, enhancement of cognitive function, loss of cognitive function associated with but not limited to Alzheimer's disease, stroke, or traumatic injury to the brain, seizures resulting from disease or injury including but not limited to epilepsy, learning disorders/disabilities, cerebral palsy. In addition, anxiety disorders may apply to personality disorders including but not limited to the following types: paranoid, antisocial, avoidant behavior, borderline personality disorders, dependent, histronic, narcissistic, obsessive-compulsive, schizoid, and schizotypal.

The term "lipid metabolic disorder" refers to abnormal clinical chemistry levels of cholesterol and triglycerides, wherein elevated levels of these lipids is an indication for atherosclerosis. Additionally, abnormal serum lipid levels may be an indication of various cardiovascular diseases including hypertension, stroke, coronary artery diseases, diabetes and/or obesity.

The phrase "eye abnormality" refers to such potential disorders of the eye as they may be related to atherosclerosis or various opthalmological abnormalities. Such disorders include but are not limited to the following: retinal dysplasia, various retinopathies, restenosis, retinal artery obstruction or occlusion; retinal degeneration causing secondary atrophy of the retinal vasculature, retinitis pigmentosa, macular dystrophies, Stargardt's disease, congenital stationary night blindness, choroideremia, gyrate atrophy, Leber's congenital amaurosis, retinoschisis disorders, Wagner's syndrome, Usher syndromes, Zellweger syndrome, Saldino-Mainzer syndrome, Senior-Loken syndrome, Bardet-Biedl syndrome, Alport's syndrome, Alstrom's syndrome, Cockayne's syndrome, dysplaisa spondyloepiphysaria congentia, Flynn-Aird syndrome, Friedreich ataxia, Hallgren syndrome, Marshall syndrome, Albers-Schnoberg disease, Refsum's disease, Kearns-Sayre syndrome, Waardenburg's syndrome, Alagile syndrome, myotonic dystrophy, olivopontocerebellar atrophy, Pierre-Marie dunsdrome, Stickler syndrome, carotinemeia, cystinosis, Wolfram syndrome, Bassen-Kornzweig syndrome, abetalipoproteinemia, incontinentia pigmenti, Batten's disease, mucopolysaccharidoses, homocystinuria, or mannosidosis. Cataracts are also considered an eye abnormality and are associated with such systemic diseases as: Human Down's syndrome, Hallerman-Streiff syndrome, Lowe syndrome, galactosemia, Marfan syndrome, Trismoy 13-15 condition, Alport syndrome, myotonic dystrophy, Fabry disease, hypothroidisms, or Conradi syndrome. Other ocular developmental anomalies include: Aniridia, anterior segment and dysgenesis syndrome. Cataracts may also occur as a result of an intraocular infection or inflammation (uveitis).

A "growth inhibitory amount" of an anti-PRO224, anti-PRO9783, anti-PRO1108, anti-PRO34000, anti-PRO240, anti-PRO943, anti-hu A33, anti-PRO230, anti-PRO178, anti-PRO1199, anti-PRO4333, anti-PRO1336, anti-PRO19598, anti-PRO1083, anti-hu TRPM2 or anti-PRO1801 antibody, PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide, PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 binding oligopeptide or PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 binding organic molecule is an amount capable of inhibiting the growth of a cell, especially tumor, e.g., cancer cell, either in vitro or in vivo. A "growth inhibitory amount" of an anti-PRO224, anti-PRO9783, anti-PRO1108, anti-PRO34000, anti-PRO240, anti-PRO943, anti-hu A33, anti-PRO230, anti-PRO178, anti-PRO1199, anti-PRO4333, anti-PRO1336, anti-PRO19598, anti-PRO1083, anti-hu TRPM2 or anti-PRO1801 antibody, PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide, PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 binding oligopeptide or PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 binding organic molecule for purposes of inhibiting neoplastic cell growth may be determined empirically and in a routine manner.

A "cytotoxic amount" of an anti-PRO224, anti-PRO9783, anti-PRO1108, anti-PRO34000, anti-PRO240, anti-PRO943, anti-hu A33, anti-PRO230, anti-PRO178, anti-PRO1199, anti-PRO4333, anti-PRO1336, anti-PRO19598, anti-PRO1083, anti-hu TRPM2 or anti-PRO1801 antibody, PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide, PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 binding oligopeptide or PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 binding organic molecule is an amount capable of causing the destruction of a cell, especially tumor, e.g., cancer cell, either in vitro or in vivo. A "cytotoxic amount" of an anti-PRO224, anti-PRO9783, anti-PRO1108, anti-PRO34000, anti-PRO240, anti-PRO943, anti-hu A33, anti-PRO230, anti-PRO178, anti-PRO1199, anti-PRO4333, anti-PRO1336, anti-PRO19598, anti-PRO1083, anti-hu TRPM2 or anti-PRO1801 antibody, PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide, PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 binding oligopeptide or PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 binding organic molecule for purposes of inhibiting neoplastic cell growth may be determined empirically and in a routine manner.

The term "antibody" is used in the broadest sense and specifically covers, for example, single anti-PRO224, anti-PRO9783, anti-PRO1108, anti-PRO34000, anti-PRO240, anti-PRO943, anti-hu A33, anti-PRO230, anti-PRO178, anti-PRO1199, anti-PRO4333, anti-PRO1336, anti-PRO19598, anti-PRO1083, anti-hu TRPM2 or anti-PRO1801 monoclonal antibodies (including agonist, antagonist, and neutralizing antibodies), anti-PRO224, anti-PRO9783, anti-PRO1108, anti-PRO34000, anti-PRO240, anti-PRO943, anti-hu A33, anti-PRO230, anti-PRO178, anti-PRO1199, anti-PRO4333, anti-PRO1336, anti-PRO19598, anti-PRO1083, anti-hu TRPM2 or anti-PRO1801 antibody compositions with polyepitopic specificity, polyclonal antibodies, single chain anti-PRO224, anti-PRO9783, anti-PRO1108, anti-PRO34000, anti-PRO240, anti-PRO943, anti-hu A33, anti-PRO230, anti-PRO178, anti-PRO1199, anti-PRO4333, anti-PRO1336, anti-PRO19598, anti-PRO1083, anti-hu TRPM2 or anti-PRO1801 antibodies, and fragments of anti-PRO224, anti-PRO9783, anti-PRO1108, anti-PRO34000, anti-PRO240, anti-PRO943, anti-hu A33, anti-PRO230, anti-PRO178, anti-PRO1199, anti-PRO4333, anti-PRO1336, anti-PRO19598, anti-PRO1083, anti-hu TRPM2 or anti-PRO1801 antibodies (see below) as long as they exhibit the desired biological or immunological activity. The term "immunoglobulin" (Ig) is used interchangeable with antibody herein.

An "isolated antibody" is one which has been identified and separated and/or recovered from a component of its natural environment. Contaminant components of its natural environment are materials which would interfere with diagnostic or therapeutic uses for the antibody, and may include enzymes, hormones, and other proteinaceous or nonproteinaceous solutes. The invention provides that the antibody will be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

The basic 4-chain antibody unit is a heterotetrameric glycoprotein composed of two identical light (L) chains and two identical heavy (H) chains (an IgM antibody consists of 5 of the basic heterotetramer unit along with an additional polypeptide called J chain, and therefore contain 10 antigen binding sites, while secreted IgA antibodies can polymerize to form polyvalent assemblages comprising 2-5 of the basic 4-chain units along with J chain). In the case of IgGs, the 4-chain unit is generally about 150,000 daltons. Each L chain is linked to a H chain by one covalent disulfide bond, while the two H chains are linked to each other by one or more disulfide bonds depending on the H chain isotype. Each H and L chain also has regularly spaced intrachain disulfide bridges. Each H chain has at the N-terminus, a variable domain ($V_H$) followed by three constant domains ($C_H$) for each of the α and γ chains and four $C_H$ domains for μ and ε isotypes. Each L chain has at the N-terminus, a variable domain ($V_L$) followed by a constant domain ($C_L$) at its other end. The $V_L$ is aligned with the $V_H$ and the $C_L$ is aligned with the first constant domain of the heavy chain ($C_H$ 1). Particular amino acid residues are believed to form an interface between the light chain and heavy chain variable domains. The pairing of a $V_H$ and $V_L$ together forms a single antigen-binding site. For the structure and properties of the different classes of antibodies, see, e.g., *Basic and Clinical Immunology,* 8th edition, Daniel P. Stites, Abba I. Terr and Tristram G. Parslow (eds.), Appleton & Lange, Norwalk, Conn., 1994, page 71 and Chapter 6.

The L chain from any vertebrate species can be assigned to one of two clearly distinct types, called kappa and lambda, based on the amino acid sequences of their constant domains. Depending on the amino acid sequence of the constant domain of their heavy chains ($C_H$), immunoglobulins can be assigned to different classes or isotypes. There are five classes of immunoglobulins: IgA, IgD, IgE, IgG, and IgM, having heavy chains designated α, δ, ε, γ, and μ, respectively. The γ and α classes are further divided into subclasses on the basis of relatively minor differences in $C_H$ sequence and function, e.g., humans express the following subclasses: IgG1, IgG2, IgG3, IgG4, IgA1, and IgA2.

The term "variable" refers to the fact that certain segments of the variable domains differ extensively in sequence among antibodies. The V domain mediates antigen binding and define specificity of a particular antibody for its particular antigen. However, the variability is not evenly distributed across the 110-amino acid span of the variable domains. Instead, the V regions consist of relatively invariant stretches called framework regions (FRs) of 15-30 amino acids separated by shorter regions of extreme variability called "hypervariable regions" that are each 9-12 amino acids long. The variable domains of native heavy and light chains each comprise four FRs, largely adopting a β-sheet configuration, connected by three hypervariable regions, which form loops connecting, and in some cases forming part of, the β-sheet structure. The hypervariable regions in each chain are held together in close proximity by the FRs and, with the hypervariable regions from the other chain, contribute to the formation of the antigen-binding site of antibodies (see Kabat et al., *Sequences of Proteins of Immunological Interest,* 5th Ed. Public Health Service, National Institutes of Health, Bethesda, Md. (1991)). The constant domains are not involved directly in binding an antibody to an antigen, but exhibit various effector functions, such as participation of the antibody in antibody dependent cellular cytotoxicity (ADCC).

The term "hypervariable region" when used herein refers to the amino acid residues of an antibody which are responsible for antigen-binding. The hypervariable region generally comprises amino acid residues from a "complementarity determining region" or "CDR" (e.g. around about residues 24-34 (L1), 50-56 (L2) and 89-97 (L3) in the $V_L$, and around about 1-35 (H1), 50-65 (H2) and 95-102 (H3) in the $V_H$; Kabat et al., *Sequences of Proteins of Immunological Interest,* 5th Ed. Public Health Service, National Institutes of Health, Bethesda, Md. (1991)) and/or those residues from a "hypervariable loop" (e.g. residues 26-32 (L1), 50-52 (L2) and 91-96 (L3) in the $V_L$, and 26-32 (H1), 53-55 (H2) and 96-101 (H3) in the $V_H$; Chothia and Lesk *J. Mol. Biol.* 196:901-917 (1987)).

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to polyclonal antibody preparations which include different antibodies directed against different determinants (epitopes), each monoclonal antibody is directed against a single determinant on the antigen. In addition to their specificity, the monoclonal antibodies are advantageous in that they may be synthesized uncontaminated by other antibodies. The modifier "monoclonal" is not to be construed as requiring production of the antibody by any particular method. For example, the monoclonal antibodies useful in the present invention may be prepared by the hybridoma methodology first described by Kohler et al., *Nature*, 256:495 (1975), or may be made using recombinant DNA methods in bacterial, eukaryotic animal or plant cells (see, e.g., U.S. Pat. No. 4,816, 567). The "monoclonal antibodies" may also be isolated from phage antibody libraries using the techniques described in Clackson et al., *Nature*, 352:624-628 (1991) and Marks et al., *J. Mol. Biol.*, 222:581-597 (1991), for example.

The monoclonal antibodies herein include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (see U.S. Pat. No. 4,816,567; and Morrison et al., *Proc. Natl. Acad. Sci. USA*, 81:6851-6855 (1984)). Chimeric antibodies of interest herein include "primatized" antibodies comprising variable domain antigen-binding sequences derived from a non-human primate (e.g. Old World Monkey, Ape etc), and human constant region sequences.

An "intact" antibody is one which comprises an antigen-binding site as well as a $C_L$ and at least heavy chain constant domains, $C_H1$, $C_H2$ and $C_H3$. The constant domains may be native sequence constant domains (e.g. human native sequence constant domains) or amino acid sequence variant thereof. Preferably, the intact antibody has one or more effector functions.

"Antibody fragments" comprise a portion of an intact antibody, preferably the antigen binding or variable region of the intact antibody. Examples of antibody fragments include Fab, Fab', F(ab')$_2$, and Fv fragments; diabodies; linear antibodies (see U.S. Pat. No. 5,641,870, Example 2; Zapata et al., *Protein Eng.* 8(10): 1057-1062 [1995]); single-chain antibody molecules; and multispecific antibodies formed from antibody fragments.

Papain digestion of antibodies produces two identical antigen-binding fragments, called "Fab" fragments, and a residual "Fc" fragment, a designation reflecting the ability to crystallize readily. The Fab fragment consists of an entire L chain along with the variable region domain of the H chain ($V_H$), and the first constant domain of one heavy chain ($C_H1$). Each Fab fragment is monovalent with respect to antigen binding, i.e., it has a single antigen-binding site. Pepsin treatment of an antibody yields a single large F(ab')$_2$ fragment which roughly corresponds to two disulfide linked Fab fragments having divalent antigen-binding activity and is still capable of cross-linking antigen. Fab' fragments differ from Fab fragments by having additional few residues at the carboxy terminus of the $C_H1$ domain including one or more cysteines from the antibody hinge region. Fab'-SH is the designation herein for Fab' in which the cysteine residue(s) of the constant domains bear a free thiol group. F(ab')$_2$ antibody fragments originally were produced as pairs of Fab' fragments which have hinge cysteines between them. Other chemical couplings of antibody fragments are also known.

The Fc fragment comprises the carboxy-terminal portions of both H chains held together by disulfides. The effector functions of antibodies are determined by sequences in the Fc region, which region is also the part recognized by Fc receptors (FcR) found on certain types of cells.

"Fv" is the minimum antibody fragment which contains a complete antigen-recognition and -binding site. This fragment consists of a dimer of one heavy- and one light-chain variable region domain in tight, non-covalent association. From the folding of these two domains emanate six hypervariable loops (3 loops each from the H and L chain) that contribute the amino acid residues for antigen binding and confer antigen binding specificity to the antibody. However, even a single variable domain (or half of an Fv comprising only three CDRs specific for an antigen) has the ability to recognize and bind antigen, although at a lower affinity than the entire binding site.

"Single-chain Fv" also abbreviated as "sFv" or "scFv" are antibody fragments that comprise the $V_H$ and $V_L$ antibody domains connected into a single polypeptide chain. Preferably, the sFv polypeptide further comprises a polypeptide linker between the $V_H$ and $V_L$ domains which enables the sFv to form the desired structure for antigen binding. For a review of sFv, see Pluckthun in *The Pharmacology of Monoclonal Antibodies*, vol. 113, Rosenburg and Moore eds., Springer-Verlag, New York, pp. 269-315 (1994); Borrebaeck 1995, infra.

The term "diabodies" refers to small antibody fragments prepared by constructing sFv fragments (see preceding paragraph) with short linkers (about 5-10 residues) between the $V_H$ and $V_L$ domains such that inter-chain but not intra-chain pairing of the V domains is achieved, resulting in a bivalent fragment, i.e., fragment having two antigen-binding sites. Bispecific diabodies are heterodimers of two "crossover" sFv fragments in which the $V_H$ and $V_L$ domains of the two antibodies are present on different polypeptide chains. Diabodies are described more fully in, for example, EP 404,097; WO 93/11161; and Hollinger et al., *Proc. Natl. Acad. Sci. USA*, 90:6444-6448 (1993).

"Humanized" forms of non-human (e.g., rodent) antibodies are chimeric antibodies that contain minimal sequence derived from the non-human antibody. For the most part, humanized antibodies are human immunoglobulins (recipient antibody) in which residues from a hypervariable region of the recipient are replaced by residues from a hypervariable region of a non-human species (donor antibody) such as mouse, rat, rabbit or non-human primate having the desired antibody specificity, affinity, and capability. In some instances, framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally also will comprise at least a portion of an immunoglobulin constant region (Fc), typically that of a human immunoglobulin. For further details, see Jones et al., Nature 321:522-525 (1986); Riechmann et al., Nature 332: 323-329 (1988); and Presta, Curr. Op. Struct. Biol. 2:593-596 (1992).

A "species-dependent antibody," e.g., a mammalian anti-human IgE antibody, is an antibody which has a stronger binding affinity for an antigen from a first mammalian species than it has for a homologue of that antigen from a second mammalian species. Normally, the species-dependent antibody "bind specifically" to a human antigen (i.e., has a binding affinity (Kd) value of no more than about $1 \times 10^{-7}$ M, preferably no more than about $1 \times 10^{-8}$ and most preferably no more than about $1 \times 10^{-9}$ M) but has a binding affinity for a homologue of the antigen from a second non-human mammalian species which is at least about 50 fold, or at least about 500 fold, or at least about 1000 fold, weaker than its binding affinity for the human antigen. The species-dependent antibody can be of any of the various types of antibodies as defined above, but preferably is a humanized or human antibody.

A "PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 binding oligopeptide" is an oligopeptide that binds, preferably specifically, to a PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide as described herein. PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 binding oligopeptides may be chemically synthesized using known oligopeptide synthesis methodology or may be prepared and purified using recombinant technology. PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 binding oligopeptides usually are or are at least about 5 amino acids in length, alternatively are or are at least about 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 amino acids in length or more, wherein such oligopeptides that are capable of binding, preferably specifically, to a PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide as described herein. PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 binding oligopeptides may be identified without undue experimentation using well known techniques. In this regard, it is noted that techniques for screening oligopeptide libraries for oligopeptides that are capable of specifically binding to a polypeptide target are well known in the art (see, e.g., U.S. Pat. Nos. 5,556,762, 5,750,373, 4,708,871, 4,833,092, 5,223,409, 5,403,484, 5,571,689, 5,663,143; PCT Publication Nos. WO 84/03506 and WO84/03564; Geysen et al., Proc. Natl. Acad. Sci. U.S.A., 81:3998-4002 (1984); Geysen et al., Proc. Natl. Acad. Sci. U.S.A., 82:178-182(1985); Geysen et al., in Synthetic Peptides as Antigens, 130-149 (1986); Geysen et al., J. Immunol. Meth., 102:259-274 (1987); Schoofs et al., J. Immunol., 140:611-616 (1988), Cwirla, S. E. et al. (1990) Proc. Natl. Acad. Sci. USA, 87:6378; Lowman, H. B. et al. (1991) Biochemistry, 30:10832; Clackson, T. et al. (1991) Nature, 352: 624; Marks, J. D. et al. (1991), J. Mol. Biol., 222:581; Kang, A. S. et al. (1991) Proc. Natl. Acad. Sci. USA, 88:8363, and Smith, G. P. (1991) Current Opin. Biotechnol., 2:668).

A "PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 binding organic molecule" is an organic molecule other than an oligopeptide or antibody as defined herein that binds, preferably specifically, to a PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide as described herein. PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 binding organic molecules may be identified and chemically synthesized using known methodology (see, e.g., PCT Publication Nos. WO00/00823 and WO00/39585). PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 binding organic molecules are usually less than about 2000 daltons in size, alternatively less than about 1500, 750, 500, 250 or 200 daltons in size, wherein such organic molecules that are capable of binding, preferably specifically, to a PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide as described herein may be identified without undue experimentation using well known techniques. In this regard, it is noted that techniques for screening organic molecule libraries for molecules that are capable of binding to a polypeptide target are well known in the art (see, e.g., PCT Publication Nos. WO00/00823 and WO00/39585).

An antibody, oligopeptide or other organic molecule "which binds" an antigen of interest, e.g. a tumor-associated polypeptide antigen target, is one that binds the antigen with sufficient affinity such that the antibody, oligopeptide or other organic molecule is preferably useful as a diagnostic and/or therapeutic agent in targeting a cell or tissue expressing the antigen, and does not significantly cross-react with other proteins. The extent of binding of the antibody, oligopeptide or other organic molecule to a "non-target" protein will be less than about 10% of the binding of the antibody, oligopeptide or other organic molecule to its particular target protein as determined by fluorescence activated cell sorting (FACS) analysis or radioimmunoprecipitation (RIA). With regard to the binding of an antibody, oligopeptide or other organic molecule to a target molecule, the term "specific binding" or "specifically binds to" or is "specific for" a particular polypeptide or an epitope on a particular polypeptide target means binding that is measurably different from a non-specific interaction. Specific binding can be measured, for example, by determining binding of a molecule compared to binding of a control molecule, which generally is a molecule of similar structure that does not have binding activity. For example, specific binding can be determined by competition with a control molecule that is similar to the target, for example, an excess of non-labeled target. In this case, specific binding is indicated if the binding of the labeled target to a probe is competitively inhibited by excess unlabeled target. The term "specific binding" or "specifically binds to" or is "specific for" a particular polypeptide or an epitope on a particular polypeptide target as used herein can be exhibited, for example, by a molecule having a Kd for the target of at least about $10^{-4}$ M, alternatively at least about $10^{-5}$ M, alternatively at least about $10^{-6}$ M, alternatively at least about $10^{-7}$ M, alternatively at least about $10^{-8}$ M, alternatively at least about $10^{-9}$ M, alternatively at least about $10^{-10}$ M, alternatively at least about $10^{-11}$ M, alternatively at least about $10^{-12}$ M, or greater. The term "specific binding" refers to binding where a molecule binds to a particular polypeptide or epitope on a particular polypeptide without substantially binding to any other polypeptide or polypeptide epitope.

An antibody, oligopeptide or other organic molecule that "inhibits the growth of tumor cells expressing a PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801" or a "growth inhibitory" antibody, oligopeptide or other organic molecule is one which results in measurable growth inhibition of cancer cells expressing or overexpressing the appropriate PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide. The PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide may be a transmembrane polypeptide expressed on the surface of a cancer cell or may be a polypeptide that is produced and secreted by a cancer cell. Preferred growth inhibitory anti-PRO224, anti-PRO9783, anti-PRO1108, anti-PRO34000, anti-PRO240, anti-PRO943, anti-hu A33, anti-PRO230, anti-PRO178, anti-PRO1199, anti-PRO4333, anti-PRO1336, anti-PRO19598, anti-PRO1083, anti-hu TRPM2 or anti-PRO1801 antibodies, oligopeptides or organic molecules inhibit growth of PRO224-, PRO9783-, PRO1108-, PRO34000-, PRO240-, PRO943-, hu A33-, PRO230-, PRO178-, PRO1199-, PRO4333-, PRO1336-, PRO19598-, PRO1083-, hu TRPM2- or PRO1801-expressing tumor cells by or by greater than 20%, preferably from about 20% to about 50%, and even more preferably, by or by greater than 50% (e.g., from about 50% to about 100%) as compared to the appropriate control, the control typically being tumor cells not treated with the antibody, oligopeptide or other organic molecule being tested. Growth inhibition can be measured at an antibody concentration of about 0.1 to 30 µg/ml or about 0.5 nM to 200 nM in cell culture, where the growth inhibition is determined 1-10 days after exposure of the tumor cells to the antibody. Growth inhibition of tumor cells in vivo can be determined in various ways. The antibody is growth inhibitory in vivo if administration of the anti-PRO224, anti-PRO9783, anti-PRO1108, anti-PRO34000, anti-PRO240, anti-PRO943, anti-hu A33, anti-PRO230, anti-PRO178, anti-PRO1199, anti-PRO4333, anti-PRO1336, anti-PRO19598, anti-PRO1083, anti-hu TRPM2 or anti-PRO1801 antibody at about 1 µg/kg to about 100 mg/kg body weight results in reduction in tumor size or tumor cell proliferation within about 5 days to 3 months from the first administration of the antibody, preferably within about 5 to 30 days.

An antibody, oligopeptide or other organic molecule which "induces apoptosis" is one which induces programmed cell death as determined by binding of annexin V, fragmentation of DNA, cell shrinkage, dilation of endoplasmic reticulum, cell fragmentation, and/or formation of membrane vesicles (called apoptotic bodies). The cell is usually one which overexpresses a PRO224, PRO9783, PRO1108, PRO34000, PRO240, PRO943, hu A33, PRO230, PRO178, PRO199, PRO4333, PRO1336, PRO19598, PRO1083, hu TRPM2 or PRO1801 polypeptide. Preferably the cell is a tumor cell, e.g., a prostate, breast, ovarian, stomach, endometrial, lung, kidney, colon, bladder cell. Various methods are available for evaluating the cellular events associated with apoptosis. For example, phosphatidyl serine (PS) translocation can be measured by annexin binding; DNA fragmentation can be evaluated through DNA laddering; and nuclear/chromatin condensation along with DNA fragmentation can be evaluated by any increase in hypodiploid cells. Preferably, the antibody, oligopeptide or other organic molecule which induces apoptosis is one which results in or in about 2 to 50 fold, preferably in or in about 5 to 50 fold, and most preferably in or in about 10 to 50 fold, induction of annexin binding relative to untreated cell in an annexin binding assay.

Antibody "effector functions" refer to those biological activities attributable to the Fc region (a native sequence Fc region or amino acid sequence variant Fc region) of an antibody, and vary with the antibody isotype. Examples of antibody effector functions include: C1q binding and complement dependent cytotoxicity; Fc receptor binding; antibody-dependent cell-mediated cytotoxicity (ADCC); phagocytosis; down regulation of cell surface receptors (e.g., B cell receptor); and B cell activation.

"Antibody-dependent cell-mediated cytotoxicity" or "ADCC" refers to a form of cytotoxicity in which secreted Ig bound onto Fc receptors (FcRs) present on certain cytotoxic cells (e.g., Natural Killer (NK) cells, neutrophils, and macrophages) enable these cytotoxic effector cells to bind specifically to an antigen-bearing target cell and subsequently kill the target cell with cytotoxins. The antibodies "arm" the cytotoxic cells and are absolutely required for such killing. The primary cells for mediating ADCC, NK cells, express FcγRIII only, whereas monocytes express FcγRI, FcγRII and FcγRIII. FcR expression on hematopoietic cells is summarized in Table 3 on page 464 of Ravetch and Kinet, *Annu. Rev. Immunol.* 9:457-92 (1991). To assess ADCC activity of a molecule of interest, an in vitro ADCC assay, such as that described in U.S. Pat. No. 5,500,362 or 5,821,337 may be performed. Useful effector cells for such assays include peripheral blood mononuclear cells (PBMC) and Natural Killer (NK) cells. Alternatively, or additionally, ADCC activity of the molecule of interest may be assessed in vivo, e.g., in a animal model such as that disclosed in Clynes et al. *Proc. Natl. Acad. Sci. U.S.A.* 95:652-656 (1998).

"Fc receptor" or "FcR" describes a receptor that binds to the Fc region of an antibody. The preferred FcR is a native sequence human FcR. Moreover, a preferred FcR is one which binds an IgG antibody (a gamma receptor) and includes receptors of the FcγRI, FcγRII and FcγRIII subclasses, including allelic variants and alternatively spliced forms of these receptors. FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain. Inhibiting receptor FcγRIIB contains an immunoreceptor tyrosine-based inhibition motif (ITIM) in its cytoplasmic domain. (see review M. in Daëron, *Annu. Rev. Immunol.* 15:203-234 (1997)). FcRs are reviewed in Ravetch and Kinet, *Annu. Rev. Immunol.* 9:457-492 (1991); Capel et al., *Immunomethods* 4:25-34 (1994); and de Haas et al., *J. Lab. Clin. Med.* 126:330-41 (1995). Other FcRs, including those to be identified in the future, are encompassed by the term "FcR" herein. The term also includes the neonatal receptor, FcRn, which is responsible for the transfer of maternal IgGs to the fetus (Guyer et al., *J. Immunol.* 117:587 (1976) and Kim et al., *J. Immunol.* 24:249 (1994)).

"Human effector cells" are leukocytes which express one or more FcRs and perform effector functions. Preferably, the cells express at least FcγRIII and perform ADCC effector function. Examples of human leukocytes which mediate ADCC include peripheral blood mononuclear cells (PBMC), natural killer (NK) cells, monocytes, cytotoxic T cells and neutrophils; with PBMCs and NK cells being preferred. The effector cells may be isolated from a native source, e.g., from blood.

"Complement dependent cytotoxicity" or "CDC" refers to the lysis of a target cell in the presence of complement. Activation of the classical complement pathway is initiated by the binding of the first component of the complement system (C1q) to antibodies (of the appropriate subclass) which are bound to their cognate antigen. To assess complement activation, a CDC assay, e.g., as described in Gazzano-Santoro et al., *J. Immunol. Methods* 202:163 (1996), may be performed.

The terms "cancer" and "cancerous" refer to or describe the physiological condition in mammals that is typically characterized by unregulated cell growth. Examples of cancer include but are not limited to, carcinoma, lymphoma, blastoma, sarcoma, and leukemia. More particular examples of such cancers include squamous cell cancer, lung cancer (including small-cell lung cancer, non-small cell lung cancer, adenocarcinoma of the lung, and squamous carcinoma of the lung), cancer of the peritoneum, hepatocellular cancer, gastric or stomach cancer (including gastrointestinal cancer), pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney or renal cancer, liver cancer, prostate cancer, vulval cancer, thyroid cancer, hepatic carcinoma and various types of head and neck cancer, as well as B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's Macroglobulinemia); chronic lymphocytic leukemia (CLL); acute lymphoblastic leukemia (ALL); Hairy cell leukemia; chronic myeloblastic leukemia; and post-transplant lymphoproliferative disorder (PTLD). Preferably, the cancer comprises a tumor that expresses an IGF receptor, more preferably breast cancer, lung cancer, colorectal cancer, or prostate cancer, and most preferably breast or prostate cancer.

A "chemotherapeutic agent" is a chemical compound useful in the treatment of cancer. Examples of chemotherapeutic agents include alkylating agents such as thiotepa and CYTOXAN® cyclophosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gamma1I and calicheamicin omega1I (see, e.g., Agnew, *Chem. Intl. Ed. Engl.*, 33: 183-186 (1994)); dynemicin, including dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL® paclitaxel (Bristol-Myers Squibb Oncology, Princeton, N.J.), ABRAXANE™ Cremophor-free, albumin-engineered nanoparticle formulation of paclitaxel (American Pharmaceutical Partners, Schaumberg, Ill.), and TAXOTERE® doxetaxel (Rhône-Poulenc Rorer, Antony, France); chloranbucil; GEMZAR® gemcitabine; 6-thioguanine; mercaptopurine; methotrexate; platinum analogs such as cisplatin and carboplatin; vinblastine; platinum; etoposide (VP-16); ifosfamide; mitoxantrone; vincristine; NAVELBINE® vinorelbine; novantrone; teniposide; edatrexate; daunomycin; aminopterin; xeloda; ibandronate; CPT-11; topoisomerase inhibitor RFS 2000; difluoromethylornithine (DMFO); retinoids such as retinoic acid; capecitabine; and pharmaceutically acceptable salts, acids or derivatives of any of the above.

Also included in this definition are anti-hormonal agents that act to regulate or inhibit hormone action on tumors such as anti-estrogens and selective estrogen receptor modulators (SERMs), including, for example, tamoxifen (including NOLVADEX® tamoxifen), raloxifene, droloxifene, 4-hydroxytamoxifen, trioxifene, keoxifene, LY117018, onapristone, and FARESTON toremifene; aromatase inhibitors that inhibit the enzyme aromatase, which regulates estrogen production in the adrenal glands, such as, for example, 4(5)-imidazoles, aminoglutethimide, MEGASE® megestrol acetate, AROMASIN® exemestane, formestanie, fadrozole, RIVISOR® vorozole, FEMARA® letrozole, and ARIMIDEX® anastrozole; and anti-androgens such as flutamide, nilutamide, bicalutamide, leuprolide, and goserelin; as well as troxacitabine (a 1,3-dioxolane nucleoside cytosine analog); antisense oligonucleotides, particularly those which inhibit expression of genes in signaling pathways implicated in abherant cell proliferation, such as, for example, PKC-alpha, Ralf and H-Ras; ribozymes such as a VEGF expression inhibitor (e.g., ANGIOZYME® ribozyme) and a HER2 expression inhibitor; vaccines such as gene therapy vaccines, for example, ALLOVECTIN® vaccine, LEUVECTIN® vaccine, and VAXID® vaccine; PROLEUKIN® rIL-2; LURTOTECAN® topoisomerase 1 inhibitor; ABARELIX® rmRH; and pharmaceutically acceptable salts, acids or derivatives of any of the above.

The terms "cell proliferative disorder" and "proliferative disorder" refer to disorders that are associated with some degree of abnormal cell proliferation. In one aspect of the invention, the cell proliferative disorder is cancer.

"Tumor", as used herein, refers to all neoplastic cell growth and proliferation, whether malignant or benign, and all precancerous and cancerous cells and tissues.

An antibody, oligopeptide or other organic molecule which "induces cell death" is one which causes a viable cell to become nonviable. The cell is one which expresses a PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide, preferably a cell that overexpresses a PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide as compared to a normal cell of the same tissue type. The PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide may be a transmembrane polypeptide expressed on the surface of a cancer cell or may be a polypeptide that is produced and secreted by a cancer cell. Preferably, the cell is a cancer cell, e.g., a breast, ovarian, stomach, endometrial, salivary gland, lung, kidney, colon, thyroid, pancreatic or bladder cell. Cell death in vitro may be determined in the absence of complement and immune effector cells to distinguish cell death induced by antibody-dependent cell-mediated cytotoxicity (ADCC) or complement dependent cytotoxicity (CDC). Thus, the assay for cell death may be performed using heat inactivated serum (i.e., in the absence of complement) and in the absence of immune effector cells. To determine whether the antibody, oligopeptide or other organic molecule is able to induce cell death, loss of membrane integrity as evaluated by uptake of propidium iodide (PI), trypan blue (see Moore et al. *Cytotechnology* 17:1-11 (1995)) or 7AAD can be assessed relative to untreated cells. Preferred cell death-inducing antibodies, oligopeptides or other organic molecules are those which induce PI uptake in the PI uptake assay in BT474 cells.

As used herein, the term "immunoadhesion" designates antibody-like molecules which combine the binding specificity of a heterologous protein (an "adhesion") with the effector functions of immunoglobulin constant domains. Structurally, the immunoadhesions comprise a fusion of an amino acid sequence with the desired binding specificity which is other than the antigen recognition and binding site of an antibody (i.e., is "heterologous"), and an immunoglobulin constant domain sequence. The adhesion part of an immunoadhesion molecule typically is a contiguous amino acid sequence comprising at least the binding site of a receptor or a ligand. The immunoglobulin constant domain sequence in the immunoadhesion may be obtained from any immunoglobulin, such as IgG-1, IgG-2, IgG-3, or IgG-4 subtypes, IgA (including IgA-1 and IgA-2), IgE, IgD or IgM.

The word "label" when used herein refers to a detectable compound or composition which is conjugated directly or indirectly to the antibody so as to generate a "labeled" antibody. The label may be detectable by itself (e.g. radioisotope labels or fluorescent labels) or, in the case of an enzymatic label, may catalyze chemical alteration of a substrate compound or composition which is detectable.

"Replication-preventing agent" is an agent wherein replication, function, and/or growth of the cells is inhibited or prevented, or cells are destroyed, no matter what the mechanism, such as by apoptosis, angiostasis, cytosis, tumoricide, mytosis inhibition, blocking cell cycle progression, arresting cell growth, binding to tumors, acting as cellular mediators, etc. Such agents include a chemotherapeutic agent, cytotoxic agent, cytokine, growth-inhibitory agent, or anti-hormonal agent, e.g., an anti-estrogen compound such as tamoxifen, an anti-progesterone such as onapristone (see, EP 616 812); or an anti-androgen such as flutamide, as well as aromidase inhibitors, or a hormonal agent such as an androgen.

The term "cytotoxic agent" as used herein refers to a substance that inhibits or prevents the function of cells and/or causes destruction of cells. The term is intended to include radioactive isotopes (e.g., $At^{211}$, $I^{131}$, $I^{125}$, $Y^{90}$, $Re^{186}$, $Re^{188}$, $Sm^{153}$, $Bi^{212}$, $P^{32}$ and radioactive isotopes of Lu), chemotherapeutic agents e.g. methotrexate, adriamicin, vinca alkaloids (vincristine, vinblastine, etoposide), doxorubicin, melphalan, mitomycin C, chlorambucil, daunorubicin or other intercalating agents, enzymes and fragments thereof such as nucleolytic enzymes, antibiotics, and toxins such as small molecule toxins or enzymatically active toxins of bacterial, fungal, plant or animal origin, including fragments and/or variants thereof, and the various antitumor or anticancer agents disclosed below. Other cytotoxic agents are described below. A tumoricidal agent causes destruction of tumor cells.

Preferred cytotoxic agents herein for the specific tumor types to use in combination with the antagonists herein are as follows:

1. Prostate cancer: androgens, docetaxel, paclitaxel, estramustine, doxorubicin, mitoxantrone, antibodies to ErbB2 domain(s) such as 2C4 (WO 01/00245; hybridoma ATCC HB-12697), which binds to a region in the extracellular domain of ErbB2 (e.g., any one or more residues in the region from about residue 22 to about residue 584 of ErbB2, inclusive), AVASTIN™ anti-vascular endothelial growth factor (VEGF), TARCEVA™ OSI-774 (erlotinib) (Genenetech and OSI Pharmaceuticals), or other epidermal growth factor receptor tyrosine kinase inhibitors (EGFR TKI's).
2. Stomach cancer: 5-fluorouracil (5FU), XELODA™ capecitabine, methotrexate, etoposide, cisplatin/carboplatin, pacliitaxel, docetaxel, gemcitabine, doxorubicin, and CPT-11 (camptothcin-1; irinotecan, USA Brand Name: CAMPTOSAR®).
3. Pancreatic cancer: gemcitabine, 5FU, XELODA™ capecitabine, CPT-11, docetaxel, paclitaxel, cisplatin, carboplatin, TARCEVA™ erlotinib, and other EGFR TKI's.
4. Colorectal cancer: 5FU, XELODA™ capecitabine, CPT-11, oxaliplatin, AVASTIN™ anti-VEGF, TARCEVA™ erlotinib and other EGFR TKI's, and ERBITUX™ (formerly known as IMC-C225) human:murine-chimerized monoclonal antibody that binds to EGFR and blocks the ability of EGF to initiate receptor activation and signaling to the tumor.

5. Renal cancer: IL-2, interferon alpha, AVASTIN™ anti-VEGF, MEGACE™ (Megestrol acetate) progestin, vinblastine, TARCEVA™ erlotinib, and other EGFR TKI's.

A "growth inhibitory agent" when used herein refers to a compound or composition which inhibits growth of a cell, especially a PRO224-, PRO9783-, PRO1108-, PRO34000-, PRO240-, PRO943-, hu A33-, PRO230-, PRO178-, PRO1199-, PRO4333-, PRO1336-, PRO19598-, PRO1083-, hu TRPM2- or PRO1801-expressing cancer cell, either in vitro or in vivo. Thus, the growth inhibitory agent may be one which significantly reduces the percentage of PRO224-, PRO9783-, PRO1108-, PRO34000-, PRO240-, PRO943-, hu A33-, PRO230-, PRO178-, PRO1199-, PRO4333-, PRO1336-, PRO19598-, PRO1083-, hu TRPM2- or PRO1801-expressing cells in S phase. Examples of growth inhibitory agents include agents that block cell cycle progression (at a place other than S phase), such as agents that induce G1 arrest and M-phase arrest. Classical M-phase blockers include the vincas (vincristine and vinblastine), taxanes, and topoisomerase II inhibitors such as doxorubicin, epirubicin, daunorubicin, etoposide, and bleomycin. Those agents that arrest G1 also spill over into S-phase arrest, for example, DNA alkylating agents such as tamoxifen, prednisone, dacarbazine, mechlorethamine, cisplatin, methotrexate, 5-fluorouracil, and ara-C. Further information can be found in *The Molecular Basis of Cancer*, Mendelsohn and Israel, eds., Chapter 1, entitled "Cell cycle regulation, oncogenes, and antineoplastic drugs" by Murakami et al. (WB Saunders: Philadelphia, 1995), especially p. 13. The taxanes (paclitaxel and docetaxel) are anticancer drugs both derived from the yew tree. Docetaxel (TAXOTERE®, Rhone-Poulenc Rorer), derived from the European yew, is a semisynthetic analogue of paclitaxel (TAXOL®, Bristol-Myers Squibb). Paclitaxel and docetaxel promote the assembly of microtubules from tubulin dimers and stabilize microtubules by preventing depolymerization, which results in the inhibition of mitosis in cells.

"Doxorubicin" is an anthracycline antibiotic. The full chemical name of doxorubicin is (8S-cis)-10-[(3-amino-2,3,6-trideoxy-α-L-lyxo-hexapyranosyl)oxy]-7,8,9,10-tetrahydro-6,8,11-trihydroxy-8-(hydroxyacetyl)-1-methoxy-5,12-naphthacenedione.

The term "cytokine" is a generic term for proteins released by one cell population which act on another cell as intercellular mediators. Examples of such cytokines are lymphokines, monokines, and traditional polypeptide hormones. Included among the cytokines are growth hormone such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor; fibroblast growth factor; prolactin; placental lactogen; tumor necrosis factor-α and -β; mullerian-inhibiting substance; mouse gonadotropin-associated peptide; inhibin; activin; vascular endothelial growth factor; integrin; thrombopoietin (TPO); nerve growth factors such as NGF-β; platelet-growth factor; transforming growth factors (TGFs) such as TGF-α and TGF-β; insulin-like growth factor-I and -II; erythropoietin (EPO); osteoinductive factors; interferons such as interferon-α, -β, and -γ; colony stimulating factors (CSFs) such as macrophage-CSF (M-CSF); granulocyte-macrophage-CSF (GM-CSF); and granulocyte-CSF (G-CSF); interleukins (ILs) such as IL-1, IL-1a, IL-2, IL-3, IL-4, IL-5, IL-6, IL-7, IL-8, IL-9, IL-11, IL-12; a tumor necrosis factor such as TNF-α or TNF-β; and other polypeptide factors including LIF and kit ligand (KL). As used herein, the term cytokine includes proteins from natural sources or from recombinant cell culture and biologically active equivalents of the native sequence cytokines.

The term "package insert" is used to refer to instructions customarily included in commercial packages of therapeutic products, that contain information about the indications, usage, dosage, administration, contraindications and/or warnings concerning the use of such therapeutic products.

The term "gene" refers to (a) a gene containing at least one of the DNA sequences disclosed herein; (b) any DNA sequence that encodes the amino acid sequence encoded by the DNA sequences disclosed herein and/or; (c)) any DNA sequence that hybridizes to the complement of the coding sequences disclosed herein. Preferably, the term includes coding as well as noncoding regions, and preferably includes all sequences necessary for normal gene expression.

The term "gene targeting" refers to a type of homologous recombination that occurs when a fragment of genomic DNA is introduced into a mammalian cell and that fragment locates and recombines with endogenous homologous sequences. Gene targeting by homologous recombination employs recombinant DNA technologies to replace specific genomic sequences with exogenous DNA of particular design.

The term "homologous recombination" refers to the exchange of DNA fragments between two DNA molecules or chromatids at the site of homologous nucleotide sequences.

The term "target gene" (alternatively referred to as "target gene sequence" or "target DNA sequence") refers to any nucleic acid molecule, polynucleotide, or gene to be modified by homologous recombination. The target sequence includes an intact gene, an exon or intron, a regulatory sequence or any region between genes. The target gene my comprise a portion of a particular gene or genetic locus in the individual's genomic DNA.

"Disruption" of a PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 gene occurs when a fragment of genomic DNA locates and recombines with an endogenous homologous sequence wherein the disruption is a deletion of the native gene or a portion thereof, or a mutation in the native gene or wherein the disruption is the functional inactivation of the native gene. Alternatively, sequence disruptions may be generated by nonspecific insertional inactivation using a gene trap vector (i.e. non-human transgenic animals containing and expressing a randomly inserted transgene; see for example U.S. Pat. No. 6,436,707 issued Aug. 20, 2002). These sequence disruptions or modifications may include insertions, missense, frameshift, deletion, or substitutions, or replacements of DNA sequence, or any combination thereof. Insertions include the insertion of entire genes, which may be of animal, plant, fungal, insect, prokaryotic, or viral origin. Disruption, for example, can alter the normal gene product by inhibiting its production partially or completely or by enhancing the normal gene product's activity. Preferably, the disruption is a null disruption, wherein there is no significant expression of the PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 gene.

The term "native expression" refers to the expression of the full-length polypeptide encoded by the PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 gene, at expression levels present in the wild-type mouse. Thus, a disruption in which there is "no native expression" of the endogenous PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 gene refers to a partial or complete reduction of the expression of at least a portion of a polypeptide encoded by an endogenous PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 gene of a single cell, selected cells, or all of the cells of a mammal.

The term "knockout" refers to the disruption of a PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 gene wherein the disruption results in: the functional inactivation of the native gene; the deletion of the native gene or a portion thereof, or a mutation in the native gene.

The term "knock-in" refers to the replacement of the mouse ortholog (or other mouse gene) with a human cDNA encoding any of the specific human PRO224-, PRO9783-, PRO1108-, PRO34000-, PRO240-, PRO943-, hu A33-, PRO230-, PRO178-, PRO1199-, PRO4333-, PRO1336-, PRO19598-, PRO1083-, hu TRPM2- or PRO1801-encoding genes or variants thereof (ie. the disruption results in a replacement of a native mouse gene with a native human gene).

The term "construct" or "targeting construct" refers to an artificially assembled DNA segment to be transferred into a target tissue, cell line or animal. Typically, the targeting construct will include a gene or a nucleic acid sequence of particular interest, a marker gene and appropriate control sequences. As provided herein, the targeting construct comprises a PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 targeting construct. A "PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 targeting construct" includes a DNA sequence homologous to at least one portion of a PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 gene and is capable of producing a disruption in a PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 gene in a host cell.

The term "transgenic cell" refers to a cell containing within its genome a PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 gene that has been disrupted, modified, altered, or replaced completely or partially by the method of gene targeting.

The term "transgenic animal" refers to an animal that contains within its genome a specific gene that has been disrupted or otherwise modified or mutated by the methods described herein or methods otherwise well known in the art. Preferably the non-human transgenic animal is a mammal. More preferably, the mammal is a rodent such as a rat or mouse. In addition, a "transgenic animal" may be a heterozygous animal (i.e., one defective allele and one wild-type allele) or a homozygous animal (i.e., two defective alleles). An embryo is considered to fall within the definition of an animal. The provision of an animal includes the provision of an embryo or foetus in utero, whether by mating or otherwise, and whether or not the embryo goes to term.

As used herein, the terms "selective marker" and "position selection marker" refer to a gene encoding a product that enables only the cells that carry the gene to survive and/or grow under certain conditions. For example, plant and animal cells that express the introduced neomycin resistance ($Neo^r$) gene are resistant to the compound G418. Cells that do not carry the $Neo^r$ gene marker are killed by G418. Other positive selection markers are known to, or are within the purview of, those of ordinary skill in the art.

The term "modulates" or "modulation" as used herein refers to the decrease, inhibition, reduction, amelioration, increase or enhancement of a PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 gene function, expression, activity, or alternatively a phenotype associated with PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 gene.

The term "ameliorates" or "amelioration" as used herein refers to a decrease, reduction or elimination of a condition, disease, disorder, or phenotype, including an abnormality or symptom.

The term "abnormality" refers to any disease, disorder, condition, or phenotype in which PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 is implicated, including pathological conditions and behavioral observations.

TABLE 2

| PRO | XXXXXXXXXXXXXXX | (Length = 15 amino acids) |
|---|---|---|
| Comparison Protein | XXXXXYYYYYYY | (Length = 12 amino acids) |

% amino acid sequence identity = (the number of identically matching amino acid residues between the two polypeptide sequences as determined by ALIGN-2) divided by (the total number of amino acid residues of the PRO polypeptide) = 5 divided by 15 = 33.3%

TABLE 3

| PRO | XXXXXXXXXX | (Length = 10 amino acids) |
|---|---|---|
| Comparison Protein | XXXXXYYYYYYZZYZ | (Length = 15 amino acids) |

% amino acid sequence identity = (the number of identically matching amino acid residues between the two polypeptide sequences as determined by ALIGN-2) divided by (the total number of amino acid residues of the PRO polypeptide) = 5 divided by 10 = 50%

TABLE 4

| PRO-DNA | NNNNNNNNNNNNNN | (Length = 14 nucleotides) |
|---|---|---|
| Comparison DNA | NNNNNNLLLLLLLLLL | (Length = 16 nucleotides) |

% nucleic acid sequence identity = (the number of identically matching nucleotides between the two nucleic acid sequences as determined by ALIGN-2) divided by (the total number of nucleotides of the PRO-DNA nucleic acid sequence) = 6 divided by 14 = 42.9%

TABLE 5

| PRO-DNA | NNNNNNNNNNNN | (Length = 12 nucleotides) |
|---|---|---|
| Comparison DNA | NNNNLLLVV | (Length = 9 nucleotides) |

% nucleic acid sequence identity = (the number of identically matching nucleotides between the two nucleic acid sequences as determined by ALIGN-2) divided by (the total number of nucleotides of the PRO-DNA nucleic acid sequence) = 4 divided by 12 = 33.3%

II. Compositions and Methods of the Invention

A. Full-Length PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 Polypeptides The present invention provides newly identified and isolated nucleotide sequences encoding polypeptides referred to in the present application as PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptides. In particular, cDNAs encoding various PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptides have been identified and isolated, as disclosed in further detail in the Examples below. It is noted that proteins produced in separate expression rounds may be given different PRO numbers but the UNQ number is unique for any given DNA and the encoded protein, and will not be changed. However, for sake of simplicity, in the present specification the protein encoded by the full length native nucleic acid molecules disclosed herein as well as all further native homologues and variants included in the foregoing definition of PRO, will be referred to as "PRO/number", regardless of their origin or mode of preparation.

As disclosed in the Examples below, various cDNA clones have been deposited with the ATCC. The actual nucleotide sequences of those clones can readily be determined by the skilled artisan by sequencing of the deposited clone using routine methods in the art. The predicted amino acid sequence can be determined from the nucleotide sequence using routine skill. For the PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptides and encoding nucleic acids described herein, Applicants have identified what is believed to be the reading frame best identifiable with the sequence information available at the time.

B. PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 Polypeptide Variants In addition to the full-length native sequence PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptides described herein, it is contemplated that PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 variants can be prepared. PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 variants can be prepared by introducing appropriate nucleotide changes into the PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 DNA, and/or by synthesis of the desired PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide. Those skilled in the art will appreciate that amino acid changes may alter post-translational processes of the PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide, such as changing the number or position of glycosylation sites or altering the membrane anchoring characteristics.

Variations in the native full-length sequence PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide or in various domains of the PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide described herein, can be made, for example, using any of the techniques and guidelines for conservative and non-conservative mutations set forth, for instance, in U.S. Pat. No. 5,364,934. Variations may be a substitution, deletion or insertion of one or more codons encoding the PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide that results in a change in the amino acid sequence of the PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide as compared with the native sequence PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide. Optionally the variation is by substitution of at least one amino acid with any other amino acid in one or more of the domains of the PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide. Guidance in determining which amino acid residue may be inserted, substituted or deleted without adversely affecting the desired activity may be found by comparing the sequence of the PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide with that of homologous known protein molecules and minimizing the number of amino acid sequence changes made in regions of high homology. Amino acid substitutions can be the result of replacing one amino acid with another amino acid having similar structural and/or chemical properties, such as the replacement of a leucine with a serine, i.e., conservative amino acid replacements. Insertions or deletions may optionally be in the range of about 1 to 5 amino acids. The variation allowed may be determined by systematically making insertions, deletions or substitutions of amino acids in the sequence and testing the resulting variants for activity exhibited by the full-length or mature native sequence.

PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide fragments are provided herein. Such fragments may be truncated at the N-terminus or C-terminus, or may lack internal residues, for example, when compared with a full length native protein. Certain fragments lack amino acid residues that are not essential for a desired biological activity of the PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide.

PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 fragments may be prepared by any of a number of conventional techniques. Desired peptide fragments may be chemically synthesized. An alternative approach involves generating PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 fragments by enzymatic digestion, e.g., by treating the protein with an enzyme known to cleave proteins at sites defined by particular amino acid residues, or by digesting the DNA with suitable restriction enzymes and isolating the desired fragment. Yet another suitable technique involves isolating and amplifying a DNA fragment encoding a desired polypeptide fragment, by polymerase chain reaction (PCR). Oligonucleotides that define the desired termini of the DNA fragment are employed at the 5' and 3' primers in the PCR. Preferably, PRO224, PRO9783, PRO1108, PRO34000; PRO240, PRO943, hu A33, PRO230, PRO178, PRO1199, PRO4333, PRO1336, PRO19598, PRO1083, hu TRPM2 or PRO1801 polypeptide fragments share at least one biological and/or immunological activity with the native PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide disclosed herein.

Conservative substitutions of interest are shown in Table 6 under the heading of preferred substitutions. If such substitutions result in a change in biological activity, then more substantial changes, denominated exemplary substitutions in Table 6, or as further described below in reference to amino acid classes, are preferably introduced and the products screened.

TABLE 6

| Original Residue | Exemplary Substitutions | Preferred Substitutions |
| --- | --- | --- |
| Ala (A) | Val; Leu; Ile | Val |
| Arg ®) | Lys; Gln; Asn | Lys |
| Asn (N) | Gln; His; Asp, Lys; Arg | Gln |
| Asp (D) | Glu; Asn | Glu |
| Cys ©) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Substantial modifications in function or immunological identity of the PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues are divided into groups based on common side-chain properties:
Amino acids may be grouped according to similarities in the properties of their side chains (in A. L. Lehninger, in Biochemistry, second ed., pp. 73-75, Worth Publishers, New York (1975)):

(1) non-polar: Ala (A), Val (V), Leu (L), Ile (I), Pro (P), Phe (F), Trp (W), Met (M)
(2) uncharged polar: Gly (G), Ser (S), Thr (T), Cys ©), Tyr (Y), Asn (N), Gln (Q)
(3) acidic: Asp (D), Glu (E)
(4) basic: Lys (K), Arg, His (H)
Alternatively, naturally occurring residues may be divided into groups based on common side-chain properties:
(1) hydrophobic: Norleucine, Met, Ala, Val, Leu, Ile;
(2) neutral hydrophilic: Cys, Ser, Thr, Asn, Gln;
(3) acidic: Asp, Glu;
(4) basic: H is, Lys, Arg;
(5) residues that influence chain orientation: Gly, Pro;
(6) aromatic: Trp, Tyr, Phe.

Non-conservative substitutions will entail exchanging a member of one of these classes for another class. Such substituted residues also may be introduced into the conservative substitution sites or, more preferably, into the remaining (non-conserved) sites.

The variations can be made using methods known in the art such as oligonucleotide-mediated (site-directed) mutagenesis, alanine scanning, and PCR mutagenesis. Site-directed mutagenesis [Carter et al., *Nucl. Acids Res.*, 13:4331 (1986); Zoller et al., *Nucl. Acids Res.*, 10:6487 (1987)], cassette mutagenesis [Wells et al., *Gene*, 34:315 (1985)], restriction selection mutagenesis [Wells et al., *Philos. Trans. R. Soc. London SerA*, 317:415 (1986)] or other known techniques can be performed on the cloned DNA to produce the PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 variant DNA.

Scanning amino acid analysis can also be employed to identify one or more amino acids along a contiguous sequence. Among the preferred scanning amino acids are relatively small, neutral amino acids. Such amino acids include alanine, glycine, serine, and cysteine. Alanine is typically a preferred scanning amino acid among this group because it eliminates the side-chain beyond the beta-carbon and is less likely to alter the main-chain conformation of the variant [Cunningham and Wells, *Science*, 244: 1081-1085 (1989)]. Alanine is also typically preferred because it is the most common amino acid. Further, it is frequently found in both buried and exposed positions [Creighton, *The Proteins*, (W.H. Freeman & Co., N.Y.); Chothia, *J. Mol. Biol.*, 150:1 (1976)]. If alanine substitution does not yield adequate amounts of variant, an isoteric amino acid can be used.

C. Modifications of PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801

Covalent modifications of PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptides are included within the scope of this invention. One type of covalent modification includes reacting targeted amino acid residues of a PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide with an organic derivatizing agent that is capable of reacting with selected side chains or the N- or C-terminal residues of the PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide. Derivatization with bifunctional agents is useful, for instance, for crosslinking PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptides to a water-insoluble support matrix or surface for use in the method for purifying anti-PRO224, anti-PRO9783, anti-PRO1108, anti-PRO34000, anti-PRO240, anti-PRO943, anti-hu A33, anti-PRO230, anti-PRO178, anti-PRO1199, anti-PRO4333, anti-PRO1336, anti-PRO19598, anti-PRO1083, anti-hu TRPM2 or anti-PRO1801 antibodies, and vice-versa. Commonly used crosslinking agents include, e.g., 1,1-bis(diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis(succinimidylpropionate), bifunctional maleimides such as bis-N-maleimido-1,8-octane and agents such as methyl-3-[(p-azidophenyl)dithio]propioimidate.

Other modifications include deamidation of glutaminyl and asparaginyl residues to the corresponding glutamyl and aspartyl residues, respectively, hydroxylation of proline and lysine, phosphorylation of hydroxyl groups of seryl or threonyl residues, methylation of the α-amino groups of lysine, arginine, and histidine side chains [T. E. Creighton, *Proteins: Structure and Molecular Properties*, W.H. Freeman & Co., San Francisco, pp. 79-86 (1983)], acetylation of the N-terminal amine, and amidation of any C-terminal carboxyl group.

Another type of covalent modification of the PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide included within the scope of this invention comprises altering the native glycosylation pattern of the polypeptide. "Altering the native glycosylation pattern" is intended for purposes herein to mean deleting one or more carbohydrate moieties found in native sequence PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptides (either by removing the underlying glycosylation site or by deleting the glycosylation by chemical and/or enzymatic means), and/or adding one or more glycosylation sites that are not present in the native sequence PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide. In addition, the phrase includes qualitative changes in the glycosylation of the native proteins, involving a change in the nature and proportions of the various carbohydrate moieties present.

Addition of glycosylation sites to the PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide may be accomplished by altering the amino acid sequence. The alteration may be made, for example, by the addition of, or substitution by, one or more serine or threonine residues to the native sequence PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 (for O-linked glycosylation sites). The PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 amino acid sequence may optionally be altered through changes at the DNA level, particularly by mutating the DNA encoding the PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide at preselected bases such that codons are generated that will translate into the desired amino acids.

Another means of increasing the number of carbohydrate moieties on the PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide is by chemical or enzymatic coupling of glycosides to the polypeptide. Such methods are described in the art, e.g., in WO 87/05330 published 11 Sep. 1987, and in Aplin and Wriston, *CRC Crit. Rev. Biochem.*, pp. 259-306 (1981).

Removal of carbohydrate moieties present on the PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide may be accomplished chemically or enzymatically or by mutational substitution of codons encoding for amino acid residues that serve as targets for glycosylation. Chemical deglycosylation techniques are known in the art and described, for instance, by Hakimuddin, et al., *Arch. Biochem. Biophys.*, 259:52 (1987) and by Edge et al., *Anal. Biochem.*, 118:131 (1981). Enzymatic cleavage of carbohydrate moieties on polypeptides can be achieved by the use of a variety of endo- and exo-glycosidases as described by Thotakura et al., *Meth. Enzymol.*, 138:350 (1987).

Another type of covalent modification of PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptides comprises linking the PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide to one of a variety of nonproteinaceous polymers, e.g., polyethylene glycol (PEG), polypropylene glycol, or polyoxyalkylenes, in the manner set forth in U.S. Pat. No. 4,640,835; 4,496,689; 4,301,144; 4,670,417; 4,791,192 or 4,179,337.

The PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptides of the present invention may also be modified in a way to form a chimeric molecule comprising the PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide fused to another, heterologous polypeptide or amino acid sequence.

Such a chimeric molecule comprises a fusion of the PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide with a tag polypeptide which provides an epitope to which an anti-tag antibody can selectively bind. The epitope tag is generally placed at the amino- or carboxyl-terminus of the PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide. The presence of such epitope-tagged forms of the PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide can be detected using an antibody against the tag polypeptide. Also, provision of the epitope tag enables the PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide to be readily purified by affinity purification using an anti-tag antibody or another type of affinity matrix that binds to the epitope tag. Various tag polypeptides and their respective antibodies are well known in the art. Examples include poly-histidine (poly-his) or poly-histidine-glycine (poly-his-gly) tags; the flu HA tag polypeptide and its antibody 12CA5 [Field et al., *Mol. Cell. Biol.*, 8:2159-2165 (1988)]; the c-myc tag and the 8F9, 3C7, 6E10, G4, B7 and 9E10 antibodies thereto [Evan et al., *Molecular and Cellular Biology*, 5:3610-3616 (1985)]; and the Herpes Simplex virus glycoprotein D (gD) tag and its antibody [Paborsky et al., *Protein Engineering*, 3(6):547-553 (1990)]. Other tag polypeptides include the Flag-peptide [Hopp et al., *BioTechnology*, 6:1204-1210 (1988)]; the KT3 epitope peptide [Martin et al., *Science*, 255:192-194 (1992)]; an α-tubulin epitope peptide [Skinner et al., *J. Biol. Chem.*, 266:15163-15166 (1991)]; and the T7 gene 10 protein peptide tag [Lutz-Freyermuth et al., *Proc. Natl. Acad. Sci. USA*, 87:6393-6397 (1990)].

The chimeric molecule may comprise a fusion of the PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide with an immunoglobulin or a particular region of an immunoglobulin. For a bivalent form of the chimeric molecule (also referred to as an "immunoadhesin"), such a fusion could be to the Fc region of an IgG molecule. The Ig fusions preferably include the substitution of a soluble (transmembrane domain deleted or inactivated) form of a PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide in place of at least one variable region within an Ig molecule. In a particularly preferred aspect of the invention, the immunoglobulin fusion includes the hinge, CH2 and CH3, or the hinge, CH1, CH2 and CH3 regions of an IgG1 molecule. For the production of immunoglobulin fusions see also U.S. Pat. No. 5,428,130 issued Jun. 27, 1995.

D. Preparation of PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 Polypeptides The description below relates primarily to production of PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptides by culturing cells transformed or transfected with a vector containing PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 nucleic acid. It is, of course, contemplated that alternative methods, which are well known in the art, may be employed to prepare PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptides. For instance, the PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 sequence, or portions thereof, may be produced by direct peptide synthesis using solid-phase techniques [see, e.g., Stewart et al., *Solid-Phase Peptide Synthesis*, W.H. Freeman Co., San Francisco, Calif. (1969); Merrifield, *J. Am. Chem. Soc.*, 85:2149-2154 (1963)]. In vitro protein synthesis may be performed using manual techniques or by automation. Automated synthesis may be accomplished, for instance, using an Applied Biosystems Peptide Synthesizer (Foster City, Calif.) using manufacturer's instructions. Various portions of the PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide may be chemically synthesized separately and combined using chemical or enzymatic methods to produce the full-length PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide.

1. Isolation of DNA Encoding PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 Polypeptides DNA encoding PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptides may be obtained from a cDNA library prepared from tissue believed to possess the PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 mRNA and to express it at a detectable level. Accordingly, human PRO224-, PRO9783-, PRO1108-, PRO34000-, PRO240-, PRO943-, hu A33-, PRO230-, PRO178-, PRO1199-, PRO4333-, PRO1336-, PRO19598-, PRO1083-, hu TRPM2- or PRO1801-DNA can be conveniently obtained from a cDNA library prepared from human tissue, such as described in the Examples. The PRO224-, PRO9783-, PRO1108-, PRO34000-, PRO240-, PRO943-, hu A33-, PRO230-, PRO178-, PRO1199-, PRO4333-, PRO1336-, PRO19598-, PRO1083-, hu TRPM2- or PRO1801-encoding gene may also be obtained from a genomic library or by known synthetic procedures (e.g., automated nucleic acid synthesis).

Libraries can be screened with probes (such as antibodies to the PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide or oligonucleotides of at least about 20-80 bases) designed to identify the gene of interest or the protein encoded by it. Screening the cDNA or genomic library with the selected probe may be conducted using standard procedures, such as described in Sambrook et al., *Molecular Cloning: A Laboratory Manual* (New York: Cold Spring Harbor Laboratory Press, 1989). An alternative means to isolate the gene encoding PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 is to use PCR methodology [Sambrook et al., supra; Dieffenbach et al., *PCR Primer: A Laboratory Manual* (Cold Spring Harbor Laboratory Press, 1995)].

The Examples below describe techniques for screening a cDNA library. The oligonucleotide sequences selected as probes should be of sufficient length and sufficiently unambiguous that false positives are minimized. The oligonucleotide is preferably labeled such that it can be detected upon hybridization to DNA in the library being screened. Methods of labeling are well known in the art, and include the use of radiolabels like $^{32}$P-labeled ATP, biotinylation or enzyme labeling. Hybridization conditions, including moderate stringency and high stringency, are provided in Sambrook et al., supra.

Sequences identified in such library screening methods can be compared and aligned to other known sequences deposited and available in public databases such as GenBank or other private sequence databases. Sequence identity (at either the amino acid or nucleotide level) within defined regions of the molecule or across the full-length sequence can be determined using methods known in the art and as described herein.

Nucleic acid having protein coding sequence may be obtained by screening selected cDNA or genomic libraries using the deduced amino acid sequence disclosed herein for the first time, and, if necessary, using conventional primer extension procedures as described in Sambrook et al., supra, to detect precursors and processing intermediates of mRNA that may not have been reverse-transcribed into cDNA.

2. Selection and Transformation of Host Cells

Host cells are transfected or transformed with expression or cloning vectors described herein for PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide production and cultured in conventional nutrient media modified as appropriate for inducing promoters, selecting transformants, or amplifying the genes encoding the desired sequences. The culture conditions, such as media, temperature, pH and the like, can be selected by the skilled artisan without undue experimentation. In general, principles, protocols, and practical techniques for maximizing the productivity of cell cultures can be found in *Mammalian Cell Biotechnology: a Practical Approach*, M. Butler, ed. (IPL Press, 1991) and Sambrook et al., supra.

Methods of eukaryotic cell transfection and prokaryotic cell transformation are known to the ordinarily skilled artisan, for example, $CaCl_2$, $CaPO_4$, liposome-mediated and electroporation. Depending on the host cell used, transformation is performed using standard techniques appropriate to such cells. The calcium treatment employing calcium chloride, as described in Sambrook et al., supra, or electroporation is generally used for prokaryotes. Infection with *Agrobacterium tumefaciens* is used for transformation of certain plant cells, as described by Shaw et al., *Gene*, 23:315 (1983) and WO 89/05859 published 29 Jun. 1989. For mammalian cells without such cell walls, the calcium phosphate precipitation method of Graham and van der Eb, *Virology*, 52:456-457 (1978) can be employed. General aspects of mammalian cell host system transfections have been described in U.S. Pat. No. 4,399,216. Transformations into yeast are typically carried out according to the method of Van Solingen et al., *J. Bact.*, 130:946 (1977) and Hsiao et al., *Proc. Natl. Acad. Sci. (USA)*, 76:3829 (1979). However, other methods for introducing DNA into cells, such as by nuclear microinjection, electroporation, bacterial protoplast fusion with intact cells, or polycations, e.g., polybrene, polyornithine, may also be used. For various techniques for transforming mammalian cells, see Keown et al., *Methods in Enzymology*, 185:527-537 (1990) and Mansour et al., *Nature*, 336:348-352 (1988).

Suitable host cells for cloning or expressing the DNA in the vectors herein include prokaryote, yeast, or higher eukaryote cells. Suitable prokaryotes include but are not limited to eubacteria, such as Gram-negative or Gram-positive organisms, for example, Enterobacteriaceae such as *E. coli*. Various *E. coli* strains are publicly available, such as *E. coli* K12 strain MM294 (ATCC 31,446); *E. coli* X1776 (ATCC 31,537); *E. coli* strain W3110 (ATCC 27,325) and K5 772 (ATCC 53,635). Other suitable prokaryotic host cells include Enterobacteriaceae such as *Escherichia*, e.g., *E. coli, Enterobacter, Erwinia, Klebsiella, Proteus, Salmonella*, e.g., *Salmonella typhimurium, Serratia*, e.g., *Serratia marcescans*, and *Shigella*, as well as *Bacilli* such as *B. subtilis* and *B. licheniformis* (e.g., *B. licheniformis* 41P disclosed in DD 266,710 published 12 Apr. 1989), *Pseudomonas* such as *P. aeruginosa*, and *Streptomyces*. These examples are illustrative rather than limiting. Strain W3110 is one particularly preferred host or parent host because it is a common host strain for recombinant DNA product fermentations. Preferably, the host cell secretes minimal amounts of proteolytic enzymes. For example, strain W3110 may be modified to effect a genetic mutation in the genes encoding proteins endogenous to the host, with examples of such hosts including *E. coli* W3110 strain 1A2, which has the complete genotype tonA; *E. coli* W3110 strain 9E4, which has the complete genotype tonA ptr3; *E. coli* W3110 strain 27C7 (ATCC 55,244), which has the complete genotype tonA ptr3 phoA E15 (argF-lac) 169 degP ompT kan$^r$; *E. coli* W3110 strain 37D6, which has the complete genotype tonA ptr3 phoA E15 (argF-lac) 169 degP ompT rbs7 ilvG kan$^r$; *E. coli* W3110 strain 40B4, which is strain 37D6 with a non-kanamycin resistant degP deletion mutation; and an *E. coli* strain having mutant periplasmic protease disclosed in U.S. Pat. No. 4,946,783 issued 7 Aug. 1990. Alternatively, in vitro methods of cloning, e.g., PCR or other nucleic acid polymerase reactions, are suitable.

In addition to prokaryotes, eukaryotic microbes such as filamentous fungi or yeast are suitable cloning or expression hosts for PRO224-, PRO9783-, PRO1108-, PRO34000-, PRO240-, PRO943-, hu A33-, PRO230-, PRO178-, PRO1199-, PRO4333-, PRO1336-, PRO19598-, PRO1083-, hu TRPM2- or PRO1801-encoding vectors. *Saccharomyces cerevisiae* is a commonly used lower eukaryotic host microorganism. Others include *Schizosaccharomyces pombe* (Beach and Nurse, *Nature*, 290: 140 [1981]; EP 139,383 published 2 May 1985); *Kluyveromyces* hosts (U.S. Pat. No. 4,943,529; Fleer et al., *Bio/Technology*, 9:968-975 (1991)) such as, e.g., *K. lactis* (MW98-8C, CBS683, CBS4574; Louvencourt et al., *J. Bacteriol.*, 154(2):737-742 [1983]), *K. fragilis* (ATCC 12,424), *K. bulgaricus* (ATCC 16,045), *K. wickeramii* (ATCC 24,178), *K. waltii* (ATCC 56,500), *K. drosophilarum* (ATCC 36,906; Van den Berg et al., *Bio/Technology*, 8:135 (1990)), *K. thermotolerans*, and *K. marxianus; yarrowia* (EP 402,226); *Pichia pastoris* (EP 183,070; Sreekrishna et al., *J. Basic Microbiol.*, 28:265-278 [1988]); *Candida; Trichoderma reesia* (EP 244,234); *Neurospora crassa* (Case et al., *Proc. Natl. Acad. Sci. USA*, 76:5259-5263 [1979]); *Schwanniomyces* such as *Schwanniomyces occidentalis* (EP 394,538 published 31 Oct. 1990); and filamentous fungi such as, e.g., *Neurospora, Penicillium, Tolypocladium* (WO 91/00357 published 10 Jan. 1991), and *Aspergillus* hosts such as *A. nidulans* (Ballance et al., *Biochem. Biophys. Res. Commun.*, 112:284-289 [1983]; Tilburn et al., *Gene*, 26:205-221 [1983]; Yelton et al., *Proc. Natl. Acad. Sci. USA*, 81: 1470-1474 [1984]) and *A. niger* (Kelly and Hynes, *EMBO J.*, 4:475-479 [1985]). Methylotropic yeasts are suitable herein and include, but are not limited to, yeast capable of growth on methanol selected from the genera consisting of *Hansenula, Candida, Kloeckera, Pichia, Saccharomyces, Torulopsis*, and *Rhodotorula*. A list of specific species that are exemplary of this class of yeasts may be found in C. Anthony, *The Biochemistry of Methylotrophs*, 269 (1982).

Suitable host cells for the expression of glycosylated PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptides are derived from multicellular organisms. Examples of invertebrate cells include insect cells such as *Drosophila* S2 and *Spodoptera* Sf9, as well as plant cells. Examples of useful mammalian host cell lines include Chinese hamster ovary (CHO) and COS cells. More specific examples include monkey kidney CV1 line transformed by SV40 (COS-7, ATCC CRL 1651); human embryonic kidney line (293 or 293 cells subcloned for growth in suspension culture, Graham et al., *J. Gen Virol.*, 36:59 (1977)); Chinese hamster ovary cells/–DHFR (CHO, Urlaub and Chasin, *Proc. Natl. Acad. Sci. USA*, 77:4216 (1980)); mouse sertoli cells (TM4, Mather, *Biol. Reprod.*, 23:243-251 (1980)); human lung cells (W138, ATCC CCL 75); human liver cells (Hep G2, HB 8065); and mouse mammary tumor (MMT 060562, ATCC CCL51). The selection of the appropriate host cell is deemed to be within the skill in the art.

3. Selection and Use of a Replicable Vector

The nucleic acid (e.g., cDNA or genomic DNA) encoding PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptides may be inserted into a replicable vector for cloning (amplification of the DNA) or for expression. Various vectors are publicly available. The vector may, for example, be in the form of a plasmid, cosmid, viral particle, or phage. The appropriate nucleic acid sequence may be inserted into the vector by a variety of procedures. In general, DNA is inserted into an appropriate restriction endonuclease site(s) using techniques known in the art. Vector components generally include, but are not limited to, one or more of a signal sequence, an origin of replication, one or more marker genes, an enhancer element, a promoter, and a transcription termination sequence. Construction of suitable vectors containing one or more of these components employs standard ligation techniques which are known to the skilled artisan.

The PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide may be produced recombinantly not only directly, but also as a fusion polypeptide with a heterologous polypeptide, which may be a signal sequence or other polypeptide having a specific cleavage site at the N-terminus of the mature protein or polypeptide. In general, the signal sequence may be a component of the vector, or it may be a part of the PRO224-, PRO9783-, PRO1108-, PRO34000-, PRO240-, PRO943-, hu A33-, PRO230-, PRO178-, PRO199-, PRO4333-, PRO1336-, PRO19598-, PRO1083-, hu TRPM2- or PRO1801-encoding DNA that is inserted into the vector. The signal sequence may be a prokaryotic signal sequence selected, for example, from the group of the alkaline phosphatase, penicillinase, Ipp, or heat-stable enterotoxin II leaders. For yeast secretion the signal sequence may be, e.g., the yeast invertase leader, alpha factor leader (including *Saccharomyces* and *Kluyveromyces* α-factor leaders, the latter described in U.S. Pat. No. 5,010,182), or acid phosphatase leader, the *C. albicans* glucoamylase leader (EP 362,179 published 4 Apr. 1990), or the signal described in WO 90/13646 published 15 Nov. 1990. In mammalian cell expression, mammalian signal sequences may be used to direct secretion of the protein, such as signal sequences from secreted polypeptides of the same or related species, as well as viral secretory leaders.

Both expression and cloning vectors contain a nucleic acid sequence that enables the vector to replicate in one or more selected host cells. Such sequences are well known for a variety of bacteria, yeast, and viruses. The origin of replication from the plasmid pBR322 is suitable for most Gram-negative bacteria, the 2μ plasmid origin is suitable for yeast, and various viral origins (SV40, polyoma, adenovirus, VSV or BPV) are useful for cloning vectors in mammalian cells.

Expression and cloning vectors will typically contain a selection gene, also termed a selectable marker. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for *Bacilli*.

An example of suitable selectable markers for mammalian cells are those that enable the identification of cells competent to take up the PRO224-, PRO9783-, PRO1108-, PRO34000-, PRO240-, PRO943-, hu A33-, PRO230-, PRO178-, PRO1199-, PRO4333-, PRO1336-, PRO19598-, PRO1083-, hu TRPM2- or PRO1801-encoding nucleic acid, such as DHFR or thymidine kinase. An appropriate host cell when wild-type DHFR is employed is the CHO cell line deficient in DHFR activity, prepared and propagated as described by Urlaub et al., *Proc. Natl. Acad. Sci. USA*, 77:4216 (1980). A suitable selection gene for use in yeast is the trp1 gene present in the yeast plasmid YRp7 [Stinchcomb et al., *Nature*, 282:39 (1979); Kingsman et al., *Gene*, 7:141 (1979); Tschemper et al., *Gene*, 10:157 (1980)]. The trp1 gene provides a selection marker for a mutant strain of yeast lacking the ability to grow in tryptophan, for example, ATCC No. 44076 or PEP4-1 [Jones, *Genetics*, 85:12 (1977)].

Expression and cloning vectors usually contain a promoter operably linked to the PRO224-, PRO9783-, PRO1108-, PRO34000-, PRO240-, PRO943-, hu A33-, PRO230-, PRO178-, PRO1199-, PRO4333-, PRO1336-, PRO19598-, PRO10837, hu TRPM2- or PRO1801-encoding nucleic acid sequence to direct mRNA synthesis. Promoters recognized by a variety of potential host cells are well known. Promoters suitable for use with prokaryotic hosts include the β-lactamase and lactose promoter systems [Chang et al., *Nature*, 275:615 (1978); Goeddel et al., *Nature*, 281:544 (1979)], alkaline phosphatase, a tryptophan (trp) promoter system [Goeddel, *Nucleic Acids Res.*, 8:4057 (1980); EP 36,776], and hybrid promoters such as the tac promoter [deBoer et al., *Proc. Natl. Acad. Sci. USA*, 80:21-25 (1983)]. Promoters for use in bacterial systems also will contain a Shine-Dalgarno (S.D.) sequence operably linked to the DNA encoding PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptides.

Examples of suitable promoting sequences for use with yeast hosts include the promoters for 3-phosphoglycerate kinase [Hitzeman et al., *J. Biol. Chem.*, 255:2073 (1980)] or other glycolytic enzymes [Hess et al., *J. Adv. Enzyme Reg.*, 7:149 (1968); Holland, Biochemistry, 17:4900 (1978)], such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in EP 73,657.

PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 transcription from vectors in mammalian host cells is controlled, for example, by promoters obtained from the genomes of viruses such as polyoma virus, fowlpox virus (UK 2,211,504 published 5 Jul. 1989), adenovirus (such as Adenovirus 2), bovine papilloma virus, avian sarcoma virus, cytomegalovirus, a retrovirus, hepatitis-B virus and Simian Virus 40 (SV40), from heterologous mammalian promoters, e.g., the actin promoter or an immunoglobulin promoter, and from heat-shock promoters, provided such promoters are compatible with the host cell systems.

Transcription of a DNA encoding the PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide by higher eukaryotes may be increased by inserting an enhancer sequence into the vector. Enhancers are cis-acting elements of DNA, usually about from 10 to 300 bp, that act on a promoter to increase its transcription. Many enhancer sequences are now known from mammalian genes (globin, elastase, albumin, α-fetoprotein, and insulin). Typically, however, one will use an enhancer from a eukaryotic cell virus. Examples include the SV40 enhancer on the late side of the replication origin (bp 100-270), the cytomegalovirus early promoter enhancer, the polyoma enhancer on the late side of the replication origin, and adenovirus enhancers. The enhancer may be spliced into the vector at a position 5' or 3' to the PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 coding sequence, but is preferably located at a site 5' from the promoter.

Expression vectors used in eukaryotic host cells (yeast, fungi, insect, plant, animal, human, or nucleated cells from other multicellular organisms) will also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptides.

Still other methods, vectors, and host cells suitable for adaptation to the synthesis of PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptides in recombinant vertebrate cell culture are described in Gething et al., Nature, 293:620-625 (1981); Mantei et al., Nature, 281:40-46 (1979); EP 117,060; and EP 117,058.

4. Detecting Gene Amplification/Expression

Gene amplification and/or expression may be measured in a sample directly, for example, by conventional Southern blotting, Northern blotting to quantitate the transcription of mRNA [Thomas, Proc. Natl. Acad. Sci. USA, 77:5201-5205 (1980)], dot blotting (DNA analysis), or in situ hybridization, using an appropriately labeled probe, based on the sequences provided herein. Alternatively, antibodies may be employed that can recognize specific duplexes, including DNA duplexes, RNA duplexes, and DNA-RNA hybrid duplexes or DNA-protein duplexes. The antibodies in turn may be labeled and the assay may be carried out where the duplex is bound to a surface, so that upon the formation of duplex on the surface, the presence of antibody bound to the duplex can be detected.

Gene expression, alternatively, may be measured by immunological methods, such as immunohistochemical staining of cells or tissue sections and assay of cell culture or body fluids, to quantitate directly the expression of gene product. Antibodies useful for immunohistochemical staining and/or assay of sample fluids may be either monoclonal or polyclonal, and may be prepared in any mammal. Conveniently, the antibodies may be prepared against a native sequence PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide or against a synthetic peptide based on the DNA sequences provided herein or against exogenous sequence fused to PRO224, PRO9783, PRO11108, PRO34000, PRO240, PRO943, hu A33, PRO230, PRO178, PRO1199, PRO4333, PRO1336, PRO19598, PRO1083, hu TRPM2 or PRO1801 DNA and encoding a specific antibody epitope.

5. Purification of Polypeptide

Forms of PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptides may be recovered from culture medium or from host cell lysates. If membrane-bound, it can be released from the membrane using a suitable detergent solution (e.g. Triton-X 100) or by enzymatic cleavage. Cells employed in expression of PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptides can be disrupted by various physical or chemical means, such as freeze-thaw cycling, sonication, mechanical disruption, or cell lysing agents.

It may be desired to purify PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptides from recombinant cell proteins or polypeptides. The following procedures are exemplary of suitable purification procedures: by fractionation on an ion-exchange column; ethanol precipitation; reverse phase HPLC; chromatography on silica or on a cation-exchange resin such as DEAE; chromatofocusing; SDS-PAGE; ammonium sulfate precipitation; gel filtration using, for example, Sephadex G-75; protein A Sepharose columns to remove contaminants such as IgG; and metal chelating columns to bind epitope-tagged forms of the PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide. Various methods of protein purification may be employed and such methods are known in the art and described for example in Deutscher, Methods in Enzymology, 182 (1990); Scopes, Protein Purification: Principles and Practice, Springer-Verlag, New York (1982). The purification step(s) selected will depend, for example, on the nature of the production process used and the particular PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide produced.

E. Uses for PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 Polypeptides Nucleotide sequences (or their complement) encoding PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptides have various applications in the art of molecular biology, including uses as hybridization probes, in chromosome and gene mapping and in the generation of anti-sense RNA and DNA. PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 nucleic acid will also be useful for the preparation of PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptides by the recombinant techniques described herein.

The full-length native sequence PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 gene, or portions thereof, may be used as hybridization probes for a cDNA library to isolate the full-length PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 cDNA or to isolate still other cDNAs (for instance, those encoding naturally-occurring variants of PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptides or PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptides from other species) which have a desired sequence identity to the native PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 sequence disclosed herein. Optionally, the length of the probes will be about 20 to about 50 bases. The hybridization probes may be derived from at least partially novel regions of the full length native nucleotide sequence wherein those regions may be determined without undue experimentation or from genomic sequences including promoters, enhancer elements and introns of native sequence PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801. By way of example, a screening method will comprise isolating the coding region of the PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 gene using the known DNA sequence to synthesize a selected probe of about 40 bases. Hybridization probes may be labeled by a variety of labels, including radionucleotides such as $^{32}P$ or $^{35}S$, or enzymatic labels such as alkaline phosphatase coupled to the probe via avidin/biotin coupling systems. Labeled probes having a sequence complementary to that of the PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 gene of the present invention can be used to screen libraries of human cDNA, genomic DNA or mRNA to determine which members of such libraries the probe hybridizes to. Hybridization techniques are described in further detail in the Examples below.

Any EST sequences disclosed in the present application may similarly be employed as probes, using the methods disclosed herein.

Other useful fragments of the PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 nucleic acids include antisense or sense oligonucleotides comprising a singe-stranded nucleic acid sequence (either RNA or DNA) capable of binding to target PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 mRNA (sense) or PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 DNA (antisense) sequences. Antisense or sense oligonucleotides, according to the present invention, comprise a fragment of the coding region of PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 DNA. Such a fragment generally comprises at least about 14 nucleotides, preferably from about 14 to 30 nucleotides. The ability to derive an antisense or a sense oligonucleotide, based upon a cDNA sequence encoding a given protein is described in, for example, Stein and Cohen (*Cancer Res.* 48:2659, 1988) and van der Krol et al. (*BioTechniques* 6:958, 1988).

Binding of antisense or sense oligonucleotides to target nucleic acid sequences results in the formation of duplexes that block transcription or translation of the target sequence by one of several means, including enhanced degradation of the duplexes, premature termination of transcription or translation, or by other means. The antisense oligonucleotides thus may be used to block expression of PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801. Antisense or sense oligonucleotides further comprise oligonucleotides having modified sugar-phosphodiester backbones (or other sugar linkages, such as those described in WO 91/06629) and wherein such sugar linkages are resistant to endogenous nucleases. Such oligonucleotides with resistant sugar linkages are stable in vivo (i.e., capable of resisting enzymatic degradation) but retain sequence specificity to be able to bind to target nucleotide sequences.

Other examples of sense or antisense oligonucleotides include those oligonucleotides which are covalently linked to organic moieties, such as those described in WO 90/10048, and other moieties that increases affinity of the oligonucleotide for a target nucleic acid sequence, such as poly-(L-lysine). Further still, intercalating agents, such as ellipticine, and alkylating agents or metal complexes may be attached to sense or antisense oligonucleotides to modify binding specificities of the antisense or sense oligonucleotide for the target nucleotide sequence.

Antisense or sense oligonucleotides may be introduced into a cell containing the target nucleic acid sequence by any gene transfer method, including, for example, $CaPO_4$-mediated DNA transfection, electroporation, or by using gene transfer vectors such as Epstein-Barr virus. In a preferred procedure, an antisense or sense oligonucleotide is inserted into a suitable retroviral vector. A cell containing the target nucleic acid sequence is contacted with the recombinant retroviral vector, either in vivo or ex vivo. Suitable retroviral vectors include, but are not limited to, those derived from the murine retrovirus M-MuLV, N2 (a retrovirus derived from M-MuLV), or the double copy vectors designated DCT5A, DCT5B and DCT5C (see WO 90/13641).

Sense or antisense oligonucleotides also may be introduced into a cell containing the target nucleotide sequence by formation of a conjugate with a ligand binding molecule, as described in WO 91/04753. Suitable ligand binding molecules include, but are not limited to, cell surface receptors, growth factors, other cytokines, or other ligands that bind to cell surface receptors. Preferably, conjugation of the ligand binding molecule does not substantially interfere with the ability of the ligand binding molecule to bind to its corresponding molecule or receptor, or block entry of the sense or antisense oligonucleotide or its conjugated version into the cell.

Alternatively, a sense or an antisense oligonucleotide may be introduced into a cell containing the target nucleic acid sequence by formation of an oligonucleotide-lipid complex, as described in WO 90/10448. The sense or antisense oligonucleotide-lipid complex is preferably dissociated within the cell by an endogenous lipase.

Antisense or sense RNA or DNA molecules are generally at least about 5 bases in length, about 10 bases in length, about 15 bases in length, about 20 bases in length, about 25 bases in length, about 30 bases in length, about 35 bases in length, about 40 bases in length, about 45 bases in length, about 50 bases in length, about 55 bases in length, about 60 bases in length, about 65 bases in length, about 70 bases in length, about 75 bases in length, about 80 bases in length, about 85 bases in length, about 90 bases in length, about 95 bases in length, about 100 bases in length, or more.

The probes may also be employed in PCR techniques to generate a pool of sequences for identification of closely related PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 coding sequences.

Nucleotide sequences encoding a PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide can also be used to construct hybridization probes for mapping the gene which encodes that PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide and for the genetic analysis of individuals with genetic disorders. The nucleotide sequences provided herein may be mapped to a chromosome and specific regions of a chromosome using known techniques, such as in situ hybridization, linkage analysis against known chromosomal markers, and hybridization screening with libraries.

When the coding sequences for PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 encode a protein which binds to another protein (for example, where the PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 is a receptor), the PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide can be used in assays to identify the other proteins or molecules involved in the binding interaction. By such methods, inhibitors of the receptor/ligand binding interaction can be identified. Proteins involved in such binding interactions can also be used to screen for peptide or small molecule inhibitors or agonists of the binding interaction. Also, the receptor PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 can be used to isolate correlative ligand(s). Screening assays can be designed to find lead compounds that mimic the biological activity of a native PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide or a receptor for PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptides. Such screening assays will include assays amenable to high-throughput screening of chemical libraries, making them particularly suitable for identifying small molecule drug candidates. Small molecules contemplated include synthetic organic or inorganic compounds. The assays can be performed in a variety of formats, including protein-protein binding assays, biochemical screening assays, immunoassays and cell based assays, which are well characterized in the art.

Nucleic acids which encode PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptides or its modified forms can also be used to generate either transgenic animals or "knock out" animals which, in turn, are useful in the development and screening of therapeutically useful reagents. A transgenic animal (e.g., a mouse or rat) is an animal having cells that contain a transgene, which transgene was introduced into the animal or an ancestor of the animal at a prenatal, e.g., an embryonic stage. A transgene is a DNA which is integrated into the genome of a cell from which a transgenic animal develops. The invention provides cDNA encoding a PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide which can be used to clone genomic DNA encoding a PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide in accordance with established techniques and the genomic sequences used to generate transgenic animals that contain cells which express DNA encoding PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptides. Any technique known in the art may be used to introduce a target gene transgene into animals to produce the founder lines of transgenic animals. Such techniques include, but are not limited to pronuclear microinjection (U.S. Pat. Nos. 4,873,191, 4,736,866 and 4,870,009); retrovirus mediated gene transfer into germ lines (Van der Putten, et al., *Proc. Natl. Acad. Sci., USA,* 82:6148-6152 (1985)); gene targeting in embryonic stem cells (Thompson, et al., *Cell,* 56:313-321 (1989)); nonspecific insertional inactivation using a gene trap vector (U.S. Pat. No. 6,436,707); electroporation of embryos (Lo, *Mol. Cell. Biol.,* 3:1803-1814 (1983)); and sperm-mediated gene transfer (Lavitrano, et al., *Cell,* 57:717-723 (1989)); etc. Typically, particular cells would be targeted for a PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 transgene incorporation with issue-specific enhancers. Transgenic animals that include a copy of a transgene encoding a PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide introduced into the germ line of the animal at an embryonic stage can be used to examine the effect of increased expression of DNA encoding PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptides. Such animals can be used as tester animals for reagents thought to confer protection from, for example, pathological conditions associated with its overexpression. In accordance with this facet of the invention, an animal is treated with the reagent and a reduced incidence of the pathological condition, compared to untreated animals bearing the transgene, would indicate a potential therapeutic intervention for the pathological condition.

Alternatively, non-human homologues of PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptides can be used to construct a PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 "knockout" animal which has a defective or altered gene encoding PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 proteins as a result of homologous recombination between the endogenous gene encoding PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptides and altered genomic DNA encoding PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptides introduced into an embryonic stem cell of the animal. Preferably the knock out animal is a mammal. More preferably, the mammal is a rodent such as a rat or mouse. For example, cDNA encoding PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptides can be used to clone genomic DNA encoding PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptides in accordance with established techniques. A portion of the genomic DNA encoding the PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide can be deleted or replaced with another gene, such as a gene encoding a selectable marker which can be used to monitor integration. Typically, several kilobases of unaltered flanking DNA (both at the 5' and 3' ends) are included in the vector [see e.g., Thomas and Capecchi, *Cell*, 51:503 (1987) for a description of homologous recombination vectors]. The vector is introduced into an embryonic stem cell line (e.g., by electroporation) and cells in which the introduced DNA has homologously recombined with the endogenous DNA are selected [see e.g., Li et al., *Cell*, 69:915 (1992)]. The selected cells are then injected into a blastocyst of an animal (e.g., a mouse or rat) to form aggregation chimeras [see e.g., Bradley, in *Teratocarcinomas and Embryonic Stem Cells: A Practical Approach*, E. J. Robertson, ed. (IRL, Oxford, 1987), pp. 113-152]. A chimeric embryo can then be implanted into a suitable pseudopregnant female foster animal and the embryo brought to term to create a "knock out" animal. Progeny harboring the homologously recombined DNA in their germ cells can be identified by standard techniques and used to breed animals in which all cells of the animal contain the homologously recombined DNA. Knockout animals can be characterized for instance, for their ability to defend against certain pathological conditions and for their development of pathological conditions due to absence of the gene encoding the PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide.

In addition, knockout mice can be highly informative in the discovery of gene function and pharmaceutical utility for a drug target, as well as in the determination of the potential on-target side effects associated with a given target. Gene function and physiology are so well conserved between mice and humans, since they are both mammals and contain similar numbers of genes, which are highly conserved between the species. It has recently been well documented, for example, that 98% of genes on mouse chromosome 16 have a human ortholog (Mural et al., *Science* 296:1661-71 (2002)).

Although gene targeting in embryonic stem (ES) cells has enabled the construction of mice with null mutations in many genes associated with human disease, not all genetic diseases are attributable to null mutations. One can design valuable mouse models of human diseases by establishing a method for gene replacement (knock-in) which will disrupt the mouse locus and introduce a human counterpart with mutation, Subsequently one can conduct in vivo drug studies targeting the human protein (Kitamoto et. Al., *Biochemical and Biophysical Res. Commun.*, 222:742-47 (1996)).

Nucleic acid encoding the PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptides may also be used in gene therapy. In gene therapy applications, genes are introduced into cells in order to achieve in vivo synthesis of a therapeutically effective genetic product, for example for replacement of a defective gene. "Gene therapy" includes both conventional gene therapy where a lasting effect is achieved by a single treatment, and the administration of gene therapeutic agents, which involves the one time or repeated administration of a therapeutically effective DNA or mRNA. Antisense RNAs and DNAs can be used as therapeutic agents for blocking the expression of certain genes in vivo. It has already been shown that short antisense oligonucleotides can be imported into cells where they act as inhibitors, despite their low intracellular concentrations caused by their restricted uptake by the cell membrane. (Zamecnik et al., *Proc. Natl. Acad. Sci. USA* 83:4143-4146 [1986]). The oligonucleotides can be modified to enhance their uptake, e.g. by substituting their negatively charged phosphodiester groups by uncharged groups.

There are a variety of techniques available for introducing nucleic acids into viable cells. The techniques vary depending upon whether the nucleic acid is transferred into cultured cells in vitro, or in vivo in the cells of the intended host. Techniques suitable for the transfer of nucleic acid into mammalian cells in vitro include the use of liposomes, electroporation, microinjection, cell fusion, DEAE-dextran, the calcium phosphate precipitation method, etc. The currently preferred in vivo gene transfer techniques include transfection with viral (typically retroviral) vectors and viral coat protein-liposome mediated transfection (Dzau et al., *Trends in Biotechnology* 11, 205-210 [1993]). In some situations it is desirable to provide the nucleic acid source with an agent that targets the target cells, such as an antibody specific for a cell surface membrane protein or the target cell, a ligand for a receptor on the target cell, etc. Where liposomes are employed, proteins which bind to a cell surface membrane protein associated with endocytosis may be used for targeting and/or to facilitate uptake, e.g. capsid proteins or fragments thereof tropic for a particular cell type, antibodies for proteins which undergo internalization in cycling, proteins that target intracellular localization and enhance intracellular half-life. The technique of receptor-mediated endocytosis is described, for example, by Wu et al., *J. Biol. Chem.* 262, 4429-4432 (1987); and Wagner et al., *Proc. Natl. Acad. Sci. USA* 87, 3410-3414 (1990). For review of gene marking and gene therapy protocols see Anderson et al., *Science* 256, 808-813 (1992).

The PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptides described herein may also be employed as molecular weight markers for protein electrophoresis purposes and the isolated nucleic acid sequences may be used for recombinantly expressing those markers.

The nucleic acid molecules encoding the PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptides or fragments thereof described herein are useful for chromosome identification. In this regard, there exists an ongoing need to identify new chromosome markers, since relatively few chromosome marking reagents, based upon actual sequence data are presently available. Each PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 nucleic acid molecule of the present invention can be used as a chromosome marker.

The PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptides and nucleic acid molecules of the present invention may also be used diagnostically for tissue typing, wherein the PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptides of the present invention may be differentially expressed in one tissue as compared to another, preferably in a diseased tissue as compared to a normal tissue of the same tissue type. PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 nucleic acid molecules will find use for generating probes for PCR, Northern analysis, Southern analysis and Western analysis.

The PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptides described herein may also be employed as therapeutic agents. The PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptides of the present invention can be formulated according to known methods to prepare pharmaceutically useful compositions, whereby the PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 product hereof is combined in admixture with a pharmaceutically acceptable carrier vehicle. Therapeutic formulations are prepared for storage by mixing the active ingredient having the desired degree of purity with optional physiologically acceptable carriers, excipients or stabilizers (*Remington's Pharmaceutical Sciences* 16th edition, Osol, A. Ed. (1980)), in the form of lyophilized formulations or aqueous solutions. Acceptable carriers, excipients or stabilizers are nontoxic to recipients at the dosages and concentrations employed, and include buffers such as phosphate, citrate and other organic acids; antioxidants including ascorbic acid; low molecular weight (less than about 10 residues) polypeptides; proteins, such as serum albumin, gelatin or immunoglobulins; hydrophilic polymers such as polyvinylpyrrolidone, amino acids such as glycine, glutamine, asparagine, arginine or lysine; monosaccharides, disaccharides and other carbohydrates including glucose, mannose, or dextrins; chelating agents such as EDTA; sugar alcohols such as mannitol or sorbitol; salt-forming counterions such as sodium; and/or nonionic surfactants such as TWEEN™, PLURONICS™ or PEG.

The formulations to be used for in vivo administration must be sterile. This is readily accomplished by filtration through sterile filtration membranes, prior to or following lyophilization and reconstitution.

Therapeutic compositions herein generally are placed into a container having a sterile access port, for example, an intravenous solution bag or vial having a stopper pierceable by a hypodermic injection needle.

The route of administration is in accord with known methods, e.g. injection or infusion by intravenous, intraperitoneal, intracerebral, intramuscular, intraocular, intraarterial or intralesional routes, topical administration, or by sustained release systems.

Dosages and desired drug concentrations of pharmaceutical compositions of the present invention may vary depending on the particular use envisioned. The determination of the appropriate dosage or route of administration is well within the skill of an ordinary physician. Animal experiments provide reliable guidance for the determination of effective doses for human therapy. Interspecies scaling of effective doses can be performed following the principles laid down by Mordenti, J. and Chappell, W. "The use of interspecies scaling in toxicokinetics" In Toxicokinetics and New Drug Development, Yacobi et al., Eds., Pergamon Press, New York 1989, pp. 42-96.

When in vivo administration of a PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide or agonist or antagonist thereof is employed, normal dosage amounts may vary from about 10 ng/kg to up to 100 mg/kg of mammal body weight or more per day, preferably about 1 µg/kg/day to 10 mg/kg/day, depending upon the route of administration. Guidance as to particular dosages and methods of delivery is provided in the literature; see, for example, U.S. Pat. Nos. 4,657,760; 5,206,344; or 5,225,212. It is anticipated that different formulations will be effective for different treatment compounds and different disorders, that administration targeting one organ or tissue, for example, may necessitate delivery in a manner different from that to another organ or tissue.

Where sustained-release administration of a PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide is desired in a formulation with release characteristics suitable for the treatment of any disease or disorder requiring administration of the PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide, microencapsulation of the PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide is contemplated. Microencapsulation of recombinant proteins for sustained release has been successfully performed with human growth hormone (rhGH), interferon- (rhIFN-), interleukin-2, and MN rgp120. Johnson et al., *Nat. Med.*, 2:795-799 (1996); *Yasuda, Biomed. Ther.*, 27:1221-1223 (1993); Hora et al., *Bio/Technology*, 8:755-758 (1990);

Cleland, "Design and Production of Single Immunization Vaccines Using Polylactide Polyglycolide Microsphere Systems," in *Vaccine Design: The Subunit and Adjuvant Approach*, Powell and Newman, eds, (Plenum Press: New York, 1995), pp. 439-462; WO 97/03692, WO 96/40072, WO 96/07399; and U.S. Pat. No. 5,654,010.

The sustained-release formulations of these proteins were developed using poly-lactic-coglycolic acid (PLGA) polymer due to its biocompatibility and wide range of biodegradable properties. The degradation products of PLGA, lactic and glycolic acids, can be cleared quickly within the human body. Moreover, the degradability of this polymer can be adjusted from months to years depending on its molecular weight and composition. Lewis, "Controlled release of bioactive agents from lactide/glycolide polymer," in: M. Chasin and R. Langer (Eds.), *Biodegradable Polymers as Drug Delivery Systems* (Marcel Dekker: New York, 1990), pp. 1-41.

This invention encompasses methods of screening compounds to identify those that mimic the PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide (agonists) or prevent the effect of the PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide (antagonists). Agonists that mimic a PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide would be especially valuable therapeutically in those instances where a negative phenotype is observed based on findings with the non-human transgenic animal whose genome comprises a disruption of the gene which encodes for the PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide. Antagonists that prevent the effects of a PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide would be especially valuable therapeutically in those instances where a positive phenotype is observed based upon observations with the non-human transgenic knockout animal. Screening assays for antagonist drug candidates are designed to identify compounds that bind or complex with the PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide encoded by the genes identified herein, or otherwise interfere with the interaction of the encoded polypeptide with other cellular proteins. Such screening assays will include assays amenable to high-throughput screening of chemical libraries, making them particularly suitable for identifying small molecule drug candidates.

The assays can be performed in a variety of formats, including protein-protein binding assays, biochemical screening assays, immunoassays, and cell-based assays, which are well characterized in the art.

All assays for antagonists are common in that they call for contacting the drug candidate with a PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide encoded by a nucleic acid identified herein under conditions and for a time sufficient to allow these two components to interact.

In binding assays, the interaction is binding and the complex formed can be isolated or detected in the reaction mixture. The PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide encoded by the gene identified herein or the drug candidate is immobilized on a solid phase, e.g., on a microtiter plate, by covalent or non-covalent attachments. Non-covalent attachment generally is accomplished by coating the solid surface with a solution of the PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide and drying. Alternatively, an immobilized antibody, e.g., a monoclonal antibody, specific for the PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide to be immobilized can be used to anchor it to a solid surface. The assay is performed by adding the non-immobilized component, which may be labeled by a detectable label, to the immobilized component, e.g., the coated surface containing the anchored component. When the reaction is complete, the non-reacted components are removed, e.g., by washing, and complexes anchored on the solid surface are detected. When the originally non-immobilized component carries a detectable label, the detection of label immobilized on the surface indicates that complexing occurred. Where the originally non-immobilized component does not carry a label, complexing can be detected, for example, by using a labeled antibody specifically binding the immobilized complex.

If the candidate compound interacts with but does not bind to a particular PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide encoded by a gene identified herein, its interaction with that polypeptide can be assayed by methods well known for detecting protein-protein interactions. Such assays include traditional approaches, such as, e.g., cross-linking, co-immunoprecipitation, and co-purification through gradients or chromatographic columns. In addition, protein-protein interactions can be monitored by using a yeast-based genetic system described by Fields and co-workers (Fields and Song, *Nature (London)*, 340:245-246 (1989); Chien et al., *Proc. Natl. Acad. Sci. USA*, 88:9578-9582 (1991)) as disclosed by Chevray and Nathans, *Proc. Natl. Acad. Sci. USA*, 89: 5789-5793 (1991). Many transcriptional activators, such as yeast GAL4, consist of two physically discrete modular domains, one acting as the DNA-binding domain, the other one functioning as the transcription-activation domain. The yeast expression system described in the foregoing publications (generally referred to as the "two-hybrid system") takes advantage of this property, and employs two hybrid proteins, one in which the target protein is fused to the DNA-binding domain of GAL4, and another, in which candidate activating proteins are fused to the activation domain. The expression of a GAL1-lacZ reporter gene under control of a GAL4-activated promoter depends on reconstitution of GAL4 activity via protein-protein interaction. Colonies containing interacting polypeptides are detected with a chromogenic substrate for β-galactosidase. A complete kit (MATCHMAKER™) for identifying protein-protein interactions between two specific proteins using the two-hybrid technique is commercially available from Clontech. This system can also be extended to map protein domains involved in specific protein interactions as well as to pinpoint amino acid residues that are crucial for these interactions.

Compounds that interfere with the interaction of a gene encoding a PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide identified herein and other intra- or extracellular components can be tested as follows: usually a reaction mixture is prepared containing the product of the gene and the intra- or extracellular component under conditions and for a time allowing for the interaction and binding of the two products. To test the ability of a candidate compound to inhibit binding, the reaction is run in the absence and in the presence of the test compound. In addition, a placebo may be added to a third reaction mixture, to serve as positive control. The binding (complex formation) between the test compound and the intra- or extracellular component present in the mixture is monitored as described hereinabove. The formation of a complex in the control reaction(s) but not in the reaction mixture containing the test compound indicates that the test compound interferes with the interaction of the test compound and its reaction partner.

To assay for antagonists, the PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide may be added to a cell along with the compound to be screened for a particular activity and the ability of the compound to inhibit the activity of interest in the presence of the PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide indicates that the compound is an antagonist to the PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide. Alternatively, antagonists may be detected by combining the PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide and a potential antagonist with membrane-bound PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide receptors or recombinant receptors under appropriate conditions for a competitive inhibition assay. The PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide can be labeled, such as by radioactivity, such that the number of PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide molecules bound to the receptor can be used to determine the effectiveness of the potential antagonist. The gene encoding the receptor can be identified by numerous methods known to those of skill in the art, for example, ligand panning and FACS sorting. Coligan et al., *Current Protocols in Immun.*, 1(2): Chapter 5 (1991). Preferably, expression cloning is employed wherein polyadenylated RNA is prepared from a cell responsive to the PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide and a cDNA library created from this RNA is divided into pools and used to transfect COS cells or other cells that are not responsive to the PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide. Transfected cells that are grown on glass slides are exposed to labeled PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide. The PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide can be labeled by a variety of means including iodination or inclusion of a recognition site for a site-specific protein kinase. Following fixation and incubation, the slides are subjected to autoradiographic analysis. Positive pools are identified and sub-pools are prepared and re-transfected using an interactive sub-pooling and re-screening process, eventually yielding a single clone that encodes the putative receptor.

As an alternative approach for receptor identification, the labeled PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide can be photoaffinity-linked with cell membrane or extract preparations that express the receptor molecule. Cross-linked material is resolved by PAGE and exposed to X-ray film. The labeled complex containing the receptor can be excised, resolved into peptide fragments, and subjected to protein micro-sequencing. The amino acid sequence obtained from micro-sequencing would be used to design a set of degenerate oligonucleotide probes to screen a cDNA library to identify the gene encoding the putative receptor.

Another approach in assessing the effect of an antagonist to a PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide, would be administering a PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 antagonist to a wild-type mouse in order to mimic a known knockout phenotype. Thus, one would initially knockout the PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 gene of interest and observe the resultant phenotype as a consequence of knocking out or disrupting the PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 gene. Subsequently, one could then assess the effectiveness of an antagonist to the PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide by administering an antagonist to the PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide to a wild-type mouse. An effective antagonist would be expected to mimic the phenotypic effect that was initially observed in the knockout animal.

Likewise, one could assess the effect of an agonist to a PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide, by administering a PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 agonist to a non-human transgenic mouse in order to ameliorate a known negative knockout phenotype. Thus, one would initially knockout the PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 gene of interest and observe the resultant phenotype as a consequence of knocking out or disrupting the PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 gene. Subsequently, one could then assess the effectiveness of an agonist to the PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide by administering an agonist to the PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide to the non-human transgenic mouse. An effective agonist would be expected to ameliorate the negative phenotypic effect that was initially observed in the knockout animal.

In another assay for antagonists, mammalian cells or a membrane preparation expressing the receptor would be incubated with a labeled PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide in the presence of the candidate compound. The ability of the compound to enhance or block this interaction could then be measured.

More specific examples of potential antagonists include an oligonucleotide that binds to the fusions of immunoglobulin with the PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide, and, in particular, antibodies including, without limitation, poly- and monoclonal antibodies and antibody fragments, single-chain antibodies, anti-idiotypic antibodies, and chimeric or humanized versions of such antibodies or fragments, as well as human antibodies and antibody fragments. Alternatively, a potential antagonist may be a closely related protein, for example, a mutated form of the PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide that recognizes the receptor but imparts no effect, thereby competitively inhibiting the action of the PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide.

Another potential PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide antagonist is an antisense RNA or DNA construct prepared using antisense technology, where, e.g., an antisense RNA or DNA molecule acts to block directly the translation of mRNA by hybridizing to targeted mRNA and preventing protein translation. Antisense technology can be used to control gene expression through triple-helix formation or antisense DNA or RNA, both of which methods are based on binding of a polynucleotide to DNA or RNA. For example, the 5' coding portion of the polynucleotide sequence, which encodes the mature PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptides herein, is used to design an antisense RNA oligonucleotide of from about 10 to 40 base pairs in length. A DNA oligonucleotide is designed to be complementary to a region of the gene involved in transcription (triple helix—see Lee et al., *Nucl. Acids Res.,* 6:3073 (1979); Cooney et al., *Science,* 241: 456 (1988); Dervan et al., *Science,* 251:1360 (1991)), thereby preventing transcription and the production of the PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide. The antisense RNA oligonucleotide hybridizes to the mRNA in vivo and blocks translation of the mRNA molecule into the PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide (antisense—Okano, *Neurochem.,* 56:560 (1991); *Oligodeoxynucleotides as Antisense Inhibitors of Gene Expression* (CRC Press: Boca Raton, Fla., 1988). The oligonucleotides described above can also be delivered to cells such that the antisense RNA or DNA may be expressed in vivo to inhibit production of the PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide. When antisense DNA is used, oligodeoxyribonucleotides derived from the translation-initiation site, e.g., between about −10 and +10 positions of the target gene nucleotide sequence, are preferred.

Potential antagonists include small molecules that bind to the active site, the receptor binding site, or growth factor or other relevant binding site of the PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide, thereby blocking the normal biological activity of the PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide. Examples of small molecules include, but are not limited to, small peptides or peptide-like molecules, preferably soluble peptides, and synthetic non-peptidyl organic or inorganic compounds.

Ribozymes are enzymatic RNA molecules capable of catalyzing the specific cleavage of RNA. Ribozymes act by sequence-specific hybridization to the complementary target RNA, followed by endonucleolytic cleavage. Specific ribozyme cleavage sites within a potential RNA target can be identified by known techniques. For further details see, e.g., Rossi, *Current Biology,* 4:469-471 (1994), and PCT publication No. WO 97/33551 (published Sep. 18, 1997).

Nucleic acid molecules in triple-helix formation used to inhibit transcription should be single-stranded and composed of deoxynucleotides. The base composition of these oligonucleotides is designed such that it promotes triple-helix formation via Hoogsteen base-pairing rules, which generally require sizeable stretches of purines or pyrimidines on one strand of a duplex. For further details see, e.g., PCT publication No. WO 97/33551, supra.

These small molecules can be identified by any one or more of the screening assays discussed hereinabove and/or by any other screening techniques well known for those skilled in the art.

Diagnostic and therapeutic uses of the herein disclosed molecules may also be based upon the positive functional assay hits disclosed and described below.

F. Anti-PRO224, Anti-PRO9783, Anti-PRO1108, Anti-PRO34000, Anti-PRO240, Anti-PRO943, Anti-hu A33, Anti-PRO230, Anti-PRO178, Anti-PRO1199, Anti-PRO4333, Anti-PRO1336, Anti-PRO19598, Anti-PRO1083, Anti-hu TRPM2 or Anti-PRO1801 Antibodies The present invention provides anti-PRO224, anti-PRO9783, anti-PRO1108, anti-PRO34000, anti-PRO240, anti-PRO943, anti-hu A33, anti-PRO230, anti-PRO178, anti-PRO1199, anti-PRO4333, anti-PRO1336, anti-PRO19598, anti-PRO1083, anti-hu TRPM2 or anti-PRO1801 antibodies which may find use herein as therapeutic and/or diagnostic agents. Exemplary antibodies include polyclonal, monoclonal, humanized, bispecific, and heteroconjugate antibodies.

1. Polyclonal Antibodies

Polyclonal antibodies are preferably raised in animals by multiple subcutaneous (sc) or intraperitoneal (ip) injections of the relevant antigen and an adjuvant. It may be useful to conjugate the relevant antigen (especially when synthetic peptides are used) to a protein that is immunogenic in the species to be immunized. For example, the antigen can be conjugated to keyhole limpet hemocyanin (KLH), serum albumin, bovine thyroglobulin, or soybean trypsin inhibitor, using a bifunctional or derivatizing agent, e.g., maleimidobenzoyl sulfosuccinimide ester (conjugation through cysteine residues), N-hydroxysuccinimide (through lysine residues), glutaraldehyde, succinic anhydride, $SOCl_2$, or $R^1N=C=NR$, where R and $R^1$ are different alkyl groups.

Animals are immunized against the antigen, immunogenic conjugates, or derivatives by combining, e.g., 100 µg or 5 µg of the protein or conjugate (for rabbits or mice, respectively) with 3 volumes of Freund's complete adjuvant and injecting the solution intradermally at multiple sites. One month later, the animals are boosted with ⅕ to ⅒ the original amount of peptide or conjugate in Freund's complete adjuvant by subcutaneous injection at multiple sites. Seven to 14 days later, the animals are bled and the serum is assayed for antibody titer. Animals are boosted until the titer plateaus. Conjugates also can be made in recombinant cell culture as protein fusions. Also, aggregating agents such as alum are suitably used to enhance the immune response.

2. Monoclonal Antibodies

Monoclonal antibodies may be made using the hybridoma method first described by Kohler et al., *Nature*, 256:495 (1975), or may be made by recombinant DNA methods (U.S. Pat. No. 4,816,567).

In the hybridoma method, a mouse or other appropriate host animal, such as a hamster, is immunized as described above to elicit lymphocytes that produce or are capable of producing antibodies that will specifically bind to the protein used for immunization. Alternatively, lymphocytes may be immunized in vitro. After immunization, lymphocytes are isolated and then fused with a myeloma cell line using a suitable fusing agent, such as polyethylene glycol, to form a hybridoma cell (Goding, *Monoclonal Antibodies: Principles and Practice*, pp. 59-103 (Academic Press, 1986)).

The hybridoma cells thus prepared are seeded and grown in a suitable culture medium which medium preferably contains one or more substances that inhibit the growth or survival of the unfused, parental myeloma cells (also referred to as fusion partner). For example, if the parental myeloma cells lack the enzyme hypoxanthine guanine phosphoribosyl transferase (HGPRT or HPRT), the selective culture medium for the hybridomas typically will include hypoxanthine, aminopterin, and thymidine (HAT medium), which substances prevent the growth of HGPRT-deficient cells.

Preferred fusion partner myeloma cells are those that fuse efficiently, support stable high-level production of antibody by the selected antibody-producing cells, and are sensitive to a selective medium that selects against the unfused parental cells. Preferred myeloma cell lines are murine myeloma lines, such as those derived from MOPC-21 and MPC-11 mouse tumors available from the Salk Institute Cell Distribution Center, San Diego, Calif. USA, and SP-2 and derivatives e.g., X63-Ag8-653 cells available from the American Type Culture Collection, Manassas, Va., USA. Human myeloma and mouse-human heteromyeloma cell lines also have been described for the production of human monoclonal antibodies (Kozbor, *J. Immunol.*, 133:3001 (1984); and Brodeur et al., *Monoclonal Antibody Production Techniques and Applications*, pp. 51-63 (Marcel Dekker, Inc., New York, 1987)).

Culture medium in which hybridoma cells are growing is assayed for production of monoclonal antibodies directed against the antigen. Preferably, the binding specificity of monoclonal antibodies produced by hybridoma cells is determined by immunoprecipitation or by an in vitro binding assay, such as radioimmunoassay (RIA) or enzyme-linked immunosorbent assay (ELISA).

The binding affinity of the monoclonal antibody can, for example, be determined by the Scatchard analysis described in Munson et al., *Anal. Biochem.*, 107:220 (1980).

Once hybridoma cells that produce antibodies of the desired specificity, affinity, and/or activity are identified, the clones may be subcloned by limiting dilution procedures and grown by standard methods (Goding, *Monoclonal Antibodies: Principles and Practice*, pp. 59-103 (Academic Press, 1986)). Suitable culture media for this purpose include, for example, D-MEM or RPMI-1640 medium. In addition, the hybridoma cells may be grown in vivo as ascites tumors in an animal e.g., by i.p. injection of the cells into mice.

The monoclonal antibodies secreted by the subclones are suitably separated from the culture medium, ascites fluid, or serum by conventional antibody purification procedures such as, for example, affinity chromatography (e.g., using protein A or protein G-Sepharose) or ion-exchange chromatography, hydroxylapatite chromatography, gel electrophoresis, dialysis, etc.

DNA encoding the monoclonal antibodies is readily isolated and sequenced using conventional procedures (e.g., by using oligonucleotide probes that are capable of binding specifically to genes encoding the heavy and light chains of murine antibodies). The hybridoma cells serve as a preferred source of such DNA. Once isolated, the DNA may be placed into expression vectors, which are then transfected into host cells such as *E. coli* cells, simian COS cells, Chinese Hamster Ovary (CHO) cells, or myeloma cells that do not otherwise produce antibody protein, to obtain the synthesis of monoclonal antibodies in the recombinant host cells. Review articles on recombinant expression in bacteria of DNA encoding the antibody include Skerra et al., *Curr. Opinion in Immunol.*, 5:256-262 (1993) and Plückthun, *Immunol. Revs.* 130: 151-188 (1992).

Monoclonal antibodies or antibody fragments can be isolated from antibody phage libraries generated using the techniques described in McCafferty et al., *Nature*, 348:552-554 (1990). Clackson et al., *Nature*, 352:624-628 (1991) and Marks et al., *J. Mol. Biol.*, 222:581-597 (1991) describe the isolation of murine and human antibodies, respectively, using phage libraries. Subsequent publications describe the production of high affinity (nM range) human antibodies by chain shuffling (Marks et al., *Bio/Technology*, 10:779-783 (1992)), as well as combinatorial infection and in vivo recombination as a strategy for constructing very large phage libraries (Waterhouse et al., *Nuc. Acids. Res.* 21:2265-2266 (1993)). Thus, these techniques are viable alternatives to traditional monoclonal antibody hybridoma techniques for isolation of monoclonal antibodies.

The DNA that encodes the antibody may be modified to produce chimeric or fusion antibody polypeptides, for example, by substituting human heavy chain and light chain constant domain ($C_H$ and $C_L$) sequences for the homologous murine sequences (U.S. Pat. No. 4,816,567; and Morrison, et al., *Proc. Natl. Acad. Sci. USA,* 81:6851 (1984)), or by fusing the immunoglobulin coding sequence with all or part of the coding sequence for a non-immunoglobulin polypeptide (heterologous polypeptide). The non-immunoglobulin polypeptide sequences can substitute for the constant domains of an antibody, or they are substituted for the variable domains of one antigen-combining site of an antibody to create a chimeric bivalent antibody comprising one antigen-combining site having specificity for an antigen and another antigen-combining site having specificity for a different antigen.

3. Human and Humanized Antibodies

The anti-PRO224, anti-PRO9783, anti-PRO1108, anti-PRO34000, anti-PRO240, anti-PRO943, anti-hu A33, anti-PRO230, anti-PRO178, anti-PRO1199, anti-PRO4333, anti-PRO1336, anti-PRO19598, anti-PRO1083, anti-hu TRPM2 or anti-PRO1801 antibodies of the invention may further comprise humanized antibodies or human antibodies. Humanized forms of non-human (e.g., murine) antibodies are chimeric immunoglobulins, immunoglobulin chains or fragments thereof (such as Fv, Fab, Fab', F(ab')$_2$ or other antigen-binding subsequences of antibodies) which contain minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin [Jones et al., *Nature* 321:522-525 (1986); Riechmann et al., *Nature* 332:323-329 (1988); and Presta, *Curr. Op. Struct. Biol,* 2:593-596 (1992)].

Methods for humanizing non-human antibodies are well known in the art. Generally, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers [Jones et al., *Nature,* 321:522-525 (1986); Riechmann et al., *Nature,* 332:323-327 (1988); Verhoeyen et al., *Science,* 239:1534-1536 (1988)], by substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

The choice of human variable domains, both light and heavy, to be used in making the humanized antibodies is very important to reduce antigenicity and HAMA response (human anti-mouse antibody) when the antibody is intended for human therapeutic use. According to the so-called "best-fit" method, the sequence of the variable domain of a rodent antibody is screened against the entire library of known human variable domain sequences. The human V domain sequence which is closest to that of the rodent is identified and the human framework region (FR) within it accepted for the humanized antibody (Sims et al., *J. Immunol.* 151:2296 (1993); Chothia et al., *J. Mol. Biol.,* 196:901 (1987)). Another method uses a particular framework region derived from the consensus sequence of all human antibodies of a particular subgroup of light or heavy chains. The same framework may be used for several different humanized antibodies (Carter et al., *Proc. Natl. Acad. Sci. USA,* 89:4285 (1992); Presta et al., *J. Immunol.* 151:2623 (1993)).

It is further important that antibodies be humanized with retention of high binding affinity for the antigen and other favorable biological properties. To achieve this goal, according to a preferred method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved. In general, the hypervariable region residues are directly and most substantially involved in influencing antigen binding.

Various forms of a humanized anti-PRO224, anti-PRO9783, anti-PRO1108, anti-PRO34000, anti-PRO240, anti-PRO943, anti-hu A33, anti-PRO230, anti-PRO178, anti-PRO1199, anti-PRO4333, anti-PRO1336, anti-PRO19598, anti-PRO1083, anti-hu TRPM2 or anti-PRO1801 antibody are contemplated. For example, the humanized antibody may be an antibody fragment, such as a Fab, which is optionally conjugated with one or more cytotoxic agent(s) in order to generate an immunoconjugate. Alternatively, the humanized antibody may be an intact antibody, such as an intact IgG1 antibody.

As an alternative to humanization, human antibodies can be generated. For example, it is now possible to produce transgenic animals (e.g., mice) that are capable, upon immunization, of producing a full repertoire of human antibodies in the absence of endogenous immunoglobulin production. For example, it has been described that the homozygous deletion of the antibody heavy-chain joining region ($J_H$) gene in chimeric and germ-line mutant mice results in complete inhibition of endogenous antibody production. Transfer of the human germ-line immunoglobulin gene array into such germ-line mutant mice will result in the production of human antibodies upon antigen challenge. See, e.g., Jakobovits et al., *Proc. Natl. Acad. Sci. USA,* 90:2551 (1993); Jakobovits et al., *Nature,* 362:255-258 (1993); Bruggemann et al., *Year in Immuno.* 7:33 (1993); U.S. Pat. Nos. 5,545,806, 5,569,825, 5,591,669 (all of GenPharm); 5,545,807; and WO 97/17852.

Alternatively, phage display technology (McCafferty et al., *Nature* 348:552-553 [1990]) can be used to produce human antibodies and antibody fragments in vitro, from immunoglobulin variable (V) domain gene repertoires from unimmunized donors. According to this technique, antibody V domain genes are cloned in-frame into either a major or minor coat protein gene of a filamentous bacteriophage, such as M13 or fd, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. Thus, the phage mimics some of the properties of the B-cell. Phage display can be performed in a variety of formats, reviewed in, e.g., Johnson, Kevin S, and Chiswell, David J., *Current Opinion in Structural Biology* 3:564-571 (1993). Several sources of V-gene segments can be used for phage display. Clackson et al., *Nature*, 352:624-628 (1991) isolated a diverse array of antioxazolone antibodies from a small random combinatorial library of V genes derived from the spleens of immunized mice. A repertoire of V genes from unimmunized human donors can be constructed and antibodies to a diverse array of antigens (including self-antigens) can be isolated essentially following the techniques described by Marks et al., *J. Mol. Biol.* 222:581-597 (1991), or Griffith et al., *EMBO J.* 12:725-734 (1993). See, also, U.S. Pat. Nos. 5,565,332 and 5,573,905.

As discussed above, human antibodies may also be generated by in vitro activated B cells (see U.S. Pat. Nos. 5,567,610 and 5,229,275).

4. Antibody Fragments

In certain circumstances there are advantages of using antibody fragments, rather than whole antibodies. The smaller size of the fragments allows for rapid clearance, and may lead to improved access to solid tumors.

Various techniques have been developed for the production of antibody fragments. Traditionally, these fragments were derived via proteolytic digestion of intact antibodies (see, e.g., Morimoto et al., *Journal of Biochemical and Biophysical Methods* 24:107-117 (1992); and Brennan et al., *Science*, 229:81 (1985)). However, these fragments can now be produced directly by recombinant host cells. Fab, Fv and ScFv antibody fragments can all be expressed in and secreted from *E. coli*, thus allowing the facile production of large amounts of these fragments. Antibody fragments can be isolated from the antibody phage libraries discussed above. Alternatively, Fab'-SH fragments can be directly recovered from *E. coli* and chemically coupled to form $F(ab')_2$ fragments (Carter et al., *Bio/Technology* 10:163-167 (1992)). According to another approach, $F(ab')_2$ fragments can be isolated directly from recombinant host cell culture. Fab and $F(ab')_2$ fragment with increased in vivo half-life comprising a salvage receptor binding epitope residues are described in U.S. Pat. No. 5,869,046. Other techniques for the production of antibody fragments will be apparent to the skilled practitioner. The antibody of choice is a single chain Fv fragment (scFv). See WO 93/16185; U.S. Pat. No. 5,571,894; and U.S. Pat. No. 5,587,458. Fv and sFv are the only species with intact combining sites that are devoid of constant regions; thus, they are suitable for reduced nonspecific binding during in vivo use. sFv fusion proteins may be constructed to yield fusion of an effector protein at either the amino or the carboxy terminus of an sFv. See *Antibody Engineering*, ed. Borrebaeck, supra. The antibody fragment may also be a "linear antibody", e.g., as described in U.S. Pat. No. 5,641,870 for example. Such linear antibody fragments may be monospecific or bispecific.

5. Bispecific Antibodies

Bispecific antibodies are antibodies that have binding specificities for at least two different epitopes. Exemplary bispecific antibodies may bind to two different epitopes of a PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 protein as described herein. Other such antibodies may combine a PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 binding site with a binding site for another protein. Alternatively, an anti-PRO224, anti-PRO9783, anti-PRO1108, anti-PRO34000, anti-PRO240, anti-PRO943, anti-hu A33, anti-PRO230, anti-PRO178, anti-PRO1199, anti-PRO4333, anti-PRO1336, anti-PRO19598, anti-PRO1083, anti-hu TRPM2 or anti-PRO1801 arm may be combined with an arm which binds to a triggering molecule on a leukocyte such as a T-cell receptor molecule (e.g. CD3), or Fc receptors for IgG (FcγR), such as FcγRI (CD64), FcγRII (CD32) and FcγRIII (CD16), so as to focus and localize cellular defense mechanisms to the PRO224-, PRO9783-, PRO1108-, PRO34000-, PRO240-, PRO943-, hu A33-, PRO230-, PRO178-, PRO1199-, PRO4333-, PRO1336-, PRO19598-, PRO1083-, hu TRPM2- or PRO1801-expressing cell. Bispecific antibodies may also be used to localize cytotoxic agents to cells which express a PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide. These antibodies possess a PRO224-, PRO9783-, PRO1108-, PRO34000-, PRO240-, PRO943-, hu A33-, PRO230-, PRO178-, PRO1199-, PRO4333-, PRO1336-, PRO19598-, PRO1083-, hu TRPM2- or PRO1801-binding arm and an arm which binds the cytotoxic agent (e.g., saporin, anti-interferon-α, vinca alkaloid, ricin A chain, methotrexate or radioactive isotope hapten). Bispecific antibodies can be prepared as full length antibodies or antibody fragments (e.g., $F(ab')_2$ bispecific antibodies).

WO 96/16673 describes a bispecific anti-ErbB2/anti-FcγRIII antibody and U.S. Pat. No. 5,837,234 discloses a bispecific anti-ErbB2/anti-FcγRI antibody. A bispecific anti-ErbB2/Fcα antibody is shown in WO98/02463. U.S. Pat. No. 5,821,337 teaches a bispecific anti-ErbB2/anti-CD3 antibody.

Methods for making bispecific antibodies are known in the art. Traditional production of full length bispecific antibodies is based on the co-expression of two immunoglobulin heavy chain-light chain pairs, where the two chains have different specificities (Millstein et al., *Nature* 305:537-539 (1983)). Because of the random assortment of immunoglobulin heavy and light chains, these hybridomas (quadromas) produce a potential mixture of 10 different antibody molecules, of which only one has the correct bispecific structure. Purification of the correct molecule, which is usually done by affinity chromatography steps, is rather cumbersome, and the product yields are low. Similar procedures are disclosed in WO 93/08829, and in Traunecker et al., *EMBO J.* 10:3655-3659 (1991).

According to a different approach, antibody variable domains with the desired binding specificity (antibody-antigen combining sites) are fused to immunoglobulin constant domain sequences. Preferably, the fusion is with an Ig heavy chain constant domain, comprising at least part of the hinge, $C_H2$, and $C_H3$ regions. It is preferred to have the first heavy-chain constant region ($C_H1$) containing the site necessary for light chain bonding, present in at least one of the fusions. DNAs encoding the immunoglobulin heavy chain fusions and, if desired, the immunoglobulin light chain, are inserted into separate expression vectors, and are co-transfected into a suitable host cell. This provides for greater flexibility in adjusting the mutual proportions of the three polypeptide fragments when unequal ratios of the three polypeptide chains used in the construction provide the optimum yield of the desired bispecific antibody. It is, however, possible to insert the coding sequences for two or all three polypeptide chains into a single expression vector when the expression of at least two polypeptide chains in equal ratios results in high yields or when the ratios have no significant affect on the yield of the desired chain combination.

The invention provides bispecific antibodies which are composed of a hybrid immunoglobulin heavy chain with a first binding specificity in one arm, and a hybrid immunoglobulin heavy chain-light chain pair (providing a second binding specificity) in the other arm. It was found that this asymmetric structure facilitates the separation of the desired bispecific compound from unwanted immunoglobulin chain combinations, as the presence of an immunoglobulin light chain in only one half of the bispecific molecule provides for a facile way of separation. This approach is disclosed in WO 94/04690. For further details of generating bispecific antibodies see, for example, Suresh et al., Methods in Enzymology 121:210 (1986).

According to another approach described in U.S. Pat. No. 5,731,168, the interface between a pair of antibody molecules can be engineered to maximize the percentage of heterodimers which are recovered from recombinant cell culture. The preferred interface comprises at least a part of the $C_H3$ domain. In this method, one or more small amino acid side chains from the interface of the first antibody molecule are replaced with larger side chains (e.g., tyrosine or tryptophan). Compensatory "cavities" of identical or similar size to the large side chain(s) are created on the interface of the second antibody molecule by replacing large amino acid side chains with smaller ones (e.g., alanine or threonine). This provides a mechanism for increasing the yield of the heterodimer over other unwanted end-products such as homodimers.

Bispecific antibodies include cross-linked or "heteroconjugate" antibodies. For example, one of the antibodies in the heteroconjugate can be coupled to avidin, the other to biotin. Such antibodies have, for example, been proposed to target immune system cells to unwanted cells (U.S. Pat. No. 4,676,980), and for treatment of HIV infection (WO 91/00360, WO 92/200373, and EP 03089). Heteroconjugate antibodies may be made using any convenient cross-linking methods. Suitable cross-linking agents are well known in the art, and are disclosed in U.S. Pat. No. 4,676,980, along with a number of cross-linking techniques.

Techniques for generating bispecific antibodies from antibody fragments have also been described in the literature. For example, bispecific antibodies can be prepared using chemical linkage. Brennan et al., Science 229:81 (1985) describe a procedure wherein intact antibodies are proteolytically cleaved to generate F(ab')$_2$ fragments. These fragments are reduced in the presence of the dithiol complexing agent, sodium arsenite, to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Recent progress has facilitated the direct recovery of Fab'-SH fragments from E. coli, which can be chemically coupled to form bispecific antibodies. Shalaby et al., J. Exp. Med. 175: 217-225 (1992) describe the production of a fully humanized bispecific antibody F(ab')$_2$ molecule. Each Fab' fragment was separately secreted from E. coli and subjected to directed chemical coupling in vitro to form the bispecific antibody. The bispecific antibody thus formed was able to bind to cells overexpressing the ErbB2 receptor and normal human T cells, as well as trigger the lytic activity of human cytotoxic lymphocytes against human breast tumor targets. Various techniques for making and isolating bispecific antibody fragments directly from recombinant cell culture have also been described. For example, bispecific antibodies have been produced using leucine zippers. Kostelny et al., J. Immunol. 148(5):1547-1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al., Proc. Natl. Acad. Sci. USA 90:6444-6448 (1993) has provided an alternative mechanism for making bispecific antibody fragments. The fragments comprise a $V_H$ connected to a $V_L$ by a linker which is too short to allow pairing between the two domains on the same chain. Accordingly, the $V_H$ and $V_L$ domains of one fragment are forced to pair with the complementary $V_L$ and $V_H$ domains of another fragment, thereby forming two antigen-binding sites. Another strategy for making bispecific antibody fragments by the use of single-chain Fv (sFv) dimers has also been reported. See Gruber et al., J. Immunol., 152:5368 (1994).

Antibodies with more than two valencies are contemplated. For example, trispecific antibodies can be prepared. Tutt et al., J. Immunol. 147:60 (1991).

6. Heteroconjugate Antibodies

Heteroconjugate antibodies are also within the scope of the present invention. Heteroconjugate antibodies are composed of two covalently joined antibodies. Such antibodies have, for example, been proposed to target immune system cells to unwanted cells [U.S. Pat. No. 4,676,980], and for treatment of HIV infection [WO 91/00360; WO 92/200373; EP 03089]. It is contemplated that the antibodies may be prepared in vitro using known methods in synthetic protein chemistry, including those involving crosslinking agents. For example, immunotoxins may be constructed using a disulfide exchange reaction or by forming a thioether bond. Examples of suitable reagents for this purpose include iminothiolate and methyl-4-mercaptobutyrimidate and those disclosed, for example, in U.S. Pat. No. 4,676,980.

7. Multivalent Antibodies

A multivalent antibody may be internalized (and/or catabolized) faster than a bivalent antibody by a cell expressing an antigen to which the antibodies bind. The antibodies of the present invention can be multivalent antibodies (which are other than of the IgM class) with three or more antigen binding sites (e.g. tetravalent antibodies), which can be readily produced by recombinant expression of nucleic acid encoding the polypeptide chains of the antibody. The multivalent antibody can comprise a dimerization domain and three or more antigen binding sites. The preferred dimerization domain comprises (or consists of) an Fc region or a hinge region. In this scenario, the antibody will comprise an Fc region and three or more antigen binding sites amino-terminal to the Fc region. The preferred multivalent antibody herein comprises (or consists of) three to about eight, but preferably four, antigen binding sites. The multivalent antibody comprises at least one polypeptide chain (and preferably two polypeptide chains), wherein the polypeptide chain(s) comprise two or more variable domains. For instance, the polypeptide chain(s) may comprise VD1-(X1)$_n$-VD2-(X2)$_n$-Fc, wherein VD1 is a first variable domain, VD2 is a second variable domain, Fc is one polypeptide chain of an Fc region, X1 and X2 represent an amino acid or polypeptide, and n is 0 or 1. For instance, the polypeptide chain(s) may comprise: VH-CH1-flexible linker-VH-CH1-Fc region chain; or VH-CH1-VH-CH1-Fc region chain. The multivalent antibody herein preferably further comprises at least two (and preferably four) light chain variable domain polypeptides. The multivalent antibody herein may, for instance, comprise from about two to about eight light chain variable domain polypeptides. The light chain variable domain polypeptides contemplated here comprise a light chain variable domain and, optionally, further comprise a CL domain.

8. Effector Function Engineering

It may be desirable to modify the antibody of the invention with respect to effector function, e.g., so as to enhance antigen-dependent cell-mediated cyotoxicity (ADCC) and/or complement dependent cytotoxicity (CDC) of the antibody. This may be achieved by introducing one or more amino acid substitutions in an Fc region of the antibody. Alternatively or additionally, cysteine residue(s) may be introduced in the Fc region, thereby allowing interchain disulfide bond formation in this region. The homodimeric antibody thus generated may have improved internalization capability and/or increased complement-mediated cell killing and antibody-dependent cellular cytotoxicity (ADCC). See Caron et al., *J. Exp Med.* 176:1191-1195 (1992) and Shopes, B. *J. Immunol.* 148:2918-2922 (1992). Homodimeric antibodies with enhanced antitumor activity may also be prepared using heterobifunctional cross-linkers as described in Wolff et al., *Cancer Research* 53:2560-2565(1993). Alternatively, an antibody can be engineered which has dual Fc regions and may thereby have enhanced complement lysis and ADCC capabilities. See Stevenson et al., *Anti-Cancer Drug Design* 3:219-230 (1989). To increase the serum half life of the antibody, one may incorporate a salvage receptor binding epitope into the antibody (especially an antibody fragment) as described in U.S. Pat. No. 5,739,277, for example. As used herein, the term "salvage receptor binding epitope" refers to an epitope of the Fc region of an IgG molecule (e.g., IgG$_1$, IgG$_2$, IgG$_3$, or IgG$_4$) that is responsible for increasing the in vivo serum half-life of the IgG molecule.

9. Immunoconjugates

The invention also pertains to immunoconjugates comprising an antibody conjugated to a cytotoxic agent such as a chemotherapeutic agent, a growth inhibitory agent, a toxin (e.g., an enzymatically active toxin of bacterial, fungal, plant, or animal origin, or fragments thereof), or a radioactive isotope (i.e., a radioconjugate).

Chemotherapeutic agents useful in the generation of such immunoconjugates have been described above. Enzymatically active toxins and fragments thereof that can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *momordica charantia* inhibitor, curcin, crotin, sapaonaria officinalis inhibitor, gelonin, mitogellin, restrictocin, phenomycin, enomycin, and the tricothecenes. A variety of radionuclides are available for the production of radioconjugated antibodies. Examples include $^{212}$Bi, $^{131}$I, $^{131}$In, $^{90}$Y, and $^{186}$Re. Conjugates of the antibody and cytotoxic agent are made using a variety of bifunctional protein-coupling agents such as N-succinimidyl-3-(2-pyridyldithiol) propionate (SPDP), iminothiolane (IT), bifunctional derivatives of imidoesters (such as dimethyl adipimidate HCL), active esters (such as disuccinimidyl suberate), aldehydes (such as glutareldehyde), bis-azido compounds (such as his (p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). For example, a ricin immunotoxin can be prepared as described in Vitetta et al., *Science,* 238: 1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026.

Conjugates of an antibody and one or more small molecule toxins, such as a calicheamicin, maytansinoids, a trichothene, and CC1065, and the derivatives of these toxins that have toxin activity, are also contemplated herein.

Maytansine and Maytansinoids

The invention provides an anti-PRO224, anti-PRO9783, anti-PRO1108, anti-PRO34000, anti-PRO240, anti-PRO943, anti-hu A33, anti-PRO230, anti-PRO178, anti-PRO1199, anti-PRO4333, anti-PRO1336, anti-PRO19598, anti-PRO1083, anti-hu TRPM2 or anti-PRO1801 antibody (full length or fragments) which is conjugated to one or more maytansinoid molecules.

Maytansinoids are mitototic inhibitors which act by inhibiting tubulin polymerization. Maytansine was first isolated from the east African shrub *Maytenus serrata* (U.S. Pat. No. 3,896,111). Subsequently, it was discovered that certain microbes also produce maytansinoids, such as maytansinol and C-3 maytansinol esters (U.S. Pat. No. 4,151,042). Synthetic maytansinol and derivatives and analogues thereof are disclosed, for example, in U.S. Pat. Nos. 4,137,230; 4,248,870; 4,256,746; 4,260,608; 4,265,814; 4,294,757; 4,307,016; 4,308,268; 4,308,269; 4,309,428; 4,313,946; 4,315,929; 4,317,821; 4,322,348; 4,331,598; 4,361,650; 4,364,866; 4,424,219; 4,450,254; 4,362,663; and 4,371,533, the disclosures of which are hereby expressly incorporated by reference.

Maytansinoid-antibody Conjugates

In an attempt to improve their therapeutic index, maytansine and maytansinoids have been conjugated to antibodies specifically binding to tumor cell antigens. Immunoconjugates containing maytansinoids and their therapeutic use are disclosed, for example, in U.S. Pat. Nos. 5,208,020, 5,416,064 and European Patent EP 0 425 235 B1, the disclosures of which are hereby expressly incorporated by reference. Liu et al., *Proc. Natl. Acad. Sci. USA* 93:8618-8623 (1996) described immunoconjugates comprising a maytansinoid designated DM1 linked to the monoclonal antibody C242 directed against human colorectal cancer. The conjugate was found to be highly cytotoxic towards cultured colon cancer cells, and showed antitumor activity in an in vivo tumor growth assay. Chari et al., *Cancer Research* 52:127-131 (1992) describe immunoconjugates in which a maytansinoid was conjugated via a disulfide linker to the murine antibody A7 binding to an antigen on human colon cancer cell lines, or to another murine monoclonal antibody TA.1 that binds the HER-2/neu oncogene. The cytotoxicity of the TA.1-maytansonoid conjugate was tested in vitro on the human breast cancer cell line SK-BR-3, which expresses 3×10$^5$ HER-2 surface antigens per cell. The drug conjugate achieved a degree of cytotoxicity similar to the free maytansonid drug, which could be increased by increasing the number of maytansinoid molecules per antibody molecule. The A7-maytansinoid conjugate showed low systemic cytotoxicity in mice.

Anti-PRO224, Anti-PRO9783, Anti-PRO1108, Anti-PRO34000, Anti-PRO240, Anti-PRO943, Anti-hu A33, Anti-PRO230, Anti-PRO178, Anti-PRO1199, Anti-PRO4333, Anti-PRO1336, Anti-PRO19598, Anti-PRO1083, Anti-hu TRPM2 or Anti-PRO1801Antibody-Maytansinoid Conjugates (Immunoconjugates)

Anti-PRO224, anti-PRO9783, anti-PRO1108, anti-PRO34000, anti-PRO240, anti-PRO943, anti-hu A33, anti-PRO230, anti-PRO178, anti-PRO1199, anti-PRO4333, anti-PRO1336, anti-PRO19598, anti-PRO1083, anti-hu TRPM2 or anti-PRO1801 antibody-maytansinoid conjugates are prepared by chemically linking an anti-PRO224, anti-PRO9783, anti-PRO1108, anti-PRO34000, anti-PRO240, anti-PRO943, anti-hu A33, anti-PRO230, anti-PRO178, anti-PRO1199, anti-PRO4333, anti-PRO1336, anti-PRO19598, anti-PRO1083, anti-hu TRPM2 or anti-PRO1801 antibody to a maytansinoid molecule without significantly diminishing the biological activity of either the antibody or the maytansinoid molecule. An average of 3-4 maytansinoid molecules conjugated per antibody molecule has shown efficacy in enhancing cytotoxicity of target cells without negatively affecting the function or solubility of the antibody, although even one molecule of toxin/antibody would be expected to enhance cytotoxicity over the use of naked antibody. Maytansinoids are well known in the art and can be synthesized by known techniques or isolated from natural sources. Suitable maytansinoids are disclosed, for example, in U.S. Pat. No. 5,208,020 and in the other patents and nonpatent publications referred to hereinabove. Preferred maytansinoids are maytansinol and maytansinol analogues modified in the aromatic ring or at other positions of the maytansinol molecule, such as various maytansinol esters.

There are many linking groups known in the art for making antibody-maytansinoid conjugates, including, for example, those disclosed in U.S. Pat. No. 5,208,020 or EP Patent 0 425 235 B1, and Chari et al., *Cancer Research* 52:127-131 (1992). The linking groups include disulfide groups, thioether groups, acid labile groups, photolabile groups, peptidase labile groups, or esterase labile groups, as disclosed in the above-identified patents, disulfide and thioether groups being preferred.

Conjugates of the antibody and maytansinoid may be made using a variety of bifunctional protein coupling agents such as N-succinimidyl-3-(2-pyridyldithio) propionate (SPDP), succinimidyl-4-(N-maleimidomethyl)cyclohexane-1-carboxylate, iminothiolane (IT), bifunctional derivatives of imidoesters (such as dimethyl adipimidate HCL), active esters (such as disuccinimidyl suberate), aldehydes (such as glutareldehyde), bis-azido compounds (such as bis(p-azidobenzoyl) hexanediamine), bis-diazonium derivatives (such as bis-(p-diazoniumbenzoyl)-ethylenediamine), diisocyanatesc (such as toluene 2,6-diisocyanate), and bis-active fluorine compounds (such as 1,5-difluoro-2,4-dinitrobenzene). Particularly preferred coupling agents include N-succinimidyl-3-(2-pyridyldithio) propionate (SPDP) (Carlsson et al., *Biochem. J.* 173:723-737 [1978]) and N-succinimidyl-4-(2-pyridylthio)pentanoate (SPP) to provide for a disulfide linkage.

The linker may be attached to the maytansinoid molecule at various positions, depending on the type of the link. For example, an ester linkage may be formed by reaction with a hydroxyl group using conventional coupling techniques. The reaction may occur at the C-3 position having a hydroxyl group, the C-14 position modified with hydroxymethyl, the C-15 position modified with a hydroxyl group, and the C-20 position having a hydroxyl group. The linkage is formed at the C-3 position of maytansinol or a maytansinol analogue.

Calicheamicin

Another immunoconjugate of interest comprises an anti-PRO224, anti-PRO9783, anti-PRO1108, anti-PRO34000, anti-PRO240, anti-PRO943, anti-hu A33, anti-PRO230, anti-PRO178, anti-PRO1199, anti-PRO4333, anti-PRO1336, anti-PRO19598, anti-PRO1083, anti-hu TRPM2 or anti-PRO1801 antibody conjugated to one or more calicheamicin molecules. The calicheamicin family of antibiotics are capable of producing double-stranded DNA breaks at sub-picomolar concentrations. For the preparation of conjugates of the calicheamicin family, see U.S. Pat. Nos. 5,712,374, 5,714,586, 5,739,116, 5,767,285, 5,770,701, 5,770,710, 5,773,001, 5,877,296 (all to American Cyanamid Company). Structural analogues of calicheamicin which may be used include, but are not limited to, $\gamma_1^I$, $\alpha_2^I$, $\alpha_3^I$, N-acetyl-$\gamma_1^I$, PSAG and $\theta_1^I$ (Hinman et al., *Cancer Research* 53:3336-3342 (1993), Lode et al., *Cancer Research* 58:2925-2928 (1998) and the aforementioned U.S. patents to American Cyanamid). Another anti-tumor drug that the antibody can be conjugated is QFA which is an antifolate. Both calicheamicin and QFA have intracellular sites of action and do not readily cross the plasma membrane. Therefore, cellular uptake of these agents through antibody mediated internalization greatly enhances their cytotoxic effects.

Other Cytotoxic Agents

Other antitumor agents that can be conjugated to the anti-PRO224, anti-PRO9783, anti-PRO1108, anti-PRO34000, anti-PRO240, anti-PRO943, anti-hu A33, anti-PRO230, anti-PRO178, anti-PRO1199, anti-PRO4333, anti-PRO1336, anti-PRO19598, anti-PRO1083, anti-hu TRPM2 or anti-PRO1801 antibodies of the invention include BCNU, streptozoicin, vincristine and 5-fluorouracil, the family of agents known collectively LL-E33288 complex described in U.S. Pat. Nos. 5,053,394, 5,770,710, as well as esperamicins (U.S. Pat. No. 5,877,296).

Enzymatically active toxins and fragments thereof which can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *momordica charantia* inhibitor, curcin, crotin, sapaonaria officinalis inhibitor, gelonin, mitogellin, restrictocin, phenomycin, enomycin and the tricothecenes. See, for example, WO 93/21232 published Oct. 28, 1993.

The present invention further contemplates an immunoconjugate formed between an antibody and a compound with nucleolytic activity (e.g., a ribonuclease or a DNA endonuclease such as a deoxyribonuclease; DNase).

For selective destruction of the tumor, the antibody may comprise a highly radioactive atom. A variety of radioactive isotopes are available for the production of radioconjugated anti-PRO224, anti-PRO9783, anti-PRO1108, anti-PRO34000, anti-PRO240, anti-PRO943, anti-hu A33, anti-PRO230, anti-PRO178, anti-PRO199, anti-PRO4333, anti-PRO1336, anti-PRO19598, anti-PRO1083, anti-hu TRPM2 or anti-PRO1801 antibodies. Examples include $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu. When the conjugate is used for diagnosis, it may comprise a radioactive atom for scintigraphic studies, for example $tc^{99m}$ or $I^{123}$, or a spin label for nuclear magnetic resonance (NMR) imaging (also known as magnetic resonance imaging, mri), such as iodine-123 again, iodine-131, indium-111, fluorine-19, carbon-13, nitrogen-15, oxygen-17, gadolinium, manganese or iron.

The radio- or other labels may be incorporated in the conjugate in known ways. For example, the peptide may be biosynthesized or may be synthesized by chemical amino acid synthesis using suitable amino acid precursors involving, for example, fluorine-19 in place of hydrogen. Labels such as $tc^{99m}$ or $I^{123}$, $Re^{186}$, $Re^{188}$ and $In^{111}$ can be attached via a cysteine residue in the peptide. Yttrium-90 can be attached via a lysine residue. The IODOGEN method (Fraker et al (1978) Biochem. Biophys. Res. Commun. 80: 49-57 can be used to incorporate iodine-123. "Monoclonal Antibodies in Immunoscintigraphy" (Chatal, CRC Press 1989) describes other methods in detail.

Conjugates of the antibody and cytotoxic agent may be made using a variety of bifunctional protein coupling agents such as N-succinimidyl-3-(2-pyridyldithio)propionate (SPDP), succinimidyl-4-(N-maleimidomethyl)cyclohexane-1-carboxylate, iminothiolane (IT), bifunctional derivatives of imidoesters (such as dimethyl adipimidate HCL), active esters (such as disuccinimidyl suberate), aldehydes (such as glutareldehyde), bis-azido compounds (such as bis(p-azidobenzoyl)hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). For example, a ricin immunotoxin can be prepared as described in Vitetta et al., *Science* 238:1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026. The linker may be a "cleavable linker" facilitating release of the cytotoxic drug in the cell. For example, an acid-labile linker, peptidase-sensitive linker, photolabile linker, dimethyl linker or disulfide-containing linker (Chari et al., *Cancer Research* 52:127-131 (1992); U.S. Pat. No. 5,208,020) may be used.

Alternatively, a fusion protein comprising the anti-PRO224, anti-PRO9783, anti-PRO1108, anti-PRO34000, anti-PRO240, anti-PRO943, anti-hu A33, anti-PRO230, anti-PRO178, anti-PRO1199, anti-PRO4333, anti-PRO1336, anti-PRO19598, anti-PRO1083, anti-hu TRPM2 or anti-PRO1801 antibody and cytotoxic agent may be made, e.g., by recombinant techniques or peptide synthesis. The length of DNA may comprise respective regions encoding the two portions of the conjugate either adjacent one another or separated by a region encoding a linker peptide which does not destroy the desired properties of the conjugate.

The invention provides that the antibody may be conjugated to a "receptor" (such streptavidin) for utilization in tumor pre-targeting wherein the antibody-receptor conjugate is administered to the patient, followed by removal of unbound conjugate from the circulation using a clearing agent and then administration of a "ligand" (e.g., avidin) which is conjugated to a cytotoxic agent (e.g., a radionucleotide).

10. Immunoliposomes

The anti-PRO224, anti-PRO9783, anti-PRO1108, anti-PRO34000, anti-PRO240, anti-PRO943, anti-hu A33, anti-PRO230, anti-PRO178, anti-PRO1199, anti-PRO4333, anti-PRO1336, anti-PRO19598, anti-PRO1083, anti-hu TRPM2 or anti-PRO1801 antibodies disclosed herein may also be formulated as immunoliposomes. A "liposome" is a small vesicle composed of various types of lipids, phospholipids and/or surfactant which is useful for delivery of a drug to a mammal. The components of the liposome are commonly arranged in a bilayer formation, similar to the lipid arrangement of biological membranes. Liposomes containing the antibody are prepared by methods known in the art, such as described in Epstein et al., *Proc. Natl. Acad. Sci. USA* 82:3688 (1985); Hwang et al., *Proc. Natl. Acad. Sci. USA* 77:4030 (1980); U.S. Pat. Nos. 4,485,045 and 4,544,545; and WO97/38731 published Oct. 23, 1997. Liposomes with enhanced circulation time are disclosed in U.S. Pat. No. 5,013,556.

Particularly useful liposomes can be generated by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter. Fab' fragments of the antibody of the present invention can be conjugated to the liposomes as described in Martin et al., *J. Biol. Chem.* 257: 286-288 (1982) via a disulfide interchange reaction. A chemotherapeutic agent is optionally contained within the liposome. See Gabizon et al., *J. National Cancer Inst.* 81(19): 1484 (1989).

11. Pharmaceutical Compositions of Antibodies

Antibodies specifically binding a PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide identified herein, as well as other molecules identified by the screening assays disclosed hereinbefore, can be administered for the treatment of various disorders in the form of pharmaceutical compositions.

If the PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide is intracellular and whole antibodies are used as inhibitors, internalizing antibodies are preferred. However, lipofections or liposomes can also be used to deliver the antibody, or an antibody fragment, into cells. Where antibody fragments are used, the smallest inhibitory fragment that specifically binds to the binding domain of the target protein is preferred. For example, based upon the variable-region sequences of an antibody, peptide molecules can be designed that retain the ability to bind the target protein sequence. Such peptides can be synthesized chemically and/or produced by recombinant DNA technology. See, e.g., Marasco et al., *Proc. Natl. Acad. Sci. USA,* 90: 7889-7893 (1993). The formulation herein may also contain more than one active compound as necessary for the particular indication being treated, preferably those with complementary activities that do not adversely affect each other. Alternatively, or in addition, the composition may comprise an agent that enhances its function, such as, for example, a cytotoxic agent, cytokine, chemotherapeutic agent, or growth-inhibitory agent. Such molecules are suitably present in combination in amounts that are effective for the purpose intended.

The active ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles, and nanocapsules) or in macroemulsions. Such techniques are disclosed in *Remington's Pharmaceutical Sciences, supra.*

The formulations to be used for in vivo administration must be sterile. This is readily accomplished by filtration through sterile filtration membranes.

Sustained-release preparations may be prepared. Suitable examples of sustained-release preparations include semipermeable matrices of solid hydrophobic polymers containing the antibody, which matrices are in the form of shaped articles, e.g., films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γ ethyl-L-glutamate, non-degradable ethylene-vinyl acetate, degradable lactic acid-glycolic acid copolymers such as the LUPRON DEPOT T™ (injectable microspheres composed of lactic acid-glycolic acid copolymer and leuprolide acetate), and poly-D-(–)-3-hydroxybutyric acid. While polymers such as ethylene-vinyl acetate and lactic acid-glycolic acid enable release of molecules for over 100 days, certain hydrogels release proteins for shorter time periods. When encapsulated antibodies remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

G. Uses for Anti-PRO224, Anti-PRO9783, Anti-PRO1108, Anti-PRO34000, Anti-PRO240, Anti-PRO943, Anti-hu A33, Anti-PRO230, Anti-PRO178, Anti-PRO1199, Anti-PRO4333, Anti-PRO1336, Anti-PRO19598, Anti-PRO1083, Anti-hu TRPM2 or Anti-PRO1801 Antibodies The anti-PRO224, anti-PRO9783, anti-PRO1108, anti-PRO34000, anti-PRO240, anti-PRO943, anti-hu A33, anti-PRO230, anti-PRO178, anti-PRO1199, anti-PRO4333, anti-PRO1336, anti-PRO19598, anti-PRO1083, anti-hu TRPM2 or anti-PRO1801 antibodies of the invention have various therapeutic and/or diagnostic utilities for a neurological disorder; a cardiovascular, endothelial or angiogenic disorder; an immunological disorder; an oncological disorder; an embryonic developmental disorder or lethality, or a metabolic abnormality. For example, anti-PRO224, anti-PRO9783, anti-PRO1108, anti-PRO34000, anti-PRO240, anti-PRO943, anti-hu A33, anti-PRO230, anti-PRO178, anti-PRO1199, anti-PRO4333, anti-PRO1336, anti-PRO19598, anti-PRO1083, anti-hu TRPM2 or anti-PRO1801 antibodies may be used in diagnostic assays for PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801, e.g., detecting its expression (and in some cases, differential expression) in specific cells, tissues, or serum. Various diagnostic assay techniques known in the art may be used, such as competitive binding assays, direct or indirect sandwich assays and immunoprecipitation assays conducted in either heterogeneous or homogeneous phases [Zola, *Monoclonal Antibodies: A Manual of Techniques*, CRC Press, Inc. (1987) pp. 147-158]. The antibodies used in the diagnostic assays can be labeled with a detectable moiety. The detectable moiety should be capable of producing, either directly or indirectly, a detectable signal. For example, the detectable moiety may be a radioisotope, such as $^3H$, $^{14}C$, $^{32}P$, $^{35}S$, or $^{125}I$, a fluorescent or chemiluminescent compound, such as fluorescein isothiocyanate, rhodamine, or luciferin, or an enzyme, such as alkaline phosphatase, beta-galactosidase or horseradish peroxidase. Any method known in the art for conjugating the antibody to the detectable moiety may be employed, including those methods described by Hunter et al., *Nature* 144:945 (1962); David et al., *Biochemistry*, 13:1014 (1974); Pain et al., *J. Immunol. Meth.*, 40:219 (1981); and Nygren, *J. Histochem. and Cytochem.*, 30:407 (1982).

Anti-PRO224, anti-PRO9783, anti-PRO1108, anti-PRO34000, anti-PRO240, anti-PRO943, anti-hu A33, anti-PRO230, anti-PRO178, anti-PRO1199, anti-PRO4333, anti-PRO1336, anti-PRO19598, anti-PRO1083, anti-hu TRPM2 or anti-PRO1801 antibodies also are useful for the affinity purification of PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptides from recombinant cell culture or natural sources. In this process, the antibodies against PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptides are immobilized on a suitable support, such a Sephadex resin or filter paper, using methods well known in the art. The immobilized antibody then is contacted with a sample containing the PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide to be purified, and thereafter the support is washed with a suitable solvent that will remove substantially all the material in the sample except the PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide, which is bound to the immobilized antibody. Finally, the support is washed with another suitable solvent that will release the PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide from the antibody.

The following examples are offered for illustrative purposes only, and are not intended to limit the scope of the present invention in any way.

All patent and literature references cited in the present specification are hereby incorporated by reference in their entirety.

EXAMPLES

Commercially available reagents referred to in the examples were used according to manufacturer's instructions unless otherwise indicated. The source of those cells identified in the following examples, and throughout the specification, by ATCC accession numbers is the American Type Culture Collection, Manassas, Va.

Example 1

Extracellular Domain Homology Screening to Identify Novel Polypeptides and cDNA Encoding Therefor The extracellular domain (ECD) sequences (including the secretion signal sequence, if any) from about 950 known secreted proteins from the Swiss-Prot public database were used to search EST databases. The EST databases included public databases (e.g., Dayhoff, GenBank), and proprietary databases (e.g. LIFESEQ™, Incyte Pharmaceuticals, Palo Alto, Calif.). The search was performed using the computer program BLAST or BLAST-2 (Altschul et al., *Methods in Enzymology*, 266:460-480 (1996)) as a comparison of the ECD protein sequences to a 6 frame translation of the EST sequences. Those comparisons with a BLAST score of 70 (or in some cases 90) or greater that did not encode known proteins were clustered and assembled into consensus DNA sequences with the program "phrap" (Phil Green, University of Washington, Seattle, Wash.).

Using this extracellular domain homology screen, consensus DNA sequences were assembled relative to the other identified EST sequences using phrap. In addition, the consensus DNA sequences obtained were often (but not always) extended using repeated cycles of BLAST or BLAST-2 and phrap to extend the consensus sequence as far as possible using the sources of EST sequences discussed above.

Based upon the consensus sequences obtained as described above, oligonucleotides were then synthesized and used to identify by PCR a cDNA library that contained the sequence of interest and for use as probes to isolate a clone of the full-length coding sequence for a PRO polypeptide. Forward and reverse PCR primers generally range from 20 to 30 nucleotides and are often designed to give a PCR product of about 100-1000 bp in length. The probe sequences are typically 40-55 bp in length. In some cases, additional oligonucleotides are synthesized when the consensus sequence is greater than about 1-1.5 kbp. In order to screen several libraries for a full-length clone, DNA from the libraries was screened by PCR amplification, as per Ausubel et al., *Current Protocols in Molecular Biology*, with the PCR primer pair. A positive library was then used to isolate clones encoding the gene of interest using the probe oligonucleotide and one of the primer pairs.

The cDNA libraries used to isolate the cDNA clones were constructed by standard methods using commercially available reagents such as those from Invitrogen, San Diego, Calif. The cDNA was primed with oligo dT containing a NotI site, linked with blunt to SalI hemikinased adaptors, cleaved with NotI, sized appropriately by gel electrophoresis, and cloned in a defined orientation into a suitable cloning vector (such as pRKB or pRKD; pRK5B is a precursor of pRK5D that does not contain the SfiI site; see, Holmes et al., *Science*, 253: 1278-1280 (1991)) in the unique XhoI and NotI sites.

Example 2

Isolation of cDNA Clones by Amylase Screening

1. Preparation of Oligo dT Primed cDNA Library mRNA was isolated from a human tissue of interest using reagents and protocols from Invitrogen, San Diego, Calif. (Fast Track 2). This RNA was used to generate an oligo dT primed cDNA library in the vector pRK5D using reagents and protocols from Life Technologies, Gaithersburg, Md. (Super Script Plasmid System). In this procedure, the double stranded cDNA was sized to greater than 1000 bp and the SalI/NotI linkered cDNA was cloned into XhoI/NotI cleaved vector. pRK5D is a cloning vector that has an sp6 transcription initiation site followed by an SfiI restriction enzyme site preceding the XhoI/NotI cDNA cloning sites.

2. Preparation of Random Primed cDNA Library

A secondary cDNA library was generated in order to preferentially represent the 5' ends of the primary cDNA clones. Sp6 RNA was generated from the primary library (described above), and this RNA was used to generate a random primed cDNA library in the vector pSST-AMY.0 using reagents and protocols from Life Technologies (Super Script Plasmid System, referenced above). In this procedure the double stranded cDNA was sized to 500-1000 bp, linkered with blunt to NotI adaptors, cleaved with SfiI, and cloned into SfiI/NotI cleaved vector. pSST-AMY.0 is a cloning vector that has a yeast alcohol dehydrogenase promoter preceding the cDNA cloning sites and the mouse amylase sequence (the mature sequence without the secretion signal) followed by the yeast alcohol dehydrogenase terminator, after the cloning sites. Thus, cDNAs cloned into this vector that are fused in frame with amylase sequence will lead to the secretion of amylase from appropriately transfected yeast colonies.

3. Transformation and Detection

DNA from the library described in paragraph 2 above was chilled on ice to which was added electrocompetent DH10B bacteria (Life Technologies, 20 ml). The bacteria and vector mixture was then electroporated as recommended by the manufacturer. Subsequently, SOC media (Life Technologies, 1 ml) was added and the mixture was incubated at 37° C. for 30 minutes. The transformants were then plated onto 20 standard 150 mm LB plates containing ampicillin and incubated for 16 hours (37° C.). Positive colonies were scraped off the plates and the DNA was isolated from the bacterial pellet using standard protocols, e.g. CsCl-gradient. The purified DNA was then carried on to the yeast protocols below.

The yeast methods were divided into three categories: (1) Transformation of yeast with the plasmid/cDNA combined vector; (2) Detection and isolation of yeast clones secreting amylase; and (3) PCR amplification of the insert directly from the yeast colony and purification of the DNA for sequencing and further analysis.

The yeast strain used was HD56-5A (ATCC-90785). This strain has the following genotype: MAT alpha, ura3-52, leu2-3, leu2-112, his3-11, his3-15, MAL$^+$, SUC$^+$, GAL$^+$. Preferably, yeast mutants can be employed that have deficient post-translational pathways. Such mutants may have translocation deficient alleles in sec71, sec72, sec62, with truncated sec71 being most preferred. Alternatively, antagonists (including antisense nucleotides and/or ligands) which interfere with the normal operation of these genes, other proteins implicated in this post translation pathway (e.g., SEC61p, SEC72p, SEC62p, SEC63p, TDJ1p or SSA1p-4p) or the complex formation of these proteins may also be preferably employed in combination with the amylase-expressing yeast.

Transformation was performed based on the protocol outlined by Gietz et al., *Nucl. Acid. Res.*, 20:1425 (1992). Transformed cells were then inoculated from agar into YEPD complex media broth (100 ml) and grown overnight at 30° C. The YEPD broth was prepared as described in Kaiser et al., *Methods in Yeast Genetics*, Cold Spring Harbor Press, Cold Spring Harbor, N.Y., p. 207 (1994). The overnight culture was then diluted to about 2×10$^6$ cells/ml (approx. OD$_{600}$=0.1) into fresh YEPD broth (500 ml) and regrown to 1×10$^7$ cells/ml (approx. OD$_{600}$=0.4-0.5).

The cells were then harvested and prepared for transformation by transfer into GS3 rotor bottles in a Sorval GS3 rotor at 5,000 rpm for 5 minutes, the supernatant discarded, and then resuspended into sterile water, and centrifuged again in 50 ml falcon tubes at 3,500 rpm in a Beckman GS-6KR centrifuge. The supernatant was discarded and the cells were subsequently washed with LiAc/TE (10 ml, 10 mM Tris-HCl, 1 mM EDTA pH 7.5, 100 mM Li$_2$OOCCH$_3$), and resuspended into LiAc/TE (2.5 ml).

Transformation took place by mixing the prepared cells (100 μl) with freshly denatured single stranded salmon testes DNA (Lofstrand Labs, Gaithersburg, Md.) and transforming DNA (1 μg, vol.<10 μl) in microfuge tubes. The mixture was mixed briefly by vortexing, then 40% PEG/TE (600 μl, 40% polyethylene glycol-4000, 10 mM Tris-HCl, 1 mM EDTA, 100 mM Li$_2$OOCCH$_3$, pH 7.5) was added. This mixture was gently mixed and incubated at 30° C. while agitating for 30 minutes. The cells were then heat shocked at 42° C. for 15 minutes, and the reaction vessel centrifuged in a microfuge at 12,000 rpm for 5-10 seconds, decanted and resuspended into TE (500 μl, 10 mM Tris-HCl, 1 mM EDTA pH 7.5) followed by recentrifugation. The cells were then diluted into TE (1 ml) and aliquots (200 μl) were spread onto the selective media previously prepared in 150 mm growth plates (VWR).

Alternatively, instead of multiple small reactions, the transformation was performed using a single, large scale reaction, wherein reagent amounts were scaled up accordingly.

The selective media used was a synthetic complete dextrose agar lacking uracil (SCD-Ura) prepared as described in Kaiser et al, *Methods in Yeast Genetics*, Cold Spring Harbor Press, Cold Spring Harbor, N.Y., p. 208-210 (1994). Transformants were grown at 30° C. for 2-3 days.

The detection of colonies secreting amylase was performed by including red starch in the selective growth media. Starch was coupled to the red dye (Reactive Red-120, Sigma) as per the procedure described by Biely et al., *Anal. Biochem.*, 172:176-179 (1988). The coupled starch was incorporated into the SCD-Ura agar plates at a final concentration of 0.15% (w/v), and was buffered with potassium phosphate to a pH of 7.0 (50-100 mM final concentration).

The positive colonies were picked and streaked across fresh selective media (onto 150 mm plates) in order to obtain well isolated and identifiable single colonies. Well isolated single colonies positive for amylase secretion were detected by direct incorporation of red starch into buffered SCD-Ura agar. Positive colonies were determined by their ability to break down starch resulting in a clear halo around the positive colony visualized directly.

4. Isolation of DNA by PCR Amplification

When a positive colony was isolated, a portion of it was picked by a toothpick and diluted into sterile water (30 μl) in a 96 well plate. At this time, the positive colonies were either frozen and stored for subsequent analysis or immediately amplified. An aliquot of cells (5 μl) was used as a template for the PCR reaction in a 25 μl volume containing: 0.5 μl Klentaq (Clontech, Palo Alto, Calif.); 4.0 μl 10 mM dNTP's (Perkin Elmer-Cetus); 2.5 μl Kentaq buffer (Clontech); 0.25 μl forward oligo 1; 0.25 μl reverse oligo 2; 12.5 μl distilled water. The sequence of the forward oligonucleotide 1 was:

(SEQ ID NO: 31)
5'-TGTAAAACGACGGCCAGTTAAATAGACCTGCAATTATTAATCT-3'

The sequence of reverse oligonucleotide 2 was:

(SEQ ID NO: 32)
5'-CAGGAAACAGCTATGACCACCTGCACACCTGCAAATCCATT-3'

PCR was then performed as follows:

| a. | | Denature | 92° C., | 5 minutes |
|---|---|---|---|---|
| b. | 3 cycles of: | Denature | 92° C., | 30 seconds |
| | | Anneal | 59° C., | 30 seconds |
| | | Extend | 72° C., | 60 seconds |
| c. | 3 cycles of: | Denature | 92° C., | 30 seconds |
| | | Anneal | 57° C., | 30 seconds |
| | | Extend | 72° C., | 60 seconds |
| d. | 25 cycles of: | Denature | 92° C., | 30 seconds |
| | | Anneal | 55° C., | 30 seconds |
| | | Extend | 72° C., | 60 seconds |
| e. | | Hold | 4° C. | |

The underlined regions of the oligonucleotides annealed to the ADH promoter region and the amylase region, respectively, and amplified a 307 bp region from vector pSST-AMY.0 when no insert was present. Typically, the first 18 nucleotides of the 5' end of these oligonucleotides contained annealing sites for the sequencing primers. Thus, the total product of the PCR reaction from an empty vector was 343 bp. However, signal sequence-fused cDNA resulted in considerably longer nucleotide sequences.

Following the PCR, an aliquot of the reaction (5 μl) was examined by agarose gel electrophoresis in a 1% agarose gel using a Tris-Borate-EDTA (TBE) buffering system as described by Sambrook et al., supra. Clones resulting in a single strong PCR product larger than 400 bp were further analyzed by DNA sequencing after purification with a 96 Qiaquick PCR clean-up column (Qiagen Inc., Chatsworth, Calif.).

Example 3

Isolation of cDNA Clones Using Signal Algorithm Analysis

Various polypeptide-encoding nucleic acid sequences were identified by applying a proprietary signal sequence finding algorithm developed by Genentech, Inc. (South San Francisco, Calif.) upon ESTs as well as clustered and assembled EST fragments from public (e.g., GenBank) and/or private (LIFESEQ®, Incyte Pharmaceuticals, Inc., Palo Alto, Calif.) databases. The signal sequence algorithm computes a secretion signal score based on the character of the DNA nucleotides surrounding the first and optionally the second methionine codon(s) (ATG) at the 5'-end of the sequence or sequence fragment under consideration. The nucleotides following the first ATG must code for at least 35 unambiguous amino acids without any stop codons. If the first ATG has the required amino acids, the second is not examined. If neither meets the requirement, the candidate sequence is not scored. In order to determine whether the EST sequence contains an authentic signal sequence, the DNA and corresponding amino acid sequences surrounding the ATG codon are scored using a set of seven sensors (evaluation parameters) known to be associated with secretion signals. Use of this algorithm resulted in the identification of numerous polypeptide-encoding nucleic acid sequences.

Using the techniques described in Examples 1 to 3 above, numerous full-length cDNA clones were identified as encoding PRO224, PRO9783, PRO1108, PRO34000, PRO240, PRO943, PRO230, PRO178, PRO1199, PRO4333, PRO1336, PRO19598, PRO1083 or PRO1801 polypeptides as disclosed herein. These cDNAs were then deposited under the terms of the Budapest Treaty with the American Type Culture Collection, University Blvd., Manassas, Va. 20110-2209, USA (ATCC) as shown in Table 7 below. In addition, the sequence of DNA98557, also known as hu A33, was identified from GenBank accession no.: AY112708. The sequence of DNA226659, also known as hu TRPM2, was identified from GenBank accession no.: AB001535.

TABLE 7

| Material | ATCC Dep. No. | Deposit Date |
|---|---|---|
| DNA33221-1133 | 209263 | Sep. 16, 1997 |
| DNA131590-2962 | PTA-2297 | Jul. 25, 2000 |
| DNA58848-1472 | 209955 | Jun. 9, 1998 |
| DNA203528-3014 | PTA-2780 | Sep. 12, 2000 |

TABLE 7-continued

| Material | ATCC Dep. No. | Deposit Date |
| --- | --- | --- |
| DNA34387-1138 | 209260 | Sep. 16, 1997 |
| DNA52192-1369 | 203042 | Jul. 1, 1998 |
| DNA33223-1136 | 209264 | Sep. 16, 1997 |
| DNA23339-1130 | 209282 | Sep. 18, 1997 |
| DNA65351-1366-2 | 209856 | May 12, 1998 |
| DNA84210-2576 | 203818 | Mar. 2, 1999 |
| DNA65423-1595 | 203227 | Sep. 15, 1998 |
| DNA145887-2849 | PTA-1532 | Mar. 21, 2000 |
| DNA50921-1458 | 209859 | May 12, 1998 |
| DNA83500-2506 | 203391 | Oct. 29, 1998 |

These deposits were made under the provisions of the Budapest Treaty on the International Recognition of the Deposit of Microorganisms for the Purpose of Patent Procedure and the Regulations thereunder (Budapest Treaty). This assures maintenance of a viable culture of the deposit for 30 years from the date of deposit. The deposits will be made available by ATCC under the terms of the Budapest Treaty, and subject to an agreement between Genentech, Inc. and ATCC, which assures permanent and unrestricted availability of the progeny of the culture of the deposit to the public upon issuance of the pertinent U.S. patent or upon laying open to the public of any U.S. or foreign patent application, whichever comes first, and assures availability of the progeny to one determined by the U.S. Commissioner of Patents and Trademarks to be entitled thereto according to 35 USC § 122 and the Commissioner's rules pursuant thereto (including 37 CFR § 1.14 with particular reference to 8860G 638).

The assignee of the present application has agreed that if a culture of the materials on deposit should die or be lost or destroyed when cultivated under suitable conditions, the materials will be promptly replaced on notification with another of the same. Availability of the deposited material is not to be construed as a license to practice the invention in contravention of the rights granted under the authority of any government in accordance with its patent laws.

Example 4

Isolation of cDNA clones Encoding Human PRO224 Polypeptides (UNQ198)

The extracellular domain (ECD) sequences (including the secretion signal, if any) of from about 950 known secreted proteins from the Swiss-Prot public protein database were used to search expressed sequence tag (EST) databases. The EST databases included public EST databases (e.g., GenBank) and a proprietary EST DNA database (LIFESEQ®, Incyte Pharmaceuticals, Palo Alto, Calif.). The search was performed using the computer program BLAST or BLAST2 (Altshul et al., Methods in Enzymology 266:460-480 (1996)) as a comparison of the ECD protein sequences to a 6 frame translation of the EST sequence. Those comparisons resulting in a BLAST score of 70 (or in some cases 90) or greater that did not encode known proteins were clustered and assembled into consensus DNA sequences with the program "phrap" (Phil Green, University of Washington, Seattle, Wash.).

A consensus DNA sequence encoding PRO224 was assembled relative to the other identified EST sequences, wherein the consensus sequence was designated herein as DNA30845. Based on the DNA30845 consensus sequence, oligonucleotides were synthesized to identify by PCR a cDNA library that contained the sequence of interest and for use as probes to isolate a clone of the full-length coding sequence for PRO224.

A pair of PCR primers (forward and reverse) were synthesized:

```
forward PCR primer
5'-AAGTTCCAGTGCCGCACCAGTGGC-3'    (SEQ ID NO: 33)

reverse PCR primer
5'-TTGGTTCCACAGCCGAGCTCGTCG-3'    (SEQ ID NO: 34)
```

Additionally, a synthetic oligonucleotide hybridization probe was constructed from the consensus DNA30845 sequence which had the following nucleotide sequence

```
hybridization probe
                                  (SEQ ID NO: 35)
5'-GAGGAGGAGTGCAGGATTGAGCCATGTACCCAGAAAGGGCAATGCCC
ACC-3'
```

In order to screen several libraries for a source of a full-length clone, DNA from the libraries was screened by PCR amplification with the PCR primer pair identified above. A positive library was then used to isolate clones encoding the PRO224 gene using the probe oligonucleotide and one of the PCR primers.

RNA for construction of the cDNA libraries was isolated from human fetal liver tissue. The cDNA libraries used to isolate the cDNA clones were constructed by standard methods using commercially available reagents such as those from Invitrogen, San Diego, Calif. The cDNA was primed with oligo dT containing a NotI site, linked with blunt to SalI hemikinased adaptors, cleaved with NotI, sized appropriately by gel electrophoresis, and cloned in a defined orientation into a suitable cloning vector (such as pRKB or pRKD; pRK5B is a precursor of pRK5D that does not contain the SfiI site; see, Holmes et al., Science, 253:1278-1280 (1991)) in the unique XhoI and NotI sites.

DNA sequencing of the clones isolated as described above gave the full-length DNA sequence for PRO224 [herein designated as UNQ198 (DNA33221-1133)] and the derived protein sequence for PRO224.

The entire nucleotide sequence of UNQ198 (DNA33221-1133) is shown in FIG. 1 (SEQ ID NO:1). Clone UNQ198 (DNA33221-1133) contains a single open reading frame with an apparent translational initiation site at nucleotide positions 96-98 [Kozak et al., supra] and ending at the stop codon at nucleotide positions 942-944 (FIG. 1; SEQ ID NO:1). The start of a transmembrane region begins at position 777. The predicted polypeptide precursor is 282 amino acids long (FIG. 2; SEQ ID NO:2). Clone UNQ198 (DNA33221-1133) has been deposited with ATCC and is assigned ATCC deposit no. 209263 on Sep. 16, 1997.

Analysis of the amino acid sequence of the full-length PRO224 suggests that it has homology to very low-density lipoprotein receptors, apolipoprotein E receptor and chicken oocyte receptors P95. Based on a BLAST and FastA sequence alignment analysis of the full-length sequence, PRO224 has amino acid identity to portions of these proteins in the range from 28% to 45%, and overall identity with these proteins in the range from 33% to 39%.

Example 5

Isolation of cDNA clones Encoding Human PRO9783 Polypeptides (UNQ2914)

The extracellular domain (ECD) sequences (including the secretion signal sequence, if any) from about 950 known secreted proteins from the Swiss-Prot public database were used to search EST databases. The EST databases included, (1) public EST databases (e.g., GenBank), (2) a proprietary EST database (LIFESEQ®, Incyte Pharmaceuticals, Palo Alto, Calif.), (3) a proprietary EST database from Genentech. The search was performed using the computer program BLAST or BLAST2 [Altschul et al., Methods in Enzymology, 266:460-480 (1996)] as a comparison of the ECD protein sequences to a 6 frame translation of the EST sequences. Those comparisons resulting in a BLAST score of 70 (or in some cases, 90) or greater that did not encode known proteins were clustered and assembled into consensus DNA sequences with the program "phrap" (Phil Green, University of Washington, Seattle, Wash.).

A consensus DNA sequence was assembled relative to other EST sequences using phrap as described above. This consensus sequence is herein designated DNA52160. In some cases, the consensus sequence derives from an intermediate consensus DNA sequence which was extended using repeated cycles of BLAST and phrap to extend that intermediate consensus sequence as far as possible using the sources of EST sequences discussed above.

Based on the DNA52160 consensus sequence, oligonucleotides were synthesized: 1) to identify by PCR a cDNA library that contained the sequence of interest, and 2) for use as probes to isolate a clone of the full-length coding sequence for PRO9783. Forward and reverse PCR primers generally range from 20 to 30 nucleotides and are often designed to give a PCR product of about 100-1000 bp in length. The probe sequences are typically 40-55 bp in length. In some cases, additional oligonucleotides are synthesized when the consensus sequence is greater than about 1-1.5 kbp. In order to screen several libraries for a full-length clone, DNA from the libraries was screened by PCR amplification, as per Ausubel et al., Current Protocols in Molecular Biology, supra, with the PCR primer pair. A positive library was then used to isolate clones encoding the gene of interest using the probe oligonucleotide and one of the primer pairs.

PCR primers (forward and reverse) were synthesized:

```
forward PCR primer 5' -- 3'    (SEQ ID NO: 36)
CGAACCTTCCTACTGGGCTCCGGTG reverse PCR primer 5' -- 3'    (SEQ ID NO: 37)
CCAACATCTATGCAGATACCTCAAGCATCTGCAAGACAGCCGTGC
```

Additionally, a synthetic oligonucleotide hybridization probe was constructed from the consensus DNA52160 sequence which had the following nucleotide sequence

```
hybridization probe
5' -- 3'   (SEQ ID NO: 38)   GCCTGACAGCAAAGATCCGGAAGG
```

RNA for construction of the cDNA libraries was isolated from human placenta tissue. The cDNA libraries used to isolate the cDNA clones were constructed by standard methods using commercially available reagents such as those from Invitrogen, San Diego, Calif. The cDNA was primed with oligo dT containing a NotI site, linked with blunt to SalI hemikinased adaptors, cleaved with NotI, sized appropriately by gel electrophoresis, and cloned in a defined orientation into a suitable cloning vector (such as pRK5B or pRK5D; pRK5B is a precursor of pRK5D that does not contain the SfiI site; see, Holmes et al., Science, 253:1278-1280 (1991)) in the unique XhoI and NotI sites.

DNA sequencing of the clones isolated as described above gave the full-length DNA sequence for a full-length PRO9783 polypeptide (designated herein as DNA131590-2962 (UNQ2914) [FIG. 3, SEQ ID NO: 3] and the derived protein sequence for that PRO9783 polypeptide.

The full length clone identified above contained a single open reading frame with an apparent translational initiation site at nucleotide positions 237-239 and a stop signal at nucleotide positions 1728-1730 (FIG. 3, SEQ ID NO:3). The predicted polypeptide precursor is 497 amino acids long, has a calculated molecular weight of approximately 55906 daltons and an estimated pI of approximately 8.43. Analysis of the full-length PRO9783 sequence shown in FIG. 4 (SEQ ID NO:4) evidences the presence of a variety of important polypeptide domains as shown in FIG. 4, wherein the locations given for those important polypeptide domains are approximate as described above. Clone DNA131590-2962 (UNQ2914) has been deposited with ATCC on Jul. 25, 2000 and is assigned ATCC deposit no. PTA-2297.

An analysis of the Dayhoff database (version 35.45 SwissProt 35), using the ALIGN-2 sequence alignment analysis of the full-length sequence shown in FIG. 4 (SEQ ID NO:4), evidenced sequence identity between the PRO9783 amino acid sequence and the following Dayhoff sequences: P_Y41738, AF109674_1, D45027_1, P_Y13392, GLIP_HUMAN, CRS3_HUMAN, TPX1_HUMAN, AF078552_1, P_Y17828, CRS1_HUMAN.

Example 6

Isolation of cDNA Clones Encoding Human PRO1108 Polypeptides (UNQ551)

The extracellular domain (ECD) sequences (including the secretion signal, if any) of from about 950 known secreted proteins from the Swiss-Prot public protein database were used to search expressed sequence tag (EST) databases. The EST databases included public EST databases (e.g., GenBank) and a proprietary EST DNA database (LIFESEQ®, Incyte Pharmaceuticals, Palo Alto, Calif.). The search was performed using the computer program BLAST or BLAST2 (Altschul et al., Methods in Enzymology 266:460-480 (1996)) as a comparison of the ECD protein sequences to a 6 frame translation of the EST sequence. Those comparisons resulting in a BLAST score of 70 (or in some cases 90) or greater that did not encode known proteins were clustered and assembled into consensus DNA sequences with the program "phrap" (Phil Green, University of Washington, Seattle, Wash.).

A consensus DNA sequence was assembled relative to other EST sequences using phrap. This consensus sequence is herein designated "Consensus". In addition, the "Consensus" DNA sequence was extended using repeated cycles of BLAST and phrap to extend the sequence as far as possible using the sources of EST sequences discussed above.

In light of the sequence homology between the "Consensus" sequence and the Incyte EST clone no. 2379881, Incyte EST clone no. 2379881 was purchased and the cDNA insert was obtained and sequenced. The sequence of this cDNA insert is shown in FIG. 5 and is herein designated DNA58848-1472.

The entire nucleotide sequence of UNQ551 (DNA58848-1472) is shown in FIG. 5 (SEQ ID NO:5). Clone UNQ551 (DNA58848-1472) contains a single open reading frame with an apparent translational initiation site at nucleotide positions 77-79 and ending at the stop codon at nucleotide positions 1445-1447 (FIG. 5). The predicted polypeptide precursor is 456 amino acids long (FIG. 6). The full-length PRO1108 protein shown in FIG. 6 has an estimated molecular weight of about 52,071 daltons and a pI of about 9.46. Analysis of the full-length PRO1108 sequence shown in FIG. 6 (SEQ ID NO:6) evidences the presence of the following: type II transmembrane domains from about amino acid 22 to about amino acid 42, from about amino acid 156 to about amino acid 176, from about amino acid 180 to about amino acid 199 and from about amino acid 369 to about amino acid 388, potential N-glycosylation sites from about amino acid 247 to about amino acid 250, from about amino acid 327 to about amino acid 330, from about amino acid 328 to about amino acid 331 and from about amino acid 362 to about amino acid 365 and an amino acid block having homology to ER lumen protein retaining receptor protein from about amino acid 153 to about amino acid 190. Clone UNQ551 (DNA58848-1472) has been deposited with ATCC on Jun. 9, 1998 and is assigned ATCC deposit no. 209955. Analysis of the amino acid sequence of the full-length PRO1108 polypeptide suggests that it possesses significant sequence similarity to the LPAAT protein, thereby indicating that PRO1108 may be a novel LPAAT homolog. More specifically, an analysis of the Dayhoff database (version 35.45 SwissProt 35) evidenced significant homology between the PRO1108 amino acid sequence and the following Dayhoff sequences, AF015811_1, CER07E3_2, YL35_CAEEL, S73863, CEF59F4_4, P_W06422, MMU41736_1, MTV008_39, P_R99248 and Y67_BPT7.

Example 7

Isolation of cDNA Clones Encoding Human PRO34000 Polypeptides (UNQ9196)

The extracellular domain (ECD) sequences (including the secretion signal sequence, if any) from about 950 known secreted proteins from the Swiss-Prot public database were used to search sequence databases. The databases included public databases (e.g., GenBank) In this instance, genomic DNA sequence from GenBank was analyzed using the gene preditiction program GENSCAN, licenced from Stanford University. GENSCAN analysis predicts gene coding regions, creating sequences which can be subjected to the ECD search. The search was performed using the computer program BLAST or BLAST2 [Altschul et al., Methods in Enzymology, 266:460-480 (1996)] as a comparison of the ECD protein sequences to a 6 frame translation of the sequences. Those comparisons resulting in a BLAST score of 70 (or in some cases, 90) or greater that did not encode known proteins were clustered and assembled into consensus DNA sequences with the program "phrap" (Phil Green, University of Washington, Seattle, Wash.) if necessary A consensus DNA sequence was assembled.

Based on the consensus sequence as described above, oligonucleotides were synthesized: 1) to identify by PCR a cDNA library that contained the sequence of interest, and 2) for use as probes to isolate a clone of the full-length coding sequence for PRO34000. Forward and reverse PCR primers generally range from 20 to 30 nucleotides and are often designed to give a PCR product of about 100-1000 bp in length. The probe sequences are typically 40-55 bp in length. In some cases, additional oligonucleotides are synthesized when the consensus sequence is greater than about 1-1.5 kbp. In order to screen several libraries for a full-length clone, DNA from the libraries was screened by PCR amplification, as per Ausubel et al., Current Protocols in Molecular Biology, supra, with the PCR primer pair. A positive library was then used to isolate clones encoding the gene of interest using the probe oligonucleotide and one of the primer pairs.

A pool of 50 different human cDNA libraries from various tissues was used in cloning. The cDNA libraries used to isolate the cDNA clones were constructed by standard methods using commercially available reagents such as those from Invitrogen, San Diego, Calif. The cDNA was primed with oligo dT containing a NotI site, linked with blunt to SalI hemikinased adaptors, cleaved with NotI, sized appropriately by gel electrophoresis, and cloned in a defined orientation into a suitable cloning vector (such as pRKB or pRKD; pRK5B is a precursor of pRK5D that does not contain the SfiI site; see, Holmes et al., Science, 253:1278-1280 (1991)) in the unique XhoI and NotI sites.

DNA sequencing of the clones isolated as described above gave the full-length DNA sequence for a full-length PRO34000 polypeptide (designated herein as DNA203528-3014 [FIGS. 7A-B, SEQ ID NO: 7) and the derived protein sequence for that PRO34000 polypeptide.

The full length clone identified above contained a single open reading frame with an apparent translational initiation site at nucleotide positions 584-586 and a stop signal at nucleotide positions 3203-3205 (FIGS. 7A-B, SEQ ID NO:7). The predicted polypeptide precursor is 873 amino acids long, has a calculated molecular weight of approximately 93996 daltons and an estimated pI of approximately 8.35. Analysis of the full-length PRO34000 sequence shown in FIGS. 8A-B (SEQ ID NO:8) evidences the presence of a variety of important polypeptide domains as shown in FIGS. 8A-B, wherein the locations given for those important polypeptide domains are approximate as described above. Clone DNA203528-3014 has been deposited with ATCC on Sep. 12, 2000 and is assigned ATCC deposit no. PTA-2780.

An analysis of the protein database (version 35.45 SwissProt 35), using the ALIGN-2 sequence alignment analysis of the full-length sequence shown in FIGS. 8A-B (SEQ ID NO:8), evidenced sequence identity between the PRO34000 amino acid sequence and the following sequences: AB019120_1.

Example 8

Isolation of cDNA Clones Encoding Human PRO240 Polypeptides (UNQ214)

The extracellular domain (ECD) sequences (including the secretion signal, if any) of from about 950 known secreted proteins from the Swiss-Prot public protein database were used to search expressed sequence tag (EST) databases. The EST databases included public EST databases (e.g., GenBank) and a proprietary EST DNA database (LIFESEQ®, Incyte Pharmaceuticals, Palo Alto, Calif.). The search was performed using the computer program BLAST or BLAST2 (Altshul et al., Methods in Enzymology 266:460-480 (1996)) as a comparison of the ECD protein sequences to a 6 frame translation of the EST sequence. Those comparisons resulting in a BLAST score of 70 (or in some cases 90) or greater that did not encode known proteins were clustered and assembled into consensus DNA sequences with the program "phrap" (Phil Green, University of Washington, Seattle, Wash.).

A consensus DNA sequence encoding PRO240 was assembled relative to the other identified EST sequences, wherein the consensus sequence was designated herein as DNA30873. Based on this consensus sequence, oligonucleotides were synthesized to identify by PCR a cDNA library that contained the sequence of interest and for use as probes to isolate a clone of the full-length coding sequence for PRO240.

A pair of PCR primers (forward and reverse) were synthesized:

```
forward PCR primer
5'-TCAGCTCCAGACTCTGATACTGCC-3'    (SEQ ID NO: 39)

reverse PCR primer
5'-TGCCTTTCTAGGAGGCAGAGCTCC-3'    (SEQ ID NO: 40)
```

Additionally, a synthetic oligonucleotide hybridization probe was constructed from the consensus DNA30873 sequence which had the following nucleotide sequence

```
hybridization probe
                                  (SEQ ID NO: 41)
5'-GGACCCAGAAATGTGTCCTGAGAATGGATCTTGTGTACCTGATGGTC

CAG-3'
```

In order to screen several libraries for a source of a full-length clone, DNA from the libraries was screened by PCR amplification with the PCR primer pair identified above. A positive library was then used to isolate clones encoding the PRO240 gene using the probe oligonucleotide and one of the PCR primers.

RNA for construction of the cDNA libraries was isolated from human fetal liver tissue. The cDNA libraries used to isolate the cDNA clones were constructed by standard methods using commercially available reagents such as those from Invitrogen, San Diego, Calif. The cDNA was primed with oligo dT containing a NotI site, linked with blunt to SalI hemikinased adaptors, cleaved with NotI, sized appropriately by gel electrophoresis, and cloned in a defined orientation into a suitable cloning vector (such as pRKB or pRKD; pRK5B is a precursor of pRK5D that does not contain the SfiI site; see, Holmes et al., Science, 253:1278-1280 (1991)) in the unique XhoI and NotI sites.

DNA sequencing of the clones isolated as described above gave the full-length DNA sequence for PRO240 [herein designated as UNQ214 (DNA34387-1138)] and the derived protein sequence for PRO240.

The entire nucleotide sequence of UNQ214 (DNA34387-1138) is shown in FIG. 9 (SEQ ID NO:9). Clone UNQ214 (DNA34387-1138) contains a single open reading frame with an apparent translational initiation site at nucleotide positions 12-14 and ending at the stop codon at nucleotide positions 699-701 (FIG. 9; SEQ ID NO:9). The predicted polypeptide precursor is 229 amino acids long (FIG. 10; SEQ ID NO:10). Clone UNQ214 (DNA34387-1138) has been deposited with ATCC on Sep. 16, 1997 and is assigned ATCC deposit no. 209260. Analysis of the amino acid sequence of the full-length PRO240 suggests that it possesses 30% and 35% amino acid identity with the serrate precursor protein from *Drospohilia melanogaster* and the C-serrate-1 protein from *Gallus gallus*.

Example 9

Isolation of cDNA Clones Encoding Human PRO943 Polypeptides (UNQ480)

The extracellular domain (ECD) sequences (including the secretion signal sequence, if any) from about 950 known secreted proteins from the Swiss-Prot public database were used to search EST databases. The EST databases included public EST databases (e.g., GenBank) and a proprietary EST database (LIFESEQ®, Incyte Pharmaceuticals, Palo Alto, Calif.). The search was performed using the computer program BLAST or BLAST2 [Altschul et al., Methods in Enzymology, 266:460-480 (1996)] as a comparison of the ECD protein sequences to a 6 frame translation of the EST sequences. Those comparisons resulting in a BLAST score of 70 (or in some cases, 90) or greater that did not encode known proteins were clustered and assembled into consensus DNA sequences with the program "phrap" (Phil Green, University of Washington, Seattle, Wash.).

A consensus DNA sequence encoding PRO943 was assembled relative to other EST sequences using phrap. This consensus sequence was then extended using repeated cycles of BLAST and phrap to extend the consensus sequence as far as possible using the sources of EST sequences discussed above. The extended consensus sequence is herein designated DNA36360.

Based on the DNA36360 consensus sequence, oligonucleotides were synthesized: 1) to identify by PCR a cDNA library that contained the sequence of interest, and 2) for use as probes to isolate a clone of the full-length coding sequence for PRO943. Forward and reverse PCR primers generally range from 20 to 30 nucleotides and are often designed to give a PCR product of about 100-1000 bp in length. The probe sequences are typically 40-55 bp in length. In some cases, additional oligonucleotides are synthesized when the consensus sequence is greater than about 1-1.5 kbp. In order to screen several libraries for a full-length clone, DNA from the libraries was screened by PCR amplification, as per Ausubel et al., Current Protocols in Molecular Biology, supra, with the PCR primer pair. A positive library was then used to isolate clones encoding the gene of interest using the probe oligonucleotide and one of the primer pairs.

PCR primers (forward and reverse) were synthesized:

```
forward PCR primer (36360.f1)
5'-CGAGATGACGCCGAGCCCCC-3'         (SEQ ID NO: 42)

reverse PCR primer (36360.r1)
5'-CGGTTCGACACGCGGCAGGTG-3'        (SEQ ID NO: 43)
```

Additionally, a synthetic oligonucleotide hybridization probe was constructed from the consensus DNA36360 sequence which had the following nucleotide sequence

```
hybridization probe (36360.p1)
                                  (SEQ ID NO: 44)
5'-TGCTGCTCCTGCTGCCGCCGCTGCTGCTGGGGGCCTTCCCGCCGG-

3'
```

In order to screen several libraries for a source of a full-length clone, DNA from the libraries was screened by PCR amplification with the PCR primer pair identified above. A positive library was then used to isolate clones encoding the PRO943 gene using the probe oligonucleotide and one of the PCR primers.

RNA for construction of the cDNA libraries was isolated from human fetal brain tissue. The cDNA libraries used to isolated the cDNA clones were constructed by standard methods using commercially available reagents such as those from Invitrogen, San Diego, Calif. The cDNA was primed with oligo dT containing a NotI site, linked with blunt to SalI hemikinased adaptors, cleaved with NotI, sized appropriately by gel electrophoresis, and cloned in a defined orientation into a suitable cloning vector (such as pRKB or pRKD; pRK5B is a precursor of pRK5D that does not contain the SfiI site; see, Holmes et al., Science, 253:1278-1280 (1991)) in the unique XhoI and NotI sites.

DNA sequencing of the clones isolated as described above gave the full-length DNA sequence for PRO943 (designated herein as DNA52192-1369 [FIG. 11, SEQ ID NO:11]; (UNQ480) and the derived protein sequence for PRO943.

The entire nucleotide sequence of UNQ480 (DNA52192-1369) is shown in FIG. 11 (SEQ ID NO:11). Clone UNQ480 (DNA52192-1369) contains a single open reading frame with an apparent translational initiation site at nucleotide positions 150-152 and ending at the stop codon at nucleotide positions 1662-1664 (FIG. 11). The predicted polypeptide precursor is 504 amino acids long (FIG. 12; SEQ ID NO:12). The full-length PRO943 protein shown in FIG. 12 has an estimated molecular weight of about 54,537 daltons and a pI of about 10.04. Analysis of the full-length PRO943 sequence shown in FIG. 12 (SEQ ID NO:12) evidences the presence of the following: a signal peptide from about amino acid 1 to about amino acid 17, a transmembrane domain from about amino acid 376 to about amino acid 396, tyrosine kinase phosphorylation sites from about amino acid 212 to about amino acid 219 and from about amino acid 329 to about amino acid 336, potential N-glycosylation sites from about amino acid 111 to about amino acid 114, from about amino acid 231 to about amino acid 234, from about amino acid 255 to about amino acid 258 and from about amino acid 293 to about amino acid 296 and an immunoglobulin and MHC protein sequence homology block from about amino acid 219 to about amino acid 236. Clone UNQ480 (DNA52192-1369) has been deposited with ATCC on Jul. 1, 1998 and is assigned ATCC deposit no. 203042.

An analysis of the Dayhoff database (version 35.45 SwissProt 35), using a WU-BLAST2 sequence alignment analysis of the full-length sequence shown in FIG. 12 (SEQ ID NO:12), evidenced significant homology between the PRO943 amino acid sequence and the following Dayhoff sequences: B49151, A39752, FGR1_XENLA, S38579, RATHBFGFRB__1, TVHU2F, FGR2_MOUSE, CEK3_CHICK, P_R21080 and A27171__1.

Example 10

Isolation of cDNA Clones Encoding Human PRO230 Polypeptides (UNQ204)

The extracellular domain (ECD) sequences (including the secretion signal, if any) of from about 950 known secreted proteins from the Swiss-Prot public protein database were used to search expressed sequence tag (EST) databases. The EST databases included public EST databases (e.g., GenBank) and a proprietary EST DNA database (LIFESEQ®, Incyte Pharmaceuticals, Palo Alto, Calif.). The search was performed using the computer program BLAST or BLAST2 (Altshul et al., Methods in Enzymology 266:460-480 (1996)) as a comparison of the ECD protein sequences to a 6 frame translation of the EST sequence. Those comparisons resulting in a BLAST score of 70 (or in some cases 90) or greater that did not encode known proteins were clustered and assembled into consensus DNA sequences with the program "phrap" (Phil Green, University of Washington, Seattle, Wash.).

A consensus DNA sequence encoding PRO230 was assembled relative to the other identified EST sequences, wherein the consensus sequence was designated herein as DNA30857. An EST proprietary to Genentech was employed in the consensus assembly.

Based on the DNA30857 consensus sequence, oligonucleotides were synthesized to identify by PCR a cDNA library that contained the sequence of interest and for use as probes to isolate a clone of the full-length coding sequence for PRO230.

A pair of PCR primers (forward and reverse) were synthesized:

```
                                              (SEQ ID NO: 45)
forward PCR primer 5'-TTCGAGGCCTCTGAGAAGTGGCCC-3'

(SEQ ID NO: 46)
reverse PCR primer 5'-GGCGGTATCTCTCTGGCCTCCC-3'
```

Additionally, a synthetic oligonucleotide hybridization probe was constructed from the consensus DNA30857 sequence which had the following nucleotide sequence
Hybridization Probe

```
                                              (SEQ ID NO: 47)
5'-TTCTCCACAGCAGCTGTGGCATCCGATCGTGTCTCAATCCATTCTCT
GGG-3'
```

In order to screen several libraries for a source of a full-length clone, DNA from the libraries was screened by PCR amplification with the PCR primer pair identified above. A positive library was then used to isolate clones encoding the PRO230 gene using the probe oligonucleotide and one of the PCR primers.

RNA for construction of the cDNA libraries was isolated from human fetal lung tissue. The cDNA libraries used to isolate the cDNA clones were constructed by standard methods using commercially available reagents such as those from Invitrogen, San Diego, Calif. The cDNA was primed with oligo dT containing a NotI site, linked with blunt to SalI hemikinased adaptors, cleaved with NotI, sized appropriately by gel electrophoresis, and cloned in a defined orientation into a suitable cloning vector (such as pRKB or pRKD; pRK5B is a precursor of pRK5D that does not contain the SfiI site; see, Holmes et al., Science, 253:1278-1280 (1991)) in the unique XhoI and NotI sites.

DNA sequencing of the clones isolated as described above gave the full-length DNA sequence for PRO230 (herein designated as UNQ204 (DNA33223-1136)) and the derived protein sequence for PRO230.

The entire nucleotide sequence of UNQ204 (DNA33223-1136) is shown in FIG. 13 (SEQ ID NO:13).

Clone UNQ204 (DNA33223-1136) contains a single open reading frame with an apparent translational initiation site at nucleotide positions 100-103 (Kozak et al., supra) and ending at the stop codon at nucleotide positions 1501-1503 (FIG. 13; SEQ ID NO:13). The predicted polypeptide precursor is 467 amino acids long (FIG. 14; SEQ ID NO:14). Clone UNQ203 (DNA33223-1136) has been deposited with ATCC on Sep. 16, 1997 and is assigned ATCC deposit no. 209264.

Example 11

Isolation of cDNA Clones Encoding Human PRO178 Polypeptides (UNQ152)

An expressed sequence tag (EST) DNA database (LIFESEQ®, Incyte Pharmaceuticals, Palo Alto, Calif.) was searched and an EST was identified which showed homology to the human TIE ligand family.

RNA for construction of cDNA libraries was then isolated from human fetal lung tissue. The cDNA libraries used to isolate the cDNA clones encoding human PRO178 were constructed by standard methods using commercially available reagents such as those from Invitrogen, San Diego, Calif. The cDNA was primed with oligo dT containing a NotI site, linked with blunt to SalI hemikinased adaptors, cleaved with NotI, sized appropriately by gel electrophoresis, and cloned in a defined orientation into a suitable cloning vector (such as pRKB or pRKD; pRK5B is a precursor of pRK5D that does not contain the SfiI site; see, Holmes et al., Science, 253: 1278-1280 (1991)) in the unique XhoI and NotI.

Oligonucleotides probes based upon the above described EST sequence were then synthesized: 1) to identify by PCR a cDNA library that contained the sequence of interest, and 2) for use as probes to isolate a clone of the full-length coding sequence for PRO178. Forward and reverse PCR primers generally range from 20 to 30 nucleotides and are often designed to give a PCR product of about 100-1000 bp in length. The probe sequences are typically 40-55 bp in length. In order to screen several libraries for a full-length clone, DNA from the libraries was screened by PCR amplification, as per Ausubel et al., Current Protocols in Molecular Biology, supra, with the PCR primer pair. A positive library was then used to isolate clones encoding the gene of interest using the probe oligonucleotide and one of the primer pairs.

The oligonucleotide probes employed were as follows:

```
                                              (SEQ ID NO: 48)
NL8.5-1:  5'-ACGTAGTTCCAGTATGGTGTGAGCAGCAACTGGA-3'

(SEQ ID NO: 49)
NL8.3-1:  5'-AGTCCAGCCTCCACCCTCCAGTTGCT-3'

(SEQ ID NO: 50)
NL8.3-2:  5'-CCCCAGTCCTCCAGGAGAACCAGCA-3'
```

A full length clone [DNA23339-1130; UNQ152] was identified that contained a single open reading frame with an apparent translational initiation site at nucleotide positions 118-120 and a stop signal at nucleotide positions 1528-1530 (FIG. 15, SEQ ID NO:15). The predicted polypeptide precursor is 470 amino acids long, has a calculated molecular weight of approximately 51,694 daltons and an estimated pI of approximately 8.86. Analysis of the full-length PRO178 sequence shown in FIG. 16 (SEQ ID NO:16) evidences the presence of a variety of important polypeptide domains as shown in FIG. 16, wherein the locations given for those important polypeptide domains are approximate as described above. Analysis of the full-length PRO178 polypeptide shown in FIG. 16 evidences the presence of the following: a signal peptide from about amino acid 1 to about amino acid 20; N-glycosylation sites from about amino acid 58 to about amino acid 62, and from about amino acid 145 to about amino acid 149; a cAMP- and cGMP-dependent protein kinase phosphorylation site from about amino acid 97 to about amino acid 101; a tyrosine kinase phosphorylation site from about amino acid 441 to about amino acid 448; N-myristoylation sites from about amino acid 16 to about amino acid 22; from about amino acid 23 to about amino acid 29, from about amino acid 87 to about amino acid 93, from about amino acid 108 to about amino acid 114, from about amino acid 121 to about amino acid 127, from about amino acid 125 to about amino acid 131, from about amino acid 129 to about amino acid 135, from about amino acid 187 to about amino acid 193, from about amino acid 293 to about amino acid 299, from about amino acid 353 to about amino acid 359, from about amino acid 378 to about amino acid 384, from about amino acid 445 to about amino acid 451, and from about amino acid 453 to about amino acid 459; a cell attachment site from about amino acid 340 to about amino acid 343; and a fibrinogen beta and gamma chains C-terminal domain signature from about amino acid 418 to about amino acid 431. Clone DNA23339-1130 has been deposited with ATCC on Sep. 18, 1997 and is assigned ATCC deposit no. 209282.

Based on a BLAST and FastA sequence alignment analysis of the full-length sequence shown in FIG. 16 (SEQ ID NO:16), PRO178 (herein designated NL8) shows a 23% amino acid sequence identity to both ligand 1 and ligand 2 of the TIE2 receptor. Ligand 1 and ligand 2 of the TIE-2 receptor are 64% identical and 40-43% identical, respectively, to PRO178. The abbreviation "TIE" is an acronym which stands for "tyrosine kinase containing Ig and EGF homology domains" and was coined to designate a new family of receptor tyrosine kinases.

Example 12

Isolation of cDNA Clones Encoding Human PRO1199 Polypeptides (UNQ407)

A public expressed sequence tag (EST) DNA database (GenBank) was searched with the full-length murine m-FIZZ1 (DNA 53517), and an EST, designated AA311223 and renamed as DNA53028 was identified, which showed homology with the m-FIZZ1 DNA.

Based on the EST sequence, oligonucleotides were synthesized to identify by PCR a cDNA library that contained the sequence of interest and for use as probes to isolate a clone of the full-length coding sequence for h-PRO1199 (also designated FIZZ3).

A pair of PCR primers (forward and reverse) and a probe were synthesized:

```
                                              (SEQ ID NO: 51)
forward primer (h-FIZZ3.f):  GGATTTGGTTAGCTGAGCCCAC
                             CGAGA (SEQ ID NO: 52)
reverse primer (h-FIZZ3.r):  GCACTGCGCGCGACCTCAGGGC
                             TGCA (SEQ ID NO: 53)
probe (h-PIZZ3.p):           CTTATTGCCCTAAATATTAGGG
                             AGCCGGCGACCTCCTGGATCCT
                             CTCATT
```

In order to screen several libraries for a source of a full-length clone, DNA from the libraries was screened by PCR amplification with the PCR primer pair identified above. A positive library was then used to isolate clones encoding the PRO1199 (hFIZZ-3) gene using the probe oligonucleotide and one of the PCR primers.

mRNA was isolated from human bone marrow tissue using reagents and protocols from Invitrogen, San Diego, Calif. (Fast Track 2). This RNA was used to generate an oligo dT primed cDNA library in the vector pRK5D using reagents and protocols from Life Technologies, Gaithersburg, Md. (Super Script Plasmid System). In this procedure, the double stranded cDNA was sized to 3-4 kb and the SalI/NotI linkered cDNA was cloned into XhoI/NotI cleaved vector. pRK5D is a cloning vector that has an sp6 transcription initiation site followed by an SfiI restriction enzyme site preceding the XhoI/NotI cDNA cloning sites.

DNA sequencing of the clones isolated as described above gave the full-length DNA sequence for hFIZZ-3 (DNA65351-1366-2; UNQ407) and the derived protein sequence for PRO1199. A cDNA clone was sequenced in entirety. The entire nucleotide sequence of DNA65351-

1366-2 (hFIZZ-3) is shown in FIG. 17 (SEQ ID NO:17). Clone DNA65351-1366-2 contains a single open reading frame with an apparent translational initiation site at nucleotide positions 25-27 (FIG. 17; SEQ ID NO:17). The predicted polypeptide precursor is 108 amino acids long (FIG. 18; SEQ ID NO:18). N-terminal amino acids 1-18 represent a putative signal peptide, and starting at position 57 we have identified a cell attachment sequence motif (RGD). Clone DNA65351-1366-2 has been deposited with ATCC on May 12, 1998 and is assigned ATCC deposit no. 209856.

Example 13

Isolation of cDNA clones Encoding Human PRO4333 Polypeptides (UNQ1888)

An expressed sequence tag (EST) DNA database (LIFESEQ®, Incyte Pharmaceuticals, Palo Alto, Calif.) was searched in a manner similar to that described above under the ECD homology procedure described above and an EST was identified which showed homology to lymphotoxin-beta receptor.

The EST served as the template to create oligonucleotide primers and probes to screen a human fetal kidney library in a manner similar to that described above under the ECD homology procedure.

The oligonucleotides created for the above procedure were the following:

```
                                        (SEQ ID NO: 54)
forward PCR primer: 5'-GCAAGAATTCAGGGATCGGTCTGG-3'

(SEQ ID NO: 55)
probe: 5'-CTGTGTTCCCTGCAACCAGTGTGGGCCAGGCATGG AGTT
GTCTAAGG-3'

(SEQ ID NO: 56)
reverse: 5'-AGATGGCATCACTG GTGGCTGAAC-3'

(SEQ ID NO: 57)
forward: 5'-CAGAAGGCAAATTGTTCAGCCACCAG-3'

(SEQ ID NO: 58)
reverse: 5'-ACAGTTTCCAGACCGATCCCTGAATTC-3'
```

The result was the isolation of the full-length DNA sequence DNA84210-2576 (SEQ ID NO:21, FIGS. 21A-B). The DNA84210-2576 (SEQ ID NO:21) clone depicted in FIGS. 21A-B contains a single open reading frame with an apparent translation initiation site at nucleotide positions 185-187, and a stop codon (TAA) at nucleotide positions 1436-1438, as indicated by bolded underline. The predicted PRO4333 polypeptide precursor (i.e., UNQ1888, SEQ ID NO:22) is 417 amino acids long. The UNQ1888 protein (SEQ ID NO:22) shown in FIG. 22 has an estimated molecular weight of about 45305 daltons and a pI of about 5.12.

Analysis of the UNQ1888 polypeptide (SEQ ID NO:22) of FIG. 22 reveals a signal peptide at about amino acid residues 1-25, a transmembrane domain at about residues 169-192, N-glycosylation sites about residues 105-109, 214-218, 319-323, 350-354, 368-372, 379-383, cAMP- and cGMP-dependent protein kinase phosphorylation sites at about residues 200-204 and 238-242, a tyrosine kinase phosphorylation site at about residues 207-214, an N-myristoylation site at about residues 55-61, 215-218 and 270-276, a prokaryotic membrane lipoprotein lipid attachment site at about residues 259-270 and a TNFR/NGFR family cysteine-rich region at about residues 89-96.

A cDNA clone containing DNA84210-2576 (SEQ ID NO:21), designated as DNA84210-2576, has been deposited with ATCC on Mar. 2, 1999 and is assigned ATCC deposit no. 203818.

Example 14

Isolation of cDNA Clones Encoding Human PRO1336 Polypeptides (UNQ691)

An EST sequence was identified and entered into a proprietary Genentech database. The EST was blasted against various EST databases. The EST databases included public EST databases (e.g., GenBank), and a proprietary EST database (LIFESEQ®, Incyte Pharmaceuticals, Palo Alto, Calif.), and proprietary ESTs from Genentech. The search was performed using the computer program BLAST or BLAST2 [Altschul et al., *Methods in Enzymology*, 266:460-480 (1996)] as a comparison of the ECD protein sequences to a 6 frame translation of the EST sequences. Those comparisons resulting in a BLAST score of 70 (or in some cases, 90) or greater that did not encode known proteins were clustered and assembled into consensus DNA sequences with the program "phrap" (Phil Green, University of Washington, Seattle, Wash.).

A consensus DNA sequence encoding PRO1336 was assembled relative to other aligned EST sequences (forming an assembly) using phrap. This consensus sequence is designated herein "DNA43319". Based on the DNA43319 consensus sequence, oligonucleotides were synthesized: 1) to identify by PCR a cDNA library that contained the sequence of interest, and 2) for use as probes to isolate a clone of the full-length coding sequence for PRO1336.

PCR primers (forward and reverse) were synthesized:

```
                                        (SEQ ID NO: 59)
forward PCR primer 5'ATGGAGATTCCTGCCAACTTGCCG3';
and (SEQ ID NO: 60)
reverse PCR primer 5'TTGTTGGCATTGAGGAGGAGCAGC3'.
```

Additionally, a synthetic oligonucleotide hybridization probe was constructed from the consensus DNA43319 sequence which had the following nucleotide sequence:
Hybridization Probe

```
                                        (SEQ ID NO: 61)
5'GAGGGCATCGTCGAAATACGCCTAGAACAGAACTCCATCAAAGCCATC
CC3'.
```

In order to screen several libraries for a source of a full-length clone, DNA from the libraries was screened by PCR amplification with the PCR primer pair identified above. A positive library was then used to isolate clones encoding the PRO1336 gene using the probe oligonucleotide and one of the PCR primers. RNA for construction of the cDNA libraries was isolated from human fetal lung tissue.

DNA sequencing of the clones isolated as described above gave the full-length DNA sequence for PRO1336 (designated herein as DNA65423-1595 [FIGS. 23A-B, SEQ ID NO:23]; and the derived protein sequence for PRO1336.

The entire coding sequence of PRO1336 is shown in FIGS. 23A-B (SEQ ID NO:23). Clone DNA65423-1595 contains a single open reading frame with an apparent translational initiation site at nucleotide positions 83-85 and an apparent stop codon at nucleotide positions 4652-4654 of SEQ ID NO:23.

The predicted polypeptide precursor is 1523 amino acids long (FIGS. 24A-B; SEQ ID NO:24). The approximate locations of the signal peptide (amino acids 1-27), aspartic acid and asparagine hydroxylation sites, EGF-like domain cystein pattern signature regions, a leucine zipper pattern region, a region conserved in immunoglobulins and major histocompatibility complexes, and N-glycosylation sites are indicated in FIGS. 24A-B. Clone DNA65423-1595 has been deposited with the ATCC on Sep. 15, 1998 and is assigned ATCC deposit no. 203227. The full-length PRO1336 protein shown in FIGS. 24A-B has an estimated molecular weight of about 167,715 daltons and a pI of about 8.06.

An analysis of the Dayhoff database (version 35.45 SwissProt 35), using a WU-BLAST2 sequence alignment analysis of the full-length sequence shown in FIGS. 24A-B (SEQ ID NO:24), revealed sequence identity between the PRO1336 amino acid sequence and the following Dayhoff sequences (data incorporated: herein): SLIT_DROME, CEF40E10__1, LCU58977__1, AF029779__1, FBP1_STRPU, NOTC_X-ENLA, AC004663__1, XELXDEL__1, P_W05835 and HSU77720__1.

Example 15

Isolation of cDNA Clones Encoding Human PRO19598 Polypeptides (UNQ5793)

The extracellular domain (ECD) sequences (including the secretion signal sequence, if any) from about 950 known secreted proteins from the Swiss-Prot public database were used to search sequence databases. The databases included public databases (e.g., GenBank) In this instance, genomic DNA sequence from GenBank was analyzed using the gene preditiction program GENSCAN, licenced from Stanford University. GENSCAN analysis predicts gene coding regions, creating sequences which can be subjected to the ECD search. The search was performed using the computer program BLAST or BLAST2 [Altschul et al., *Methods in Enzymology*, 266:460-480 (1996)] as a comparison of the ECD protein sequences to a 6 frame translation of the sequences. Those comparisons resulting in a BLAST score of 70 (or in some cases, 90) or greater that did not encode known proteins were clustered and assembled into consensus DNA sequences with the program "phrap" (Phil Green, University of Washington, Seattle, Wash.).

A consensus DNA sequence was assembled. This consensus sequence is herein designated DNA132879.

Based on the DNA132879 consensus sequence, oligonucleotides were synthesized: 1) to identify by PCR a cDNA library that contained the sequence of interest, and 2) for use as probes to isolate a clone of the full-length coding sequence for PRO19598. Forward and reverse PCR primers generally range from 20 to 30 nucleotides and are often designed to give a PCR product of about 100-1000 bp in length. The probe sequences are typically 40-55 bp in length. In some cases, additional oligonucleotides are synthesized when the consensus sequence is greater than about 1-1.5 kbp. In order to screen several libraries for a full-length clone, DNA from the libraries was screened by PCR amplification, as per Ausubel et al., *Current Protocols in Molecular Biology*, supra, with the PCR primer pair. A positive library was then used to isolate clones encoding the gene of interest using the probe oligonucleotide and one of the primer pairs.

PCR primers (forward and reverse) were synthesized:
Forward PCR Primer (SEQ ID NO: 62)
><H3 ecd.snf1 5'CTGGCAACAGCAGTGTCTATTTTGTGC 3'

Reverse PCR Primer (SEQ ID NO: 63)
><H3 ecd.snr1 5'TAAGTGCCCTCCCAGGCTGCC 3'

Additionally, a synthetic oligonucleotide hybridization probe was constructed from the consensus DNA132879 sequence which had the following nucleotide sequence
Hybridization Probe (SEQ ID NO: 64)
5'TCCTCCAGTCATGAATATAACCCAAGTCAATGGCTCTTTGTTGGTAAT

TCTC 3'

A pool of 50 different human cDNA libraries from various tissues was used in cloning. The cDNA libraries used to isolate the cDNA clones were constructed by standard methods using commercially available reagents such as those from Invitrogen, San Diego, Calif. The cDNA was primed with oligo dT containing a NotI site, linked with blunt to SalI hemikinased adaptors, cleaved with NotI, sized appropriately by gel electrophoresis, and cloned in a defined orientation into a suitable cloning vector (such as pRKB or pRKD; pRK5B is a precursor of pRK5D that does not contain the SfiI site; see, Holmes et al., *Science*, 253:1278-1280 (1991)) in the unique XhoI and NotI sites.

DNA sequencing of the clones isolated as described above gave the full-length DNA sequence for a full-length PRO19598 polypeptide (designated herein as DNA145887-2849 [FIG. 25, SEQ ID NO: 25) and the derived protein sequence for that PRO19598 polypeptide.

The full length clone identified above contained a single open reading frame with an apparent translational initiation site at nucleotide positions 241-243 and a stop signal at nucleotide positions 1027-1030 (FIG. 25, SEQ ID NO:25). The predicted polypeptide precursor is 262 amino acids long, has a calculated molecular weight of approximately 30419 daltons and an estimated pI of approximately 8.44 Analysis of the full-length PRO19598 sequence shown in FIG. 26 (SEQ ID NO:26) evidences the presence of a variety of important polypeptide domains as shown in FIG. 26, wherein the locations given for those important polypeptide domains are approximate as described above. Clone DNA145887-2849 has been deposited with ATCC on Mar. 21, 2000 and is assigned ATCC deposit no. PTA-1532.

An analysis of the Dayhoff database (version 35.45 SwissProt 35), using the ALIGN-2 sequence alignment analysis of the full-length sequence shown in FIG. 26 (SEQ ID NO:26), evidenced sequence identity between the PRO19598 amino acid sequence and the following Dayhoff sequence: AF184971__1.

Example 16

Isolation of cDNA Clones Encoding Human PRO1083 Polypeptides (UNQ540)

A cDNA sequence was identified using the amylase screening technique described in EXAMPLE 2 above. That cDNA sequence was then compared and aligned with other known EST sequences as described in Example 1 above to obtain a consensus DNA sequence which is designated herein as DNA43422. Based on the DNA 43422 consensus sequence, oligonucleotides were synthesized: 1) to identify by PCR a cDNA library that contained the sequence of interest, and 2) for use as probes to isolate a clone of the full-length coding sequence for PRO1083.

A pair of PCR primers (forward and reverse) were synthesized:

```
forward PCR primer
5'-GGCATTGGAGCAGTGCTGGGTG-3';    (SEQ ID NO: 65)

reverse PCR primer
5'-TGGAGGCCTAGATGCGGCTGGACG-3'.  (SEQ ID NO: 66)
```

In order to screen several libraries for a source of a full-length clone, DNA from the libraries was screened by PCR amplification with the PCR primer pair identified above. A positive library was then used to isolate clones encoding the PRO1083 gene using the reverse PCR primer. RNA for construction of the cDNA libraries was isolated from human fetal kidney tissue (LIB227).

DNA sequencing of the clones isolated as described above gave the full-length DNA sequence for PRO1083 [herein designated as UNQ540 (DNA50921-1458)] (SEQ ID NO:27; FIG. 27) and the derived protein sequence for PRO1083.

The entire nucleotide sequence of UNQ540 (DNA50921-1458) is shown in FIG. 27 (SEQ ID NO:27). Clone UNQ540 (DNA50921-1458) contains a single open reading frame with an apparent translational initiation site at nucleotide positions 214-216 and ending at the stop codon at nucleotide positions 2293-2295 (FIG. 27). The predicted polypeptide precursor is 693 amino acids long (FIG. 28; SEQ ID NO:28). The full-length PRO1083 protein shown in FIG. 28 has an estimated molecular weight of about 77,738 daltons and a pI of about 8.87. Clone UNQ540 (DNA50921-1458) has been deposited with the ATCC on May 12, 1998, under ATCC deposit no. 209859. Regarding the sequence, it is understood that the deposited clone contains the correct sequence, and the sequences provided herein are based on known sequencing techniques.

Still analyzing the amino acid sequence of SEQ ID NO:28, the putative signal peptide is at about amino acids 1-25 of SEQ ID NO:28. The transmembrane domains are at about amino acids 382-398, 402-420, 445-468, 473-491, 519-537, 568-590 and 634-657 of SEQ ID NO:28. A microbodies C-terminal targeting signal is at about amino acids 691-693 of SEQ ID NO:28. cAMP- and cGMP-dependent protein kinase phosphorylation sites are at about amino acids 198-201 and 370-373 of SEQ ID NO:28. N-glycosylation sites are at about amino acids 39-42, 148-151, 171-174, 234-237, 303-306, 324-227 and 341-344 of SEQ ID NO:28. A G-protein coupled receptor family domain is at about amino acids 475-504 of SEQ ID NO:28. The corresponding nucleotides can be routinely determined given the sequences provided herein.

Example 17

Isolation of cDNA Clones Encoding Human PRO1801 Polypeptides (UNQ852)

A proprietary expressed sequence tag (EST) DNA database (LIFESEQ®, Incyte Pharmaceuticals, Palo Alto, Calif.) was searched and an EST was identified which showed homology to the IL-19 protein. This EST sequence is Incyte EST clone no. 819592 and is herein designated DNA79293. Based on the DNA79293 sequence, oligonucleotides were synthesized: 1) to identify by PCR a cDNA library that contained the sequence of interest, and 2) for use as probes to isolate a clone of the full-length coding sequence for PRO1801.

PCR primers (forward and reverse) were synthesized:

```
forward PCR primer
5'-CTCCTGTGGTCTCCAGATTTCAGGCCTA-3'  (SEQ ID NO: 69)

reverse PCR primer
5'-AGTCCTCCTTAAGATTCTGATGTCAA-3'    (SEQ ID NO: 70)
```

RNA for construction of the cDNA libraries was isolated from human fetal kidney tissue. The cDNA libraries used to isolated the cDNA clones were constructed by standard methods using commercially available reagents such as those from Invitrogen, San Diego, Calif. The cDNA was primed with oligo dT containing a NotI site, linked with blunt to SalI hemikinased adaptors, cleaved with NotI, sized appropriately by gel electrophoresis, and cloned in a defined orientation into a suitable cloning vector (such as pRKB or pRKD; pRK5B is a precursor of pRK5D that does not contain the SfiI site; see, Holmes et al., *Science,* 253:1278-1280 (1991)) in the unique XhoI and NotI sites.

DNA sequencing of the clones isolated as described above gave the full-length DNA sequence for PRO1801 (designated herein as DNA83500-2506 [FIG. 31, SEQ ID NO:67]; and the derived protein sequence for PRO1801.

The entire nucleotide sequence of DNA83500-2506 is shown in FIG. 31 (SEQ ID NO:67). Clone DNA83500-2506 contains a single open reading frame with an apparent translational initiation site at nucleotide positions 109-111 and ending at the stop codon at nucleotide positions 892-894 (FIG. 31). The predicted polypeptide precursor is 261 amino acids long (FIG. 32). The full-length PRO1801 protein shown in FIG. 32 has an estimated molecular weight of about 29,667 daltons and a pI of about 8.76. Analysis of the full-length PRO1801 sequence shown in FIG. 32 (SEQ ID NO:68) evidences the presence of the following: a signal peptide from about amino acid 1 to about amino acid 42, cAMP- and cGMP-dependent protein kinase phosphorylation sites from about amino acid 192 to about amino acid 195 and from about amino acid 225 to about amino acid 228 and potential N-myristolation sites from about amino acid 42 to about amino acid 47, from about amino acid 46 to about amino acid 51 and from about amino acid 136 to about amino acid 141. Clone DNA83500-2506 has been deposited with ATCC on Oct. 29, 1998 and is assigned ATCC deposit no. 203391.

An analysis of the Dayhoff database (version 35.45 SwissProt 35), using a WU-BLAST2 sequence alignment analysis of the full-length sequence shown in FIG. 32 (SEQ ID NO:68), evidenced significant homology between the PRO1801 amino acid sequence and the following Dayhoff sequences: P_W37935, HGS_B477, P_R32277, IL10_MACFA, P_W46585, P_R39714, P_R71471, P_R10159, IL10_RAT and P_W57201.

Example 18

Generation and Analysis of Mice Comprising PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 Gene Disruptions To investigate the role of PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 genes were produced by homologous recombination. Specifically, transgenic mice comprising disruptions in PRO224, PRO1108, PRO9783, PRO34000, PRO240, PRO943, hu A33, PRO230, PRO178, PRO1199, PRO4333, PRO1336, PRO19598, PRO1083, hu TRPM2 or PRO1801 genes (i.e., knockout mice) were created by either gene targeting or gene trapping. Mutations were confirmed by southern blot analysis to confirm correct targeting on both the 5' and 3' ends. Gene-specific genotyping was also performed by genomic PCR to confirm the loss of the endogenous native transcript as demonstrated by RT-PCR using primers that anneal to exons flanking the site of insertion. Targeting vectors were electroporated into 129 strain ES cells and targeted clones were identified. Targeted clones were microinjected into host blastocysts to produce chimeras. Chimeras were bred with C57 animals to produce F1 heterozygotes. Heterozygotes were intercrossed to produce F2 wildtype, heterozygote and homozygote cohorts which were used for phenotypic analysis. Rarely, if not enough F1 heterozygotes were produced, the F1 hets were bred to wildtype C57 mice to produce sufficient heterozygotes to breed for cohorts to be analyzed for a phenotype. All phenotypic analysis was performed from 12-16 weeks after birth.

Overall Phenotypic Observation Summaries:

A. Generation and Analysis of Mice Comprising DNA33221-1133 (UNQ198) Gene Disruptions In these knockout experiments, the gene encoding PRO224 polypeptides (designated as DNA33221-1133) [UNQ198] was disrupted. The gene specific information for these studies is as follows: the mutated mouse gene corresponds to nucleotide reference: NM_019421 or *Mus musculus* hypothetical protein 425018-1, protein reference: NP_062294 or hypothetical protein 425018-1; putative VLDL lipoprotein receptor precursor; DNA segment, Chr 17, ERATO Doi 716, expressed [*Mus musculus*]; the human gene sequence reference: BC007083 or *Homo sapiens*, 8D6 antigen, clone MGC: 14623 IMAGE: 4076237; the human protein sequence corresponds to reference: NP_057663 or 8D6 antigen (*Homo sapiens*).

The mutated mouse gene encodes hypothetical protein 425018-1 (LocusLink 54219), which may be orthologus to human 8D6 antigen (8D6A). Aliases and synonyms include putative VLDL lipoprotein receptor precursor, DNA segment Chr 17 ERATO Doi 716, LOC51293, cDNA DKFZp56401762, D17Ertd716e and NG29.

The protein is a member of the family of low-density lipoprotein (LDL) receptors, class A (Pfam accession number PF000057) with unknown biological function. LDL receptors play an important role in cholesterol metabolism, and such motifs are observed in several extracellular and membrane proteins (Daly et al., Proc. Natl. Acad. Sci. USA, 92(14):6334-8 (1995)). The hypothetical protein is 56% similar (over 281 amino acids) to human 8D6 antigen (LocusLink 51293), a follicular dendritic cell signal molecule that stimulates B cell growth (Li et al., J. Exp. Med., 191(6):1077-84 (2000)).

Targeted or gene trap mutations were generated in strain 129SvEv$^{Brd}$-derived embryonic stem (ES) cells. The chimeric mice were bred to C57BL/6J albino mice to generate F1 heterozygous animals. These progeny were intercrossed to generate F2 wild type, heterozygous, and homozygous mutant progeny. On rare occasions, for example when very few F1 mice were obtained from the chimera, F1 heterozygous mice were crossed to 129SvEv$^{Brd}$/C57 hybrid mice to yield additional heterozygous animals for the intercross to generate the F2 mice. Retroviral insertion (OST) occurred; insertion appeared to be in the forward direction prior to the exon encoding amino acid 45.

|  | wt | het | hom | Total |
|---|---|---|---|---|
| Observed | 22 | 39 | 18 | 79 |
| Expected | 19.75 | 39.5 | 19.75 | 79 |

Chi-Sq. = 0.42 Significance = 0.81151 (hom/n) = 0.23 Avg. Litter Size = 0

Wild-type expression of the target gene was detected in embryonic stem (ES) cells and, of the 13 adult tissue samples tested by RT-PCR, only in kidney, testis, and adipose. RT-PCR analysis revealed that the transcript was absent in the (−/−) mouse analyzed.

Phenotypic analysis was performed on mice from this generation as described below.

1. Phenotypic Analysis (for Disrupted Gene: DNA33221-1133 (UNQ198)

(a) Cardiovascular Phenotypic Analysis:

In the area of cardiovascular biology, phenotypic testing was performed to identify potential targets for the treatment of cardiovascular, endothelial or angiogenic disorders. One such phenotypic test included optic fundus photography and angiography to determine the retinal arteriovenous ratio (A/V ratio) in order to flag various eye abnormalities. An abnormal A/V ratio signals such systemic diseases or disorders that may be related to the vascular disease of hypertension (and any disease that causes hypertension, e.g. atherosclerosis), diabetes or other ocular diseases corresponding to opthalmological disorders. Such eye abnormalities may include but are not limited to the following: retinal abnormality is retinal dysplasia, various retinopathies, restenosis, retinal artery obstruction or occlusion; retinal degeneration causing secondary atrophy of the retinal vasculature, retinitis pigmentosa, macular dystrophies, Stargardt's disease, congenital stationary night blindness, choroideremia, gyrate atrophy, Leber's congenital amaurosis, retinoschisis disorders, Wagner's syndrome, Usher syndromes, Zellweger syndrome, Saldino-Mainzer syndrome, Senior-Loken syndrome, Bardet-Biedl syndrome, Alport's syndrome, Alstom's syndrome, Cockayne's syndrome, dysplaisa spondyloepiphysaria congentia, Flynn-Aird syndrome, Friedreich ataxia, Hallgren syndrome, Marshall syndrome, Albers-Schnoberg disease, Refsum's disease, Kearns-Sayre syndrome, Waardenburg's syndrome, Alagile syndrome, myotonic dystrophy, olivopontocerebellar atrophy, Pierre-Marie dunsdrome, Stickler syndrome, carotinemeia, cystinosis, Wolfram syndrome, Bassen-Kornzweig syndrome, abetalipoproteinemia, incontinentia pigmenti, Batten's disease, mucopolysaccharidoses, homocystinuria, or mannosidosis.

Procedure: A cohort of 4 wild type, 4 heterozygotes and 8 homozygotes were tested in this assay. Optic fundus photography was performed on conscious animals using a Kowa Genesis small animal fundus camera modified according to Hawes and coauthors (Hawes et al., 1999 Molecular Vision 1999; 5:22). Intra-peritoneal injection of fluorescein permitted the acquisition of direct light fundus images and fluorescent angiograms for each examination. In addition to direct opthalmological changes, this test can detect retinal changes associated with systemic diseases such as diabetes and atherosclerosis or other retinal abnormalities. Pictures were provided of the optic fundus under normal light. The angiographic pictures allowed examination of the arteries and veins of the eye. In addition an artery to vein (A/V) ratio was determined for the eye.

Opthalmology analysis was performed on generated F2 wild type, heterozygous, and homozygous mutant progeny using the protocol described above. Specifically, the A/V ratio was measured and calculated according to the fundus images with Kowa COMIT+ software. This test takes color photographs through a dilated pupil: the images help in detecting and classifying many diseases. The artery to vein ratio (A/V) is the ratio of the artery diameter to the vein diameter (measured before the bifurcation of the vessels). Many diseases will influence the ratio, i.e., diabetes, cardiovascular disorders, papilledema, optic atrophy or other eye abnormalities such as retinal degeneration (known as retinitis pigmentosa) or retinal dysplasia, vision problems or blindness. Thus, phenotypic observations which result in an increased artery-to-vein ratio in homozygous (−/−) and heterozygous (+/−) mutant progeny compared to wildtype (+/+) littermates would be indicative of such pathological conditions.

Results: In this study, the (−/−) and (+/−) mice exhibited an increased mean artery-to-vein (A/V) ratio when compared with their (+/+) littermates indicating retinal degeneration. In summary, by knocking out the gene identified as DNA33221-1133 encoding PRO224 polypeptides, both heterozygous and homozygous mutant progeny exhibit phenotypes which are associated with retinal degeneration. Such detected retinal changes are most commonly associated with cardiovascular systemic diseases or disorders that may be related to the vascular disease of hypertension (and any disease that causes hypertension, e.g. atherosclerosis), diabetes or other ocular diseases corresponding to opthalmological disorders such as retinal degeneration. Thus, antagonists of PRO224 encoding genes would lead to similar pathological retinal changes, whereas agonists would be useful as therapeutic agents in the treatment of hypertension, atherosclerosis or other opthamological disorders including retinal degeneration and diseases associated with this condition (as indicated above).

B. Generation and Analysis of Mice Commising DNA131590-2962 (UNQ2914) Gene Disruptions In these knockout experiments, the gene encoding PRO9783 polypeptides (designated as DNA131590-2962) [UNQ2914] was disrupted. The gene specific information for these studies is as follows: the mutated mouse gene nucleotide reference corresponds to: NM_030209 or *Mus musculus* RIKEN cDNA 1810049K24 gene (1810049K24Rik), protein reference: NP_084485 or RIKEN cDNA 1810049K24 [*Mus musculus*]; the human nucleotide reference corresponds to: NM_031476, protein reference: NP_113664 or *Homo sapiens* hypothetical protein DKFZp434B044 (DKFZP434B044).

The disrupted mouse gene is represented by RIKEN cDNA 1810049K24Rik, ortholog of human hypothetical protein DKFZp434B044. The putative proteins are members of the SCP-like (Pfam PF00188) and LCCP (Pfam PF03815) families of extracellular domain containing proteins. While the individual members of these families have diverse physiological functions, proteins containing LCCP domains are suspected to be involved in protein folding.

The mouse protein has the greatest similarity to mouse cocoacrisp (cysteine-rich secretory protein or CRISP) and trypsin inhibitors, which also contain LCCL and SCP-like extracellular domains. CRISP proteins are typically secreted and expressed in the male genital tract. They are thought to mediate cell-cell interactions of male germ cells with other cells during sperm maturation or during fertilization (Giese et al., Gene, 299(1-2):101-9 (2002)). Overall, this is a large and diverse family of eukaryotic proteins that includes wasp allergens, plant PR-type proteins, snail proteases, and even a component of a reptile toxin (Milne et al., J. Biol. Chem., 278(33):31105-10 (2003)).

Targeted or gene trap mutations were generated in strain 129SvEv$^{Brd}$-derived embryonic stem (ES) cells. The wild-type expression panel resulted in the following observation: expression of the target gene was detected in embryonic stem (ES) cells and, among the 13 adult tissue samples tested by RT-PCR, in bone, skin fibroblast, adipose, and tail. Disruption of the target gene was confirmed by Southern hybridization analysis. The chimeric mice were bred to C57BL/6J albino mice to generate F1 heterozygous animals. These progeny were intercrossed to generate F2 wild type, heterozygous, and homozygous mutant progeny. On rare occasions, for example when very few F1 mice were obtained from the chimera, F1 heterozygous mice were crossed to 129SvEv$^{Brd}$/C57 hybrid mice to yield additional heterozygous animals for the intercross to generate the F2 mice.

|  | wt | het | hom | Total |
|---|---|---|---|---|
| Observed | 22 | 50 | 28 | 100 |
| Expected | 25 | 50 | 25 | 100 |

Chi-Sq. = 0.72 Significance = 0.69768 (hom/n) = 0.28 Avg. Litter Size = 0

Phenotypic analysis was performed on mice from this generation as described below.

1. Phenotypic Analysis (for Disrupted Gene: DNA131590-2962 (UNQ2914)

(a) Overall Phenotypic Summary:

The homozygous mutant mice exhibited numerous immunological abnormalities when compared with their wild-type littermates and the historical mean. The male homozygous mutant mice also exhibited enhanced glucose tolerance at all 3 time intervals tested and exhibited notably decreased bone-related measurements when compared with their gender-matched wild-type littermates and the historical means. Female (−/−) mice showed a decreased skin fibroblast proliferation rate. Disruption of the target gene was confirmed by Southern hybridization analysis.

(b) Phenotypic Analysis: Metabolism—Blood Chemistry

In the area of metabolism, targets may be identified for the treatment of various cardiovascular diseases, diabetes and/or obesity. Blood chemistry phenotypic analysis includes glucose tolerance tests to measure insulin sensitivity and changes in glucose metabolism. Abnormal glucose tolerance test results may indicate but may not be limited to the following disorders or conditions: Diabetes Type 1 and Type 2, Syndrome X, various cardiovascular diseases or obesity.

Procedure: A cohort of 2 wild type and 4 homozygote males were used in this assay. The glucose tolerance test is the standard for defining impaired glucose homeostasis in mammals. Glucose tolerance tests were performed using a Lifescan glucometer. Animals were injected IP at 2 g/kg with D-glucose delivered as a 20% solution and blood glucose levels were measured at 0, 30, 60 and 90 minutes after injection.

Results: These studies indicated that male (−/−) mice exhibit enhanced glucose tolerance in the presence of normal fasting glucose at all 3 intervals tested when compared with their gender-matched (+/+) littermates and the historical means. In addition, hyperinsulinemia was not apparent in the (−/−) mice. Thus, knockout mice exhibited the opposite phenotypic pattern of an impaired glucose homeostasis, and as such antagonists to PRO9783 polypeptides or its encoding gene would be useful in the treatment of impaired glucose homeostasis and/or various cardiovascular diseases such as diabetes.

(c) Immunology Phenotypic Analysis

Immune related and inflammatory diseases are the manifestation or consequence of fairly complex, often multiple interconnected biological pathways which in normal physiology are critical to respond to insult or injury, initiate repair from insult or injury, and mount innate and acquired defense against foreign organisms. Disease or pathology occurs when these normal physiological pathways cause additional insult or injury either as directly related to the intensity of the response, as a consequence of abnormal regulation or excessive stimulation, as a reaction to self, or as a combination of these.

Though the genesis of these diseases often involves multistep pathways and often multiple different biological systems/pathways, intervention at critical points in one or more of these pathways can have an ameliorative or therapeutic effect. Therapeutic intervention can occur by either antagonism of a detrimental process/pathway or stimulation of a beneficial process/pathway.

T lymphocytes (T cells) are an important component of a mammalian immune response. T cells recognize antigens which are associated with a self-molecule encoded by genes within the major histocompatibility complex (MHC). The antigen may be displayed together with MHC molecules on the surface of antigen presenting cells, virus infected cells, cancer cells, grafts, etc. The T cell system eliminates these altered cells which pose a health threat to the host mammal. T cells include helper T cells and cytotoxic T cells. Helper T cells proliferate extensively following recognition of an antigen-MHC complex on an antigen presenting cell. Helper T cells also secrete a variety of cytokines, i.e., lymphokines, which play a central role in the activation of B cells, cytotoxic T cells and a variety of other cells which participate in the immune response.

In many immune responses, inflammatory cells infiltrate the site of injury or infection. The migrating cells may be neutrophilic, eosinophilic, monocytic or lymphocytic as can be determined by histologic examination of the affected tissues. Current Protocols in Immunology, ed. John E. Coligan, 1994, John Wiley & Sons, Inc.

Many immune related diseases are known and have been extensively studied. Such diseases include immune-mediated inflammatory diseases (such as rheumatoid arthritis, immune mediated renal disease, hepatobiliary diseases, inflammatory bowel disease (IBD), psoriasis, and asthma), non-immune-mediated inflammatory diseases, infectious diseases, immunodeficiency diseases, neoplasia, and graft rejection, etc. In the area of immunology, targets were identified for the treatment of inflammation and inflammatory disorders.

In the area of immunology, targets have been identified herein for the treatment of inflammation and inflammatory disorders. Immune related diseases, in one instance, could be treated by suppressing the immune response. Using neutralizing antibodies that inhibit molecules having immune stimulatory activity would be beneficial in the treatment of immune-mediated and inflammatory diseases. Molecules which inhibit the immune response can be utilized (proteins directly or via the use of antibody agonists) to inhibit the immune response and thus ameliorate immune related disease.

The Following Tests were Performed:

Flourescence-activated Cell-sorting (FACS) Analysis

Procedure: FACS analysis of immune cell composition from peripheral blood was performed including analysis of CD4, CD8 and T cell receptors to evaluate T lymphocytes, CD19 for B lymphocytes, CD45 as a leukocyte marker and pan NK for natural killer cells. The FACS analysis was carried out on 2 wild type and 6 homozygous mice and included cells derived from thymus, spleen, bone marrow and lymph node.

In these studies, analyzed cells were isolated from thymus, peripheral blood, spleen, bone marrow and lymph nodes. Flow cytometry was designed to determine the relative proportions of CD4 and CD8 positive T cells, B cells, NK cells and monocytes in the mononuclear cell population. A Becton-Dickinson FACSCalibur 3-laser FACS machine was used to assess immune status. For Phenotypic Assays and Screening, this machine records CD4+/CD8−, CD8+/CD4−, NK, B cell and monocyte numbers in addition to the CD4+/CD8+ ratio.

The mononuclear cell profile was derived by staining a single sample of lysed peripheral blood from each mouse with a panel of six lineage-specific antibodies: CD45 PerCP, anti-TCRb APC, CD4 PE, CD8 FITC, pan-NK PE, and CD19 FITC. The two FITC and PE labeled antibodies stain mutually exclusive cell types. The samples were analyzed using a Becton Dickinson FACSCalibur flow cytometer with CellQuest software.

Results: FACS analysis gave the following results: The male (−/−) mice exhibited a decreased mean percentage of B cells when compared with their (+/+) littermates and the historical mean.

Ovalbumin Challenge

Procedure: This assay was carried out on 6 wild types and 14 homozygotes. Chicken ovalbumin (OVA) is a T-cell dependent antigen, which is commonly used as a model protein for studying antigen-specific immune responses in mice. OVA is non-toxic and inert and therefore will not cause harm to the animals even if no immune response is induced. The murine immune response to OVA has been well characterized, to the extent that the immunodominant peptides for eliciting T cell responses have been identified. Anti-OVA antibodies are detectable 8 to 10 days after immunization using enzyme-linked immunosorbent assay (ELIZA), and determination of different isotypes of antibodies gives further information on the complex processes that may lead to a deficient response in genetically engineered mice.

As noted above, this protocol assesses the ability of mice to raise an antigen-specific immune response. Animals were injected IP with 50 mg of chicken ovalbumin emulsified in Complete Feund's Adjuvant and 14 days later the serum titer of anti-ovalbumin antibodies (IgM, IgG1 and IgG2 subclasses) was measured. The amount of OVA-specific antibody in the serum sample is proportional to the Optical Density (OD) value generated by an instrument that scans a 96-well sample plate. Data was collected for a set of serial dilutions of each serum sample. [Analyzed wt/het/hom: 6/4/14]

Results of this challenge: The male (−/−) mice exhibited a decreased mean serum IgG2a response to the ovalbumin challenge when compared with their (+/+) littermates. Thus, these knockout mice exhibited a decreased ability to elicit an OVA-specific antibody response to the T-cell dependent OVA antigen.

In summary, both FACS analysis of immune cell composition from peripheral blood and the ovalbumin challenge studies indicate that knockout mice deficient in the gene encoding PRO9783 polypeptides exhibit immunological abnormalities when compared with their wild-type littermates. In one instance, the mutant mice exhibited a decreased ability to elicit an immunological response when challenged with the T-cell dependent OVA antigen. This coupled with the immune cell composition analysis of peripheral blood, suggests that PRO9783 polypeptides or their agonists would be useful for stimulating the immune system (such as T cell proliferation) and would find utility in the cases wherein this effect would be beneficial to the individual such as in the case of leukemia, and other types of cancer, and in immunocompromised patients, such as AIDS sufferers. Accordingly, inhibitors (antagonists) of PRO9783 polypeptides would be useful in inhibiting the immune response and would be useful candidates for suppressing harmful immune responses, e.g. in the case of graft rejection or graft-versus-host diseases.

(d) Oncology Phenotypic Analysis

In the area of oncology, targets were identified herein for the treatment of solid tumors, lymphomas and leukemia.

Adult Skin Cell Proliferation:

Procedure: Skin cells were isolated from 16 week old animals (2 wild type and 4 homozygotes). These were developed into primary fibroblast cultures and the fibroblast proliferation rates were measured in a strictly controlled protocol. The ability of this assay to detect hyper-proliferative and hypo-proliferative phenotypes has been demonstrated with p53 and Ku80. Proliferation was measured using Brdu incorporation.

Specifically, in these studies the skin fibroblast proliferation assay was used. An increase in the number of cells in a standardized culture was used as a measure of relative proliferative capacity. Primary fibroblasts were established from skin biopsies taken from wild type and mutant mice. Duplicate or triplicate cultures of 0.05 million cells were plated and allowed to grow for six days. At the end of the culture period, the number of cells present in the culture was determined using a electronic particle counter.

Results: The female (−/−) mice exhibited a decreased skin fibroblast proliferation rate when compared with their gender-matched (+/+) littermates and the historical mean. [Analyzed wt/het/hom: 2/0/4]

Thus, homozygous mutant mice demonstrated a hypo-proliferative phenotype. As suggested by these observations, antagonists of a PRO9783 polypeptide or its encoding gene would be useful in decreasing abnormal cell proliferation.

(e) Bone Metabolism: Radiology Phenotypic Analysis

In the area of bone metabolism, targets were identified herein for the treatment of arthritis, osteoporosis, osteopenia and osteopetrosis as well as identifying targets that promote bone healing. Tests included:

DEXA for measurement of bone mineral density on femur and vertebra

MicroCT for very high resolution and very high sensitivity measurements of bone mineral density for both trabecular and cortical bone.

Dexa Analysis—Test Description:

Procedure: A cohort of 4 wild type, 4 heterozygotes and 8 homozygotes were tested in this assay. Dual Energy X-ray Absorptiometry (DEXA) has been used successfully to identify changes in bone. Anesthetized animals were examined and bone mineral content (BMC), BMC/LBM ratios, volumetric bone mineral density (vBMD), total body BMD, femur BMD and vertebra BMD were measured.

The mouse was anesthetized by intraperitoneal injection of Avertin (1.25% 2,2,2,-tribromoethanol, 20 ml/kg body weight), body length and weight were measured, and then the mouse was placed in a prone position on the platform of the PIXImus™ Densitometer (Lunar Inc.) for a DEXA scan. Using Lunar PIXImus software, the bone mineral density (BMD) and fat composition (% fat) and total tissue mass (TTM) were determined in the regions of interest (ROI) [i.e., whole body, vertebrae, and both femurs].

DEXA Results: The male (−/−) mice exhibited decreased mean bone mineral content, volumetric bone mineral density, bone mineral content index (BMC/LBM), and bone mineral density in total body, femur, and vertebrae when compared with their gender-matched (+/+) littermates and the historical means.

Bone microCT Analysis:

Procedure: MicroCT was also used to get very sensitive measurements of BMD. One vertebra and 1 femur were taken from a cohort of 4 wild type and 8 homozygous mice. Measurements were taken of lumbar 5 veterbra traebecular bone volume, traebecular thickness, connectivity density and midshaft femur total bone area and cortical thickness. The μCT40 scans provided detailed information on bone mass and architecture. Multiple bones were placed into sample holders and scanned automatically. Instrument software was used to select regions of interest for analysis. Trabecular bone parameters were analyzed in the fifth lumbar vertebrae (LV5) at 16 micrometer resolution and cortical bone parameters were analyzed in the femur midshaft at a resolution of 20 micrometers.

Micro-CT Analysis Results: The male (−/−) mice exhibited a notably decreased mean lumbar 5 vertebral trabecular bone volume, number, thickness, and connectivity density when compared with their gender-matched (+/+) littermates and the historical means. These mutants also exhibited notably decreased mean femoral midshaft cross-sectional area. [Analyzed wt/het/hom: 4/4/8]

These results demonstrate that knockout mutant male mice deficient in the gene encoding PRO9783 polypeptides exhibit abnormal bone metabolism with significant bone loss characterized by a decrease in bone mass with decreased density and possibly fragility leading to bone fractures. No hypercalcemia, hyperglycemia, or increased alkaline phosphate was detected in blood chemistry tests to suggest renal, parathyroid, or adrenal dysfunction that might be related to the decrease in bone mineral density seen on the DEXA scan. As the bone mineral density defect was only seen in male knockout mice, this bone abnormality observation suggests testosterone deficiency. Thus, it appears that PRO9783 polypeptides or agonists thereof would be useful in maintaining bone homeostasis mediated by male hormones such as testosterone. In addition, PRO9783 polypeptides or its encoding gene would be useful in maintaining bone homeostasis and could be important in bone healing or for the treatment of arthritis or osteoporosis; whereas antagonists to PRO9783 polypeptides or its encoding gene would lead to abnormal or pathological bone disorders including inflammatory diseases associated with abnormal bone metabolism such as arthritis, osteoporosis, and osteopenia.

C. Generation and Analysis of Mice Comprising DNA58848-1472 (UNQ551) Gene Disruptions In these knockout experiments, the gene encoding PRO1108 polypeptides (designated as DNA58848-1472) [UNQ551] was disrupted. The gene specific information for these studies is as follows: mouse nucleotide reference corresponds to: NM_018743 or *Mus musculus* putative lysophosphatidic acid acyltransferase (LOC55933), protein reference: NP_061213 or putative lysophosphatidic acid acyltransferase [*Mus musculus*]; the human nucleotide reference corresponds to: AF317516 or *Homo sapiens* putative lysophosphatidic acid acyltransferase, protein reference: AAG33063 or putative lysophosphatidic acid acyltransferase [*Homo sapiens*]. Retroviral Insertion (OST) appeared to be in the forward direction prior to the start codon of a predicted protein about 295 amino acids in length.

The gene that is mutated in these animals is represented by NCBI sequence NM_018743 (expressed sequence AU041707), which is the ortholog of human sequence AF317516 (DKFZp586M1819). Both loci encode a hypothetical putative lysophosphatidic acid acyltransferase. DKFZp586M1819 is likely to be an enzyme that catalyzes the biosynthesis of glycerolipids or phospholipids. DKFZp586M1819 contains a phosphate acyltransferase domain, which is found in enzymes that have glycerolphosphate, 1-acylglycerolphosphate, or 2-acylglycerolphosphoethanolamine acyltransferase activities (SMART SM00563).

DKFZp586M1819 has some similarity (33% similar over 270 residues) with 1-acylglycerol-3-phosphate O-acyltransferase 1 (AGPAT1; OMIM 603099). AGPAT1 catalyzes the conversion of lysophosphatidic acid to phosphatidic acid. Lysophosphatidic acid and phosphatidic acid are involved in signal transduction and lipid biosynthesis (Leung, D. W., Front Biosci., 6:D944-53 (2001)).

Targeted or gene trap mutations were generated in strain 129SvEv$^{Brd}$-derived embryonic stem (ES) cells. The chimeric mice were bred to C57BL/6J albino mice to generate F1 heterozygous animals. These progeny were intercrossed to generate F2 wild type, heterozygous, and homozygous mutant progeny. On rare occasions, for example when very few F1 mice were obtained from the chimera, F1 heterozygous mice were crossed to 129SvEv$^{Brd}$/C57 hybrid mice to yield additional heterozygous animals for the intercross to generate the F2 mice.

|          | wt    | het  | hom   | Total |
|----------|-------|------|-------|-------|
| Observed | 19    | 34   | 0     | 53    |
| Expected | 13.25 | 26.5 | 13.25 | 53    |

Chi-Sq. = 17.87 Significance = 0.00013 (hom/n) = 0.00 Avg. Litter Size = 0

In the wild-type animals, expression of the target gene was detected in embryonic stem (ES) cells and in all 13 adult tissue samples tested by RT-PCR, except bone and tail. Genetic data indicate that this retroviral insertion resulted in lethality of the homozygous mutants. Due to lethality, transcript expression analysis was not performed. It is not clear when lethality occurs. Expression of the gene starts at E8.5, continues in all subsequent stages examined thus far (up to E13). Normal expression is ubiquitous as shown by in situ hybridization.

Discussion Related to Embryonic Developmental Abnormality of Lethality:

Embryonic lethality in knockout mice usually results from various serious developmental problems including but not limited to neurodegenerative diseases, angiogenic disorders, inflammatory diseases, or where the gene/protein has an important role in basic cell signaling processes in many cell types. In addition, embryonic lethals are useful as potential cancer models. Likewise, the corresponding heterozygous (+/−) mutant animals are particularly useful when they exhibit a phenotype and/or a pathology report which reveals highly informative clues as to the function of the knocked-out gene. For instance, EPO knockout animals were embryonic lethals, but the pathology reports on the embryos showed a profound lack of RBCs.

In the present example, UNQ 551 is a novel lysophophatidic acid acyltransferase which catalyses the conversion of lysophophatidic acid (LPA) to phosphatidic acid (PA). LPA is a naturally occurring component of phospholipid and is known to have growth factor like activity in the regulation of numerous cellular responses through the activation of specific G-protein coupled receptors. LPA has recently been recognized as diagnostic marker for ovarian cancer thus indicating that a UNQ 551 mediated pathway is implicated in cancer progression (*Cancer Epidemiol Biomarkers Prev.* 13(7):1185-91 (2004)).

1. Phenotypic Analysis (for Disrupted Gene: DNA58848-1472 (UNQ551))

(a) Overall Phenotypic Summary:

The heterozygous (−/+) mutant mice exhibited immunological abnormalities when compared with their wild-type littermates and the historical mean. Serum IgM, IgG1, IgG2b and IgG3 were decreased in heterozygous adults.

(b) Further Embryonic Analysis

UNQ551 is expressed during the early stages of embryonic mouse development. A day after gastrulation at 8.5d UNQ551 is expressed in the newly formed mesoderm and also in the ectoplacental cone, a structure that will eventually contribute to the placenta. A day later, UNQ551 expression becomes widespread and uniform until at least mid-gestation. By 12.5d the placenta is fully formed and functional. The placenta provides an interface between mother and embryo to allow exchange of gases, nutrients and wastes. The placenta is also a source of hormones and growth factors and is involved in immune protection of the embryo. Deficiencies in any of these properties can lead to growth retardation and death. UNQ551 is expressed in the spongiotrophoblast layer of the placenta.

Homozygous UNQ551 mutant embryos start dying around 14.5 days. Mutants can first be identified at 12.5d by their small placentas. Also the amniotic fluid of mutants is yellow and the yolk sac vasculature is reduced. Both observations are characteristic of unhealthy embryos that are dying and undergoing resorption. Examination of placental histology at 12.5d revealed that projections of the labyrinthine layer into the spongiotrophoblast layer are reduced in number and extent in the mutants. Marker gene analysis confirms that the spongiotrophoblast layer that expresses UNQ551 is reduced in size.

The labyrinthine layer of the placenta is where the maternal and fetal blood circulations are juxtaposed for metabolic exchange. The reduction in branching and therefore reduced surface area in contact between the two systems in the UNQ551 mutant embryos leads to insufficient oxygen/nutrient exchange resulting in death of the embryo. UNQ551 is important in placental development especially in mediating the invasion of one tissue type into another as seen in the placenta. A similar role for UNQ551 can occur during metastasis.

(c) Immunology Phenotypic Analysis

Immune related and inflammatory diseases are the manifestation or consequence of fairly complex, often multiple interconnected biological pathways which in normal physiology are critical to respond to insult or injury, initiate repair from insult or injury, and mount innate and acquired defense against foreign organisms. Disease or pathology occurs when these normal physiological pathways cause additional insult or injury either as directly related to the intensity of the response, as a consequence of abnormal regulation or excessive stimulation, as a reaction to self, or as a combination of these.

Though the genesis of these diseases often involves multistep pathways and often multiple different biological systems/pathways, intervention at critical points in one or more of these pathways can have an ameliorative or therapeutic effect. Therapeutic intervention can occur by either antagonism of a detrimental process/pathway or stimulation of a beneficial process/pathway.

T lymphocytes (T cells) are an important component of a mammalian immune response. T cells recognize antigens which are associated with a self-molecule encoded by genes within the major histocompatibility complex (MHC). The antigen may be displayed together with MHC molecules on the surface of antigen presenting cells, virus infected cells, cancer cells, grafts, etc. The T cell system eliminates these altered cells which pose a health threat to the host mammal. T cells include helper T cells and cytotoxic T cells. Helper T cells proliferate extensively following recognition of an antigen-MHC complex on an antigen presenting cell. Helper T cells also secrete a variety of cytokines, i.e., lymphokines, which play a central role in the activation of B cells, cytotoxic T cells and a variety of other cells which participate in the immune response.

In many immune responses, inflammatory cells infiltrate the site of injury or infection. The migrating cells may be neutrophilic, eosinophilic, monocytic or lymphocytic as can be determined by histologic examination of the affected tissues. Current Protocols in Immunology, ed. John E. Coligan, 1994, John Wiley & Sons, Inc.

Many immune related diseases are known and have been extensively studied. Such diseases include immune-mediated inflammatory diseases (such as rheumatoid arthritis, immune mediated renal disease, hepatobiliary diseases, inflammatory bowel disease (IBD), psoriasis, and asthma), non-immune-mediated inflammatory diseases, infectious diseases, immunodeficiency diseases, neoplasia, and graft rejection, etc. In the area of immunology, targets were identified for the treatment of inflammation and inflammatory disorders.

In the area of immunology, targets have been identified herein for the treatment of inflammation and inflammatory disorders. Immune related diseases, in one instance, could be treated by suppressing the immune response. Using neutralizing antibodies that inhibit molecules having immune stimulatory activity would be beneficial in the treatment of immune-mediated and inflammatory diseases. Molecules which inhibit the immune response can be utilized (proteins directly or via the use of antibody agonists) to inhibit the immune response and thus ameliorate immune related disease.

The Following Tests were Performed:
Serum Immunoglobulin Isotyping Assay:

The Serum Immunoglobulin Isotyping Assay is performed using a Cytometric Bead Array (CBA) kit. This assay is used to rapidly identify the heavy and light chain isotypes of a mouse monoclonal antibody in a single sample. The values expressed are "relative fluorescence units" and are based on the detection of kappa light chains. Any value<6 is not significant.

Results:

The serum immunoglobulin isotyping assay revealed that heterozygous adults exhibited decreased serum IgM, IgG1, IgG2a, IgG2b and IgG3 levels. Thus, heterozygotes showed an abnormally low serum immunoglobulin levels compared with the (+/+) littermates. Homozygous mutant mice resulted in embryonic lethality. Thus, PRO1108 polypeptides or the gene encoding PRO1108 is essential for embryonic development. In addition, the gene encoding PRO1108 is essential for making immunoglobulins (or gamma globulins). A disease associated with the failure to make gamma globulins has been characterized as agammaglobulinemia linked to a single-gene defect on the X chromosome and thus occurs mainly in males. This single-gene defect in antibody production causes the absence of immunoglobulin isotypes known as IgM, IgA and several subclasses of IgG. Most inherited immunodeficiency diseases are caused by recessive gene defects. Recessive defects thus lead to disease or death only when both chromosomes are defective. In this case, the heterozygous mutant mice present an excellent model for studying an immunodeficiency disease such as agammaglobulinemia.

D. Generation and Analysis of Mice Comprising DNA203528-3014 (UNQ9196) Gene Disruptions In these knockout experiments, the gene encoding PRO34000 polypeptides (designated as DNA203528-3014) [UNQ9196] was disrupted. The gene specific information for these studies is as follows: the mutated mouse gene corresponds to nucleotide reference: BY731963 or BY731963 RIKEN full-length enriched, 8 cells embryo Mus musculus; the human nucleotide reference corresponds to: NM_153835 or homo sapiens G protein-coupled receptor 113 (GPR113), protein reference: NP_722577 or G-protein coupled receptor 113 [Homo sapiens].

The mutated mouse gene is represented by NCBI cDNA BY731963, which is orthologous to human GPR113 (G-protein coupled receptor 113). Aliases include PGR23 and hGPCR37. A single publication documents the existence of the human and mouse loci under the name PGR23 (Vassilatis et al., Proc. Natl. Acad. Sci. USA, 100(8):4903-8 (2003)). The SwissProt record for GPR113 (Q8IZF5) notes that the sequence was uploaded electronically under the title: New human G-protein coupled receptors with long N-terminals containing GPS domains and Ser/Thr rich regions.

Bioinformatic analysis of the human protein predicts a region of weak similarity to the hormone-receptor domain (HRM, Pfam 02793) encoded within residues 428-481, and a secretin-type G protein-coupled receptor motif at the C-terminus (Pfam 01825, Pfam 00002). The N-terminus (amino acids 20-427) is composed of nearly 20% serine or threonine residues.

GPR113 is not closely related to other human G protein-coupled receptors. However, it is about 40% similar over 780 residues to GPR116 (KIAA0758 protein), another orphan receptor.

Targeted or gene trap mutations were generated in strain 129SvEv$^{Brd}$-derived embryonic stem (ES) cells. The chimeric mice were bred to C57BL/6J albino mice to generate F1 heterozygous animals. These progeny were intercrossed to generate F2 wild type, heterozygous, and homozygous mutant progeny. On rare occasions, for example when very few F1 mice were obtained from the chimera, F1 heterozygous mice were crossed to 129SvEv$^{Brd}$/C57 hybrid mice to yield additional heterozygous animals for the intercross to generate the F2 mice.

|  | wt | het | hom | Total |
|---|---|---|---|---|
| Observed | 23 | 46 | 31 | 100 |
| Expected | 25 | 50 | 25 | 100 |

Chi-Sq. = 1.92
Significance = 0.38289
(hom/n) = 0.31
Avg. Litter Size = 0

Level I phenotypic analysis was performed on mice from this generation as described below.

Wild-type expression of the target gene was detected in embryonic stem (ES) cells and, among the 44 adult and fetal tissue samples tested by RT-PCR, in thymus, spleen, testis, salivary gland, skeletal muscle, uterus, adipose, bladder, thyroid, aorta, eye, placenta, 9.5 day embryo, 12.5 day embryo, fetal brain, and fetal lung. Disruption of the target gene was confirmed by Southern hybridization analysis.

1. Phenotypic Analysis (for Disrupted Gene: DNA203528-3014 (UNQ9196)

(a) Overall Phenotypic Summary

Mutation of the gene encoding the ortholog of a human predicted G protein-coupled receptor 113 (GPR113) resulted in decreased trabecular bone volume, thickness, and connectivity density in (−/−) mutants. Knockouts also showed an abnormal glucose tolerance. Gene disruption was confirmed by Southern blot.

(b) Bone Metabolism: Radiology Phenotypic Analysis

Procedure:

In the area of bone metabolism, targets were identified herein for the treatment of arthritis, osteoporosis, osteopenia and osteopetrosis as well as identifying targets that promote bone healing. Tests included microCT for very high resolution and very high sensitivity measurements of bone mineral density for both trabecular and cortical bone.

Bone MicroCT Analysis:

Procedure: MicroCT was also used to get very sensitive measurements of BMD. One vertebra and 1 femur were taken from a cohort of 4 wild type and 8 homozygous mice. Measurements were taken of lumbar 5 veterbra traebecular bone volume, traebecular thickness, connectivity density and midshaft femur total bone area and cortical thickness. The μCT40 scans provided detailed information on bone mass and architecture. Multiple bones were placed into sample holders and scanned automatically. Instrument software was used to select regions of interest for analysis. Trabecular bone parameters were analyzed in the fifth lumbar vertebrae (LV5) at 16 micrometer resolution and cortical bone parameters were analyzed in the femur midshaft at a resolution of 20 micrometers.

Micro-CT Analysis Results: The (−/−) mice exhibited notably decreased mean vertebral trabecular bone volume, number, thickness, and connectivity density when compared with their gender-matched (+/+) littermates and the historical means. [Analyzed wt/het/hom: 4/0/8]

These results demonstrate that knockout mutant mice exhibit abnormal bone metabolism with significant bone loss similar to osteoporosis characterized by decrease in bone mass with decreased density and possibly fragility leading to bone fractures. Thus, it appears that PRO34000 polypeptides or agonists thereof would be useful in maintaining bone homeostasis. In addition, PRO34000 polypeptides or its encoding gene would be useful in maintaining bone homeostasis and would be important in bone healing or for the treatment of arthritis or osteoporosis; whereas antagonists to PRO34000 polypeptides or its encoding gene would lead to abnormal or pathological bone disorders including inflammatory diseases associated with abnormal bone metabolism including arthritis, osteoporosis, and osteopenia.

(c) Phenotypic Analysis: Metabolism—Blood Chemistry

In the area of metabolism, targets may be identified for the treatment of diabetes. Blood chemistry phenotypic analysis includes glucose tolerance tests to measure insulin sensitivity and changes in glucose metabolism. Abnormal glucose tolerance test results may indicate but may not be limited to the following disorders or conditions: Diabetes Type 1 and Type 2, Syndrome X, various cardiovascular diseases and/or obesity.

Procedure: A cohort of 2 wild type and 4 homozygote mice were used in this assay. The glucose tolerance test is the standard for defining impaired glucose homeostasis in mammals. Glucose tolerance tests were performed using a Lifescan glucometer. Animals were injected IP at 2 g/kg with D-glucose delivered as a 20% solution and blood glucose levels were measured at 0, 30, 60 and 90 minutes after injection.

Results: These studies indicated that (−/−) mice exhibit enhanced glucose tolerance in the presence of normal fasting glucose at all 3 intervals tested when compared with their gender-matched (+/+) littermates and the historical means. In addition, hyperinsulinemia was not apparent in the (−/−) mice. No abnormality was seen in the remaining clinical chemistry data. Thus, knockout mice exhibited the opposite phenotypic pattern of an impaired glucose homeostasis, and as such antagonists to PRO34000 polypeptides or its encoding gene would be useful in the treatment of impaired glucose homeostasis and/or diabetes.

E. Generation and Analysis of Mice Comprising DNA34387-1138 (UNQ214) Gene Disruptions In these knockout experiments, the gene encoding PRO240 polypeptides (designated as DNA34387-1138) [UNQ214] was disrupted. The gene specific information for these studies is as follows: the mutated mouse gene corresponds to nucleotide reference: AK002276 or *Mus musculus* adult male kidney cDNA, RIKEN full-length enriched library, clone: 0610007C21: homolog to HSPC013, full insert sequence, protein reference is BAB21981 or data source: SPTR, source key: Q9Y2R7, evidence: ISS-homolog to HSPC013-putative [*Mus musculus*]. The human gene sequence is as follows: nucleotide reference: BC021237 or *Homo sapiens*, clone IMAGE: 4303513; protein reference: AAH11006. Unknown (protein for MGC: 13322) [*Homo sapiens*].

The gene that is mutated in these animals is represented by mouse UniGene cluster Mm.28144, which is the ortholog of human UniGene cluster Hs.9527 (APR-3). APR-3 encodes apoptosis related protein APR-3. The protein is also known as p18, HSPC013, and p18 protein.

SMART (Shultz et al., *Nucleic Acids Res.*, 28(1):231-4 (2000)) analysis predicts an EGF-like domain (Pfam PF00008) and a cleavable signal peptide in the hypothetical protein, as well as a possible transmembrane domain. EGF-like domains are a common feature found in secreted proteins and the extracellular portions of membrane-bound proteins.

Little specific information is available concerning APR-3, but it may be involved in apoptosis and may be involved in hematopoietic development and differentiation (Zhang et al., *Genome Res.*, 10(10): 1546-60(2000)). There are several alternate splice forms of the mouse and human APR-3 gene.

Targeted or gene trap mutations were generated in strain 129SvEv$^{Brd}$-derived embryonic stem (ES) cells. The chimeric mice were bred to C57BL/6J albino mice to generate F1 heterozygous animals. These progeny were intercrossed to generate F2 wild type, heterozygous, and homozygous mutant progeny. On rare occasions, for example when very few F1 mice were obtained from the chimera, F1 heterozygous mice were crossed to 129SvEv$^{Brd}$/C57 hybrid mice to yield additional heterozygous animals for the intercross to generate the F2 mice. Level I phenotypic analysis was performed on mice from this generation as described below.

|  | wt | het | hom | Total |
|---|---|---|---|---|
| Observed | 12 | 31 | 17 | 60 |
| Expected | 15 | 30 | 15 | 60 |

Chi-Sq. = 0.90
Significance = 0.63763
(hom/n) = 0.28
Avg. Litter Size = 0

Retroviral insertion appears to be in the forward direction near amino acid 30 out of about 225. Wild-type expression of the target gene was detected in embryonic stem (ES) cells and in all 13 adult tissues tested by RT-PCR. RT-PCR analysis revealed that the transcript was absent in the (−/−) mouse analyzed (F-91).

1. Phenotypic Analysis (for Disrupted Gene: DNA34387-1138 (UNQ214)

(a) Cardiovascular Phenotypic Analysis:

In the area of cardiovascular biology, phenotypic testing was performed to identify potential targets for the treatment of cardiovascular, endothelial or angiogenic disorders. One such phenotypic test included optic fundus photography and angiography to determine the retinal arteriovenous ratio (A/V ratio) in order to flag various eye abnormalities. An abnormal A/V ratio signals such systemic diseases or disorders that may be related to the vascular disease of hypertension (and any disease that causes hypertension, e.g. atherosclerosis), diabetes or other ocular diseases corresponding to opthalmological disorders. Such eye abnormalities may include but are not limited to the following: retinal abnormality is retinal dysplasia, various retinopathies, restenosis, retinal artery obstruction or occlusion; retinal degeneration causing secondary atrophy of the retinal vasculature, retinitis pigmentosa, macular dystrophies, Stargardt's disease, congenital stationary night blindness, choroideremia, gyrate atrophy, Leber's congenital amaurosis, retinoschisis disorders, Wagner's syndrome, Usher syndromes, Zellweger syndrome, Saldino-Mainzer syndrome, Senior-Loken syndrome, Bardet-Biedl syndrome, Alport's syndrome, Alstom's syndrome, Cockayne's syndrome, dysplaisa spondyloepiphysaria congentia, Flynn-Aird syndrome, Friedreich ataxia, Hallgren syndrome, Marshall syndrome, Albers-Schnoberg disease, Refsum's disease, Kearns-Sayre syndrome, Waardenburg's syndrome, Alagile syndrome, myotonic dystrophy, olivopontocerebellar atrophy, Pierre-Marie dunsdrome, Stickler syndrome, carotinemeia, cystinosis, Wolfram syndrome, Bassen-Kornzweig syndrome, abetalipoproteinemia, incontinentia pigmenti, Batten's disease, mucopolysaccharidoses, homocystinuria, or mannosidosis.

In addition, optic fundus photography and angiography may be used to determine cataract formation. Cataracts are associated with such systemic diseases as: Human Down's syndrome, Hallerman-Streiff syndrome, Lowe syndrome, galactosemia, Marfan syndrome, Trismoy 13-15 condition, Alport syndrome, myotonic dystrophy, Fabry disease, hypothroidisms, or Conradi syndrome. Other ocular developmental anomalies include: Aniridia, anterior segment and dysgenesis syndrome. Cataracts may also occur as a result of an intraocular infection or inflammation (uveitis).

Procedure:

A cohort of 4 wild type, 4 heterozygotes and 8 homozygotes were tested in this assay. Optic fundus photography was performed on conscious animals using a Kowa Genesis small animal fundus camera modified according to Hawes and coauthors (Hawes et al., 1999 Molecular Vision 1999; 5:22). Intra-peritoneal injection of fluorescein permitted the acquisition of direct light fundus images and fluorescent angiograms for each examination. In addition to direct opthalmological changes, this test can detect retinal changes associated with systemic diseases such as diabetes and atherosclerosis. Pictures were provided of the optic fundus under normal light. The angiographic pictures allowed examination of the arteries and veins of the eye. In addition an artery to vein (A/V) ratio was determined for the eye.

Opthalmology analysis was performed on generated F2 wild type, heterozygous, and homozygous mutant progeny using the protocol described above. Specifically, the A/V ratio was measured and calculated according to the fundus images with Kowa COMIT+ software. This test takes color photographs through a dilated pupil: the images help in detecting and classifying many diseases. The artery to vein ratio (A/V) is the ratio of the artery diameter to the vein diameter (measured before the bifurcation of the vessels). Many diseases will influence the ratio, i.e., diabetes, cardiovascular disorders, papilledema, optic atrophy or other eye abnormalities such as retinal degeneration (known as retinitis pigmentosa) or retinal dysplasia, vision problems or blindness. Thus, phenotypic observations which result in an increased artery-to-vein ratio in homozygous (−/−) and heterozygous (+/−) mutant progeny compared to wildtype (+/+) littermates would be indicative of such pathological conditions.

Results:

In this study, developing cataracts were observed in 6 (−/−) mice (F-97, -115, -117, F-120, -134, and -137) and 1 (+/−) mice (F-99), being more severe in the (−/−) mice. The male (−/−) mouse examined (-141) exhibited a cataract in the right eye. A slight increase in artery to ratio was also seen. In summary, by knocking out the gene identified as DNA34387-1138 (UNQ214) which encodes PRO240 polypeptides, both heterozygous and homozygous mutant progeny exhibit phenotypes which are associated with cataract formation and/or other opthalmological disorders. Such detected opthalmology changes are most commonly associated with cardiovascular systemic diseases. In particular, cataract formation may be indicative of a cardiovascular complication related to disturbances in the blood coagulation cascade. Cataracts are also associated with such systemic diseases as: Human Down's syndrome, Hallerman-Streiff syndrome, Lowe syndrome, galactosemia, Marfan syndrome, Trismoy 13-15 condition, Alport syndrome, myotonic dystrophy, Fabry disease, hypothroidisms, Conradi syndrome. Thus, antagonists of PRO240 polypeptides or its encoding genes would lead to similar pathological changes, whereas agonists would be useful as therapeutic agents in the prevention of cataract formation and/or the underlying cardiovascular disease or opthalmological disorder.

F. Generation and Analysis of Mice Comprising DNA52192-1369 (UNQ480) Gene Disruptions In these knockout experiments, the gene encoding PRO943 polypeptides (designated as DNA52192-1369) [UNQ480] was disrupted. The gene specific information for these studies is as follows: the mouse nucleotide reference corresponds to: NM_054071 or *Mus musculus* fibroblast growth factor receptor-like 1 (Fgfrl1); protein reference: NP_473-412 or fibroblast growth factor receptor-like 1; fibroblast growth factor receptor 5 [*Mus musculus*]; the human nucleotide reference corresponds to: NM_021923 or *Homo sapiens* fibroblast growth factor receptor-like 1 (FGFRL1), protein reference: NP_068742 or fibroblast growth factor receptor-like 1 precursor [*Homo sapiens*].

The gene that is mutated in these animals is represented by mouse UniGene cluster Mm.35691, which is the ortholog of human UniGene cluster Hs.193326 (FGFRL1). FGFRL1 encodes fibroblast growth factor, receptor-like 1. The protein is also known as FGFR5, FGFR5beta, FGFR5gamma, and fibroblast growth factor receptor 5.

FGFRL1, a member of the fibroblast growth factor receptor family, contains a signal peptide, three extracellular Ig-like modules, six cysteines, an acidic box with no HAV motif, a transmembrane segment, and a short intracellular domain lacking the usual tyrosine kinase domain required for signal transduction by transphosphorylation (Wiedemann, M., and Trued, B., Genomics, 69(2):275-9 (2000); Kim et al., Biocim Biophys Acta, 1518(1-2):152-6 (2001); Wiedemann, M. and Trued, B., Biochim Biophys Acta, 1520(3):247-50 (2001), Sleeman et al., Gene, 271(2):171-82 (2001)) further classified FGFRL1 as a member of the I-set subgroup of the Ig-superfamily, consistent with the known FGFRs.

Although no precise function has been attributed to FGFRL1, Wiedemann, M. and Trued, B. suggested that FGFRL1 may play a role in modulating FGF receptor activity. FGFRL1 is expressed at high levels in the pancreas, suggesting that FGFRL1 may regulate pancreatic function (Kim et al, 2001 supra). In addition to kidney, FGFRL1 expression is high in brain and lung (Sleeman et al, 2001 supra).

Targeted or gene trap mutations were generated in strain 129SvEv$^{Brd}$-derived embryonic stem (ES) cells. The chimeric mice were bred to C57BL/6J albino mice to generate F1 heterozygous animals. These progeny were intercrossed to generate F2 wild type, heterozygous, and homozygous mutant progeny. On rare occasions, for example when very few F1 mice were obtained from the chimera, F1 heterozygous mice were crossed to 129SvEv$^{Brd}$/C57 hybrid mice to yield additional heterozygous animals for the intercross to generate the F2 mice.

|  | wt | het | hom | Total |
|---|---|---|---|---|
| Observed | 30 | 68 | 1 | 99 |
| Expected | 24.75 | 49.5 | 24.75 | 99 |

Chi-Sq. = 30.82
Significance = 0.00000
(hom/n) = 0.01
Avg. Litter Size = 0

In the wild-type animals, expression of the target gene was detected in embryonic stem (ES) cells and in all 13 adult tissue samples tested by RT-PCR. Disruption of the target gene was confirmed by Southern hybridization analysis. Genetic data indicate that this mutation resulted in lethality of the homozygous mutants. No notable phenotype was observed for the heterozygous mice. Due to lethality, transcript expression analysis was not performed.

1. Phenotypic Analysis (for Disrupted Gene: DNA52192-1369 (UNQ480)

Mutation of the target gene (UNQ480) resulted in embryonic lethality. Heterozygous male (+/−) mice exhibited an increased mean femoral midshaft cross-sectional area when compared with their gender-matched littermates and the historical mean.

Discussion Related to Developmental Abnormality of Embryonic Lethality for UNQ480 and the Negative Phenotype Associated with Heterozygous Male Mutant Mice:

Embryonic lethality in knockout mice usually results from various serious developmental problems including but not limited to neurodegenerative diseases, angiogenic disorders, inflammatory diseases, or where the gene/protein has an important role in basic cell signaling processes in many cell types. In addition, embryonic lethals are useful as potential cancer models. Likewise, the corresponding heterozygous (+/−) mutant animals are particularly useful when they exhibit a phenotype and/or a pathology report which reveals highly informative clues as to the function of the knocked-out gene. For instance, EPO knockout animals were embryonic lethals, but the pathology reports on the embryos showed a profound lack of RBCs.

With regards to UNQ480, the disease conditions more likely to be associated with the embryonic lethality are as follows:
chondrodyplasia
osteoarthritis
pancreatic diseases
vascular development
multiple sclerosis During embryonic development UNQ480 is preferentially expressed in the cartilage of skeletal tissues indicating involvement in the control of proliferation and differentiation of chondrocytes. Mutations in cartilage proteins can cause severe congenital disorders, including various forms of chondrodyplasia. In the adult, degeneration of the cartilage can lead to osteoarthritis.

UNQ480 is also expressed at high levels in the developing foregut endoderm which will give rise to the pancreatic analage. In adult human tissues UNQ480 is preferentially expressed in the pancreas. Several FGFs and their receptors are expressed in human pancreatic cancer cell lines and are overexpressed in human pancreatic cancers or in the pancreas of chronic pancreatitis. Therefore, overexpression of UNQ480 is involved in the pathobiology of pancreatic diseases.

UNQ480 also plays a role in vascular development as it binds FGF2 which is known to be involved in this process. FGF2 has also been shown to play a role in demyelination and thus can be involved in demyelination diseases such as multiple sclerosis; by inference so might UNQ480.

(a) Bone Metabolism: Radiology Phenotypic Analysis
Procedure:
In the area of bone metabolism, targets were identified herein for the treatment of arthritis, osteoporosis, osteopenia and osteopetrosis as well as identifying targets that promote bone healing. Tests included microCT for very high resolution and very high sensitivity measurements of bone mineral density for both trabecular and cortical bone.

Bone MicroCT Analysis:
Procedure: MicroCT was also used to get very sensitive measurements of BMD. One vertebra and 1 femur were taken from a cohort of 4 wild type and 8 heterozygous mice. Measurements were taken of lumbar 5 veterbra traebecular bone volume, traebecular thickness, connectivity density and midshaft femur total bone area and cortical thickness. The μCT40 scans provided detailed information on bone mass and architecture. Multiple bones were placed into sample holders and scanned automatically. Instrument software was used to select regions of interest for analysis. Trabecular bone parameters were analyzed in the fifth lumbar vertebrae (LV5) at 16 micrometer resolution and cortical bone parameters were analyzed in the femur midshaft at a resolution of 20 micrometers.

Micro-CT Analysis Results: The male (+/−) mice exhibited an increased mean femoral midshaft cross-sectional area when compared with their gender-matched (+/+) littermates and the historical mean.

(b) Further Pathology Observations
In addition to the above discussion, UNQ480 knockout mice were further investigated to determine what factors were involved which contributed to the embryonic lethality phenotype for the homozygous mice. The results of these studies show that UNQ480 (designated as FGFRL1) is essential for kidney development and can play a positive role in FGF signaling.

FGFRL1 is expressed during embryonic development in the intermediate mesoderm that gives rise to the two precursor cell populations of the kidney; the metenephric mesenchyme and the Wolffian duct. Kidney development starts at embryonic day 10.5 when the metenephric mesenchyme signals to the adjacent epithelial Wolffian duct to induce ureteric bud formation. FGFRL1 is expressed in the metenephric mesenchyme at this stage. The ureteric bud grows and branches in response to signals from the metenephric mesenchyme to form the collecting duct system of the mature kidney. Reciprocal signals from the ureteric bud cause the metenephric mesenchyme to undergo a mesenchymal to epithelial transition to form the excretory portion of the kidney, the nephron.

UNQ480 homozygous mutants die around birth and exhibit kidney agenesis. The initial ureteric bud forms normally in the UNQ480 mutants as illustrated by the normal expression pattern of c-ret at embryonic day 10.5. However, a day later the ureteric bud fails to branch and form the characteristic T-shape structure. Wnt-11 is expressed in the ureteric bud prior to branching but little to no Wnt-11 is expressed in the UNQ480 mutants. Pax2 is expressed in mesenchyme condensing around the tips of the ureteric bud, although Pax2 is expressed in the UNQ480 mutants, the numbers of cells and levels of expression is greatly reduced. These observations suggest that FGFRL1 signals from the metenephric mesenchyme to the ureteric bud to undergo branching morphogenesis. By 13.5d the ureteric bud has normally branched many times as illustrated by c-ret expression. Similarly Wnt-11 marks the branch termini at these stages. Both these genes are either missing or greatly down regulated in the UNQ480 mutants.

Little detail is known about the role of FGF signaling during the early stages of kidney development. However, over expression of a dominant negative form of FGFR2 blocks ureteric branching providing compelling evidence that FGF signaling plays a key role. The endogenous receptor affected in the dominant negative model is unknown because the FGFR2 knock out develops kidneys normally. However, FGFRL1 plays a role in this process.

In summary we have identified UNQ480 (FGFRL1) as a key regulator during the early stages of kidney development. This data suggests that FGFRL1 plays a positive role in FGF signaling.

G. Generation and Analysis of Mice Comprising DNA98557 (UNQ1425) Gene Disruptions In these knockout experiments, the gene encoding hu A33 polypeptides (designated as DNA98557) [UNQ1425] was disrupted. The gene specific information for these studies is as follows: the mouse nucleotide reference corresponds to: NM_021610 or *Mus musculus* glycoprotein A33 (transmembrane) (Gpa33), the protein reference: NP_067623 or glycoprotein A33 (transmembrane); A33 antigen [*Mus musculus*]; the human nucleotide reference corresponds to: NM_005814 or *Homo sapiens* glycoprotein A33 (transmembrane) (GPA33), protein reference: NP_005805 or transmembrane glycoprotein A33 precursor [*Homo sapiens*]. Retroviral insertion disrupted the gene prior to the exon encoding amino acid 3 in a protein of 315 amino acids (mouse NCBI accession number NP_067623).

The disrupted mouse gene is glycoprotein A33 (GPA33), ortholog of human GPA33. Aliases include cell surface antigen A33; A33, A33 antigen, and cell surface A33 antigen.

GPA33 is a transmembrane protein containing two immunoglobulin domains (Pfam PF00047) and is expressed almost exclusively in intestinal epithelial cells (Abud et al., Mech. Dev., 98(1-2): 111-4 (2000)).

Targeted or gene trap mutations were generated in strain 129SvEv$^{Brd}$-derived embryonic stem (ES) cells. The chimeric mice were bred to C57BL/6J albino mice to generate F1 heterozygous animals. These progeny were intercrossed to generate F2 wild type, heterozygous, and homozygous mutant progeny. On rare occasions, for example when very few F1 mice were obtained from the chimera, F1 heterozygous mice were crossed to 129SvEv$^{Brd}$/C57 hybrid mice to yield additional heterozygous animals for the intercross to generate the F2 mice. Level I phenotypic analysis was performed on mice from this generation Wild-type expression of the target gene was detected in embryonic stem (ES) cells and, among the 13 adult tissue samples tested by RT-PCR, in thymus, testis, and small intestine and colon. RT-PCR analysis revealed that the transcript was absent in the (−/−) mouse analyzed (F-99).

|  | wt | het | hom | Total |
| --- | --- | --- | --- | --- |
| Observed | 29 | 47 | 24 | 100 |
| Expected | 25 | 50 | 25 | 100 |

Chi-Sq. = 0.86
Significance = 0.65051
(hom/n) = 0.24
Avg. Litter Size = 0

1. Phenotypic Analysis (for Disrupted Gene: DNA98557 (UNQ1425)

(a) Overall Phenotypic Summary:

The homozygous mutant mice exhibited an increased mean percentage of CD4 cells and a decreased mean percentage of CD8 cells in the spleen and thymus when compared with their wild-type littermates. In addition, the mutants exhibited a decreased mean percentage of CD21hiCD23med B cells in the lymph node. RT-PCR analysis revealed that the transcript was absent in the homozygous mutant mice.

The male (−/−) mice also exhibited an increased mean serum cholesterol level when compared with their gender-matched (+/+) littermates and the historical mean.

(b) Phenotypic Analysis: Cardiology

In the area of cardiovascular biology, targets were identified herein for the treatment of hypertension, atherosclerosis, heart failure, stroke, various coronary artery diseases, dyslipidemias such as high cholesterol (hypercholesterolemia) and elevated serum triglycerides (hypertriglyceridemia), cancer and/or obesity.

The phenotypic tests included the measurement of serum cholesterol and triglycerides. In addition, inflammation assays were performed to identify potential targets for the inflammatory component of atherosclerosis.

Blood Lipids

Procedure:

A cohort of 5 wild type, 4 heterozygotes and 8 homozygotes were tested in this assay. High cholesterol levels are recognized risk factors in the development of cardiovascular disease. Measuring blood lipids allowed finding of the biological switches that regulate blood lipid levels and that upon inhibition would lead to a reduction in the risk for cardiovascular disease. Cholesterol measurements were recorded. The COBAS Integra 400 (mfr: Roche) was used for running blood chemistry tests on mice.

Results:

As summarized above, the (−/−) mice exhibited a 35% increased mean serum cholesterol level when compared with their gender-matched (+/+) littermates and the historical mean. No change in triglycerides was observed. (Analyzed wt/het/hom: 5/4/8)

Thus, mutant mice deficient in the A33 gene can serve as a model for cardiovascular disease. A33 polypeptides or its encoding gene would be useful in regulating blood lipids and in particular maintaining normal cholesterol metabolism. Thus A33 polypeptides would be useful for the treatment of such cardiovascular diseases as: hypertension, atherosclerosis, heart failure, stroke, various coronary artery diseases or diabetes.

(c) Immunology Phenotypic Analysis

Immune related and inflammatory diseases are the manifestation or consequence of fairly complex, often multiple interconnected biological pathways which in normal physiology are critical to respond to insult or injury, initiate repair from insult or injury, and mount innate and acquired defense against foreign organisms. Disease or pathology occurs when these normal physiological pathways cause additional insult or injury either as directly related to the intensity of the response, as a consequence of abnormal regulation or excessive stimulation, as a reaction to self, or as a combination of these.

Though the genesis of these diseases often involves multi-step pathways and often multiple different biological systems/pathways, intervention at critical points in one or more of these pathways can have an ameliorative or therapeutic effect. Therapeutic intervention can occur by either antagonism of a detrimental process/pathway or stimulation of a beneficial process/pathway.

T lymphocytes (T cells) are an important component of a mammalian immune response. T cells recognize antigens which are associated with a self-molecule encoded by genes within the major histocompatibility complex (MHC). The antigen may be displayed together with MHC molecules on the surface of antigen presenting cells, virus infected cells, cancer cells, grafts, etc. The T cell system eliminates these altered cells which pose a health threat to the host mammal. T cells include helper T cells and cytotoxic T cells. Helper T cells proliferate extensively following recognition of an antigen-MHC complex on an antigen presenting cell. Helper T cells also secrete a variety of cytokines, i.e., lymphokines, which play a central role in the activation of B cells, cytotoxic T cells and a variety of other cells which participate in the immune response.

In many immune responses, inflammatory cells infiltrate the site of injury or infection. The migrating cells may be neutrophilic, eosinophilic, monocytic or lymphocytic as can be determined by histologic examination of the affected tissues. Current Protocols in Immunology, ed. John E. Coligan, 1994, John Wiley & Sons, Inc.

Many immune related diseases are known and have been extensively studied. Such diseases include immune-mediated inflammatory diseases (such as rheumatoid arthritis, immune mediated renal disease, hepatobiliary diseases, inflammatory bowel disease (IBD), psoriasis, and asthma), non-immune-mediated inflammatory diseases, infectious diseases, immunodeficiency diseases, neoplasia, and graft rejection, etc.

In the area of immunology, targets were identified herein for the treatment of inflammation and inflammatory disorders. Immune related diseases could be treated by suppressing the immune response. Using neutralizing antibodies that inhibit molecules having immune stimulatory activity would be beneficial in the treatment of immune-mediated and inflammatory diseases. Molecules which inhibit the immune response can be utilized (proteins directly or via the use of antibody agonists) to inhibit the immune response and thus ameliorate immune related disease.

The Following Tests were Performed:

Flourescence-activated Cell-sorting (FACS) Analysis Procedure:

FACS analysis of immune cell composition from peripheral blood was performed including CD4, CD8 and T cell receptor to evaluate T lymphocytes, CD19 for B lymphocytes, CD45 as a leukocyte marker and pan NK for natural killer cells. The FACS analysis was carried out on 2 wild type and 6 homozygous mice and included cells derived from thymus, spleen, bone marrow and lymph node.

In these studies, analyzed cells were isolated from thymus, peripheral blood, spleen, bone marrow and lymph nodes. Flow cytometry was designed to determine the relative proportions of CD4 and CD8 positive T cells, B cells, NK cells and monocytes in the mononuclear cell population. A Becton-Dickinson FACSCalibur 3-laser FACS machine was used to assess immune status. For Phenotypic Assays and Screening, this machine records CD4+/CD8−, CD8+/CD4−, NK, B cell and monocyte numbers in addition to the CD4+/CD8+ ratio.

The mononuclear cell profile was derived by staining a single sample of lysed peripheral blood from each mouse with a panel of six lineage-specific antibodies: CD45 PerCP, anti-TCRb APC, CD4 PE, CD8 FITC, pan-NK PE, and CD19 FITC. The two FITC and PE labeled antibodies stain mutually exclusive cell types. The samples were analyzed using a Becton Dickinson FACSCalibur flow cytometer with CellQuest software.

Results:

The homozygous mutant mice exhibited an increased mean percentage of CD4+/CD8− cells and a decreased mean percentage of CD4−/CD8+ cells in the spleen and thymus when compared with their wild-type littermates. In addition, tissue-specific FACS analysis resulted in the following observations: The (−/−) mice exhibited a decreased mean percentage of CD21hiCD23med B cells in the lymph node when compared with their (+/+) littermates; the (−/−) mice also showed decreased mean percentages of B220dim CD43dim and B220Med IgD-cells in bone marrow.

In summary, FACS analysis of immune cell composition from peripheral blood indicates that knockout mice exhibit immunological differences with respect to CD4 and CD8 cells when compared with their wild-type littermates. Thus, antagonists of A33 polypeptides or its encoding gene would be expected to mimic these effects. The co-receptor CD4 molecule cooperates with the T-cell receptor which differentially recognizes MHC class II molecules in the antigen recognition process. An increased mean percentage of CD4 cells plays a central role in B cell activation.

H. Generation and Analysis of Mice Comprising DNA33223-1136 (UNQ204) Gene Disruptions In these knockout experiments, the gene encoding PRO230 polypeptides (designated as DNA33223-1136) [UNQ204] was disrupted. The gene specific information for these studies is as follows: mouse nucleotide reference: NM_023476 or *Mus musculus* lipocalin 7 (Lcn7); mouse protein reference: NP_075965 or lipocalin 7; androgen-regulated gene 1 [*Mus musculus*]; human gene nucleotide reference: NM_022164 or *Homo sapiens* lipocalin 7 (LCN7), protein reference: NP_071447 or P3ECSL; glucocorticoid-inducible protein; oxidized-LDL responsive gene 2; tubulointerstitial nephritis antigen-related protein precursor; likely ortholog of lipocalin 7; androgen-regulated gene 1 [*Homo sapiens*].

The targeted mouse gene is lipocalin 7 (Lcn7), ortholog of human lipocalin 7 (LCN7). Aliases include androgen-regulated gene 1, Arg1, P3ECSL, oxidized-LDL responsive gene 2, glucocorticoid-inducible protein, and tubulointerstitial nephritis antigen-related protein precursor.

LCN7 is a secreted protein with weak homology to cathepsin-like proteases. The protein of about 460 amino acids contains a signal peptide, epidermal growth factor-like repeats, and a proteolytically inactive cathepsin B-related domain (Mukai et al., J. Biol. Chem., 278(19):17084-92

(2003)). LCN7 also contains a lipocalin signature, which typically binds with small hydrophobic molecules (Kobayashi et al., J. Steroid Biochem. Mol. Biol., 77(2-3): 109-15 (2001)). The molecular function of LCN7 is not known; it does not have proteolytic activity though it has features of a protease.

LCN7 expression is induced by androgens in androgen-dependent mouse mammary Shionogi carcinoma SC-3 cells and in prostate. LCN7 is also detected in kidney, heart, lung, spleen, and liver (Kobayashi et al, 2001 supra). Expression of the protein may be restricted to vascular smooth muscle cells as well as skeletal muscle, cardiac muscle, and kidney cells (Wex et al., Biochemistry, 40(5):1350-7 (2001)). LCN7 may be involved in zonal differentiation in the adrenal cortex (Mukai et al, 2003 supra) or in endosomal trafficking (Bromme et al., Biochem. Biophys. Res. Commun., 271(2):474-80 (2000)). It may also be a structural or regulatory protein.

Targeted or gene trap mutations were generated in strain 129SvEv$^{Brd}$-derived embryonic stem (ES) cells. The chimeric mice were bred to C57BL/6J albino mice to generate F1 heterozygous animals. These progeny were intercrossed to generate F2 wild type, heterozygous, and homozygous mutant progeny. On rare occasions, for example when very few F1 mice were obtained from the chimera, F1 heterozygous mice were crossed to 129SvEv$^{Brd}$/C57 hybrid mice to yield additional heterozygous animals for the intercross to generate the F2 mice. Level I phenotypic analysis was performed on mice from this generation as shown below.

|  | wt | het | hom | Total |
|---|---|---|---|---|
| Observed | 27 | 51 | 22 | 100 |
| Expected | 25 | 50 | 25 | 100 |

Chi-Sq. = 0.54
Significance = 0.76338
(hom/n) = 0.22
Avg. Litter Size = 0

Wild-type expression of the target gene was detected in all 13 adult tissue samples tested by RT-PCR, except brain, skeletal muscle, bone, stomach, small intestine, and colon, and adipose. Disruption of the target gene was confirmed by Southern hybridization analysis.

1. Phenotypic Analysis (for Disrupted Gene: DNA33223-1136 (UNQ204)

(a) Overall Phenotypic Summary:

The female homozygous mutant mice exhibited a decreased anxiety-like response during open field activity testing when compared with their gender-matched wild-type littermates and the historical mean. The homozygous mutant mice also showed an increased response to the ovalbumin challenge. Disruption of the target gene was confirmed by Southern hybridization analysis.

(b) Phenotypic Analysis: CNS/Neurology

In the area of neurology, analysis focused herein on identifying in vivo validated targets for the treatment of neurological and psychiatric disorders. Neurological disorders include but are not limited to: depression, generalized anxiety disorders, attention deficit disorder, sleep disorder, hyperactivity disorder, obsessive compulsive disorder, schizophrenia, cognitive disorders, hyperalgesia and sensory disorders, mild to moderate anxiety, anxiety disorder due to a general medical condition, anxiety disorder not otherwise specified, generalized anxiety disorder, panic attack, panic disorder with agoraphobia, panic disorder without agoraphobia, posttraumatic stress disorder, social phobia, social anxiety, autism, specific phobia, substance-induced anxiety disorder, acute alcohol withdrawal, obsessive compulsive disorder, agoraphobia, monopolar disorders, bipolar disorder I or II, bipolar disorder not otherwise specified, cyclothymic disorder, depressive disorder, major depressive disorder, mood disorder, substance-induced mood disorder, enhancement of cognitive function, loss of cognitive function associated with but not limited to Alzheimer's disease, stroke, or traumatic injury to the brain, seizures resulting from disease or injury including but not limited to epilepsy, learning disorders/disabilities, cerebral palsy. In addition, anxiety disorders may apply to personality disorders including but not limited to the following types: paranoid, antisocial, avoidant behavior, borderline personality disorders, dependent, histronic, narcissistic, obsessive-compulsive, schizoid, and schizotypal.

Procedure:

Behavioral screens were performed on a cohort of 4 wild type, 4 heterozygous and 8 homozygous mutant mice. All behavioral tests were done between 12 and 16 weeks of age unless reduced viability necessitates earlier testing. These tests included open field to measure anxiety, activity levels and exploration.

Open Field Test:

Several targets of known drugs have exhibited phenotypes in the open field test. These include knockouts of the seratonin transporter, the dopamine transporter (Giros et al., Nature. 1996 Feb. 15; 379(6566):606-12), and the GABA receptor (Homanics et al., Proc Natl Acad Sci USA. 1997 Apr. 15; 94(8):4143-8). An automated open-field assay was customized to address changes related to affective state and exploratory patterns related to learning. First, the field (40×40 cm) was selected to be relatively large for a mouse, thus designed to pick up changes in locomotor activity associated with exploration. In addition, there were 4 holes in the floor to allow for nose-poking, an activity specifically related to exploration. Several factors were also designed to heighten the affective state associated with this test. The open-field test is the first experimental procedure in which the mice are tested, and the measurements that were taken were the subjects' first experience with the chamber. In addition, the open-field was brightly lit. All these factors will heighten the natural anxiety associated with novel and open spaces. The pattern and extent of exploratory activity, and especially the center-to-total distance traveled ratio, may then be able to discern changes related to susceptibility to anxiety or depression. A large arena (40 cm×40 cm, VersaMax animal activity monitoring system from AccuScan Instruments) with infrared beams at three different levels was used to record rearing, hole poke, and locomotor activity. The animal was placed in the center and its activity was measured for 20 minutes. Data from this test was analyzed in five, 4-minute intervals. The total distance traveled (cm), vertical movement number (rearing), number of hole pokes, and the center to total distance ratio were recorded.

The propensity for mice to exhibit normal habituation responses to a novel environment is assessed by determining the overall change in their horizontal locomotor activity across the 5 time intervals. This calculated slope of the change in activity over time is determined using normalized, rather than absolute, total distance traveled. The slope is determined from the regression line through the normalized activity at each of the 5 time intervals. Normal habituation is represented by a negative slope value.

Results: A notable difference was observed during open field activity testing. The female (−/−) mice exhibited an increased median sum time in the center area when compared with their gender-matched (+/+) littermates, which is indicative of a decreased anxiety-like response in the mutants. Thus, knockout mice demonstrated a phenotype consistent with depression, generalized anxiety disorders, attention deficit disorder, sleep disorder, cognitive disorders, hyperalgesia and sensory disorders depressive disorders. Thus, PRO230 polypeptides and agonists thereof would be useful for the treatment or amelioration of the symptoms associated with such depressive disorders.

(c) Immunology Phenotypic Analysis

Immune related and inflammatory diseases are the manifestation or consequence of fairly complex, often multiple interconnected biological pathways which in normal physiology are critical to respond to insult or injury, initiate repair from insult or injury, and mount innate and acquired defense against foreign organisms. Disease or pathology occurs when these normal physiological pathways cause additional insult or injury either as directly related to the intensity of the response, as a consequence of abnormal regulation or excessive stimulation, as a reaction to self, or as a combination of these.

Though the genesis of these diseases often involves multistep pathways and often multiple different biological systems/pathways, intervention at critical points in one or more of these pathways can have an ameliorative or therapeutic effect. Therapeutic intervention can occur by either antagonism of a detrimental process/pathway or stimulation of a beneficial process/pathway.

T lymphocytes (T cells) are an important component of a mammalian immune response. T cells recognize antigens which are associated with a self-molecule encoded by genes within the major histocompatibility complex (MHC). The antigen may be displayed together with MHC molecules on the surface of antigen presenting cells, virus infected cells, cancer cells, grafts, etc. The T cell system eliminates these altered cells which pose a health threat to the host mammal. T cells include helper T cells and cytotoxic T cells. Helper T cells proliferate extensively following recognition of an antigen-MHC complex on an antigen presenting cell. Helper T cells also secrete a variety of cytokines, i.e., lymphokines, which play a central role in the activation of B cells, cytotoxic T cells and a variety of other cells which participate in the immune response.

In many immune responses, inflammatory cells infiltrate the site of injury or infection. The migrating cells may be neutrophilic, eosinophilic, monocytic or lymphocytic as can be determined by histologic examination of the affected tissues. Current Protocols in Immunology, ed. John E. Coligan, 1994, John Wiley & Sons, Inc.

Many immune related diseases are known and have been extensively studied. Such diseases include immune-mediated inflammatory diseases (such as rheumatoid arthritis, immune mediated renal disease, hepatobiliary diseases, inflammatory bowel disease (IBD), psoriasis, and asthma), non-immune-mediated inflammatory diseases, infectious diseases, immunodeficiency diseases, neoplasia, and graft rejection, etc. In the area of immunology, targets were identified for the treatment of inflammation and inflammatory disorders.

In the area of immunology, targets have been identified herein for the treatment of inflammation and inflammatory disorders. Immune related diseases, in one instance, could be treated by suppressing the immune response. Using neutralizing antibodies that inhibit molecules having immune stimulatory activity would be beneficial in the treatment of immune-mediated and inflammatory diseases. Molecules which inhibit the immune response can be utilized (proteins directly or via the use of antibody agonists) to inhibit the immune response and thus ameliorate immune related disease.

The Following Test was Performed:

Ovalbumin Challenge

Procedure: This assay was carried out on 6 wild types and 14 homozygotes. Chicken ovalbumin (OVA) is a T-cell dependent antigen, which is commonly used as a model protein for studying antigen-specific immune responses in mice. OVA is non-toxic and inert and therefore will not cause harm to the animals even if no immune response is induced. The murine immune response to OVA has been well characterized, to the extent that the immunodominant peptides for eliciting T cell responses have been identified. Anti-OVA antibodies are detectable 8 to 10 days after immunization using enzyme-linked immunosorbent assay (ELIZA), and determination of different isotypes of antibodies gives further information on the complex processes that may lead to a deficient response in genetically engineered mice.

As noted above, this protocol assesses the ability of mice to raise an antigen-specific immune response. Animals were injected IP with 50 mg of chicken ovalbumin emulsified in Complete Feund's Adjuvant and 14 days later the serum titer of anti-ovalbumin antibodies (IgM, IgG1 and IgG2 subclasses) was measured. The amount of OVA-specific antibody in the serum sample is proportional to the Optical Density (OD) value generated by an instrument that scans a 96-well sample plate. Data was collected for a set of serial dilutions of each serum sample. [Analyzed wt/het/hom: 6/4/14]

Results of this challenge: The (−/−) mice exhibited a trend towards an increased mean serum IgG2a response to the ovalbumin challenge when compared with their (+/+) littermates. Thus, these knockout mice exhibited an increased ability to elicit an OVA-specific antibody response to the T-cell dependent OVA antigen. Inhibitors (antagonists) of PRO230 polypeptides would be expected to also stimulate the immune system and would find utility in the cases wherein this effect would be beneficial to the individual such as in the case of leukemia, and other types of cancer, and in immunocompromised patients, such as AIDS sufferers. Accordingly, PRO230 polypeptides or agonists thereof would be useful in inhibiting the immune response and would be useful candidates for suppressing harmful immune responses, e.g. in the case of graft rejection or graft-versus-host diseases.

I. Generation and Analysis of Mice Comprising DNA23339-1130 (UNQ152) Gene Disruptions In these knockout experiments, the gene encoding PRO178 polypeptides (designated as DNA23339-1130) [UNQ152] was disrupted. The gene specific information for these studies is as follows: mouse gene sequence nucleotide reference: NM_145154 or accession: NM_145154 NID: gi 21699061 ref NM_145154.1, *Mus musculus* RIKEN cDNA 6330404E11 gene (6330404E11Rik), protein reference: Q9CU50 or accession: Q9CU50 NID: *Mus musculus* (Mouse) or 6330404E11RIK protein (fragment) or MOUSESPTRNRDB; human gene sequence nucleotide reference: NM_031917 or accession: NM_031917 NID: 13994284 *Homo sapiens [Homo sapiens* angiopoietin-related protein 5 (ARP5)], protein reference: Q9BZZ0 or accession: Q9BZZ0 NID: *Homo sapiens* (Human) or ANGIOPOIETIN-RELATED PROTEIN 5. HUMANSPTRNRDB. Insertion appears to be in forward direction near amino acid 180 out of about 460.

The gene that is mutated in these animals is represented by mouse UniGene cluster Mm.34019, which is the ortholog of human UniGene cluster Hs.306971 (ARP5). ARP5 encodes angiopoietin-related protein 5. The protein is also known as ARP3 or ANGPTL5.

Angiopoietin-related proteins 1, 3 and 5 suffer from nomenclature problems and ensuing confusion. All three have been called ARP3 at one time or another (in mouse or human). Additionally, other proteins have an b ARPb prefix (e.g., actin-related proteins).

ARP5 is predicted to encode a domain known as b C-terminal globular domain of fibrinogen beta and gamma chainsb (Pfam 00147; FBG). This domain is up to 270 residues in length and contains 4 conserved cysteines that participate in 2 disulfide bonds. The FBG motif is found in the C-terminus of the beta and gamma chains of fibrinogen, but not the alpha chain.

Examination of SwissProt records shows that the motif is found in various, typically extracellular or surface, human proteins including angiopoietin-1 and b 2 (Q15389, O15123), angiopoietin-related protein 2 (Q9UKU9), neurexin 4 (P78357), ficolin 2 (Q15485), and microfibril-associated glycoprotein 4 (P55083). Additionally, the FBG domain is present in 2 fibrinogen-like proteins of sea urchin (Xu, X. and Doolittle, R. F., Proc. Natl. Acad. Sci. USA, 87(6):2097-101 (1990)) and the *Drosophila* scabrous protein (P21520).

Because a signal peptide is predicted and membrane-anchoring mechanisms were not, and also because related proteins are secreted, the protein may be secreted.

Targeted or gene trap mutations were generated in strain 129SvEv$^{Brd}$-derived embryonic stem (ES) cells. The chimeric mice were bred to C57BL/6J albino mice to generate F1 heterozygous animals. These progeny were intercrossed to generate F2 wild type, heterozygous, and homozygous mutant progeny. On rare occasions, for example when very few F1 mice were obtained from the chimera, F1 heterozygous mice were crossed to 129SvEv$^{Brd}$/C57 hybrid mice to yield additional heterozygous animals for the intercross to generate the F2 mice. Level I phenotypic analysis was performed on mice from this generation as shown below.

|  | wt | het | hom | Total |
|---|---|---|---|---|
| Observed | 31 | 29 | 22 | 82 |
| Expected | 20.5 | 41 | 20.5 | 82 |

Chi-Sq. = 9.00
Significance = 0.01111
(hom/n) = 0.27
Avg. Litter Size = 0

Wild-type expression of the target gene was detected in embryonic stem (ES) cells and, among the 13 adult tissue samples tested by RT-PCR, in brain, thymus, liver, and skin fibroblast. RT-PCR analysis revealed that the transcript was absent in the (−/−) mouse analyzed (M-68).

1. Phenotypic Analysis (for Disrupted Gene: DNA23339-1130 (UNQ152)

(a) Overall Phenotypic Summary

The male homozygous mutant mice exhibited notably increased mean serum triglyceride and cholesterol levels when compared with their gender-matched wild-type littermates and the historical means. No other notable phenotype was observed for the homozygous mutant mice. RT-PCR analysis revealed that the transcript was absent in the homozygous mutant mice.

(b) Phenotypic Analysis: Cardiology

In the area of cardiovascular biology, targets were identified herein for the treatment of hypertension, atherosclerosis, heart failure, stroke, various coronary artery diseases, dyslipidemias such as high cholesterol (hypercholesterolemia) and elevated serum triglycerides (hypertriglyceridemia), diabetes and/or obesity. The phenotypic tests included the measurement of serum cholesterol and triglycerides.

Blood Lipids

Procedure: A cohort of 4 wild type, 4 heterozygotes and 8 homozygotes were tested in this assay. High cholesterol levels and increased triglyceride blood levels are recognized risk factors in the development of cardiovascular disease and/or diabetes. Measuring blood lipids facilitates the finding of biological switches that regulate blood lipid levels. Inhibition of factors which elevate blood lipid levels may be useful for reducing the risk for cardiovascular disease. In these blood chemistry tests, cholesterol measurements were recorded using the COBAS Integra 400 (mfr: Roche).

Results: As summarized above, the male (−/−) mice exhibited notably increased triglyceride and cholesterol levels when compared with their gender-matched (+/+) littermates and the historical means for the male (+/+) mice. Thus, mutant mice deficient in the PRO178 gene can serve as a model for cardiovascular disease. PRO178 polypeptides or its encoding gene would be useful in regulating blood lipids such as cholesterol and triglycerides. Thus, PRO178 polypeptides or agonists thereof would be useful in the treatment of such cardiovascular diseases as hypertension, atherosclerosis, heart failure, stroke, various coronary diseases, hypercholesterolemia, hypertriglyceridemia, diabetes and/or obesity.

J. Generation and Analysis of Mice Comprising DNA65351-1366-2 (UNQ407) Gene Disruptions In these knockout experiments, the gene encoding PRO1199 polypeptides (designated as DNA65351-1366-2) [UNQ407] was disrupted. The gene specific information for these studies is as follows: mouse gene sequence nucleotide reference: NM_022984 or *Mus musculus* resistin (Retn), protein reference: NP_075360 or resistin; found in inflammatory zone 3; adipocyte-specific secretory factor; Fizz3-pending [*Mus musculus*]; human gene sequence nucleotide reference: NM_020415 or *Homo sapiens* resistin (RETN), protein reference: NP_065148 or resistin [*Homo sapiens*].

The mutated gene is resistin (Retn), ortholog of human resistin (RETN). Aliases include ADSF, RSTN, FIZZ3, RETN1, found in inflammatory zone 3, C/EBP-epsilon regulated myeloid-specific secreted cysteine-rich protein, cysteine-rich secreted protein A12-alpha-like 2, cysteine-rich secreted protein FIZZ3, and adipocyte-specific secretory factor.

RETN contains an N-terminal signal peptide and a cysteine-rich C-terminus. The spacing of the C-terminal cysteines is highly conserved among FIZZ family members (Holcomb et al., EMBO J., 19(15):4046-55 (2000); Steppan et al., Nature, 409:307-312 (2001); OMIM 605565). RETN belongs to the RESISTIN/FIZZ family of proteins, which are involved in inflammation.

RETN is a hormone expressed mainly in white adipose tissue that suppresses insulin-stimulated glucose uptake into fat cells and insulin action in peripheral tissues. In obese individuals, RETN is reported to be overexpressed in adipose tissue; thus, RETN may contribute to insulin resistance (Steppan et al, 2001 supra; Pizzuti et al., J. Clin. Endocr. Metab., 87:4403-4406 (2002)). However, other studies failed to find RETN overexpression in adipose tissues (Beltowski, J., Med. Sci. Monit., 9(2):RA55-61 (2003)).

Targeted or gene trap mutations were generated in strain 129SvEv$^{Brd}$-derived embryonic stem (ES) cells. The chimeric mice were bred to C57BL/6J albino mice to generate F1 heterozygous animals. These progeny were crossed to hybrid 129SvEv$^{Brd}$/C57 Cre homozygous mice to generate mice carrying both the mutant and Cre alleles (compound heterozygous mice). The male compound heterozygous mice were then crossed to hybrid 129SvEv$^{Brd}$/C57 F1 mice, derived from crossing 129SvEv$^{Brd}$ mice to C57BL/6J mice, to generate heterozygous Cre-excised animals. Finally, these progeny were intercrossed to generate wild-type, Cre-excised heterozygous, and Cre-excised homozygous mice. Level I phenotypic analysis was performed on mice from this generation as shown below.

Wild-type expression of the target gene was detected in all 13 adult tissue samples tested by RT-PCR, except brain, liver, testis, stomach, and skin fibroblast. Disruption of the target gene was confirmed by Southern hybridization analysis.

|  | wt | het | hom | Total |
|---|---|---|---|---|
| Observed | 29 | 48 | 23 | 100 |
| Expected | 25 | 50 | 25 | 100 |

Chi-Sq. = 0.88
Significance = 0.64404
(hom/n) = 0.23
Avg. Litter Size = 0

1. Phenotypic Analysis (for Disrupted Gene: DNA65351-1366-2 (UNQ407)

(a) Overall Phenotypic Summary

The homozygous mutant mice exhibited an increased response to an inflammatory stimulus when compared with their wild-type littermate and the historical range. In addition, the female homozygous mutant mice exhibited an increased mean total tissue mass and lean body mass and an increased mean serum triglyceride level.

(b) Immunology Phenotypic Analysis

Immune related and inflammatory diseases are the manifestation or consequence of fairly complex, often multiple interconnected biological pathways which in normal physiology are critical to respond to insult or injury, initiate repair from insult or injury, and mount innate and acquired defense against foreign organisms. Disease or pathology occurs when these normal physiological pathways cause additional insult or injury either as directly related to the intensity of the response, as a consequence of abnormal regulation or excessive stimulation, as a reaction to self, or as a combination of these.

Though the genesis of these diseases often involves multi-step pathways and often multiple different biological systems/pathways, intervention at critical points in one or more of these pathways can have an ameliorative or therapeutic effect. Therapeutic intervention can occur by either antagonism of a detrimental process/pathway or stimulation of a beneficial process/pathway.

T lymphocytes (T cells) are an important component of a mammalian immune response. T cells recognize antigens which are associated with a self-molecule encoded by genes within the major histocompatibility complex (MHC). The antigen may be displayed together with MHC molecules on the surface of antigen presenting cells, virus infected cells, cancer cells, grafts, etc. The T cell system eliminates these altered cells which pose a health threat to the host mammal. T cells include helper T cells and cytotoxic T cells. Helper T cells proliferate extensively following recognition of an antigen-MHC complex on an antigen presenting cell. Helper T cells also secrete a variety of cytokines, i.e., lymphokines, which play a central role in the activation of B cells, cytotoxic T cells and a variety of other cells which participate in the immune response.

In many immune responses, inflammatory cells infiltrate the site of injury or infection. The migrating cells may be neutrophilic, eosinophilic, monocytic or lymphocytic as can be determined by histologic examination of the affected tissues. Current Protocols in Immunology, ed. John E. Coligan, 1994, John Wiley & Sons, Inc.

Many immune related diseases are known and have been extensively studied. Such diseases include immune-mediated inflammatory diseases (such as rheumatoid arthritis, immune mediated renal disease, hepatobiliary diseases, inflammatory bowel disease (IBD), psoriasis, and asthma), non-immune-mediated inflammatory diseases, infectious diseases, immunodeficiency diseases, neoplasia, and graft rejection, etc.

In the area of immunology, targets were identified herein for the treatment of inflammation and inflammatory disorders. Immune related diseases could be treated by suppressing the immune response. Using neutralizing antibodies that inhibit molecules having immune stimulatory activity would be beneficial in the treatment of immune-mediated and inflammatory diseases. Molecules which inhibit the immune response can be utilized (proteins directly or via the use of antibody agonists) to inhibit the immune response and thus ameliorate immune related disease.

The Following Tests were Performed:

Zymosan Challenge Assay—Peritoneal Inflammation:

Procedure: A cohort of 1 wild type and 2 homozygous mutants were used in this assay. Peritoneal leukocyte recruitment assays were used to identify targets that may regulate the inflammatory component of atherosclerosis. These assays detect abnormalities in immune cell recruitment to a site of inflammation. Zymosan (an agent which induces inflammation) was injected into the intraperitoneal cavity and fluid was later removed and measurements were taken of total WBC counts, neutrophil/monocyte ratio and percent granulocytes, monocytes, lymphocytes and eosinophils in the ip fluid.

Results: The (−/−) mice exhibited a notably increased total white blood cell count after zymosan challenge when compared with their (+/+) littermate and the historical range, suggestive of an increased response to an inflammatory stimulus in these mutants.

In summary, the zymosan challenge studies indicate that knockout mice deficient in the gene encoding PRO1199 polypeptides exhibit a proinflammatory response when compared with their wild-type littermates. Thus, antagonists of PRO1199 polypeptides would be important agents which would stimulate the immune system (such as T cell proliferation) and would find utility in the cases wherein this effect would be beneficial to the individual such as in the case of leukemia, and other types of cancer, and in immunocompromised patients, such as AIDS sufferers. Accordingly, PRO1199 polypeptides or agonists thereto would be useful in inhibiting the immune response and would be useful candidates for suppressing harmful immune responses, e.g. in the case of graft rejection or graft-versus-host diseases.

(c) Phenotypic Analysis: Cardiology

In the area of cardiovascular biology, targets were identified for the treatment of hypertension, atherosclerosis, heart failure, stroke, coronary artery diseases, and dislipidemias such as high cholesterol and triglyceride serum levels. The phenotypic tests included the measurement of serum cholesterol and triglycerides.

Blood Lipids

Procedure: A cohort of 4 wild type, 4 heterozygotes and 8 homozygotes were tested in this assay. High serum trigylcerides levels are recognized risk factors in the development of cardiovascular disease. In addition, dislipidemia can be associated with obesity and diabetes. Measuring blood lipids facilitates the finding of biological switches that regulate blood lipid levels. Inhibition of factors which elevate blood lipid levels may be useful for reducing the risk for cardiovascular disease.

As summarized above, the female homozygous mutant mice exhibited an increased mean total tissue mass and lean body mass and an increased mean serum triglyceride level in homozygous knockout mice (167% of wild-type littermates). Thus, mutant mice deficient in the PRO1199 gene can serve as a model for cardiovascular disease and/or dislipidemia associated with obesity and diabetes. PRO1199 or its encoding gene would be useful in regulating blood lipids and in particular may play a role in maintaining normal lipid metabolism.

(d) Dexa Analysis—Test Description:

Procedure: A cohort of 4 wild type, 4 heterozygotes and 8 homozygotes were tested in this assay. Dual Energy X-ray Absorptiometry (DEXA) has been used successfully to identify changes in total tissue mass (TTM).

The mouse was anesthetized by intraperitoneal injection of Avertin (1.25% 2,2,2,-tribromoethanol, 20 ml/kg body weight), body length and weight were measured, and then the mouse was placed in a prone position on the platform of the PIXImus™ Densitometer (Lunar Inc.) for a DEXA scan. Using Lunar PIXImus software, the bone mineral density (BMD) and fat composition (% fat) and total tissue mass (TTM) were determined in the regions of interest (ROI, i.e., whole body, vertebrae, and both femurs).

DEXA Results: As summarized above, the female homozygous mutant mice exhibited slightly increased mean total tissue mass and lean body mass beginning at 8 weeks; at 18 weeks, the female knockout mice are 18% heavier than their gender-matched (+/+) littermates and the historical means.

These studies suggest that mutant (−/−) non-human transgenic animals exhibit a negative phenotype that can be associated with obesity. Thus, PRO1199 polypeptides or agonists thereof would be useful in the treatment of obesity.

K. Generation and Analysis of Mice Comprising DNA84210-2576 (UNQ1888) Gene Disruptions In these knockout experiments, the gene encoding PRO4333 polypeptides (designated as DNA84210-2576 (UNQ1888) was disrupted. The gene specific information for these studies is as follows: mouse gene sequence nucleotide reference: NM_013869 or *Mus musculus* tumor necrosis factor receptor superfamily, member 19 (Tnfrsf19), protein reference: NP_038897 or tumor necrosis factor receptor superfamily, member 19; tumor necrosis factor receptor superfamily, member 20 [*Mus musculus*]; human gene sequence nucleotide reference: NM_018647 or *Homo sapiens* tumor necrosis factor receptor superfamily, member 19 (TNFRSF19), protein reference: NP_061117 or tumor necrosis factor receptor superfamily, member 19 [*Homo sapiens*].

The disrupted mouse gene is tumor necrosis factor receptor superfamily, member 19 (Tnfrsf19), ortholog of human TNFRSF19. Aliases and synonyms include TAJ; Troy; TAJ-ALPHA; Tnfrsf20; tumor necrosis factor receptor superfamily, member 20; TRADE; and toxicity and JNK inducer.

TNFRSF19 consists of an extracellular ligand-binding domain, a transmembrane domain, and a cytoplasmic domain that contains a tumor necrosis factor receptor-associated factor (TRAF) 2-binding consensus sequence but no death domain. TNFRSF19 recruits binding of TRAFs, and activates nuclear factor kappa B (NF-kB) and c-Jun N-terminal kinase (Eby et al., J. Biol. Chem., 275(20): 15336-42 (2000); Kojima et al., J. Biol. Chem., 275(27):20742-7 (2000); Hu et al., Genomics, 62(1):103-7 (1999)).

In the developing mouse embryo, TNFRSF19 is expressed at high levels in skin, whereas expression is high in brain and moderate in heart, lung, liver and hair follicles in post natal mice. Activation of TNFRSF19 also induces caspace-independent cell death. The function of TNFRSF19 is likely to be pleiotropic and important in embryonic development and skin and hair follicle development (OMIM 606122).

In mouse, alternative splicing gives rise to 2 additional variants; one may function as a soluble receptor and the other may function as a decoy receptor.

Targeted or gene trap mutations were generated in strain 129SvEv$^{Brd}$-derived embryonic stem (ES) cells. The chimeric mice were bred to 129SvEv$^{Brd}$ mice to generate F1 heterozygous animals. These progeny were intercrossed to generate F2 wild type, heterozygous, and homozygous mutant mice. On rare occasions, for example when very few F1 mice were obtained from the chimera, F1 heterozygous mice were crossed to 129SvEv$^{Brd}$ mice to yield additional heterozygous animals for the intercross to generate the F2 mice. Expression of the target gene was detected in embryonic stem (ES) cells and, of 13 adult tissues samples tested by RT-PCR, only in brain. RT-PCR analysis revealed that the transcript was absent in the (−/−) mouse analyzed (M-66). Level I phenotypic analysis was performed on mice from this generation.

|  | wt | het | hom | Total |
| --- | --- | --- | --- | --- |
| Observed | 25 | 46 | 15 | 86 |
| Expected | 21.5 | 43 | 21.5 | 86 |

Chi-Sq. = 2.74
Significance = 0.25358
(hom/n) = 0.17
Avg. Litter Size = 0

1. Phenotypic Analysis (for Disrupted Gene: DNA84210-2576 (UNQ1888)

(a) Overall Phenotypic Summary

The homozygous mutant mice exhibited a decreased exploratory response and hypoactivity when compared with their wild-type littermates. The (−/−) mice exhibited decreased serum IgA levels. In addition, these mutants exhibited enhanced glucose tolerance at all 3 intervals tested. The (−/−) mutant mice also exhibited a decreased mean total tissue mass and lean body mass. The male (−/−) mutant mice exhibited a notably decreased femoral midshaft cross-sectional area when compared with the histroical mean.

(b) Phenotypic Analysis: CNS/Neurology

In the area of neurology, analysis focused herein on identifying in vivo validated targets for the treatment of neurological and psychiatric disorders. Neurological disorders include but are not limited to: depression, generalized anxiety disorders, attention deficit disorder, sleep disorder, hyperactivity disorder, obsessive compulsive disorder, schizophrenia, cognitive disorders, hyperalgesia and sensory disorders, mild to moderate anxiety, anxiety disorder due to a general medical condition, anxiety disorder not otherwise specified, generalized anxiety disorder, panic attack, panic disorder with agoraphobia, panic disorder without agoraphobia, posttraumatic stress disorder, social phobia, social anxiety, autism, specific phobia, substance-induced anxiety disorder, acute alcohol withdrawal, obsessive compulsive disorder, agoraphobia, monopolar disorders, bipolar disorder I or II, bipolar disorder not otherwise specified, cyclothymic disorder, depressive disorder, major depressive disorder, mood disorder, substance-induced mood disorder, enhancement of cognitive function, loss of cognitive function associated with but not limited to Alzheimer's disease, stroke, or traumatic injury to the brain, seizures resulting from disease or injury including but not limited to epilepsy, learning disorders/disabilities, cerebral palsy. In addition, anxiety disorders may apply to personality disorders including but not limited to the following types: paranoid, antisocial, avoidant behavior, borderline personality disorders, dependent, histronic, narcissistic, obsessive-compulsive, schizoid, and schizotypal.

Procedure:

Behavioral screens were performed on a cohort of 4 wild type, 4 heterozygous and 8 homozygous mutant mice. All behavioral tests were done between 12 and 16 weeks of age unless reduced viability necessitates earlier testing. These tests included open field to measure anxiety, activity levels and exploration.

Open Field Test:

Several targets of known drugs have exhibited phenotypes in the open field test. These include knockouts of the seratonin transporter, the dopamine transporter (Giros et al., Nature. 1996 Feb. 15; 379(6566):606-12), and the GABA receptor (Homanics et al., Proc Natl Acad Sci USA. 1997 Apr. 15; 94(8):4143-8). An automated open-field assay was customized to address changes related to affective state and exploratory patterns related to learning. First, the field (40×40 cm) was selected to be relatively large for a mouse, thus designed to pick up changes in locomotor activity associated with exploration. In addition, there were 4 holes in the floor to allow for nose-poking, an activity specifically related to exploration. Several factors were also designed to heighten the affective state associated with this test. The open-field test is the first experimental procedure in which the mice are tested, and the measurements that were taken were the subjects' first experience with the chamber. In addition, the open-field was brightly lit. All these factors will heighten the natural anxiety associated with novel and open spaces. The pattern and extent of exploratory activity, and especially the center-to-total distance traveled ratio, may then be able to discern changes related to susceptibility to anxiety or depression. A large arena (40 cm×40 cm, VersaMax animal activity monitoring system from AccuScan Instruments) with infrared beams at three different levels was used to record rearing, hole poke, and locomotor activity. The animal was placed in the center and its activity was measured for 20 minutes. Data from this test was analyzed in five, 4-minute intervals. The total distance traveled (cm), vertical movement number (rearing), number of hole pokes, and the center to total distance ratio were recorded.

The propensity for mice to exhibit normal habituation responses to a novel environment is assessed by determining the overall change in their horizontal locomotor activity across the 5 time intervals. This calculated slope of the change in activity over time is determined using normalized, rather than absolute, total distance traveled. The slope is determined from the regression line through the normalized activity at each of the 5 time intervals. Normal habituation is represented by a negative slope value.

Results:

As indicated in the phenotypic analysis summary, notable differences were observed during open field activity testing. The (−/−) mice demonstrated a decrease in locomotor activity, rearing, and hole poke activity over all intervals when compared with the (+/+) mice, suggesting a hypoactive and decreased exploratory response. Thus, knockout mice demonstrated a phenotype consistent with various neural degenerative diseases which may include consistent with depression, generalized anxiety disorders, attention deficit disorder, sleep disorder, cognitive disorders, hyperalgesia and sensory disorders, schizophrenia and/or bipolar disorders. Thus, PRO4333 polypeptides and agonists thereof would be useful for the treatment or amelioration of the symptoms associated with such depressive disorders.

(c) Bone Metabolism: Radiology Phenotypic Analysis

Procedure:

In the area of bone metabolism, targets were identified herein for the treatment of arthritis, osteoporosis, osteopenia and osteopetrosis as well as identifying targets that promote bone healing. Tests included microCT for very high resolution and very high sensitivity measurements of bone mineral density for both trabecular and cortical bone.

DEXA Analysis—Test Description:

Procedure: A cohort of 4 wild type, 4 heterozygotes and 8 homozygotes were tested in this assay. Dual Energy X-ray Absorptiometry (DEXA) has been used successfully to identify changes in total tissue mass (TTM).

The mouse was anesthetized by intraperitoneal injection of Avertin (1.25% 2,2,2,-tribromoethanol, 20 ml/kg body weight), body length and weight were measured, and then the mouse was placed in a prone position on the platform of the PIXImus™ Densitometer (Lunar Inc.) for a DEXA scan. Using Lunar PIXImus software, the bone mineral density (BMD) and fat composition (% fat) and total tissue mass (TTM) were determined in the regions of interest (ROI, i.e., whole body, vertebrae, and both femurs).

DEXA Results: As summarized above, The male (−/−) mice exhibited decreased mean total tissue mass and lean body mass when compared with their gender-matched (+/−) littermates and the historical means.

Bone microCT Analysis:

Procedure: MicroCT was also used to get very sensitive measurements of BMD. The µCT40 scans dissected bones and provides detailed information on bone mass and architecture. One vertebra and 1 femur were taken from a cohort of 4 wild type and 8 homozygous mice. Measurements were taken of lumbar 5 veterbra traebecular bone volume, traebecular thickness, connectivity density and midshaft femur total bone area and cortical thickness. The µCT40 scans provided detailed information on bone mass and architecture. Multiple bones were placed into sample holders and scanned automatically. Instrument software was used to select regions of interest for analysis. Trabecular bone parameters were analyzed in the fifth lumbar vertebrae (LV5) at 16 micrometer resolution and cortical bone parameters were analyzed in the femur midshaft at a resolution of 20 micrometers.

Micro-CT Analysis Results: The male (−/−) mutant exhibited a notably decreased femoral midshaft cross-sectional area when compared with gender-matched (+/+) littermates and the historical means.

These results demonstrate that knockout mutant mice exhibit abnormal bone metabolism with significant bone loss similar to osteoporosis characterized by decrease in bone mass with decreased density and possibly fragility leading to bone fractures. Blood chemistry tests also showed an increased alkaline phosphatase activity in (−/−) mutant mice which is commonly associated with osteoporosis. Thus, it appears that PRO4333 polypeptides or its encoding gene would be useful in maintaining bone homeostasis or would be useful for bone healing or for the treatment of arthritis or osteoporosis, whereas antagonists would lead to abnormal or pathological bone disorders similar to osteoporosis. In addition to these studies, (−/−) mutant mice showed signs of growth retardation. Such growth disorders may be associated with the phenotype or physiological condition associated with tissue wasting diseases such as diabetes or cachexia. Thus, PRO4333 polypeptides or agonists thereof would be useful for treating diabetes or cachexia.

(d) Phenotypic Analysis: Metabolism—Blood Chemistry

In the area of metabolism, targets may be identified for the treatment of diabetes. Blood chemistry phenotypic analysis includes glucose tolerance tests to measure insulin sensitivity and changes in glucose metabolism. Abnormal glucose tolerance test results may indicate the following disorders or conditions: cachexia, Diabetes Type 1 and Type 2, Syndrome X, various cardiovascular diseases.

Procedure: A cohort of 4 wild type, 4 heterozygote and 8 homozygote mice were used in this assay. The glucose tolerance test is the standard for defining impaired glucose homeostasis in mammals. The intraperitoneal glucose tolerance test (IPGTT) measures glucose levels following administration of a glucose challenge. Glucose tolerance tests were performed using a Lifescan glucometer. Animals were injected IP at 2 g/kg with D-glucose delivered as a 20% solution and blood glucose levels were measured at 0, 30, 60 and 90 minutes after injection.

Results: These studies indicated that male (−/−) mice exhibit enhanced glucose tolerance in the presence of normal fasting glucose at all 3 intervals tested when compared with their gender-matched (+/+) littermates and the historical means. In addition, hyperinsulinemia was not apparent in the (−/−) mice.

(e) Immunology Phenotypic Analysis

Immune related and inflammatory diseases are the manifestation or consequence of fairly complex, often multiple interconnected biological pathways which in normal physiology are critical to respond to insult or injury, initiate repair from insult or injury, and mount innate and acquired defense against foreign organisms. Disease or pathology occurs when these normal physiological pathways cause additional insult or injury either as directly related to the intensity of the response, as a consequence of abnormal regulation or excessive stimulation, as a reaction to self, or as a combination of these.

Though the genesis of these diseases often involves multi-step pathways and often multiple different biological systems/pathways, intervention at critical points in one or more of these pathways can have an ameliorative or therapeutic effect. Therapeutic intervention can occur by either antagonism of a detrimental process/pathway or stimulation of a beneficial process/pathway.

T lymphocytes (T cells) are an important component of a mammalian immune response. T cells recognize antigens which are associated with a self-molecule encoded by genes within the major histocompatibility complex (MHC). The antigen may be displayed together with MHC molecules on the surface of antigen presenting cells, virus infected cells, cancer cells, grafts, etc. The T cell system eliminates these altered cells which pose a health threat to the host mammal. T cells include helper T cells and cytotoxic T cells. Helper T cells proliferate extensively following recognition of an antigen-MHC complex on an antigen presenting cell. Helper T cells also secrete a variety of cytokines, i.e., lymphokines, which play a central role in the activation of B cells, cytotoxic T cells and a variety of other cells which participate in the immune response.

In many immune responses, inflammatory cells infiltrate the site of injury or infection. The migrating cells may be neutrophilic, eosinophilic, monocytic or lymphocytic as can be determined by histologic examination of the affected tissues. Current Protocols in Immunology, ed. John E. Coligan, 1994, John Wiley & Sons, Inc.

Many immune related diseases are known and have been extensively studied. Such diseases include immune-mediated inflammatory diseases (such as rheumatoid arthritis, immune mediated renal disease, hepatobiliary diseases, inflammatory bowel disease (IBD), psoriasis, and asthma), non-immune-mediated inflammatory diseases, infectious diseases, immunodeficiency diseases, neoplasia, and graft rejection, etc. In the area of immunology, targets were identified for the treatment of inflammation and inflammatory disorders.

In the area of immunology, targets have been identified herein for the treatment of inflammation and inflammatory disorders. Immune related diseases, in one instance, could be treated by suppressing the immune response. Using neutralizing antibodies that inhibit molecules having immune stimulatory activity would be beneficial in the treatment of immune-mediated and inflammatory diseases. Molecules which inhibit the immune response can be utilized (proteins directly or via the use of antibody agonists) to inhibit the immune response and thus ameliorate immune related disease.

The Following Tests were Performed:

Serum Immunoglobulin Isotyping Assay:

The Serum Immunoglobulin Isotyping Assay is performed using a Cytometric Bead Array (CBA) kit. This assay is used to rapidly identify the heavy and light chain isotypes of a mouse monoclonal antibody in a single sample. The values expressed are "relative fluorescence units" and are based on the detection of kappa light chains. Any value<6 is not significant.

Results:

The serum immunoglobulin isotyping assay revealed that homozygous adults exhibited decreased serum IgA levels compared with the (+/+) littermates. These results suggest that the phenotype associated with these knockout mice is immunoglobulin deficiency in IgA. The most common inherited form of immunoglobulin deficiency is selective IgA deficiency, which is seen in about one person in 800. Although no obvious disease susceptibility is associated with selective IgA defects, they are commoner in people with chronic lung disease than in the general population. This suggests that lack of IgA may result in a predisposition to lung infections with various pathogens and is consistent with the role of IgA in defense at the body surfaces. Thus PRO4333 polypeptides or agonists thereof, would be useful for natural immunity protection against skin infections and more importantly could prevent susceptibility to lung infections.

L. Generation and Analysis of Mice Comprising DNA65423-1595 (UNQ691) Gene Disruptions In these knockout experiments, the gene encoding PRO1336 polypeptides (designated as DNA65423-1595 (UNQ691) was disrupted. The gene specific information for these studies is as follows: mouse gene sequence nucleotide reference: AF144629 or *Mus musculus* SLIT3 (Slit3), protein reference: AAD44760 or SLIT3 [*Mus musculus*]; human gene sequence nucleotide reference: NM_003062 or *Homo sapiens* slit homolog 3 (Drosophila) (SLIT3), protein reference: NP_003053 or slit homolog 3 (Drosophila); slit (Drosophila) homolog 3; slit (Drosophila) homolog 2; slit2 [*Homo sapiens*].

The gene that is mutated in these animals is represented by mouse UniGene cluster Mm.28509, which is the ortholog of human UniGene cluster Hs.57929 (SLIT3). SLIT3 encodes slit homolog 3 (Drosophila). The protein is also known as MEGF5, SLIL2, SLIT1, SLIT-3, slit2, slit (Drosophila)

homolog 2, slit (Drosophila) homolog 3 and multiple epidermal growth factor-like domains 5. The *Drosophila* and vertebrate SLIT proteins are large extracellular glycoproteins that have been characterized as secreted chemo-repellents recognized by the ROBO receptor proteins that function principally for the guidance of neuronal axons and neurons. *Drosophila* SLIT3 expression is restricted to the future chondrogenic core of the limb bud in early development, and in later stages, it is expressed in proliferating chondrocytes during cartilage development (Holmes et al., Dev. Dyn., 222(2): 301-7 (2001)).

The SLIT3 protein is targeted to and localized at two distinct sites within mouse kidney epithelial cells: the mitochondria, and then, in more confluent cells, the cell surface. The investigators concluded that their results indicated that SLIT3 has potentially unique functions not shared by other SLIT proteins (Little et al., Am J Physiol Cell Physiol, 281(2): C486-95 (August 2001)).

Targeted or gene trap mutations were generated in strain 129SvEv$^{Brd}$-derived embryonic stem (ES) cells. The chimeric mice were bred to C57BL/6J albino mice to generate F1 heterozygous animals. These progeny were crossed to hybrid 129SvEv$^{Brd}$/C57 Cre homozygous mice to generate mice carrying both the mutant and Cre alleles (compound heterozygous mice). The male compound heterozygous mice were then crossed to hybrid 129SvEv$^{Brd}$/C57 F1 mice, derived from crossing 129SvEv$^{Brd}$ mice to C57BL/6J mice, to generate heterozygous Cre-excised animals. Finally, these progeny were intercrossed to generate wild-type, Cre-excised heterozygous, and Cre-excised homozygous mice.

Wild-type expression of the target gene was detected in embryonic stem (ES) cells and in all 13 adult tissue samples tested by RT-PCR. RT-PCR analysis revealed that the transcript was absent in kidney and barely detectable in lung in the (−/−) mouse analyzed (M-107). Gene expression of the neo transcript was detected in stomach, adrenal gland cortex, kidney collecting tubule, small intestine renal tubule, heart parenchyma, and brain hippocampus. [Analyzed wt/het/hom: 0/1/5]. RT-PCR analysis revealed that the transcript was absent in the homozygous mutant mice. Level I phenotypic analysis was performed on mice from this generation as shown below.

|  | wt | het | hom | Total |
|---|---|---|---|---|
| Observed | 22 | 39 | 22 | 83 |
| Expected | 20.75 | 41.5 | 20.75 | 83 |

Chi-Sq. = 0.30
Significance = 0.86019
(hom/n) = 0.27
Avg. Litter Size = 0

1. Phenotypic Analysis (for Disrupted Gene: DNA65423-1595 (UNQ691)
   (a) Overall Phenotypic Summary At 2 weeks of age, the homozygous mutant neonates exhibited balding; however, their hair grew in and appeared normal at adulthood. Half of the homozygous mutant mice exhibited signs of growth retardation at 16 weeks of age, namely decreased body weight and length, total tissue mass, and lean body mass, when compared with their wild-type littermates. The homozygous mutant mice also exhibited a diaphragmatic hernia and decreased exploratory activity and a decreased anxiety-related response during open field testing.

(b) Phenotypic Analysis: CNS/Neurology

In the area of neurology, analysis focused herein on identifying in vivo validated targets for the treatment of neurological and psychiatric disorders. Neurological disorders include but are not limited to: depression, generalized anxiety disorders, attention deficit disorder, sleep disorder, hyperactivity disorder, obsessive compulsive disorder, schizophrenia, cognitive disorders, hyperalgesia and sensory disorders, mild to moderate anxiety, anxiety disorder due to a general medical condition, anxiety disorder not otherwise specified, generalized anxiety disorder, panic attack, panic disorder with agoraphobia, panic disorder without agoraphobia, posttraumatic stress disorder, social phobia, social anxiety, autism, specific phobia, substance-induced anxiety disorder, acute alcohol withdrawal, obsessive compulsive disorder, agoraphobia, monopolar disorders, bipolar disorder I or II, bipolar disorder not otherwise specified, cyclothymic disorder, depressive disorder, major depressive disorder, mood disorder, substance-induced mood disorder, enhancement of cognitive function, loss of cognitive function associated with but not limited to Alzheimer's disease, stroke, or traumatic injury to the brain, seizures resulting from disease or injury including but not limited to epilepsy, learning disorders/disabilities, cerebral palsy. In addition, anxiety disorders may apply to personality disorders including but not limited to the following types: paranoid, antisocial, avoidant behavior, borderline personality disorders, dependent, histronic, narcissistic, obsessive-compulsive, schizoid, and schizotypal.

Procedure:

Behavioral screens were performed on a cohort of 4 wild type, 4 heterozygous and 8 homozygous mutant mice. All behavioral tests were done between 12 and 16 weeks of age unless reduced viability necessitates earlier testing. These tests included open field to measure anxiety, activity levels and exploration.

Open Field Test:

Several targets of known drugs have exhibited phenotypes in the open field test. These include knockouts of the seratonin transporter, the dopamine transporter (Giros et al., Nature. 1996 Feb. 15; 379(6566):606-12), and the GABA receptor (Homanics et al., Proc Natl Acad Sci USA. 1997 Apr. 15; 94(8):4143-8). An automated open-field assay was customized to address changes related to affective state and exploratory patterns related to learning. First, the field (40×40 cm) was selected to be relatively large for a mouse, thus designed to pick up changes in locomotor activity associated with exploration. In addition, there were 4 holes in the floor to allow for nose-poking, an activity specifically related to exploration. Several factors were also designed to heighten the affective state associated with this test. The open-field test is the first experimental procedure in which the mice are tested, and the measurements that were taken were the subjects' first experience with the chamber. In addition, the open-field was brightly lit. All these factors will heighten the natural anxiety associated with novel and open spaces. The pattern and extent of exploratory activity, and especially the center-to-total distance traveled ratio, may then be able to discern changes related to susceptibility to anxiety or depression. A large arena (40 cm×40 cm, VersaMax animal activity monitoring system from AccuScan Instruments) with infrared beams at three different levels was used to record rearing, hole poke, and locomotor activity. The animal was placed in the center and its activity was measured for 20 minutes. Data from this test was analyzed in five, 4-minute intervals. The total distance traveled (cm), vertical movement number (rearing), number of hole pokes, and the center to total distance ratio were recorded.

The propensity for mice to exhibit normal habituation responses to a novel environment is assessed by determining the overall change in their horizontal locomotor activity across the 5 time intervals. This calculated slope of the change in activity over time is determined using normalized, rather than absolute, total distance traveled. The slope is determined from the regression line through the normalized activity at each of the 5 time intervals. Normal habituation is represented by a negative slope value.

Results:

With regards to general and exploratory activity/anxiety behavior, notable differences were observed during open field activity testing. The (−/−) mice demonstrated a decrease in rearing and hole poke activity when compared to the (+/+) mice, suggesting a decreased exploratory response in the (−/−) mice. The (−/−) mice also demonstrated a decrease in center-to-total distance traveled ratio at intervals 2, 3, and 5 when compared to the (+/+) mice, suggesting a decreased anxiety-like response in the (−/−) mice. Thus, knockout mice demonstrated a phenotype consistent with various neural degenerative diseases which may include consistent with depression, generalized anxiety disorders, attention deficit disorder, sleep disorder, cognitive disorders, hyperalgesia and sensory disorders, schizophrenia and/or bipolar disorders. Thus, PRO1336 polypeptides and agonists thereof would be useful for the treatment or amelioration of the symptoms associated with such depressive disorders.

Functional Observational Battery (FOB) Test

The FOB is a series of situations applied to the animal to determine gross sensory and motor deficits. A subset of tests from the Irwin neurological screen that evaluates gross neurological function is used. In general, short-duration, tactile, olfactory, and visual stimuli are applied to the animal to determine their ability to detect and respond normally. These simple tests take approximately 10 minutes and the mouse is returned to its home cage at the end of testing.

Results:

As summarized above, a notable difference was observed during the functional observational battery. Male heterozygous (−/+) mice exhibited moderate exophthalmus (an abnormal protrusion of the eyeball); whereas female homozygous (−/−) mutant mice exhibited severe exophthalmus. Both male and female (−/−) mice also exhibited piloerection. Piloerection is an involuntary erection or bristling of hairs due to a sympathetic reflex usually triggered by cold, shock, or fright or due to a sympatho-mimetic agent. All of the (−/−) mice exhibited balding at 2 weeks of age with bald hair patches around the snout. However, their hair grew in and appeared normal at adulthood. Thus, functional observational battery testing showed that the mutant mice exhibited a decreased exploratory activity phenotype. Neurological disorders associated with this type of behavior may involve such anxiety disorders of panic or a panic disorder associated with agoraphobia, agoraphobia or cyclothymic disorder. Cyclothymic disorders are characterized by the alteration of depressed moods with elevated, expansive, or irritable moods without psychotic features such as hallucinations or delusions.

(c) Phenotype Analysis: Body Mass:

Dexa Analysis—Test Description:

Procedure: A cohort of 4 wild type, 4 heterozygotes and 6 homozygotes were tested in this assay. Dual Energy X-ray Absorptiometry (DEXA) has been used successfully to identify changes in total tissue mass (TTM).

The mouse was anesthetized by intraperitoneal injection of Avertin (1.25% 2,2,2,-tribromoethanol, 20 ml/kg body weight), body length and weight were measured, and then the mouse was placed in a prone position on the platform of the PIXImus™ Densitometer (Lunar Inc.) for a DEXA scan. Using Lunar PIXImus software, the bone mineral density (BMD) and fat composition (% fat) and total tissue mass (TTM) were determined in the regions of interest (ROI, i.e., whole body, vertebrae, and both femurs).

Results:

The (−/−) mice analyzed by DEXA exhibited notably decreased total tissue mass and lean body mass when compared with their (+/+) littermates, suggestive of growth retardation in these mutants. These mutants also exhibited a notably increased bone mineral content index (BMC/LBM). Blood chemistry analysis indicated that male (−/−) mice showed a decreased mean insulin level when compared with their gender-matched (+/+) littermates and the historical mean. This in conjunction with the observations of a decreased mean body weight and decreased mean body length suggests a tissue wasting condition such as cachexia, diabetes type 1 and type 2. Thus, PRO1336 polypeptides or agonists thereof would be useful in the treatment or prevention of cachexia and/or diabetes.

CAT-Scan Protocol:

Mice were injected with a CT contrast agent, Omnipaque 300 (Nycomed Amershan, 300 mg of iodine per ml, 0.25 ml per animal, or 2.50-3.75 g iodine/kg of body weight) intraperitoneally. After resting in the cage for ~10 minutes, the mouse was then sedated by intraperitoneal injection of Avertin (1.25% 2,2,2,-tribromoethanol, 20 ml/kg body weight). A CAT-scan was performed using a MicroCAT scanner (ImTek, Inc.) with the anesthetized animal lying prone on the test bed. Three dimensional images were reconstructed by the Feldkamp algorithm in a cluster of workstations using an ImTek 3D RECON software.

Results:

Of the five (−/−) mutant mice that were examined, four exhibited a developmental defect of the diaphragm (diaphragmatic hernia). In addition, the (−/−) mice exhibited an enlarged right atrium. Microscopic observations were as follows: Histological analysis of these mutants revealed a variety of lesions, including hepatic atrophy, congestion, periportal fibrosis, aortic atherosclerosis, and gastric inflammation. However, all of these lesions were considered to be secondary to the diaphragmatic hernia, rather than being primary gene-related lesions.

M. Generation and Analysis of Mice Comprising DNA145887-2849 (UNQ5793) Gene Disruptions In these knockout experiments, the gene encoding PRO19598 polypeptides (designated as DNA145887-2849 (UNQ5793) was disrupted. The gene specific information for these studies is as follows: mouse gene sequence nucleotide reference: XM_136951 or *Mus musculus* similar to interleukin-22 binding protein (LOC237310), protein reference: XP_136951 similar to interleukin-22 binding protein [*Mus musculus*]; human gene sequence nucleotide reference: NM_052962 or *Homo sapiens* class II cytokine receptor (IL22RA2), protein reference: NP_443194 or class II cytokine receptor; interleukin 22-binding protein [*Homo sapiens*].

The gene that is mutated in these animals is represented by mouse nucleotide sequence XM_136951, which is the ortholog of human UniGene cluster Hs. 126891 (IL22RA2). IL22RA2 encodes interleukin 22 receptor alpha-2. The protein is also known as interleukin 22-binding protein (IL22BP) and class II cytokine receptor, IL22BP, CRF2-S1, and IL-22BP.

IL22RA2, containing 2 cytokine-binding fibronectin type III domains, is a secreted glycoprotein resembling the extracellular domain of cytokine receptors IL20RA and IL22R (33% identity) (Dumoutier et al, J. Immunol., 166(12):7090-5 (2001)); Xu et al, Proc. Natl. Acad. Sci. USA, 98(17):9511-6 (2001)). IL22RA2 binds with IL22, a cytokine produced by T cells, and was shown to inhibit IL22 signaling in numerous cell lines. Thus, IL22RA2 is likely to be a negative regulator of inflammatory responses induced by IL22 (Dumoutier et al, 2001 supra; Xu et al, 2001 supra; Kotenko et al, J. Immunol., 166(12):7096-103 (2001)). IL22RA2 was detected in breast, lung, colon, skin, placenta, spleen, mononuclear cells, and to a lesser extent in several other tissues (Dumoutier et al, 2001 supra; Xu et al, 2001 supra; Kotenko et al, 2001 supra). Highest IL22RA2 expression occurred in mononuclear cells, plasma cells, and epithelium in inflammatory infiltration sites. IL22RA2 expression was also detected in certain types of tumors (see U.S. Patent Application Publication No. US-2002-0137909-A1 published Sep. 26, 2002).

Targeted or gene trap mutations were generated in strain 129SvEv$^{Brd}$-derived embryonic stem (ES) cells. The chimeric mice were bred to C57BL/6J albino mice to generate F1 heterozygous animals. These progeny were intercrossed to generate F2 wild type, heterozygous, and homozygous mutant progeny. On rare occasions, for example when very few F1 mice were obtained from the chimera, F1 heterozygous mice were crossed to 129SvEv$^{Brd}$/C57 hybrid mice to yield additional heterozygous animals for the intercross to generate the F2 mice. Disruption of the target gene was confirmed by Southern hybridization analysis. Level I phenotypic analysis was performed on mice from this generation.

|  | wt | het | hom | Total |
|---|---|---|---|---|
| Observed | 22 | 52 | 23 | 97 |
| Expected | 24.25 | 48.5 | 24.25 | 97 |

Chi-Sq. = 0.53
Significance = 0.76883
(hom/n) = 0.24
Avg. Litter Size = 0

1. Phenotypic Analysis (for Disrupted Gene: DNA145887-2849 (UNQ5793)

(a) Overall Phenotypic Summary

Mutant (−/−) mice exhibited elevation of serum immunoglobulins compared to their gender-matched (+/+) littermates. In addition, (−/−) mice exhibited elevated levels of alanine aminotransferase (ALT) and aspartate aminotransferase (AST) levels when the mice after inducing a hepatitis phenotype with ConA compared to the controls and wild-type littermates.

(b) Immunology Phenotypic Analysis

Immune related and inflammatory diseases are the manifestation or consequence of fairly complex, often multiple interconnected biological pathways which in normal physiology are critical to respond to insult or injury, initiate repair from insult or injury, and mount innate and acquired defense against foreign organisms. Disease or pathology occurs when these normal physiological pathways cause additional insult or injury either as directly related to the intensity of the response, as a consequence of abnormal regulation or excessive stimulation, as a reaction to self, or as a combination of these.

Though the genesis of these diseases often involves multistep pathways and often multiple different biological systems/pathways, intervention at critical points in one or more of these pathways can have an ameliorative or therapeutic effect. Therapeutic intervention can occur by either antagonism of a detrimental process/pathway or stimulation of a beneficial process/pathway.

T lymphocytes (T cells) are an important component of a mammalian immune response. T cells recognize antigens which are associated with a self-molecule encoded by genes within the major histocompatibility complex (MHC). The antigen may be displayed together with MHC molecules on the surface of antigen presenting cells, virus infected cells, cancer cells, grafts, etc. The T cell system eliminates these altered cells which pose a health threat to the host mammal. T cells include helper T cells and cytotoxic T cells. Helper T cells proliferate extensively following recognition of an antigen-MHC complex on an antigen presenting cell. Helper T cells also secrete a variety of cytokines, i.e., lymphokines, which play a central role in the activation of B cells, cytotoxic T cells and a variety of other cells which participate in the immune response.

In many immune responses, inflammatory cells infiltrate the site of injury or infection. The migrating cells may be neutrophilic, eosinophilic, monocytic or lymphocytic as can be determined by histologic examination of the affected tissues. Current Protocols in Immunology, ed. John E. Coligan, 1994, John Wiley & Sons, Inc.

Many immune related diseases are known and have been extensively studied. Such diseases include immune-mediated inflammatory diseases (such as rheumatoid arthritis, immune mediated renal disease, hepatobiliary diseases, inflammatory bowel disease (IBD), psoriasis, and asthma), non-immune-mediated inflammatory diseases, infectious diseases, immunodeficiency diseases, neoplasia, and graft rejection, etc.

In the area of immunology, targets were identified herein for the treatment of inflammation and inflammatory disorders. Immune related diseases could be treated by suppressing the immune response. Using neutralizing antibodies that inhibit molecules having immune stimulatory activity would be beneficial in the treatment of immune-mediated and inflammatory diseases. Molecules which inhibit the immune response can be utilized (proteins directly or via the use of antibody agonists) to inhibit the immune response and thus ameliorate immune related disease.

Serum Immunoglobulin Isotyping Assay:

The Serum Immunoglobulin Isotyping Assay was performed using a Cytometric Bead Array (CBA) kit. This assay was used to rapidly identify the heavy and light chain isotypes of a mouse monoclonal antibody in a single sample. The values expressed are "relative fluorescence units" and are based on the detection of kappa light chains. Any value<6 is not significant.

Results:

Mutant (−/−) mice exhibited elevation of IgM, IgG1, IgG2a and IgG2b serum immunoglobulins compared to their gender-matched (+/+) littermates. IgM immunoglobulins are the first to be produced in a humoral immune response for neutralization of bacterial toxins and are particularly important in activating the complement system. Likewise, IgG immunoglobulins have neutralization effects and to a lesser extent are important for activation of the complement system. The observed phenotype suggests that the PRO19598 polypeptide is a negative regulator of inflammatory responses. These immunological abnormalities suggest that inhibitors (antagonists) of PRO19598 polypeptides would be useful in stimulating the immune system (such as T cell proliferation) and would find utility in the cases wherein this effect would be beneficial to the individual such as in the case of leukemia, and other types of cancer, and in immunocompromised patients, such as AIDS sufferers. Accordingly, PRO9783 polypeptides or agonists thereof would be useful in inhibiting the immune response and would be useful candidates for suppressing harmful immune responses, e.g. in the case of graft rejection or graft-versus-host diseases.

ConA-induced Hepatitis

Studies were performed to see the effects of ConA-induced hepatitis on homozygous and heterozygous mutant mice in comparison to their wild-type gender-matched littermates.

Procedure:

The effect of ConA-induced hepatitis was studied in UNQ5793 knockout mice. Groups used for this study include wild-type (+/+) mice, heterozygous (+/−) mice, UNQ5793 homozygous (−/−) mice, and untreated C57B16 mice. All mice except for the C57B16 control group were injected with 10 mg/kg of ConA in 100 ul saline by intravenous injection. Sixteen hours later, mice were sacrificed and serum was collected for analysis of alanine aminotransferase (ALT) and aspartate aminotransferase (AST) levels. Serum was diluted 1:3 in water and placed on a Roche reagent cassette and read using a Chemistry analyzer (Integra 400). Livers were also collected at 16 hours. The liver samples were fixed and stained with hematoxylin and eosin in order to determine the extent of liver damage.

Results:

Both the homozygous (−/−) and heterozygous (+/−) mutant mice exhibited significantly elevated levels of serum alanine aminotransferase (ALT) and aspartate aminotransferase (AST) 16 hours after injection with ConA compared with untreated C57B16 controls and their wild-type (+/+) gender-matched littermates. In addition, histological findings showed significant liver damage in the mutant (+/−) and (−/−) mice compared with the untreated controls and wild-type littermates. The knockout (−/−) mice showed marked to severe multifocal bridging acute hepatocellular necrosis. Likewise, the heterozygotes (+/−) showed marked to moderate multifocal acute hepatocellular necrosis indicative of extensive liver damage. Thus, the mutant knockout mice appeared to have an exacerbated liver damage when hepatitis was induced with ConA, suggestive of an enhanced inflammatory response. These studies indicate that PRO9783 polypeptides or agonists thereof would be useful in inhibiting or suppressing harmful immune responses and in particular would be useful in the treatment of hepatitis.

N. Generation and Analysis of Mice Comprising DNA50921-1458 (UNQ540) Gene Disruptions In these knockout experiments, the gene encoding PRO1083 polypeptides (designated as DNA50921-1458 (UNQ540) was disrupted. The gene specific information for these studies is as follows: mouse gene sequence nucleotide reference: NM_018882 or *Mus musculus* G protein-coupled receptor 56 (Gpr56), protein reference: NP_061370 or serpentine receptor; secretin receptor [*Mus musculus*]; human gene sequence nucleotide reference: NM_005682 or *Homo sapiens* G protein-coupled receptor 56 (GPR56), protein reference: NP_005673 or G protein-coupled receptor 56; EGF-TM7-like [*Homo sapiens*].

The gene that is mutated in these animals is represented by mouse UniGene cluster Mm. 13799, which is the ortholog of human UniGene cluster Hs.6527 (GPR56). GPR56 encodes G protein-coupled receptor 56. The protein is also known as Cyt28, TM7LN4, TM7XN1, secretin receptor, serpentine receptor, and EGF-TM7-like. GPR56 is strongly expressed in hippocampus and hypothalamic nuclei (Liu et al., Genomics, 55(3):296-305 (1999)) and was strongly downregulated in highly metastatic cell lines (Zendman et al, FEBS Lett., 446 (2-3):292-8 (Mar. 12, 1999)). The presence of an extracellular mucin-like domain suggests a possible role for the protein in cell-cell interactions.

Targeted or gene trap mutations were generated in strain 129SvEv$^{Brd}$-derived embryonic stem (ES) cells. The chimeric mice were bred to C57BL/6J albino mice to generate F1 heterozygous animals. These progeny were intercrossed to generate F2 wild type, heterozygous, and homozygous mutant progeny. On rare occasions, for example when very few F1 mice were obtained from the chimera, F1 heterozygous mice were crossed to 129SvEv$^{Brd}$/C57 hybrid mice to yield additional heterozygous animals for the intercross to generate the F2 mice. Level I phenotypic analysis was performed on mice from this generation. Wild-type expression of the target gene was detected in embryonic stem (ES) cells and in all 13 adult tissue samples tested by RT-PCR, except adipose. Disruption of the target gene was confirmed by Southern hybridization analysis.

|  | wt | het | hom | Total |
|---|---|---|---|---|
| Observed | 14 | 43 | 16 | 73 |
| Expected | 18.25 | 36.5 | 18.25 | 73 |

Chi-Sq. = 2.42 Significance = 0.29750 (hom/n) = 0.22 Avg. Litter Size = 0

1. Phenotypic Analysis (for Disrupted Gene: DNA50921-1458 (UNQ540)

(a) Overall Phenotypic Summary

The (−/−) mice exhibited an increased mean serum IgM level and notably increased mean serum IgA and IgG3 levels when compared with their (+/+) littermates and the historical means. The female (−/−) mice exhibited slightly increased mean total tissue mass, lean body mass, bone mineral content, and total body and femoral bone mineral density when compared with their gender-matched (+/+) littermates.

(b) Immunology Phenotypic Analysis

Immune related and inflammatory diseases are the manifestation or consequence of fairly complex, often multiple interconnected biological pathways which in normal physiology are critical to respond to insult or injury, initiate repair from insult or injury, and mount innate and acquired defense against foreign organisms. Disease or pathology occurs when these normal physiological pathways cause additional insult or injury either as directly related to the intensity of the response, as a consequence of abnormal regulation or excessive stimulation, as a reaction to self, or as a combination of these.

Though the genesis of these diseases often involves multistep pathways and often multiple different biological systems/pathways, intervention at critical points in one or more of these pathways can have an ameliorative or therapeutic effect. Therapeutic intervention can occur by either antagonism of a detrimental process/pathway or stimulation of a beneficial process/pathway.

T lymphocytes (T cells) are an important component of a mammalian immune response. T cells recognize antigens which are associated with a self-molecule encoded by genes within the major histocompatibility complex (MHC). The antigen may be displayed together with MHC molecules on the surface of antigen presenting cells, virus infected cells, cancer cells, grafts, etc. The T cell system eliminates these altered cells which pose a health threat to the host mammal. T cells include helper T cells and cytotoxic T cells. Helper T cells proliferate extensively following recognition of an antigen-MHC complex on an antigen presenting cell. Helper T cells also secrete a variety of cytokines, i.e., lymphokines, which play a central role in the activation of B cells, cytotoxic T cells and a variety of other cells which participate in the immune response.

In many immune responses, inflammatory cells infiltrate the site of injury or infection. The migrating cells may be neutrophilic, eosinophilic, monocytic or lymphocytic as can be determined by histologic examination of the affected tissues. Current Protocols in Immunology, ed. John E. Coligan, 1994, John Wiley & Sons, Inc.

Many immune related diseases are known and have been extensively studied. Such diseases include immune-mediated inflammatory diseases (such as rheumatoid arthritis, immune mediated renal disease, hepatobiliary diseases, inflammatory bowel disease (IBD), psoriasis, and asthma), non-immune-mediated inflammatory diseases, infectious diseases, immunodeficiency diseases, neoplasia, and graft rejection, etc.

In the area of immunology, targets were identified herein for the treatment of inflammation and inflammatory disorders. Immune related diseases could be treated by suppressing the immune response. Using neutralizing antibodies that inhibit molecules having immune stimulatory activity would be beneficial in the treatment of immune-mediated and inflammatory diseases. Molecules which inhibit the immune response can be utilized (proteins directly or via the use of antibody agonists) to inhibit the immune response and thus ameliorate immune related disease.

Serum Immunoglobulin Isotyping Assay:

The Serum Immunoglobulin Isotyping Assay was performed using a Cytometric Bead Array (CBA) kit. This assay was used to rapidly identify the heavy and light chain isotypes of a mouse monoclonal antibody in a single sample. The values expressed are "relative fluorescence units" and are based on the detection of kappa light chains. Any value<6 is not significant.

Results:

Mutant (−/−) mice exhibited elevation of IgM, IgA, and IgG3 serum immunoglobulins compared to their gender-matched (+/+) littermates. IgM immunoglobulins are the first to be produced in a humoral immune response for neutralization of bacterial toxins and are particularly important in activating the complement system. Likewise, IgG immunoglobulins have neutralization effects and to a lesser extent are important for activation of the complement system. IgA mainly functions as an epithelial cell protector which can neutralize bacterial toxins and viruses. Although no obvious disease susceptibility is associated with selective IgA defects, they are commoner in people with chronic lung disease than in the general population. This suggests that lack of IgA may result in a predisposition to lung infections with various pathogens and is consistent with the role of IgA in defense at the body surfaces. In this case, the phenotype observed for knockout mice resulted in an increase in IgA serum levels suggesting that inhibitors (antagonists) of PRO1083 polypeptides would be useful for natural immunity protection against skin infections and more importantly would prevent susceptibility to lung infections. The observed phenotype suggests that the PRO1083 polypeptide is a negative regulator of inflammatory responses. These immunological abnormalities suggest that inhibitors (antagonists) of PRO1083 polypeptides would be useful as important agents which could stimulate the immune system (such as T cell proliferation) and would find utility in the cases wherein this effect would be beneficial to the individual such as in the case of leukemia, and other types of cancer, and in immunocompromised patients, such as AIDS sufferers. Accordingly, PRO1083 polypeptides or agonists thereof would be useful in inhibiting the immune response and would be useful candidates for suppressing harmful immune responses, e.g. in the case of graft rejection or graft-versus-host diseases.

(c) Bone Metabolism: Radiology Phenotypic Analysis

In the area of bone metabolism, targets were identified herein for the treatment of arthritis, osteoporosis, osteopenia and osteopetrosis as well as identifying targets that promote bone healing. Tests included:

DEXA for measurement of bone mineral density on femur and vertebra

MicroCT for very high resolution and very high sensitivity measurements of bone mineral density for both trabecular and cortical bone.

Dexa Analysis—Test Description:

Procedure: A cohort of 4 wild type, 4 heterozygotes and 8 homozygotes were tested in this assay. Dual Energy X-ray Absorptiometry (DEXA) has been used successfully to identify changes in bone. Anesthetized animals were examined and bone mineral content (BMC), BMC/LBM ratios, volumetric bone mineral density (vBMD), total body BMD, femur BMD and vertebra BMD were measured.

The mouse was anesthetized by intraperitoneal injection of Avertin (1.25% 2,2,2,-tribromoethanol, 20 ml/kg body weight), body length and weight were measured, and then the mouse was placed in a prone position on the platform of the PIXImus™ Densitometer (Lunar Inc.) for a DEXA scan. Using Lunar PIXImus software, the bone mineral density (BMD) and fat composition (% fat) and total tissue mass (TTM) were determined in the regions of interest (ROI) [i.e., whole body, vertebrae, and both femurs].

DEXA Results:

The female (−/−) mice exhibited increased mean total tissue mass, lean body mass, bone mineral content, and total body and femoral bone mineral density when compared with their gender-matched (+/+) littermates. These results indicate that the knockout mutant phenotype may be associated with such bone abnormalities as osteopetrosis. Osteopetrosis is a condition characterized by abnormal thickening and hardening of bone and abnormal fragility of the bones. As such, PRO1083 polypeptides or agonists thereof would be useful for the treatment of osteopetrosis. A phenotype associated with an increased bone mineral content, and total body and femoral bone mineral density suggests that agents which mimic these effects (e.g. antagonists of PRO1083 polypeptides) would be useful in bone healing.

O. Generation and Analysis of Mice Comprising DNA226659 (UNQ5070) Gene Disruptions In these knockout experiments, the gene encoding hu TRPM2 polypeptides (designated as DNA226659 (UNQ5070) was disrupted. The gene specific information for these studies is as follows: mouse gene sequence nucleotide reference: NM_138301 or *Mus musculus* transient receptor potential cation channel, subfamily M, member 2 (Trpm2), protein reference: NP_612174 or transient receptor potential cation channel, subfamily M, member 2; transient receptor potential channel 7; transient receptor protein 7 [*Mus musculus*]; human gene sequence nucleotide reference: NM_003307 or *Homo sapiens* transient receptor potential cation channel, subfamily M, member 2 (TRPM2), protein reference: NP_003298 or transient receptor potential cation channel, subfamily M, member 2; transient receptor potential-related channel 7, a novel putative Ca2+ channel protein; transient receptor potential channel 7 [*Homo sapiens*].

The disrupted mouse gene is transient receptor potential cation channel, subfamily M, member 2 (Trpm2), ortholog of human transient receptor potential cation channel, subfamily M, member 2 (TRPM2). Aliases include TRPC7; Trrp7;

LTRPC2; transient receptor protein 7; transient receptor potential channel 7; KNP3; and transient receptor potential-related channel 7, a novel putative Ca2+ channel protein.

TRPM2, a member of the short subfamily of transient receptor potential channels, functions as a Ca2+-permeable nonselective cation channel highly expressed in brain and immunocytes (OMIM 603749). The protein contains an ion transport protein domain (Pfam PF00520) and a NUDIX domain (Pfam PF00293), which functions as a specific ADP-ribose pyrophosphatase.

ADP-ribose, which is a breakdown product of the calcium-release second messenger cyclic ADP-ribose and NAD hydrolysis, activates TRPM2 by binding to the C-terminal Nudix domain. ADP-ribose-activated TRPM2 is likely to play an important role in triggering immune responses in certain types of immune cells (Sano et al., Science, 293(5533):1327-30 (Aug. 17, 2001); Perraud et al, Nature, 411(6837):595-9 (May 31, 2001)).

A specific TRPM2 variant lacking the C-terminal Nudix domain is activated by hydrogen peroxide but not ADP-ribose and is thus activated by oxidative stress. This variant is expressed in neutrophil granulocytes and is likely to play a role in respiratory burst, which generates high concentrations of superoxide anions and free radicals (Wehage et al, J. Biol. Chem., 277(26):23150-6 (2002)). Moreover, the TRPM2 variant with the Nudix domain is also activated by hydrogen peroxide. Since it is widely expressed, this TRPM2 variant may play a more general role in necrosis and apoptosis in response to oxidative stress (Hara et al, Mol. Cell., 9(1):163-73 (2002)).

Targeted or gene trap mutations were generated in strain 129SvEv$^{Brd}$-derived embryonic stem (ES) cells. The chimeric mice were bred to C57BL/6J albino mice to generate F1 heterozygous animals. These progeny were intercrossed to generate F2 wild type, heterozygous, and homozygous mutant progeny. On rare occasions, for example when very few F1 mice were obtained from the chimera, F1 heterozygous mice were crossed to 129SvEv$^{Brd}$/C57 hybrid mice to yield additional heterozygous animals for the intercross to generate the F2 mice. Level I phenotypic analysis was performed on mice from this generation. Wild-type expression of the target gene was detected in embryonic stem (ES) cells and, among the 19 adult tissue samples tested by RT-PCR, in spleen, liver, bone, stomach, small intestine and colon, skin fibroblast, prostate, heart, and aortic tree. Disruption of the target gene was confirmed by Southern hybridization analysis.

|  | wt | het | hom | Total |
|---|---|---|---|---|
| Observed | 22 | 43 | 22 | 87 |
| Expected | 21.75 | 43.5 | 21.75 | 87 |

Chi-Sq. = 0.01 Significance = 0.99427 (hom/n) = 0.25 Avg. Litter Size = 0

1. Phenotypic Analysis (for Disrupted Gene: DNA226659 (UNQ5070)
  (a) Overall Phenotypic Summary The male (−/−) mice exhibited decreased mean vertebral trabecular bone volume, thickness, and connectivity density and decreased mean femoral midshaft cortical thickness, and cross-sectional area when compared with their gender-matched (+/+) littermates and the historical means.

(b) Bone Metabolism: Radiology Phenotypic Analysis

In the area of bone metabolism, targets were identified herein for the treatment of arthritis, osteoporosis, osteopenia and osteopetrosis as well as identifying targets that promote bone healing. Tests included:

DEXA for measurement of bone mineral density on femur and vertebra

MicroCT for very high resolution and very high sensitivity measurements of bone mineral density for both trabecular and cortical bone.

Dexa Analysis—Test Description:

Procedure: A cohort of 4 wild type, 4 heterozygotes and 8 homozygotes were tested in this assay. Dual Energy X-ray Absorptiometry (DEXA) has been used successfully to identify changes in bone. Anesthetized animals were examined and bone mineral content (BMC), BMC/LBM ratios, volumetric bone mineral density (vBMD), total body BMD, femur BMD and vertebra BMD were measured.

The mouse was anesthetized by intraperitoneal injection of Avertin (1.25% 2,2,2,-tribromoethanol, 20 ml/kg body weight), body length and weight were measured, and then the mouse was placed in a prone position on the platform of the PIXImus™ Densitometer (Lunar Inc.) for a DEXA scan. Using Lunar PIXImus software, the bone mineral density (BMD) and fat composition (% fat) and total tissue mass (TTM) were determined in the regions of interest (ROI) [i.e., whole body, vertebrae, and both femurs].

Bone microCT Analysis:

Procedure:

MicroCT was also used to get very sensitive measurements of BMD. One vertebra and 1 femur were taken from a cohort of 4 wild type and 8 homozygous mice. Measurements were taken of lumbar 5 veterbra traebecular bone volume, traebecular thickness, connectivity density and midshaft femur total bone area and cortical thickness. The μCT40 scans provided detailed information on bone mass and architecture. Multiple bones were placed into sample holders and scanned automatically. Instrument software was used to select regions of interest for analysis. Trabecular bone parameters were analyzed in the fifth lumbar vertebrae (LV5) at 16 micrometer resolution and cortical bone parameters were analyzed in the femur midshaft at a resolution of 20 micrometers.

Micro-CT Analysis Results: The male (−/−) mice exhibited notably decreased mean lumbar 5 vertebral trabecular bone volume, number, thickness, and connectivity density when compared with their gender-matched (+/+) littermates and the historical means. These mutants also exhibited notably decreased mean femoral midshaft cortical thickness and cross-sectional area when compared with their gender-matched (+/+) littermates and the historical mean. [Analyzed wt/het/hom: 5/4/8]

These results demonstrate that knockout mutant male mice deficient in the gene encoding hu TRPM2 polypeptides exhibit abnormal bone metabolism with significant bone loss characterized by a decrease in bone mass with decreased density and possibly fragility leading to bone fractures. Thus, it appears that hu TRPM2 or its encoding gene would be useful in maintaining bone homeostasis and would be important in bone healing or for the treatment of arthritis or osteoporosis; whereas antagonists to hu TRPM2 or its encoding gene would lead to abnormal or pathological bone disorders including inflammatory diseases associated with abnormal bone metabolism including arthritis, osteoporosis, and osteopenia.

P. Generation and Analysis of Mice Comprising DNA83500-2506 (UNQ852) Gene Disruptions In these knockout experiments, the gene encoding PRO1801 polypeptides (designated as DNA83500-2506) (UNQ852) was disrupted. The gene specific information for these studies is as follows: the mutated mouse gene corresponds to nucleotide reference: NM_021380 or *Mus musculus* interleukin 20 (Il20); protein reference: NP_067355 or interleukin 20; four helix bundle cytokine 10 [*Mus musculus*]; the human gene sequence reference: NM_018724 or *Homo sapiens* interleukin 20 (IL20); the human protein sequence corresponds to reference: NP_061194 or interleukin 20 [*Homo sapiens*]

The gene that is mutated in these animals is interleukin 20 (Il20), which is the ortholog of human IL20. Aliases include IL-20, IL10D, ZCYTO10, and four alpha helix cytokine.

IL20 is most closely related by sequence to several members of the IL10 family: IL19, MDA7, and IL10 (OMIM 605619). Northern blot studies demonstrate that the gene is expressed in skin, and trachea. Overexpression of the gene in mouse caused neonatal death as well as skin abnormalities. An IL20 receptor molecule is also expressed in skin.

IL20 is reported to share receptor complexes with IL19 and IL24, however the biological consequences of ligand-receptor interactions are very different for the three cytokines. IL20 is reported to enhance hematopoiesis, and has been proposed as a target for inflammatory skin disease treatments.

Targeted or gene trap mutations were generated in strain 129SvEv$^{Brd}$-derived embryonic stem (ES) cells. The chimeric mice were bred to C57BL/6J albino mice to generate F1 heterozygous animals. These progeny were intercrossed to generate F2 wild type, heterozygous, and homozygous mutant progeny. On rare occasions, for example when very few F1 mice were obtained from the chimera, F1 heterozygous mice were crossed to 129SvEv$^{Brd}$/C57 hybrid mice to yield additional heterozygous animals for the intercross to generate the F2 mice. Level I phenotypic analysis was performed on mice from this generation. Wild-type expression of the target gene was detected in embryonic stem (ES) cells and, among the 19 adult tissue samples tested by RT-PCR, in spleen, liver, bone, stomach, small intestine and colon, skin fibroblast, prostate, heart, and aortic tree. Disruption of the target gene was confirmed by Southern hybridization analysis.

|          | wt   | het | hom  | Total |
|----------|------|-----|------|-------|
| Observed | 18   | 34  | 18   | 70    |
| Expected | 17.5 | 35  | 17.5 | 70    |

Chi-Sq. = 0.06 Significance = 0.97183 (hom/n) = 0.26 Avg. Litter Size = 8

41.1.1. Phenotypic Analysis (for Disrupted Gene: DNA83500-2506) (UNQ852)

(a) Overall Phenotypic Summary:

Mutation of the gene encoding the ortholog of human interleukin 20 (IL-20) resulted in a notably increased inflammatory response in the (−/−) mice. Gene disruption was confirmed by Southern blot.

(b) Immunology Phenotypic Analysis

Immune related and inflammatory diseases are the manifestation or consequence of fairly complex, often multiple interconnected biological pathways which in normal physiology are critical to respond to insult or injury, initiate repair from insult or injury, and mount innate and acquired defense against foreign organisms. Disease or pathology occurs when these normal physiological pathways cause additional insult or injury either as directly related to the intensity of the response, as a consequence of abnormal regulation or excessive stimulation, as a reaction to self, or as a combination of these.

Though the genesis of these diseases often involves multi-step pathways and often multiple different biological systems/pathways, intervention at critical points in one or more of these pathways can have an ameliorative or therapeutic effect. Therapeutic intervention can occur by either antagonism of a detrimental process/pathway or stimulation of a beneficial process/pathway.

T lymphocytes (T cells) are an important component of a mammalian immune response. T cells recognize antigens which are associated with a self-molecule encoded by genes within the major histocompatibility complex (MHC). The antigen may be displayed together with MHC molecules on the surface of antigen presenting cells, virus infected cells, cancer cells, grafts, etc. The T cell system eliminates these altered cells which pose a health threat to the host mammal. T cells include helper T cells and cytotoxic T cells. Helper T cells proliferate extensively following recognition of an antigen-MHC complex on an antigen presenting cell. Helper T cells also secrete a variety of cytokines, i.e., lymphokines, which play a central role in the activation of B cells, cytotoxic T cells and a variety of other cells which participate in the immune response.

In many immune responses, inflammatory cells infiltrate the site of injury or infection. The migrating cells may be neutrophilic, eosinophilic, monocytic or lymphocytic as can be determined by histologic examination of the affected tissues. Current Protocols in Immunology, ed. John E. Coligan, 1994, John Wiley & Sons, Inc.

Many immune related diseases are known and have been extensively studied. Such diseases include immune-mediated inflammatory diseases (such as rheumatoid arthritis, immune mediated renal disease, hepatobiliary diseases, inflammatory bowel disease (IBD), psoriasis, and asthma), non-immune-mediated inflammatory diseases, infectious diseases, immunodeficiency diseases, neoplasia, and graft rejection, etc.

In the area of immunology, targets were identified herein for the treatment of inflammation and inflammatory disorders. Immune related diseases could be treated by suppressing the immune response. Using neutralizing antibodies that inhibit molecules having immune stimulatory activity would be beneficial in the treatment of immune-mediated and inflammatory diseases. Molecules which inhibit the immune response can be utilized (proteins directly or via the use of antibody agonists) to inhibit the immune response and thus ameliorate immune related disease.

DSS-Induced Colitis:

Both male wildtype and homozygous (−/−) mutant mice were given 3% DSS (dextran sulfate sodium) in their drinking water from day 0 to day 7. On day 7, the drinking water was replaced with regular water. The mice were weighed and colons were analyzed by histology on day 7 and day 14. The knockout (−/−) mice showed a markedly decreased survival rate on Day 7 (60% survival) compared to their wild-type littermate controls (100% survival). The knockout (−/−) mice were much more susceptible to the DSS challenge (inducing a colitis condition) and they exhibited an enhanced inflammatory response compared to their gender-matched littermate controls. Thus, PRO1801 polypeptides or agonists thereof would be useful in the healing process of inflammatory conditions of the colon such as occurs in colitis or irritable bowel disorders.

Example 19

Use of PRO224, PRO9783, PRO1108, PRO34000, PRO240, PRO943, hu A33, PRO230, PRO178, PRO199, PRO4333, PRO1336, PRO19598, PRO1083, hu TRPM2 or PRO1801 as a Hybridization Probe The following method describes use of a nucleotide sequence encoding a PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide as a hybridization probe.

DNA comprising the coding sequence of full-length or mature PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptides as disclosed herein is employed as a probe to screen for homologous DNAs (such as those encoding naturally-occurring variants of PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptides) in human tissue cDNA libraries or human tissue genomic libraries.

Hybridization and washing of filters containing either library DNAs is performed under the following high stringency conditions. Hybridization of radiolabeled PRO224-, PRO9783-, PRO1108-, PRO34000-, PRO240-, PRO943-, hu A33-, PRO230-, PRO178-, PRO1199-, PRO4333-, PRO1336-, PRO19598-, PRO1083-, hu TRPM2- or PRO1801-derived probe to the filters is performed in a solution of 50% formamide, 5×SSC, 0.1% SDS, 0.1% sodium pyrophosphate, 50 mM sodium phosphate, pH 6.8, 2×Denhardt's solution, and 10% dextran sulfate at 42° C. for 20 hours. Washing of the filters is performed in an aqueous solution of 0.1×SSC and 0.1% SDS at 42° C.

DNAs having a desired sequence identity with the DNA encoding full-length native sequence PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptides can then be identified using standard techniques known in the art.

Example 20

Expression of PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 in *E. coli*

This example illustrates preparation of an unglycosylated form of PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptides by recombinant expression in *E. coli*.

The DNA sequence encoding a PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide is initially amplified using selected PCR primers. The primers should contain restriction enzyme sites which correspond to the restriction enzyme sites on the selected expression vector. A variety of expression vectors may be employed. An example of a suitable vector is pBR322 (derived from *E. coli*; see Bolivar et al., *Gene*, 2:95 (1977)) which contains genes for ampicillin and tetracycline resistance. The vector is digested with restriction enzyme and dephosphorylated. The PCR amplified sequences are then ligated into the vector. The vector will preferably include sequences which encode for an antibiotic resistance gene, a trp promoter, a polyhis leader (including the first six STII codons, polyhis sequence, and enterokinase cleavage site), the PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 coding region, lambda transcriptional terminator, and an argU gene.

The ligation mixture is then used to transform a selected *E. coli* strain using the methods described in Sambrook et al., supra. Transformants are identified by their ability to grow on LB plates and antibiotic resistant colonies are then selected. Plasmid DNA can be isolated and confirmed by restriction analysis and DNA sequencing.

Selected clones can be grown overnight in liquid culture medium such as LB broth supplemented with antibiotics. The overnight culture may subsequently be used to inoculate a larger scale culture. The cells are then grown to a desired optical density, during which the expression promoter is turned on.

After culturing the cells for several more hours, the cells can be harvested by centrifugation. The cell pellet obtained by the centrifugation can be solubilized using various agents known in the art, and the solubilized PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 protein can then be purified using a metal chelating column under conditions that allow tight binding of the protein.

PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 may be expressed in *E. coli* in a poly-His tagged form, using the following procedure. The DNA encoding PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 is initially amplified using selected PCR primers. The primers will contain restriction enzyme sites which correspond to the restriction enzyme sites on the selected expression vector, and other useful sequences providing for efficient and reliable translation initiation, rapid purification on a metal chelation column, and proteolytic removal with enterokinase. The PCR-amplified, poly-His tagged sequences are then ligated into an expression vector, which is used to transform an *E. coli* host based on strain 52 (W3110 fuhA(tonA) lon galE rpoHts(htpRts) clpP(lacIq). Transformants are first grown in LB containing 50 mg/ml carbenicillin at 30° C. with shaking until an O.D.600 of 3-5 is reached. Cultures are then diluted 50-100 fold into CRAP media (prepared by mixing 3.57 g $(NH_4)_2SO_4$, 0.71 g sodium citrate•$2H_2O$, 1.07 g KCl, 5.36 g Difco yeast extract, 5.36 g Sheffield hycase SF in 500 mL water, as well as 110 mM MPOS, pH 7.3, 0.55% (w/v) glucose and 7 mM $MgSO_4$) and grown for approximately 20-30 hours at 30° C. with shaking. Samples are removed to verify expression by SDS-PAGE analysis, and the bulk culture is centrifuged to pellet the cells. Cell pellets are frozen until purification and refolding.

*E. coli* paste from 0.5 to 1 L fermentations (6-10 g pellets) is resuspended in 10 volumes (w/v) in 7 M guanidine, 20 mM Tris, pH 8 buffer. Solid sodium sulfite and sodium tetrathionate is added to make final concentrations of 0.1M and 0.02 M, respectively, and the solution is stirred overnight at 4° C. This step results in a denatured protein with all cysteine residues blocked by sulfitolization. The solution is centrifuged at 40,000 rpm in a Beckman Ultracentifuge for 30 min. The supernatant is diluted with 3-5 volumes of metal chelate column buffer (6 M guanidine, 20 mM Tris, pH 7.4) and filtered through 0.22 micron filters to clarify. The clarified extract is loaded onto a 5 ml Qiagen Ni-NTA metal chelate column equilibrated in the metal chelate column buffer. The column is washed with additional buffer containing 50 mM imidazole (Calbiochem, Utrol grade), pH 7.4. The protein is eluted with buffer containing 250 mM imidazole. Fractions containing the desired protein are pooled and stored at 4° C.

Protein concentration is estimated by its absorbance at 280 nm using the calculated extinction coefficient based on its amino acid sequence.

The proteins are refolded by diluting the sample slowly into freshly prepared refolding buffer consisting of: 20 mM Tris, pH 8.6, 0.3 M NaCl, 2.5 M urea, 5 mM cysteine, 20 mM glycine and 1 mM EDTA. Refolding volumes are chosen so that the final protein concentration is between 50 to 100 micrograms/ml. The refolding solution is stirred gently at 4° C. for 12-36 hours. The refolding reaction is quenched by the addition of TFA to a final concentration of 0.4% (pH of approximately 3). Before further purification of the protein, the solution is filtered through a 0.22 micron filter and acetonitrile is added to 2-10% final concentration. The refolded protein is chromatographed on a Poros R1/H reversed phase column using a mobile buffer of 0.1% TFA with elution with a gradient of acetonitrile from 10 to 80%. Aliquots of fractions with A280 absorbance are analyzed on SDS polyacrylamide gels and fractions containing homogeneous refolded protein are pooled. Generally, the properly refolded species of most proteins are eluted at the lowest concentrations of acetonitrile since those species are the most compact with their hydrophobic interiors shielded from interaction with the reversed phase resin. Aggregated species are usually eluted at higher acetonitrile concentrations. In addition to resolving misfolded forms of proteins from the desired form, the reversed phase step also removes endotoxin from the samples.

Fractions containing the desired folded PRO224, PRO9783, PRO1.108, PRO34000, PRO240, PRO943, hu A33, PRO230, PRO178, PRO199, PRO4333, PRO1336, PRO19598, PRO1083, hu TRPM2 or PRO1801 polypeptide are pooled and the acetonitrile removed using a gentle stream of nitrogen directed at the solution. Proteins are formulated into 20 mM Hepes, pH 6.8 with 0.14 M sodium chloride and 4% mannitol by dialysis or by gel filtration using G25 Superfine (Pharmacia) resins equilibrated in the formulation buffer and sterile filtered.

Example 21

Expression of PRO224, PRO9783, PRO1108, PRO34000, PRO240, PRO943, hu A33. PRO230, PRO178, PRO199, PRO4333, PRO1336, PRO19598, PRO1083, hu TRPM2 or PRO1801 in Mammalian Cells This example illustrates preparation of a potentially glycosylated form of a PRO224, PRO9783, PRO1108, PRO34000, PRO240, PRO943, hu A33, PRO230, PRO178, PRO199, PRO4333, PRO1336, PRO19598, PRO1083, hu TRPM2 or PRO1801 polypeptide by recombinant expression in mammalian cells.

The vector, pRK5 (see EP 307,247, published Mar. 15, 1989), is employed as the expression vector. Optionally, the PRO224, PRO9783, PRO1108, PRO34000, PRO240, PRO943, hu A33, PRO230, PRO178, PRO199, PRO4333, PRO1336, PRO19598, PRO1083, hu TRPM2 or PRO1801 DNA is ligated in to pRK5 with selected restriction enzymes to allow insertion of the PRO224, PRO9783, PRO1108, PRO34000, PRO240, PRO943, hu A33, PRO230, PRO178, PRO199, PRO4333, PRO1336, PRO19598, PRO1083, hu TRPM2 or PRO1801 DNA using ligation methods such as described in Sambrook et al., supra. The resulting vector is called pRK5-PRO224, pRK5-PRO9783, pRK5-PRO1108, pRK5-PRO34000, pRK5-PRO240, pRK5-PRO943, pRK5-hu A33, pRK5-PRO230, pRK5-PRO178, pRK5-PRO199, pRK5-PRO4333, pRK5-PRO1336, pRK5-PRO19598, pRK5-PRO1083, pRK5-hu TRPM2 or pRK5-PRO1801.

In one embodiment, the selected host cells may be 293 cells. Human 293 cells (ATCC CCL 1573) are grown to confluence in tissue culture plates in medium such as DMEM supplemented with fetal calf serum and optionally, nutrient components and/or antibiotics. About 10 µg pRK5-PRO224, pRK5-PRO9783, pRK5-PRO1108, pRK5-PRO34000, pRK5-PRO240, pRK5-PRO943, pRK5-hu A33, pRK5-PRO230, pRK5-PRO178, pRK5-PRO199, pRK5-PRO4333, pRK5-PRO1336, pRK5-PRO19598, pRK5-PRO1083, pRK5-hu TRPM2 or pRK5-PRO1801 DNA is mixed with about 1 µg DNA encoding the VA RNA gene [Thimmappaya et al., Cell, 31:543 (1982)] and dissolved in 500 µl of 1 mM Tris-HCl, 0.1 mM EDTA, 0.227 M $CaCl_2$. To this mixture is added, dropwise, 500 µl of 50 mM HEPES (pH 7.35), 280 mM NaCl, 1.5 mM $NaPO_4$, and a precipitate is allowed to form for 10 minutes at 25° C. The precipitate is suspended and added to the 293 cells and allowed to settle for about four hours at 37° C. The culture medium is aspirated off and 2 ml of 20% glycerol in PBS is added for 30 seconds. The 293 cells are then washed with serum free medium, fresh medium is added and the cells are incubated for about 5 days.

Approximately 24 hours after the transfections, the culture medium is removed and replaced with culture medium (alone) or culture medium containing 200 µCi/ml $^{35}$S-cysteine and 200 µCi/ml $^{35}$S-methionine. After a 12 hour incubation, the conditioned medium is collected, concentrated on a spin filter, and loaded onto a 15% SDS gel. The processed gel may be dried and exposed to film for a selected period of time to reveal the presence of PRO224, PRO9783, PRO1108, PRO34000, PRO240, PRO943, hu A33, PRO230, PRO178, PRO199, PRO4333, PRO1336, PRO19598, PRO1083, hu TRPM2 or PRO1801 polypeptides. The cultures containing transfected cells may undergo further incubation (in serum free medium) and the medium is tested in selected bioassays.

In an alternative technique, PRO224, PRO9783, PRO1108, PRO34000, PRO240, PRO943, hu A33, PRO230, PRO178, PRO199, PRO4333, PRO1336, PRO19598, PRO1083, hu TRPM2 or PRO1801 may be introduced into 293 cells transiently using the dextran sulfate method described by Somparyrac et al., Proc. Natl. Acad. Sci., 12:7575 (1981). 293 cells are grown to maximal density in a spinner flask and 700 µg pRK5-PRO224, pRK5-PRO9783, pRK5-PRO1108, pRK5-PRO34000, pRK5-PRO240, pRK5-PRO943, pRK5-hu A33, pRK5-PRO230, pRK5-PRO178, pRK5-PRO199, pRK5-PRO4333, pRK5-PRO1336, pRK5-PRO19598, pRK5-PRO1083, pRK5-hu TRPM2 or pRK5-PRO1801 DNA is added. The cells are first concentrated from the spinner flask by centrifugation and washed with PBS. The DNA-dextran precipitate is incubated on the cell pellet for four hours. The cells are treated with 20% glycerol for 90 seconds, washed with tissue culture medium, and re-introduced into the spinner flask containing tissue culture medium, 5 µg/ml bovine insulin and 0.1 µg/ml bovine transferrin. After about four days, the conditioned media is centrifuged and filtered to remove cells and debris. The sample containing expressed PRO224, PRO9783, PRO1108, PRO34000, PRO240, PRO943, hu A33, PRO230, PRO178, PRO199, PRO4333, PRO1336, PRO19598, PRO1083, hu TRPM2 or PRO1801 can then be concentrated and purified by any selected method, such as dialysis and/or column chromatography.

In another embodiment, PRO224, PRO9783, PRO1108, PRO34000, PRO240, PRO943, hu A33, PRO230, PRO178, PRO199, PRO4333, PRO1336, PRO19598, PRO1083, hu TRPM2 or PRO1801 can be expressed in CHO cells. The pRK5-PRO224, pRK5-PRO9783, pRK5-PRO1108, pRK5-

PRO34000, pRK5-PRO240, pRK5-PRO943, pRK5-hu A33, pRK5-PRO230, pRK5-PRO178, pRK5-PRO1199, pRK5-PRO4333, pRK5-PRO1336, pRK5-PRO19598, pRK5-PRO1083, pRK5-hu TRPM2 or pRK5-PRO1801 can be transfected into CHO cells using known reagents such as $CaPO_4$ or DEAE-dextran. As described above, the cell cultures can be incubated, and the medium replaced with culture medium (alone) or medium containing a radiolabel such as $^{35}S$-methionine. After determining the presence of PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide, the culture medium may be replaced with serum free medium. Preferably, the cultures are incubated for about 6 days, and then the conditioned medium is harvested. The medium containing the expressed PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 can then be concentrated and purified by any selected method.

Epitope-tagged PRO224, PRO9783, PRO1108, PRO34000, PRO240, PRO943, hu A33, PRO230, PRO178, PRO199, PRO4333, PRO1336, PRO19598, PRO1083, hu TRPM2 or PRO1801 may also be expressed in host CHO cells. The PRO224, PRO9783, PRO1108, PRO34000, PRO240, PRO943, hu A33, PRO230, PRO178, PRO199, PRO4333, PRO1336, PRO19598, PRO1083, hu TRPM2 or PRO1801 may be subcloned out of the pRK5 vector. The subclone insert can undergo PCR to fuse in frame with a selected epitope tag such as a poly-his tag into a Baculovirus expression vector. The poly-his tagged PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 insert can then be subcloned into a SV40 driven vector containing a selection marker such as DHFR for selection of stable clones. Finally, the CHO cells can be transfected (as described above) with the SV40 driven vector. Labeling may be performed, as described above, to verify expression. The culture medium containing the expressed poly-His tagged PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 can then be concentrated and purified by any selected method, such as by $Ni^{2+}$-chelate affinity chromatography.

PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 may also be expressed in CHO and/or COS cells by a transient expression procedure or in CHO cells by another stable expression procedure.

Stable expression in CHO cells is performed using the following procedure. The proteins are expressed as an IgG construct (immunoadhesin), in which the coding sequences for the soluble forms (e.g. extracellular domains) of the respective proteins are fused to an IgG1 constant region sequence containing the hinge, CH2 and CH2 domains and/or is a poly-His tagged form.

Following PCR amplification, the respective DNAs are subcloned in a CHO expression vector using standard techniques as described in Ausubel et al., *Current Protocols of Molecular Biology*, Unit 3.16, John Wiley and Sons (1997). CHO expression vectors are constructed to have compatible restriction sites 5' and 3'of the' DNA of interest to allow the convenient shuttling of cDNA's. The vector used expression in CHO cells is as described in Lucas et al., *Nucl. Acids Res.* 24:9 (1774-1779 (1996), and uses the SV40 early promoter/enhancer to drive expression of the cDNA of interest and dihydrofolate reductase (DHFR). DHFR expression permits selection for stable maintenance of the plasmid following transfection.

Twelve micrograms of the desired plasmid DNA is introduced into approximately 10 million CHO cells using commercially available transfection reagents Superfect® (Qiagen), Dosper® or Fugene® (Boehringer Mannheim). The cells are grown as described in Lucas et al., supra. Approximately $3 \times 10^7$ cells are frozen in an ampule for further growth and production as described below.

The ampules containing the plasmid DNA are thawed by placement into water bath and mixed by vortexing. The contents are pipetted into a centrifuge tube containing 10 mLs of media and centrifuged at 1000 rpm for 5 minutes. The supernatant is aspirated and the cells are resuspended in 10 mL of selective media (0.2 µm filtered PS20 with 5% 0.2 µm diafiltered fetal bovine serum). The cells are then aliquoted into a 100 mL spinner containing 90 mL of selective media. After 1-2 days, the cells are transferred into a 250 mL spinner filled with 150 mL selective growth medium and incubated at 37° C. After another 2-3 days, 250 mL, 500 mL and 2000 mL spinners are seeded with $3 \times 10^5$ cells/mL. The cell media is exchanged with fresh media by centrifugation and resuspension in production medium. Although any suitable CHO media may be employed, a production medium described in U.S. Pat. No. 5,122,469, issued Jun. 16, 1992 may actually be used. A 3 L production spinner is seeded at $1.2 \times 10^6$ cells/mL. On day 0, the cell number pH ie determined. On day 1, the spinner is sampled and sparging with filtered air is commenced. On day 2, the spinner is sampled, the temperature shifted to 33° C., and 30 mL of 500 g/L glucose and 0.6 mL of 10% antifoam (e.g., 35% polydimethylsiloxane emulsion, Dow Corning 365 Medical Grade Emulsion) taken. Throughout the production, the pH is adjusted as necessary to keep it at around 7.2. After 10 days, or until the viability dropped below 70%, the cell culture is harvested by centrifugation and filtering through a 0.22 µm filter. The filtrate was either stored at 4° C. or immediately loaded onto columns for purification.

For the poly-His tagged constructs, the proteins are purified using a Ni-NTA column (Qiagen). Before purification, imidazole is added to the conditioned media to a concentration of 5 mM. The conditioned media is pumped onto a 6 ml Ni-NTA column equilibrated in 20 mM Hepes, pH 7.4, buffer containing 0.3 M NaCl and 5 mM imidazole at a flow rate of 4-5 ml/min. at 4° C. After loading, the column is washed with additional equilibration buffer and the protein eluted with equilibration buffer containing 0.25 M imidazole. The highly purified protein is subsequently desalted into a storage buffer containing 10 mM Hepes, 0.14 M NaCl and 4% mannitol, pH 6.8, with a 25 ml G25 Superfine (Pharmacia) column and stored at −80° C.

Immunoadhesin (Fc-containing) constructs are purified from the conditioned media as follows. The conditioned medium is pumped onto a 5 ml Protein A column (Pharmacia) which had been equilibrated in 20 mM Na phosphate buffer, pH 6.8. After loading, the column is washed extensively with equilibration buffer before elution with 100 mM citric acid, pH 3.5. The eluted protein is immediately neutralized by collecting 1 ml fractions into tubes containing 275 µL of 1 M Tris buffer, pH 9. The highly purified protein is subsequently desalted into storage buffer as described above for the poly-His tagged proteins. The homogeneity is assessed by SDS polyacrylamide gels and by N-terminal amino acid sequencing by Edman degradation.

Example 22

Expression of PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 in Yeast

The following method describes recombinant expression of PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 in yeast.

First, yeast expression vectors are constructed for intracellular production or secretion of PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 from the ADH2/GAPDH promoter. DNA encoding PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 and the promoter is inserted into suitable restriction enzyme sites in the selected plasmid to direct intracellular expression of PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801. For secretion, DNA encoding PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 can be cloned into the selected plasmid, together with DNA encoding the ADH2/GAPDH promoter, a native PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 signal peptide or other mammalian signal peptide, or, for example, a yeast alpha-factor or invertase secretory signal/leader sequence, and linker sequences (if needed) for expression of PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801.

Yeast cells, such as yeast strain AB110, can then be transformed with the expression plasmids described above and cultured in selected fermentation media. The transformed yeast supernatants can be analyzed by precipitation with 10% trichloroacetic acid and separation by SDS-PAGE, followed by staining of the gels with Coomassie Blue stain.

Recombinant PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 can subsequently be isolated and purified by removing the yeast cells from the fermentation medium by centrifugation and then concentrating the medium using selected cartridge filters. The concentrate containing PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 may further be purified using selected column chromatography resins.

Example 23

Expression of PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 in Baculovirus-Infected Insect Cells

The following method describes recombinant expression of PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 in Baculovirus-infected insect cells.

The sequence coding for PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 is fused upstream of an epitope tag contained within a baculovirus expression vector. Such epitope tags include poly-his tags and immunoglobulin tags (like Fc regions of IgG). A variety of plasmids may be employed, including plasmids derived from commercially available plasmids such as pVL1393 (Novagen). Briefly, the sequence encoding PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 or the desired portion of the coding sequence of PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 such as the sequence encoding the extracellular domain of a transmembrane protein or the sequence encoding the mature protein if the protein is extracellular is amplified by PCR with primers complementary to the 5' and 3' regions. The 5' primer may incorporate flanking (selected) restriction enzyme sites. The product is then digested with those selected restriction enzymes and subcloned into the expression vector.

Recombinant baculovirus is generated by co-transfecting the above plasmid and BaculoGold™ virus DNA (Pharmingen) into *Spodoptera frugiperda* ("Sf9") cells (ATCC CRL 1711) using lipofectin (commercially available from GIBCO-BRL). After 4-5 days of incubation at 28° C., the released viruses are harvested and used for further amplifications. Viral infection and protein expression are performed as described by O'Reilley et al., *Baculovirus expression vectors: A Laboratory Manual*, Oxford: Oxford University Press (1994).

Expressed poly-his tagged PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 can then be purified, for example, by $Ni^{2+}$-chelate affinity chromatography as follows. Extracts are prepared from recombinant virus-infected Sf9 cells as described by Rupert et al., *Nature*, 362:175-179 (1993). Briefly, Sf9 cells are washed, resuspended in sonication buffer (25 mL Hepes, pH 7.9; 12.5 mM $MgCl_2$; 0.1 mM EDTA; 10% glycerol; 0.1% NP-40; 0.4 M KCl), and sonicated twice for 20 seconds on ice. The sonicates are cleared by centrifugation, and the supernatant is diluted 50-fold in loading buffer (50 mM phosphate, 300 mM NaCl, 10% glycerol, pH 7.8) and filtered through a 0.45 µm filter. A $Ni^{2+}$-NTA agarose column (commercially available from Qiagen) is prepared with a bed volume of 5 mL, washed with 25 mL of water and equilibrated with 25 mL of loading buffer. The filtered cell extract is loaded onto the column at 0.5 mL per minute. The column is washed to baseline $A_{280}$ with loading buffer, at which point fraction collection is started. Next, the column is washed with a secondary wash buffer (50 mM phosphate; 300 mM NaCl, 10% glycerol, pH 6.0), which elutes nonspecifically bound protein. After reaching $A_{280}$ baseline again, the column is developed with a 0 to 500 mM Imidazole gradient in the secondary wash buffer. One mL fractions are collected and analyzed by SDS-PAGE and silver staining or Western blot with $Ni^{2+}$-NTA-conjugated to alkaline phosphatase (Qiagen). Fractions containing the eluted $His_{10}$-tagged PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 are pooled and dialyzed against loading buffer.

Alternatively, purification of the IgG tagged (or Fc tagged) PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 can be performed using known chromatography techniques, including for instance, Protein A or protein G column chromatography.

Example 24

Preparation of Antibodies that Bind PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801Polypeptides This example illustrates preparation of monoclonal antibodies which can specifically bind PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptides.

Techniques for producing the monoclonal antibodies are known in the art and are described, for instance, in Goding, supra. Immunogens that may be employed include purified PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptides, fusion proteins containing PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptides, and cells expressing recombinant PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptides on the cell surface. Selection of the immunogen can be made by the skilled artisan without undue experimentation.

Mice, such as Balb/c, are immunized with the PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 immunogen emulsified in complete Freund's adjuvant and injected subcutaneously or intraperitoneally in an amount from 1-100 micrograms. Alternatively, the immunogen is emulsified in MPL-TDM adjuvant (Ribi Immunochemical Research, Hamilton, Mont.) and injected into the animal's hind foot pads. The immunized mice are then boosted 10 to 12 days later with additional immunogen emulsified in the selected adjuvant. Thereafter, for several weeks, the mice may also be boosted with additional immunization injections. Serum samples may be periodically obtained from the mice by retro-orbital bleeding for testing in ELISA assays to detect anti-PRO224, anti-PRO9783, anti-PRO1108, anti-PRO34000, anti-PRO240, anti-PRO943, anti-hu A33, anti-PRO230, anti-PRO178, anti-PRO1199, anti-PRO4333, anti-PRO1336, anti-PRO19598, anti-PRO1083, anti-hu TRPM2 or anti-PRO1801 antibodies.

After a suitable antibody titer has been detected, the animals "positive" for antibodies can be injected with a final intravenous injection of PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801. Three to four days later, the mice are sacrificed and the spleen cells are harvested. The spleen cells are then fused (using 35% polyethylene glycol) to a selected murine myeloma cell line such as P3X63AgU. 1, available from ATCC, No. CRL 1597. The fusions generate hybridoma cells which can then be plated in 96 well tissue culture plates containing HAT (hypoxanthine, aminopterin, and thymidine) medium to inhibit proliferation of non-fused cells, myeloma hybrids, and spleen cell hybrids.

The hybridoma cells will be screened in an ELISA for reactivity against PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801. Determination of "positive" hybridoma cells secreting the desired monoclonal antibodies against PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 is within the skill in the art.

The positive hybridoma cells can be injected intraperitoneally into syngeneic Balb/c mice to produce ascites containing the anti-PRO224, anti-PRO9783, anti-PRO1108, anti-PRO34000, anti-PRO240, anti-PRO943, anti-hu A33, anti-PRO230, anti-PRO178, anti-PRO1199, anti-PRO4333, anti-PRO1336, anti-PRO19598, anti-PRO1083, anti-hu TRPM2 or anti-PRO1801 monoclonal antibodies. Alternatively, the hybridoma cells can be grown in tissue culture flasks or roller bottles. Purification of the monoclonal antibodies produced in the ascites can be accomplished using ammonium sulfate precipitation, followed by gel exclusion chromatography. Alternatively, affinity chromatography based upon binding of antibody to protein A or protein G can be employed.

Example 25

Purification of PRO224, PRO9783, PRO1108, PRO34000, PRO240, PRO943, hu A33, PRO230, PRO178, PRO199, PRO4333, PRO1336, PRO19598, PRO1083, hu TRPM2 or PRO1801 Polypeptides Using Specific Antibodies Native or recombinant PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptides may be purified by a variety of standard techniques in the art of protein purification. For example, pro-PRO224, pro-PRO9783, pro-PRO1108, pro-PRO34000, pro-PRO240, pro-PRO943, pro-hu A33, pro-PRO230, pro-PRO178, pro-PRO1199, pro-PRO4333, pro-PRO1336, pro-PRO19598, pro-PRO1083, pro-hu TRPM2 or pro-PRO1801 polypeptide, mature PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide, or pre-PRO224, pre-PRO9783, pre-PRO1108, pre-PRO34000, pre-PRO240, pre-PRO943, pre-hu A33, pre-PRO230, pre-PRO178, pre-PRO1199, pre-PRO4333, pre-PRO1336, pre-PRO19598, pre-PRO1083, pre-hu TRPM2 or pre-PRO1801 polypeptide is purified by immunoaffinity chromatography using antibodies specific for the PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide of interest. In general, an immunoaffinity column is constructed by covalently coupling the anti-PRO224, anti-PRO9783, anti-PRO1108, anti-PRO34000, anti-PRO240, anti-PRO943, anti-hu A33, anti-PRO230, anti-PRO178, anti-PRO1199, anti-PRO4333, anti-PRO1336, anti-PRO19598, anti-PRO1083, anti-hu TRPM2 or anti-PRO1801 polypeptide antibody to an activated chromatographic resin.

Polyclonal immunoglobulins are prepared from immune sera either by precipitation with ammonium sulfate or by purification on immobilized Protein A (Pharmacia LKB Biotechnology, Piscataway, N.J.). Likewise, monoclonal antibodies are prepared from mouse ascites fluid by ammonium sulfate precipitation or chromatography on immobilized Protein A. Partially purified immunoglobulin is covalently attached to a chromatographic resin such as CnBr-activated SEPHAROSE™ (Pharmacia LKB Biotechnology). The antibody is coupled to the resin, the resin is blocked, and the derivative resin is washed according to the manufacturer's instructions.

Such an immunoaffinity column is utilized in the purification of PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide by preparing a fraction from cells containing PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide in a soluble form. This preparation is derived by solubilization of the whole cell or of a subcellular fraction obtained via differential centrifugation by the addition of detergent or by other methods well known in the art. Alternatively, soluble PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide containing a signal sequence may be secreted in useful quantity into the medium in which the cells are grown.

A soluble PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide-containing preparation is passed over the immunoaffinity column, and the column is washed under conditions that allow the preferential absorbance of PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide (e.g., high ionic strength buffers in the presence of detergent). Then, the column is eluted under conditions that disrupt antibody/PRO224, antibody/PRO9783, antibody/PRO1108, antibody/PRO34000, antibody/PRO240, antibody/PRO943, antibody/hu A33, antibody/PRO230, antibody/PRO178, antibody/PRO1199, antibody/PRO4333, antibody/PRO1336, antibody/PRO19598, antibody/PRO1083, antibody/hu TRPM2 or antibody/PRO1801 polypeptide binding (e.g., a low pH buffer such as approximately pH 2-3, or a high concentration of a chaotrope such as urea or thiocyanate ion), and PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide is collected.

Example 26

Drug Screening

This invention is particularly useful for screening compounds by using PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptides or binding fragment thereof in any of a variety of drug screening techniques. The PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide or fragment employed in such a test may either be free in solution, affixed to a solid support, borne on a cell surface, or located intracellularly. One method of drug screening utilizes eukaryotic or prokaryotic host cells which are stably transformed with recombinant nucleic acids expressing the PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide or fragment. Drugs are screened against such transformed cells in competitive binding assays. Such cells, either in viable or fixed form, can be used for standard binding assays. One may measure, for example, the formation of complexes between PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide or a fragment and the agent being tested. Alternatively, one can examine the diminution in complex formation between the PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide and its target cell or target receptors caused by the agent being tested.

Thus, the present invention provides methods of screening for drugs or any other agents which can affect a PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide-associated disease or disorder. These methods comprise contacting such an agent with an PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide or fragment thereof and assaying (i) for the presence of a complex between the agent and the PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide or fragment, or (ii) for the presence of a complex between the PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide or fragment and the cell, by methods well known in the art. In such competitive binding assays, the PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide or fragment is typically labeled. After suitable incubation, free PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide or fragment is separated from that present in bound form, and the amount of free or uncomplexed label is a measure of the ability of the particular agent to bind to PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide or to interfere with the PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide/cell complex.

Another technique for drug screening provides high throughput screening for compounds having suitable binding affinity to a polypeptide and is described in detail in WO 84/03564, published on Sep. 13, 1984. Briefly stated, large numbers of different small peptide test compounds are synthesized on a solid substrate, such as plastic pins or some other surface. As applied to a PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide, the peptide test compounds are reacted with PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide and washed. Bound PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide is detected by methods well known in the art. Purified PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide can also be coated directly onto plates for use in the aforementioned drug screening techniques. In addition, non-neutralizing antibodies can be used to capture the peptide and immobilize it on the solid support.

This invention also contemplates the use of competitive drug screening assays in which neutralizing antibodies capable of binding PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide specifically compete with a test compound for binding to PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide or fragments thereof. In this manner, the antibodies can be used to detect the presence of any peptide which shares one or more antigenic determinants with PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide.

Example 27

Rational Drug Design

The goal of rational drug design is to produce structural analogs of biologically active polypeptide of interest (i.e., a PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide) or of small molecules with which they interact, e.g., agonists, antagonists, or inhibitors. Any of these examples can be used to fashion drugs which are more active or stable forms of the PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide or which enhance or interfere with the function of the PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide in vivo (cf., Hodgson, Bio/Technology, 9: 19-21 (1991)).

In one approach, the three-dimensional structure of the PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide, or of a PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide-inhibitor complex, is determined by x-ray crystallography, by computer modeling or, most typically, by a combination of the two approaches. Both the shape and charges of the PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide must be ascertained to elucidate the structure and to determine active site(s) of the molecule. Less often, useful information regarding the structure of the PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide may be gained by modeling based on the structure of homologous proteins. In both cases, relevant structural information is used to design analogous PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide-like molecules or to identify efficient inhibitors. Useful examples of rational drug design may include molecules which have improved activity or stability as shown by Braxton and Wells, Biochemistry, 31:7796-7801 (1992) or which act as inhibitors, agonists, or antagonists of native peptides as shown by Athauda et al., J. Biochem., 113:742-746 (1993).

It is also possible to isolate a target-specific antibody, selected by functional assay, as described above, and then to solve its crystal structure. This approach, in principle, yields a pharmacore upon which subsequent drug design can be based. It is possible to bypass protein crystallography altogether by generating anti-idiotypic antibodies (anti-ids) to a functional, pharmacologically active antibody. As a mirror image of a mirror image, the binding site of the anti-ids would be expected to be an analog of the original receptor. The anti-id could then be used to identify and isolate peptides from banks of chemically or biologically produced peptides. The isolated peptides would then act as the pharmacore.

By virtue of the present invention, sufficient amounts of the PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide may be made available to perform such analytical studies as X-ray crystallography. In addition, knowledge of the PRO224, PRO9783, PRO1108, PRO34000, PRO240, PRO943, hu A33, PRO230, PRO178, PRO1199, PRO4333, PRO1336, PRO19598, PRO1083, hu TRPM2 or PRO1801 polypeptide amino acid sequence provided herein will provide guidance to those employing computer modeling techniques in place of or in addition to x-ray crystallography.

What is claimed is:

1. A method of identifying an agent that modulates a retinal abnormality, the method comprising: (a) providing a transgenic mouse whose genome comprises a knockout of the gene which encodes for the native sequence PRO224 polypeptide, said mouse comprising a retinal abnormality resulting from said PRO224 gene knockout; (b) measuring a physiological characteristic of a retina of the transgenic mouse of (a); (c) comparing the measured physiological characteristic of (b) with that of a gender matched wild-type mouse, wherein the physiological characteristic of a retina of the transgenic mouse that differs from the physiological characteristic of a retina of the wild-type mouse is identified as a retinal abnormality resulting from the PRO224 gene knockout in the transgenic mouse; (d) administering a test agent to the transgenic mouse of (a); and (e) determining whether the test agent modulates said retinal abnormality, whereby an agent which is determined to modulate a retinal abnormality is identified.

2. The method of claim 1, wherein the retinal abnormality comprises a retinal artery obstruction or occlusion.

3. The method of claim 1, wherein the retinal abnormality is a vascular retinal abnormality.

4. The method of claim 1, wherein the retinal abnormality causes vision problems or blindness.

5. The method of claim 1, wherein the retinal abnormality is retinitis pigmentosa.

6. The method of claim 1, wherein the retinal abnormality is characterized by retinal degeneration or retinal dysplasia.

7. The method of claim 1, wherein the retinal abnormality is selected from the group consisting of retinal dysplasia, a retinopathy, retinopathy of prematurity, retrolental fibroplasia, neovascular glaucoma, age-related macular degeneration, diabetic macular edema, retinal/choroidal neovascularization, neovascularization of the angle (rubeosis), ocular neovascular disease, vascular restenosis, arteriovenous malformations (AVM), meningioma, hemangioma, angiofibroma, thyroid hyperplasia, Grave's disease, retinal artery obstruction or occlusion, retinal degeneration causing secondary atrophy of the retinal vasculature, retinitis pigmentosa, macular dystrophies, Stargardt's disease, congenital stationary night blindness, choroideremia, gyrate atrophy, Leber's congenital amaurosis, retinoschisis disorders, Wagner's syndrome, Usher syndrome, Zellweger syndrome, Saldino-Mainzer syndrome, Senior-Loken syndrome, Bardet-Biedl syndrome, Alport's syndrome, Alstrom's syndrome, Cockayne's syndrome, dysplasia spondyloepiphysaria congentia, Flynn-Aird syndrome, Marshall syndrome, Albers-Schnoberg disease, Refsum's disease, Keams-Sayre syndrome, Stickler syndrome, Wolfram syndrome, Bassen-Kornzweig syndrome, abetalipoproteinemia, incontinentia pigmenti, Batten's disease, mucopolysaccharidoses, homocystinuria, and mannosidosis.

8. The method of claim 1, wherein the transgenic mouse exhibits an increased mean artery-to-vein ratio associated with retinal degeneration, as compared with gender-matched wild-type littermates.

* * * * *

UNITED STATES PATENT AND TRADEMARK OFFICE
CERTIFICATE OF CORRECTION

PATENT NO.        : 8,067,664 B2                                    Page 1 of 18
APPLICATION NO.   : 10/583466
DATED             : November 29, 2011
INVENTOR(S)       : Wenhu Huang It is certified that error appears in the above-identified patent and that said Letters Patent is hereby corrected as shown below:

Col. 9, line 51 should read, --(c) comparing the measured physiological characteristic--

Col. 13, line 9 should read, --(c) comparing the measured physiological characteristic--

Col. 16, line 33 should read, --(c) comparing the measured physiological characteristic--

Col. 17, line 55 should read, --(c) comparing the observed behavior of (b) with that of a--

Col. 19, line 9 should read, --(c) determining whether the test agent ameliorates or--

Col. 23, line 6 should read, --(c) comparing the measured physiological characteristic--

Col. 26, line 35 should read, --(c) determining whether the test agent ameliorates or--

Col. 82, line 15 should read, --the DNA sequences disclosed herein and /or; (c) and DNA--

Signed and Sealed this
Nineteenth Day of June, 2012

David J. Kappos
*Director of the United States Patent and Trademark Office*

CERTIFICATE OF CORRECTION (continued)
U.S. Pat. No. 8,067,664 B2

On Column 84 after Line 31 please insert Table 1:

Table 1

```
/*
 *
 * C-C increased from 12 to 15
 * Z is average of EQ
 * B is average of ND
 * match with stop is _M; stop-stop = 0; J (joker) match = 0
 */
define  _M      -8         /* value of a match with a stop */ int      _day[26][26] = {
/*       A B C D E F G H I J K L M N O P Q R S T U V W X Y Z*/
/* A */  { 2, 0,-2, 0, 0,-4, 1,-1,-1, 0,-1,-2,-1, 0,_M, 1, 0,-2, 1, 1, 0, 0,-6, 0,-3, 0},
/* B */  { 0, 3,-4, 3, 2,-5, 0, 1,-2, 0, 0,-3,-2, 2,_M,-1, 1, 0, 0, 0, 0,-2,-5, 0,-3, 1},
/* C */  {-2,-4,15,-5,-5,-4,-3,-3,-2, 0,-5,-6,-5,-4,_M,-3,-5,-4, 0,-2, 0,-2,-8, 0, 0,-5},
/* D */  { 0, 3,-5, 4, 3,-6, 1, 1,-2, 0, 0,-4,-3, 2,_M,-1, 2,-1, 0, 0, 0,-2,-7, 0,-4, 2},
/* E */  { 0, 2,-5, 3, 4,-5, 0, 1,-2, 0, 0,-3,-2, 1,_M,-1, 2,-1, 0, 0, 0,-2,-7, 0,-4, 3},
/* F */  {-4,-5,-4,-6,-5, 9,-5,-2, 1, 0,-5, 2, 0,-4,_M,-5,-5,-4,-3,-3, 0,-1, 0, 0, 7,-5},
/* G */  { 1, 0,-3, 1, 0,-5, 5,-2,-3, 0,-2,-4,-3, 0,_M,-1,-1,-3, 1, 0, 0,-1,-7, 0,-5, 0},
/* H */  {-1, 1,-3, 1, 1,-2,-2, 6,-2, 0, 0,-2,-2, 2,_M, 0, 3, 2,-1,-1, 0,-2,-3, 0, 0, 2},
/* I */  {-1,-2,-2,-2,-2, 1,-3,-2, 5, 0,-2, 2, 2,-2,_M,-2,-2,-2,-1, 0, 0, 4,-5, 0,-1,-2},
/* J */  { 0, 0, 0, 0, 0, 0, 0, 0, 0, 0, 0, 0, 0, 0,_M, 0, 0, 0, 0, 0, 0, 0, 0, 0, 0, 0},
/* K */  {-1, 0,-5, 0, 0,-5,-2, 0,-2, 0, 5,-3, 0, 1,_M,-1, 1, 3, 0, 0, 0,-2,-3, 0,-4, 0},
/* L */  {-2,-3,-6,-4,-3, 2,-4,-2, 2, 0,-3, 6, 4,-3,_M,-3,-2,-3,-3,-1, 0, 2,-2, 0,-1,-2},
/* M */  {-1,-2,-5,-3,-2, 0,-3,-2, 2, 0, 0, 4, 6,-2,_M,-2,-1, 0,-2,-1, 0, 2,-4, 0,-2,-1},
/* N */  { 0, 2,-4, 2, 1,-4, 0, 2,-2, 0, 1,-3,-2, 2,_M,-1, 1, 0, 1, 0, 0,-2,-4, 0,-2, 1},
/* O */  {_M,_M,_M,_M,_M,_M,_M,_M,_M,_M,_M,_M,_M,_M, 0,_M,_M,_M,_M,_M,_M,_M,_M,_M,_M,_M},
/* P */  { 1,-1,-3,-1,-1,-5,-1, 0,-2, 0,-1,-3,-2,-1,_M, 6, 0, 0, 1, 0, 0,-1,-6, 0,-5, 0},
/* Q */  { 0, 1,-5, 2, 2,-5,-1, 3,-2, 0, 1,-2,-1, 1,_M, 0, 4, 1,-1,-1, 0,-2,-5, 0,-4, 3},
/* R */  {-2, 0,-4,-1,-1,-4,-3, 2,-2, 0, 3,-3, 0, 0,_M, 0, 1, 6, 0,-1, 0,-2, 2, 0,-4, 0},
/* S */  { 1, 0, 0, 0, 0,-3, 1,-1,-1, 0, 0,-3,-2, 1,_M, 1,-1, 0, 2, 1, 0,-1,-2, 0,-3, 0},
/* T */  { 1, 0,-2, 0, 0,-3, 0,-1, 0, 0, 0,-1,-1, 0,_M, 0,-1,-1, 1, 3, 0, 0,-5, 0,-3, 0},
/* U */  { 0, 0, 0, 0, 0, 0, 0, 0, 0, 0, 0, 0, 0, 0,_M, 0, 0, 0, 0, 0, 0, 0, 0, 0, 0, 0},
/* V */  { 0,-2,-2,-2,-2,-1,-1,-2, 4, 0,-2, 2, 2,-2,_M,-1,-2,-2,-1, 0, 0, 4,-6, 0,-2,-2},
/* W */  {-6,-5,-8,-7,-7, 0,-7,-3,-5, 0,-3,-2,-4,-4,_M,-6,-5, 2,-2,-5, 0,-6,17, 0, 0,-6},
/* X */  { 0, 0, 0, 0, 0, 0, 0, 0, 0, 0, 0, 0, 0, 0,_M, 0, 0, 0, 0, 0, 0, 0, 0, 0, 0, 0},
/* Y */  {-3,-3, 0,-4,-4, 7,-5, 0,-1, 0,-4,-1,-2,-2,_M,-5,-4,-4,-3,-3, 0,-2, 0, 0,10,-4},
/* Z */  { 0, 1,-5, 2, 3,-5, 0, 2,-2, 0, 0,-2,-1, 1,_M, 0, 3, 0, 0, 0, 0,-2,-6, 0,-4, 4}
};
```

--

Table 1 (cont')

```
/*
*/
#include <stdio.h>
include <ctype.h> define  MAXJMP   16      /* max jumps in a diag */
define  MAXGAP   24      /* don't continue to penalize gaps larger than this */
#define  JMPS     1024    /* max jmps in an path */
define  MX       4       /* save if there's at least MX-1 bases since last jmp */ define  DMAT     3       /* value of matching bases */
define  DMIS     0       /* penalty for mismatched bases */
#define  DINS0    8       /* penalty for a gap */
#define  DINS1    1       /* penalty per base */
#define  PINS0    8       /* penalty for a gap */
define  PINS1    4       /* penalty per residue */ struct jmp {
        short           n[MAXJMP];      /* size of jmp (neg for dely) */
        unsigned short  x[MAXJMP];      /* base no. of jmp in seq x */
};                                      /* limits seq to 2^16 -1 */ struct diag {
        int         score;      /* score at last jmp */
        long        offset;     /* offset of prev block */
        short       ijmp;       /* current jmp index */
        struct jmp  jp;         /* list of jmps */
};

struct path {
        int    spc;             /* number of leading spaces */
        short  n[JMPS];/* size of jmp (gap) */
        int    x[JMPS];/* loc of jmp (last elem before gap) */
};

char            *ofile;         /* output file name */
char            *namex[2];      /* seq names: getseqs() */
char            *prog;          /* prog name for err msgs */
char            *seqx[2];       /* seqs: getseqs() */
int             dmax;           /* best diag: nw() */
int             dmax0;          /* final diag */
int             dna;            /* set if dna: main() */
int             endgaps;        /* set if penalizing end gaps */
int             gapx, gapy;     /* total gaps in seqs */
int             len0, len1;     /* seq lens */
int             ngapx, ngapy;   /* total size of gaps */
int             smax;           /* max score: nw() */
int             *xbm;           /* bitmap for matching */
long            offset;         /* current offset in jmp file */
struct diag     *dx;            /* holds diagonals */
struct path     pp[2];          /* holds path for seqs */ char            *calloc(), *malloc(), *index(), *strcpy();
char            *getseq(), *g_calloc();
```

Table 1 (cont')

```
/* Needleman-Wunsch alignment program
*
* usage: progs file1 file2
*   where file1 and file2 are two dna or two protein sequences.
*   The sequences can be in upper- or lower-case an may contain ambiguity
*   Any lines beginning with ';', '>' or '<' are ignored
*   Max file length is 65535 (limited by unsigned short x in the jmp struct)
*   A sequence with 1/3 or more of its elements ACGTU is assumed to be DNA
*   Output is in the file "align.out"
*
* The program may create a tmp file in /tmp to hold info about traceback.
* Original version developed under BSD 4.3 on a vax 8650
*/
include "nw.h"
#include "day.h"

static    _dbval[26] = {
          1,14,2,13,0,0,4,11,0,0,12,0,3,15,0,0,0,5,6,8,8,7,9,0,10,0
};

static    _pbval[26] = {
          1, 2|(1<<('D'-'A'))|(1<<('N'-'A')), 4, 8, 16, 32, 64,
          128, 256, 0xFFFFFFF, 1<<10, 1<<11, 1<<12, 1<<13, 1<<14,
          1<<15, 1<<16, 1<<17, 1<<18, 1<<19, 1<<20, 1<<21, 1<<22,
          1<<23, 1<<24, 1<<25|(1<<('E'-'A'))|(1<<('Q'-'A'))
};

main(ac, av)                                                                    main
          int       ac;
          char      *av[];
{
          prog = av[0];
          if (ac != 3) {
                    fprintf(stderr,"usage: %s file1 file2\n", prog);
                    fprintf(stderr,"where file1 and file2 are two dna or two protein sequences.\n");
                    fprintf(stderr,"The sequences can be in upper- or lower-case\n");
                    fprintf(stderr,"Any lines beginning with ';' or '<' are ignored\n");
                    fprintf(stderr,"Output is in the file \"align.out\"\n");
                    exit(1);
          }
          namex[0] = av[1];
          namex[1] = av[2];
          seqx[0] = getseq(namex[0], &len0);
          seqx[1] = getseq(namex[1], &len1);
          xbm = (dna)? _dbval : _pbval;

endgaps = 0;            /* 1 to penalize endgaps */
          ofile = "align.out";    /* output file */ nw();                   /* fill in the matrix, get the possible jmps */
          readjmps();             /* get the actual jmps */
          print();                /* print stats, alignment */ cleanup(0);             /* unlink any tmp files */}
```

Table 1 (cont')

```
/* do the alignment, return best score: main()
 * dna: values in Fitch and Smith, PNAS, 80, 1382-1386, 1983
 * pro: PAM 250 values
 * When scores are equal, we prefer mismatches to any gap, prefer
 * a new gap to extending an ongoing gap, and prefer a gap in seqx
 * to a gap in seq y.
 */
nw()                                                                            nw
{
        char            *px, *py;           /* seqs and ptrs */
        int             *ndely, *dely;      /* keep track of dely */
        int             ndelx, delx;        /* keep track of delx */
        int             *tmp;               /* for swapping row0, row1 */
        int             mis;                /* score for each type */
        int             ins0, ins1;         /* insertion penalties */
        register        id;                 /* diagonal index */
        register        ij;                 /* jmp index */
        register        *col0, *col1;       /* score for curr, last row */
        register        xx, yy;             /* index into seqs */ dx = (struct diag *)g_calloc("to get diags", len0+len1+1, sizeof(struct diag));
        ndely = (int *)g_calloc("to get ndely", len1+1, sizeof(int));
        dely = (int *)g_calloc("to get dely", len1+1, sizeof(int));
        col0 = (int *)g_calloc("to get col0", len1+1, sizeof(int));
        col1 = (int *)g_calloc("to get col1", len1+1, sizeof(int));
        ins0 = (dna)? DINS0 : PINS0;
        ins1 = (dna)? DINS1 : PINS1;
        smax = -10000;
        if (endgaps) {
                for (col0[0] = dely[0] = -ins0, yy = 1; yy <= len1; yy++) {
                        col0[yy] = dely[yy] = col0[yy-1] - ins1;
                        ndely[yy] = yy;
                }
                col0[0] = 0;    /* Waterman Bull Math Biol 84 */
        }
        else
                for (yy = 1; yy <= len1; yy++)
                        dely[yy] = -ins0;
        /* fill in match matrix
         */
        for (px = seqx[0], xx = 1; xx <= len0; px++, xx++) {
                /* initialize first entry in col
                 */
                if (endgaps) {
                        if (xx == 1)
                                col1[0] = delx = -(ins0+ins1);
                        else
                                col1[0] = delx = col0[0] - ins1;
                        ndelx = xx;
                }
                else {
                        col1[0] = 0;
                        delx = -ins0;
                        ndelx = 0;
                }
```

Table 1 (cont')

...nw

```
for (py = seqx[1], yy = 1; yy <= len1; py++, yy++) {
        mis = col0[yy-1];
        if (dna)
                mis += (xbm[*px-'A']&xbm[*py-'A'])? DMAT : DMIS;
        else
                mis += _day[*px-'A'][*py-'A'];

/* update penalty for del in x seq;
         * favor new del over ongong del
         * ignore MAXGAP if weighting endgaps
         */
        if (endgaps || ndely[yy] < MAXGAP) {
                if (col0[yy] - ins0 >= dely[yy]) {
                        dely[yy] = col0[yy] - (ins0+ins1);
                        ndely[yy] = 1;
                } else {
                        dely[yy] -= ins1;
                        ndely[yy]++;
                }
        } else {
                if (col0[yy] - (ins0+ins1) >= dely[yy]) {
                        dely[yy] = col0[yy] - (ins0+ins1);
                        ndely[yy] = 1;
                } else
                        ndely[yy]++;
        }

/* update penalty for del in y seq;
         * favor new del over ongong del
         */
        if (endgaps || ndelx < MAXGAP) {
                if (col1[yy-1] - ins0 >= delx) {
                        delx = col1[yy-1] - (ins0+ins1);
                        ndelx = 1;
                } else {
                        delx -= ins1;
                        ndelx++;
                }
        } else {
                if (col1[yy-1] - (ins0+ins1) >= delx) {
                        delx = col1[yy-1] - (ins0+ins1);
                        ndelx = 1;
                } else
                        ndelx++;
        }

/* pick the maximum score; we're favoring
         * mis over any del and delx over dely
         */
```

...nw

```
        id = xx - yy + len1 - 1;
        if (mis >= delx && mis >= dely[yy])
                col1[yy] = mis;
```

Table 1 (cont')

```
                else if (delx >= dely[yy]) {
                        col1[yy] = delx;
                        ij = dx[id].ijmp;
                        if (dx[id].jp.n[0] && (!dna || (ndelx >= MAXJMP
                                && xx > dx[id].jp.x[ij]+MX) || mis > dx[id].score+DINS0)) {
                                dx[id].ijmp++;
                                if (++ij >= MAXJMP) {
                                        writejmps(id);
                                        ij = dx[id].ijmp = 0;
                                        dx[id].offset = offset;
                                        offset += sizeof(struct jmp) + sizeof(offset);
                                }
                        }
                        dx[id].jp.n[ij] = ndelx;
                        dx[id].jp.x[ij] = xx;
                        dx[id].score = delx;
                }
                else {
                        col1[yy] = dely[yy];
                        ij = dx[id].ijmp;
        if (dx[id].jp.n[0] && (!dna || (ndely[yy] >= MAXJMP
                                && xx > dx[id].jp.x[ij]+MX) || mis > dx[id].score+DINS0)) {
                                dx[id].ijmp++;
                                if (++ij >= MAXJMP) {
                                        writejmps(id);
                                        ij = dx[id].ijmp = 0;
                                        dx[id].offset = offset;
                                        offset += sizeof(struct jmp) + sizeof(offset);
                                }
                        }
                        dx[id].jp.n[ij] = -ndely[yy];
                        dx[id].jp.x[ij] = xx;
                        dx[id].score = dely[yy];
                }
                if (xx == len0 && yy < len1) {
                        /* last col
                        */
                        if (endgaps)
                                col1[yy] -= ins0+ins1*(len1-yy);
                        if (col1[yy] > smax) {
                                smax = col1[yy];
                                dmax = id;
                        }
                }
        }
        if (endgaps && xx < len0)
                col1[yy-1] -= ins0+ins1*(len0-xx);
        if (col1[yy-1] > smax) {
                smax = col1[yy-1];
                dmax = id;
        }
        tmp = col0; col0 = col1; col1 = tmp;              }
(void) free((char *)ndely);
(void) free((char *)dely);
(void) free((char *)col0);
(void) free((char *)col1);                        }
```

Table 1 (cont')

```
/*
 *
 * print() -- only routine visible outside this module
 *
 * static:
 * getmat() -- trace back best path, count matches: print()
 * pr_align() -- print alignment of described in array p[]: print()
 * dumpblock() -- dump a block of lines with numbers, stars: pr_align()
 * nums() -- put out a number line: dumpblock()
 * putline() -- put out a line (name, [num], seq, [num]): dumpblock()
 * stars() - -put a line of stars: dumpblock()
 * stripname() -- strip any path and prefix from a seqname
 */ include "nw.h"

define SPC      3
#define P_LINE   256    /* maximum output line */
define P_SPC    3      /* space between name or num and seq */ extern   _day[26][26];
int      olen;              /* set output line length */
FILE     *fx;               /* output file */ print()
{
         int     lx, ly, firstgap, lastgap;      /* overlap */ if ((fx = fopen(ofile, "w")) == 0) {
                 fprintf(stderr,"%s: can't write %s\n", prog, ofile);
                 cleanup(1);
         }
         fprintf(fx, "<first sequence: %s (length = %d)\n", namex[0], len0);
         fprintf(fx, "<second sequence: %s (length = %d)\n", namex[1], len1);
         olen = 60;
         lx = len0;
         ly = len1;
         firstgap = lastgap = 0;
         if (dmax < len1 - 1) {          /* leading gap in x */
                 pp[0].spc = firstgap = len1 - dmax - 1;
                 ly -= pp[0].spc;
         }
         else if (dmax > len1 - 1) {     /* leading gap in y */
                 pp[1].spc = firstgap = dmax - (len1 - 1);
                 lx -= pp[1].spc;
         }
         if (dmax0 < len0 - 1) {         /* trailing gap in x */
                 lastgap = len0 - dmax0 -1;
                 lx -= lastgap;
         }
         else if (dmax0 > len0 - 1) {    /* trailing gap in y */
                 lastgap = dmax0 - (len0 - 1);
                 ly -= lastgap;
         }
         getmat(lx, ly, firstgap, lastgap);
         pr_align();          }
``` print

Table 1 (cont')

```
/*
 * trace back the best path, count matches
 */
static
getmat(lx, ly, firstgap, lastgap)
        int     lx, ly;                 /* "core" (minus endgaps) */
        int     firstgap, lastgap;      /* leading trailing overlap */
{
        int             nm, i0, i1, siz0, siz1;
        char            outx[32];
        double          pct;
        register        n0, n1;
        register char   *p0, *p1;
        /* get total matches, score
         */
        i0 = i1 = siz0 = siz1 = 0;
        p0 = seqx[0] + pp[1].spc;
        p1 = seqx[1] + pp[0].spc;
        n0 = pp[1].spc + 1;
        n1 = pp[0].spc + 1;
        nm = 0;
        while ( *p0 && *p1 ) {
                if (siz0) {
                        p1++;
                        n1++;
                        siz0--;
                }
                else if (siz1) {
                        p0++;
                        n0++;
                        siz1--;
                }
                else {
                        if (xbm[*p0-'A']&xbm[*p1-'A'])
                                nm++;
                        if (n0++ == pp[0].x[i0])
                                siz0 = pp[0].n[i0++];
                        if (n1++ == pp[1].x[i1])
                                siz1 = pp[1].n[i1++];
                        p0++;
                        p1++;
                }
        }

/* pct homology:
         * if penalizing endgaps, base is the shorter seq
         * else, knock off overhangs and take shorter core
         */
        if (endgaps)
                lx = (len0 < len1)? len0 : len1;
        else
                lx = (lx < ly)? lx : ly;
        pct = 100.*(double)nm/(double)lx;
        fprintf(fx, "\n");
        fprintf(fx, "<%d match%s in an overlap of %d: %.2f percent similarity\n",
                nm, (nm == 1)? "" : "es", lx, pct);
``` getmat

Table 1 (cont')

```
                fprintf(fx, "<gaps in first sequence: %d", gapx);                              ...getmat
                if (gapx) {
                        (void) sprintf(outx, " (%d %s%s)",
                                ngapx, (dna)? "base":"residue", (ngapx == 1)? "":"s");
                        fprintf(fx,"%s", outx);
                fprintf(fx, ", gaps in second sequence: %d", gapy);
                if (gapy) {
                        (void) sprintf(outx, " (%d %s%s)",
                                ngapy, (dna)? "base":"residue", (ngapy == 1)? "":"s");
                        fprintf(fx,"%s", outx);
                }
                if (dna)
                        fprintf(fx,
                        "\n<score: %d (match = %d, mismatch = %d, gap penalty = %d + %d per base)\n",
                        smax, DMAT, DMIS, DINS0, DINS1);
                else
                        fprintf(fx,
                        "\n<score: %d (Dayhoff PAM 250 matrix, gap penalty = %d + %d per residue)\n",
                        smax, PINS0, PINS1);
                if (endgaps)
                        fprintf(fx,
                        "<endgaps penalized. left endgap: %d %s%s, right endgap: %d %s%s\n",
                        firstgap, (dna)? "base" : "residue", (firstgap == 1)? "" : "s",
                        lastgap, (dna)? "base" : "residue", (lastgap == 1)? "" : "s");
                else
                        fprintf(fx, "<endgaps not penalized\n");
        }
        static          nm;             /* matches in core -- for checking */
        static          lmax;           /* lengths of stripped file names */
        static          ij[2];          /* jmp index for a path */
        static          nc[2];          /* number at start of current line */
        static          ni[2];          /* current elem number -- for gapping */
        static          siz[2];
        static char     *ps[2];         /* ptr to current element */
        static char     *po[2];         /* ptr to next output char slot */
        static char     out[2][P_LINE]; /* output line */
        static char     star[P_LINE];   /* set by stars() */
        /*
        * print alignment of described in struct path pp[]
        */
        static
        pr_align()                                                                             pr_align
        {
                int             nn;     /* char count */
                int             more;
                register        i;

for (i = 0, lmax = 0; i < 2; i++) {
                        nn = stripname(namex[i]);
                        if (nn > lmax)
                                lmax = nn;
                        nc[i] = 1;
                        ni[i] = 1;
                        siz[i] = ij[i] = 0;
                        ps[i] = seqx[i];
                        po[i] = out[i];                         }
```

Table 1 (cont')

```
         for (nn = nm = 0, more = 1; more; ) {                              ...pr_align
                 for (i = more = 0; i < 2; i++) {
                         /*
                          * do we have more of this sequence?
                          */
                         if (!*ps[i])
                                 continue;
                         more++;
                         if (pp[i].spc) {      /* leading space */
                                 *po[i]++ = ' ';
                                 pp[i].spc--;
                         }
                         else if (siz[i]) {     /* in a gap */
                                 *po[i]++ = '-';
                                 siz[i]--;
                         }
                         else {                 /* we're putting a seq element
                                                 */
                                 *po[i] = *ps[i];
                                 if (islower(*ps[i]))
                                         *ps[i] = toupper(*ps[i]);
                                 po[i]++;
                                 ps[i]++;
                                 /*
                                  * are we at next gap for this seq?
                                  */
                                 if (ni[i] == pp[i].x[ij[i]]) {
                                         /*
                                          * we need to merge all gaps
                                          * at this location
                                          */
                                         siz[i] = pp[i].n[ij[i]++];
                                         while (ni[i] == pp[i].x[ij[i]])
                                                 siz[i] += pp[i].n[ij[i]++];
                                 }
                                 ni[i]++;
                         }
                 }
                 if (++nn == olen || !more && nn) {
                         dumpblock();
                         for (i = 0; i < 2; i++)
                                 po[i] = out[i];
                         nn = 0;
                 }
         }
}
/*
 * dump a block of lines, including numbers, stars: pr_align()
 */
static
dumpblock()                                                                 dumpblock
{
        register i;
        for (i = 0; i < 2; i++)
                *po[i]-- = '\0';
```

Table 1 (cont')

...dumpblock

```
                (void) putc('\n', fx);
                for (i = 0; i < 2; i++) {
                        if (*out[i] && (*out[i] != ' ' || *(po[i]) != ' ')) {
                                if (i == 0)
                                        nums(i);
                                if (i == 0 && *out[1])
                                        stars();
                                putline(i);
                                if (i == 0 && *out[1])
                                        fprintf(fx, star);
                                if (i == 1)
                                        nums(i);
                        }
                }
}
/*
 * put out a number line: dumpblock()
 */
static
nums(ix)                                                                          nums
        int     ix;       /* index in out[] holding seq line */
{
        char            nline[P_LINE];
        register        i, j;
        register char   *pn, *px, *py;
        for (pn = nline, i = 0; i < lmax+P_SPC; i++, pn++)
                *pn = ' ';
        for (i = nc[ix], py = out[ix]; *py; py++, pn++) {
                if (*py == ' ' || *py == '-')
                        *pn = ' ';
                else {
                        if (i%10 == 0 || (i == 1 && nc[ix] != 1)) {
                                j = (i < 0)? -i : i;
                                for (px = pn; j; j /= 10, px--)
                                        *px = j%10 + '0';
                                if (i < 0)
                                        *px = '-';
                        }
                        else
                                *pn = ' ';
                        i++;
                }
        }
        *pn = '\0';
        nc[ix] = i;
        for (pn = nline; *pn; pn++)
                (void) putc(*pn, fx);
        (void) putc('\n', fx);
}
/*
 * put out a line (name, [num], seq, [num]): dumpblock()
 */
static
putline(ix)                                                                       putline
        int     ix;                     {
```

Table 1 (cont')

...putline

```
        int             i;
        register char   *px;

for (px = namex[ix], i = 0; *px && *px != ':'; px++, i++)
                (void) putc(*px, fx);
        for (; i < lmax+P_SPC; i++)
                (void) putc(' ', fx);

/* these count from 1:
         * ni[] is current element (from 1)
         * nc[] is number at start of current line
         */
        for (px = out[ix]; *px; px++)
                (void) putc(*px&0x7F, fx);
        (void) putc('\n', fx);
}

/*
 * put a line of stars (seqs always in out[0], out[1]): dumpblock()
 */
static
stars()
{
        int             i;
        register char   *p0, *p1, cx, *px;

if (!*out[0] || (*out[0] == ' ' && *(po[0]) == ' ') ||
            !*out[1] || (*out[1] == ' ' && *(po[1]) == ' '))
                return;
        px = star;
        for (i = lmax+P_SPC; i; i--)
                *px++ = ' ';

for (p0 = out[0], p1 = out[1]; *p0 && *p1; p0++, p1++) {
                if (isalpha(*p0) && isalpha(*p1)) {
                        if (xbm[*p0-'A']&xbm[*p1-'A']) {
                                cx = '*';
                                nm++;
                        }
                        else if (!dna && _day[*p0-'A'][*p1-'A'] > 0)
                                cx = '.';
                        else
                                cx = ' ';
                }
                else
                        cx = ' ';
                *px++ = cx;
        }
        *px++ = '\n';
        *px = '\0';
}
``` stars

Table 1 (cont')

```
/*
 * strip path or prefix from pn, return len: pr_align()
 */
static
stripname(pn)                                                              stripname
        char       *pn;     /* file name (may be path) */
{
        register char    *px, *py;

py = 0;
        for (px = pn; *px; px++)
                if (*px == '/')
                        py = px + 1;
        if (py)
                (void) strcpy(pn, py);
        return(strlen(pn));

}
```

Table 1 (cont')

```
/*
 * cleanup() -- cleanup any tmp file
 * getseq() -- read in seq, set dna, len, maxlen
 * g_calloc() -- calloc() with error checkin
 * readjmps() -- get the good jmps, from tmp file if necessary
 * writejmps() -- write a filled array of jmps to a tmp file: nw()
 */
include "nw.h"
include <sys/file.h> char      *jname = "/tmp/homgXXXXXX";          /* tmp file for jmps */
FILE      *fj;
int       cleanup();                            /* cleanup tmp file */
long      lseek();
/*
 * remove any tmp file if we blow
 */
cleanup(i)                                                                          cleanup
        int       i;
{
        if (fj)
                (void) unlink(jname);
        exit(i);
}
/*
 * read, return ptr to seq, set dna, len, maxlen
 * skip lines starting with ';', '<', or '>'
 * seq in upper or lower case
 */
char      *
getseq(file, len)                                                                   getseq
        char      *file;      /* file name */
        int       *len;       /* seq len */
{
        char      line[1024], *pseq;
        register char *px, *py;
        int       natgc, tlen;
        FILE      *fp;
        if ((fp = fopen(file,"r")) == 0) {
                fprintf(stderr,"%s: can't read %s\n", prog, file);
                exit(1);
        }
        tlen = natgc = 0;
        while (fgets(line, 1024, fp)) {
                if (*line == ';' || *line == '<' || *line == '>')
                        continue;
                for (px = line; *px != '\n'; px++)
                        if (isupper(*px) || islower(*px))
                                tlen++;
        }
        if ((pseq = malloc((unsigned)(tlen+6))) == 0) {
                fprintf(stderr,"%s: malloc() failed to get %d bytes for %s\n", prog, tlen+6, file);
                exit(1);
        }
        pseq[0] = pseq[1] = pseq[2] = pseq[3] = '\0';
```

Table 1 (cont')

...getseq

```
            py = pseq + 4;
        *len = tlen;
        rewind(fp);
        while (fgets(line, 1024, fp)) {
                    if (*line == ';' || *line == '<' || *line == '>')
                            continue;
                    for (px = line; *px != '\n'; px++) {
                            if (isupper(*px))
                                    *py++ = *px;
                            else if (islower(*px))
                                    *py++ = toupper(*px);
                            if (index("ATGCU",*(py-1)))
                                    natgc++;
                    }
        }
        *py++ = '\0';
        *py = '\0';
        (void) fclose(fp);
        dna = natgc > (tlen/3);
        return(pseq+4);
}
char    *
g_calloc(msg, nx, sz)
        char    *msg;       /* program, calling routine */
        int     nx, sz;     /* number and size of elements */
{
        char            *px, *calloc();
        if ((px = calloc((unsigned)nx, (unsigned)sz)) == 0) {
                    if (*msg) {
                            fprintf(stderr, "%s: g_calloc() failed %s (n=%d, sz=%d)\n", prog, msg, nx, sz);
                            exit(1);
                    }
        }
        return(px);
}

/*
 * get final jmps from dx[] or tmp file, set pp[], reset dmax: main()
 */
readjmps()
{
        int             fd = -1;
        int             siz, i0, i1;
        register        i, j, xx;
        if (fj) {
                    (void) fclose(fj);
                    if ((fd = open(jname, O_RDONLY, 0)) < 0) {
                            fprintf(stderr, "%s: can't open() %s\n", prog, jname);
                            cleanup(1);
                    }
        }
        for (i = i0 = i1 = 0, dmax0 = dmax, xx = len0; ; i++) {
                    while (1) {
                            for (j = dx[dmax].ijmp; j >= 0 && dx[dmax].jp.x[j] >= xx; j--)
                                    ;
``` g_calloc readjmps

Table 1 (cont')

...readjmps

```
                if (j < 0 && dx[dmax].offset && fj) {
                        (void) lseek(fd, dx[dmax].offset, 0);
                        (void) read(fd, (char *)&dx[dmax].jp, sizeof(struct jmp));
                        (void) read(fd, (char *)&dx[dmax].offset, sizeof(dx[dmax].offset));
                        dx[dmax].ijmp = MAXJMP-1;                    }
                else
                        break;              }
        if (j >= JMPS) {
                fprintf(stderr, "%s: too many gaps in alignment\n", prog);
                cleanup(1);
        }
        if (j >= 0) {
                siz = dx[dmax].jp.n[j];
                xx = dx[dmax].jp.x[j];
                dmax += siz;
                if (siz < 0) {              /* gap in second seq */
                        pp[1].n[i1] = -siz;
                        xx += siz;
                        /* id = xx - yy + len1 - 1                    */
                        pp[1].x[i1] = xx - dmax + len1 - 1;
                        gapy++;
                        ngapy -= siz;
/* ignore MAXGAP when doing endgaps */
                        siz = (-siz < MAXGAP || endgaps)? -siz : MAXGAP;
                        i1++;
                }
                else if (siz > 0) {    /* gap in first seq */
                        pp[0].n[i0] = siz;
                        pp[0].x[i0] = xx;
                        gapx++;
                        ngapx += siz;
/* ignore MAXGAP when doing endgaps */
                        siz = (siz < MAXGAP || endgaps)? siz : MAXGAP;
                        i0++;
                }
        }
        else
                break;
}
/* reverse the order of jmps    */
for (j = 0, i0--; j < i0; j++, i0--) {
        i = pp[0].n[j]; pp[0].n[j] = pp[0].n[i0]; pp[0].n[i0] = i;
        i = pp[0].x[j]; pp[0].x[j] = pp[0].x[i0]; pp[0].x[i0] = i;
}
for (j = 0, i1--; j < i1; j++, i1--) {
        i = pp[1].n[j]; pp[1].n[j] = pp[1].n[i1]; pp[1].n[i1] = i;
        i = pp[1].x[j]; pp[1].x[j] = pp[1].x[i1]; pp[1].x[i1] = i;
}
if (fd >= 0)
        (void) close(fd);
if (fj) {
        (void) unlink(jname);
        fj = 0;
        offset = 0;
}                                          }
```

Table 1 (cont')

```
/*
 * write a filled jmp struct offset of the prev one (if any): nw()
 */
writejmps(ix)                                                                writejmps
        int     ix;
{
        char    *mktemp();

if (!fj) {
                if (mktemp(jname) < 0) {
                        fprintf(stderr, "%s: can't mktemp() %s\n", prog, jname);
                        cleanup(1);
                }
                if ((fj = fopen(jname, "w")) == 0) {
                        fprintf(stderr, "%s: can't write %s\n", prog, jname);
                        exit(1);
                }
        }
        (void) fwrite((char *)&dx[ix].jp, sizeof(struct jmp), 1, fj);
        (void) fwrite((char *)&dx[ix].offset, sizeof(dx[ix].offset), 1, fj);
}
```

--

Col. 88, line 3 should read, --(2) uncharged polar: Gly (G), Ser (S), Thr (T), Cys (c), Tyr--

SEQUENCE LISTING

<160> NUMBER OF SEQ ID NOS: 70

<210> SEQ ID NO 1
<211> LENGTH: 1210
<212> TYPE: DNA
<213> ORGANISM: Homo sapiens -continued

```
<400> SEQUENCE: 1
cagcgcgtgg ccggcgccgc tgtggggaca gcatgagcgg cggttggatg         50
gcgcaggttg gagcgtggcg aacaggggct ctgggcctgg cgctgctgct        100
gctgctcggc ctcggactag gcctggaggc cgccgcgagc ccgctttcca        150
ccccgacctc tgcccaggcc gcaggcccca gctcaggctc gtgcccaccc        200
accaagttcc agtgccgcac cagtggctta tgcgtgcccc tcacctggcg        250
ctgcgacagg gacttggact gcagcgatgg cagcgatgag gaggagtgca        300
ggattgagcc atgtacccag aaagggcaat gcccaccgcc ccctggcctc        350
ccctgcccct gcaccggcgt cagtgactgc tctggggaa ctgacaagaa         400 actgcgcaac tgcagccgcc tggcctgcct agcaggcgag ctccgttgca        450
cgctgagcga tgactgcatt ccactcacgt ggcgctgcga cggccaccca        500
gactgtcccg actccagcga cgagctcggc tgtggaacca atgagatcct        550
cccggaaggg gatgccacaa ccatggggcc ccctgtgacc ctggagagtg        600
tcacctctct caggaatgcc acaaccatgg gcccctgt gaccctggag          650 agtgtcccct ctgtcgggaa tgccacatcc tcctctgccg agaccagtc         700 tggaagccca actgcctatg gggttattgc agctgctgcg gtgctcagtg        750
caagcctggt caccgccacc ctcctccttt tgtcctggct ccgagcccag        800
gagcgcctcc gcccactggg gttactggtg gccatgaagg agtccctgct        850
gctgtcagaa cagaagacct cgctgccctg aggacaagca cttgccacca        900
ccgtcactca gccctgggcg tagccggaca ggaggagagc agtgatgcgg        950
atgggtaccc gggcacacca gccctcagag acctgagttc ttctggccac       1000
gtggaacctc gaacccgagc tcctgcagaa gtggccctgg agattgaggg       1050
tccctggaca ctccctatgg agatccgggg agctaggatg gggaacctgc       1100
cacagccaga actgagggc tggccccagg cagctcccag ggggtagaac        1150
ggccctgtgc ttaagacact ccctgctgcc ccgtctgagg gtggcgatta       1200
aagttgcttc                                                    1210
```

```
<210> SEQ ID NO 2
<211> LENGTH: 282
<212> TYPE: PRT
<213> ORGANISM: Homo sapiens

<400> SEQUENCE: 2

Met Ser Gly Gly Trp Met Ala Gln Val Gly Ala Trp Arg Thr Gly
  1               5                  10                  15

Ala Leu Gly Leu Ala Leu Leu Leu Leu Gly Leu Gly Leu Gly
                 20                  25                  30

Leu Glu Ala Ala Ala Ser Pro Leu Ser Thr Pro Thr Ser Ala Gln
                 35                  40                  45

Ala Ala Gly Pro Ser Ser Gly Ser Cys Pro Pro Thr Lys Phe Gln
                 50                  55                  60

Cys Arg Thr Ser Gly Leu Cys Val Pro Leu Thr Trp Arg Cys Asp
                 65                  70                  75

Arg Asp Leu Asp Cys Ser Asp Gly Ser Asp Glu Glu Cys Arg
                 80                  85                  90

Ile Glu Pro Cys Thr Gln Lys Gly Gln Cys Pro Pro Pro Gly
```

|  | 95 |  |  | 100 |  |  | 105 |  |  |  |
|---|---|---|---|---|---|---|---|---|---|---|

Leu Pro Cys Pro Cys Thr Gly Val Ser Asp Cys Ser Gly Gly Thr
           110              115              120

Asp Lys Lys Leu Arg Asn Cys Ser Arg Leu Ala Cys Leu Ala Gly
           125               130              135

Glu Leu Arg Cys Thr Leu Ser Asp Asp Cys Ile Pro Leu Thr Trp
           140               145              150

Arg Cys Asp Gly His Pro Asp Cys Pro Asp Ser Ser Asp Glu Leu
           155               160              165

Gly Cys Gly Thr Asn Glu Ile Leu Pro Glu Gly Asp Ala Thr Thr
           170               175              180

Met Gly Pro Pro Val Thr Leu Glu Ser Val Thr Ser Leu Arg Asn
           185               190              195

Ala Thr Thr Met Gly Pro Pro Val Thr Leu Glu Ser Val Pro Ser
           200               205              210

Val Gly Asn Ala Thr Ser Ser Ser Ala Gly Asp Gln Ser Gly Ser
           215               220              225

Pro Thr Ala Tyr Gly Val Ile Ala Ala Ala Ala Val Leu Ser Ala
           230               235              240

Ser Leu Val Thr Ala Thr Leu Leu Leu Ser Trp Leu Arg Ala
           245               250              255

Gln Glu Arg Leu Arg Pro Leu Gly Leu Leu Val Ala Met Lys Glu
           260               265              270

Ser Leu Leu Leu Ser Glu Gln Lys Thr Ser Leu Pro
           275               280

<210> SEQ ID NO 3
<211> LENGTH: 1867
<212> TYPE: DNA
<213> ORGANISM: Homo sapiens

<400> SEQUENCE: 3

| | |
|---|---|
| acactggcca aacactcgca tcccagggcg tctccggctg ctcccattga | 50 |
| gctgtctgct cgctgtgccc gctgtgcctg ctgtgcccgc gctgtcgccg | 100 |
| ctgctaccgc gtctgctgga cgcgggagac gccagcgagc tggtgattgg | 150 |
| agccctgcgg agagctcaag cgcccagctc tgcccgagga gcccaggctg | 200 |
| ccccgtgagt cccatagttg ctgcaggagt ggagcctttc cctttgcgat | 250 |
| cgctaaacca ccatgagctg cgtcctgggt ggtgtcatcc ccttggggct | 300 |
| gctgttcctg gtctgcggat cccaaggcta cctcctgccc aacgtcactc | 350 |
| tcttagagga gctgctcagc aaataccagc acaacgagtc tcactcccgg | 400 |
| gtccgcagag ccatccccag ggaggacaag gaggagatcc tcatgctgca | 450 |
| caacaagctt cggggccagg tgcagcctca ggcctccaac atggagtaca | 500 |
| tgacctggga tgacgaactg agaagtctgc tgcagcgtgt ggccagtcag | 550 |
| tgcatctggg agcacgggcc caccagtctg ctggtgtcca tcgggcagaa | 600 |
| cctgggcgct cactggggca ggtatcgctc tccggggttc catgtgcagt | 650 |
| cctggtatga cgaggtgaag gactacacct accctaccc gagcgagtgc | 700 |
| aacccctggt gtccagagag gtgctcgggg cctatgtgca cgcactacac | 750 |
| acagatagtt tgggccacca ccaacaagat cggttgtgct gtgaacacct | 800 |
| gccggaagat gactgtctgg ggagaagttt gggagaacgc ggtctacttt | 850 |

```
gtctgcaatt attctccaaa ggggaactgg attggagaag cccctacaa          900 gaatggccgg ccctgctctg agtgcccacc cagctatgga ggcagctgca          950
ggaacaactt gtgttaccga aagaaacct acactccaaa acctgaaacg          1000
gacgagatga atgaggtgga aacggctccc attcctgaag aaaaccatgt         1050
ttggctccaa ccgagggtga tgagacccac caagcccaag aaaacctctg         1100
cggtcaacta catgacccaa gtcgtcagat gtgacaccaa gatgaaggac         1150
aggtgcaaag ggtccacgtg taacaggtac cagtgcccag caggctgcct         1200
gaaccacaag gcgaagatct ttggaagtct gttctatgaa agctcgtcta         1250
gcatatgccg cgccgccatc cactacggga tcctggatga caagggaggc         1300
ctggtggata tcaccaggaa cgggaaggtc cccttcttcg tgaagtctga         1350
gagacacggc gtgcagtccc tcagcaaata caaaccttcc agctcattca         1400
tggtgtcaaa agtgaaagtg caggatttgg actgctacac gaccgttgct         1450
cagctgtgcc cgtttgaaaa gccagcaact cactgcccaa gaatccattg         1500
tccggcacac tgcaaagacg aaccttccta ctgggctccg tgtgtttggaa        1550 ccaacatcta tgcagatacc tcaagcatct gcaagacagc tgtgcacgcg         1600
ggagtcatca gcaacgagag tgggggtgac gtggacgtga tgcccgtgga         1650
taaaaagaag acctacgtgg gctcgctcag gaatggagtt cagtctgaaa         1700
gcctggggac tcctcgggat ggaaaggcct tccggatctt tgctgtcagg         1750 catttcccctt tgcggccgcg tgaatttcca gcaccagggg agaagggggcg       1800 tcttcaggag ggcttcgggg ttttgctttt attttattt tgtcattgcg          1850 gggtatatgg agagtca                                              1867
```

<210> SEQ ID NO 4
<211> LENGTH: 497
<212> TYPE: PRT
<213> ORGANISM: Homo sapiens

<400> SEQUENCE: 4

```
Met Ser Cys Val Leu Gly Gly Val Ile Pro Leu Gly Leu Leu Phe
  1               5                  10                  15

Leu Val Cys Gly Ser Gln Gly Tyr Leu Leu Pro Asn Val Thr Leu
                 20                  25                  30

Leu Glu Glu Leu Leu Ser Lys Tyr Gln His Asn Glu Ser His Ser
                 35                  40                  45

Arg Val Arg Arg Ala Ile Pro Arg Glu Asp Lys Glu Glu Ile Leu
                 50                  55                  60

Met Leu His Asn Lys Leu Arg Gly Gln Val Gln Pro Gln Ala Ser
                 65                  70                  75

Asn Met Glu Tyr Met Thr Trp Asp Asp Glu Leu Glu Lys Ser Ala
                 80                  85                  90

Ala Ala Trp Ala Ser Gln Cys Ile Trp Glu His Gly Pro Thr Ser
                 95                 100                 105

Leu Leu Val Ser Ile Gly Gln Asn Leu Gly Ala His Trp Gly Arg
                110                 115                 120

Tyr Arg Ser Pro Gly Phe His Val Gln Ser Trp Tyr Asp Glu Val
                125                 130                 135

Lys Asp Tyr Thr Tyr Pro Tyr Pro Ser Glu Cys Asn Pro Trp Cys
                140                 145                 150
```

```
Pro Glu Arg Cys Ser Gly Pro Met Cys Thr His Tyr Thr Gln Ile
            155                 160                 165

Val Trp Ala Thr Thr Asn Lys Ile Gly Cys Ala Val Asn Thr Cys
            170                 175                 180

Arg Lys Met Thr Val Trp Gly Glu Val Trp Glu Asn Ala Val Tyr
            185                 190                 195

Phe Val Cys Asn Tyr Ser Pro Lys Gly Asn Trp Ile Gly Glu Ala
            200                 205                 210

Pro Tyr Lys Asn Gly Arg Pro Cys Ser Glu Cys Pro Pro Ser Tyr
            215                 220                 225

Gly Gly Ser Cys Arg Asn Asn Leu Cys Tyr Arg Glu Glu Thr Tyr
            230                 235                 240

Thr Pro Lys Pro Glu Thr Asp Glu Met Asn Glu Val Glu Thr Ala
            245                 250                 255

Pro Ile Pro Glu Glu Asn His Val Trp Leu Gln Pro Arg Val Met
            260                 265                 270

Arg Pro Thr Lys Pro Lys Lys Thr Ser Ala Val Asn Tyr Met Thr
            275                 280                 285

Gln Val Val Arg Cys Asp Thr Lys Met Lys Asp Arg Cys Lys Gly
            290                 295                 300

Ser Thr Cys Asn Arg Tyr Gln Cys Pro Ala Gly Cys Leu Asn His
            305                 310                 315

Lys Ala Lys Ile Phe Gly Ser Leu Phe Tyr Glu Ser Ser Ser
            320                 325                 330

Ile Cys Arg Ala Ala Ile His Tyr Gly Ile Leu Asp Asp Lys Gly
            335                 340                 345

Gly Leu Val Asp Ile Thr Arg Asn Gly Lys Val Pro Phe Phe Val
            350                 355                 360

Lys Ser Glu Arg His Gly Val Gln Ser Leu Ser Lys Tyr Lys Pro
            365                 370                 375

Ser Ser Ser Phe Met Val Ser Lys Val Lys Val Gln Asp Leu Asp
            380                 385                 390

Cys Tyr Thr Thr Val Ala Gln Leu Cys Pro Phe Glu Lys Pro Ala
            395                 400                 405

Thr His Cys Pro Arg Ile His Cys Pro Ala His Cys Lys Asp Glu
            410                 415                 420

Pro Ser Tyr Trp Ala Pro Val Phe Gly Thr Asn Ile Tyr Ala Asp
            425                 430                 435

Thr Ser Ser Ile Cys Lys Thr Ala Val His Ala Gly Val Ile Ser
            440                 445                 450

Asn Glu Ser Gly Gly Asp Val Asp Val Met Pro Val Asp Lys Lys
            455                 460                 465

Lys Thr Tyr Val Gly Ser Leu Arg Asn Gly Val Gln Ser Glu Ser
            470                 475                 480

Leu Gly Thr Pro Arg Asp Gly Lys Ala Phe Arg Ile Phe Ala Val
            485                 490                 495

Arg Gln

<210> SEQ ID NO 5
<211> LENGTH: 2359
<212> TYPE: DNA
<213> ORGANISM: Homo sapiens

<400> SEQUENCE: 5
ctgtcaggaa ggaccatctg aaggctgcaa tttgttctta gggaggcagg                50
```

| | |
|---|---|
| tgctggcctg gcctggatct tccaccatgt tcctgttgct gccttttgat | 100 |
| agcctgattg tcaaccttct gggcatctcc ctgactgtcc tcttcaccct | 150 |
| ccttctcgtt ttcatcatag tgccagccat ttttggagtc tcctttggta | 200 |
| tccgcaaact ctacatgaaa agtctgttaa aaatctttgc gtgggctacc | 250 |
| ttgagaatgg agcgaggagc caaggagaag aaccaccagc tttacaagcc | 300 |
| ctacaccaac ggaatcattg caaaggatcc cacttcacta gaagaagaga | 350 |
| tcaaagagat tcgtcgaagt ggtagtagta aggctctgga caacactcca | 400 |
| gagttcgagc tctctgacat tttctacttt tgccggaaag gaatggagac | 450 |
| cattatggat gatgaggtga caaagagatt ctcagcagaa gaactggagt | 500 |
| cctggaacct gctgagcaga accaattata acttccagta catcagcctt | 550 |
| cggctcacgg tcctgtgggg gttaggagtg ctgattcggt actgctttct | 600 |
| gctgccgctc aggatagcac tggctttcac agggattagc cttctggtgg | 650 |
| tgggcacaac tgtggtggga tacttgccaa atgggaggtt taaggaattc | 700 |
| atgagtaaac atgttcactt aatgtgttac cggatctgcg tgcgagcgct | 750 |
| gacagccatc atcacctacc atgacaggga aaacagacca agaaatggtg | 800 |
| gcatctgtgt ggccaatcat acctcaccga tcgatgtgat catcttggcc | 850 |
| agcgatggct attatgccat ggtgggtcaa gtgcacgggg gactcatggg | 900 |
| tgtgattcag agagccatgg tgaaggcctg cccacacgtc tggtttgagc | 950 |
| gctcggaagt gaaggatcgc cacctggtgg ctaagagact gactgaacat | 1000 |
| gtgcaagata aaagcaagct gcctatcctc atcttcccag aaggaacctg | 1050 |
| catcaataat acatcggtga tgatgttcaa aagggaagt tttgaaattg | 1100 |
| gagccacagt ttaccctgtt gctatcaagt atgaccctca atttggcgat | 1150 |
| gccttctgga acagcagcaa atacgggatg gtgacgtacc tgctgcgaat | 1200 |
| gatgaccagc tgggccattg tctgcagcgt gtggtacctg cctcccatga | 1250 |
| ctagagaggc agatgaagat gctgtccagt ttgcgaatag ggtgaaatct | 1300 |
| gccattgcca ggcagggagg acttgtggac ctgctgtggg atgggggcct | 1350 |
| gaagagggag aaggtgaagg acacgttcaa ggaggagcag cagaagctgt | 1400 |
| acagcaagat gatcgtgggg aaccacaagg acaggagccg ctcctgagcc | 1450 |
| tgcctccagc tggctggggc caccgtgcgg ggtgccaacg ggctcagagc | 1500 |
| tggagttgcc gccgccgccc ccactgctgt gtccttccca gactccaggg | 1550 |
| ctccccgggc tgctctggat cccaggactc cggctttcgc cgagccgcag | 1600 |
| cgggatccct gtgcacccgg cgcagcctac ccttggtggt ctaaacggat | 1650 |
| gctgctgggt gttgcgaccc aggacgagat gccttgtttc ttttacaata | 1700 |
| agtcgttgga ggaatgccat taaagtgaac tccccacctt tgcacgctgt | 1750 |
| gcgggctgag tggttgggga gatgtggcca tggtcttgtg ctagagatgg | 1800 |
| cggtacaaga gtctgttatg caagcccgtg tgccagggat gtgctggggg | 1850 |
| cggccacccg ctctccagga aaggcacagc tgaggcactg tggctggctt | 1900 |
| cggcctcaac atcgcccccca gccttggagc tctgcagaca tgataggaag | 1950 |
| gaaactgtca tctgcagggg cttttcagcaa aatgaagggt tagatttta | 2000 |
| tgctgctgct gatggggtta ctaaagggag gggaagaggc caggtgggcc | 2050 |

```
gctgactggg ccatggggag aacgtgtgtt cgtactccag gctaaccctg        2100
aactccccat gtgatgcgcg ctttgttgaa tgtgtgtctc ggtttcccca        2150
tctgtaatat gagtcggggg gaatggtggt gattcctacc tcacagggct        2200
gttgtgggga ttaaagtgct gcgggtgagt gaaggacaca tcacgttcag        2250
tgtttcaagt acaggcccac aaaacggggc acggcaggcc tgagctcaga        2300
gctgctgcac tgggctttgg atttgttctt gtgagtaaat aaaactggct        2350
ggtgaatga                                                     2359
```

<210> SEQ ID NO 6
<211> LENGTH: 456
<212> TYPE: PRT
<213> ORGANISM: Homo sapiens

<400> SEQUENCE: 6

```
Met Phe Leu Leu Leu Pro Phe Asp Ser Leu Ile Val Asn Leu Leu
 1               5                   10                  15

Gly Ile Ser Leu Thr Val Leu Phe Thr Leu Leu Leu Val Phe Ile
             20                  25                  30

Ile Val Pro Ala Ile Phe Gly Val Ser Phe Gly Ile Arg Lys Leu
             35                  40                  45

Tyr Met Lys Ser Leu Lys Ile Phe Ala Trp Ala Thr Leu Arg
             50                  55                  60

Met Glu Arg Gly Ala Lys Glu Lys Asn His Gln Leu Tyr Lys Pro
             65                  70                  75

Tyr Thr Asn Gly Ile Ile Ala Lys Asp Pro Thr Ser Leu Glu Glu
             80                  85                  90

Glu Ile Lys Glu Ile Arg Arg Ser Gly Ser Ser Lys Ala Leu Asp
             95                 100                 105

Asn Thr Pro Glu Phe Glu Leu Ser Asp Ile Phe Tyr Phe Cys Arg
            110                 115                 120

Lys Gly Met Glu Thr Ile Met Asp Asp Glu Val Thr Lys Arg Phe
            125                 130                 135

Ser Ala Glu Glu Leu Glu Ser Trp Asn Leu Leu Ser Arg Thr Asn
            140                 145                 150

Tyr Asn Phe Gln Tyr Ile Ser Leu Arg Leu Thr Val Leu Trp Gly
            155                 160                 165

Leu Gly Val Leu Ile Arg Tyr Cys Phe Leu Pro Leu Arg Ile
            170                 175                 180

Ala Leu Ala Phe Thr Gly Ile Ser Leu Leu Val Val Gly Thr Thr
            185                 190                 195

Val Val Gly Tyr Leu Pro Asn Gly Arg Phe Lys Glu Phe Met Ser
            200                 205                 210

Lys His Val His Leu Met Cys Tyr Arg Ile Cys Val Arg Ala Leu
            215                 220                 225

Thr Ala Ile Ile Thr Tyr His Asp Arg Glu Asn Arg Pro Arg Asn
            230                 235                 240

Gly Gly Ile Cys Val Ala Asn His Thr Ser Pro Ile Asp Val Ile
            245                 250                 255

Ile Leu Ala Ser Asp Gly Tyr Tyr Ala Met Val Gly Gln Val His
            260                 265                 270

Gly Gly Leu Met Gly Val Ile Gln Arg Ala Met Val Lys Ala Cys
            275                 280                 285
```

```
Pro His Val Trp Phe Glu Arg Ser Glu Val Lys Asp Arg His Leu
            290                 295                 300

Val Ala Lys Arg Leu Thr Glu His Val Gln Asp Lys Ser Lys Leu
        305                 310                 315

Pro Ile Leu Ile Phe Pro Glu Gly Thr Cys Ile Asn Asn Thr Ser
    320                 325                 330

Val Met Met Phe Lys Lys Gly Ser Phe Glu Ile Gly Ala Thr Val
335                 340                 345

Tyr Pro Val Ala Ile Lys Tyr Asp Pro Gln Phe Gly Asp Ala Phe
            350                 355                 360

Trp Asn Ser Ser Lys Tyr Gly Met Val Thr Tyr Leu Leu Arg Met
        365                 370                 375

Met Thr Ser Trp Ala Ile Val Cys Ser Val Trp Tyr Leu Pro Pro
    380                 385                 390

Met Thr Arg Glu Ala Asp Glu Asp Ala Val Gln Phe Ala Asn Arg
395                 400                 405

Val Lys Ser Ala Ile Ala Arg Gln Gly Gly Leu Val Asp Leu Leu
            410                 415                 420

Trp Asp Gly Gly Leu Lys Arg Glu Lys Val Lys Asp Thr Phe Lys
        425                 430                 435

Glu Glu Gln Gln Lys Leu Tyr Ser Lys Met Ile Val Gly Asn His
    440                 445                 450

Lys Asp Arg Ser Arg Ser
455

<210> SEQ ID NO 7
<211> LENGTH: 3493
<212> TYPE: DNA
<213> ORGANISM: Homo sapiens

<400> SEQUENCE: 7 ctcccttca tctggtggcc ctagcgccac aagctgccgc ttaggaagtc          50
cctgccggga gcagaagtgg agacatcagc aggatggcat cggcaagtcg        100
ctcccctccc gggcctcatc tgccaaacga tcatctcctc ctccgaagtt        150
gtatgcatga caggcgagtg gaaacttcac taaaatgaag gcgattgaca        200
caacagaagg aactccatcc tttcgggggc ttacgaaaat aataagttta        250
aaaaaaatag gaagggaatt ccctcgctcc atgatcactg agcgctctcc        300
taaggaaaag gaaatctccc gggggtgcc gactacgggc ggcgggctta         350
ggatgctccc acgctccccg accccccaatc cccaggaccc gcaggacctc       400
cggaggaacg cccgccagcc cgcccggagc acgcggcac aaggtgacac         450 ggaccgcgcc gcgcgggccc ctcagccgcc tgggcgaggc cgggagcagg        500 gagagggca tccgccggcc cgcggtacct tgtacttatc aaagccagcc         550
agctgctccg ggctcacgta ttcgtagcca gccatgacga cccgaaaact        600
gagcgcccac tcggcagcga ctcccggcta caaggctgtg acacacaagc        650
accacaccgg ctgggcaagg atggcaaaga ctgggctgcc cgagaaggga        700
cagagtcagg ctggagggga atctggatct gggcagctcc tggaccaaga        750
gaatggagca ggggaatcag cgctggtctc cgtctatgta catctggact        800
ttccagataa gacctggccc ctgaactct ccaggacact gactctccct         850
gctgcctcag cttcctcttc cccaaggcct cttctcactg gcctcagact        900
```

-continued

| | |
|---|---|
| cacaacaggt gagtacatga gctgcttcga ggcccagggc ttcaagtgga | 950 |
| acctgtatga ggtggtgagg gtgcccttga aggcgacaga tgtggctcga | 1000 |
| cttccatacc agctgtccat ctcctgtgtc acctcccctg gcttccagct | 1050 |
| gagctgctgc atcccagca caaacctggc ctacaccgcg gcctggagcc | 1100 |
| ctggagaggg cagcaaagct tcctccttca acgagtcagg ctctcagtgc | 1150 |
| tttgtgctgc tgttcagcg ctgcccgatg gctgacacca cgtacacttg | 1200 |
| tgacctgcag agcctgggcc tggctccact cagggtcccc atctccatca | 1250 |
| ccatcatcca ggatggagac atcacctgcc ctgaggacgc ctcggtgctc | 1300 |
| acctggaatg tcaccaaggc tggccacgtg gcacaggccc catgtcctga | 1350 |
| gagcaagagg ggcatagtga ggaggctctg tggggctgac ggagtctggg | 1400 |
| ggccggtcca cagcagctgc acagatgcga ggctcctggc cttgttcact | 1450 |
| agaaccaagc tgctgcaggc aggccagggc agtcctgctg aggaggtgcc | 1500 |
| acagatcctg gcacagctgc cagggcaggc ggcagaggca agttcaccct | 1550 |
| ccgacttact gaccctgctg agcaccatga aatacgtggc caaggtggtg | 1600 |
| gcagaggcca gaatacagct tgaccgcaga gccctgaaga atctcctgat | 1650 |
| tgccacagac aaggtcctag atatggacac caggtctctg tggaccctgg | 1700 |
| cccaagcccg gaagccctgg gcaggctcga ctctcctgct ggctgtggag | 1750 |
| accctggcat gcagcctgtg cccacaggac tacccttcg ccttcagctt | 1800 |
| acccaatgtg ctgctgcaga gccagctgtt tggacccacg tttcctgctg | 1850 |
| actacagcat ctccttccct actcgtcccc cactgcaggc tcagattccc | 1900 |
| aggcactcac tggccccatt ggtccgtaat ggaactgaaa taagtattac | 1950 |
| tagcctggtg ctgcgaaaac tggaccacct tctgccctca aactatggac | 2000 |
| aagggctggg ggattccctc tatgccactc ctggcctggt ccttgtcatt | 2050 |
| tccatcatgg caggtgaccg ggccttcagc cagggagagg tcatcatgga | 2100 |
| ctttgggaac acagatggtt ccctcactg tgtcttctgg gatcacagtc | 2150 |
| tcttccaggg caggggggt tggtccaaag aagggtgcca ggcacaggtg | 2200 |
| gccagtgcca gccccactgc tcagtgcctc tgccagcacc tcactgcctt | 2250 |
| ctccgtcctc atgtccccac acactgttcc ggaagaaccc gctctggcgc | 2300 |
| tgctgactca agtgggcttg ggagcttcca tactggcgct gcttgtgtgc | 2350 |
| ctgggtgtgt actggctggt gtggagagtc gtggtgcgga acaagatctc | 2400 |
| ctatttccgc cacgccgccc tgctcaacat ggtgttctgc ttgctggccg | 2450 |
| cagacacttg cttcctgggc gccccattcc tctctccagg gccccgaagc | 2500 |
| ccgctctgcc ttgctgccgc cttcctctgt catttcctct acctggccac | 2550 |
| cttttctgg atgctggcgc aggccctggt gttggcccac cagctgctat | 2600 |
| ttgtctttca ccagctggca aagcaccgag ttctccccct catggtgctc | 2650 |
| ctgggctacc tgtgcccact ggggttggca ggtgtcaccc tggggctcta | 2700 |
| cctacctcaa gggcaatacc tgagggaggg ggaatgctgg ttggatggga | 2750 |
| agggaggggc gttatacacc ttcgtggggc cagtgctggc catcataggc | 2800 |
| gtgaatgggc tggtactagc catggccatg ctgaagttgc tgagaccttc | 2850 |
| gctgtcagag ggaccccag cagagaagcg ccaagctctg ctggggtga | 2900 |

-continued

```
tcaaagccct gctcattctt acacccatct ttggcctcac ctgggggctg      2950
ggcctggcca ctctgttaga ggaagtctcc acggtccctc attacatctt      3000
caccattctc aacaccctcc agggcgtctt catcctattg tttggttgcc      3050
tcatggacag gaagatacaa gaagctttgc gcaaacgctt ctgccgcgcc      3100
caagccccca gctccaccat ctccctggcc acaaatgaag gctgcatctt      3150
ggaacacagc aaaggaggaa gcgacactgc caggaagaca gatgcttcag      3200
agtgaaccac acacggaccc atgttcctgc aagggagttg aggctgtgtg      3250
cttgaaccca ccagatgagc cctggcccaa tgctctgaac tcttcccgcc      3300
tcccggagct cagcccttga gaaagttatg aagaaggat gacttacttg       3350 acaggaacct ctgatctttc aaacattgga gatgaagggc agaatttggt      3400
ttgtcttttc aagtttagga aaaggtgaag ttaattggtc cctctttctt      3450
taacctttaa aaaatcaata taaaatgtaa gtttcttaac cat             3493
```

<210> SEQ ID NO 8
<211> LENGTH: 873
<212> TYPE: PRT
<213> ORGANISM: Homo sapiens

<400> SEQUENCE: 8

```
Met Thr Thr Arg Lys Leu Ser Ala His Ser Ala Ala Thr Pro Gly
  1               5                  10                  15

Tyr Lys Ala Val Thr His Lys His His Thr Gly Trp Ala Arg Met
                 20                  25                  30

Ala Lys Thr Gly Leu Pro Glu Lys Gly Gln Ser Gln Ala Gly Gly
                 35                  40                  45

Glu Ser Gly Ser Gly Gln Leu Leu Asp Gln Glu Asn Gly Ala Gly
                 50                  55                  60

Glu Ser Ala Leu Val Ser Val Tyr Val His Leu Asp Phe Pro Asp
                 65                  70                  75

Lys Thr Trp Pro Pro Glu Leu Ser Arg Thr Leu Thr Leu Pro Ala
                 80                  85                  90

Ala Ser Ala Ser Ser Pro Arg Pro Leu Leu Thr Gly Leu Arg
                 95                 100                 105

Leu Thr Thr Gly Glu Tyr Met Ser Cys Phe Glu Ala Gln Gly Phe
                110                 115                 120

Lys Trp Asn Leu Tyr Glu Val Val Arg Val Pro Leu Lys Ala Thr
                125                 130                 135

Asp Val Ala Arg Leu Pro Tyr Gln Leu Ser Ile Ser Cys Val Thr
                140                 145                 150

Ser Pro Gly Phe Gln Leu Ser Cys Cys Ile Pro Ser Thr Asn Leu
                155                 160                 165

Ala Tyr Thr Ala Ala Trp Ser Pro Gly Glu Gly Ser Lys Ala Ser
                170                 175                 180

Ser Phe Asn Glu Ser Gly Ser Gln Cys Phe Val Leu Ala Val Gln
                185                 190                 195

Arg Cys Pro Met Ala Asp Thr Thr Tyr Thr Cys Asp Leu Gln Ser
                200                 205                 210

Leu Gly Leu Ala Pro Leu Arg Val Pro Ile Ser Ile Thr Ile Ile
                215                 220                 225

Gln Asp Gly Asp Ile Thr Cys Pro Glu Asp Ala Ser Val Leu Thr
                230                 235                 240
```

-continued

```
Trp Asn Val Thr Lys Ala Gly His Val Ala Gln Ala Pro Cys Pro
                245                 250                 255

Glu Ser Lys Arg Gly Ile Val Arg Arg Leu Cys Gly Ala Asp Gly
            260                 265                 270

Val Trp Gly Pro Val His Ser Ser Cys Thr Asp Ala Arg Leu Leu
        275                 280                 285

Ala Leu Phe Thr Arg Thr Lys Leu Leu Gln Ala Gly Gln Gly Ser
    290                 295                 300

Pro Ala Glu Glu Val Pro Gln Ile Leu Ala Gln Leu Pro Gly Gln
305                 310                 315

Ala Ala Glu Ala Ser Ser Pro Ser Asp Leu Leu Thr Leu Leu Ser
                320                 325                 330

Thr Met Lys Tyr Val Ala Lys Val Val Ala Glu Ala Arg Ile Gln
            335                 340                 345

Leu Asp Arg Arg Ala Leu Lys Asn Leu Leu Ile Ala Thr Asp Lys
        350                 355                 360

Val Leu Asp Met Asp Thr Arg Ser Leu Trp Thr Leu Ala Gln Ala
    365                 370                 375

Arg Lys Pro Trp Ala Gly Ser Thr Leu Leu Ala Val Glu Thr
380                 385                 390

Leu Ala Cys Ser Leu Cys Pro Gln Asp Tyr Pro Phe Ala Phe Ser
                395                 400                 405

Leu Pro Asn Val Leu Leu Gln Ser Gln Leu Phe Gly Pro Thr Phe
            410                 415                 420

Pro Ala Asp Tyr Ser Ile Ser Phe Pro Thr Arg Pro Pro Leu Gln
        425                 430                 435

Ala Gln Ile Pro Arg His Ser Leu Ala Pro Leu Val Arg Asn Gly
    440                 445                 450

Thr Glu Ile Ser Ile Thr Ser Leu Val Leu Arg Lys Leu Asp His
455                 460                 465

Leu Leu Pro Ser Asn Tyr Gly Gln Gly Leu Gly Asp Ser Leu Tyr
                470                 475                 480

Ala Thr Pro Gly Leu Val Leu Val Ile Ser Ile Met Ala Gly Asp
            485                 490                 495

Arg Ala Phe Ser Gln Gly Glu Val Ile Met Asp Phe Gly Asn Thr
        500                 505                 510

Asp Gly Ser Pro His Cys Val Phe Trp Asp His Ser Leu Phe Gln
    515                 520                 525

Gly Arg Gly Gly Trp Ser Lys Glu Gly Cys Gln Ala Gln Val Ala
530                 535                 540

Ser Ala Ser Pro Thr Ala Gln Cys Leu Cys Gln His Leu Thr Ala
                545                 550                 555

Phe Ser Val Leu Met Ser Pro His Thr Val Pro Glu Glu Pro Ala
            560                 565                 570

Leu Ala Leu Leu Thr Gln Val Gly Leu Gly Ala Ser Ile Leu Ala
        575                 580                 585

Leu Leu Val Cys Leu Gly Val Tyr Trp Leu Val Trp Arg Val Val
    590                 595                 600

Val Arg Asn Lys Ile Ser Tyr Phe Arg His Ala Ala Leu Leu Asn
605                 610                 615

Met Val Phe Cys Leu Leu Ala Ala Asp Thr Cys Phe Leu Gly Ala
                620                 625                 630

Pro Phe Leu Ser Pro Gly Pro Arg Ser Pro Leu Cys Leu Ala Ala
            635                 640                 645
```

```
Ala Phe Leu Cys His Phe Leu Tyr Leu Ala Thr Phe Trp Met
            650                 655                 660

Leu Ala Gln Ala Leu Val Leu Ala His Gln Leu Leu Phe Val Phe
        665                 670                 675

His Gln Leu Ala Lys His Arg Val Leu Pro Leu Met Val Leu Leu
        680                 685                 690

Gly Tyr Leu Cys Pro Leu Gly Leu Ala Gly Val Thr Leu Gly Leu
        695                 700                 705

Tyr Leu Pro Gln Gly Gln Tyr Leu Arg Glu Gly Glu Cys Trp Leu
        710                 715                 720

Asp Gly Lys Gly Gly Ala Leu Tyr Thr Phe Val Gly Pro Val Leu
        725                 730                 735

Ala Ile Ile Gly Val Asn Gly Leu Val Leu Ala Met Ala Met Leu
        740                 745                 750

Lys Leu Leu Arg Pro Ser Leu Ser Glu Gly Pro Pro Ala Glu Lys
        755                 760                 765

Arg Gln Ala Leu Leu Gly Val Ile Lys Ala Leu Leu Ile Leu Thr
        770                 775                 780

Pro Ile Phe Gly Leu Thr Trp Gly Leu Gly Leu Ala Thr Leu Leu
        785                 790                 795

Glu Glu Val Ser Thr Val Pro His Tyr Ile Phe Thr Ile Leu Asn
        800                 805                 810

Thr Leu Gln Gly Val Phe Ile Leu Leu Phe Gly Cys Leu Met Asp
        815                 820                 825

Arg Lys Ile Gln Glu Ala Leu Arg Lys Arg Phe Cys Arg Ala Gln
        830                 835                 840

Ala Pro Ser Ser Thr Ile Ser Leu Ala Thr Asn Glu Gly Cys Ile
        845                 850                 855

Leu Glu His Ser Lys Gly Gly Ser Asp Thr Ala Arg Lys Thr Asp
        860                 865                 870

Ala Ser Glu
```

<210> SEQ ID NO 9
<211> LENGTH: 932
<212> TYPE: DNA
<213> ORGANISM: Homo sapiens
<220> FEATURE:
<221> NAME/KEY: Unsure
<222> LOCATION: 911
<223> OTHER INFORMATION: Unknown base

<400> SEQUENCE: 9

```
gggaacggaa aatggcgcct cacggcccgg gtagtcttac gaccctggtg          50
ccctgggctg ccgccctgct cctcgctctg ggcgtggaaa gggctctggc         100
gctacccgag atatgcaccc aatgtccagg gagcgtgcaa aatttgtcaa         150
aagtggcctt ttattgtaaa acgacacgag agctaatgct gcatgcccgt         200
tgctgcctga atcagaaggg caccatcttg gggctggatc tccagaactg         250
ttctctggag gaccctggtc caaactttca tcaggcacat accactgtca         300
tcatagacct gcaagcaaac cccctcaaag gtgacttggc caacaccttc         350
cgtggcttta ctcagctcca gactctgata ctgccacaac atgtcaactg         400
tcctggagga attaatgcct ggaatactat cacctcttat atagacaacc         450
aaatctgtca agggcaaaag aacctttgca ataacactgg ggacccagaa         500
```

```
atgtgtcctg agaatggatc ttgtgtacct gatggtccag gtcttttgca        550
gtgtgtttgt gctgatggtt tccatggata caagtgtatg cgccagggct        600
cgttctcact gcttatgttc ttcgggattc tgggagccac cactctatcc        650
gtctccattc tgctttgggc gacccagcgc cgaaaagcca agacttcatg        700
aactacatag gtcttaccat tgacctaaga tcaatctgaa ctatcttagc        750
ccagtcaggg agctctgctt cctagaaagg catctttcgc cagtggattc        800
gcctcaaggt tgaggccgcc attggaagat gaaaaattgc actcccttgg        850
tgtagacaaa taccagttcc cattggtgtt gttgcctata ataaacactt        900
tttcttttt naaaaaaaaa aaaaaaaaa  aa                            932
```

<210> SEQ ID NO 10
<211> LENGTH: 229
<212> TYPE: PRT
<213> ORGANISM: Homo sapiens
<400> SEQUENCE: 10

```
Met Ala Pro His Gly Pro Gly Ser Leu Thr Thr Leu Val Pro Trp
 1               5                  10                  15

Ala Ala Ala Leu Leu Leu Ala Leu Gly Val Glu Arg Ala Leu Ala
             20                  25                  30

Leu Pro Glu Ile Cys Thr Gln Cys Pro Gly Ser Val Gln Asn Leu
         35                  40                  45

Ser Lys Val Ala Phe Tyr Cys Lys Thr Thr Arg Glu Leu Met Leu
     50                  55                  60

His Ala Arg Cys Cys Leu Asn Gln Lys Gly Thr Ile Leu Gly Leu
 65                  70                  75

Asp Leu Gln Asn Cys Ser Leu Glu Asp Pro Gly Pro Asn Phe His
             80                  85                  90

Gln Ala His Thr Thr Val Ile Ile Asp Leu Gln Ala Asn Pro Leu
         95                 100                 105

Lys Gly Asp Leu Ala Asn Thr Phe Arg Gly Phe Thr Gln Leu Gln
        110                 115                 120

Thr Leu Ile Leu Pro Gln His Val Asn Cys Pro Gly Gly Ile Asn
    125                 130                 135

Ala Trp Asn Thr Ile Thr Ser Tyr Ile Asp Asn Gln Ile Cys Gln
        140                 145                 150

Gly Gln Lys Asn Leu Cys Asn Asn Thr Gly Asp Pro Glu Met Cys
    155                 160                 165

Pro Glu Asn Gly Ser Cys Val Pro Asp Gly Pro Gly Leu Leu Gln
        170                 175                 180

Cys Val Cys Ala Asp Gly Phe His Gly Tyr Lys Cys Met Arg Gln
    185                 190                 195

Gly Ser Phe Ser Leu Leu Met Phe Phe Gly Ile Leu Gly Ala Thr
        200                 205                 210

Thr Leu Ser Val Ser Ile Leu Leu Trp Ala Thr Gln Arg Arg Lys
    215                 220                 225

Ala Lys Thr Ser
```

<210> SEQ ID NO 11
<211> LENGTH: 3402
<212> TYPE: DNA
<213> ORGANISM: Homo sapiens
<400> SEQUENCE: 11

-continued

| | |
|---|---|
| gccgccccgc cccgagaccg ggcccggggg cgcggggcgg cgggatgcgg | 50 |
| cgcccggggc ggcgatgacc gcggagcgca cgccgcgggc ccggccctga | 100 |
| ccccgccgcc cgcccgctga gccccccgcc gaggtccgga caggccgaga | 150 |
| tgacgccgag cccctgttg ctgctcctgc tgccgccgct gctgctgggg | 200 |
| gccttcccac cggccgccgc cgcccgaggc cccccaaaga tggcggacaa | 250 |
| ggtggtccca cggcaggtgg cccggctggg ccgcactgtg cggctgcagt | 300 |
| gcccagtgga gggggacccg ccgccgctga ccatgtggac caaggatggc | 350 |
| cgcaccatcc acagcggctg gagccgcttc cgcgtgctgc cgcaggggct | 400 |
| gaaggtgaag caggtggagc gggaggatgc cggcgtgtac gtgtgcaagg | 450 |
| ccaccaacgg cttcggcagc ctgagcgtca actacaccct cgtcgtgctg | 500 |
| gatgacatta gcccagggaa ggagagcctg ggcccgaca gctcctctgg | 550 |
| gggtcaagag gaccccgcca gccagcagtg gcacgaccg cgcttcacac | 600 |
| agccctccaa gatgaggcgc cgggtgatcg cacggcccgt gggtagctcc | 650 |
| gtgcggctca agtgcgtggc cagcgggcac cctcggcccg acatcacgtg | 700 |
| gatgaaggac gaccaggcct tgacgcgccc agaggccgct gagcccagga | 750 |
| agaagaagtg gacactgagc ctgaagaacc tgcggccgga ggacagcggc | 800 |
| aaatacacct gccgcgtgtc gaaccgcgcg ggcgccatca acgccaccta | 850 |
| caaggtggat gtgatccagc ggacccgttc caagcccgtg ctcacaggca | 900 |
| cgcaccccgt gaacacgacg gtggacttcg ggggaccac gtccttccag | 950 |
| tgcaaggtgc gcagcgacgt gaagccggtg atccagtggc tgaagcgcgt | 1000 |
| ggagtacggc gccgagggcc gccacaactc caccatcgat gtgggcggcc | 1050 |
| agaagtttgt ggtgctgccc acgggtgacg tgtggtcgcg gcccgacggc | 1100 |
| tcctacctca ataagctgct catcacccgt gcccgccagg acgatgcggg | 1150 |
| catgtacatc tgccttggcg ccaacaccat gggctacagc ttccgcagcg | 1200 |
| ccttcctcac cgtgctgcca gacccaaaac cgccagggcc acctgtggcc | 1250 |
| tcctcgtcct cggccactag cctgccgtgg cccgtggtca tcggcatccc | 1300 |
| agccggcgct gtcttcatcc tgggcaccct gctcctgtgg ctttgccagg | 1350 |
| cccagaagaa gccgtgcacc cccgcgcctg cccctcccct gcctgggcac | 1400 |
| cgcccgccgg ggacggcccg cgaccgcagc ggagacaagg accttccctc | 1450 |
| gttggccgcc ctcagcgctg gccctggtgt ggggctgtgt gaggagcatg | 1500 |
| ggtctccggc agccccccag cacttactgg gcccaggccc agttgctggc | 1550 |
| cctaagttgt accccaaaact ctacacagac atccacacac acacacacac | 1600 |
| acactctcac acacactcac acgtggaggg caaggtccac cagcacatcc | 1650 |
| actatcagtg ctagacggca ccgtatctgc agtgggcacg ggggggccgg | 1700 |
| ccagacaggc agactgggag gatggaggac ggagctgcag acgaaggcag | 1750 |
| gggacccatg gcgaggagga atggccagcc cccaggcag tctgtgtgtg | 1800 |
| aggcatagcc cctggacaca cacacacaga cacacacact acctggatgc | 1850 |
| atgtatgcac acacatgcgc gcacacgtgc tccctgaagg cacacgtacg | 1900 |
| cacacgcaca tgcacagata tgccgcctgg gcacacagat aagctgccca | 1950 |
| aatgcacgca cacgcacaga gacatgccag aacatacaag gacatgctgc | 2000 |

| | |
|---|---|
| ctgaacatac acacgcacac ccatgcgcag atgtgctgcc tggacacaca | 2050 |
| cacacacacg gatatgctgt ctggacgcac acacgtgcag atatggtatc | 2100 |
| cggacacaca cgtgcacaga tatgctgcct ggacacacag ataatgctgc | 2150 |
| cttgacacac acatgcacgg atattgcctg acacacaca cacacacacg | 2200 |
| cgtgcacaga tatgctgtct ggacacgcac acacatgcag atatgctgcc | 2250 |
| tggacacaca cttccagaca cacgtgcaca ggcgcagata tgctgcctgg | 2300 |
| acacacgcag atatgctgtc tagtcacaca cacacgcaga catgctgtcc | 2350 |
| ggacacacac acgcatgcac agatatgctg tccggacaca cacacgcacg | 2400 |
| cagatatgct gcctggacac acacacagat aatgctgcct caacactcac | 2450 |
| acacgtgcag atattgcctg acacacaca tgtgcacaga tatgctgtct | 2500 |
| ggacatgcac acacgtgcag atatgctgtc cggatacaca cgcacgcaca | 2550 |
| catgcagata tgctgcctgg gcacacactt ccggacacac atgcacacac | 2600 |
| aggtgcagat atgctgcctg gacacacaca cagataatgc tgcctcaaca | 2650 |
| ctcacacacg tgcagatatt gcctggacac acacatgtgc acagatatgc | 2700 |
| tgtctggaca tgcacacacg tgcagatatg ctgtccggat acacacgcac | 2750 |
| gcacacatgc agatatgctg cctgggcaca cacttccgga cacacatgca | 2800 |
| cacacaggtg cagatatgct gcctggacac acgcagactg acgtgctttt | 2850 |
| gggagggtgt gccgtgaagc ctgcagtacg tgtgccgtga ggctcatagt | 2900 |
| tgatgaggga ctttccctgc tccaccgtca ctcccccaac tctgcccgcc | 2950 |
| tctgtccccg cctcagtccc cgcctccatc ccgcctctg tcccctggcc | 3000 |
| ttggcggcta ttttttgccac ctgccttggg tgcccaggag tcccctactg | 3050 |
| ctgtgggctg gggttggggg cacagcagcc caagcctga gaggctggag | 3100 |
| cccatggcta gtggctcatc cccagtgcat tctccccctg acacagagaa | 3150 |
| ggggccttgg tatttatatt taagaaatga agataatatt aataatgatg | 3200 |
| gaaggaagac tgggttgcag ggactgtggt ctctcctggg gcccgggacc | 3250 |
| cgcctggtct ttcagccatg ctgatgacca caccccgtcc aggccagaca | 3300 |
| ccacccccca ccccactgtc gtggtggccc cagatctctg taattttatg | 3350 |
| tagagtttga gctgaagccc cgtatattta atttattttg ttaaacacaa | 3400 |
| aa | 3402 |

<210> SEQ ID NO 12
<211> LENGTH: 504
<212> TYPE: PRT
<213> ORGANISM: Homo sapiens

<400> SEQUENCE: 12

```
Met Thr Pro Ser Pro Leu Leu Leu Leu Leu Pro Pro Leu Leu
 1               5                  10                  15

Leu Gly Ala Phe Pro Ala Ala Ala Ala Arg Gly Pro Pro Lys
                20                  25                  30

Met Ala Asp Lys Val Val Pro Arg Gln Val Ala Arg Leu Gly Arg
                35                  40                  45

Thr Val Arg Leu Gln Cys Pro Val Glu Gly Asp Pro Pro Leu
                50                  55                  60

Thr Met Trp Thr Lys Asp Gly Arg Thr Ile His Ser Gly Trp Ser
```

```
                    65                  70                  75
Arg Phe Arg Val Leu Pro Gln Gly Leu Lys Val Lys Gln Val Glu
                80                  85                  90
Arg Glu Asp Ala Gly Val Tyr Val Cys Lys Ala Thr Asn Gly Phe
                95                 100                 105
Gly Ser Leu Ser Val Asn Tyr Thr Leu Val Val Leu Asp Asp Ile
               110                 115                 120
Ser Pro Gly Lys Glu Ser Leu Gly Pro Asp Ser Ser Gly Gly
               125                 130                 135
Gln Glu Asp Pro Ala Ser Gln Gln Trp Ala Arg Pro Arg Phe Thr
               140                 145                 150
Gln Pro Ser Lys Met Arg Arg Val Ile Ala Arg Pro Val Gly
               155                 160                 165
Ser Ser Val Arg Leu Lys Cys Val Ala Ser Gly His Pro Arg Pro
               170                 175                 180
Asp Ile Thr Trp Met Lys Asp Asp Gln Ala Leu Thr Arg Pro Glu
               185                 190                 195
Ala Ala Glu Pro Arg Lys Lys Lys Trp Thr Leu Ser Leu Lys Asn
               200                 205                 210
Leu Arg Pro Glu Asp Ser Gly Lys Tyr Thr Cys Arg Val Ser Asn
               215                 220                 225
Arg Ala Gly Ala Ile Asn Ala Thr Tyr Lys Val Asp Val Ile Gln
               230                 235                 240
Arg Thr Arg Ser Lys Pro Val Leu Thr Gly Thr His Pro Val Asn
               245                 250                 255
Thr Thr Val Asp Phe Gly Gly Thr Thr Ser Phe Gln Cys Lys Val
               260                 265                 270
Arg Ser Asp Val Lys Pro Val Ile Gln Trp Leu Lys Arg Val Glu
               275                 280                 285
Tyr Gly Ala Glu Gly Arg His Asn Ser Thr Ile Asp Val Gly Gly
               290                 295                 300
Gln Lys Phe Val Val Leu Pro Thr Gly Asp Val Trp Ser Arg Pro
               305                 310                 315
Asp Gly Ser Tyr Leu Asn Lys Leu Leu Ile Thr Arg Ala Arg Gln
               320                 325                 330
Asp Asp Ala Gly Met Tyr Ile Cys Leu Gly Ala Asn Thr Met Gly
               335                 340                 345
Tyr Ser Phe Arg Ser Ala Phe Leu Thr Val Leu Pro Asp Pro Lys
               350                 355                 360
Pro Pro Gly Pro Pro Val Ala Ser Ser Ser Ala Thr Ser Leu
               365                 370                 375
Pro Trp Pro Val Val Ile Gly Ile Pro Ala Gly Ala Val Phe Ile
               380                 385                 390
Leu Gly Thr Leu Leu Leu Trp Leu Cys Gln Ala Gln Lys Lys Pro
               395                 400                 405
Cys Thr Pro Ala Pro Ala Pro Pro Leu Pro Gly His Arg Pro Pro
               410                 415                 420
Gly Thr Ala Arg Asp Arg Ser Gly Asp Lys Asp Leu Pro Ser Leu
               425                 430                 435
Ala Ala Leu Ser Ala Gly Pro Gly Val Gly Leu Cys Glu Glu His
               440                 445                 450
Gly Ser Pro Ala Ala Pro Gln His Leu Leu Gly Pro Gly Pro Val
               455                 460                 465
```

Ala Gly Pro Lys Leu Tyr Pro Lys Leu Tyr Thr Asp Ile His Thr
        470                 475                 480

His Thr His Thr His Ser His Thr His Ser His Val Glu Gly Lys
        485                 490                 495

Val His Gln His Ile His Tyr Gln Cys
        500

<210> SEQ ID NO 13
<211> LENGTH: 2197
<212> TYPE: DNA
<213> ORGANISM: Homo sapiens

<400> SEQUENCE: 13

| | | | | |
|---|---|---|---|---|
| cggacgcgtg ggcgtccggc ggtcgcagag ccaggaggcg gaggcgcgcg | | | | 50 |
| ggccagcctg ggccccagcc cacaccttca ccagggccca ggagccacca | | | | 100 |
| tgtggcgatg tccactgggg ctactgctgt tgctgccgct ggctggccac | | | | 150 |
| ttggctctgg gtgcccagca gggtcgtggg cgccggagc tagcaccggg | | | | 200 |
| tctgcacctg cggggcatcc gggacgcggg aggccggtac tgccaggagc | | | | 250 |
| aggacctgtg ctgccgcggc cgtgccgacg actgtgccct gccctacctg | | | | 300 |
| ggcgccatct gttactgtga cctcttctgc aaccgcacgg tctccgactg | | | | 350 |
| ctgccctgac ttctgggact tctgcctcgg cgtgccaccc ccttttcccc | | | | 400 |
| cgatccaagg atgtatgcat ggaggtcgta tctatccagt cttgggaacg | | | | 450 |
| tactgggaca actgtaaccg ttgcacctgc aggagaaca ggcagtggca | | | | 500 |
| tggtggatcc agacatgatc aaagccatca accagggcaa ctatggctgg | | | | 550 |
| caggctggga accacagcgc cttctggggc atgaccctgg atgagggcat | | | | 600 |
| tcgctaccgc ctgggcacca tccgcccatc ttcctcggtc atgaacatgc | | | | 650 |
| atgaaattta cagtgctg aacccagggg aggtgcttcc cacagccttc | | | | 700 |
| gaggcctctg agaagtggcc caacctgatt catgagcctc ttgaccaagg | | | | 750 |
| caactgtgca ggctcctggg ccttctccac agcagctgtg catccgatc | | | | 800 |
| gtgtctcaat ccattctctg ggacacatga cgcctgtcct gtcgcccag | | | | 850 |
| aacctgctgt cttgtgacac ccaccagcag cagggctgcc gcggtgggcg | | | | 900 |
| tctcgatggt gcctggtggt tcctgcgtcg ccgaggggtg gtgtctgacc | | | | 950 |
| actgctaccc cttctcgggc cgtgaacgag acgaggctgg ccctgcgccc | | | | 1000 |
| ccctgtatga tgcacagccg agccatgggt cggggcaagc gccaggccac | | | | 1050 |
| tgcccactgc cccaacagct atgttaataa caatgacatc taccaggtca | | | | 1100 |
| ctcctgtcta ccgcctcggc tccaacgaca aggagatcat gaaggagctg | | | | 1150 |
| atggagaatg ccctgtcca gccctcatg gaggtgcatg aggacttctt | | | | 1200 |
| cctatacaag ggaggcatct acagccacac gccagtgagc cttgggaggc | | | | 1250 |
| cagagagata ccgccggcat ggacccact cagtcaagat cacaggatgg | | | | 1300 |
| ggagaggaga cgctgccaga tggaaggacg ctcaaatact ggactgcggc | | | | 1350 |
| caactcctgg ggcccagcct ggggcgagag gggccacttc cgcatcgtgc | | | | 1400 |
| gcggcgtcaa tgagtcgac atcgagagct tcgtgctggg cgtctgggc | | | | 1450 |
| cgcgtgggca tggaggacat gggtcatcac tgaggctgcg gcaccacgc | | | | 1500 |
| ggggtccggc ctgggatcca ggctaagggc cggcggaaga ggcccaatg | | | | 1550 |
| gggcggtgac cccagcctcg cccgacagag cccggggcgc aggcgggcgc | | | | 1600 |

| | |
|---|---|
| cagggcgcta atcccggcgc gggttccgct gacgcagcgc cccgcctggg | 1650 |
| agccgcgggc aggcgagact ggcggagccc ccagacctcc cagtggggac | 1700 |
| ggggcagggc ctggcctggg aagagcacag ctgcagatcc caggcctctg | 1750 |
| gcgcccccac tcaagactac caaagccagg acacctcaag tctccagccc | 1800 |
| caataccccca ccccaatccc gtattctttt ttttttttttt ttagacaggg | 1850 |
| tcttgctccg ttgcccaggt tggagtgcag tggcccatca gggctcactg | 1900 |
| taacctccga ctcctgggtt caagtgaccc tcccacctca gcctctcaag | 1950 |
| tagctgggac tacaggtgca ccaccacacc tggctaattt ttgtattttt | 2000 |
| tgtaaagagg ggggtctcac tgtgttgccc aggctggttt cgaactcctg | 2050 |
| ggctcaagcg gtccacctgc ctccgcctcc caaagtgctg ggattgcagg | 2100 |
| catgagccac tgcacccagc cctgtattct tattcttcag atatttattt | 2150 |
| ttcttttcac tgttttaaaa taaaaccaaa gtattgataa  aaaaaaa | 2197 |

<210> SEQ ID NO 14
<211> LENGTH: 164
<212> TYPE: PRT
<213> ORGANISM: Homo sapiens

<400> SEQUENCE: 14

Met Trp Arg Cys Pro Leu Gly Leu Leu Leu Leu Pro Leu Ala
1               5                   10                  15

Gly His Leu Ala Leu Gly Ala Gln Gln Gly Arg Gly Arg Glu
            20                  25                  30

Leu Ala Pro Gly Leu His Leu Arg Gly Ile Arg Asp Ala Gly Gly
        35                  40                  45

Arg Tyr Cys Gln Glu Gln Asp Leu Cys Arg Gly Arg Ala Asp
    50                  55                  60

Asp Cys Ala Leu Pro Tyr Leu Gly Ala Ile Cys Tyr Cys Asp Leu
                65                  70                  75

Phe Cys Asn Arg Thr Val Ser Asp Cys Cys Pro Asp Phe Trp Asp
            80                  85                  90

Phe Cys Leu Gly Val Pro Pro Phe Pro Pro Ile Gln Gly Cys
        95                  100                 105

Met His Gly Gly Arg Ile Tyr Pro Val Leu Gly Thr Tyr Trp Asp
            110                 115                 120

Asn Cys Asn Arg Cys Thr Cys Gln Glu Asn Arg Gln Trp His Gly
        125                 130                 135

Gly Ser Arg His Asp Gln Ser His Gln Pro Gly Gln Leu Trp Leu
    140                 145                 150

Ala Gly Trp Glu Pro Gln Arg Leu Leu Gly His Asp Pro Gly
            155                 160

<210> SEQ ID NO 15
<211> LENGTH: 1780
<212> TYPE: DNA
<213> ORGANISM: Homo sapiens

<400> SEQUENCE: 15

| | |
|---|---|
| ggctcagagg ccccactgga ccctcggctc ttccttggac ttcttgtgtg | 50 |
| ttctgtgagc ttcgctggat tcagggtctt gggcatcaga ggtgagaggg | 100 |
| tgggaaggtc cgccgcgatg gggaagccct ggctgcgtgc gctacagctg | 150 |

```
ctgctcctgc tgggcgcgtc gtgggcgcgg gcgggcgccc cgcgctgcac      200
ctacaccttc gtgctgcccc cgcagaagtt cacgggcgct gtgtgctgga      250
gcggccccgc atccacgcgg gcgacgcccg aggccgccaa cgccagcgag      300
ctggcggcgc tgcgcatgcg cgtcggccgc cacgaggagc tgttacgcga      350
gctgcagagg ctggcggcgg ccgacggcgc cgtggccggc gaggtgcgcg      400
cgctgcgcaa ggagagccgc ggcctgagcg cgcgcctggg ccagttgcgc      450
gcgcagctgc agcacgaggc ggggcccggg gcgggcccgg ggcggatct       500
gggggcggag cctgccgcgg cgctggcgct gctcggggag cgcgtgctca      550
acgcgtccgc cgaggctcag cgcgcagccg cccggttcca ccagctggac      600
gtcaagttcc gcgagctggc gcagctcgtc acccagcaga gcagtctcat      650
cgcccgcctg gagcgcctgt gcccgggagg cgcgggcggg cagcagcagg      700
tcctgccgcc accccactg tgcctgtgg ttccggtccg tcttgtgggt        750
agcaccagtg acaccagtag gatgctggac ccagccccag agccccagag      800
agaccagacc cagagacagc aggagcccat ggcttctccc atgcctgcag      850
gtcaccctgc ggtccccacc aagcctgtgg gcccgtggca ggattgtgca      900
gaggcccgcc aggcaggcca tgaacagagt ggagtgtatg aactgcgagt      950
gggccgtcac gtagtgtcag tatggtgtga gcagcaactg gagggtggag     1000
gctggactgt gatccagcgg aggcaagatg gttcagtcaa cttcttcact     1050
acctggcagc actataaggc gggctttggg cggccagacg gagaatactg     1100
gctgggcctt gaacccgtgt atcagctgac cagccgtggg gaccatgagc     1150
tgctggttct cctggaggac tggggggggcc gtggagcacg tgcccactat    1200
gatggcttct ccctggaacc cgagagcgac cactaccgcc tgcggcttgg     1250
ccagtaccat ggtgatgctg agactctct ttcctggcac aatgacaagc      1300
ccttcagcac cgtggatagg gaccgagact cctattctgg taactgtgcc     1350
ctgtaccagc ggggaggctg gtggtaccat gcctgtgccc actccaacct     1400
caacggtgtg tggcaccacg gcggccacta ccgaagccgc taccaggatg     1450
gtgtctactg ggctgagttt cgtggtgggg catattctct caggaaggcc     1500
gccatgctca ttcggcccct gaagctgtga ctctgtgttc ctctgtcccc     1550
taggccctag aggacattgg tcagcaggag cccaagttgt tctggccaca     1600
ccttctttgt ggctcagtgc caatgtgtcc cacagaactt cccactgtgg     1650
atctgtgacc ctgggcgctg aaaatgggac ccaggaatcc ccccgtcaa      1700
tatcttggcc tcagatggct ccccaaggtc attcatatct cggtttgagc     1750
tcatatctta taataacaca aagtagccac                           1780
```

<210> SEQ ID NO 16
<211> LENGTH: 470
<212> TYPE: PRT
<213> ORGANISM: Homo sapiens

<400> SEQUENCE: 16

Met Gly Lys Pro Trp Leu Arg Ala Leu Gln Leu Leu Leu Leu
 1               5                   10                  15

Gly Ala Ser Trp Ala Arg Ala Gly Ala Pro Arg Cys Thr Tyr Thr
                20                  25                  30

-continued

```
Phe Val Leu Pro Pro Gln Lys Phe Thr Gly Ala Val Cys Trp Ser
             35                  40                  45

Gly Pro Ala Ser Thr Arg Ala Thr Pro Glu Ala Ala Asn Ala Ser
     50                  55                  60

Glu Leu Ala Ala Leu Arg Met Arg Val Gly Arg His Glu Glu Leu
 65                  70                  75

Leu Arg Glu Leu Gln Arg Leu Ala Ala Ala Asp Gly Ala Val Ala
             80                  85                  90

Gly Glu Val Arg Ala Leu Arg Lys Glu Ser Arg Gly Leu Ser Ala
         95                 100                 105

Arg Leu Gly Gln Leu Arg Ala Gln Leu Gln His Glu Ala Gly Pro
                 110                 115                 120

Gly Ala Gly Pro Gly Ala Asp Leu Gly Ala Glu Pro Ala Ala Ala
             125                 130                 135

Leu Ala Leu Leu Gly Glu Arg Val Leu Asn Ala Ser Ala Glu Ala
             140                 145                 150

Gln Arg Ala Ala Ala Arg Phe His Gln Leu Asp Val Lys Phe Arg
                 155                 160                 165

Glu Leu Ala Gln Leu Val Thr Gln Gln Ser Ser Leu Ile Ala Arg
                 170                 175                 180

Leu Glu Arg Leu Cys Pro Gly Gly Ala Gly Gly Gln Gln Gln Val
                 185                 190                 195

Leu Pro Pro Pro Pro Leu Val Pro Val Val Pro Val Arg Leu Val
                 200                 205                 210

Gly Ser Thr Ser Asp Thr Ser Arg Met Leu Asp Pro Ala Pro Glu
                 215                 220                 225

Pro Gln Arg Asp Gln Thr Gln Arg Gln Glu Pro Met Ala Ser
                 230                 235                 240

Pro Met Pro Ala Gly His Pro Ala Val Pro Thr Lys Pro Val Gly
                 245                 250                 255

Pro Trp Gln Asp Cys Ala Glu Ala Arg Gln Ala Gly His Glu Gln
                 260                 265                 270

Ser Gly Val Tyr Glu Leu Arg Val Gly Arg His Val Val Ser Val
                 275                 280                 285

Trp Cys Glu Gln Gln Leu Glu Gly Gly Gly Trp Thr Val Ile Gln
                 290                 295                 300

Arg Arg Gln Asp Gly Ser Val Asn Phe Phe Thr Thr Trp Gln His
                 305                 310                 315

Tyr Lys Ala Gly Phe Gly Arg Pro Asp Gly Glu Tyr Trp Leu Gly
                 320                 325                 330

Leu Glu Pro Val Tyr Gln Leu Thr Ser Arg Gly Asp His Glu Leu
                 335                 340                 345

Leu Val Leu Leu Glu Asp Trp Gly Gly Arg Gly Ala Arg Ala His
                 350                 355                 360

Tyr Asp Gly Phe Ser Leu Glu Pro Glu Ser Asp His Tyr Arg Leu
                 365                 370                 375

Arg Leu Gly Gln Tyr His Gly Asp Ala Gly Asp Ser Leu Ser Trp
                 380                 385                 390

His Asn Asp Lys Pro Phe Ser Thr Val Asp Arg Asp Arg Asp Ser
                 395                 400                 405

Tyr Ser Gly Asn Cys Ala Leu Tyr Gln Arg Gly Gly Trp Trp Tyr
                 410                 415                 420

His Ala Cys Ala His Ser Asn Leu Asn Gly Val Trp His His Gly
                 425                 430                 435
```

```
Gly His Tyr Arg Ser Arg Tyr Gln Asp Gly Val Tyr Trp Ala Glu
                440                 445                 450

Phe Arg Gly Gly Ala Tyr Ser Leu Arg Lys Ala Ala Met Leu Ile
            455                 460                 465

Arg Pro Leu Lys Leu
            470

<210> SEQ ID NO 17
<211> LENGTH: 462
<212> TYPE: DNA
<213> ORGANISM: Homo sapiens

<400> SEQUENCE: 17
agcccaccga gaggcgcctg caggatgaaa gctctctgtc tcctcctcct        50
ccctgtcctg gggctgttgg tgtctagcaa gaccctgtgc tccatggaag       100
aagccatcaa tgagaggatc caggaggtcg ccggctccct aatatttagg       150
gcaataagca gcattggcct ggagtgccag agcgtcacct ccagggggga       200
cctggctact tgcccccgag gcttcgccgt caccggctgc acttgtggct       250
ccgcctgtgg ctcgtgggat gtgcgcgccg agaccacatg tcactgccag       300
tgcgcgggca tggactggac cggagcgcgc tgctgtcgtg tgcagccctg       350
aggtcgcgcg cagcgcgtgc acagcgcggg cggaggcggc tccaggtccg       400
gaggggttgc gggggagctg gaaataaacc tggagatgat gatgatgatg       450
atgatggaaa aa                                                462

<210> SEQ ID NO 18
<211> LENGTH: 108
<212> TYPE: PRT
<213> ORGANISM: Homo sapiens

<400> SEQUENCE: 18

Met Lys Ala Leu Cys Leu Leu Leu Pro Val Leu Gly Leu Leu
 1               5                  10                  15

Val Ser Ser Lys Thr Leu Cys Ser Met Glu Glu Ala Ile Asn Glu
                20                  25                  30

Arg Ile Gln Glu Val Ala Gly Ser Leu Ile Phe Arg Ala Ile Ser
                35                  40                  45

Ser Ile Gly Leu Glu Cys Gln Ser Val Thr Ser Arg Gly Asp Leu
                50                  55                  60

Ala Thr Cys Pro Arg Gly Phe Ala Val Thr Gly Cys Thr Cys Gly
                65                  70                  75

Ser Ala Cys Gly Ser Trp Asp Val Arg Ala Glu Thr Thr Cys His
                80                  85                  90

Cys Gln Cys Ala Gly Met Asp Trp Thr Gly Ala Arg Cys Cys Arg
                95                  100                 105

Val Gln Pro

<210> SEQ ID NO 19
<211> LENGTH: 3228
<212> TYPE: DNA
<213> ORGANISM: Homo sapiens

<400> SEQUENCE: 19
tcagggtcag gtgattctcc cacctcagcc tcctgagtag ctgggagtac         50
aggcacatgc caccacaccc agataatttt taaattttttt gtagagatgg       100
```

```
ggtctcactg tgttgcccag gctggtctcg agctcctggg ctgaagtgat         150
ccatccacct ccgtccacca aagtgctggg attacaggtg tgagccaccg         200
tgccctgcct gcatttcttt taatagacat gtctctggat ggtcaactgg         250
acagttgtgc tcaccctcca catttcctcc cctctactca caccccaagg         300
tgataatgga ttggcaaccc tgggtgactt aagaattcca tgagcttcat         350
aaatgtcaaa taagctgtct taccctacta accccctctac catcacaatg        400
atcaaagcaa agccaaatag cccacacctc tcatcccaca cataccatag         450
tcatcctttc atccatttat ccatccattt accaacttaa aatattcatt         500
gattacctac tacatatgac actttacttg accaaaattg gcaaaacaca         550
tagcttaaag ttgtctttct tcctagttag gtggaatgat gcctggtata         600
tcgtatcatt agaaatggct gaatgaatga gctcactgtt tattaggaga         650
atgagacaca gaccaaataa ctcaagcata agagagaatg tagttagtgt         700
cctaaaagag atccagagtg ctgtgtgagt tcaaggtga gaaagagccc          750
ttctgactga agaaatcagg aaagacttca tagaagcagt ggtgatatat         800
gagctgactt ctaaaggaca agtaagatta taatagcaga tatagtaggg         850
gaagggaatt accgaggggg tggcatcaat aaagttttgg gggtaaggaa         900
gtatgagttc tgggtatgaa aatatgtcta acttggtcag agcataaatt         950
acgtattctg gaaggtagac tgtgtttgag aacaaatgct agaataccct         1000
aaaagctaat ttgttaggtt ctgcagagtc agtgatagga cccaagcaga         1050
caagtaatta ggaagactaa tttggcaaag atattataaa atgttggggc         1100
tgaacaatta ttacatataa taagagaatt aacaaggtgc ctgagtgaaa         1150
tgtaataaac agaaaacaac aaattttgta tgtcaaccaa acctagcagt         1200
caaaaggatt aataacaata agtcatgtag gatactatga attcataaca         1250
caaagaaatg ctaggggaaa tatttgcaat gcttatcaca tccaaaagtt         1300
cctttcccta atatacaaag atctgctaga agtcaacaag ctaaagatca         1350
acagctcaat agaaatatgg ccaaacggct ggacgtggtg gctcatgcct         1400
gtaatcccag catttgtggga gactgaggca ggattgcttg agcccaggaa        1450
ttcaagacca gcctggtcaa cgtagcgaga ttctgtgtct atattttaa          1500
aaatttatta aaaaagaaa tacgggcaaa tgagctacct agtctcagaa          1550
aagaaaatat atatgatgtg caactatatt aaaagatttt caatttcact         1600
aataattttt ttttttgaga cagagtcttg ctctgtcgcc aggctggagt         1650
gcagtggcac catcttggct cactgcaagc tctgcctccc gagttcacca         1700
ttctcctgcc tcagcctccc aagtagctgg gattacaggc gcacaccacc         1750
acacctggct aatgttttgt attttagta gaggcggggt ttcaccgtgt          1800
tagccaggat ggcctcgatc tcttgacctc gtgatcagcc caccttggcc         1850
tctcaaagtg ctgtgattac aggcgtgagc caccgcgcct ggccaaattt         1900
cactaataat tttaaaaagt aaattatata tacatgggat atcatgttca         1950
cttagattgg cgatgagcag aaagtttgat aactgtgtca taaacacttg         2000
gtaactgtgt tagtgagtgt gtggggagat aggtatcctt atatgctgct         2050
aataggagtg taggctgtaa aattctcatg gtagctagtt tagcaatatc         2100
```

```
tataaaaatt acaaatatgc ataactttca gtgagtcaga aatttttactt           2150 ttaagaattt atcttacatg tataatcaca acacgtgtga aatatcgtac           2200
acataataga tattggttgc aatctttttca tagttgtgaa agatgaggaa          2250
aaacaatctt aaaagtagtt tggttaaata aatcatgtca ctcatataca           2300
gtgaaatatc atccccattt taaaaagatg atggtggtgg tgctatacat           2350
accgatacag aaagctttct aaaacctttc attaaatgaa aaatgaataa           2400
atcattgcag aacagtgtat atatatctaa aatatctatg gaagaaacca          2450
gcaacagcca ctgctcctgg agaattatgg tcccacacca ctgatcattc          2500
tttcagtagg gtgaccatca tccaaatttg cttgggactg aggggggttcc         2550 ttttggtttg aaaaccagga cagtcctagg aaaagtgaga caagttggtc          2600
acatgtcccc aagatgatct tctttcactt atgaacttgc tactttccca          2650
gtcagaatat aaactctgag gggggagact tcctgttttc ttcatgacta          2700
tatctcttgc gcactgtggg gtggaggctg tagaagagga gagaagtaga          2750
gaaacagatc acattgtgtc ttgaagtgtt tcagcaaata tgggcaacac          2800
ccttctttta ctagcttgga accctacctc tgagtgcatt tcccttttta         2850
ttatttattt cctgtcagtt ataagagagg cctacccctt tgtgagcagt          2900
ctaggacttt gtacacctgc taagtaggga aaggcaggg gaggtggctg           2950 gtttaagggg aacttgaggg aagtagggaa gactcctctc gggacctttg          3000
gagtaggtga cacatgagcc cagccccagc tcacctgcca atccagctga          3050
ggagctcacc tgccaatcca gctgaggctg gcagaggtg ggtgagaaga           3100 gggaaaattg cagggacctc cagttgggcc aggccagaag ctgctgtagc          3150
tttaaccaga cagctcagac ctgtatggag gctgccagtg acaggttagg          3200
tttagggcag agaagaagca  agaccatg                                  3228
```

<210> SEQ ID NO 20
<211> LENGTH: 319
<212> TYPE: PRT
<213> ORGANISM: Homo sapiens

<400> SEQUENCE: 20

```
Met Val Gly Lys Met Trp Pro Val Leu Trp Thr Leu Cys Ala Val
  1               5                  10                  15

Arg Val Thr Val Asp Ala Ile Ser Val Glu Thr Pro Gln Asp Val
                 20                  25                  30

Leu Arg Ala Ser Gln Gly Lys Ser Val Thr Leu Pro Cys Thr Tyr
                 35                  40                  45

His Thr Ser Thr Ser Ser Arg Glu Gly Leu Ile Gln Trp Asp Lys
                 50                  55                  60

Leu Leu Leu Thr His Thr Glu Arg Val Val Ile Trp Pro Phe Ser
             65                  70                      75

Asn Lys Asn Tyr Ile His Gly Glu Leu Tyr Lys Asn Arg Val Ser
                 80                  85                  90

Ile Ser Asn Asn Ala Glu Gln Ser Asp Ala Ser Ile Thr Ile Asp
                 95                 100                 105

Gln Leu Thr Met Ala Asp Asn Gly Thr Tyr Glu Cys Ser Val Ser
                110                 115                 120

Leu Met Ser Asp Leu Glu Gly Asn Thr Lys Ser Arg Val Arg Leu
```

125                 130                 135
Leu Val Leu Val Pro Ser Lys Pro Glu Cys Gly Ile Glu Gly
                140                 145                 150
Glu Thr Ile Ile Gly Asn Asn Ile Gln Leu Thr Cys Gln Ser Lys
                155                 160                 165
Glu Gly Ser Pro Thr Pro Gln Tyr Ser Trp Lys Arg Tyr Asn Ile
                170                 175                 180
Leu Asn Gln Glu Gln Pro Leu Ala Gln Pro Ala Ser Gly Gln Pro
                185                 190                 195
Val Ser Leu Lys Asn Ile Ser Thr Asp Thr Ser Gly Tyr Tyr Ile
                200                 205                 210
Cys Thr Ser Ser Asn Glu Glu Gly Thr Gln Phe Cys Asn Ile Thr
                215                 220                 225
Val Ala Val Arg Ser Pro Ser Met Asn Val Ala Leu Tyr Val Gly
                230                 235                 240
Ile Ala Val Gly Val Val Ala Ala Leu Ile Ile Gly Ile Ile
                245                 250                 255
Ile Tyr Cys Cys Cys Cys Arg Gly Lys Asp Asp Asn Thr Glu Asp
                260                 265                 270
Lys Glu Asp Ala Arg Pro Asn Arg Glu Ala Tyr Glu Glu Pro Pro
                275                 280                 285
Glu Gln Leu Arg Glu Leu Ser Arg Glu Arg Glu Glu Asp Asp
                290                 295                 300
Tyr Arg Gln Glu Glu Gln Arg Ser Thr Gly Arg Glu Ser Pro Asp
                305                 310                 315
His Leu Asp Gln

<210> SEQ ID NO 21
<211> LENGTH: 2870
<212> TYPE: DNA
<213> ORGANISM: Homo sapiens

<400> SEQUENCE: 21

```
cgcggagccc tgcgctggga ggtgcacggt gtgcacgctg gactggaccc           50
ccatgcaacc ccgcgccctg cgccttaacc aggactgctc cgcgcgcccc          100
tgagcctcgg gctccggccc ggacctgcag cctcccaggt ggctgggaag          150
aactctccaa caataaatac atttgataag aaagatggct ttaaaagtgc          200
tactagaaca agagaaaacg tttttcactc ttttagtatt actaggctat          250
ttgtcatgta aagtgacttg tgaatcagga gactgtagac agcaagaatt          300
cagggatcgg tctggaaact gtgttccctg caaccagtgt gggccaggca          350
tggagttgtc taaggaatgt ggcttcggct atggggagga tgcacagtgt          400
gtgacgtgcc ggctgcacag gttcaaggag gactgggggct tccagaaatg          450
caagccctgt ctggactgcg cagtggtgaa ccgctttcag aaggcaaatt          500
gttcagccac cagtgatgcc atctgcgggg actgcttgcc aggatttat            550
aggaagacga aacttgtcgg ctttcaagac atggagtgtg tgccttgtgg          600
agaccctcct cctccttacg aaccgcactg tgccagcaag gtcaacctcg          650
tgaagatcgc gtccacggcc tccagcccac gggacacggc gctggctgcc          700
gttatctgca gcgctctggc caccgtcctg ctggccctgc tcatcctctg          750
tgtcatctat tgtaagagac agtttatgga gaagaaaccc agctggtctc          800
```

```
tgcggtcgca ggacattcag tacaacggct ctgagctgtc gtgttttgac        850
agacctcagc tccacgaata tgcccacaga gcctgctgcc agtgccgccg        900
tgactcagtg cagacctgcg ggccggtgcg cttgctccca tccatgtgct        950
gtgaggaggc ctgcagcccc aacccggcga ctcttggttg tggggtgcat       1000
tctgcagcca gtcttcaggc aagaaacgca ggcccagccg gggagatggt       1050
gccgactttc ttcggatccc tcacgcagtc catctgtggc gagttttcag       1100
atgcctggcc tctgatgcag aatcccatgg gtggtgacaa catctctttt       1150
tgtgactctt atcctgaact cactggagaa gacattcatt ctctcaatcc       1200
agaacttgaa agctcaacgt ctttggattc aaatagcagt caagatttgg       1250
ttggtggggc tgttccagtc cagtctcatt ctgaaaactt tacagcagct       1300
actgatttat ctagatataa caacacactg gtagaatcag catcaactca       1350
ggatgcacta actatgagaa gccagctaga tcaggagagt ggcgctgtca       1400
tccacccagc cactcagacg tccctccagg aagcttaaag aacctgcttc       1450
tttctgcagt agaagcgtgt gctggaaccc aaagagtact cctttgttag       1500
gcttatggac tgagcagtct ggaccttgca tggcttctgg ggcaaaaata       1550
aatctgaacc aaactgacgg catttgaagc ctttcagcca gttgcttctg       1600
agccagacca gctgtaagct gaaacctcaa tgaataacaa gaaaagactc       1650
caggccgact catgatactc tgcatctttc ctacatgaga agcttctctg       1700
ccacaaaagt gacttcaaag actgatgggt tgagctggca gcctatgaga       1750
ttgtggacat ataacaagaa acagaaatgc cctcatgctt attttcatgg       1800
tgattgtggt tttacaagac tgaagaccca gagtatactt tttctttcca       1850
gaaataattt cataccgcct atgaaatatc agataaatta ccttagcttt       1900
tatgtagaat gggttcaaaa gtgagtgttt ctatttgaga aggacacttt       1950
ttcatcatct aaactgattc gcataggtgg ttagaatggc cctcatattg       2000
cctgcctaaa tcttgggttt attagatgaa gtttactgaa tcagaggaat       2050
cagacagagg aggatagctc tttccagaat ccacacttct gacctcagcc       2100
tcggtctcat gaacacccgc tgatctcagg agaaacctg ggctagggaa        2150 tgtggtcgag aaagggcagc ccattgccca gaattaacac atattgtaga       2200
gacttgtatg caaaggttgg catatttata tgaaaattag ttgctataga       2250
aacatttgtt gcatctgtcc ctctgcctga gcttagaagg ttatagaaaa       2300
agggtattta taaacataaa tgacctttta cttgcattgt atcttatact       2350
aaaggcttta gaaattacaa catatcaggt tcccctacta ctgaagtagc       2400
cttccgtgag aacacaccac atgttaggac tagaagaaaa tgcacaattt       2450
gtaggggttt ggatgaagca gctgtaactg ccctagtgta gtttgaccag       2500
gacattgtcg tgctccttcc aattgtgtaa gattagttag cacatcatct       2550
cctactttag ccatccggtg ttggatttaa gaggacggtg cttctttcta       2600
ttaaagtgct ccatccccta ccatctacac attagcattg tctctagagc       2650
taagacagaa attaaccccg ttcagtcaca aagcagggaa tggttcattt       2700
actcttaatc tttatgccct ggagaagacc tacttgaaca gggcatattt       2750
tttagacttc tgaacatcag tatgttcgag ggtactatga tatttggtt        2800
```

```
tggaattgcc ctgcccaagt cactgtcttt taacttttaa actgaatatt          2850
aaaatgtatc tgtctttcct                                           2870
```

<210> SEQ ID NO 22
<211> LENGTH: 417
<212> TYPE: PRT
<213> ORGANISM: Homo sapiens

<400> SEQUENCE: 22

```
Met Ala Leu Lys Val Leu Leu Glu Gln Glu Lys Thr Phe Phe Thr
 1               5                  10                  15

Leu Leu Val Leu Leu Gly Tyr Leu Ser Cys Lys Val Thr Cys Glu
                20                  25                  30

Ser Gly Asp Cys Arg Gln Gln Glu Phe Arg Asp Arg Ser Gly Asn
                35                  40                  45

Cys Val Pro Cys Asn Gln Cys Gly Pro Gly Met Glu Leu Ser Lys
                50                  55                  60

Glu Cys Gly Phe Gly Tyr Gly Glu Asp Ala Gln Cys Val Thr Cys
                65                  70                  75

Arg Leu His Arg Phe Lys Glu Asp Trp Gly Phe Gln Lys Cys Lys
                80                  85                  90

Pro Cys Leu Asp Cys Ala Val Val Asn Arg Phe Gln Lys Ala Asn
                95                 100                 105

Cys Ser Ala Thr Ser Asp Ala Ile Cys Gly Asp Cys Leu Pro Gly
               110                 115                 120

Phe Tyr Arg Lys Thr Lys Leu Val Gly Phe Gln Asp Met Glu Cys
               125                 130                 135

Val Pro Cys Gly Asp Pro Pro Pro Tyr Glu Pro His Cys Ala
               140                 145                 150

Ser Lys Val Asn Leu Val Lys Ile Ala Ser Thr Ala Ser Ser Pro
               155                 160                 165

Arg Asp Thr Ala Leu Ala Ala Val Ile Cys Ser Ala Leu Ala Thr
               170                 175                 180

Val Leu Leu Ala Leu Leu Ile Leu Cys Val Ile Tyr Cys Lys Arg
               185                 190                 195

Gln Phe Met Glu Lys Lys Pro Ser Trp Ser Leu Arg Ser Gln Asp
               200                 205                 210

Ile Gln Tyr Asn Gly Ser Glu Leu Ser Cys Phe Asp Arg Pro Gln
               215                 220                 225

Leu His Glu Tyr Ala His Arg Ala Cys Cys Gln Cys Arg Arg Asp
               230                 235                 240

Ser Val Gln Thr Cys Gly Pro Val Arg Leu Leu Pro Ser Met Cys
               245                 250                 255

Cys Glu Glu Ala Cys Ser Pro Asn Pro Ala Thr Leu Gly Cys Gly
               260                 265                 270

Val His Ser Ala Ala Ser Leu Gln Ala Arg Asn Ala Gly Pro Ala
               275                 280                 285

Gly Glu Met Val Pro Thr Phe Phe Gly Ser Leu Thr Gln Ser Ile
               290                 295                 300

Cys Gly Glu Phe Ser Asp Ala Trp Pro Leu Met Gln Asn Pro Met
               305                 310                 315

Gly Gly Asp Asn Ile Ser Phe Cys Asp Ser Tyr Pro Glu Leu Thr
               320                 325                 330

Gly Glu Asp Ile His Ser Leu Asn Pro Glu Leu Glu Ser Ser Thr
               335                 340                 345
```

```
Ser Leu Asp Ser Asn Ser Ser Gln Asp Leu Val Gly Gly Ala Val
            350                 355                 360

Pro Val Gln Ser His Ser Glu Asn Phe Thr Ala Ala Thr Asp Leu
        365                 370                 375

Ser Arg Tyr Asn Asn Thr Leu Val Glu Ser Ala Ser Thr Gln Asp
            380                 385                 390

Ala Leu Thr Met Arg Ser Gln Leu Asp Gln Glu Ser Gly Ala Val
        395                 400                 405

Ile His Pro Ala Thr Gln Thr Ser Leu Gln Glu Ala
            410                 415

<210> SEQ ID NO 23
<211> LENGTH: 4842
<212> TYPE: DNA
<213> ORGANISM: Homo sapiens

<400> SEQUENCE: 23
```

| | | | |
|---|---|---|---|
| cgcgctcccc gcgcgcctcc tcgggctcca cgcgtcttgc cccgcagagg | | | 50 |
| cagcctcctc caggagcggg gccctgcaca ccatggcccc cgggtgggca | | | 100 |
| ggggtcggcg ccgccgtgcg cgcccgcctg gcgctggcct tggcgctggc | | | 150 |
| gagcgtcctg agtgggcctc cagccgtcgc ctgccccacc aagtgtacct | | | 200 |
| gctccgctgc cagcgtggac tgccacgggc tgggcctccg cgcggttcct | | | 250 |
| cggggcatcc cccgcaacgc tgagcgcctt gacctggaca gaaataatat | | | 300 |
| caccaggatc accaagatgg acttcgctgg gctcaagaac ctccgagtct | | | 350 |
| tgcatctgga agacaaccag gtcagcgtca tcgagagagg cgccttccag | | | 400 |
| gacctgaagc agctagagcg actgcgcctg aacaagaata gctgcaagt | | | 450 |
| ccttccagaa ttgctttttc cagagcacgc cgaagctcac cagactagatt | | | 500 |
| tgagtgaaaa ccagatccag gggatcccga ggaaggcgtt ccgcggcatc | | | 550 |
| accgatgtga agaacctgca actggacaac aaccacatca gctgcattga | | | 600 |
| agatggagcc ttccgagcgc tgcgcgattt ggagatcctt accctcaaca | | | 650 |
| acaacaacat cagtcgcatc ctggtcacca gcttcaacca catgccgaag | | | 700 |
| atccgaactc tgcgcctcca ctccaaccac ctctactgcg actgccacct | | | 750 |
| ggcctggctc tcggattggc tgcgacagcg acggacagtt ggccagttca | | | 800 |
| cactctgcat ggctcctgtg catttgaggg gcttcaacgt ggcggatgtg | | | 850 |
| cagaagaagg agtacgtgtg cccagccccc actcggagc ccccatcctg | | | 900 |
| caatgccaac tccatctcct gcccttcgcc ctgcacgtgc agcaataaca | | | 950 |
| tcgtggactg tcgaggaaag ggcttgatgg agattcctgc caacttgccg | | | 1000 |
| gagggcatcg tcgaaatacg cctagaacag aactccatca agccatccc | | | 1050 |
| tgcaggagcc ttcacccagt acaagaaact gaagcgaata gacatcagca | | | 1100 |
| agaatcagat atcggatatt gctccagatg ccttccaggg cctgaaatca | | | 1150 |
| ctcacatcgc tggtcctgta tgggaacaag atcaccgaga ttgccaaggg | | | 1200 |
| actgtttgat gggctggtgt ccctacagct gctcctcctc aatgccaaca | | | 1250 |
| agatcaactg cctgcgggtg aacacgtttc aggacctgca gaacctcaac | | | 1300 |
| ttgctctccc tgtatgacaa caagctgcag accatcagca ggggctctt | | | 1350 |
| cgccccctct gcagtccatc agacactcca cttagcccaa aacccatttg | | | 1400 |

```
tgtgcgactg ccacttgaag tggctggccg actacctcca ggacaacccc      1450
atcgagacaa gcggggcccg ctgcagcagc ccgcgccgac tcgccaacaa      1500
gcgcatcagc cagatcaaga gcaagaagtt ccgctgctca ggctccgagg      1550
attaccgcag caggttcagc agcgagtgct tcatggacct cgtgtgcccc      1600
gagaagtgtc gctgtgaggg cacgattgtg gactgctcca accagaagct      1650
ggtccgcatc ccaagccacc tccctgaata tgtcaccgac ctgcgactga      1700
atgacaatga ggtatctgtt ctggaggcca ctggcatctt caagaagttg      1750
cccaacctgc ggaaaataaa tctgagtaac aataagatca aggaggtgcg      1800
agagggagct ttcgatggag cagccagcgt gcaggagctg atgctgacag      1850
ggaaccagct ggagaccgtg cacgggcgcg tgttccgtgg cctcagtggc      1900
ctcaaaacct tgatgctgag gagtaacttg atcagctgtg tgagtaatga      1950
cacctttgcc ggcctgagtt cggtgagact gctgtccctc tatgacaatc      2000
ggatcaccac catcacccct ggggccttca ccacgcttgt ctccctgtcc      2050
accataaacc tcctgtccaa ccccttcaac tgcaactgcc acctggcctg      2100
gctcggcaag tggttgagga agaggcggat cgtcagtggg aaccctaggt      2150
gccagaagcc attttcctc aaggagattc ccatccagga tgtggccatc      2200
caggacttca cctgtgatgg caacgaggag agtagctgcc agctgagccc      2250
gcgctgcccg gagcagtgca cctgtatgga gacagtggtg cgatgcagca      2300
acaagggct ccgcgccctc cccagaggca tgcccaagga tgtgaccgag      2350
ctgtacctgg aaggaaacca cctaacagcc gtgcccagag agctgtccgc      2400
cctccgacac ctgacgctta ttgacctgag caacaacagc atcagcatgc      2450
tgaccaatta caccttcagt aacatgtctc acctctccac tctgatcctg      2500
agctacaacc ggctgaggtg catccccgtc cacgccttca cgggctgcg      2550
gtccctgcga gtgctaaccc tccatggcaa tgacatttcc agcgttcctg      2600
aaggctcctt caacgacctc acatctcttt cccatctggc gctgggaacc      2650
aacccactcc actgtgactg cagtcttcgg tggctgtcgg agtgggtgaa      2700
ggcggggtac aaggagcctg gcatcgcccg ctgcagtagc cctgagccca      2750
tggctgacag gctcctgctc accaccccaa cccaccgctt ccagtgcaaa      2800
gggccagtgg acatcaacat tgtggccaaa tgcaatgcct gcctctccag      2850
cccgtgcaag aataacggga catgcaccca ggaccctgtg gagctgtacc      2900
gctgtgcctg cccctacagc tacaagggca aggactgcac tgtgcccatc      2950
aacacctgca tccagaaccc ctgtcagcat ggaggcacct gccacctgag      3000
tgacagccac aaggatgggt tcagctgctc ctgccctctg ggctttgagg      3050
ggcagcggtg tgagatcaac ccagatgact gtgaggacaa cgactgcgaa      3100
aacaatgcca cctgcgtgga cgggatcaac aactacgtgt gtatctgtcc      3150
gcctaactac acaggtgagc tatgcgacga ggtgattgac cactgtgtgc      3200
ctgagctgaa cctctgtcag catgaggcca agtgcatccc cctggacaaa      3250
ggattcagct gcgagtgtgt ccctggctac agcgggaagc tctgtgagac      3300
agacaatgat gactgtgtgg cccacaagtg ccgccacggg gcccagtgcg      3350
tggacacaat caatggctac acatgcacct gccccccagg cttcagtgga      3400
```

| | |
|---|---|
| cccttctgtg aacaccccec acccatggtc ctactgcaga ccagcccatg | 3450 |
| cgaccagtac gagtgccaga acggggccca gtgcatcgtg gtgcagcagg | 3500 |
| agcccacctg ccgctgccca ccaggcttcg ccggcccag atgcgagaag | 3550 |
| ctcatcactg tcaacttcgt gggcaaagac tcctacgtgg aactggcctc | 3600 |
| cgccaaggtc cgaccccagg ccaacatctc cctgcaggtg gccactgaca | 3650 |
| aggacaacgg catccttctc tacaaaggag acaatgaccc cctggcactg | 3700 |
| gagctgtacc agggccacgt gcggctggtc tatgacagcc tgagttcccc | 3750 |
| tccaaccaca gtgtacagtg tggagacagt gaatgatggg cagtttcaca | 3800 |
| gtgtggagct ggtgacgcta accagaccc tgaacctagt agtggacaaa | 3850 |
| ggaactccaa agagcctggg gaagctccag aagcagccag cagtgggcat | 3900 |
| caacagcccc ctctaccttg gaggcatccc cacctccacc ggcctctccg | 3950 |
| ccttgcgcca gggcacggac cggcctctag gcggcttcca cggatgcatc | 4000 |
| catgaggtgc gcatcaacaa cgagctgcag gacttcaagg ccctcccacc | 4050 |
| acagtccctg ggggtgtcac caggctgcaa gtcctgcacc gtgtgcaagc | 4100 |
| acggcctgtg ccgctccgtg gagaaggaca gcgtggtgtg cgagtgccgc | 4150 |
| ccaggctgga ccggcccact ctgcgaccag gaggcccggg acccctgcct | 4200 |
| cggccacaga tgccaccatg gaaaatgtgt ggcaactggg acctcataca | 4250 |
| tgtgcaagtg tgccgagggc tatgaggggg acttgtgtga caacaagaat | 4300 |
| gactctgcca atgcctgctc agccttcaag tgtcaccatg ggcagtgcca | 4350 |
| catctcagac caaggggagc cctactgcct gtgccagccc ggctttagcg | 4400 |
| gcgagcactg ccaacaagag aatccgtgcc tgggacaagt agtccgagag | 4450 |
| gtgatccgcc gccagaaagg ttatgcatca tgtgccacag cctccaaggt | 4500 |
| gcccatcatg gaatgtcgtg ggggctgtgg gccccagtgc tgccagccca | 4550 |
| cccgcagcaa gcggcggaaa tacgtcttcc agtgcacgga cggctcctcg | 4600 |
| tttgtagaag aggtggagag acacttagag tgcggctgcc tcgcgtgttc | 4650 |
| ctaagcccct gccgcctgc ctgccacctc tcggactcca gcttgatgga | 4700 |
| gttgggacag ccatgtggga cccctggtg attcagcatg aaggaaatga | 4750 |
| agctggagag gaaggtaaag aagaagagaa tattaagtat attgtaaaat | 4800 |
| aaacaaaaaa tagaacttaa aaaaaaaaaa aaaaaaaaa aa | 4842 |

<210> SEQ ID NO 24
<211> LENGTH: 1523
<212> TYPE: PRT
<213> ORGANISM: Homo sapiens

<400> SEQUENCE: 24

Met Ala Pro Gly Trp Ala Gly Val Gly Ala Ala Val Arg Ala Arg
1               5                   10                  15

Leu Ala Leu Ala Leu Ala Leu Ala Ser Val Leu Ser Gly Pro Pro
                20                  25                  30

Ala Val Ala Cys Pro Thr Lys Cys Thr Cys Ser Ala Ala Ser Val
                35                  40                  45

Asp Cys His Gly Leu Gly Leu Arg Ala Val Pro Arg Gly Ile Pro
                50                  55                  60

Arg Asn Ala Glu Arg Leu Asp Leu Asp Arg Asn Asn Ile Thr Arg
                65                  70                  75

Ile Thr Lys Met Asp Phe Ala Gly Leu Lys Asn Leu Arg Val Leu
                 80                  85                  90

His Leu Glu Asp Asn Gln Val Ser Val Ile Glu Arg Gly Ala Phe
                 95                 100                 105

Gln Asp Leu Lys Gln Leu Glu Arg Leu Arg Leu Asn Lys Asn Lys
                110                 115                 120

Leu Gln Val Leu Pro Glu Leu Leu Phe Gln Ser Thr Pro Lys Leu
                125                 130                 135

Thr Arg Leu Asp Leu Ser Glu Asn Gln Ile Gln Gly Ile Pro Arg
                140                 145                 150

Lys Ala Phe Arg Gly Ile Thr Asp Val Lys Asn Leu Gln Leu Asp
                155                 160                 165

Asn Asn His Ile Ser Cys Ile Glu Asp Gly Ala Phe Arg Ala Leu
                170                 175                 180

Arg Asp Leu Glu Ile Leu Thr Leu Asn Asn Asn Asn Ile Ser Arg
                185                 190                 195

Ile Leu Val Thr Ser Phe Asn His Met Pro Lys Ile Arg Thr Leu
                200                 205                 210

Arg Leu His Ser Asn His Leu Tyr Cys Asp Cys His Leu Ala Trp
                215                 220                 225

Leu Ser Asp Trp Leu Arg Gln Arg Arg Thr Val Gly Gln Phe Thr
                230                 235                 240

Leu Cys Met Ala Pro Val His Leu Arg Gly Phe Asn Val Ala Asp
                245                 250                 255

Val Gln Lys Lys Glu Tyr Val Cys Pro Ala Pro His Ser Glu Pro
                260                 265                 270

Pro Ser Cys Asn Ala Asn Ser Ile Ser Cys Pro Ser Pro Cys Thr
                275                 280                 285

Cys Ser Asn Asn Ile Val Asp Cys Arg Gly Lys Gly Leu Met Glu
                290                 295                 300

Ile Pro Ala Asn Leu Pro Glu Gly Ile Val Glu Ile Arg Leu Glu
                305                 310                 315

Gln Asn Ser Ile Lys Ala Ile Pro Ala Gly Ala Phe Thr Gln Tyr
                320                 325                 330

Lys Lys Leu Lys Arg Ile Asp Ile Ser Lys Asn Gln Ile Ser Asp
                335                 340                 345

Ile Ala Pro Asp Ala Phe Gln Gly Leu Lys Ser Leu Thr Ser Leu
                350                 355                 360

Val Leu Tyr Gly Asn Lys Ile Thr Glu Ile Ala Lys Gly Leu Phe
                365                 370                 375

Asp Gly Leu Val Ser Leu Gln Leu Leu Leu Asn Ala Asn Lys
                380                 385                 390

Ile Asn Cys Leu Arg Val Asn Thr Phe Gln Asp Leu Gln Asn Leu
                395                 400                 405

Asn Leu Leu Ser Leu Tyr Asp Asn Lys Leu Gln Thr Ile Ser Lys
                410                 415                 420

Gly Leu Phe Ala Pro Leu Gln Ser Ile Gln Thr Leu His Leu Ala
                425                 430                 435

Gln Asn Pro Phe Val Cys Asp Cys His Leu Lys Trp Leu Ala Asp
                440                 445                 450

Tyr Leu Gln Asp Asn Pro Ile Glu Thr Ser Gly Ala Arg Cys Ser
                455                 460                 465

Ser Pro Arg Arg Leu Ala Asn Lys Arg Ile Ser Gln Ile Lys Ser

```
                    470                 475                 480
Lys Lys Phe Arg Cys Ser Gly Ser Glu Asp Tyr Arg Ser Arg Phe
                485                 490                 495
Ser Ser Glu Cys Phe Met Asp Leu Val Cys Pro Glu Lys Cys Arg
                500                 505                 510
Cys Glu Gly Thr Ile Val Asp Cys Ser Asn Gln Lys Leu Val Arg
                515                 520                 525
Ile Pro Ser His Leu Pro Glu Tyr Val Thr Asp Leu Arg Leu Asn
                530                 535                 540
Asp Asn Glu Val Ser Val Leu Glu Ala Thr Gly Ile Phe Lys Lys
                545                 550                 555
Leu Pro Asn Leu Arg Lys Ile Asn Leu Ser Asn Asn Lys Ile Lys
                560                 565                 570
Glu Val Arg Glu Gly Ala Phe Asp Gly Ala Ala Ser Val Gln Glu
                575                 580                 585
Leu Met Leu Thr Gly Asn Gln Leu Glu Thr Val His Gly Arg Val
                590                 595                 600
Phe Arg Gly Leu Ser Gly Leu Lys Thr Leu Met Leu Arg Ser Asn
                605                 610                 615
Leu Ile Ser Cys Val Ser Asn Asp Thr Phe Ala Gly Leu Ser Ser
                620                 625                 630
Val Arg Leu Leu Ser Leu Tyr Asp Asn Arg Ile Thr Thr Ile Thr
                635                 640                 645
Pro Gly Ala Phe Thr Thr Leu Val Ser Leu Ser Thr Ile Asn Leu
                650                 655                 660
Leu Ser Asn Pro Phe Asn Cys Asn Cys His Leu Ala Trp Leu Gly
                665                 670                 675
Lys Trp Leu Arg Lys Arg Arg Ile Val Ser Gly Asn Pro Arg Cys
                680                 685                 690
Gln Lys Pro Phe Phe Leu Lys Glu Ile Pro Ile Gln Asp Val Ala
                695                 700                 705
Ile Gln Asp Phe Thr Cys Asp Gly Asn Glu Glu Ser Ser Cys Gln
                710                 715                 720
Leu Ser Pro Arg Cys Pro Glu Gln Cys Thr Cys Met Glu Thr Val
                725                 730                 735
Val Arg Cys Ser Asn Lys Gly Leu Arg Ala Leu Pro Arg Gly Met
                740                 745                 750
Pro Lys Asp Val Thr Glu Leu Tyr Leu Glu Gly Asn His Leu Thr
                755                 760                 765
Ala Val Pro Arg Glu Leu Ser Ala Leu Arg His Leu Thr Leu Ile
                770                 775                 780
Asp Leu Ser Asn Asn Ser Ile Ser Met Leu Thr Asn Tyr Thr Phe
                785                 790                 795
Ser Asn Met Ser His Leu Ser Thr Leu Ile Leu Ser Tyr Asn Arg
                800                 805                 810
Leu Arg Cys Ile Pro Val His Ala Phe Asn Gly Leu Arg Ser Leu
                815                 820                 825
Arg Val Leu Thr Leu His Gly Asn Asp Ile Ser Ser Val Pro Glu
                830                 835                 840
Gly Ser Phe Asn Asp Leu Thr Ser Leu Ser His Leu Ala Leu Gly
                845                 850                 855
Thr Asn Pro Leu His Cys Asp Cys Ser Leu Arg Trp Leu Ser Glu
                860                 865                 870
```

-continued

```
Trp Val Lys Ala Gly Tyr Lys Glu Pro Gly Ile Ala Arg Cys Ser
            875                 880                 885

Ser Pro Glu Pro Met Ala Asp Arg Leu Leu Leu Thr Thr Pro Thr
            890                 895                 900

His Arg Phe Gln Cys Lys Gly Pro Val Asp Ile Asn Ile Val Ala
            905                 910                 915

Lys Cys Asn Ala Cys Leu Ser Ser Pro Cys Lys Asn Asn Gly Thr
            920                 925                 930

Cys Thr Gln Asp Pro Val Glu Leu Tyr Arg Cys Ala Cys Pro Tyr
            935                 940                 945

Ser Tyr Lys Gly Lys Asp Cys Thr Val Pro Ile Asn Thr Cys Ile
            950                 955                 960

Gln Asn Pro Cys Gln His Gly Gly Thr Cys His Leu Ser Asp Ser
            965                 970                 975

His Lys Asp Gly Phe Ser Cys Ser Cys Pro Leu Gly Phe Glu Gly
            980                 985                 990

Gln Arg Cys Glu Ile Asn Pro Asp Asp Cys Glu Asp Asn Asp Cys
            995                 1000                1005

Glu Asn Asn Ala Thr Cys Val Asp Gly Ile Asn Asn Tyr Val Cys
            1010                1015                1020

Ile Cys Pro Pro Asn Tyr Thr Gly Glu Leu Cys Asp Glu Val Ile
            1025                1030                1035

Asp His Cys Val Pro Glu Leu Asn Leu Cys Gln His Glu Ala Lys
            1040                1045                1050

Cys Ile Pro Leu Asp Lys Gly Phe Ser Cys Glu Cys Val Pro Gly
            1055                1060                1065

Tyr Ser Gly Lys Leu Cys Glu Thr Asp Asn Asp Asp Cys Val Ala
            1070                1075                1080

His Lys Cys Arg His Gly Ala Gln Cys Val Asp Thr Ile Asn Gly
            1085                1090                1095

Tyr Thr Cys Thr Cys Pro Gln Gly Phe Ser Gly Pro Phe Cys Glu
            1100                1105                1110

His Pro Pro Pro Met Val Leu Leu Gln Thr Ser Pro Cys Asp Gln
            1115                1120                1125

Tyr Glu Cys Gln Asn Gly Ala Gln Cys Ile Val Val Gln Gln Glu
            1130                1135                1140

Pro Thr Cys Arg Cys Pro Pro Gly Phe Ala Gly Pro Arg Cys Glu
            1145                1150                1155

Lys Leu Ile Thr Val Asn Phe Val Gly Lys Asp Ser Tyr Val Glu
            1160                1165                1170

Leu Ala Ser Ala Lys Val Arg Pro Gln Ala Asn Ile Ser Leu Gln
            1175                1180                1185

Val Ala Thr Asp Lys Asp Asn Gly Ile Leu Leu Tyr Lys Gly Asp
            1190                1195                1200

Asn Asp Pro Leu Ala Leu Glu Leu Tyr Gln Gly His Val Arg Leu
            1205                1210                1215

Val Tyr Asp Ser Leu Ser Ser Pro Pro Thr Thr Val Tyr Ser Val
            1220                1225                1230

Glu Thr Val Asn Asp Gly Gln Phe His Ser Val Glu Leu Val Thr
            1235                1240                1245

Leu Asn Gln Thr Leu Asn Leu Val Val Asp Lys Gly Thr Pro Lys
            1250                1255                1260

Ser Leu Gly Lys Leu Gln Lys Gln Pro Ala Val Gly Ile Asn Ser
            1265                1270                1275
```

```
Pro Leu Tyr Leu Gly Gly Ile Pro Thr Ser Thr Gly Leu Ser Ala
            1280                1285                1290

Leu Arg Gln Gly Thr Asp Arg Pro Leu Gly Gly Phe His Gly Cys
        1295                1300                1305

Ile His Glu Val Arg Ile Asn Asn Glu Leu Gln Asp Phe Lys Ala
        1310                1315                1320

Leu Pro Pro Gln Ser Leu Gly Val Ser Pro Gly Cys Lys Ser Cys
        1325                1330                1335

Thr Val Cys Lys His Gly Leu Cys Arg Ser Val Glu Lys Asp Ser
        1340                1345                1350

Val Val Cys Glu Cys Arg Pro Gly Trp Thr Gly Pro Leu Cys Asp
        1355                1360                1365

Gln Glu Ala Arg Asp Pro Cys Leu Gly His Arg Cys His His Gly
        1370                1375                1380

Lys Cys Val Ala Thr Gly Thr Ser Tyr Met Cys Lys Cys Ala Glu
        1385                1390                1395

Gly Tyr Gly Gly Asp Leu Cys Asp Asn Lys Asn Asp Ser Ala Asn
        1400                1405                1410

Ala Cys Ser Ala Phe Lys Cys His His Gly Gln Cys His Ile Ser
        1415                1420                1425

Asp Gln Gly Glu Pro Tyr Cys Leu Cys Gln Pro Gly Phe Ser Gly
        1430                1435                1440

Glu His Cys Gln Gln Glu Asn Pro Cys Leu Gly Gln Val Val Arg
        1445                1450                1455

Glu Val Ile Arg Arg Gln Lys Gly Tyr Ala Ser Cys Ala Thr Ala
        1460                1465                1470

Ser Lys Val Pro Ile Met Glu Cys Arg Gly Gly Cys Gly Pro Gln
        1475                1480                1485

Cys Cys Gln Pro Thr Arg Ser Lys Arg Arg Lys Tyr Val Phe Gln
        1490                1495                1500

Cys Thr Asp Gly Ser Ser Phe Val Glu Glu Val Glu Arg His Leu
        1505                1510                1515

Glu Cys Gly Cys Leu Ala Cys Ser
        1520

<210> SEQ ID NO 25
<211> LENGTH: 1318
<212> TYPE: DNA
<213> ORGANISM: Homo sapiens

<400> SEQUENCE: 25
cagtttcttc atctgtaaca tcaaatgaat aataatacca atctcctaga              50
cttcataaga ggattaacaa agacaaaata tgggaaaaac ataacatggc             100
gtcccataat tattagatct tattattgac actaaaatgg cattaaaatt             150
accaaaagga agacagcatc tgtttcctct ttggtcctga gctggttaaa             200
aggaacactg gttgcctgaa cagtcacact tgcaaccatg atgcctaaac             250
attgctttct aggcttcctc atcagtttct tccttactgg tgtagcagga             300
actcagtcaa cgcatgagtc tctgaagcct cagagggtac aatttcagtc             350
ccgaaatttt cacaacattt gcaatggca gcctgggagg gcacttactg              400
gcaacagcag tgtctatttt gtgcagtaca aaatcatgtt ctcatgcagc             450
atgaaaagct ctcaccagaa gccaagtgga tgctggcagc acatttcttg             500
```

```
taacttccca ggctgcagaa cattggctaa atatggacag agacaatgga         550
aaaataaaga agactgttgg ggtactcaag aactctcttg tgaccttacc         600
agtgaaacct cagacataca ggaaccttat tacgggaggg tgagggcggc         650
ctcggctggg agctactcag aatggagcat gacgccgcgg ttcactccct         700
ggtgggaaac aaaaatagat cctccagtca tgaatataac ccaagtcaat         750
ggctctttgt tggtaattct ccatgctcca aatttaccat atagatacca         800
aaaggaaaaa aatgtatcta tagaagatta ctatgaacta ctataccgag         850 ttttataat taacaattca ctagaaaagg agcaaaaggt ttatgaaggg          900
gctcacagag cggttgaaat tgaagctcta acaccacact ccagctactg         950
tgtagtggct gaaatatatc agcccatgtt agacagaaga agtcagagaa         1000
gtgaagagag atgtgtggaa attccatgac ttgtggaatt tggcattcag         1050
caatgtggaa attctaaagc tccctgagaa caggatgact cgtgtttgaa         1100
ggatcttatt taaaattgtt tttgtatttt cttaaagcaa tattcactgt         1150
tacaccttgg ggacttcttt gtttatccat tcttttatcc tttatatttc         1200
atttgtaaac tatatttgaa cgacattccc cccgaaaaat tgaaatgtaa         1250
agatgaggca gagaataaag tgttctatga aaaaaaaaa aaaaaaaaa          1300 aaaaaaaaa aaaaaaaa                                             1318

<210> SEQ ID NO 26
<211> LENGTH: 262
<212> TYPE: PRT
<213> ORGANISM: Homo sapiens

<400> SEQUENCE: 26

Met Pro Lys His Cys Phe Leu Gly Phe Leu Ile Ser Phe Phe Leu
  1               5                  10                  15

Thr Gly Val Ala Gly Thr Gln Ser Thr His Glu Ser Leu Lys Pro
                 20                  25                  30

Gln Arg Val Gln Phe Gln Ser Arg Asn Phe His Asn Ile Leu Gln
                 35                  40                  45

Trp Gln Pro Gly Arg Ala Leu Thr Gly Asn Ser Ser Val Tyr Phe
                 50                  55                  60

Val Gln Tyr Lys Ile Met Phe Ser Cys Ser Met Lys Ser Ser His
                 65                  70                  75

Gln Lys Pro Ser Gly Cys Trp Gln His Ile Ser Cys Asn Phe Pro
                 80                  85                  90

Gly Cys Arg Thr Leu Ala Lys Tyr Gly Gln Arg Gln Trp Lys Asn
                 95                 100                 105

Lys Glu Asp Cys Trp Gly Thr Gln Glu Leu Ser Cys Asp Leu Thr
                110                 115                 120

Ser Glu Thr Ser Asp Ile Gln Glu Pro Tyr Tyr Gly Arg Val Arg
                125                 130                 135

Ala Ala Ser Ala Gly Ser Tyr Ser Glu Trp Ser Met Thr Pro Arg
                140                 145                 150

Phe Thr Pro Trp Trp Glu Thr Lys Ile Asp Pro Pro Val Met Asn
                155                 160                 165

Ile Thr Gln Val Asn Gly Ser Leu Leu Val Ile Leu His Ala Pro
                170                 175                 180

Asn Leu Pro Tyr Arg Tyr Gln Lys Glu Lys Asn Val Ser Ile Glu
                185                 190                 195
```

```
Asp Tyr Tyr Glu Leu Leu Tyr Arg Val Phe Ile Ile Asn Asn Ser
            200                 205                 210

Leu Glu Lys Glu Gln Lys Val Tyr Glu Gly Ala His Arg Ala Val
            215                 220                 225

Glu Ile Glu Ala Leu Thr Pro His Ser Ser Tyr Cys Val Val Ala
            230                 235                 240

Glu Ile Tyr Gln Pro Met Leu Asp Arg Arg Ser Gln Arg Ser Glu
            245                 250                 255

Glu Arg Cys Val Glu Ile Pro
            260

<210> SEQ ID NO 27
<211> LENGTH: 3819
<212> TYPE: DNA
<213> ORGANISM: Homo sapiens

<400> SEQUENCE: 27
ggaaggggag gagcaggcca cacaggcaca ggccggtgag ggacctgccc         50
agacctggag ggtctcgctc tgtcacacag gctggagtgc agtggtgtga        100
tcttggctca tcgtaacctc cacctcccgg gttcaagtga ttctcatgcc        150
tcagcctccc gagtagctgg gattacaggt ggtgacttcc aagagtgact        200
ccgtcggagg aaaatgactc cccagtcgct gctgcagacg acactgttcc        250
tgctgagtct gctcttcctg gtccaaggtg cccacggcag gggccacagg        300
gaagactttc gcttctgcag ccagcggaac cagacacaca ggagcagcct        350
ccactacaaa cccacaccag acctgcgcat ctccatcgag aactccgaag        400
aggccctcac agtccatgcc ctttccctg cagcccaccc tgcttcccga         450
tccttccctg accccagggg cctctaccac ttctgcctct actggaaccg        500
acatgctggg agattacatc ttctctatgg caagcgtgac ttcttgctga        550
gtgacaaagc ctctagcctc tctgcttcc agcaccagga ggagagcctg         600
gctcagggcc ccccgctgtt agccacttct gtcacctcct ggtggagccc        650
tcagaacatc agcctgccca gtgccgccag cttcaccttc tccttccaca        700 gtcctccca cacggccgct cacaatgcct cggtggacat gtgcgagctc         750
aaaagggacc tccagctgct cagccagttc ctgaagcatc cccagaaggc        800
ctcaaggagg ccctcggctg cccccgccag ccagcagttg cagagcctgg        850
agtcgaaact gacctctgtg agattcatgg gggacatggt gtccttcgag        900
gaggaccgga tcaacgccac ggtgtggaag ctccagccca cagccggcct        950
ccaggacctg cacatccact cccggcagga ggaggagcag agcgagatca       1000
tggagtactc ggtgctgctg cctcgaacac tcttccagag gacgaaaggc       1050
cggagcgggg aggctgagaa gagactcctc ctggtggact tcagcagcca       1100
agccctgttc caggacaaga attccagcca agtcctgggt gagaaggtct       1150
tggggattgt ggtacagaac accaaagtag ccaacctcac ggagcccgtg       1200
gtgctcactt tccagcacca gctacagccg aagaatgtga ctctgcaatg       1250
tgtgttctgg gttgaagacc ccacattgag cagcccgggg cattggagca       1300
gtgctgggtg tgagaccgtc aggagagaaa cccaaacatc ctgcttctgc       1350
aaccacttga cctactttgc agtgctgatg gtctcctcgg tggaggtgga       1400
```

```
cgccgtgcac aagcactacc tgagcctcct ctcctacgtg ggctgtgtcg      1450
tctctgccct ggcctgcctt gtcaccattg ccgcctacct ctgctccagg      1500
gtgcccctgc cgtgcaggag gaaacctcgg gactacacca tcaaggtgca      1550
catgaacctg ctgctggccg tcttcctgct ggacacgagc ttcctgctca      1600
gcgagccggt ggccctgaca ggctctgagg ctggctgccg agccagtgcc      1650
atcttcctgc acttctccct gctcacctgc ctttcctgga tgggcctcga      1700
ggggtacaac ctctaccgac tcgtggtgga ggtcttggc acctatgtcc       1750 ctggctacct actcaagctg agcgccatgg gctggggctt ccccatcttt      1800
ctggtgacgc tggtggccct ggtggatgtg acaactatg gccccatcat       1850 cttggctgtg cataggactc cagagggcgt catctaccct tccatgtgct      1900
ggatccggga ctccctggtc agctacatca ccaacctggg cctcttcagc      1950
ctggtgtttc tgttcaacat ggccatgcta gccaccatgg tggtgcagat      2000
cctgcggctg cgccccaca cccaaaagtg gtcacatgtg ctgacactgc       2050
tgggcctcag cctggtcctt ggcctgccct gggccttgat cttcttctcc      2100
tttgcttctg gcaccttcca gcttgtcgtc ctctacctt tcagcatcat       2150 cacctccttc caaggcttcc tcatcttcat ctggtactgg tccatgcggc      2200
tgcaggcccg gggtggcccc tccctctga agagcaactc agacagcgcc       2250
aggctcccca tcagctcggg cagcacctcg tccagccgca tctaggcctc      2300
cagcccacct gcccatgtga tgaagcagag atgcggcctc gtcgcacact      2350
gcctgtggcc cccgagccag gcccagcccc aggccagtca gccgcagact      2400
ttggaaagcc caacgaccat ggagagatgg gccgttgcca tggtggacgg      2450
actcccgggc tgggcttttg aattggcctt ggggactact cggctctcac      2500
tcagctccca cgggactcag aagtgcgccg ccatgctgcc tagggtactg      2550
tccccacatc tgtcccaacc cagctggagg cctggtctct ccttacaacc      2600
cctgggccca ccctcattg ctgggggcca ggccttggat cttgagggtc       2650
tggcacatcc ttaatcctgt gccctgcct gggacagaaa tgtggctcca       2700
gttgctctgt ctctcgtggt caccctgagg gcactctgca tcctctgtca      2750
ttttaacctc aggtggcacc cagggcgaat ggggcccagg gcagaccttc      2800
agggccagag ccctggcgga ggagaggcc tttgccagga gcacagcagc       2850
agctcgccta cctctgagcc caggcccct ccctccctca gccccccagt       2900
cctccctcca tcttccctgg ggttctcctc ctctcccagg gcctccttgc      2950
tccttcgttc acagctgggg gtccccgatt ccaatgctgt tttttgggga      3000
gtggtttcca ggagctgcct ggtgtctgct gtaaatgttt gtctactgca      3050
caagcctcgg cctgcccctg agccaggctc ggtaccgatg cgtgggctgg      3100
gctaggtccc tctgtccatc tgggcctttg tatgagctgc attgcccttg      3150
ctcaccctga ccaagcacac gcctcagagg ggccctcagc ctctcctgaa      3200
gccctcttgt ggcaagaact gtggaccatg ccagtcccgt ctggtttcca      3250
tcccaccact ccaaggactg agactgacct cctctggtga cactggccta      3300
gagcctgaca ctctcctaag aggttctctc caagcccca aatagctcca       3350 ggcgccctcg gccgcccatc atggttaatt ctgtccaaca aacacacacg      3400
```

-continued

| | |
|---|---|
| ggtagattgc tggcctgttg taggtggtag ggacacagat gaccgacctg | 3450 |
| gtcactcctc ctgccaacat tcagtctggt atgtgaggcg tgcgtgaagc | 3500 |
| aagaactcct ggagctacag ggacagggag ccatcattcc tgcctgggaa | 3550 |
| tcctggaaga cttcctgcag gagtcagcgt tcaatcttga ccttgaagat | 3600 |
| gggaaggatg ttcttttac gtaccaattc ttttgtcttt tgatattaaa | 3650 |
| aagaagtaca tgttcattgt agagaatttg gaaactgtag aagagaatca | 3700 |
| agaagaaaaa taaaaatcag ctgttgtaat cgcctagcaa aaaaaaaaa | 3750 |
| aaaaaaaaaa aaaaaaaaaa aaaaaaaaaa aaaaaaaaaa aaaaaaaaaa | 3800 |
| aaaaaaaaaa  aaaaaaaaa | 3819 |

<210> SEQ ID NO 28
<211> LENGTH: 693
<212> TYPE: PRT
<213> ORGANISM: Homo sapiens

<400> SEQUENCE: 28

```
Met Thr Pro Gln Ser Leu Leu Gln Thr Thr Leu Phe Leu Leu Ser
 1               5                  10                  15

Leu Leu Phe Leu Val Gln Gly Ala His Gly Arg Gly His Arg Glu
                20                  25                  30

Asp Phe Arg Phe Cys Ser Gln Arg Asn Gln Thr His Arg Ser Ser
                35                  40                  45

Leu His Tyr Lys Pro Thr Pro Asp Leu Arg Ile Ser Ile Glu Asn
                50                  55                  60

Ser Glu Glu Ala Leu Thr Val His Ala Pro Phe Pro Ala Ala His
                65                  70                  75

Pro Ala Ser Arg Ser Phe Pro Asp Pro Arg Gly Leu Tyr His Phe
                80                  85                  90

Cys Leu Tyr Trp Asn Arg His Ala Gly Arg Leu His Leu Leu Tyr
                95                  100                 105

Gly Lys Arg Asp Phe Leu Leu Ser Asp Lys Ala Ser Ser Leu Leu
                110                 115                 120

Cys Phe Gln His Gln Glu Glu Ser Leu Ala Gln Gly Pro Pro Leu
                125                 130                 135

Leu Ala Thr Ser Val Thr Ser Trp Trp Ser Pro Gln Asn Ile Ser
                140                 145                 150

Leu Pro Ser Ala Ala Ser Phe Thr Phe Ser Phe His Ser Pro Pro
                155                 160                 165

His Thr Ala Ala His Asn Ala Ser Val Asp Met Cys Glu Leu Lys
                170                 175                 180

Arg Asp Leu Gln Leu Leu Ser Gln Phe Leu Lys His Pro Gln Lys
                185                 190                 195

Ala Ser Arg Arg Pro Ser Ala Ala Pro Ala Ser Gln Gln Leu Gln
                200                 205                 210

Ser Leu Glu Ser Lys Leu Thr Ser Val Arg Phe Met Gly Asp Met
                215                 220                 225

Val Ser Phe Glu Glu Asp Arg Ile Asn Ala Thr Val Trp Lys Leu
                230                 235                 240

Gln Pro Thr Ala Gly Leu Gln Asp Leu His Ile His Ser Arg Gln
                245                 250                 255

Glu Glu Glu Gln Ser Glu Ile Met Glu Tyr Ser Val Leu Leu Pro
                260                 265                 270
```

-continued

```
Arg Thr Leu Phe Gln Arg Thr Lys Gly Arg Ser Gly Glu Ala Glu
                275                 280                 285
Lys Arg Leu Leu Leu Val Asp Phe Ser Ser Gln Ala Leu Phe Gln
            290                 295                 300
Asp Lys Asn Ser Ser Gln Val Leu Gly Glu Lys Val Leu Gly Ile
        305                 310                 315
Val Val Gln Asn Thr Lys Val Ala Asn Leu Thr Glu Pro Val Val
    320                 325                 330
Leu Thr Phe Gln His Gln Leu Gln Pro Lys Asn Val Thr Leu Gln
        335                 340                 345
Cys Val Phe Trp Val Glu Asp Pro Thr Leu Ser Ser Pro Gly His
        350                 355                 360
Trp Ser Ser Ala Gly Cys Glu Thr Val Arg Arg Glu Thr Gln Thr
        365                 370                 375
Ser Cys Phe Cys Asn His Leu Thr Tyr Phe Ala Val Leu Met Val
        380                 385                 390
Ser Ser Val Glu Val Asp Ala Val His Lys His Tyr Leu Ser Leu
        395                 400                 405
Leu Ser Tyr Val Gly Cys Val Ser Ala Leu Ala Cys Leu Val
        410                 415                 420
Thr Ile Ala Ala Tyr Leu Cys Ser Arg Val Pro Leu Pro Cys Arg
        425                 430                 435
Arg Lys Pro Arg Asp Tyr Thr Ile Lys Val His Met Asn Leu Leu
        440                 445                 450
Leu Ala Val Phe Leu Leu Asp Thr Ser Phe Leu Leu Ser Glu Pro
        455                 460                 465
Val Ala Leu Thr Gly Ser Glu Ala Gly Cys Arg Ala Ser Ala Ile
        470                 475                 480
Phe Leu His Phe Ser Leu Leu Thr Cys Leu Ser Trp Met Gly Leu
        485                 490                 495
Glu Gly Tyr Asn Leu Tyr Arg Leu Val Val Glu Val Phe Gly Thr
        500                 505                 510
Tyr Val Pro Gly Tyr Leu Leu Lys Leu Ser Ala Met Gly Trp Gly
        515                 520                 525
Phe Pro Ile Phe Leu Val Thr Leu Val Ala Leu Val Asp Val Asp
        530                 535                 540
Asn Tyr Gly Pro Ile Ile Leu Ala Val His Arg Thr Pro Glu Gly
        545                 550                 555
Val Ile Tyr Pro Ser Met Cys Trp Ile Arg Asp Ser Leu Val Ser
        560                 565                 570
Tyr Ile Thr Asn Leu Gly Leu Phe Ser Leu Val Phe Leu Phe Asn
        575                 580                 585
Met Ala Met Leu Ala Thr Met Val Val Gln Ile Leu Arg Leu Arg
        590                 595                 600
Pro His Thr Gln Lys Trp Ser His Val Leu Thr Leu Gly Leu
        605                 610                 615
Ser Leu Val Leu Gly Leu Pro Trp Ala Leu Ile Phe Phe Ser Phe
        620                 625                 630
Ala Ser Gly Thr Phe Gln Leu Val Val Leu Tyr Leu Phe Ser Ile
        635                 640                 645
Ile Thr Ser Phe Gln Gly Phe Leu Ile Phe Ile Trp Tyr Trp Ser
        650                 655                 660
Met Arg Leu Gln Ala Arg Gly Gly Pro Ser Pro Leu Lys Ser Asn
        665                 670                 675
```

```
Ser Asp Ser Ala Arg Leu Pro Ile Ser Ser Gly Ser Thr Ser Ser
            680                 685                 690

Ser Arg Ile

<210> SEQ ID NO 29
<211> LENGTH: 6220
<212> TYPE: DNA
<213> ORGANISM: Homo sapiens

<400> SEQUENCE: 29
tgtgcagaat tgtacagttg cgaaaccatg tcgctggcag ctggtgctgg        50
cggtggagac ttccctgtgc ggtgctcagt gcatctgcac ccgtggggga       100
gggagctctt tctctggccc tgcagtcacc tgaggttgtt accattatga       150
acggccgctg ggaccccgc atgtgcatgt actccccag agtgtccggg         200 ggccccagcc aagggacaca tctcacgcag ctgggaacat gtgcaggctg       250
atgaagagaa ccggatgagg gcttcacatg aggaagcatg tggccaggtc       300
ctctcagaac atcagcctca tcttcctgtc tctgatctat ttcaccaacc       350
accccatgtg tctctagaac cccagtgtag cgagctggag agaggactgt       400
cctgagggca gcaggcctgg ttgcagctgg cgtgggggtc tcagaatgga       450
gccctcagcc ctgaggaaag ctggctcgga gcaggaggag ggctttgagg       500
ggctgcccag aagggtcact gacctgggga tggtctccaa tctccggcgc       550
agcaacagca gcctcttcaa gagctggagg ctacagtgcc ccttcggcaa       600
caatgacaag caagaaagcc tcagttcgtg gattcctgaa acatcaaga        650 agaaagaatg cgtgtatttt gtggaaagtt ccaaactgtc tgatgctggg       700
aaggtggtgt gtcagtgtgg ctacacgcat gagcagcact tggaggaggc       750
taccaagccc cacaccttcc agggcacaca gtgggaccca agaaacatg        800 tccaggagat gccaaccgat gccttggcg acatcgtctt cacgggcctg        850
agccagaagg tgaaaaagta cgtccgagtc tcccaggaca cgccctccag       900
cgtgatctac cacctcatga cccagcactg ggggctggac gtccccaatc       950
tcttgatctc ggtgaccggg ggggccaaga acttcaacat gaagccgcgg       1000
ctgaagagca ttttccgcag aggcctggtc aaggtggctc agaccacagg       1050
ggcctggatc atcacagggg ggtcccacac cggcgtcatg aagcaggtag       1100
gcgaggcggt gcgggacttc agcctgagca gcagctacaa ggaaggcgag       1150
ctcatcacca tcgagtcgc cacctggggc actgtccacc gccgcgaggg       1200
cctgatccat cccacgggca gcttccccgc cgagtacata ctggatgagg       1250
atggccaagg gaacctgacc tgcctagaca gcaaccactc tcacttcatc       1300
ctcgtggacg acgggaccca cggccagtac ggggtggaga ttcctctgag       1350
gaccaggctg gagaagttca tatcggagca gaccaaggaa agaggaggtg       1400
tggccatcaa gatccccatc gtgtgcgtgg tgctggaggg cggcccgggc       1450
acgttgcaca ccatcgacaa cgccaccacc aacggcaccc cctgtgtggt       1500
tgtggagggc tcgggccgcg tggccgacgt cattgcccag gtggccaacc       1550
tgcctgtctc ggacatcact atctccctga tccagcagaa actgagcgtg       1600
ttcttccagg agatgtttga gaccttcacg gaaagcagga ttgtcgagtg       1650
```

```
gaccaaaaag atccaagata ttgtccggag gcggcagctg ctgactgtct      1700
tccgggaagg caaggatggt cagcaggacg tggatgtggc catcttgcag      1750
gccttgctga aagcctcacg gagccaagac cactttggcc acgagaactg      1800
ggaccaccag ctgaaactgg cagtggcatg gaatcgcgtg acattgccc       1850 gcagtgagat cttcatggat gagtggcagt ggaagccttc agatctgcac      1900
cccacgatga cagctgcact catctccaac aagcctgagt tgtgaagct       1950 cttcctggaa aacggggtgc agctgaagga gtttgtcacc tgggacacct      2000
tgctctacct gtacgagaac ctggacccct cctgcctgtt ccacagcaag      2050
ctgcaaaagg tgctggtgga ggatcccgag cgcccggctt gcgcgcccgc      2100
ggcgccccgc ctgcagatgc accacgtggc ccaggtgctg cggagctgc       2150 tgggggactt cacgcagccg ctttatcccc ggccccggca caacgaccgg      2200
ctgcggctcc tgctgcccgt tccccacgtc aagctcaacg tgcagggagt      2250
gagcctccgg tccctctaca gcgttcctc aggccatgtg accttcacca       2300
tggaccccat ccgtgacctt ctcatttggg ccattgtcca gaaccgtcgg      2350
gagctggcag gaatcatctg ggctcagagc caggactgca tcgcagcggc      2400
cttggcctgc agcaagatcc tgaaggaact gtccaaggag gaggaggaca      2450
cggacagctc ggaggagatg ctggcgctgg cggaggagta tgagcacaga      2500
gccatcgggg tcttcaccga gtgctaccgg aaggacgaag agagagccca      2550
gaaactgctc acccgcgtgt ccgaggcctg ggggaagacc acctgcctgc      2600
agctcgccct ggaggccaag gacatgaagt ttgtgtctca cggggggcatc     2650 caggccttcc tgaccaaggt gtggtgggc cagctctccg tggacaatgg       2700
gctgtggcgt gtgaccctgt gcatgctggc ctcccgctg ctcctcaccg       2750 gcctcatctc cttcagggag aagaggctgc aggatgtggg cacccccgcg      2800
gcccgcgccc gtgccttctt caccgcaccc gtggtggtct tccacctgaa      2850
catcctctcc tacttcgcct tcctctgcct gttcgcctac gtgctcatgg      2900
tggacttcca gcctgtgccc tcctggtgcg agtgtgccat ctacctctgg      2950
ctcttctcct tggtgtgcga ggagatgcgg cagctcttct atgaccctga      3000
cgagtgcggg ctgatgaaga aggcagcctt gtacttcagt gacttctgga      3050
ataagctgga cgtcggcgca atcttgctct tcgtggcagg gctgacctgc      3100
aggctcatcc cggcgacgct gtaccccggg cgcgtcatcc tctctctgga      3150
cttcatcctg ttctgcctcc ggctcatgca cattttacc atcagtaaga       3200 cgctggggcc caagatcatc attgtgaagc ggatgatgaa ggacgtcttc      3250
ttcttcctct tcctgctggc tgtgtgggtg tgtccttcg gggtggccaa       3300 gcaggccatc ctcatccaca acgagcgccg ggtggactgg ctgttccgag      3350
gggccgtcta ccactcctac ctcaccatct tcgggcagat cccgggctac      3400
atcgacggtg tgaacttcaa cccggagcac tgcagcccca tggcaccga      3450 cccctacaag cctaagtgcc ccgagagcga cgcgacgcag cagaggccgg      3500
ccttccctga gtggctgacg gtcctcctac tctgcctcta cctgctcttc      3550
accaacatcc tgctgctcaa cctcctcatc gccatgttca actacacctt      3600
ccagcaggtg caggagcaca cggaccagat ttggaagttc cagcgccatg      3650
```

-continued

```
acctgatcga ggagtaccac ggccgccccg ccgcgccgcc cccttcatc    3700
ctcctcagcc acctgcagct cttcatcaag agggtggtcc tgaagactcc    3750
ggccaagagg cacaagcagc tcaagaacaa gctggagaag aacgaggagg    3800
cggccctgct atcctgggag atctacctga aggagaacta cctccagaac    3850
cgacagttcc agcaaaagca gcggcccgag cagaagatcg aggacatcag    3900
caataaggtt gacgccatgg tggacctgct ggacctggac ccactgaaga    3950
ggtcgggctc catggagcag aggttggcct ccctggagga gcaggtggcc    4000
cagacagccc gagccctgca ctggatcgtg aggacgctgc gggccagcgg    4050
cttcagctcg gaggcggacg tccccactct ggcctcccag aaggccgcgg    4100
aggagccgga tgctgagccg ggaggcagga agaagacgga ggagccgggc    4150
gacagctacc acgtgaatgc ccggcacctc ctctacccca actgccctgt    4200
cacgcgcttc cccgtgccca acgagaaggt gccctgggag acggagttcc    4250
tgatctatga cccacccttt tacacggcag agaggaagga cgcggccgcc    4300
atggacccca tgggagacac cctggagcca ctgtccacga tccagtacaa    4350
cgtggtggat ggcctgaggg accgccggag cttccacggg ccgtacacag    4400
tgcaggccgg gttgccctg aaccccatgg gccgcacagg actgcgtggg     4450
cgcgggagcc tcagctgctt cggacccaac cacacgctgt accccatggt    4500
cacgcggtgg aggcggaacg aggatggagc catctgcagg aagagcataa    4550
agaagatgct ggaagtgctg gtggtgaagc tccctctctc cgagcactgg    4600
gccctgcctg ggggctcccg ggagccaggg gagatgctac ctcggaagct    4650
gaagcggatc ctccggcagg agcactggcc gtctttgaa aacttgctga     4700
agtgcggcat ggaggtgtac aaaggctaca tggatgaccc gaggaacacg    4750
gacaatgcct ggatcgagac ggtggccgtc agcgtccact ccaggacca    4800
gaatgacgtg gagctgaaca ggctgaactc taacctgcac gcctgcgact    4850
cgggggcctc catccgatgg caggtggtgg acaggcgcat cccactctat    4900
gcgaaccaca gaccctcct ccagaaggca gccgctgagt tcggggctca     4950
ctactgactg tgccctcagg ctgggcggct ccagtccata gacgttcccc    5000
ccagaaacca gggcttctct ctcctgagcc tggccaggac tcaggctgtt    5050
cctgggccct gcacatgatg gggtttggtg gacccagtgc ccctcacggc    5100
tgccgcaagt ctgctgcaga tgacctcatg aactggaagg ggtcaaggtg    5150
acccgggagg agagctcaag acagggcaca ggctactcag agctgagggg    5200
cccctgggac ccttggccat caggcgaggg gctgggcctg tgcagctggg    5250
cccttggcca gagtccactc ccttcctggc tgtgtcaccc cgagcagctc    5300
atccaccatg gaggtcattg gcctgaggca agttccccgg agagtcggga    5350
tccctgtgg ccccctcagg cctatgtctg tgaggaaggg gccctgccac      5400
tctccccaag agggcctcca tgtttcgagg tgcctcaaca tggagccttg    5450
cctgcctgg gctaggggca ctgtctgaac tcctgactgt caggataaac      5500
tccgtggggg tacaggagcc cagacaaagc ccaggcctgt caagagacgc    5550
agagggcccc tgccagggtt ggccccaggg accctgggac gaggctgcag    5600
aagctctccc tccctactcc ctgggagcca cgtgctggcc atgtggccag    5650
```

```
ggacggcatg agcaggaggc ggggacgtgg gggccttctg gtttggtgtc          5700
aacagctcac aggagcgtga accatgaggg ccctcaggag gggaacgtgg          5750
taaaacccaa gacattaaat ctgccatctc aggcctggct ggctcttctg          5800
tgctttccac aaataaagtt cctgacacgt ccagggccag gggctgtgtg          5850
acggctgcct gaagttctcc tcgatccccc ggtgagcttc ctgcagcctg          5900
tggatgtcct gcagcccctc agccctaccc ccaagtttct cctctgaccc          5950
atcagctccc tgtcttcatt ttcctaaacc tgggctccag catcgtcccc          6000
aagcccacca ggccaggatg caggcatcca catgccctcc tccttggctt          6050
cccctgcgtg gtggtgccaa tgtgccctgg caccccctgca gaggctccgg         6100 atggagcctg gggctgcctg gccactgagc actggccgag gtgatgccca          6150
cccttccctg gacaggcctc tgtcttccac ctgacccaaa gctctctagc          6200
cacccccttg tccccagtat                                          6220
```

<210> SEQ ID NO 30
<211> LENGTH: 1503
<212> TYPE: PRT
<213> ORGANISM: Homo sapiens

<400> SEQUENCE: 30

```
Met Glu Pro Ser Ala Leu Arg Lys Ala Gly Ser Glu Gln Glu Glu
 1               5                  10                  15

Gly Phe Glu Gly Leu Pro Arg Arg Val Thr Asp Leu Gly Met Val
                20                  25                  30

Ser Asn Leu Arg Arg Ser Asn Ser Ser Leu Phe Lys Ser Trp Arg
                35                  40                  45

Leu Gln Cys Pro Phe Gly Asn Asn Asp Lys Gln Glu Ser Leu Ser
                50                  55                  60

Ser Trp Ile Pro Glu Asn Ile Lys Lys Lys Cys Val Tyr Phe
                65                  70                  75

Val Glu Ser Ser Lys Leu Ser Asp Ala Gly Lys Val Val Cys Gln
                80                  85                  90

Cys Gly Tyr Thr His Glu Gln His Leu Glu Glu Ala Thr Lys Pro
                95                 100                 105

His Thr Phe Gln Gly Thr Gln Trp Asp Pro Lys Lys His Val Gln
               110                 115                 120

Glu Met Pro Thr Asp Ala Phe Gly Asp Ile Val Phe Thr Gly Leu
               125                 130                 135

Ser Gln Lys Val Lys Lys Tyr Val Arg Val Ser Gln Asp Thr Pro
               140                 145                 150

Ser Ser Val Ile Tyr His Leu Met Thr Gln His Trp Gly Leu Asp
               155                 160                 165

Val Pro Asn Leu Leu Ile Ser Val Thr Gly Gly Ala Lys Asn Phe
               170                 175                 180

Asn Met Lys Pro Arg Leu Lys Ser Ile Phe Arg Arg Gly Leu Val
               185                 190                 195

Lys Val Ala Gln Thr Thr Gly Ala Trp Ile Ile Thr Gly Gly Ser
               200                 205                 210

His Thr Gly Val Met Lys Gln Val Gly Glu Ala Val Arg Asp Phe
               215                 220                 225

Ser Leu Ser Ser Ser Tyr Lys Glu Gly Glu Leu Ile Thr Ile Gly
               230                 235                 240
```

-continued

```
Val Ala Thr Trp Gly Thr Val His Arg Arg Glu Gly Leu Ile His
                245                 250                 255

Pro Thr Gly Ser Phe Pro Ala Glu Tyr Ile Leu Asp Glu Asp Gly
                260                 265                 270

Gln Gly Asn Leu Thr Cys Leu Asp Ser Asn His Ser His Phe Ile
                275                 280                 285

Leu Val Asp Asp Gly Thr His Gly Gln Tyr Gly Val Glu Ile Pro
                290                 295                 300

Leu Arg Thr Arg Leu Glu Lys Phe Ile Ser Glu Gln Thr Lys Glu
                305                 310                 315

Arg Gly Gly Val Ala Ile Lys Ile Pro Ile Val Cys Val Val Leu
                320                 325                 330

Glu Gly Gly Pro Gly Thr Leu His Thr Ile Asp Asn Ala Thr Thr
                335                 340                 345

Asn Gly Thr Pro Cys Val Val Glu Gly Ser Gly Arg Val Ala
                350                 355                 360

Asp Val Ile Ala Gln Val Ala Asn Leu Pro Val Ser Asp Ile Thr
                365                 370                 375

Ile Ser Leu Ile Gln Gln Lys Leu Ser Val Phe Phe Gln Glu Met
                380                 385                 390

Phe Glu Thr Phe Thr Glu Ser Arg Ile Val Glu Trp Thr Lys Lys
                395                 400                 405

Ile Gln Asp Ile Val Arg Arg Arg Gln Leu Leu Thr Val Phe Arg
                410                 415                 420

Glu Gly Lys Asp Gly Gln Gln Asp Val Asp Val Ala Ile Leu Gln
                425                 430                 435

Ala Leu Leu Lys Ala Ser Arg Ser Gln Asp His Phe Gly His Glu
                440                 445                 450

Asn Trp Asp His Gln Leu Lys Leu Ala Val Ala Trp Asn Arg Val
                455                 460                 465

Asp Ile Ala Arg Ser Glu Ile Phe Met Asp Glu Trp Gln Trp Lys
                470                 475                 480

Pro Ser Asp Leu His Pro Thr Met Thr Ala Ala Leu Ile Ser Asn
                485                 490                 495

Lys Pro Glu Phe Val Lys Leu Phe Leu Glu Asn Gly Val Gln Leu
                500                 505                 510

Lys Glu Phe Val Thr Trp Asp Thr Leu Leu Tyr Leu Tyr Glu Asn
                515                 520                 525

Leu Asp Pro Ser Cys Leu Phe His Ser Lys Leu Gln Lys Val Leu
                530                 535                 540

Val Glu Asp Pro Glu Arg Pro Ala Cys Ala Pro Ala Ala Pro Arg
                545                 550                 555

Leu Gln Met His His Val Ala Gln Val Leu Arg Glu Leu Leu Gly
                560                 565                 570

Asp Phe Thr Gln Pro Leu Tyr Pro Arg Pro Arg His Asn Asp Arg
                575                 580                 585

Leu Arg Leu Leu Leu Pro Val Pro His Val Lys Leu Asn Val Gln
                590                 595                 600

Gly Val Ser Leu Arg Ser Leu Tyr Lys Arg Ser Ser Gly His Val
                605                 610                 615

Thr Phe Thr Met Asp Pro Ile Arg Asp Leu Leu Ile Trp Ala Ile
                620                 625                 630

Val Gln Asn Arg Arg Glu Leu Ala Gly Ile Ile Trp Ala Gln Ser
                635                 640                 645
```

```
Gln Asp Cys Ile Ala Ala Leu Ala Cys Ser Lys Ile Leu Lys
            650                 655                 660

Glu Leu Ser Lys Glu Glu Asp Thr Asp Ser Ser Glu Glu Met
            665                 670                 675

Leu Ala Leu Ala Glu Glu Tyr Glu His Arg Ala Ile Gly Val Phe
            680                 685                 690

Thr Glu Cys Tyr Arg Lys Asp Glu Glu Arg Ala Gln Lys Leu Leu
            695                 700                 705

Thr Arg Val Ser Glu Ala Trp Gly Lys Thr Thr Cys Leu Gln Leu
            710                 715                 720

Ala Leu Glu Ala Lys Asp Met Lys Phe Val Ser His Gly Gly Ile
            725                 730                 735

Gln Ala Phe Leu Thr Lys Val Trp Trp Gly Gln Leu Ser Val Asp
            740                 745                 750

Asn Gly Leu Trp Arg Val Thr Leu Cys Met Leu Ala Phe Pro Leu
            755                 760                 765

Leu Leu Thr Gly Leu Ile Ser Phe Arg Glu Lys Arg Leu Gln Asp
            770                 775                 780

Val Gly Thr Pro Ala Ala Arg Ala Arg Ala Phe Phe Thr Ala Pro
            785                 790                 795

Val Val Val Phe His Leu Asn Ile Leu Ser Tyr Phe Ala Phe Leu
            800                 805                 810

Cys Leu Phe Ala Tyr Val Leu Met Val Asp Phe Gln Pro Val Pro
            815                 820                 825

Ser Trp Cys Glu Cys Ala Ile Tyr Leu Trp Leu Phe Ser Leu Val
            830                 835                 840

Cys Glu Glu Met Arg Gln Leu Phe Tyr Asp Pro Asp Glu Cys Gly
            845                 850                 855

Leu Met Lys Lys Ala Ala Leu Tyr Phe Ser Asp Phe Trp Asn Lys
            860                 865                 870

Leu Asp Val Gly Ala Ile Leu Leu Phe Val Ala Gly Leu Thr Cys
            875                 880                 885

Arg Leu Ile Pro Ala Thr Leu Tyr Pro Gly Arg Val Ile Leu Ser
            890                 895                 900

Leu Asp Phe Ile Leu Phe Cys Leu Arg Leu Met His Ile Phe Thr
            905                 910                 915

Ile Ser Lys Thr Leu Gly Pro Lys Ile Ile Val Lys Arg Met
            920                 925                 930

Met Lys Asp Val Phe Phe Leu Phe Leu Leu Ala Val Trp Val
            935                 940                 945

Val Ser Phe Gly Val Ala Lys Gln Ala Ile Leu Ile His Asn Glu
            950                 955                 960

Arg Arg Val Asp Trp Leu Phe Arg Gly Ala Val Tyr His Ser Tyr
            965                 970                 975

Leu Thr Ile Phe Gly Gln Ile Pro Gly Tyr Ile Asp Gly Val Asn
            980                 985                 990

Phe Asn Pro Glu His Cys Ser Pro Asn Gly Thr Asp Pro Tyr Lys
            995                 1000                1005

Pro Lys Cys Pro Glu Ser Asp Ala Thr Gln Gln Arg Pro Ala Phe
            1010                1015                1020

Pro Glu Trp Leu Thr Val Leu Leu Leu Cys Leu Tyr Leu Leu Phe
            1025                1030                1035

Thr Asn Ile Leu Leu Leu Asn Leu Leu Ile Ala Met Phe Asn Tyr
```

-continued

```
                1040                1045                1050
Thr Phe Gln Gln Val Gln Glu His Thr Asp Gln Ile Trp Lys Phe
                1055                1060                1065
Gln Arg His Asp Leu Ile Glu Glu Tyr His Gly Arg Pro Ala Ala
                1070                1075                1080
Pro Pro Pro Phe Ile Leu Leu Ser His Leu Gln Leu Phe Ile Lys
                1085                1090                1095
Arg Val Val Leu Lys Thr Pro Ala Lys Arg His Lys Gln Leu Lys
                1100                1105                1110
Asn Lys Leu Glu Lys Asn Glu Glu Ala Ala Leu Leu Ser Trp Glu
                1115                1120                1125
Ile Tyr Leu Lys Glu Asn Tyr Leu Gln Asn Arg Gln Phe Gln Gln
                1130                1135                1140
Lys Gln Arg Pro Glu Gln Lys Ile Glu Asp Ile Ser Asn Lys Val
                1145                1150                1155
Asp Ala Met Val Asp Leu Leu Asp Leu Asp Pro Leu Lys Arg Ser
                1160                1165                1170
Gly Ser Met Glu Gln Arg Leu Ala Ser Leu Glu Glu Gln Val Ala
                1175                1180                1185
Gln Thr Ala Arg Ala Leu His Trp Ile Val Arg Thr Leu Arg Ala
                1190                1195                1200
Ser Gly Phe Ser Ser Glu Ala Asp Val Pro Thr Leu Ala Ser Gln
                1205                1210                1215
Lys Ala Ala Glu Glu Pro Asp Ala Glu Pro Gly Gly Arg Lys Lys
                1220                1225                1230
Thr Glu Glu Pro Gly Asp Ser Tyr His Val Asn Ala Arg His Leu
                1235                1240                1245
Leu Tyr Pro Asn Cys Pro Val Thr Arg Phe Pro Val Pro Asn Glu
                1250                1255                1260
Lys Val Pro Trp Glu Thr Glu Phe Leu Ile Tyr Asp Pro Pro Phe
                1265                1270                1275
Tyr Thr Ala Glu Arg Lys Asp Ala Ala Ala Met Asp Pro Met Gly
                1280                1285                1290
Asp Thr Leu Glu Pro Leu Ser Thr Ile Gln Tyr Asn Val Val Asp
                1295                1300                1305
Gly Leu Arg Asp Arg Arg Ser Phe His Gly Pro Tyr Thr Val Gln
                1310                1315                1320
Ala Gly Leu Pro Leu Asn Pro Met Gly Arg Thr Gly Leu Arg Gly
                1325                1330                1335
Arg Gly Ser Leu Ser Cys Phe Gly Pro Asn His Thr Leu Tyr Pro
                1340                1345                1350
Met Val Thr Arg Trp Arg Arg Asn Glu Asp Gly Ala Ile Cys Arg
                1355                1360                1365
Lys Ser Ile Lys Lys Met Leu Glu Val Leu Val Val Lys Leu Pro
                1370                1375                1380
Leu Ser Glu His Trp Ala Leu Pro Gly Gly Ser Arg Glu Pro Gly
                1385                1390                1395
Glu Met Leu Pro Arg Lys Leu Lys Arg Ile Leu Arg Gln Glu His
                1400                1405                1410
Trp Pro Ser Phe Glu Asn Leu Leu Lys Cys Gly Met Glu Val Tyr
                1415                1420                1425
Lys Gly Tyr Met Asp Asp Pro Arg Asn Thr Asp Asn Ala Trp Ile
                1430                1435                1440
```

```
Glu Thr Val Ala Val Ser Val His Phe Gln Asp Gln Asn Asp Val
                1445                1450                1455

Glu Leu Asn Arg Leu Asn Ser Asn Leu His Ala Cys Asp Ser Gly
            1460                1465                1470

Ala Ser Ile Arg Trp Gln Val Val Asp Arg Arg Ile Pro Leu Tyr
        1475                1480                1485

Ala Asn His Lys Thr Leu Leu Gln Lys Ala Ala Ala Glu Phe Gly
    1490                1495                1500

Ala His Tyr

<210> SEQ ID NO 31
<211> LENGTH: 43
<212> TYPE: DNA
<213> ORGANISM: Artificial sequence
<220> FEATURE:
<223> OTHER INFORMATION: oligonucleotide probe

<400> SEQUENCE: 31
tgtaaaacga cggccagtta aatagacctg caattattaa  tct                    43

<210> SEQ ID NO 32
<211> LENGTH: 41
<212> TYPE: DNA
<213> ORGANISM: Artificial sequence
<220> FEATURE:
<223> OTHER INFORMATION: oligonucleotide probe

<400> SEQUENCE: 32
caggaaacag ctatgaccac ctgcacacct gcaaatccat  t                      41

<210> SEQ ID NO 33
<211> LENGTH: 24
<212> TYPE: DNA
<213> ORGANISM: Artificial sequence
<220> FEATURE:
<223> OTHER INFORMATION: oligonucleotide probe

<400> SEQUENCE: 33
aagttccagt gccgcaccag  tggc                                         24

<210> SEQ ID NO 34
<211> LENGTH: 24
<212> TYPE: DNA
<213> ORGANISM: Artificial sequence
<220> FEATURE:
<223> OTHER INFORMATION: oligonucleotide probe

<400> SEQUENCE: 34
ttggttccac agccgagctc  gtcg                                         24

<210> SEQ ID NO 35
<211> LENGTH: 50
<212> TYPE: DNA
<213> ORGANISM: Artificial sequence
<220> FEATURE:
<223> OTHER INFORMATION: oligonucleotide probe

<400> SEQUENCE: 35
gaggaggagt gcaggattga gccatgtacc cagaaagggc aatgcccacc               50

<210> SEQ ID NO 36
<211> LENGTH: 25
<212> TYPE: DNA
<213> ORGANISM: Artificial sequence
<220> FEATURE:
```

<223> OTHER INFORMATION: oligonucleotide probe

<400> SEQUENCE: 36
cgaaccttcc tactgggctc cggtg    25

<210> SEQ ID NO 37
<211> LENGTH: 45
<212> TYPE: DNA
<213> ORGANISM: Artificial sequence
<220> FEATURE:
<223> OTHER INFORMATION: oligonucleotide probe

<400> SEQUENCE: 37
ccaacatcta tgcagatacc tcaagcatct gcaagacagc cgtgc    45

<210> SEQ ID NO 38
<211> LENGTH: 24
<212> TYPE: DNA
<213> ORGANISM: Artificial sequence
<220> FEATURE:
<223> OTHER INFORMATION: oligonucleotide probe

<400> SEQUENCE: 38
gcctgacagc aaagatccgg aagg    24

<210> SEQ ID NO 39
<211> LENGTH: 24
<212> TYPE: DNA
<213> ORGANISM: Artificial sequence
<220> FEATURE:
<223> OTHER INFORMATION: oligonucleotide probe

<400> SEQUENCE: 39
tcagctccag actctgatac tgcc    24

<210> SEQ ID NO 40
<211> LENGTH: 24
<212> TYPE: DNA
<213> ORGANISM: Artificial sequence
<220> FEATURE:
<223> OTHER INFORMATION: oligonucleotide probe

<400> SEQUENCE: 40
tgcctttcta ggaggcagag ctcc    24

<210> SEQ ID NO 41
<211> LENGTH: 50
<212> TYPE: DNA
<213> ORGANISM: Artificial sequence
<220> FEATURE:
<223> OTHER INFORMATION: oligonucleotide probe

<400> SEQUENCE: 41
ggacccagaa atgtgtcctg agaatggatc ttgtgtacct gatggtccag    50

<210> SEQ ID NO 42
<211> LENGTH: 20
<212> TYPE: DNA
<213> ORGANISM: Artificial sequence
<220> FEATURE:
<223> OTHER INFORMATION: oligonucleotide probe

<400> SEQUENCE: 42
cgagatgacg ccgagccccc    20

<210> SEQ ID NO 43

```
<211> LENGTH: 21
<212> TYPE: DNA
<213> ORGANISM: Artificial sequence
<220> FEATURE:
<223> OTHER INFORMATION: oligonucleotide probe

<400> SEQUENCE: 43
cggttcgaca cgcggcaggt g                                        21

<210> SEQ ID NO 44
<211> LENGTH: 45
<212> TYPE: DNA
<213> ORGANISM: Artificial sequence
<220> FEATURE:
<223> OTHER INFORMATION: oligonucleotide probe

<400> SEQUENCE: 44
tgctgctcct gctgccgccg ctgctgctgg gggccttccc gccgg              45

<210> SEQ ID NO 45
<211> LENGTH: 24
<212> TYPE: DNA
<213> ORGANISM: Artificial sequence
<220> FEATURE:
<223> OTHER INFORMATION: oligonucleotide probe

<400> SEQUENCE: 45
ttcgaggcct ctgagaagtg gccc                                     24

<210> SEQ ID NO 46
<211> LENGTH: 22
<212> TYPE: DNA
<213> ORGANISM: Artificial sequence
<220> FEATURE:
<223> OTHER INFORMATION: oligonucleotide probe

<400> SEQUENCE: 46
ggcggtatct ctctggcctc cc                                       22

<210> SEQ ID NO 47
<211> LENGTH: 50
<212> TYPE: DNA
<213> ORGANISM: Artificial sequence
<220> FEATURE:
<223> OTHER INFORMATION: oligonucleotide probe

<400> SEQUENCE: 47
ttctccacag cagctgtggc atccgatcgt gtctcaatcc attctctggg         50

<210> SEQ ID NO 48
<211> LENGTH: 34
<212> TYPE: DNA
<213> ORGANISM: Artificial sequence
<220> FEATURE:
<223> OTHER INFORMATION: oligonucleotide probe

<400> SEQUENCE: 48
acgtagttcc agtatggtgt gagcagcaac tgga                          34

<210> SEQ ID NO 49
<211> LENGTH: 26
<212> TYPE: DNA
<213> ORGANISM: Artificial sequence
<220> FEATURE:
<223> OTHER INFORMATION: oligonucleotide probe

<400> SEQUENCE: 49
```

```
agtccagcct ccaccctcca gttgct                                            26
```

<210> SEQ ID NO 50
<211> LENGTH: 25
<212> TYPE: DNA
<213> ORGANISM: Artificial sequence
<220> FEATURE:
<223> OTHER INFORMATION: oligonucleotide probe

<400> SEQUENCE: 50

```
ccccagtcct ccaggagaac cagca                                             25
```

<210> SEQ ID NO 51
<211> LENGTH: 27
<212> TYPE: DNA
<213> ORGANISM: Artificial sequence
<220> FEATURE:
<223> OTHER INFORMATION: oligonucleotide probe

<400> SEQUENCE: 51

```
ggatttggtt agctgagccc accgaga                                           27
```

<210> SEQ ID NO 52
<211> LENGTH: 26
<212> TYPE: DNA
<213> ORGANISM: Artificial sequence
<220> FEATURE:
<223> OTHER INFORMATION: oligonucleotide probe

<400> SEQUENCE: 52

```
gcactgcgcg cgacctcagg gctgca                                            26
```

<210> SEQ ID NO 53
<211> LENGTH: 50
<212> TYPE: DNA
<213> ORGANISM: Artificial sequence
<220> FEATURE:
<223> OTHER INFORMATION: oligonucleotide probe

<400> SEQUENCE: 53

```
cttattgccc taaatattag ggagccggcg acctcctgga tcctctcatt                  50
```

<210> SEQ ID NO 54
<211> LENGTH: 24
<212> TYPE: DNA
<213> ORGANISM: Artificial sequence
<220> FEATURE:
<223> OTHER INFORMATION: oligonucleotide probe

<400> SEQUENCE: 54

```
gcaagaattc agggatcggt ctgg                                              24
```

<210> SEQ ID NO 55
<211> LENGTH: 47
<212> TYPE: DNA
<213> ORGANISM: Artificial sequence
<220> FEATURE:
<223> OTHER INFORMATION: oligonucleotide probe

<400> SEQUENCE: 55

```
ctgtgttccc tgcaaccagt gtgggccagg catggagttg tctaagg                     47
```

<210> SEQ ID NO 56
<211> LENGTH: 24
<212> TYPE: DNA
<213> ORGANISM: Artificial sequence
<220> FEATURE:

-continued

<223> OTHER INFORMATION: oligonucleotide probe

<400> SEQUENCE: 56
agatggcatc actggtggct gaac                                          24

<210> SEQ ID NO 57
<211> LENGTH: 26
<212> TYPE: DNA
<213> ORGANISM: Artificial sequence
<220> FEATURE:
<223> OTHER INFORMATION: oligonucleotide probe

<400> SEQUENCE: 57
cagaaggcaa attgttcagc caccag                                        26

<210> SEQ ID NO 58
<211> LENGTH: 27
<212> TYPE: DNA
<213> ORGANISM: Artificial sequence
<220> FEATURE:
<223> OTHER INFORMATION: oligonucleotide probe

<400> SEQUENCE: 58
acagtttcca gaccgatccc tgaattc                                       27

<210> SEQ ID NO 59
<211> LENGTH: 24
<212> TYPE: DNA
<213> ORGANISM: Artificial sequence
<220> FEATURE:
<223> OTHER INFORMATION: oligonucleotide probe

<400> SEQUENCE: 59
atggagattc ctgccaactt gccg                                          24

<210> SEQ ID NO 60
<211> LENGTH: 24
<212> TYPE: DNA
<213> ORGANISM: Artificial sequence
<220> FEATURE:
<223> OTHER INFORMATION: oligonucleotide probe

<400> SEQUENCE: 60
ttgttggcat tgaggaggag cagc                                          24

<210> SEQ ID NO 61
<211> LENGTH: 50
<212> TYPE: DNA
<213> ORGANISM: Artificial sequence
<220> FEATURE:
<223> OTHER INFORMATION: oligonucleotide probe

<400> SEQUENCE: 61
gagggcatcg tcgaaatacg cctagaacag aactccatca aagccatccc              50

<210> SEQ ID NO 62
<211> LENGTH: 27
<212> TYPE: DNA
<213> ORGANISM: Artificial sequence
<220> FEATURE:
<223> OTHER INFORMATION: oligonucleotide probe

<400> SEQUENCE: 62
ctggcaacag cagtgtctat tttgtgc                                       27

<210> SEQ ID NO 63

```
<211> LENGTH: 21
<212> TYPE: DNA
<213> ORGANISM: Artificial sequence
<220> FEATURE:
<223> OTHER INFORMATION: oligonucleotide probe

<400> SEQUENCE: 63
taagtgccct cccaggctgc c                                      21

<210> SEQ ID NO 64
<211> LENGTH: 52
<212> TYPE: DNA
<213> ORGANISM: Artificial sequence
<220> FEATURE:
<223> OTHER INFORMATION: oligonucleotide probe

<400> SEQUENCE: 64
tcctccagtc atgaatataa cccaagtcaa tggctctttg ttggtaattc         50
tc                                                            52

<210> SEQ ID NO 65
<211> LENGTH: 22
<212> TYPE: DNA
<213> ORGANISM: Artificial sequence
<220> FEATURE:
<223> OTHER INFORMATION: oligonucleotide probe

<400> SEQUENCE: 65
ggcattggag cagtgctggg tg                                      22

<210> SEQ ID NO 66
<211> LENGTH: 24
<212> TYPE: DNA
<213> ORGANISM: Artificial sequence
<220> FEATURE:
<223> OTHER INFORMATION: oligonucleotide probe

<400> SEQUENCE: 66
tggaggccta gatgcggctg gacg                                    24

<210> SEQ ID NO 67
<211> LENGTH: 1571
<212> TYPE: DNA
<213> ORGANISM: Homo sapiens

<400> SEQUENCE: 67
gatggcgcag ccacagcttc tgtgagattc gatttctccc cagttcccct         50
gtgggtctga ggggaccaga agggtgagct acgttggctt tctggaaggg        100
gaggctatat gcgtcaattc cccaaaacaa gttttgacat ttcccctgaa        150
atgtcattct ctatctattc actgcaagtg cctgctgttc caggccttac        200
ctgctgggca ctaacggcgg agccaggatg gggacagaat aaaggagcca        250
cgacctgtgc caccaactcg cactcagact ctgaactcag acctgaaatc        300
ttctcttcac gggaggcttg gcagtttttc ttactcctgt ggtctccaga        350
tttcaggcct aagatgaaag cctctagtct tgccttcagc cttctctctg        400
ctgcgtttta tctcctatgg actccttcca ctggactgaa gacactcaat        450
ttgggaagct gtgtgatcgc cacaaacctt caggaaatac gaaatggatt        500
ttctgagata cggggcagtg tgcaagccaa agatggaaac attgacatca        550
gaatcttaag gaggactgag tctttgcaag acacaaagcc tgcgaatcga        600
```

```
tgctgcctcc tgcgccattt gctaagactc tatctggaca gggtatttaa        650
aaactaccag acccctgacc attatactct ccggaagatc agcagcctcg        700
ccaattcctt tcttaccatc aagaaggacc tccggctctc tcatgcccac        750
atgacatgcc attgtgggga ggaagcaatg aagaaataca gccagattct        800
gagtcacttt gaaaagctgg aacctcaggc agcagttgtg aaggctttgg        850
gggaactaga cattcttctg caatggatgg aggagacaga ataggaggaa        900
agtgatgctg ctgctaagaa tattcgaggt caagagctcc agtcttcaat        950
acctgcagag gaggcatgac cccaaaccac catctcttta ctgtactagt       1000
cttgtgctgg tcacagtgta tcttatttat gcattacttg cttccttgca       1050
tgattgtctt tatgcatccc caatcttaat gagaccata cttgtataag        1100
attttgtaa tatctttctg ctattggata tatttattag ttaatatatt        1150
tatttatttt ttgctattta atgtatttat tttttacttt ggacatgaaa       1200
ctttaaaaaa attcacagat tatatttata acctgactag agcaggtgat       1250
gtatttttat acagtaaaaa aaaaaaacct tgtaaattct agaagagtgg       1300
ctagggggt tattcatttg tattcaacta aggacatatt tactcatgct        1350
gatgctctgt gagatatttg aaattgaacc aatgactact taggatgggt       1400
tgtggaataa gttttgatgt ggaattgcac atctaccta caattactga       1450
ccatccccag tagactcccc agtcccataa ttgtgtatct tccagccagg       1500
aatcctacac ggccagcatg tatttctaca aataaagttt tctttgcata       1550
ccaaaaaaaa aaaaaaaaa  a                                      1571

<210> SEQ ID NO 68
<211> LENGTH: 176
<212> TYPE: PRT
<213> ORGANISM: Homo sapiens

<400> SEQUENCE: 68

Met Lys Ala Ser Ser Leu Ala Phe Ser Leu Leu Ser Ala Ala Phe
 1               5                  10                  15

Tyr Leu Leu Trp Thr Pro Ser Thr Gly Leu Lys Thr Leu Asn Leu
                20                  25                  30

Gly Ser Cys Val Ile Ala Thr Asn Leu Gln Glu Ile Arg Asn Gly
                35                  40                  45

Phe Ser Glu Ile Arg Gly Ser Val Gln Ala Lys Asp Gly Asn Ile
                50                  55                  60

Asp Ile Arg Ile Leu Arg Arg Thr Glu Ser Leu Gln Asp Thr Lys
                65                  70                  75

Pro Ala Asn Arg Cys Cys Leu Leu Arg His Leu Leu Arg Leu Tyr
                80                  85                  90

Leu Asp Arg Val Phe Lys Asn Tyr Gln Thr Pro Asp His Tyr Thr
                95                 100                 105

Leu Arg Lys Ile Ser Ser Leu Ala Asn Ser Phe Leu Thr Ile Lys
               110                 115                 120

Lys Asp Leu Arg Leu Ser His Ala His Met Thr Cys His Cys Gly
               125                 130                 135

Glu Glu Ala Met Lys Lys Tyr Ser Gln Ile Leu Ser His Phe Glu
               140                 145                 150

Lys Leu Glu Pro Gln Ala Ala Val Val Lys Ala Leu Gly Glu Leu
               155                 160                 165
```

```
Asp Ile Leu Leu Gln Trp Met Glu Glu Thr Glu
            170                 175

<210> SEQ ID NO 69
<211> LENGTH: 28
<212> TYPE: DNA
<213> ORGANISM: Artificial sequence
<220> FEATURE:
<223> OTHER INFORMATION: oligonucleotide probe

<400> SEQUENCE: 69
ctcctgtggt ctccagattt  caggccta                                       28

<210> SEQ ID NO 70
<211> LENGTH: 26
<212> TYPE: DNA
<213> ORGANISM: Artificial sequence
<220> FEATURE:
<223> OTHER INFORMATION: oligonucleotide probe

<400> SEQUENCE: 70
agtcctcctt aagattctga  tgtcaa                                         26
```